US012366579B2

(12) United States Patent
Hsu et al.

(10) Patent No.: US 12,366,579 B2
(45) Date of Patent: Jul. 22, 2025

(54) SULFUR-HETEROCYCLE EXCHANGE CHEMISTRY AND USES THEREOF

(71) Applicant: University of Virginia Patent Foundation, Charlottesville, VA (US)

(72) Inventors: Ku-Lung Hsu, Charlottesville, VA (US); Heung Sik Hahm, Atlanta, GA (US); Emmanuel K. Toroitich, Charlottesville, VA (US); Jeffrey W. Brulet, Glen Allen, VA (US); Adam L. Borne, Charlottesville, VA (US); Adam Herman Libby, Charlottesville, VA (US); Kun Yuan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 895 days.

(21) Appl. No.: 17/441,544

(22) PCT Filed: Mar. 23, 2020

(86) PCT No.: PCT/US2020/024286
§ 371 (c)(1),
(2) Date: Sep. 21, 2021

(87) PCT Pub. No.: WO2020/214336
PCT Pub. Date: Oct. 22, 2020

(65) Prior Publication Data
US 2022/0214355 A1 Jul. 7, 2022

Related U.S. Application Data

(60) Provisional application No. 62/929,473, filed on Nov. 1, 2019, provisional application No. 62/821,478, filed on Mar. 21, 2019.

(51) Int. Cl.
*G01N 33/68* (2006.01)
*C07D 249/04* (2006.01)
*C07D 249/08* (2006.01)
*C07K 2/00* (2006.01)
*C12N 5/00* (2006.01)
*G01N 33/58* (2006.01)

(52) U.S. Cl.
CPC ....... *G01N 33/6845* (2013.01); *C07D 249/04* (2013.01); *C07D 249/08* (2013.01); *C07K 2/00* (2013.01); *C12N 5/0018* (2013.01); *G01N 33/58* (2013.01); *G01N 33/6848* (2013.01); *C12N 2500/32* (2013.01); *C12N 2501/73* (2013.01); *G01N 2458/15* (2013.01)

(58) Field of Classification Search
USPC ...................................................... 548/262
See application file for complete search history.

(56) References Cited

U.S. PATENT DOCUMENTS

| | | | |
|---|---|---|---|
| 4,710,509 A | 12/1987 | Saito et al. | |
| 2011/0245308 A1 | 10/2011 | Brueggemeier et al. | |
| 2013/0190330 A1 | 7/2013 | Furstner et al. | |
| 2016/0252509 A1 | 9/2016 | Cravatt et al. | |
| 2017/0115303 A1 | 4/2017 | Cravatt et al. | |
| 2017/0326125 A1* | 11/2017 | Short | A61K 31/4196 |
| 2018/0372751 A1 | 12/2018 | Cravatt et al. | |
| 2019/0204336 A1 | 7/2019 | Matthews | |
| 2022/0251085 A1 | 8/2022 | Hsu et al. | |
| 2024/0210412 A1 | 6/2024 | Hsu et al. | |

FOREIGN PATENT DOCUMENTS

| | | | |
|---|---|---|---|
| CN | 104087145 A | * | 10/2014 |
| CN | 105541774 A | | 5/2016 |
| CN | 108368051 A | | 8/2018 |
| CN | 113853372 | | 12/2021 |
| WO | WO2011/104322 A1 | * | 9/2011 |
| WO | WO2012/016133 A2 | * | 2/2012 |
| WO | WO2013/019469 A1 | * | 2/2013 |
| WO | WO2015/191630 A1 | * | 12/2015 |
| WO | WO2018/233633 A1 | * | 12/2018 |
| WO | WO 2019/204740 A1 | | 10/2019 |
| WO | WO-2020/214336 A2 | | 10/2020 |
| WO | WO 2021/016262 | | 1/2021 |
| WO | WO2022/221451 | | 10/2022 |
| WO | WO 2023/023376 | | 2/2023 |
| WO | WO 2023/023664 | | 2/2023 |
| WO | WO2024/097262 | | 5/2024 |

OTHER PUBLICATIONS

Spyrakis et al., ACS Med Chem letters (2018) 9(1): 45-50.*
Szabo et al., Tetrahed (2017) 73(27-28), 3810-22.*
Behrouz et al., J Chem Res (2016) 40(2), 101-106.*
Wu et al., Synth Commun (2016), 46(17), 1432-37.*
Vaillancourt et al., e-EROS Encyclopedia Reagents for org Synth (2001), 1 pp.*
Kornienko et al., Chem Heterocyclics Comp (2014) 50(1), 76-86.*
Foks et al., Heteroatom Chem (2012) 23(1), 49-58.*
Adibekian A., et al., "Click-generated triazole ureas as ultrapotent in vivo-active serine hydrolase inhibitors", Nat Chem Biol, Jul. 2011, vol. 7, No. 7, pp. 469-478.
Ahn K., et al., "Discovery of a Selective Covalent Inhibitor of Lysophospholipase-like 1 (LYPLAL1) as a Tool to Evaluate the Role of this Serine Hydrolase in Metabolism", ACS Chem Biol, vol. 11, No. 9, Jul. 8, 2016, pp. 2529-2540.

(Continued)

*Primary Examiner* — Taofiq A Solola
(74) *Attorney, Agent, or Firm* — Jenkins, Taylor & Hunt, P.A.

(57) ABSTRACT

Sulfonyl-triazole compounds and related sulfonyl-heterocycle compounds are described. The compounds can be used to identify reactive nucleophilic amino acid residues, such as reactive tyrosines and reactive lysines, in proteins and to modify the activity of proteins with reactive nucleophilic amino acid residues via the formation of protein adducts comprising a fragment of the compounds. Methods are also described for screening the compounds to identify ligands of proteins comprising a reactive lysine or a reactive tyrosine.

16 Claims, 69 Drawing Sheets

Specification includes a Sequence Listing.

(56) References Cited

OTHER PUBLICATIONS

Allocati N., et al., "Glutathione transferases: substrates, inhibitors and pro-drugs in cancer and neurodegenerative diseases", Oncogenesis, vol. 7(1):8, 2018, pp. 1:15.
Bachovchin D. A., et al., "The pharmacological landscape and therapeutic potential of serine hydrolases", Nature Reviews | Drug Discovery, vol. 11, No. 1, Jan. 2012, pp. 52-68.
Backus, K. M., et al., "Proteome-wide covalent ligand discovery in native biological systems", Nature 2016, vol. 534, No. 7608, pp. 570-574.
Belousova Z. P., et al., "Synthesis of 2,4,6-Triisopropylbenzenesulfonic Acid N-Azolides and Their Regulatory Effect on Cell Proliferation, Energy Expenditure, and Apoptosis Processes", Pharmaceutical Chemistry Journal. Vo. 43, No. 6, Jun. 6-9, 2009.
Bereman M. S., et al., "An Automated Pipeline to Monitor System Performance in Liquid Chromatography-Tandem Mass Spectrometry Proteomic Experiments", J Proteome Res, vol. 15, No. 12, 2016, pp. 4763-4769.
Bern .M., et al., "Byonic: advanced peptide and protein identification software", Current Protocols in Bioinformatics, Chapter 13: Unit13.20, Dec. 2012, pp. 1-14.
Bezerra G. A., et al., "Entropy-driven binding of opioid peptides induces a large domain motion in human dipeptidyl peptidase III", Proc Natl Acad Sci U S A, vol. 109. No. 17, Apr. 24, 2012, pp. 6525-6530.
Bicker K. L., et al., "Seeing Citrulline: Development of a Phenylglyoxal-Based Probe to Visualize Protein Citrullination", Journal of the American Chemical Society, vol. 134, No. 41, 2012, pp. 17015-17018.
Bos, J., et al., "A Chemical Probe for Protein Crotonylation", J Am Chem Soc 2018, vol. 140, No. 14, pp. 4757-4760.
Bradshaw J. M., et al., "Prolonged and tunable residence time using reversible covalent kinase inhibitors" nature Chemical Biology, vol. 11, No. 7, 2015, pp. 525-531.
Chang, T-K., et al., "Uba1 functions in Atg7- and Atg3-independent autophagy", Nat Cell Biol, Sep. 2013, vol. 15, No. 9, pp. 1067-1078.
Charton M., "Electrical Effect Substituent Constants for Correlation Analysis", In Progress in Physical Organic Chemistry, vol. 13, pp. 119-251.
Chen H., et al., "VennDiagram: a package for the generation of highly-customizable Venn and Euler diagrams in R", BMC Bioinformatics, vol. 12:35, 2011, pp. 1-7.
Chen W, Dong J, Plate L, Mortenson DE, Brighty GJ, Li S, et al. Arylfluorosulfates Inactivate Intracellular Lipid Binding Protein(s) through Chemoselective SuFEx Reaction with a Binding Site Tyr Residue. J Am Chem Soc 2016. 138(23): 7353-7364.
Choi E. J., et al., "Chemoselective Tyrosine Bioconjugation through Sulfate Click Reaction", Chemistry, vol. 24, No. 43, 2018, pp. 10948-10952.
Cravatt B. F., et al., "Activity-Based Protein Profiling: From Enzyme Chemistry to Proteomic Chemistry", Annual Review of Biochemistry, vol. 77, Mar. 26, 2008, pp. 383-414.
Decker C. J., et al., "P-Bodies and Stress Granules: Possible Roles in the Control of Translation and mRNA Degradation", Cold Spring Harb Perspect Biol, vol. 4(9): a012286, 2012, pp. 1-18.
Deu E., et al., "New approaches for dissecting protease functions to improve probe development and drug discovery"., nature structural & molecular biology, vol. 19(1), Jan. 2012, pp. 9-16.
Dong J, et al., "SuFEx-based synthesis of polysulfates", Angew Chem Int Ed Engl, vol. 53, No. 36, Sep. 1, 2014, pp. 9466-9470.
Ei-Zemity Saad R et al: "Structure and Acaricidal Activity Relationship of Some Sulfonamide Derivatives Against the Two-spotted Spider Mite, Tetranychus urticae (Koch)", International Journal of Agriculture & Biology, Jan. 1, 2006 (Jan. 1, 2006) pp. 661-665.
Erlanson D. A., et al., "Twenty years on: the impact of fragments on drug discovery", Nature Reviews Drug Discovery, vol. 15, No. 9, Sep. 2016, pp. 605-619.
Extended European Search Report corresponding to European Patent Application Serial No. 20791052.2 dated Feb. 17, 2023.

Fadeyi OO, Hoth LR, Choi C, Feng X, Gopalsamy A, Hett EC, et al. Covalent Enzyme Inhibition through Fluorosulfate Modification of a Noncatalytic Serine Residue. ACS Chem Biol 2017, 12(8): 2015-2020.
Foks H., et al., "Studies on pyrazine derivatives LII: Antibacterial and antifungal activity of nitrogen heterocyclic compounds obtained by pyrazinamidrazone usage", Heteroatom Chemistry, vol. 23, No. 1, Sep. 14, 2011 (Sep. 14, 2011), pp. 49-58.
Franks C.E., et al., "The Ligand Binding Landscape of Diacylglycerol Kinases", Cell Chemical Biology, vol. 24 (7), 2017, pp. 870-880 e875.
Gait M.J., "Oligonucleotide Synthesis: A Practical Approach", IRL Press, Oxford, England, 1984, pp. 217.
Gao B., et al., "Bifluoride-catalysed sulfur(VI) fluoride exchange reaction for the synthesis of polysulfates and polysulfonates", Nature Chemistry, vol. 9, No. 11, Jun. 19, 2017, pp. 1083-1088.
Gavin, A. L., et al., "PLD3 and PLD4 are single-stranded acid exonucleases that regulate endosomal nucleic-acid sensing", Nat Immunol, Sep. 2018, vol. 19, No. 9, pp. 942-953.
Grimster N. P., et al., "Aromatic Sulfonyl Fluorides Covalently Kinetically Stabilize Transthyretin to Prevent Amyloidogenesis while Affording a Fluorescent Conjugate", Journal of the American Chemical Society, vol. 135, No. 15, 2013, pp. 5656-5668.
Gu C., et al., "Chemical proteomics with sulfonyl fluoride probes reveals selective labeling of functional tyrosines in glutathione transferases", Chemistry & Biology, vol. 20, No. 4, Apr. 18, 2013, pp. 541-548.
Hacker S. M., et al., "Global profiling of lysine reactivity and ligandability in the human proteome". Nature Chemistry, vol. 9, No. 12, Dec. 2017, pp. 1181-1190.
Hargous Y., et al., "Molecular basis of RNA recognition and TAP binding by the SR proteins SRp20 and 9G8", The EMBO Journal, vol. 25, No. 21, 2006, pp. 5126-5137.
Harris T. K., et al., "Structural Basis of Perturbed pKa Values of Catalytic Groups in Enzyme Active Sites", IUBMB Life, vol. 53, No. 2, 2002, pp. 85-98.
Hast B. E., et al., "Proteomic Analysis of Ubiquitin Ligase KEAP1 Reveals Associated Proteins That Inhibit NRF2 Ubiquitination", Cancer Research, vol. 73, No. 7, 2013, pp. 2199-2210.
Hentze M. W., et al., "A brave new world of RNA-binding proteins", Nature Reviews | Molecular Cell Biology, vol. 19, No. 5, May 2018, pp. 327-341.
Hett E. C., et al., "Rational Targeting of Active-Site Tyrosine Residues Using Sulfonyl Fluoride Probes", ACS Chemical Biology, vol. 10, No. 4, Jan. 29, 2015 (Jan. 29, 2015), pp. 1094-1098, XP055962185, ISSN: 1554-8929.
Hilger M., et al., "Systems-wide Analysis of a Phosphatase Knockdown by Quantitative Proteomics and Phosphoproteomics", Molecular & Cellular Proteomics, vol. 8(8), 2009, pp. 1906-1920.
Hitosugi T., et al., "Tyrosine phosphorylation inhibits PKM2 to promote the Warburg effect and tumor growth", Science Signaling, vol. 2(97): ra73, 2009, pp. 1-7.
Hong J.Y., et al., "Phosphorylation and isoform use in p120-catenin during development and tumorigenesis", Biochimica et Biophysica Acta, vol. 1863(1), 2016, pp. 102-114.
Hopkins A. L., et al., "The role of ligand efficiency metrics in drug discovery", Nature Reviews | Drug Discovery, vol. 13, No. 2, Feb. 2014, pp. 105-121.
Hornbeck P. V., et al., "PhosphoSitePlus, 2014: mutations, PTMs and recalibrations", Nucleic Acids Research, vol. 43, (Database issue), 2015, pp. D512-520.
Horning B. D., et al., "Chemical Proteomic Profiling of Human Methyltransferases", Journal of the American Chemical Society, vol. 138, No. 40, 2016, pp. 13335-13343.
Matthews M. L., et al., "Chemoproteomic profiling and discovery of protein electrophiles in human cells", Nature Chemistry, vol. 9, No. 3, Mar. 2017, pp. 234-243.
Mi H., et al., "Large-scale gene function analysis with the Panther classification system", nature protocols, vol. 8, No. 8, 2013, pp. 1551-1566.
Mortenson D. E., et al., "Inverse Drug Discovery" Strategy to Identify Proteins That are Targeted by Latent Electrophiles as

(56) References Cited

OTHER PUBLICATIONS

Exemplified by Aryl Fluorosulfates. Journal of the American Chemical Society, vol. 140, No. 1, 2018, pp. 200-210.

Niphakis M.J., et al., "Enzyme Inhibitor Discovery by Activity-Based Protein Profiling", Annual Review of Biochemistry, vol. 83, 2014, pp. 341-377.

Office Action corresponding to Chinese Patent Application Serial No. 202080037292X dated Oct. 12, 2023 (English translation).

Office Action corresponding to Chinese Patent Application Serial No. 202080037292X dated May 1, 2024 (English translation).

Okamura T., et al., "Tyrosine Phosphorylation of the Human Glutathione S-Transferase P1 by Epidermal Growth Factor Receptor", Journal of Biological Chemistry, vol. 284, No. 25, Jun. 19, 2009, pp. 16979-16989.

Paoletta S., et al., "Rational Design of Sulfonated A3 Adenosine Receptor-Selective Nucleosides as Pharmacological Tools to Study Chronic Neuropathic Pain", Journal of Medicinal Chemistry, vol. 56, No. 4, 2013, pp. 5949-5963.

Park, E., et al., "Architecture of autoinhibited and active BRAF-MEK1-14-3-3 complexes", Nature 2019, vol. 575, No. 7783, pp. 545-550.

Parker C.G., et al., "Ligand and Target Discovery by Fragment-Based Screening in Human Cells", Cell 2017, vol. 168, No. 3, pp. 527-541, e529.

Patricelli M. P., et al., "Functional Interrogation of the Kinome Using Nucleotide Acyl Phosphates", Biochemistry, vol. 46(2), 2007, pp. 350-358.

Patricelli M. P., et al., "In Situ Kinase Profiling Reveals Functionally Relevant Properties of Native Kinases", Chemistry & Biology, vol. 18, No. 6, 2011, pp. 699-710. 66.

Potapova I A et al., "Synthesis and Biological Activity of Aliphatic and Aromatic Sulfonic Acid Azolides", Pharmaceutical Chemistry Journal, Nov. 1, 2001 (Nov. 1, 2001), pp. 588-590.

Purygin et al. (2002) "Synthesis and Antibacterial Activity of 2-Naphthalenesulfonic Acid Azolides," Pharmaceutical Chemistry Journal, 16-17.

Raushel, J., et al., "Efficient Synthesis of 1-Sulfonyl-1,2,3-triazoles", Org. Lett, 2010, vol. 12, No. 21, pp. 4952-4955.

Resnick E., et al., "Rapid Covalent-Probe Discovery by Electrophile-Fragment Screening", Journal of the American Chemical Society, vol. 141, No. 22, 2019, pp. 8951-8968.

Humphrey S. J., et al., "Dynamic Adipocyte Phosphoproteome Reveals that Akt Directly Regulates mTORC2", Cell Metabolism, vol. 17, No. 6, Jun. 4, 2013, pp. 1009-1020.

International Preliminary Report on Patentability corresponding to International Patent Application No. PCT/US2020/024286 dated Sep. 30, 2021.

Kheirabadi, M., et al., "Leveraging a"Catch-Release" Logic Gate Process for the Synthesis and Nonchromatographic Purification of Thioether- or Amine-Bridged Macrocyclic Peptides", J. Org. Chem. 2018, 83(8), 4323-4335.

Kumar S., et al., "Activity-based probes for protein tyrosine phosphatases", Proceedings of the National Academy of Sciences of the United States of America, vol. 101, No. 21, May 25, 2004, pp. 7943-7948.

Lazreg, F., et.al., "Copper(I)-N-Heterocyclic Carbene Complexes as Efficient Catalysts for the Synthesis of 1,4-Disubstituted 1,2,3-Sulfonyltriazoles in Air", Organometallics, vol. 37, 2018, pp. 679-683.

Lee I., et al., "Structural Insights into E1-Catalyzed Ubiquitin Activation and Transfer to Conjugating Enzymes", Cell, vol. 134, No. 2, Jul. 25, 2008, pp. 268-278.

Lee J., et al., "N-[4-(Methylsulfonylamino) benzyl]thiourea analogues as vanilloid receptor antagonists: analysis of structure-activity relationships for the'C-Region'", Bioorganic & Medicinal Chemistry, vol. 12, 2004, pp. 371-385.

Lin S., et al., "Redox-based reagents for chemoselective methionine bioconjugation", Science, vol. 355, No. 6325, Feb. 10, 2017, pp. 597-602.

Lin Y, Lang SA. New Synthesis of Diacylamines. Synthesis-Stuttgart 1980(2): 119-121.

Lin Y-I., et al., "New synthesis of 1,2,4-triazoles and 1,2,4-oxadiazoles", The Journal of Organic Chemistry, 1979, vol. 44, No. 23, pp. 4160-4164.

Liu Q., et al., "Developing Irreversible Inhibitors of the Protein Kinase Cysteinome", Chemistry & Biology, vol. 20, No. 2, Feb. 21, 2013, pp. 146-159.

Liu X., et al., "Orthogonal ubiquitin transfer identifies ubiquitination substrates under differential control by the two ubiquitin activating enzymes", Nature Communications, vol. 8:14286, 2017, pp. 1-12.

Liu Y., et al., "Activity-based protein profiling: The serine hydrolases", Proceedings of the National Academy of Sciences of the United States of America, vol. 96, No. 26, Dec. 21, 1999, pp. 14694-14699.

Liu Z., et al., "SuFEx Click Chemistry Enabled Late-Stage Drug Functionalization", Journal of the American Chemical Society, vol. 140, No. 8, 2018, pp. 2919-2925.

Lundby A, et al., "Quantitative maps of protein phosphorylation sites across 14 different rat organs and tissues", nature communications, vol. 3: 876, 2012, pp. 1-10.

Makhija M.T., et al., "De novo design and synthesis of HIV-1 integrase inhibitors", Bioorganic & Medicinal Chemistry, vol. 12, Jan. 1, 2004, pp. 2317-2333.

Mangubat-Medina., et al., "A Vinylogous Photocleavage Strategy Allows Direct Photocaging of Backbone Amide Structure", Journal of the American Chemical Society, vol. 140, 2018, 140, pp. 8401-8404.

Manley J. L., et al., "A rational nomenclature for serine/arginine-rich protein splicing factors (SR proteins)", Genes & Development, vol. 24, No. 11, 2010, pp. 1073-1074.

Mann M., "Functional and quantitative proteomics using SILAC". Nature Reviews | Molecular Cell Biology, vol. 7, No. 12, Dec. 2006, pp. 952-958.

Sadaghiani A. M., "Tagging and detection strategies for activity-based proteomics", Current Opinion in Chemical Biology, vol. 11, No. 1, 2007, pp. 20-28.

Schreiber S. L., et al., "Advancing Biological Understanding and Therapeutics Discovery with Small-Molecule Probes", Cell, vol. 161, No. 6, 2015, pp. 1252-1265.

Scott D. E., et al., "Fragment-Based Approaches in Drug Discovery and Chemical Biology", Biochemistry, vol. 51, No. 25, 2012, pp. 4990-5003.

Selezneva E S et al: "Adaptation of *Staphylococcus aureus* to synthetic triazolides", Pharmaceutical Chemistry Journal, Kluwer Academic Publishers-Consultants Bureau, NE, vol. 40, No. 3, Mar. 1, 2006 (Mar. 1, 2006), pp. 145-148.

Shannon D. A., et al., "Investigating the Proteome Reactivity and Selectivity of Aryl Halides", Journal of the American Chemical Society, vol. 136, No. 9, 2014, pp. 3330-3333.

Shin M., et al., "Isoform-selective activity-based profiling of ERK signaling", Chemical Science, vol. 9, No. 9, 2018, pp. 2419-2431.

Sigrist C. J., et al., "New and continuing developments at Prosite", Nucleic Acids Research, vol. 41 (Database issue), 2013, pp. D344-D347.

Simaga S., et al., "Dipeptidyl Peptidase III in Malignant and Non-malignant Gynaecological Tissue", Eur J Cancer, vol. 34, No. 3, 1998, pp. 399-405.

Singh J., et al., "The resurgence of covalent drugs", Nature Reviews | Drug Discovery, vol. 10, No. 4, 2011, pp. 307-317.

Song G., et al., "Proteome-wide Tyrosine Phosphorylation Analysis Reveals Dysregulated Signaling Pathways in Ovarian Tumors", Molecular & Cellular Proteomics, vol. 18, No. 3, 2019, pp. 448-460.

Song L., et al., "Activation of Stat3 by receptor tyrosine kinases and cytokines regulates survival in human non-small cell carcinoma cells", Oncogene, vol. 22, No. 27, 2003, pp. 4150-4165.

Spradlin J. N., et al., "Harnessing the anti-cancer natural product nimbolide for targeted protein degradation". Nature Chemical Biology, vol. 15, No. 7, Jul. 2019, pp. 747-755.

Thirukovela N.S., et al., "Regioselective synthesis of some new 1,4-disubstituted sulfonyl-1,2,3-triazoles and their antibacterial activity studies", Medicinal Chemistry Research, Birkhaeuser, Boston, US, vol. 26, No. 9, May 29, 2017 (May 29, 2017), pp. 2190-2195.

(56) References Cited

OTHER PUBLICATIONS

Turner S. C., et al., "A New Class of Histamine H3-Receptor Antagonists: Synthesis and Structure—Activity Relationships of 7,8,9,10-Tetrahydro-6H-cyclohepta[b]quinolines", Bioorg. Med. Chem. Lett. vol. 13, Accepted Apr. 9, 2003, pp. 2131-2135.

Vocadlo D. J., et al., "A Strategy for Functional Proteomic Analysis of Glycosidase Activity from Cell Lysates", Angew. Chem. Int. Ed., vol. 43, No. 40, 2004, pp. 5338-5342.

Wang R., et al., "Profiling Genome-Wide Chromatin Methylation with Engineered Posttranslation Apparatus within Living Cells", Journal of the American Chemical Society, vol. 135, No. 3, 2013, pp. 1048-1056.

Wang Y., et al., "Expedited mapping of the ligandable proteome using fully functionalized enantiomeric probe pairs", Nature Chemistry, vol. 11, No. 12, 2019, pp. 1113-1123.

Ware, T.B., et al., "Reprogramming fatty acyl specificity of lipid kinases via C1 domain engineering", Nat. Chem. Biol., 2020, vol. 16, pp. 170-178.

Weerapana E., et al., "Disparate proteome reactivity profiles of carbon electrophiles", Nature Chemical Biology, vol. 4, No. 7, Jul. 2008, pp. 405-407.

Weerapana E., et al., "Quantitative reactivity profiling predicts functional cysteines in proteomes", Nature, vol. 468, No. 7325, Dec. 9, 2010, pp. 790-795.

Wishart D. S., et al., "DrugBank 5.0: a major update to the DrugBank database for 2018", Nucleic Acids Research, vol. 46(D1), 2018, pp. D1074-D1082.

Yaffe MB., "Phosphotyrosine-Binding Domains in Signal Transduction". Nature Reviews | Molecular Cell Biology, vol. 3, No. 3, Mar. 2002, pp. 177-186.

Yamauchi M., et al., "Preparation of 2-Sulfonyl-1,2,3-Triazoles by Base-Promoted 1,2-Rearrangement of a Sulfonyl Group", Heterocycles, vol. 80, No. 1, 2010, pp. 177-181.

Yang B., et al., "Genetically Introducing Biochemically Reactive Amino Acids Dehydroalanine and Dehydrobutyrine in Proteins", Journal of the American Chemical Society, vol. 141, No. 19, 2019, pp. 7698-7703.

Yang X., et al., "An Affinity-Based Probe for the Human Adenosine A2A Receptor", Journal of Medicinal Chemistry, vol. 61, No. 17, 2018, pp. 7892-7901.

Yoo, E., et al., "Defining the Determinants of Specificity of Plasmodium Proteasome Inhibitors", J Am Chem Soc, Se2018, vol. 140, No. 36, pp. 11424-11437.

Yusubov M. S., et al., "Potassium 4-Iodylbenzenesulfonate: Preparation, Structure, and Application as a Reagent for Oxidative Iodination of Arenes", Eur. J. Org. Chem, vol. 30, 2012, pp. 5935-5942.

Zhang L., et al., "Comprehensive Review in Current Developments of Imidazole-Based Medicinal Chemistry", Medicinal Research Reviews, vol. 34, No. 2, 2014, pp. 340-437.

International Search Report and Written Opinion corresponding to International Patent Application No. PCT/US2020/024286 dated Jan. 22, 2021.

Hahm et al. (2019) "Global Targeting of Functional Tyrosines Using Sulfur Triazole Exchange Chemistry," Nat. Chem. Biol., vol. 16, No. 2, pp. 150-159.

Liu et al. (2008) "Aryl Vinyl Sulfonates and Sulfones as Active Site-Directed and Mechanism-Based Probes for Protein Tyrosine Phosphatases," J. Am. Chem. Soc., vol. 130, No. 26, pp. 8251-8260.

Narayanan et al. (2015) "Sulfonyl Fluorides as Privileged Warheads in Chemical Biology," Chem. Sci., vol. 6, pp. 2650-2659.

PubChem-CID-11045411, created Oct. 26, 2006.

PubChem-CID-12585520, created Feb. 8, 2007.

PubChem-CID-69947416, created Dec. 1, 2012.

PubChem-CID-71376695, created May 22, 2013.

Office Action corresponding to European Patent Application Serial No. 20791052.2 dated Nov. 12, 2024.

Fahrney, D.E., et al., "Sulfonyl Fluorides as Inhibitors of Esterases. I. Rates of Reaction with Acetylcholinesterase, α-Chymotrypsin, and Trypsin," Journal of the American Chemical Society, vol. 85, No. 07, 1963, pp. 997-1000.

Sato, T., et al., "Characterization of Rh (I) complexes bearing• N-2-nitrobenzenesulfonyl substituted, N-heterocyclic Carbenes," Journal of Organometallic Chemistry, vol. 753, pp. 20-26, Mar. 1, 2014.

Shannon, D.A., et al., "Sulfonyl Fluoride Analogues as Activity-based Probes for Serine Proteases," ChemBioChem, vol. 13, No. 16, 2012, pp. 2327-2330.

Yang, B., et al., "Proximity-enhanced SuFEx Chemical Cross-linker for Specific and Multitargeting Cross-linking Mass Spectrometry," Proceedings of the National Academy of Sciences of the United States of America, vol. 115, No. 44, 2018, pp. 11162-11167.

Zhang, X., et al., "Electrophilic PROTACs that Degrade Nuclear Proteins by Engaging DCAF16," Nature Chemical Biology, vol. 15, No. 07, 2019, pp. 737-746.

Zhao, Q., et al., "Broad-Spectrum Kinase Profiling in Live Cells with Lysine-Targeted Sulfonyl Fluoride Probes," Journal of the American Chemical Society, vol. 139, No. 02, 2017, pp. 680-685.

Zheng, Q., et al., "SuFEx-enabled, Agnostic Discovery of Covalent Inhibitors of Human Neutrophil Elastase," Proceedings of the National Academy of Sciences of the United States of America, vol. 116, No. 38, 2019, pp. 18808-18814.

\* cited by examiner

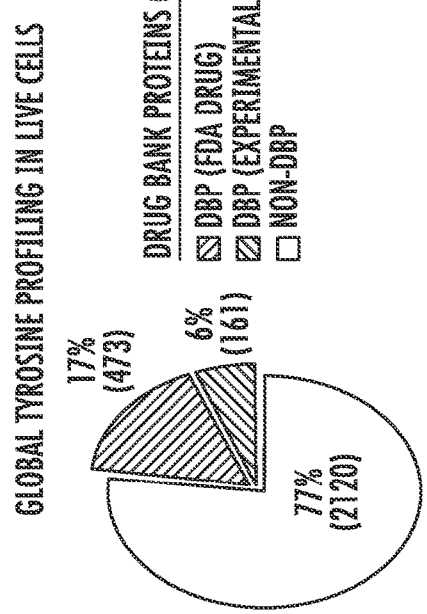
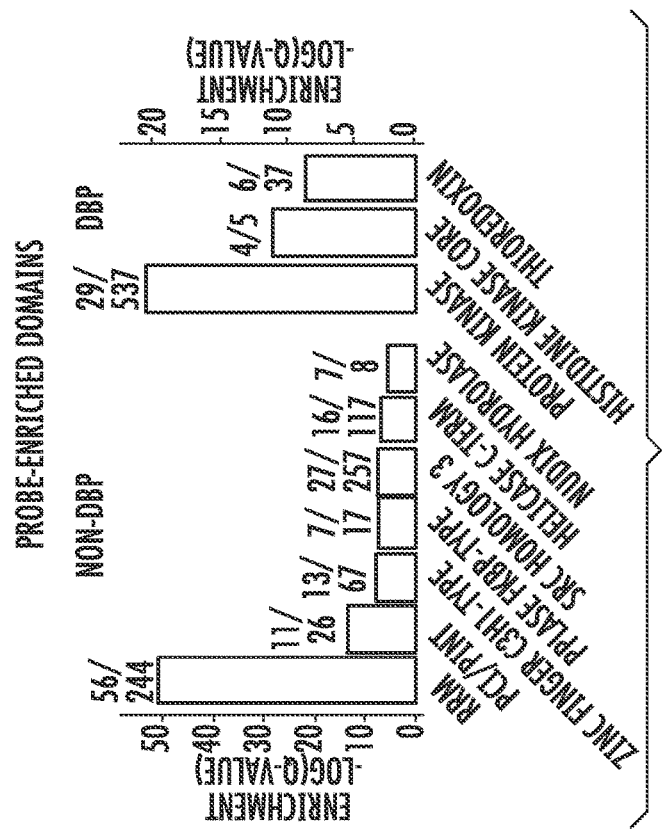
FIG. 2D
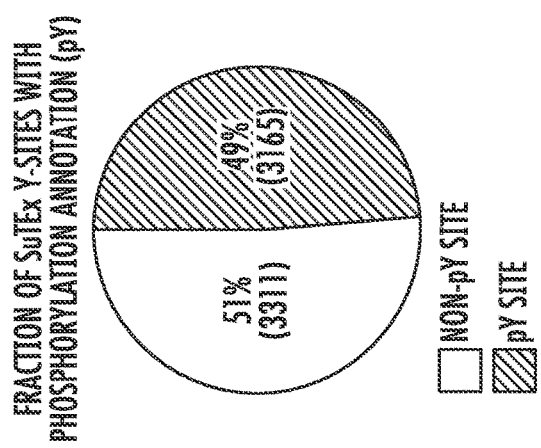
FIG. 2C

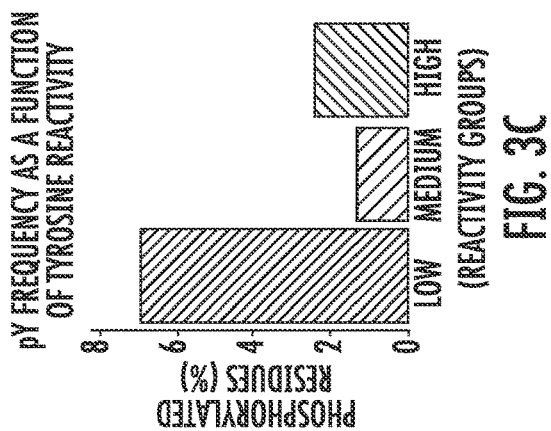
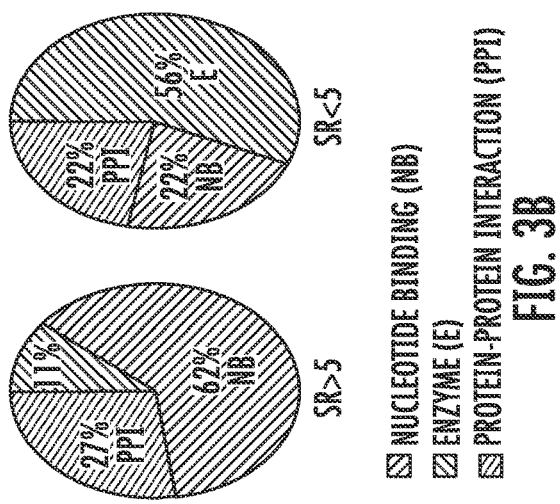
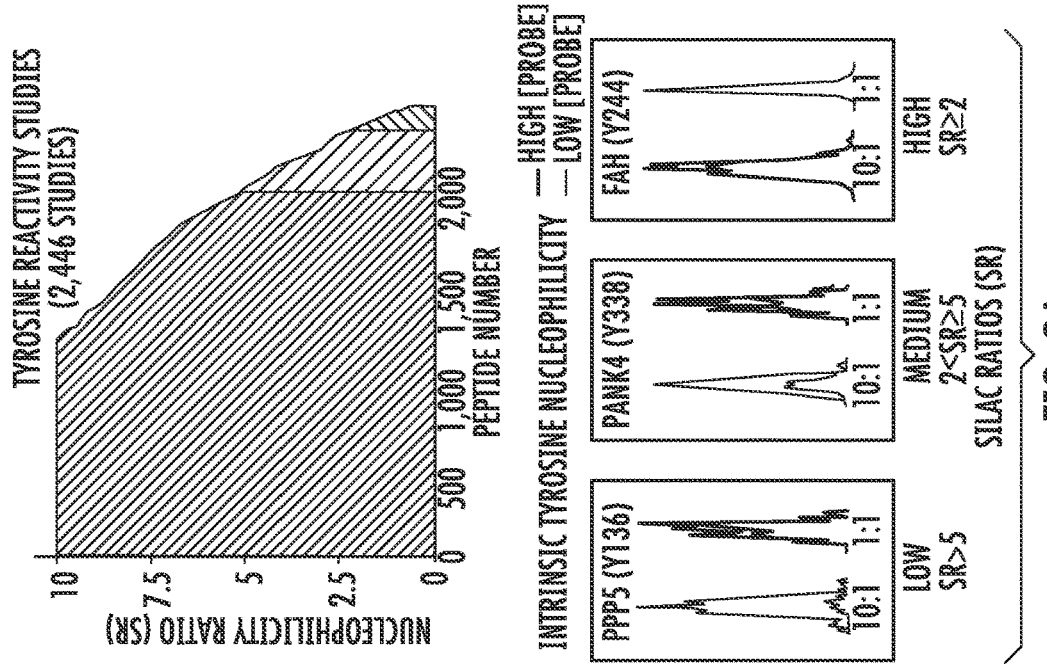
FIG. 3C
FIG. 3B
FIG. 3A

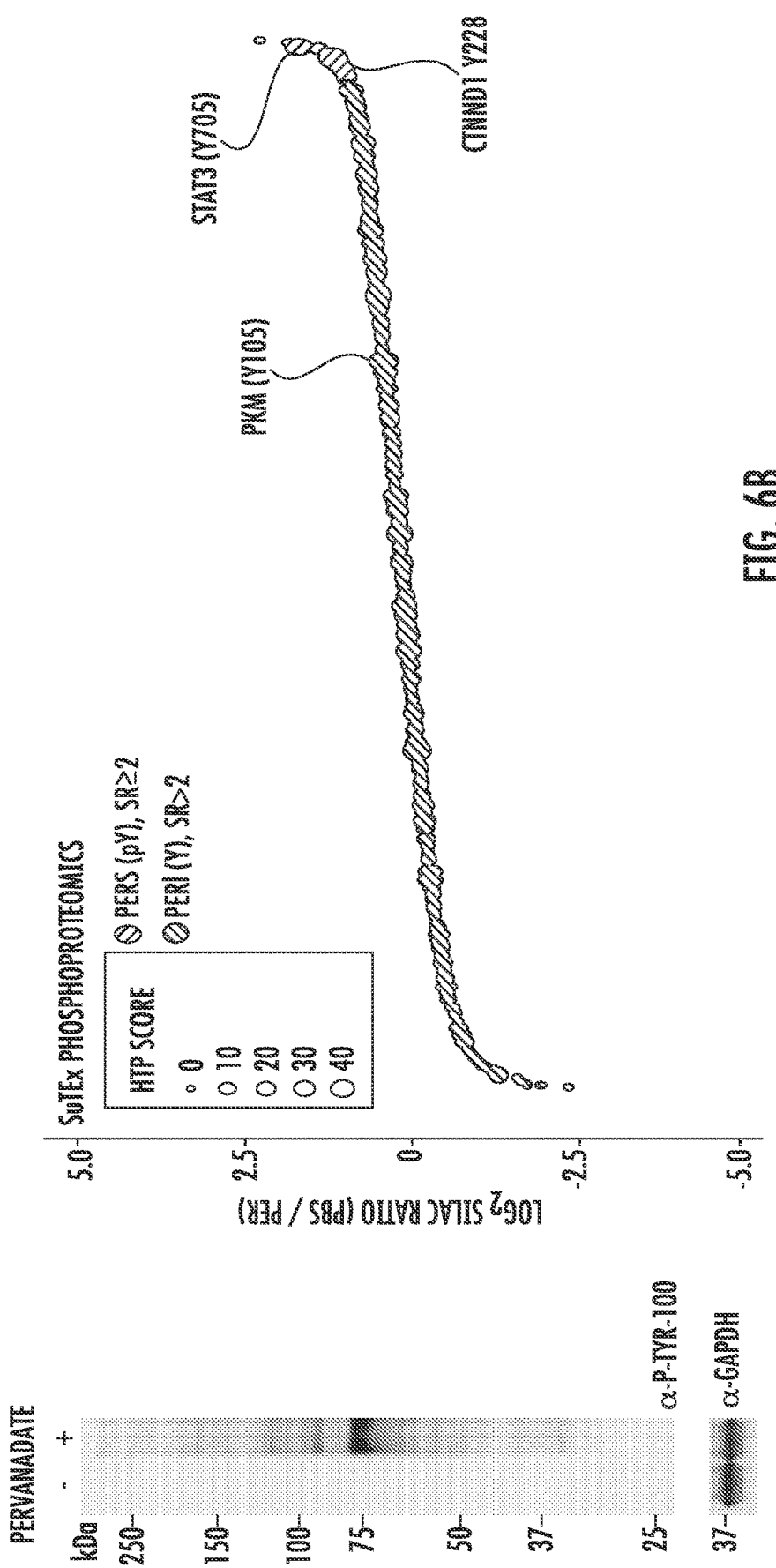

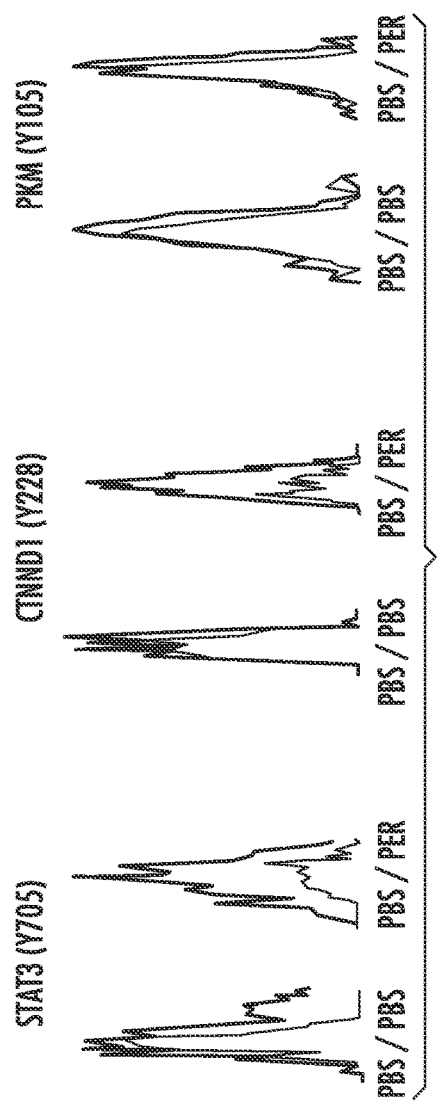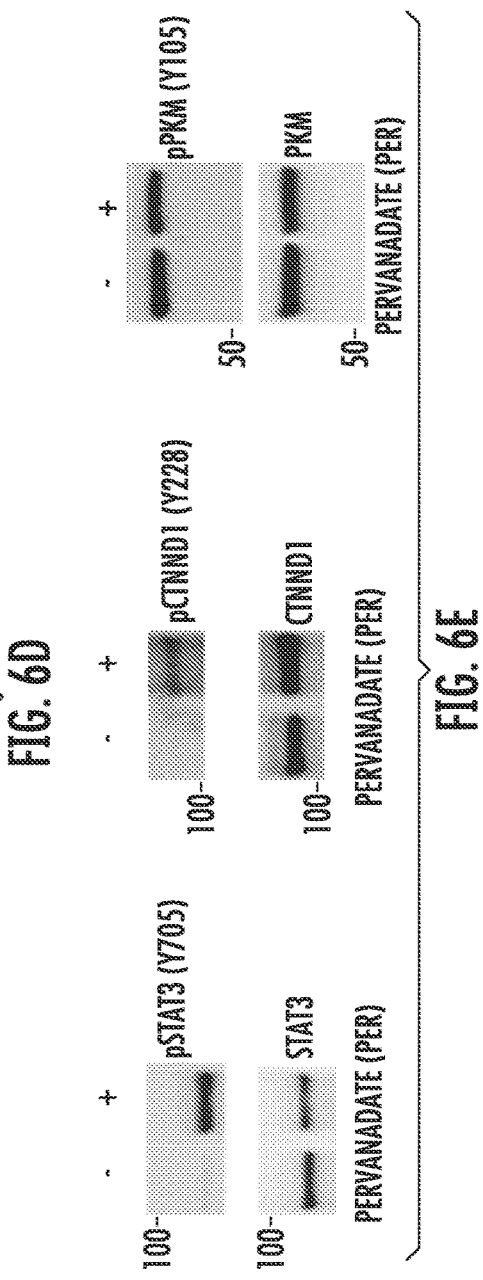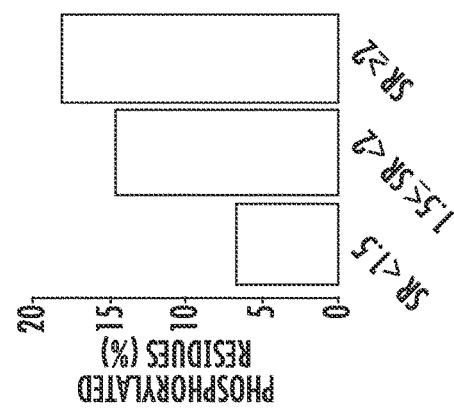
FIG. 6D
FIG. 6E
FIG. 6C

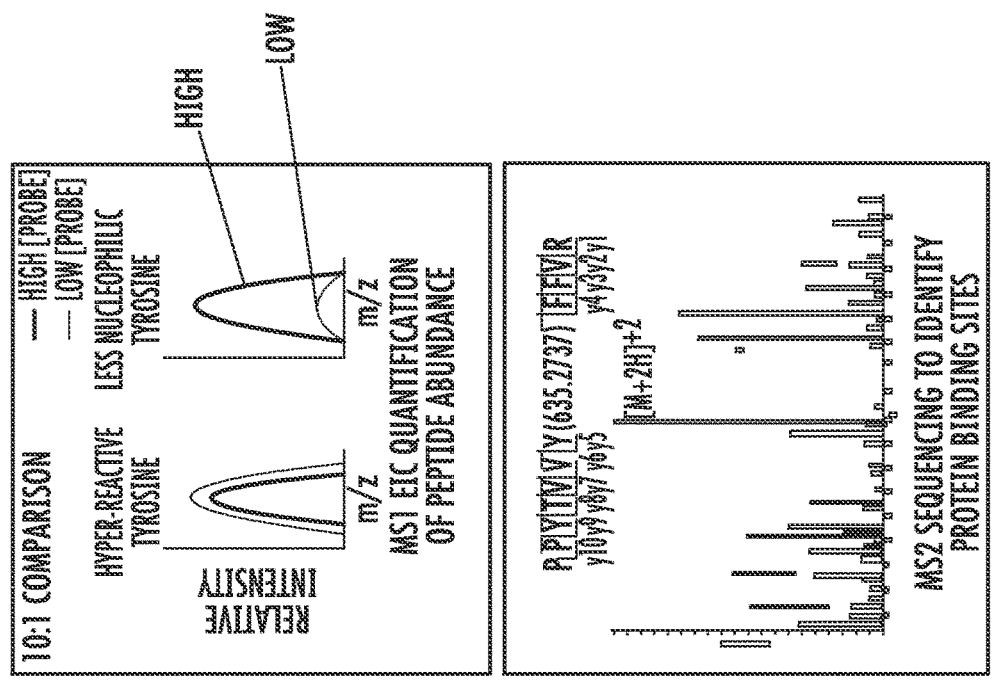
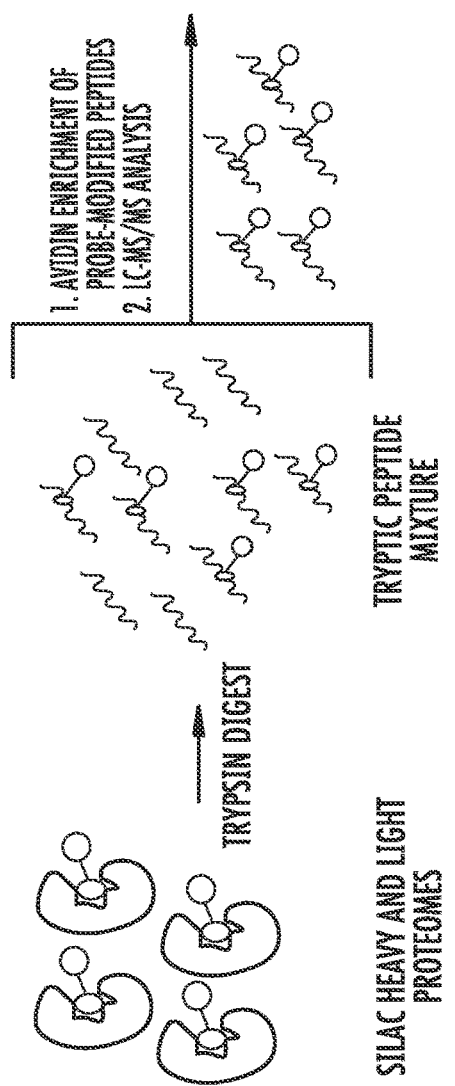
FIG. 11

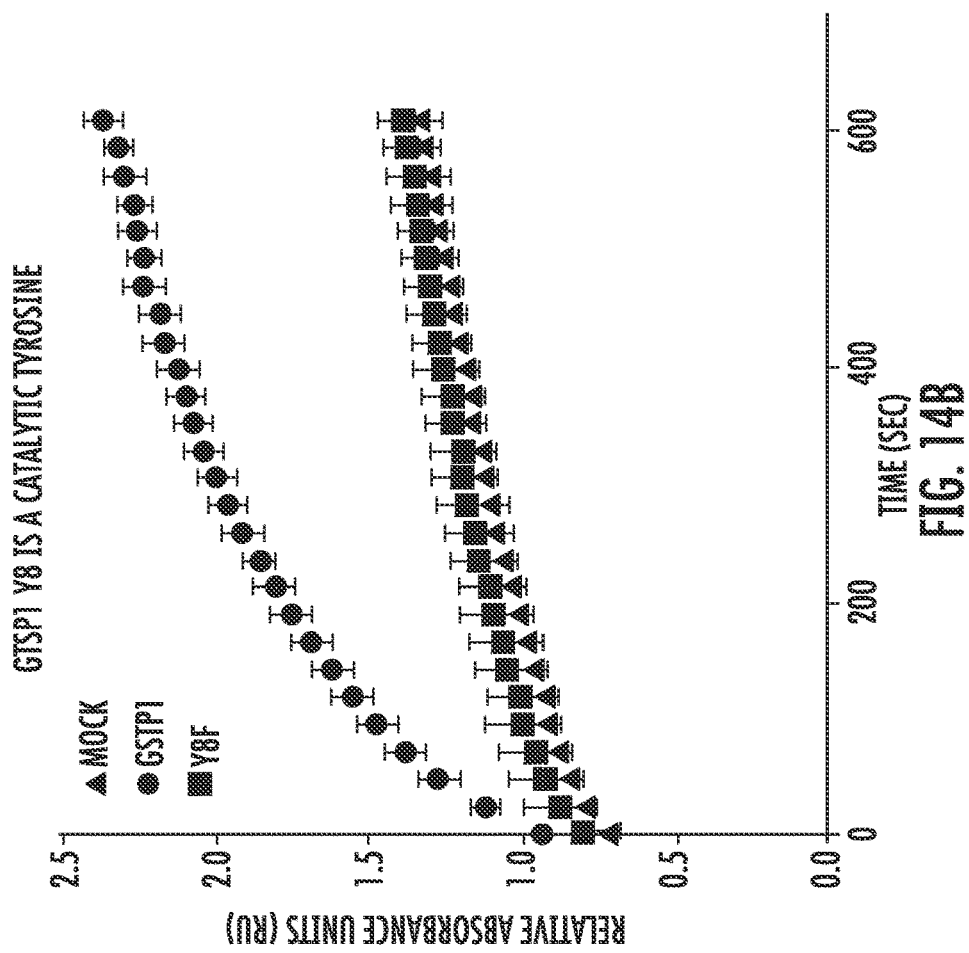
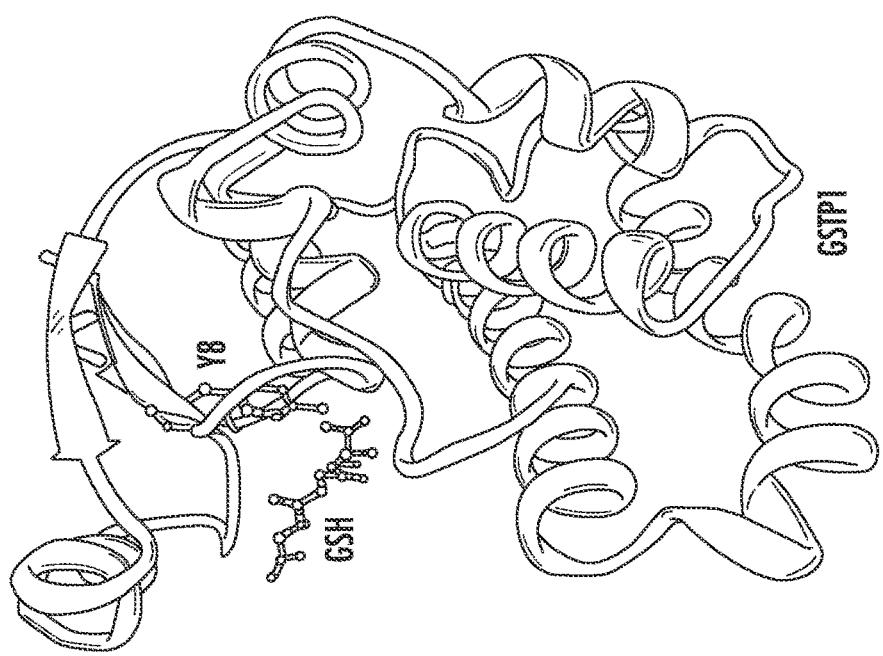
FIG. 14A
FIG. 14B

DPP3 (ACTIVE SITE)

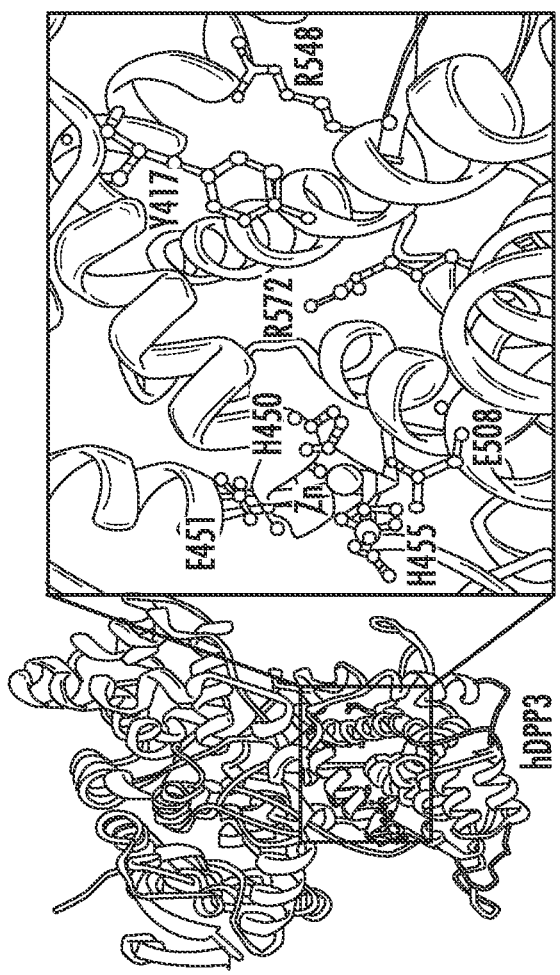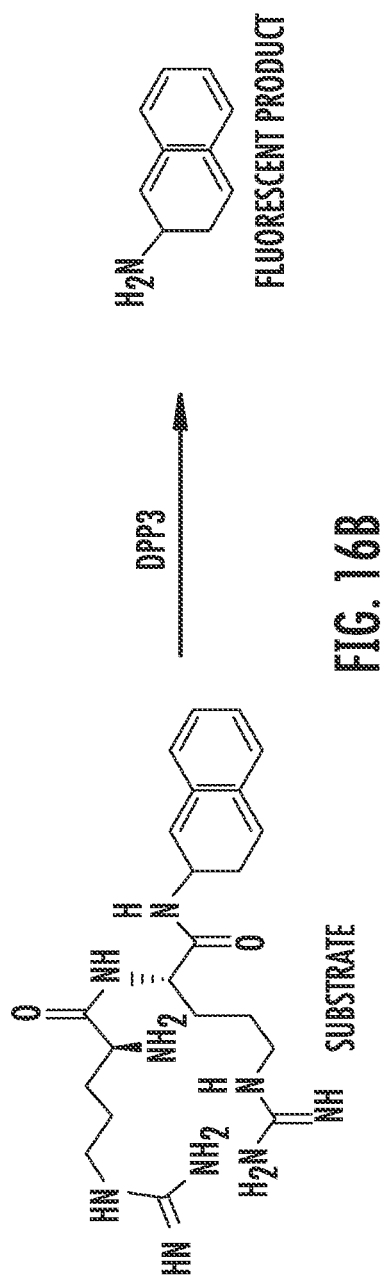
FIG. 16A
FIG. 16B

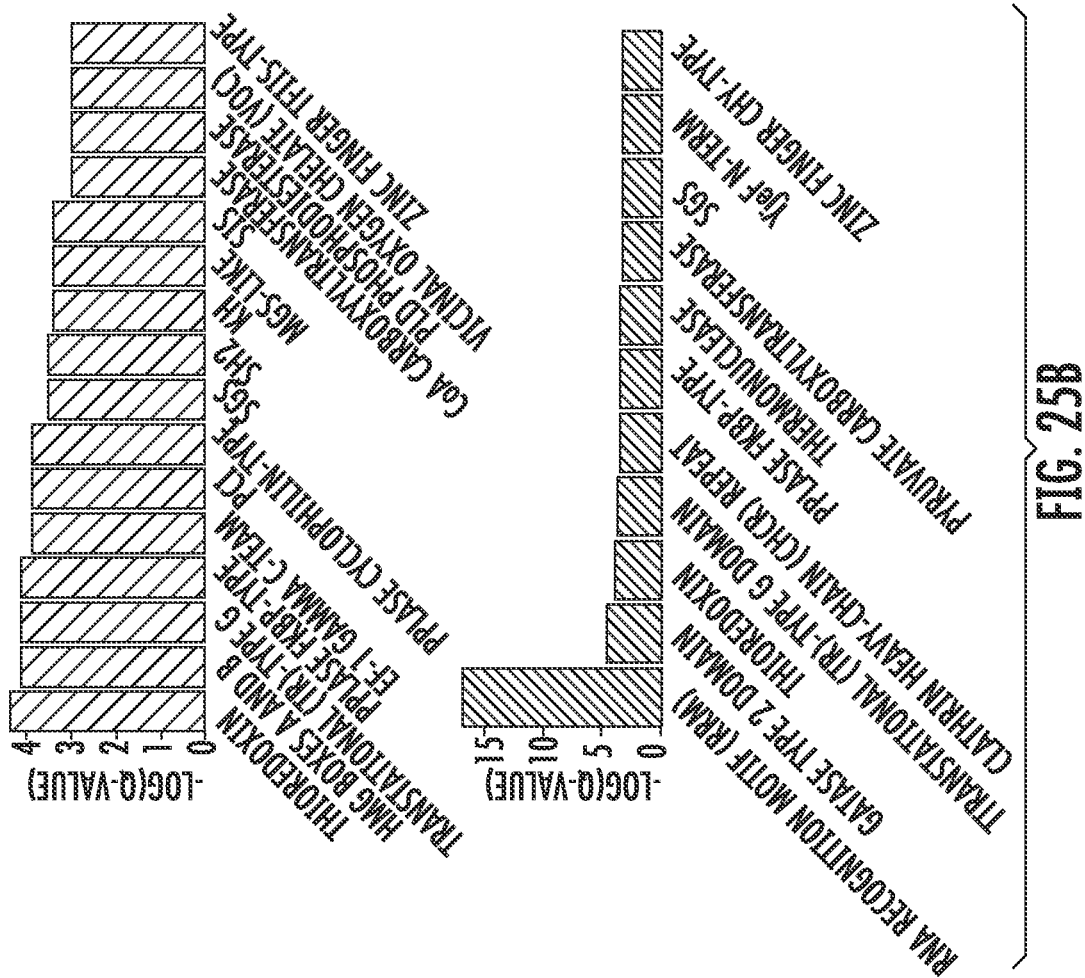
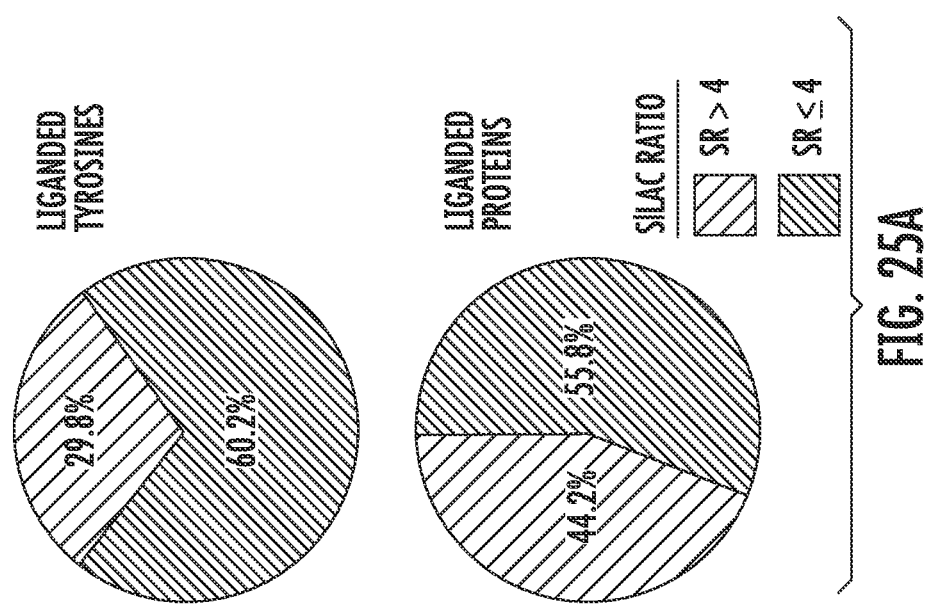
FIG. 25A
FIG. 25B

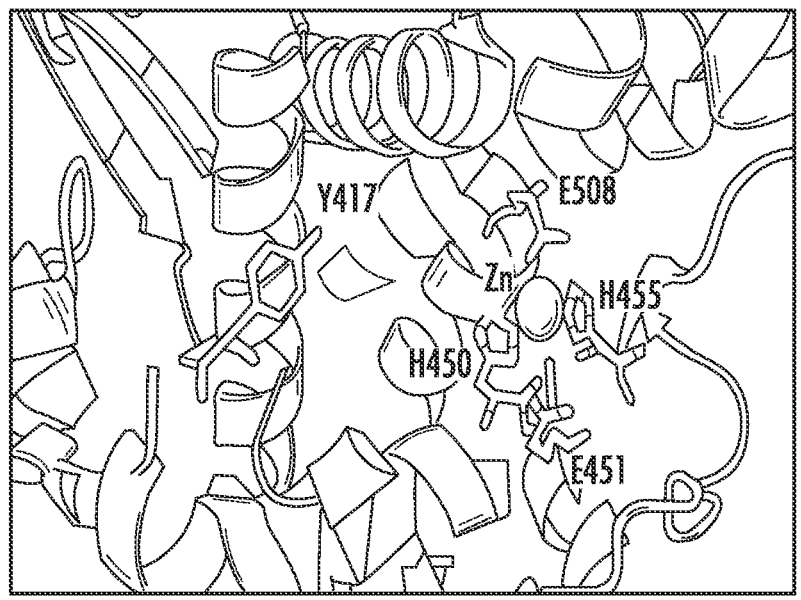
FIG. 27A
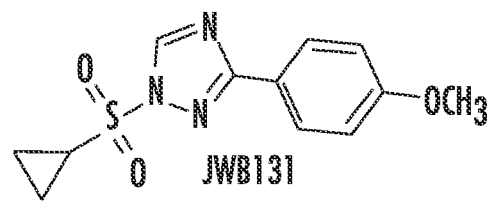
JWB131
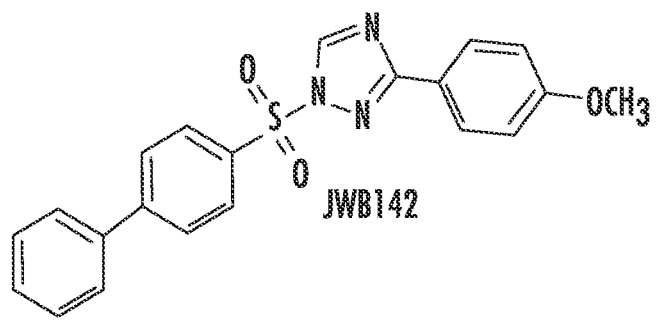
JWB142
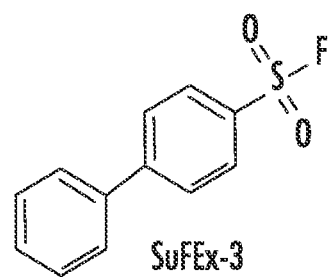
SuFEx-3
FIG. 27B

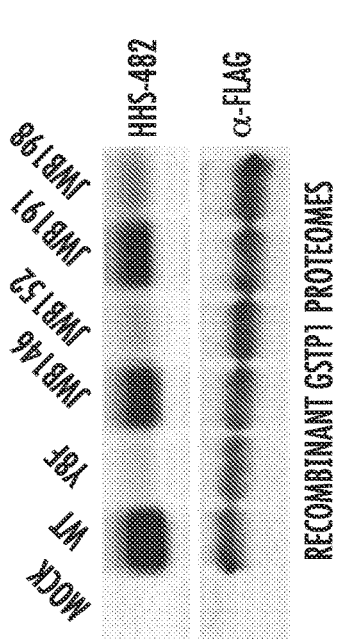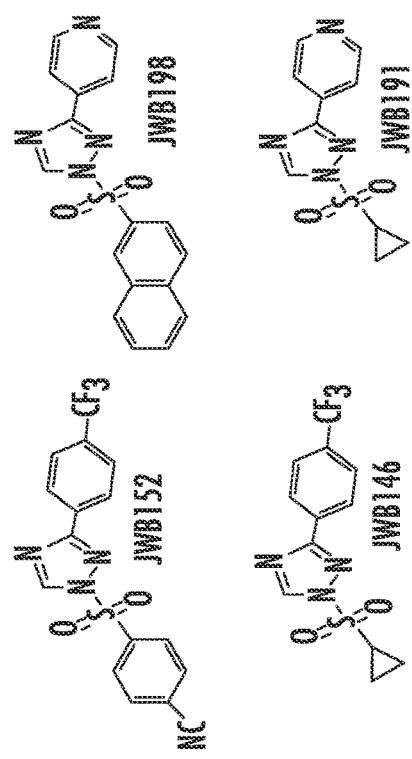
FIG. 32A
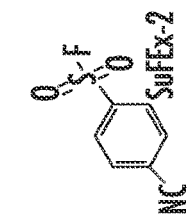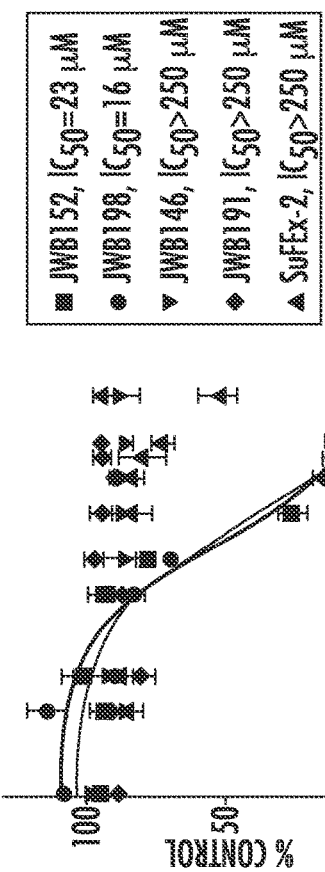
FIG. 32B

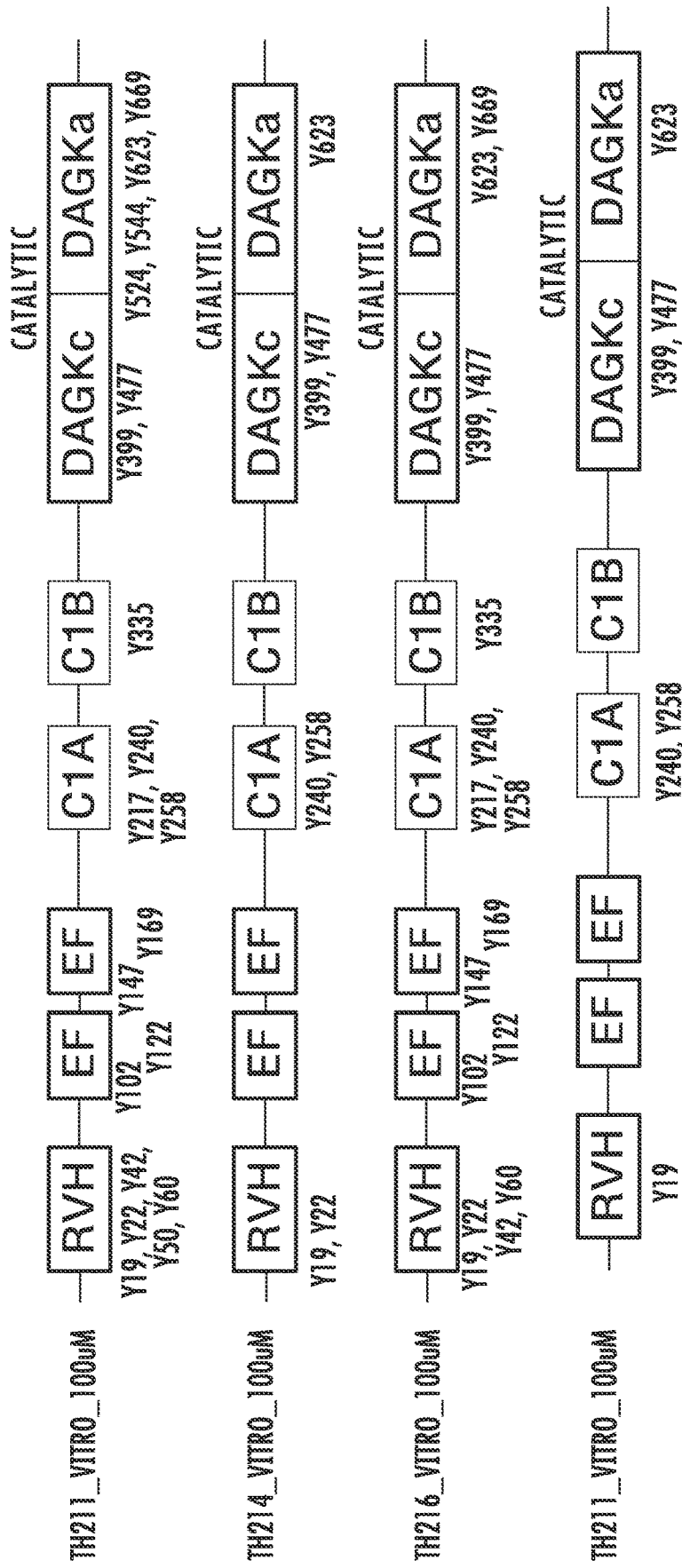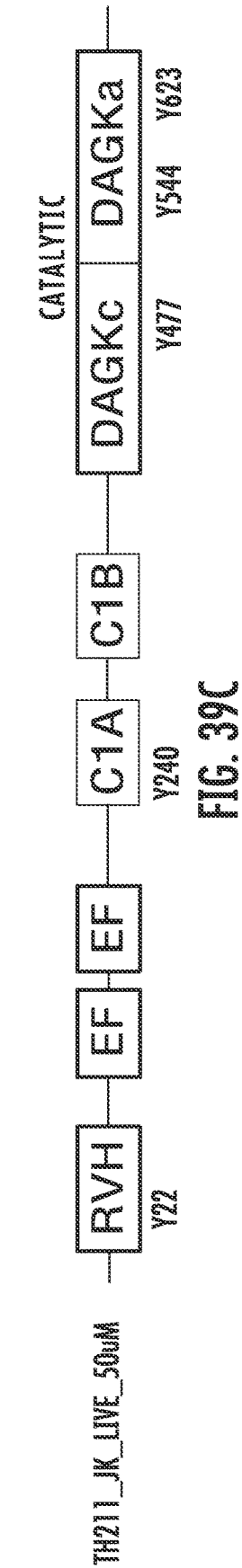
FIG. 39B
FIG. 39C

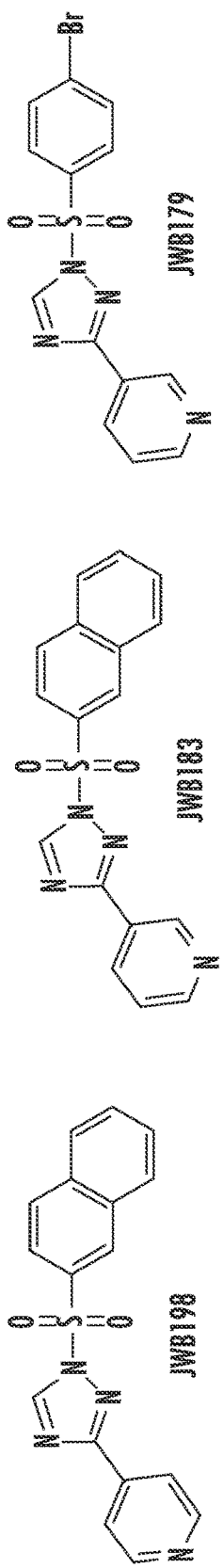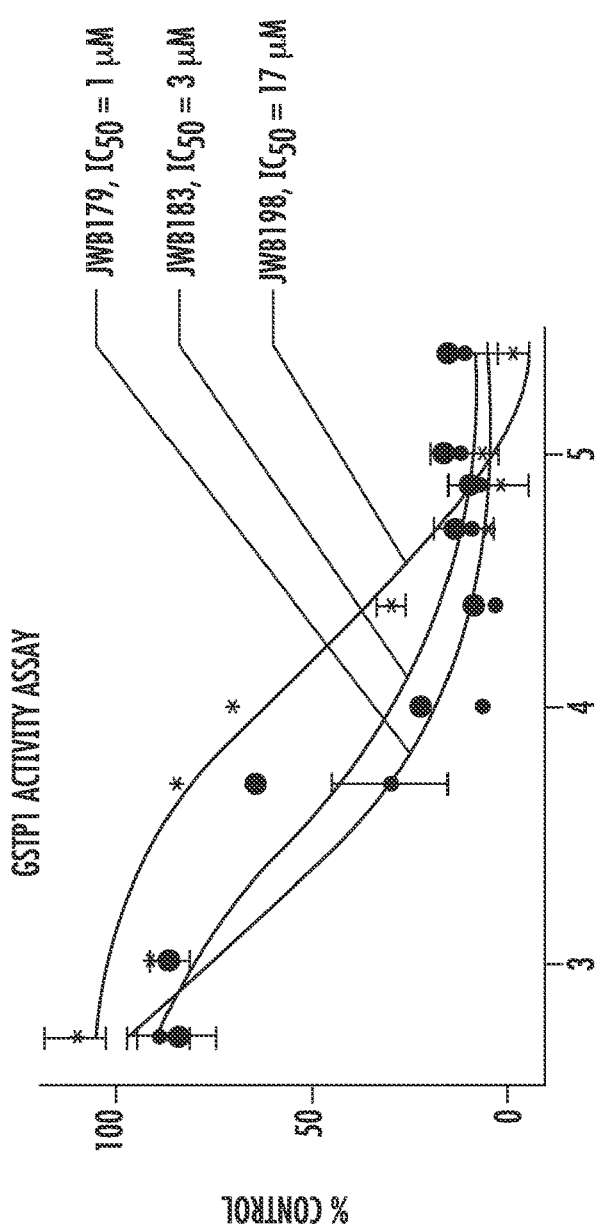
FIG. 40

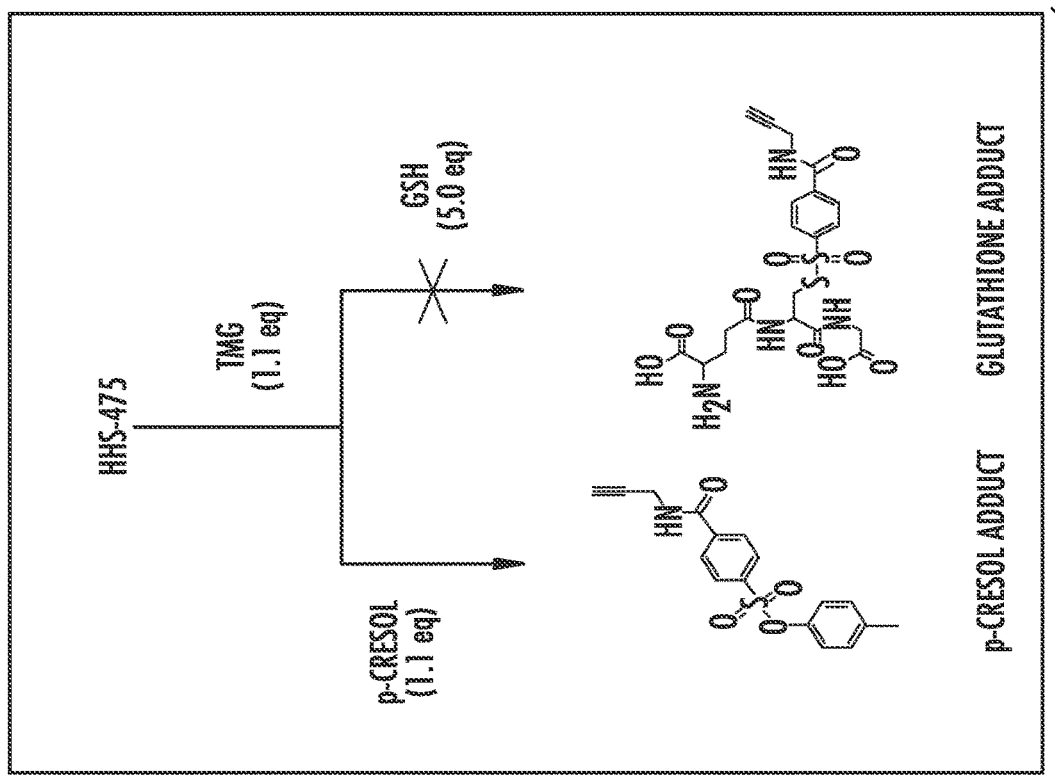
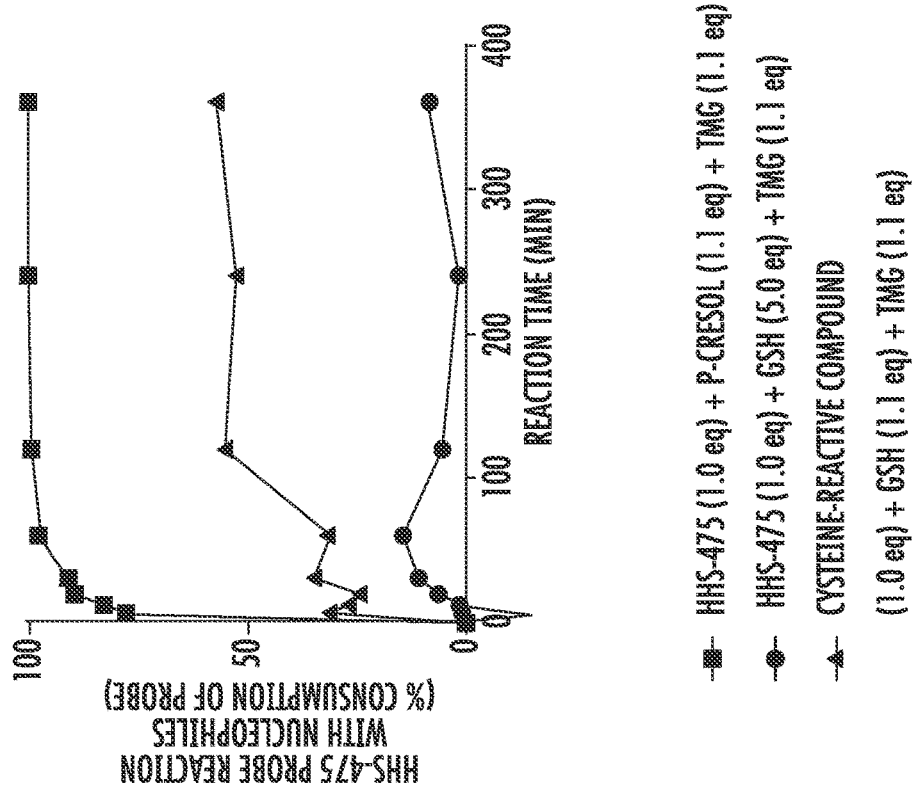
FIG. 41

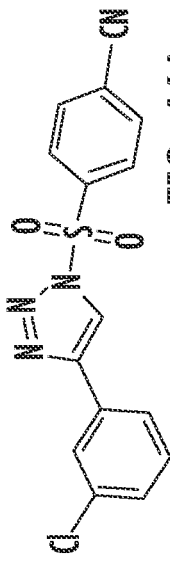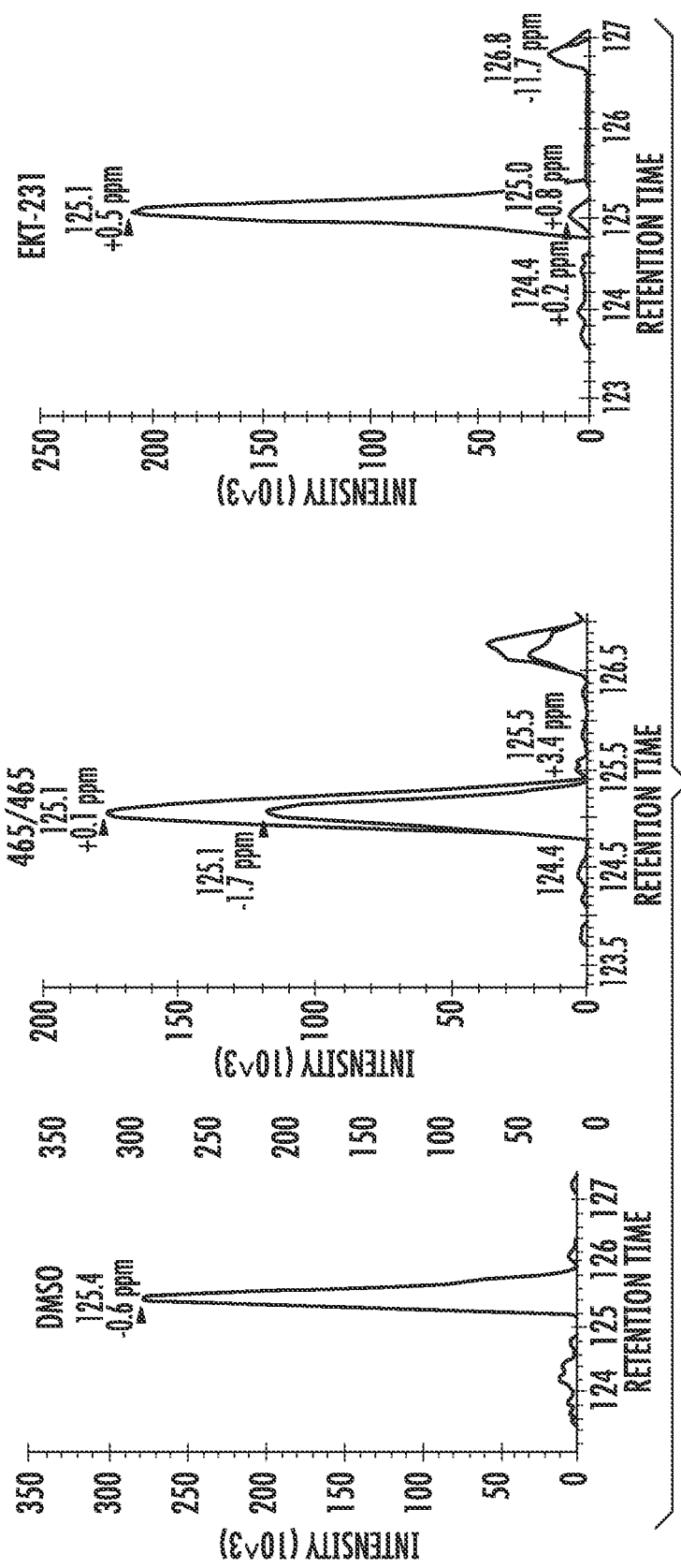
FIG. 46A
FIG. 46B

SEQUENCE LISTING

```
<160> NUMBER OF SEQ ID NOS: 2

<210> SEQ ID NO 1
<211> LENGTH: 10
<212> TYPE: PRT
<213> ORGANISM: Homo sapiens
<220> FEATURE:
<221> NAME/KEY: Mod_Res
<222> LOCATION: (2)..(2)
<223> OTHER INFORMATION: site of chemical conjugation

<400> SEQUENCE: 1

His Tyr Gly Gly Leu Thr Gly Leu Asn Lys
1               5                   10

<210> SEQ ID NO 2
<211> LENGTH: 11
<212> TYPE: PRT
<213> ORGANISM: Homo sapiens
<220> FEATURE:
<221> NAME/KEY: Mod_Res
<222> LOCATION: (7)..(7)
<223> OTHER INFORMATION: site of chemical conjugation

<400> SEQUENCE: 2

Pro Pro Tyr Thr Val Val Tyr Phe Pro Val Arg
1               5                   10
```

SULFUR-HETEROCYCLE EXCHANGE CHEMISTRY AND USES THEREOF

CROSS-REFERENCE TO RELATED APPLICATION

This application claims the benefit of U.S. Provisional Patent Application Ser. No. 62/821,478, filed Mar. 21, 2019, and of U.S. Provisional Patent Application Ser. No. 62/929,473, filed Nov. 1, 2019, the disclosure of each of which is incorporated herein by reference in its entirety.

GRANT STATEMENT

This invention was made with government support under Grant No. W81XWH-17-1-0487, awarded by the Department of Defense, and Grant Nos. DA035864 and DA043571, awarded by the National Institutes of Health. The government has certain rights in the invention.

INTRODUCTION

Chemical proteomics is a powerful technology for ascribing function to the vast number of uncharacterized proteins in the human proteome[1,2]. This proteomic method employs probes designed with reactive groups that exploit accessibility and reactivity of binding sites to covalently label active proteins with reporter tags for function assignment and inhibitor development[3]. Selective probes resulting from competitive screening efforts serve as enabling, and often first-in-class, tools for uncovering biochemical and cellular functions of proteins (e.g. serine hydrolases[4], proteases[5], kinases[6], phosphatases[7], and glycosidases[8]) and their roles in contributing to human physiology and disease. The basic and translational opportunities afforded by chemical proteomics has prompted exploration of new biocompatible chemistries for broader exploration of the proteome.

Covalent probes used for chemical proteomics range from highly chemoselective fluorophosphonates for catalytic serines[9] to general thiol alkylating agents and amine-reactive esters of cysteines[10] and lysines[11], respectively. The ability to globally measure protein functional states and selectively perturb proteins of interest has substantially augmented our basic understanding of protein function in cell and animal models[1,3] Exploration of new redox-based oxaziridine chemistry, for example, identified a conserved hyper-reactive methionine residue (M169) in redox regulation of mammalian enolase[12]. Hydrazine probes revealed a novel N-terminal glyoxylyl post-translational modification on the poorly characterized protein SCRN3[13]. More recent exploration of photoaffinity probes facilitate global evaluation of reversible small molecule-protein interactions to expand the scope of proteins available for chemical proteomic profiling[14].

Sulfonyl-fluorides[15] (—SO$_2$F) and fluorosulfates[16,17] (—OSO$_2$F) have emerged as a promising scaffold for covalent probe development because of the wide range of amino acids (e.g. serine[18,19], tyrosine[20], lysine[21], histidine[22]) and diverse protein targets (proteases[18,19], kinases[21], GPCRs[23]) available for sulfur-fluoride exchange chemistry (SuFEx[24]). Reactivity of SuFEx is driven largely through stabilization of the fluorine leaving group (LG) at protein sites during covalent reaction[25,26]. The sensitivity of SuFEx to protein microenvironments allows, for example, the ability to target orthogonal nucleophilic residues in the same nucleotide-binding site of decapping enzymes[27]. The broad reactivity and context-dependent activation of SuFEx present opportunities for modulating the sulfur electrophile to target novel, and potentially functional, sites of proteins[21,25,26,28] The reliance on fluorine, while key for activating SuFEx chemistry, is limiting in terms of LG modifications to modify reactivity, specificity, and binding affinity at protein sites across the proteome.

Accordingly, there is a need for additional covalent probes for use in chemical proteomics. In particular, there is a need for additional covalent probes with tunable selectivity, particularly for tyrosine residues.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter provides a method of identifying a reactive tyrosine of a protein, the method comprising: (a) providing a protein sample comprising isolated proteins, living cells, or a cell lysate; (b) contacting the protein sample with a probe compound of Formula (I) for a period of time sufficient for the probe compound to react with at least one reactive tyrosine in a protein in the protein sample, thereby forming at least one modified reactive tyrosine residue; and (c) analyzing proteins in the protein sample to identify at least one modified tyrosine residue, thereby identifying at least one reactive tyrosine of a protein; wherein the probe compound has a structure of Formula (I):

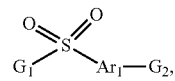

wherein: G$_1$ is a monovalent moiety comprising an alkyne moiety, a fluorophore moiety, a detectable labeling group, or a combination thereof; Ar$_1$ is heteroaryl, optionally five-membered heteroaryl and/or nitrogen-containing heteroaryl; and G$_2$ is H or an aryl group substituent; optionally wherein G$_2$ is selected from the group comprising H, alkyl, substituted alkyl, aralkyl, substituted aralkyl, aryl, heteroaryl, substituted aryl, and substituted heteroaryl; and wherein the at least one modified reactive tyrosine residue comprises a modified tyrosine residue comprising a structure of Formula (II):

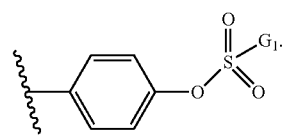

In some embodiments, G$_1$ is a group having the formula —Ar$_2$-G$_3$ and the probe compound has a structure of Formula (I) has a structure of Formula (Ia):

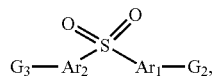

wherein: $Ar_2$ is aryl, optionally selected from phenyl, naphthyl, and pyridyl; $G_3$ is a monovalent moiety comprising an alkyne moiety, a fluorophore moiety, a detectable labeling group, or a combination thereof; and $Ar_1$ and $G_2$ are as defined for Formula (I). In some embodiments, $Ar_1$ is selected from the group comprising triazole, imidazole, pyrazole, and tetrazole.

In some embodiments, $Ar_1$ is triazole, and wherein the probe compound of Formula (Ia) has a structure of Formula (Ib):

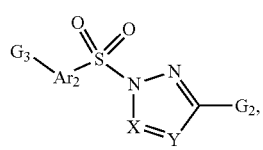

wherein: X and Y are each selected from C and N, subject to the proviso that one of X and Y is N and one of X and Y is C; $G_2$ is H or an aryl group substituent, optionally wherein $G_2$ is selected from H, alkyl, substituted alkyl, aryl, heteroaryl, substituted aryl, and substituted heteroaryl; $Ar_2$ is aryl, optionally phenyl; and $G_3$ is a monovalent moiety comprising an alkyne moiety, a fluorophore moiety, a detectable labeling group, or a combination thereof. In some embodiments, the probe compound of Formula (Ib) has a structure of Formula (Ic):

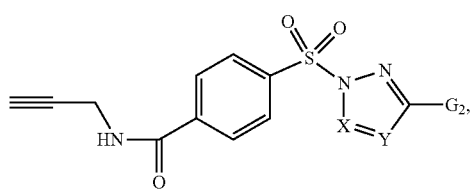

wherein X, Y, and $G_2$ are as defined for the probe compound of Formula (Ib).

In some embodiments, $G_2$ is selected from H, phenyl, and substituted phenyl, optionally wherein the substituted phenyl is phenyl substituted with one or more substituent selected from the group comprising halo, alkoxy, alkyl, and perfluoroalkyl. In some embodiments, $G_2$ is selected from H, phenyl and substituted phenyl, wherein substituted phenyl is phenyl substituted one or more substituent selected from halo, methoxy, and —$CF_3$.

In some embodiments, the probe compound is selected from the group comprising:

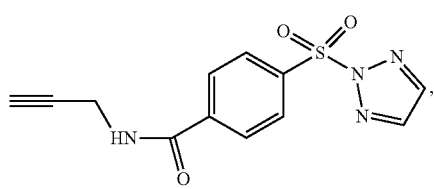 [SMILES: C#CCNC(=O)c1ccc(S(=O)(=O)n2nccn2)cc1]

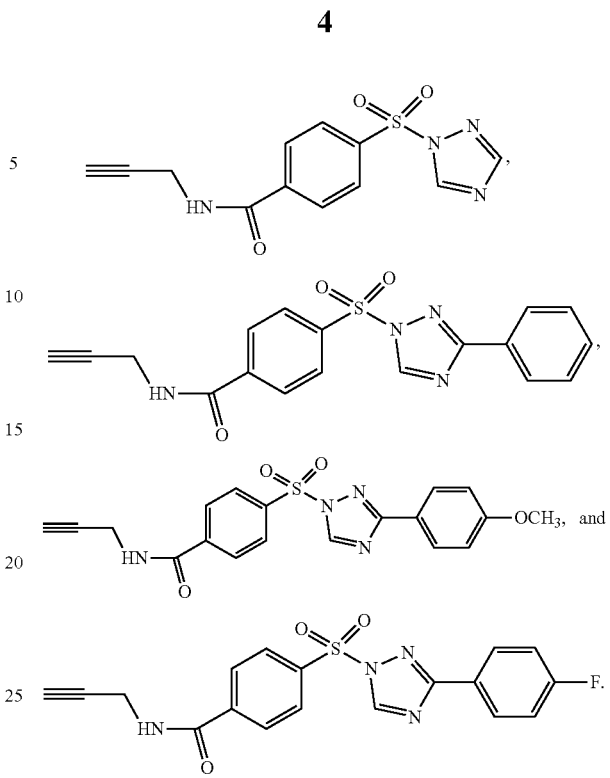

In some embodiments, the probe compound of Formula (I) is selected from the group comprising:

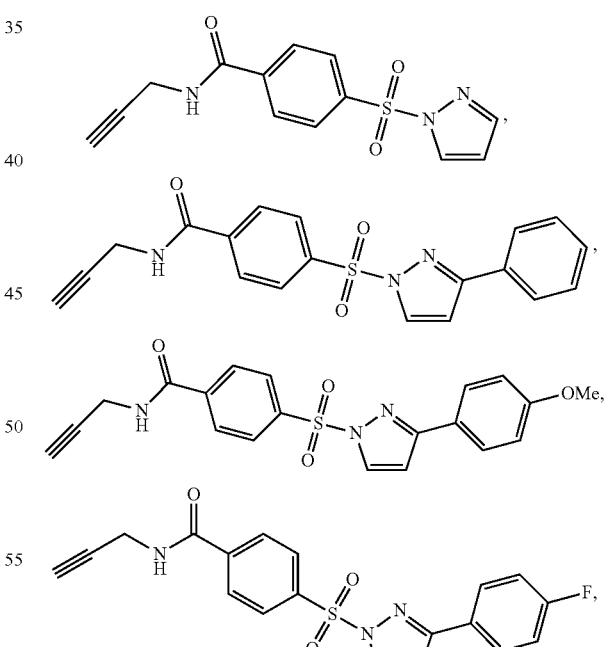

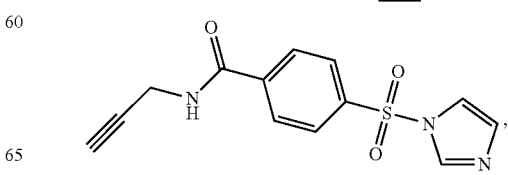

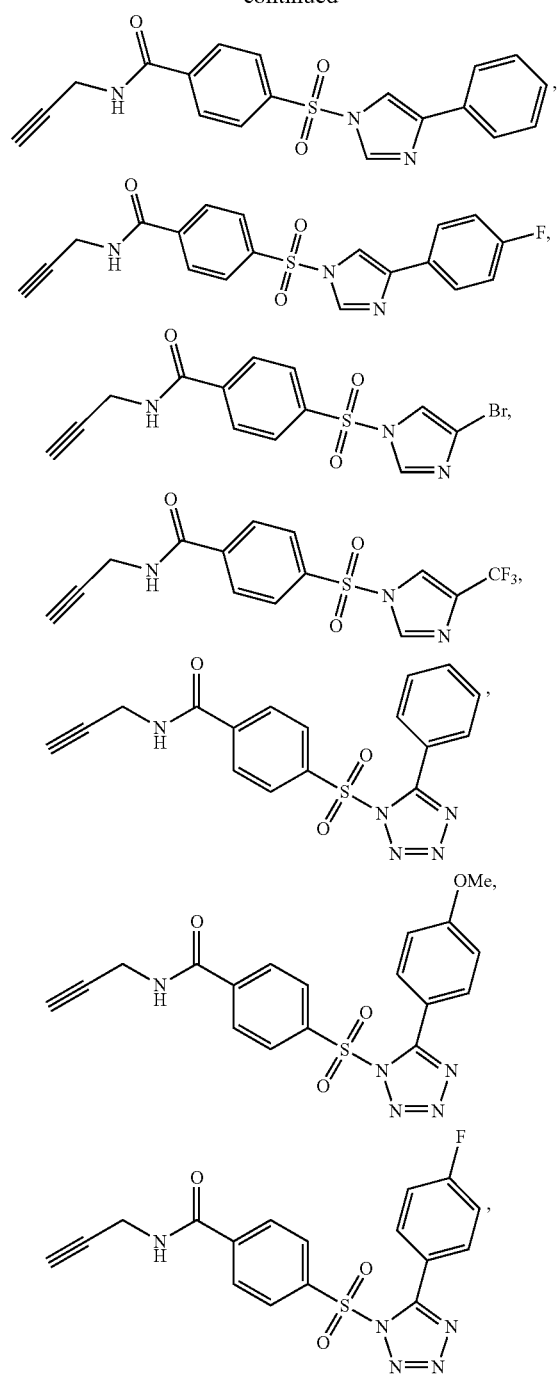
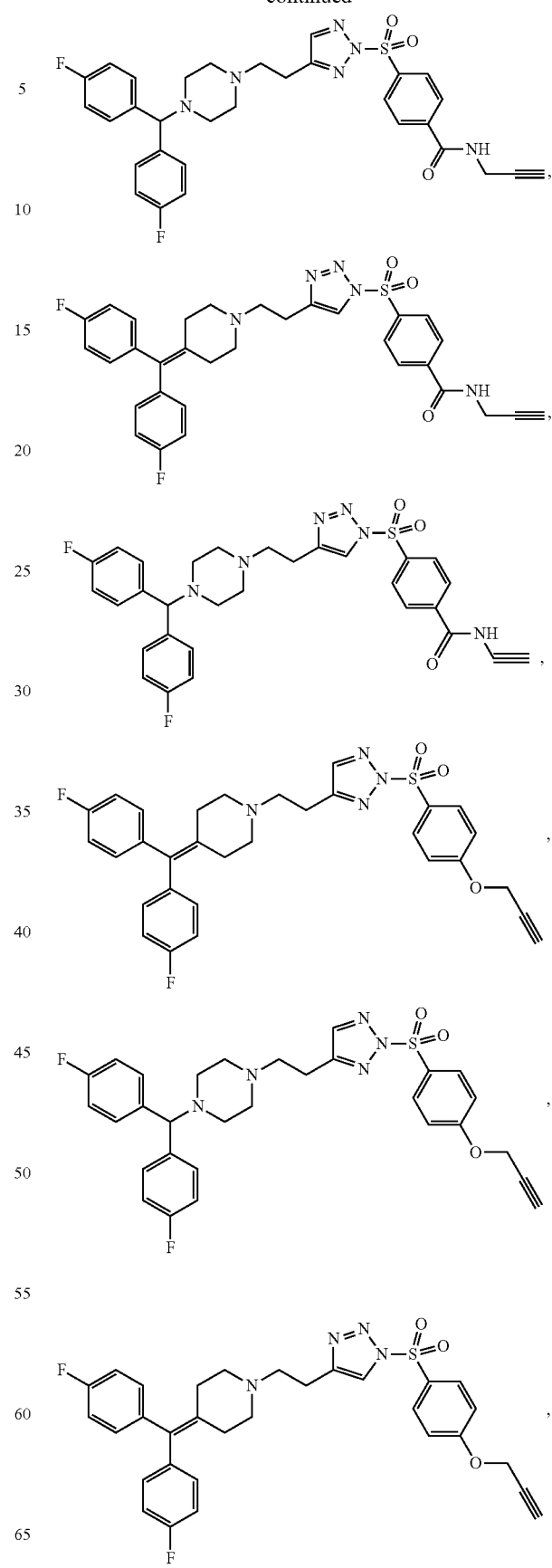

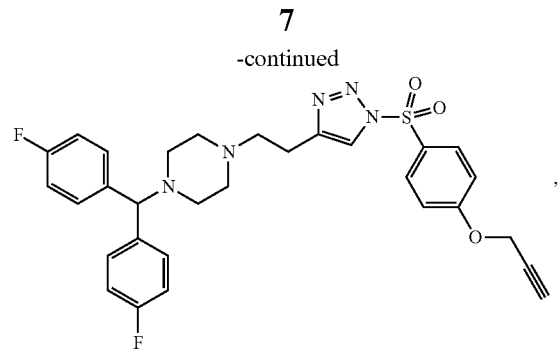

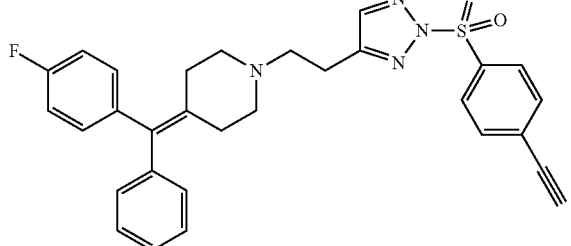

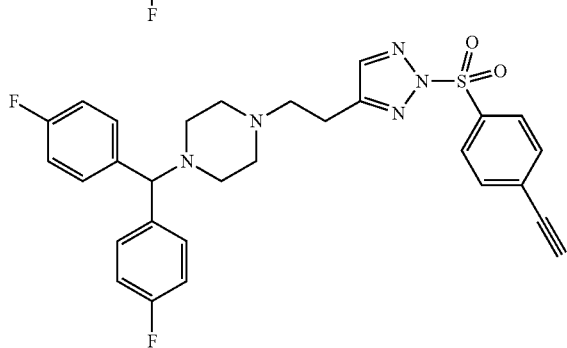

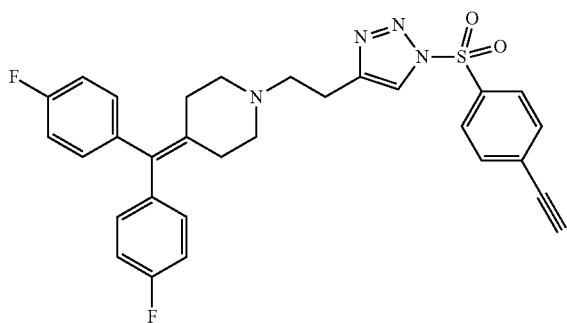

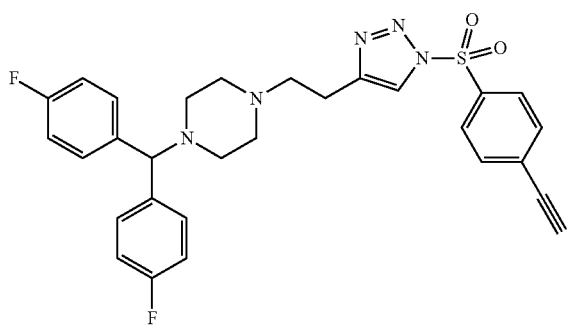

In some embodiments, the analyzing of step (c) further comprises tagging the at least one modified reactive tyrosine residue with a compound comprising detectable labeling group, thereby forming at least one tagged reactive tyrosine residue comprising said detectable labeling group. In some embodiments, the detectable labeling group comprises biotin or a biotin derivative, optionally wherein the biotin derivative is desthiobiotin. In some embodiments, the tagging comprises reacting an alkyne group in the $G_1$ moiety of the at least one tagged reactive tyrosine residue with a compound comprising an (i) an azide moiety and (ii) the detectable labeling group, optionally via a copper-catalyzed azide-alkyne cycloaddition (CuAAC) coupling reaction.

In some embodiments, the analyzing further comprises digesting the protein sample with trypsin to provide a digested protein sample comprising a protein fragment comprising the at least one tagged reactive tyrosine moiety comprising the detectable group. In some embodiments, the analyzing further comprises enriching the digested protein sample for the detectable labeling group, optionally wherein the enriching comprises contacting the digested protein sample with a solid support comprising a binding partner of the detectable labeling group. In some embodiments, the analyzing further comprises analyzing the enriched digested protein sample via liquid chromatography-mass spectrometry.

In some embodiments, providing the protein sample further comprises separating the protein sample into a first protein sample and a second protein sample; contacting the protein sample with a probe compound of Formula (I) comprises contacting the first protein sample with a first probe compound of Formula (I) at a first probe concentration for a first period of time and contacting the second protein sample with one of the group comprising: (b1) a second probe compound of Formula (I) at the first probe concentration for the first period of time, (b2) the first probe compound of Formula (I) at a second probe concentration for the first period of time, and (b3) the first probe compound of Formula (I) at the first probe concentration for a second period of time; thereby forming at least one modified reactive tyrosine residue in said first and/or said second protein sample; and analyzing proteins comprises analyzing the first and second protein samples to determine the presence and/or identity of a modified reactive tyrosine residue in the first sample and the presence and/or identity of a modified reactive tyrosine residue in the second sample.

In some embodiments, the protein sample comprises living cells and providing the protein sample further comprises separating the protein sample into a first protein sample and a second protein sample and culturing the first protein sample in a first cell culture medium comprising heavy isotopes prior to the contacting of step (b), optionally wherein the first cell culture medium comprises $^{13}$C- and/or $^{15}$N-labeled amino acids, further optionally wherein the first cell culture medium comprises $^{13}$C-,$^{15}$N-labeled lysine and arginine; and culturing the second protein sample in a second cell culture medium, wherein said second cell culture medium comprises a naturally occurring isotope distribution, prior to the contacting of step (b). In some embodiments, one of the first and the second protein sample is cultured in the presence of a tyrosine phosphatase inhibitor, optionally pervanadate. In some embodiments, the probe compound of Formula (I) comprises a detectable labeling group comprising a heavy isotope or wherein the analyzing of step (c) further comprises tagging the at least one modified tyrosine residue with a compound comprising a detectable labeling group comprising a heavy isotope, optionally wherein the heavy isotope is carbon-13. In some embodiments, during the contacting step (b), the probe compound of Formula (I) reacts with at least one reactive lysine in a protein in the protein sample, thereby forming at least one modified reactive lysine residue, and wherein the analyzing step (c) further comprises analyzing the proteins in the protein sample to identify the at least one modified lysine residue, thereby identifying at least one reactive lysine of a protein.

In some embodiments, the presently disclosed subject matter provides a probe compound for detecting a reactive tyrosine in a protein, wherein the probe compound has a structure of Formula (I):

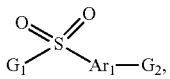

wherein: G$_1$ is a monovalent moiety comprising an alkyne moiety, a fluorophore moiety, a detectable labeling group, or a combination thereof; Ar$_1$ is heteroaryl, optionally five-membered heteroaryl and/or nitrogen-containing heteroaryl; and G$_2$ is H or an aryl group substituent; optionally wherein G$_2$ is selected from the group comprising H, alkyl, substituted alkyl, aralkyl, substituted aralkyl, aryl, heteroaryl, substituted aryl, and substituted heteroaryl. In some embodiments, the probe compound having a structure of Formula (I) has a structure of Formula (Ia):

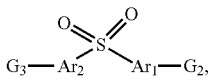

wherein: Ar$_2$ is an aryl group, optionally phenyl, naphthyl, or pyridiyl; G$_3$ is a monovalent moiety comprising an alkyne moiety, a fluorophore moiety, a detectable labeling group, or a combination thereof; and Ar$_1$ and G$_2$ are as defined for Formula (I). In some embodiments, Ar$_1$ is selected from the group comprising triazole, imidazole, pyrazole and tetrazole. In some embodiments, Ar$_2$ is phenyl and G$_3$ is —C(=O)—NH—CH$_2$—C≡CH, —C≡CH, or —O—CH$_2$—C≡CH.

In some embodiments, the probe compound of Formula (Ia) has a structure of Formula (Ib):

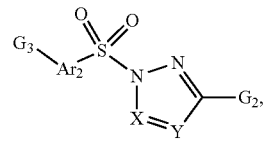

wherein: X and Y are each selected from C and N, subject to the proviso that one of X and Y is N and one of X and Y is C; G$_2$ is H or an aryl group substituent, optionally wherein G$_2$ is selected from H, alkyl, substituted alkyl, aralkyl, substituted aralkyl, aryl, heteroaryl, substituted aryl, and substituted heteroaryl, Ar$_2$ is aryl, optionally phenyl, and G$_3$ is a monovalent moiety comprising an alkyne moiety, a fluorophore moiety, a detectable labeling group, or a combination thereof. In some embodiments, the probe compound of Formula (Ib) has a structure of Formula (Ic):

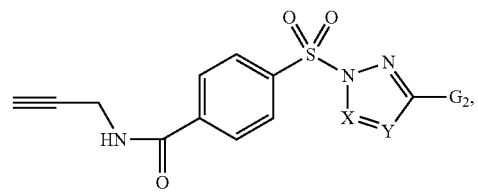

wherein X, Y, and G$_2$ are as defined for the probe compound of Formula (Ib).

In some embodiments, G$_2$ is selected from H, phenyl, and substituted phenyl, optionally wherein the substituted phenyl is phenyl substituted with one or more substituent selected from the group comprising halo, alkoxy, alkyl, and perfluoralkyl. In some embodiments, G$_2$ is selected from H, phenyl and substituted phenyl, wherein substituted phenyl is phenyl substituted with one of the group selected from halo, methoxy, and —CF$_3$.

In some embodiments, the probe compound is selected from the group comprising:

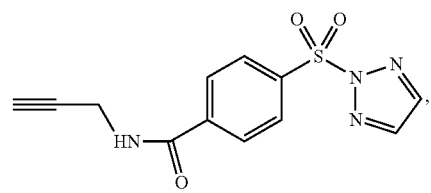

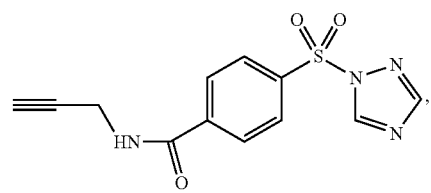 [SMILES: C#CCNC(=O)c1ccc(S(=O)(=O)n2nccn2)cc1]

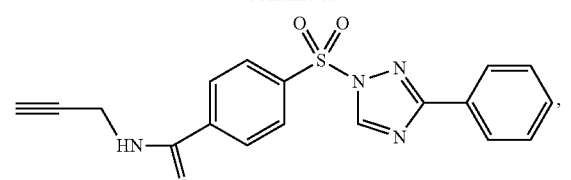, 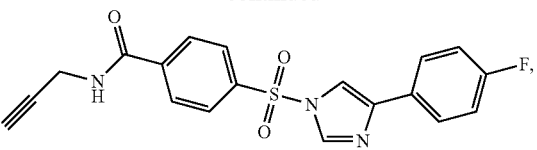
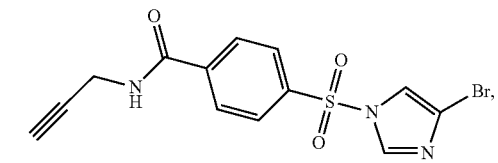
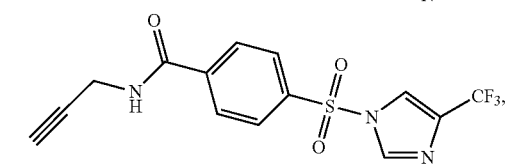
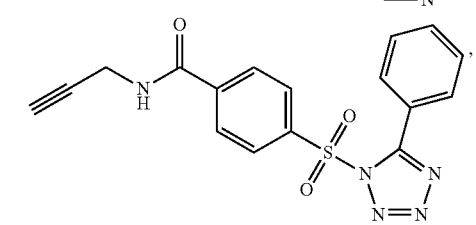
In some embodiments the probe compound is selected from the group comprising:
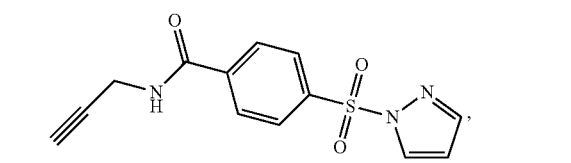
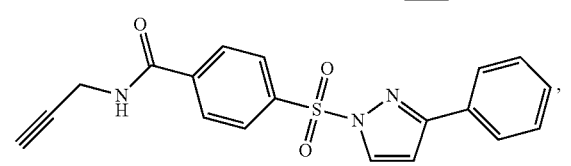
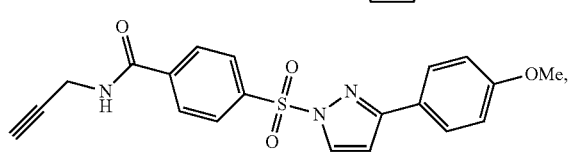
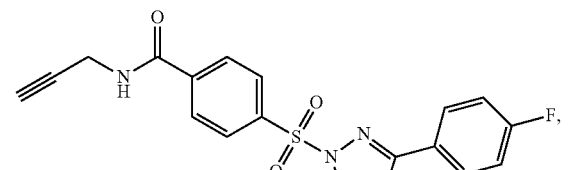
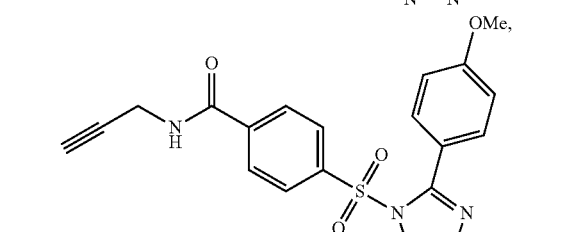
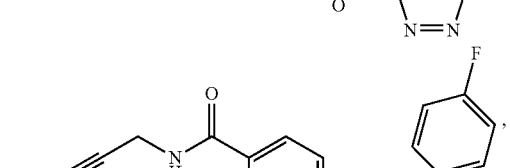
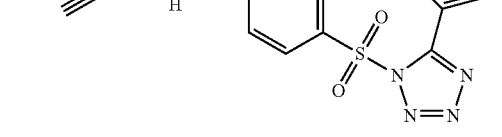
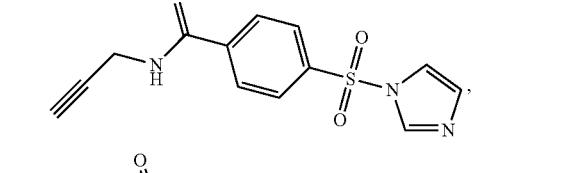
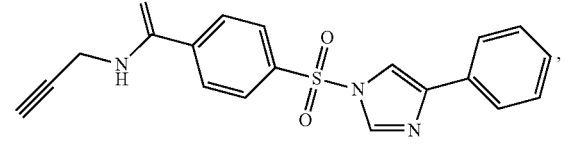
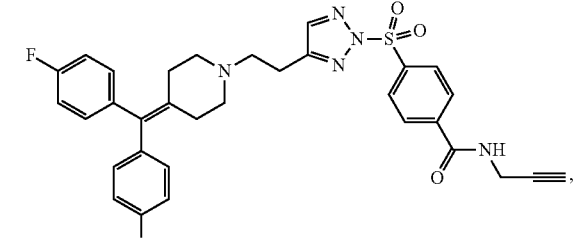
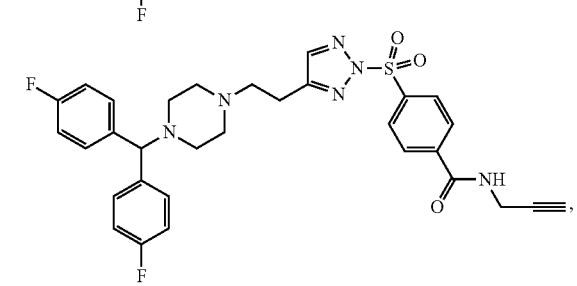

13
-continued
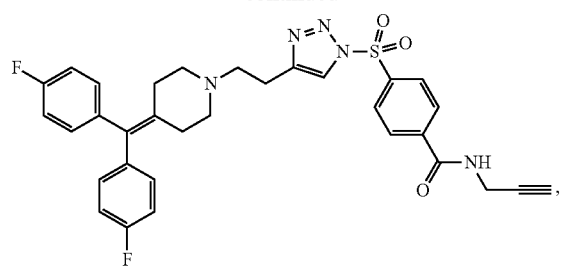,
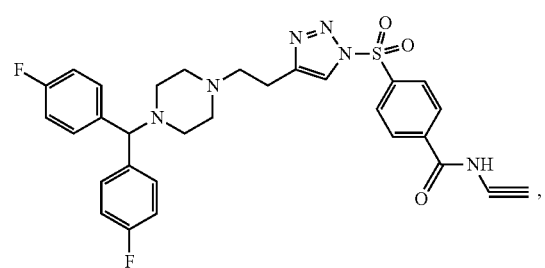,
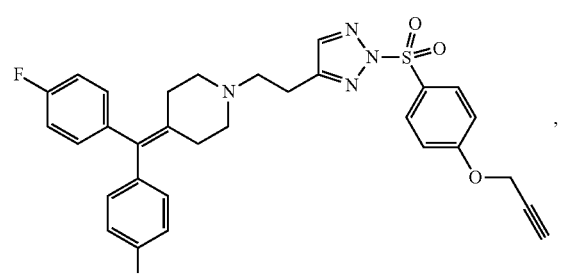,
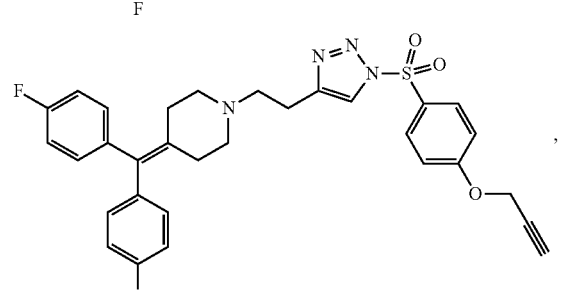,
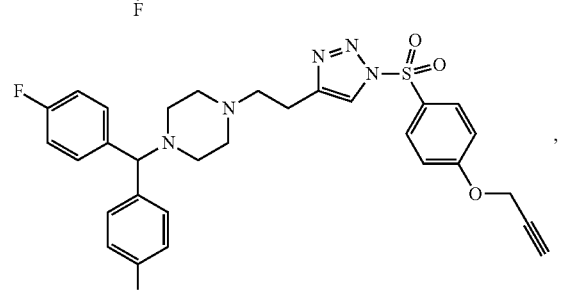,
14
-continued
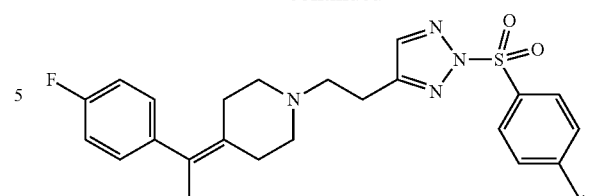,
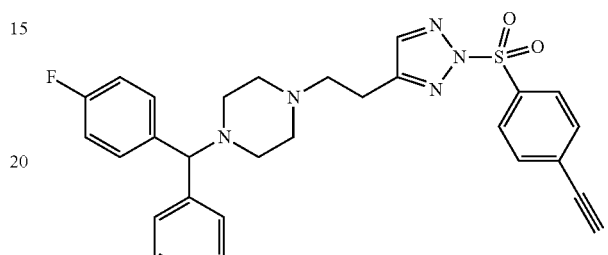,
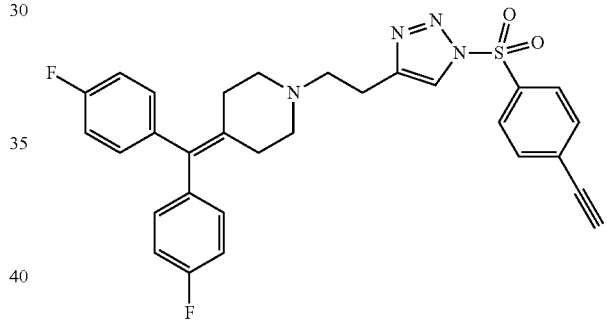,
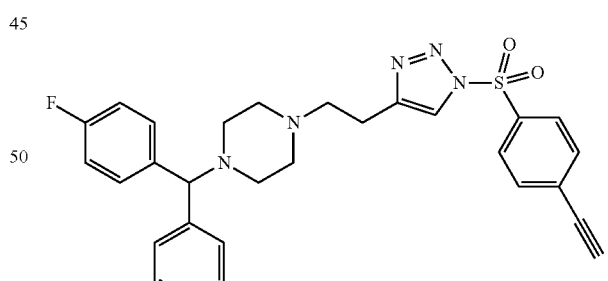,
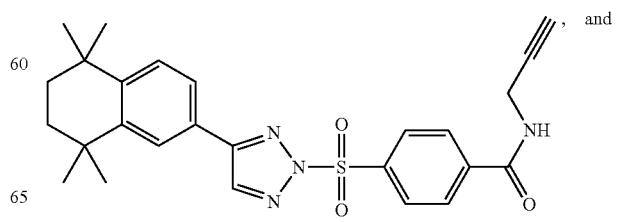, and

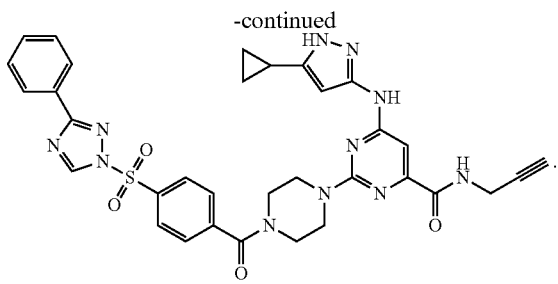

In some embodiments, the presently disclosed subject matter provides a modified tyrosine-containing protein comprising modified tyrosine residue comprising a structure of Formula (II):

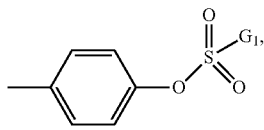

wherein $G_1$ is a monovalent moiety comprising an alkyne moiety, a fluorophore moiety, a detectable labeling group, or a combination thereof, and wherein the —S(=O)$_2$-$G_1$ group is the fragment of a non-naturally occurring synthetic molecule. In some embodiments, $G_1$ has a structure of the formula: —Ar$_2$-$G_3$, wherein Ar$_2$ is an aryl group, optionally a phenyl, naphthyl, or pyridyl group; and $G_3$ is a monovalent moiety comprising an alkylene moiety, a fluorophore moiety, a detectable labeling group, or a combination thereof.

In some embodiments, the presently disclosed subject matter provides a tyrosine-reactive compound having a structure of Formula (III):

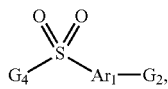

wherein: Ar$_1$ is selected from the group comprising 1,2,4-triazole, imidazole, pyrazole, and tetrazole; $G_2$ is H or an aryl group substituent, optionally wherein $G_2$ is selected from H, aryl, and substituted aryl; and $G_4$ is selected from the group comprising alkyl, substituted alkyl, cycloalkyl, substituted cycloalkyl, heterocycyl, aralkyl, substituted aralkyl, aryl, substituted aryl, heteroaryl, and substituted heteroaryl. In some embodiments, $G_4$ is selected from the group comprising phenyl, naphthyl, pyridyl, substituted pyridyl, or substituted phenyl. In some embodiments, $G_4$ is phenyl or substituted phenyl, optionally wherein the substituted phenyl is para-substituted phenyl and/or phenyl substituted with one or more aryl group substituents selected from the group comprising halo, alkoxy, cyano, perfluoroalkoxy, aryl, —C(=O)—NH(alkyl), —C(=O)—NH(cycloalkyl), and —C(=O)—NH(aralkyl). In some embodiments, $G_2$ is selected from the group comprising phenyl, pyridyl, thiophenyl, and substituted phenyl, optionally wherein said substituted phenyl is phenyl substituted with halo, alkoxy, or perfluoroalkyl.

In some embodiments, the tyrosine reactive compound has a structure of Formula (IV):

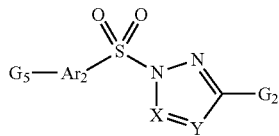

wherein: Ar$_2$ is selected from the group comprising phenyl, naphthyl, and pyridyl; $G_2$ is selected from the group comprising aryl, heteroaryl, substituted aryl, and substituted heteroaryl; and $G_5$ is selected from the group comprising H, halo, perhaloalkyl, alkoxy, cyano, perhaloalkoxy, aryl, —C(=O)—NH(alkyl), —C(=O)—NH(cycloalkyl), and —C(=O)—NH(aralkyl). In some embodiments, $G_2$ is —Ar$_3$-$G_6$, wherein Ar$_3$ is selected from phenyl, pyridyl, and thiophenyl and $G_6$ is an aryl group substituent, optionally selected from the group comprising H, halo, alkoxy, and perhaloalkyl.

In some embodiments, the presently disclosed subject matter provides a modified tyrosine-containing protein comprising a modified tyrosine residue wherein the modified tyrosine residue is formed by the reaction of a tyrosine residue with a non-naturally occurring compound having a structure of Formula (III):

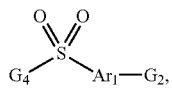

wherein: Ar$_1$ is selected from the group comprising 1,2,4-triazole, imidazole, pyrazole, and tetrazole; $G_2$ is H or an aryl group substituent, optionally wherein $G_2$ is selected from H, aryl, and substituted aryl; and $G_4$ is selected from the group comprising alkyl, substituted alkyl, cycloalkyl, substituted cycloalkyl, heterocycyl, aralkyl, substituted aralkyl, aryl, substituted aryl, heteroaryl, and substituted heteroaryl. In some embodiments, the modified tyrosine residue comprises a structure of Formula (II"):

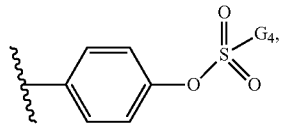

wherein: $G_4$ is selected from the group comprising alkyl, substituted alkyl, cycloalkyl, substituted cycloalkyl, heterocycyl, aralkyl, substituted aralkyl, aryl, substituted aryl, heteroaryl, and substituted heteroaryl.

In some embodiments, the tyrosine-containing protein comprises a tyrosine residue site denoted in Table 2 or Table 3. In some embodiments, the modified tyrosine-containing protein is modified at a tyrosine residue in a RNA-recognition motif (RRM) or at a domain mediating protein-protein interactions, optionally a proteasome/COP9/IF3 (PCI/PINT) or SRC homology 3 (SH3) domain. In some embodiments, the modified tyrosine-containing protein is an enzyme.

In some embodiments, the modified tyrosine-containing protein is selected from the group comprising glutathione-S-transferase Pi (GSTP1), phosphoglycerate mutase 1 (PGAM1), enhancer of mRNA-decapping protein 3 (EDC3), dipeptidyl peptidase 3 (DPP3), fumarylacetoacetase (FAAA), and prostaglandin reductase 2 (PTGR2). In some embodiments, the modified tyrosine-containing protein is DPP3 modified at tyrosine position 417, optionally wherein the modified tyrosine residue is formed by reaction of the tyrosine residue with a compound having a structure:

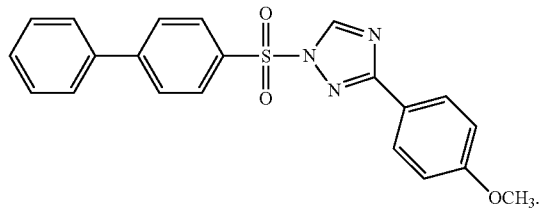 [SMILES: COc1ccc(-c2ncn(S(=O)(=O)c3ccc(-c4ccccc4)cc3)n2)cc1]

In some embodiments, the modified tyrosine-containing protein is PGAM1 modified at tyrosine position 92. In some embodiments, the modified tyrosine-containing protein is GSTP1 modified at tyrosine position 8, optionally wherein the modified tyrosine residue is formed by reaction of the tyrosine residue with a compound having a structure selected from the group consisting of:

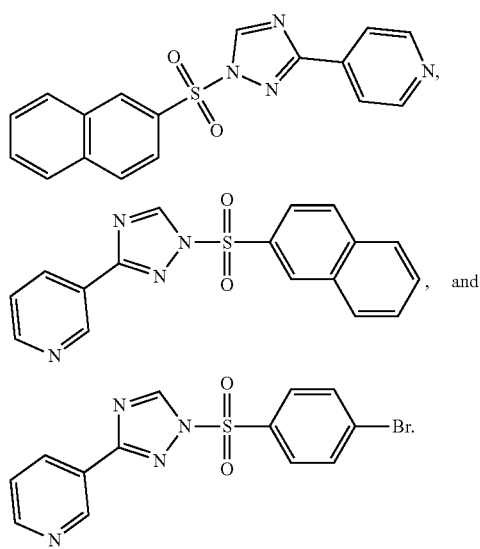

In some embodiments, the modified tyrosine-containing protein is EDC3 modified at tyrosine position 475, optionally wherein the modified tyrosine residue is formed by reaction of the tyrosine residue with a compound having a structure:

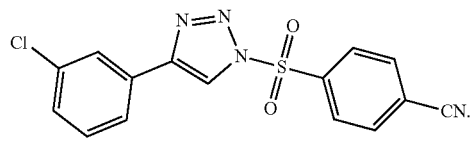 [SMILES: N#Cc1ccc(S(=O)(=O)n2cc(-c3cccc(Cl)c3)nn2)cc1]

In some embodiments, the modified tyrosine-containing protein is FAAA modified at tyrosine position 244, optionally wherein the modified tyrosine residue is formed by reaction of the tyrosine residue with a compound having a structure:

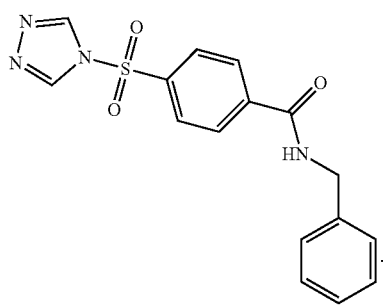 [SMILES: O=C(NCc1ccccc1)c1ccc(S(=O)(=O)n2cnnc2)cc1]

In some embodiments, the modified tyrosine-containing protein is PTGR2 modified at tyrosine position 100, optionally wherein the modified tyrosine residue is formed by reaction of the tyrosine residue with a compound having a structure

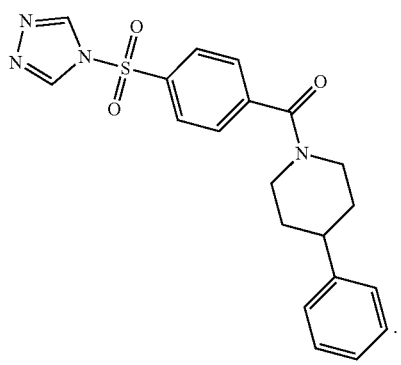 [SMILES: O=C(c1ccc(S(=O)(=O)n2cnnc2)cc1)N1CCC(c2ccccc2)CC1]

In some embodiments, the presently disclosed subject matter provides a method of identifying a reactive lysine of a protein, the method comprising: (a) providing a protein sample comprising isolated proteins, living cells, or a cell lysate; (b) contacting the protein sample with a probe compound of Formula (I) for a period of time sufficient for the probe compound to react with at least one reactive lysine in a protein in the protein sample, thereby forming at least one modified reactive lysine residue; and (c) analyzing proteins in the protein sample to identify at least one modified lysine residue, thereby identifying at least one reactive lysine of a protein; wherein the probe compound has a structure of Formula (I):

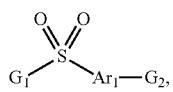

wherein: $G_1$ is a monovalent moiety comprising an alkyne moiety, a fluorophore moiety, a detectable labeling group, or a combination thereof; $Ar_1$ is heteroaryl, optionally five-membered heteroaryl and/or nitrogen-containing heteroaryl; and $G_2$ is H or an aryl group substituent; optionally wherein $G_2$ is selected from the group comprising H, alkyl, substituted alkyl, aralkyl, substituted aralkyl, aryl, heteroaryl, substituted aryl, and substituted heteroaryl; and wherein the at least one modified reactive lysine residue comprises a modified lysine residue comprising a structure of Formula (II'):

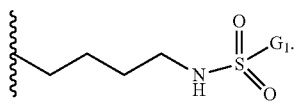

In some embodiments, the probe compound of Formula (I) has a structure selected from:

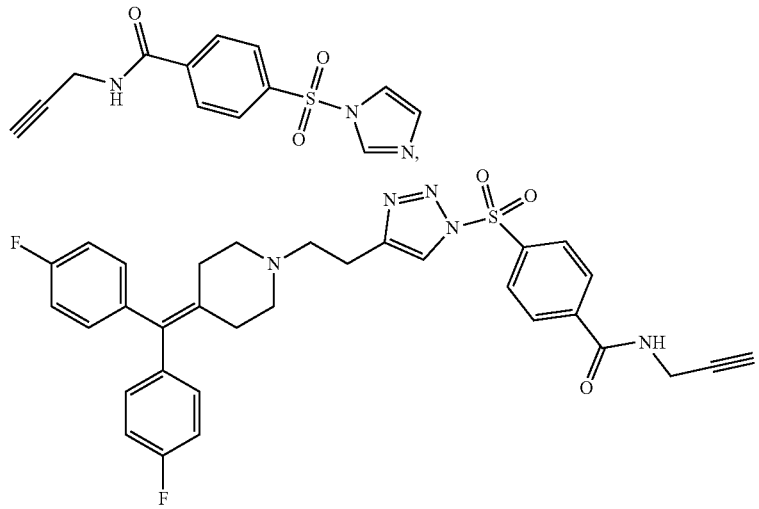

, and

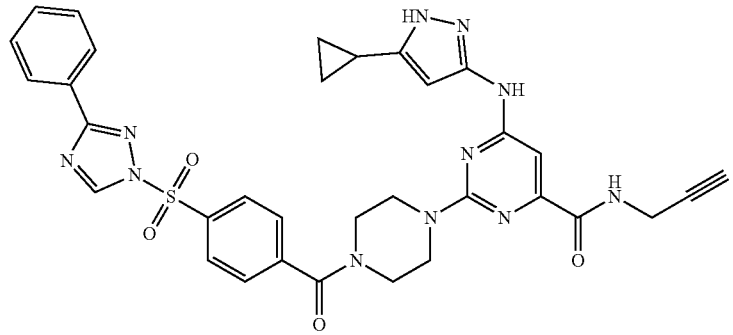

Accordingly, it is an object of the presently disclosed subject matter to provide methods of identifying reactive tyrosines and lysines in proteins, and related covalent probes, tyrosine-reactive compounds, and modified proteins. This and other objects are achieved in whole or in part by the presently disclosed subject matter. Further, an object of the presently disclosed subject matter having been stated above, other objects and advantages of the presently disclosed subject matter will become apparent to those skilled in the art after a study of the following description, Figures, and Examples.

BRIEF DESCRIPTIONS OF THE FIGURES

FIGS. 1A-1D: Development of sulfur-triazole exchange (SuTEx) chemistry for chemical proteomics. FIG. 1A is a schematic diagram showing the development of sulfonyl-triazoles as a hybrid of sulfonyl-fluoride and triazole-ureas for use as covalent probes with reactivity that can be modulated through the triazole leaving group (LG). FIG. 1B is a schematic diagram showing the chemical structures of 1,2,3- and 1,2,4-sulfonyl triazoles HHS-465 and HHS-475, respectively. FIG. 1C is a schematic diagram showing the proposed reaction mechanism of sulfur-triazole exchange (SuTEx) chemistry and LC-MS/MS workflow to identify proteins and corresponding binding sites from SuTEx reaction. FIG. 1D is a graph showing the tandem mass spectrometry (MS2) spectrum annotation of an HHS-475-modified tyrosine site (Y92) found in PGAM1. Covalent reaction with HHS-465 and HHS-475 adds +635.2737 Da to the modified amino acid (Y92 from PGAM1 shown as a representative example) as determined from analysis of a modified PGAM1 peptide fragment of the sequence HY*GGLTGLNK (SEQ ID NO:1, modified at the starred tyrosine residue) from a digested modified PGAM1 sample and supports the proposed SuTEx reaction mechanism. Data shown are representative of two experiments (n=2 biologically independent experiments).

FIGS. 2A-2D: Functional tyrosine profiling in proteomes and live cells. FIG. 2A is a schematic diagram showing the comparison of HHS-465- and HHS-475-tyrosine modified sites identified from human cell proteomes (HEK293T, A549, DM93, H82, and Jurkat cells) treated with SuTEx probes (100 μM, 1 hr, 25° C.). FIG. 2B is a graph showing the distribution of protein domain groups that are significantly overrepresented using probe-modified tyrosine sites from in situ chemical proteomic studies. Enriched domain annotations are those with a Q-value <0.01 after Benjamini- Hochberg correction of a two-sided binomial test. FIG. 2C is a pair of graphs showing (top) overlap between in situ HHS-465- and HHS-475-modified tyrosine sites that are also phosphorylation sites (number of phosphotyrosine high throughput annotation on PhosphoSitePlus (HTP score); HTP≥1); and (bottom) coverage of phospho-tyrosine sites (HTP≥10) that were detected by in situ chemical proteomics of HEK293T and Jurkat cells (HHS-465 and -475). FIG. 2D is a pair of graphs showing (top) the comparison of HHS-465 and HHS-475 in situ probe-modified proteins with DrugBank proteins (DBP group) and Non-DBP proteins (which are proteins that did not match a DrugBank entry); and (bottom) probe-enriched domains from DBP and non-DBP groups. Enriched domain annotations are those with a Q-value <0.01 after Benjamini-Hochberg correction of a two-sided binomial test. All data shown are representative of two experiments (n=2 biologically independent experiments).

FIGS. 3A-3D: SuTEx-enabled discovery of intrinsically nucleophilic tyrosines in human cell proteomes. HEK293T SILAC heavy and light soluble proteomes were treated with 250 or 25 μM HHS-465 (10:1 comparison), respectively. The resulting SILAC ratios (SR) were quantified using the area under the curve of MS1 extracted ion chromatograms (EIC) to determine tyrosine nucleophilicity. FIG. 3A is a waterfall plot of nucleophilicity ratio (median SR values) as a function or probe-modified tyrosine sites to quantitate tyrosine reactivity across the proteome. A MS1 EIC is shown for SR values that represent each nucleophilicity group (low-black, medium-grey, and high-red). FIG. 3B is a pair of graphs showing the distribution of protein domain groups that contain tyrosines quantified as low (SR>5) or medium/high (SR<5) reactivity. Domain annotations shown were significantly enriched (Q-value <0.01 after Benjamini-Hochberg correction of a two-sided binomial test) with HHS-465. FIG. 3C is a bar plot depicting tyrosines with medium to high nucleophilicity are less likely to be phosphorylated (HTP≥10, PhosphoSitePlus) compared with less reactive tyrosines. FIG. 3D is a series of graphs and gel images showing proteins containing a hyper-reactive tyrosine (GSTP1 Y8, EDC3 Y475) or single probe-modified tyrosine (DPP3 Y417) can be site-specifically labeled with SuTEx probes (50 μM, 30 min, 37° C.). Recombinant wild-type (WT) protein or corresponding tyrosine (Y)-to-phenylalanine (F) mutant HEK293T proteomes were treated with HHS-475 (GSTP1, DPP3, PGAM1) or HHS-465 (EDC3) and analyzed by gel-based chemical proteomics. Proteins that contain less nucleophilic tyrosines (PGAM1 Y92) are labeled at multiple sites and show negligible differences in probe labeling between WT and tyrosine mutant. Western blots show equivalent expression of recombinant WT and mutant proteins. All data shown are representative of two experiments (n=2 biologically independent experiments).

FIGS. 4A-4D: Tuning SuTEx probes for tyrosine chemoselectivity in cell proteomes. HEK293T soluble proteomes were treated with SuFEx and SuTEx probes. FIG. 4A is a graph showing the global reactivity [total number of tyrosine (Y) and lysine (K) sites] and specificity (Y/K ratio) of probe-labeled sites from LC-MS chemical proteomic experiments. FIG. 4B is a bar plot showing distribution of HHS-482-modified sites (high confidence sites; Byonic score >600) against nucleophilic amino acid residues detected in proteomes. FIG. 4C is a schematic diagram showing overlap of tyrosine-modified sites from proteomes treated with sulfonyl-triazoles (HHS-482) compared with -fluorides (HHS-SF-1). FIG. 4D is a schematic diagram comparing probe-modified tyrosine sites from LC-MS chemical proteomic studies using 1,2,4-sulfonyl-triazoles. Each 1,2,4-sulfonyl-triazole probe was able to modify unique tyrosine sites to increase overall tyrosine coverage. All data shown are representative of two experiments (n=2 biologically independent experiments).

FIGS. 5A-5B: Triazole LG enhances phenol reactivity of sulfonyl probes in solution. FIG. 5A is a series of graphs showing the HPLC analysis of a mixture of HHS-475 (peak 3), HHS-SF-1 (peak 4), and HHS-482 (peak 7) was incubated with p-cresol in the presence of increasing amounts of tetramethylguanidine (TMG) base and time dependent covalent reaction monitored by reduction of respective probe signal. Formation of the common p-cresol-probe adduct (peak 8) was confirmed by retention time that matched synthetic standard KY-2-48. Shaded block arrows denote the time points when each respective probe was consumed, and the asterisks denote time points corresponding to substantial but not complete probe depletion. FIG. 5B is (left) a graph showing the reduced reactivity of n-butylamine against sulfonyl probes under high TMG conditions (3.3 equivalents). Formation of the n-butylamine-probe adduct (peak 9) was validated by retention time that matched the KY-2-42 synthetic standard; and (right) a schematic diagram of the reactions of the probes with p-cresol or n-butylamine. Data shown are representative of three independent experiments (n=3).

FIGS. 6A-6E: Chemical phosphotyrosine-proteomics by SuTEx. FIG. 6A is an image of Western blot analysis confirming activation of global tyrosine phosphorylation (detected via a phospho-tyrosine monoclonal antibody, P-Tyr-100) with pervanadate treatment conditions of A549 cells (100 μM, 30 min) used for chemical proteomic studies. FIG. 6B is a graph of HHS-475-modified tyrosine sites (represented by individual circles) as a function of SILAC ratios (SR, light (PBS)/heavy (pervanadate or PER)). Size of circles reflect the HTP score (PhosphoSitePlus). Tyrosine sites were further segregated into pervanadate-insensitive (Pern) and -sensitive (PerS) groups based on SR<2 or ≥2, respectively. Soluble proteomes from pervanadate activated-A549 cells were labeled with HHS-475 (100 μM) for 30 min at 37° C. FIG. 6C is a bar plot showing trend towards increased number of phosphotyrosine annotations (HTP≥10) on tyrosine sites with enhanced pervanadate sensitivity. Validation that blockade of HHS-475 labeling (FIG. 6D) of individual tyrosine sites on STAT3 (Y705), CTNND1 (Y228), and PKM (Y105) coincides with increased phosphorylation at respective sites with pervanadate activation (FIG. 6E). Equivalent protein loading was confirmed by western blot analysis of non-phosphorylated protein counterparts. All data shown are representative of two experiments (n=2 biologically independent experiments).

FIG. 7 is a synthetic diagram showing a general strategy for preparing alkyne-modified sulfonyl-triazole probes.

FIG. 8 is a pair of graphs showing the distribution of HHS-465-(left) and HHS-475-(right) modified sites (high confidence sites; Byonic score >600) against nucleophilic amino acid residues detected in proteomes. Data shown are representative of two experiments (n=2 biologically independent experiments).

FIG. 9: Gel Images showing concentration-dependent labeling of live HEK293T cells treated with SuTEx probes. HEK293T cells were treated with the indicated concentrations of HHS-465 (left) or HHS-475 (right) for 2 h at 37° C. After treatment, cells were lysed, probe-modified proteomes (1 mg/mL) subjected to CuAAC with rhodamine-azide followed by SDS-PAGE analysis and in-gel fluorescence scanning. Data shown are representative of two experiments (n=2 biologically independent experiments).

FIG. 10: Gel Images showing time-dependent labeling of live HEK293T cells treated with SuTEx probes. HEK293T cells are treated for the indicated times with 25 μM of HHS-465 (left) or HHS-475 (right) at 37° C. After treatment, cells were lysed, probe-modified proteomes (1 mg/mL) subjected to CuAAC with rhodamine-azide followed by SDS-PAGE analysis and in-gel fluorescence scanning. Data shown are representative of two experiments (n=2 biologically independent experiments).

FIG. 11: Quantitative chemical proteomics for profiling tyrosine reactivity. Experimental workflow for quantitative chemical proteomics to measure intrinsic tyrosine nucleophilicity (i.e., reactivity). HEK293T cells were cultured in SILAC media supplemented with either "light" 12C, 14N-labeled lysine and arginine or "heavy" 13C, 15N-labeled lysine and arginine. Heavy and light HEK293T proteomes were treated with 250 (high [probe]) or 25 μM (low [probe]) HHS-465, respectively (10:1 comparison). The resulting SILAC ratios (SR) were quantified using the area under the curve of MS1 extracted ion chromatograms. Hyper-reactive tyrosines are expected to show equivalent probe labeling intensity at high and low [probe] (left MS1, SR~1) while less nucleophilic tyrosines show concentration dependent probe labeling (right MS1, SR>>1). A separate experiment where heavy and light proteomes are treated with equivalent [probe] (1:1 comparison) is used as a control for potential false quantifications. Peptide sequencing and validation of the site of probe binding are determined using MS2 (fragmentation) spectra, as shown in the lower right corner, which illustrates the MS2 spectrum of a peptide fragment of sequence PPYTVVY*FPVR (SEQ ID NO: 2) modified at the starred tyrosine residue.

FIG. 12: Quantitative analysis of tyrosine reactivity. Quantitative comparison of tyrosine nucleophilicity between sites detected in human GSTP1 (Y8), DPP2 (Y417), PGAM1 (Y92), and EDC (Y475). Heavy and light MS1 extracted ion chromatograms were used to calculate the SILAC ratio (SR) for 10:1 and 1:1 probe (HHS-465) comparisons. Data shown are representative of two experiments (n=2 biologically independent experiments).

FIG. 13 is a graph of the number of hyper-reactive (high nucleophiliciy) and quantified tyrosines per protein that contained at least a single hyper-reactive tyrosine. Data shown are representative of two experiments (n=2 biologically independent experiments).

FIGS. 14A-14D. SuTEx probes target reactive catalytic and non-catalytic tyrosines of enzymes. FIG. 14A is a schematic diagram of the crystal structure of human GSTP1 (PDB accession code 6G22) shows tyrosine 8 (Y8) is located in the GSH binding site. FIG. 14B is a graph showing loss of biochemical activity in GSTP1 Y8F mutant supports tyrosine 8 as a catalytic residue. Biochemical activity of recombinant GSTP1-HEK293T proteomes (1 mg/mL) was assessed using a substrate assay measuring GSTP1-catalyzed conjugation of GSH to BDNB (10 min, 37° C.). Data shown are mean±s.e.m.; n=7 biologically independent experiments. FIG. 14C is a schematic diagram of the crystal structure of human DPP3 (PDB accession code 3FVY) showing the location of residues involved in zinc metal binding (H450, H455, E508), the catalytic glutamate (E451) and a non-catalytic tyrosine 417 (Y417) identified by SuTEx. Positively-charged arginines (R548, R572) are found in close proximity to Y417. FIG. 14D is a graph showing that recombinant DPP3- and Y417F mutant-HEK293T soluble proteomes (1 mg/mL) showed comparable activity in a peptidase substrate assay supporting Y417 as a non-catalytic tyrosine. Data are shown as mean±s.e.m.; n=4 biologically independent experiments.

FIG. 15: GSTP1 biochemical substrate assay. GSTP1 catalytic activity was evaluated by monitoring transfer of glutathione (GSH) to 1-bromo-2,4-dinitrobenzene (BDNB), which produces a dinitrophenyl thioether that can be detected spectrophotometrically by measuring absorbance at 340 nm.

FIGS. 16A and 16B: Substrate assay for evaluating DPP3 tyrosine 417 mutant. FIG. 16A is a schematic diagram showing the crystal structure of human DPP3 (PDB accession code 3FVY) showing location of residues involved in zinc metal binding (H450, H455, E508), the catalytic glutamate (E451), and a non-catalytic tyrosine 417 identified by SuTEx. Positively-charged arginines (R548, R572) are found in close proximity to Y417. FIG. 16B is a schematic diagram showing DPP3 cleavage of Arg-Argp-naphthylamide substrate to the colored naphthylamide product that can be detected spectrophotometrically by measuring fluorescence at 450 nm.

FIG. 17: Schematic of a SuTEx platform for global tyrosine phosphoproteomic studies. Activation of tyrosine phosphorylation (pY) using a general tyrosine phosphatase inhibitor (pervanadate) can reduce availability of tyrosines (Y) for SuTEx probe labeling, which can be readout by quantitative chemical proteomics (SILAC).

FIG. 18: Chemical prophotyrosine-proteomics by HHS-481. A bar plot showing a trend towards increased phosphotyrosine annotation (HTP≥10) in tyrosine sites with enhanced pervanadate sensitivity.

Figure 22A:
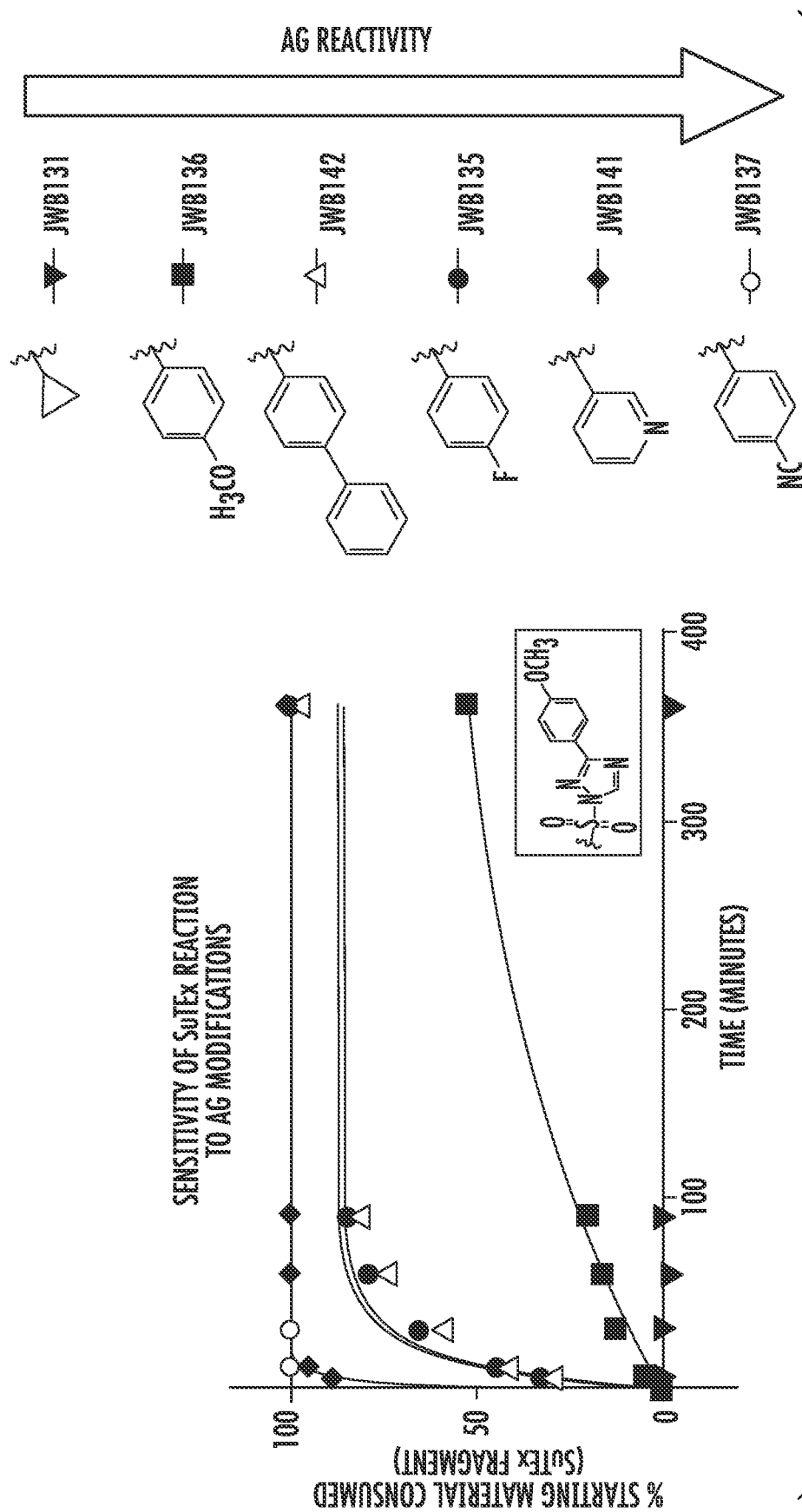
Figure 22B:
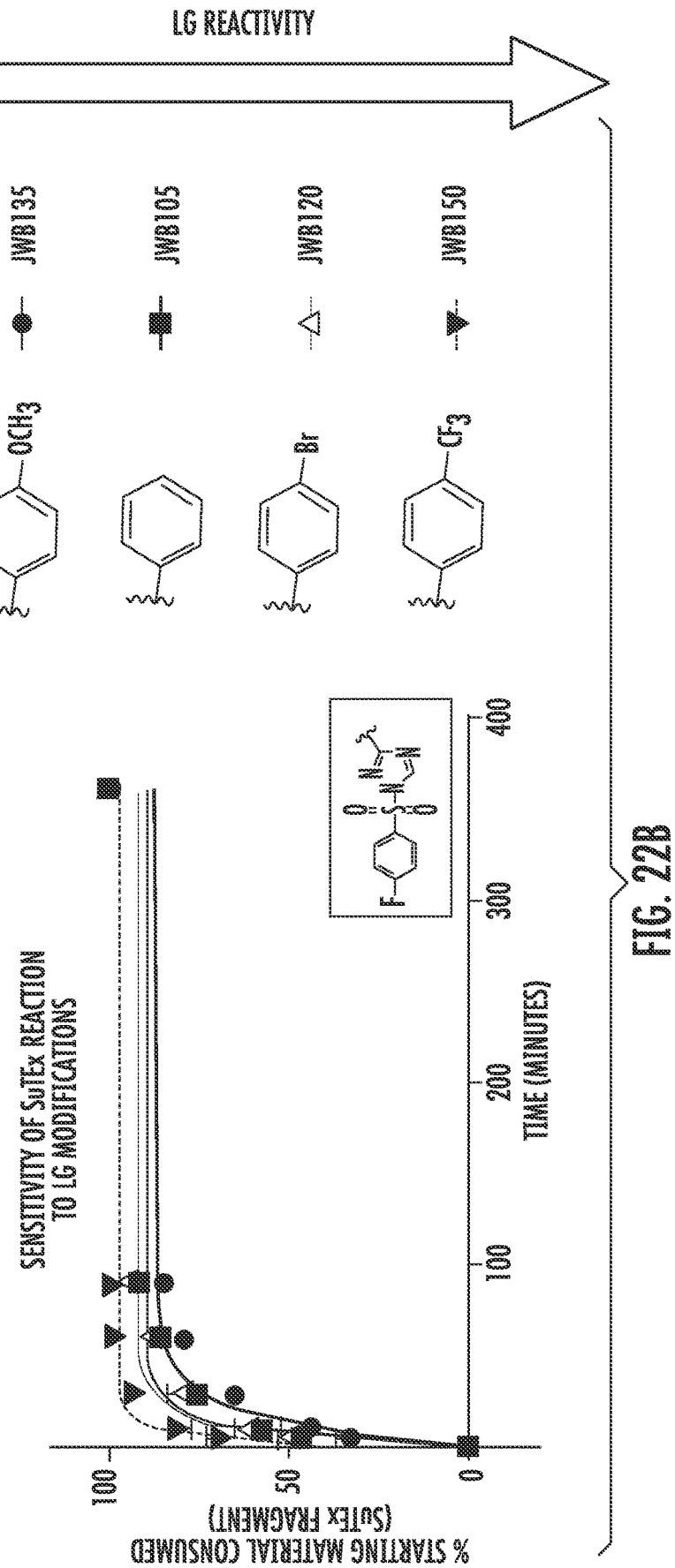

FIGS. 22A and 22B. Tuning reactivity of the sulfur electrophile. SuTEx ligands were incubated with p-cresol in the presence of tetramethylguanidine (TMG, 1.1 equivalents) base and time-dependent covalent reaction monitored by the reduction of respective ligand starting material. Modifications to the adduct group (AG; FIG. 22A) and triazole leaving group (LG; FIG. 22B) could alter solution reactivity of SuTEx ligands. Formation of the p-cresol adduct was confirmed by retention time that matched synthetic standards for respective reaction products. Data shown are representative of n=3 independent experiments.

Figure 23:
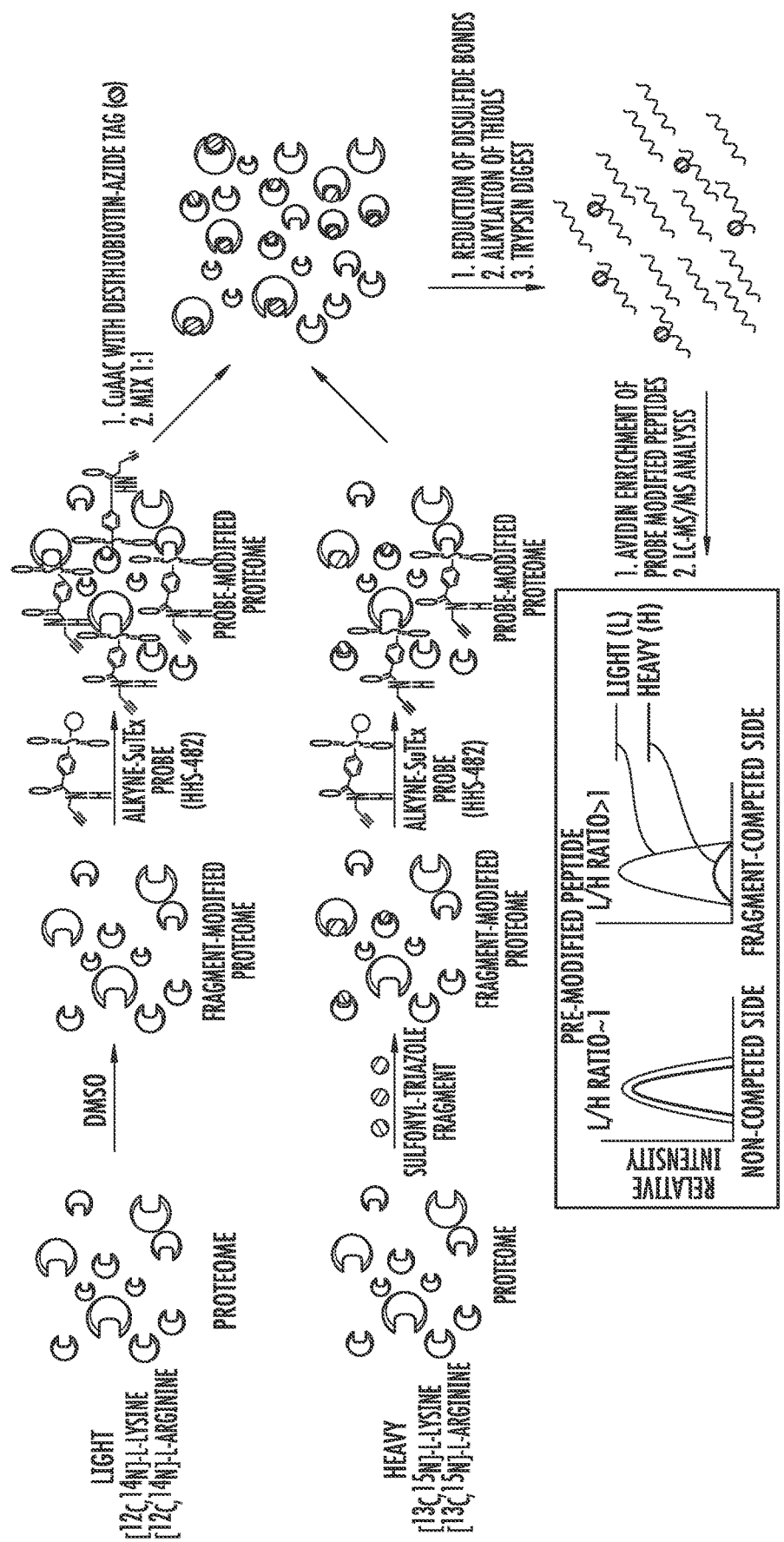

FIG. 23. Quantitative chemical proteomics for evaluating proteome-wide activity of SuTEx ligands. Experimental workflow for quantitative chemical proteomics evaluation of ligand reactivity and specificity in proteomes. DM93 cells were cultured in SILAC media supplemented with either "light" $^{12}C$, $^{14}N$-labeled lysine and arginine or "heavy" $^{13}C$, $^{15}N$-labeled lysine and arginine. Heavy and light DM93 proteomes were treated with DMSO vehicle or SuTEx ligand (50 μM, 37° C., 30 min) followed by HHS-482 probe labeling using the same reaction conditions. The resulting SILAC ratios (SR) were quantified using the area under the curve of MS1 extracted ion chromatograms. Non-liganded tyrosines are expected to show equivalent probe labeling intensity in vehicle and ligand treated conditions (left MS1, SR~1). Ligand-competed tyrosines (i.e. liganded tyrosine) are identified by sites showing substantial reduction in enrichment by HHS-482 compared with DMSO vehicle control (right MS1, SR>>1).

Figure 3D:
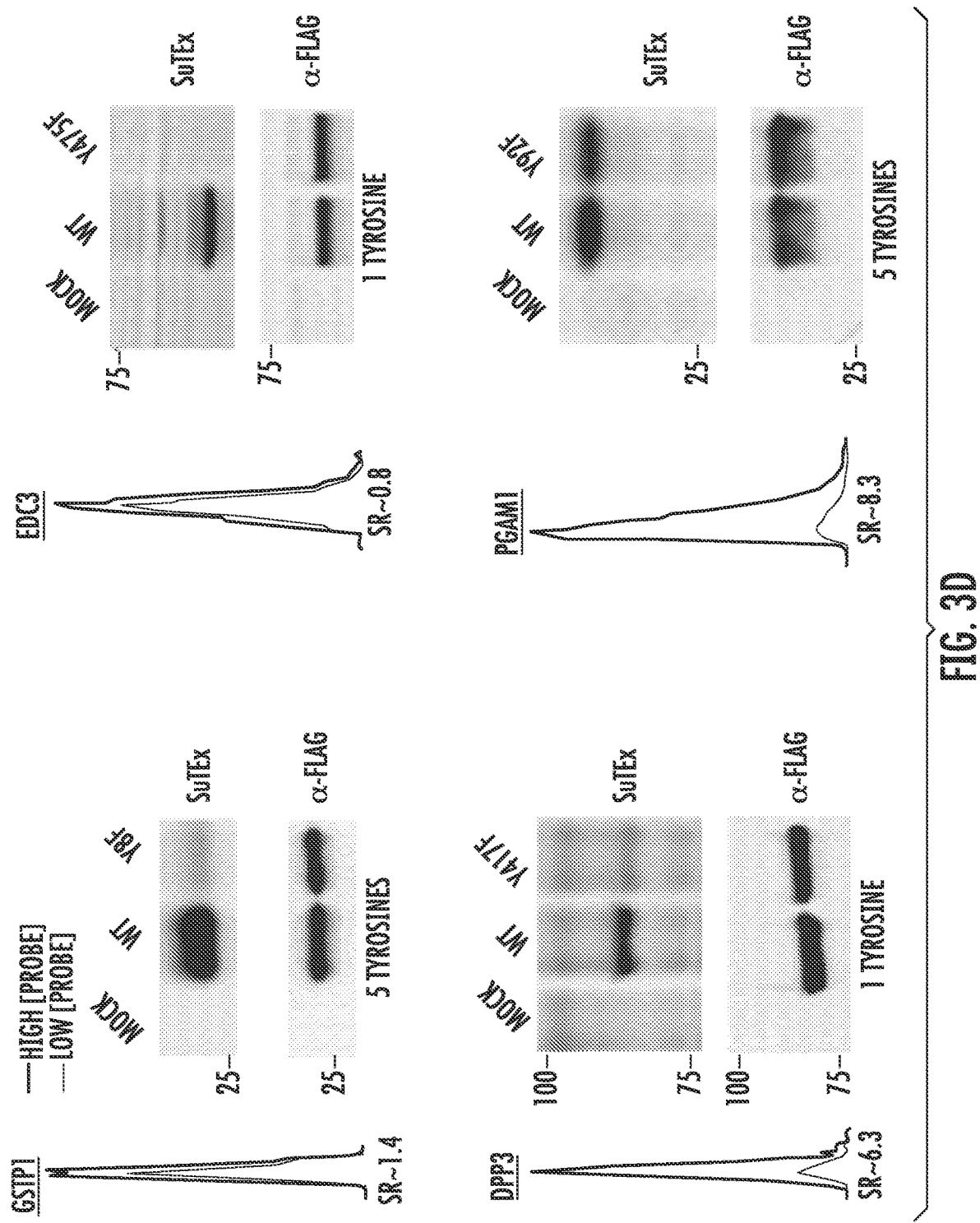
Figure 24A:
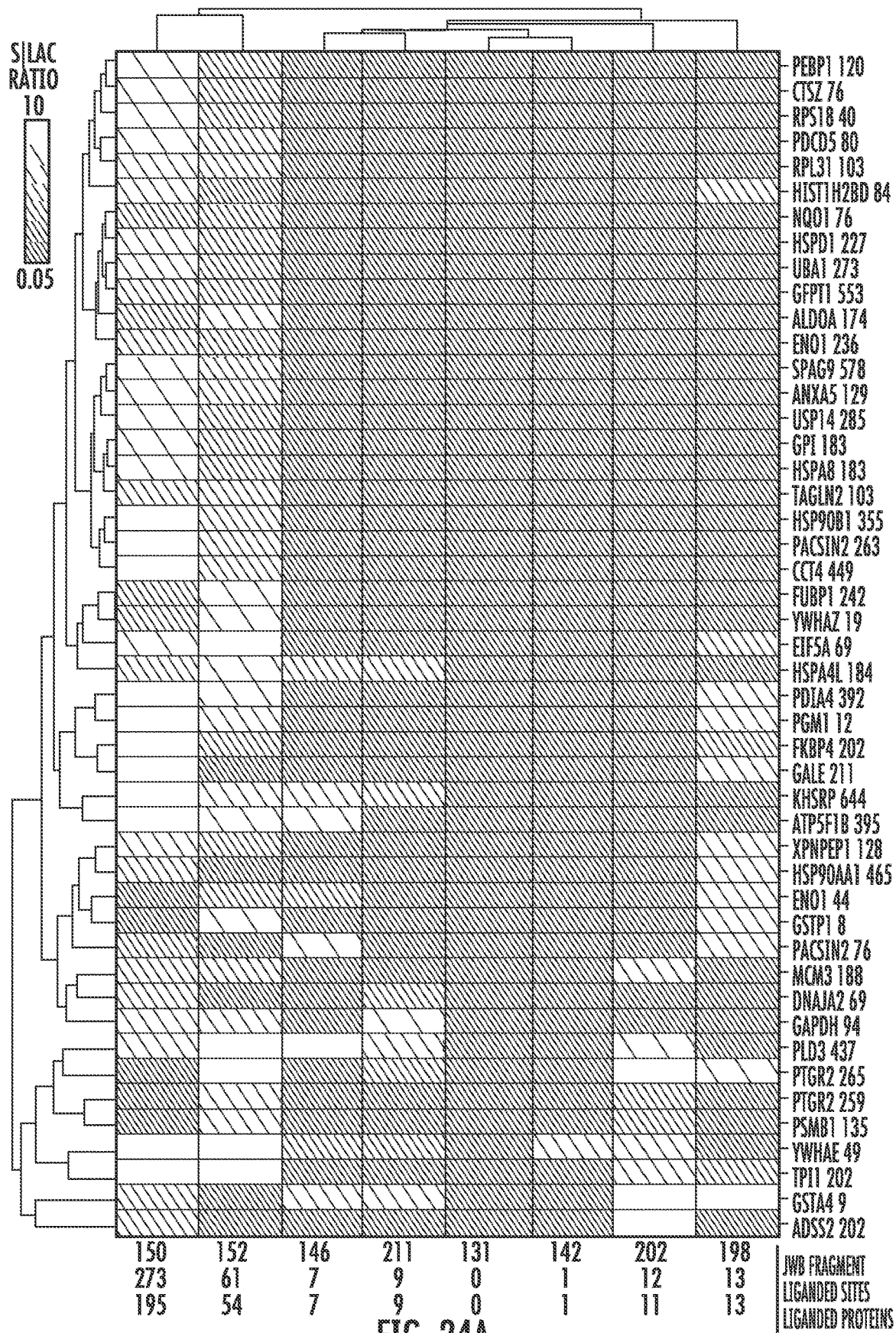
Figure 24B:
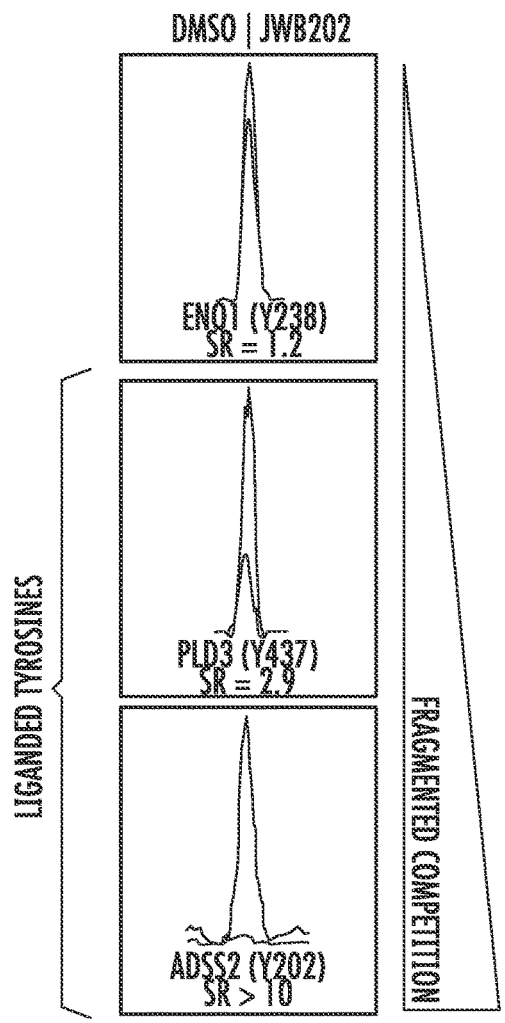
Figure 24C:
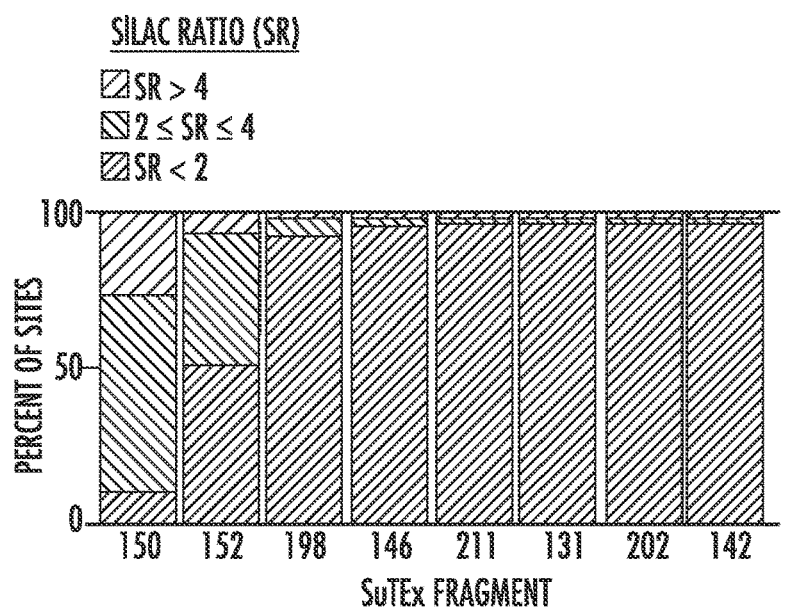

FIGS. 24A-24C: Fragment-based ligand discovery using SuTEx. FIG. 24A is a heat map showing SILAC ratios (SR) of representative tyrosines competed by fragments and organized by hierarchical clustering. Fragment competition at tyrosine sites were quantified using the area under the curve of MS1 extracted ion chromatograms (EIC) from HHS-482-labelled peptides in DMSO (light) versus fragment-treated (heavy) DM93 soluble proteomes. Competitive chemical proteomic studies were performed as shown in Supplementary FIG. 3. Tyrosine sites shown are liganded (SR>4) by at least 2 fragments with the number of liganded sites and proteins listed for each molecule. Y-axis lists the protein name and quantified tyrosine site. FIG. 24B shows representative MS1 EICs of tyrosine sites from quantitative LC-MS chemical proteomics: non-liganded (top (SR<2), partially-liganded (middle, 2≤SR≤4), and liganded (bottom, SR>4). FIG. 24C shows reactivity of fragments was assessed by comparing the fraction of tyrosine sites competed: non-liganded (SR<2), partially-liganded (2≤SR≤4), and liganded (SR>4). All data shown are representative of n=2-3 biologically independent experiments.

Figure 25C:
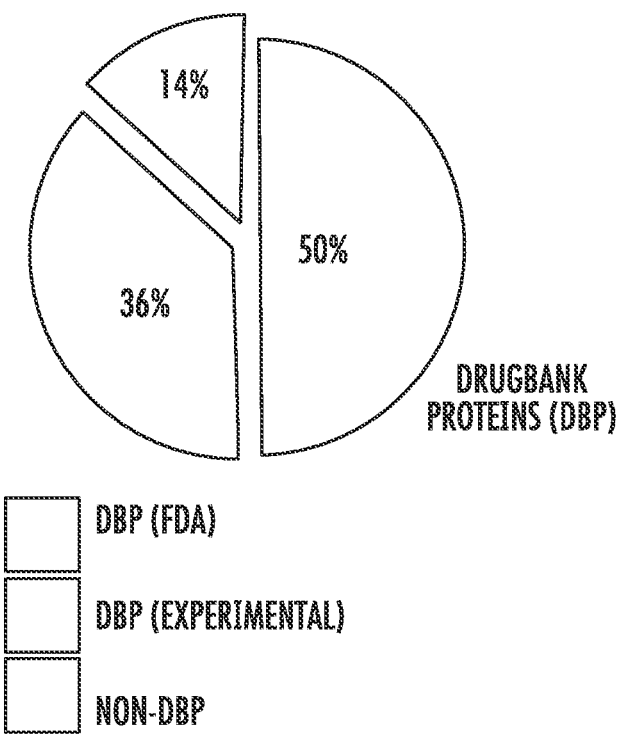

FIGS. 25A-25C: Analysis of tyrosines and proteins liganded by SuTEx fragments. (FIG. 25A) Distribution of liganded and non-liganded tyrosine sites and proteins from chemical proteomic analyses of DM93 soluble proteomes. Data shown for quantified tyrosines (top) and proteins (bottom) that were liganded (SR>4) by at least 1 fragment. (FIG. 25B) Enriched domain annotations are those with a Q<0.05 after Benjamini-Hochberg correction of a two-sided binomial test. (FIG. 25C) Distribution of liganded proteins (SR>4) found in DrugBank (DBP group) compared with proteins that did not match a DrugBank entry (non-DBP). All data shown are representative of n=2-3 biologically independent experiments.

Figure 26:
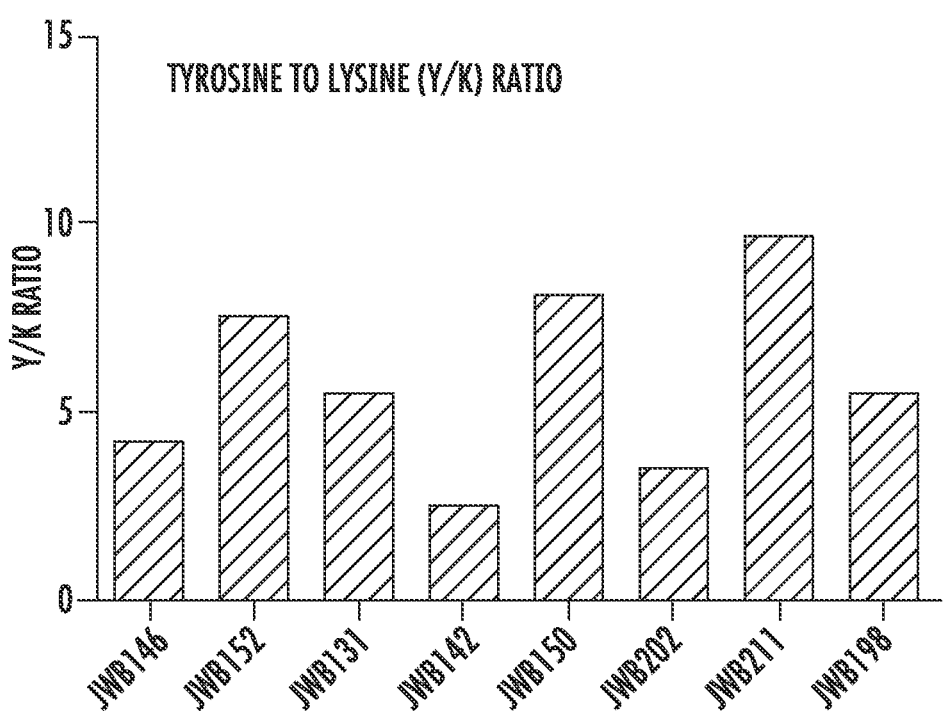
Figure 27C:
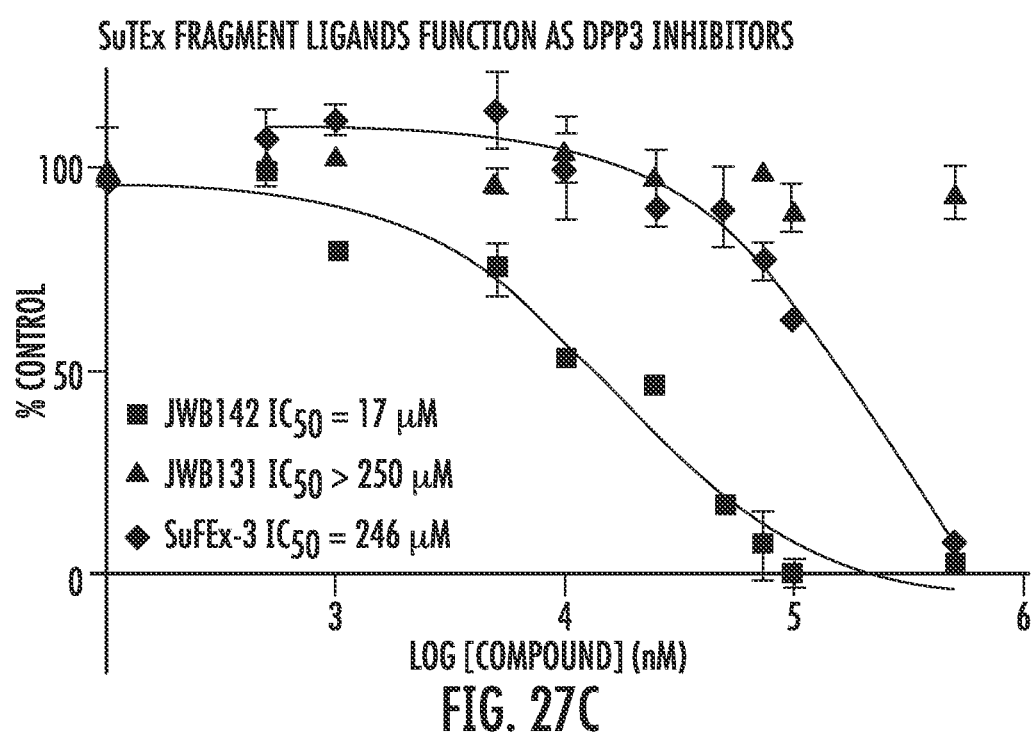
Figure 27D:
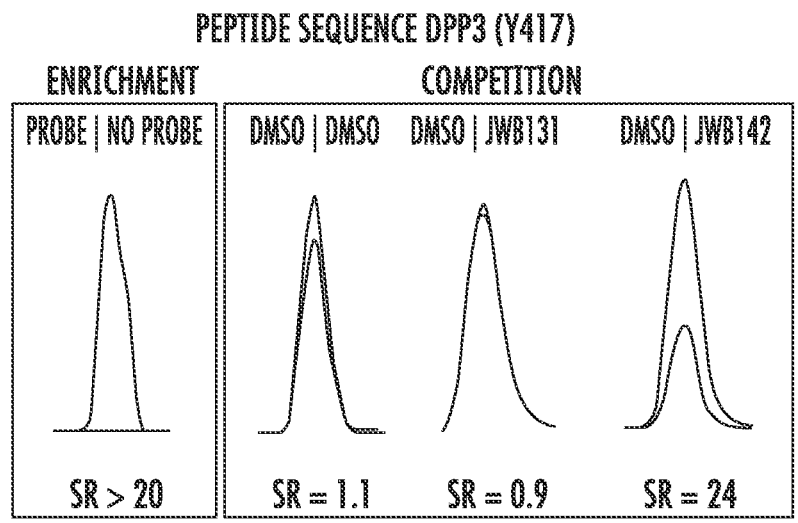

FIG. 26: Chemoselectivity of SuTEx fragments. Ratio of the number of tyrosine to lysine sites liganded (SR>2) by each respective fragment. Data shown are representative of n=2-3 biologically independent experiments.

FIGS. 27A-27D: Liganding non-catalytic tyrosines for blockade of protein activity. (FIG. 27A) Crystal structure of human DPP3 active site (PDB accession code 3FVY). The location of residues involved in zinc metal binding (H450, H455, E508), the catalytic glutamate (E451), and a non-catalytic tyrosine 417 (Y417) identified by SuTEx are highlighted. (FIG. 27B) Lead SuTEx fragments (JWB142) and negative control probe (JWB131) identified from a gel-based chemical proteomic screen against recombinant DPP3 proteomes. (FIG. 27C) JWB142 but not JWB131 blocked catalytic activity of purified DPP3 in a concentration-dependent manner as measured by substrate assay: JWB142, $IC_{50}$=17 μM, 95% confidence intervals: 11-27 μM. JWB142 showed >10-fold increase in inhibitory activity compared with the SuFEx counterpart: SuFEx-3, $IC_{50}$=246 μM, 95% confidence intervals: 117-519 μM. Data are shown as mean±s.e.m.; n=3 biologically independent experiments. (FIG. 27D) DPP3 Y417 site is liganded (~50% blockade) by JWB142 but not JWB131 fragment as judged by quantitative chemical proteomic analysis of recombinant human DPP3-HEK293T soluble cell proteome. All data shown are representative of n=2 biologically independent experiments.

Figure 28:
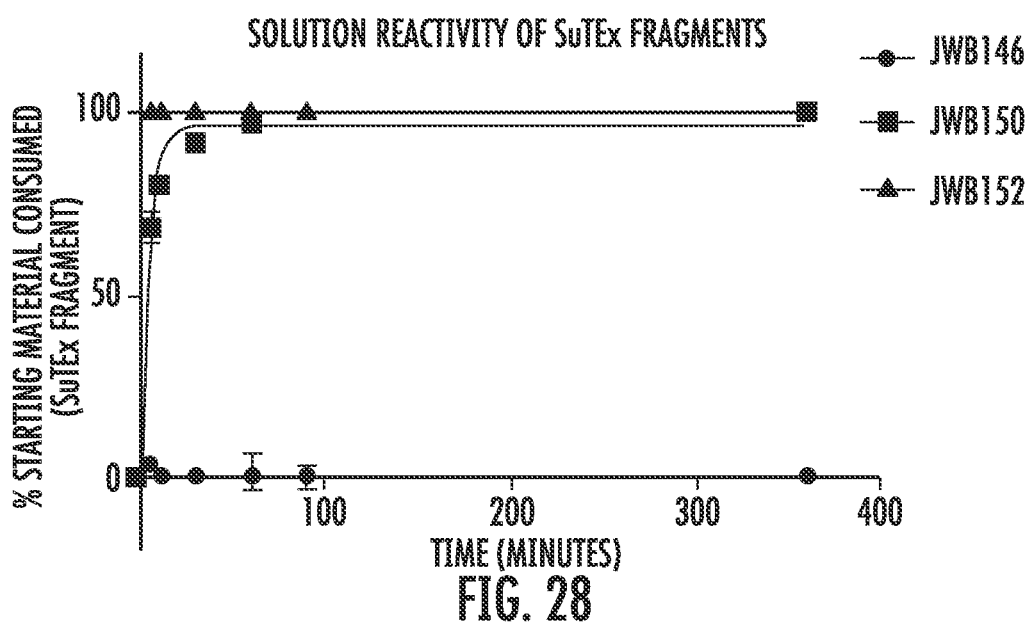

FIG. 28. Evaluating reactivity of fragment electrophiles in solution. JWB150 and JWB152 fragment electrophiles showed comparable reaction with p-cresol nucleophile while JWB146 was largely unreactive as judged by HPLC assay. Data shown are normalized to an internal caffeine standard and representative of n=3 independent experiments.

Figure 19:
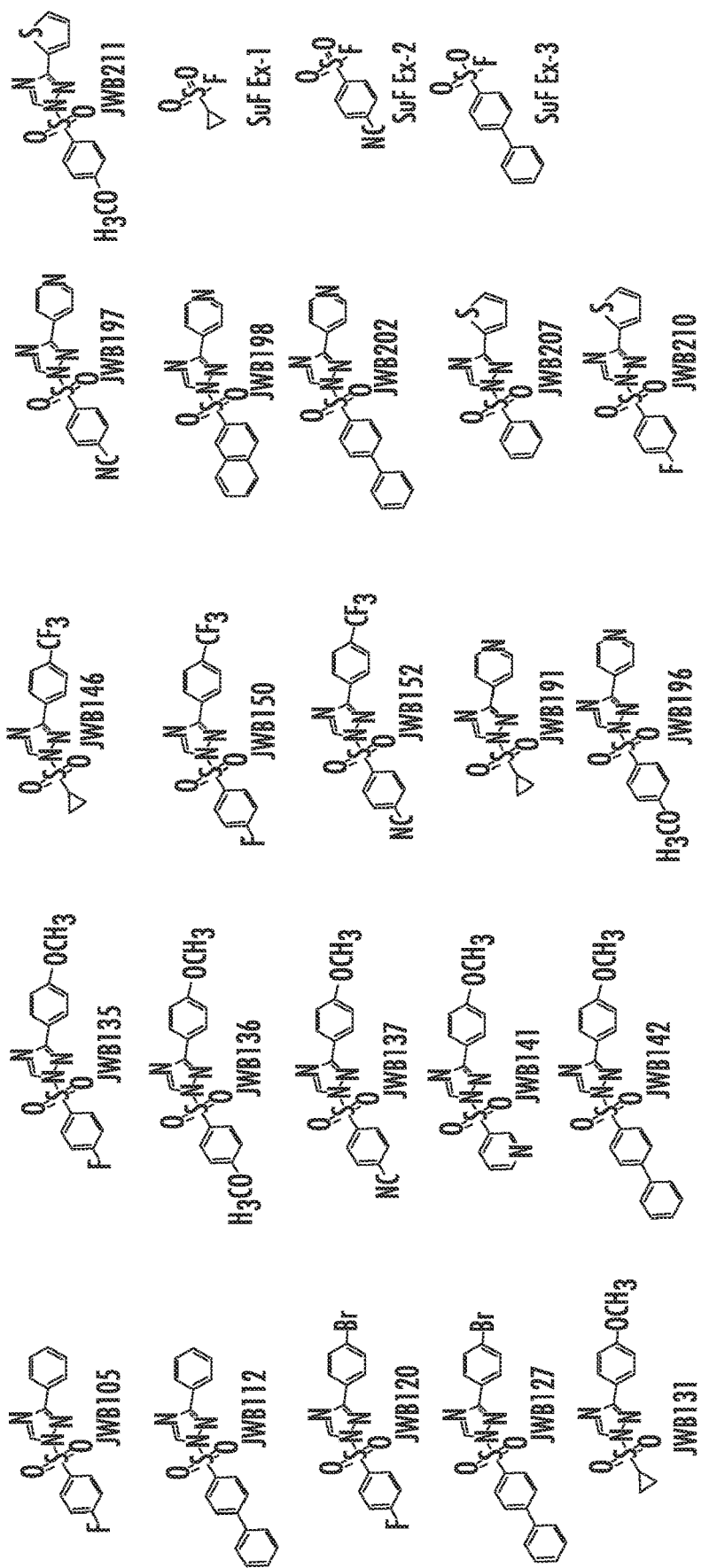
FIG. 19 is a schematic diagram showing chemical structures of a SuTEx ligand library displaying adduct- and leaving-group diversity.
Figure 29:
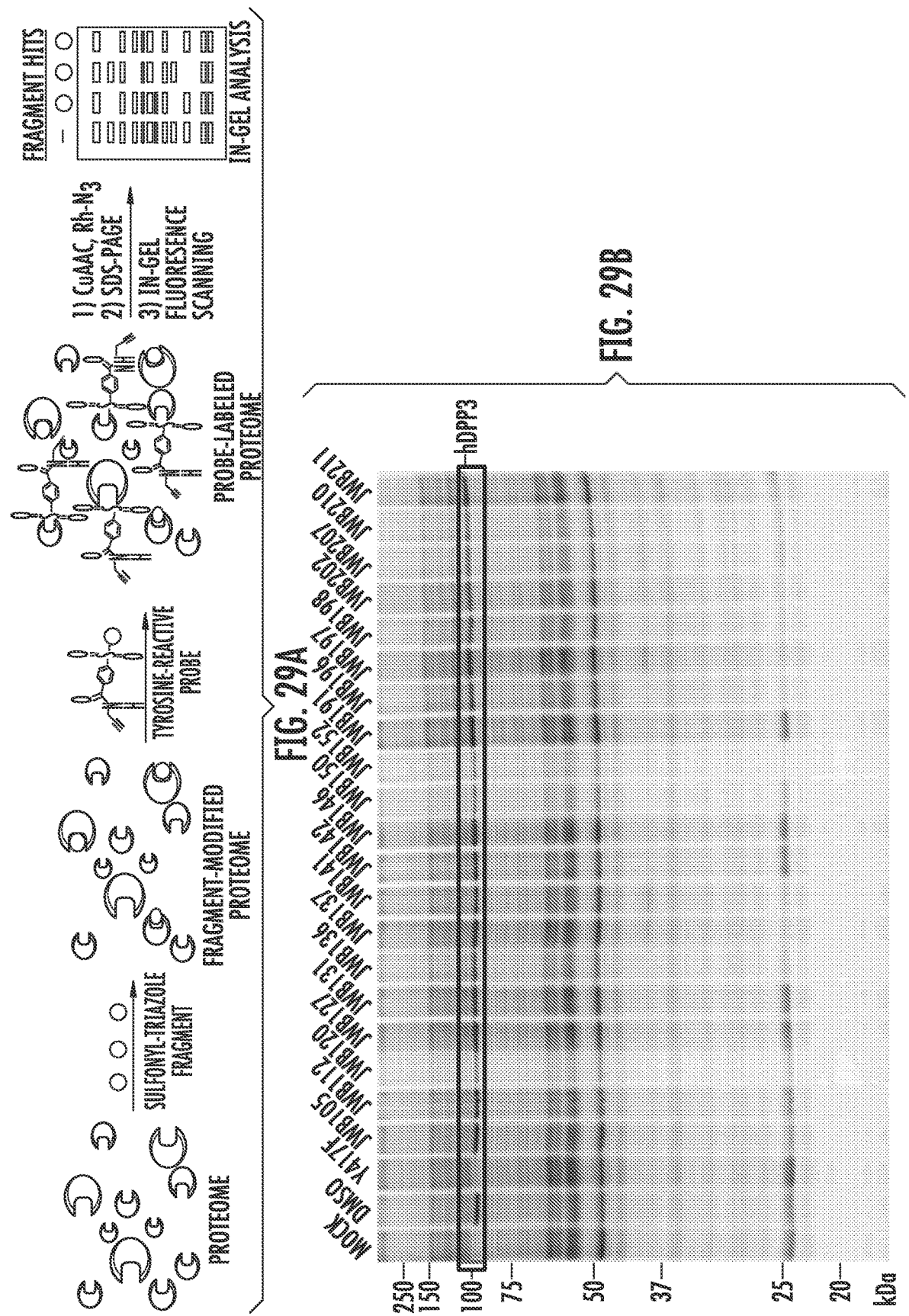

FIG. 29: Gel-based chemical proteomic screen for DPP3 fragment ligands. (FIG. 29, top) Schematic of gel-based competitive chemical proteomic assay to identify lead SuTEx fragments as ligands for perturbing human DPP3 (hDPP3) function. Proteomes were screened against the SuTEx fragment library shown in FIG. 19. (FIG. 29, bottom) Recombinant hDPP3-HEK293T soluble proteomes (1 mg/mL) were pretreated with indicated fragment (100 μM, 30 min, 37° C.) followed by labeling with HHS-482 (50 μM, 30 min, 37° C.). DPP3 Y417F mutant showed near-complete loss of HHS-482 labeling, which supports single site labeling at this tyrosine site. Data shown are representative of n=3 biologically independent experiments.

Figure 30:
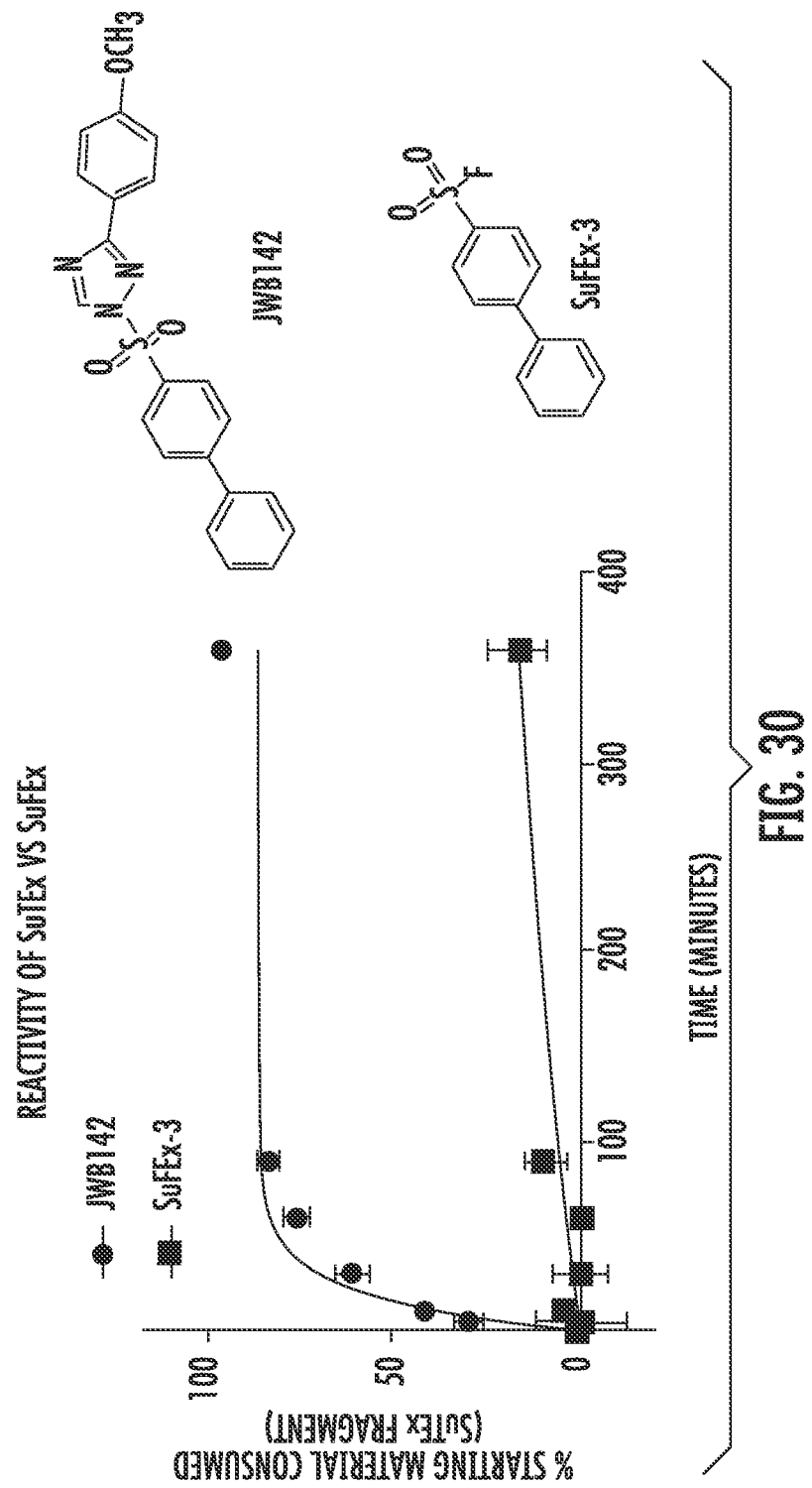

FIG. 30: Comparison of SuTEx and SuFEx reactivity in solution. JWB142 fragment electrophile shows enhanced reaction with p-cresol nucleophile compared with the SuFEx analog SuFEx-3. Data shown are normalized to an internal caffeine standard and representative of n=3 independent experiments.

Figure 31:
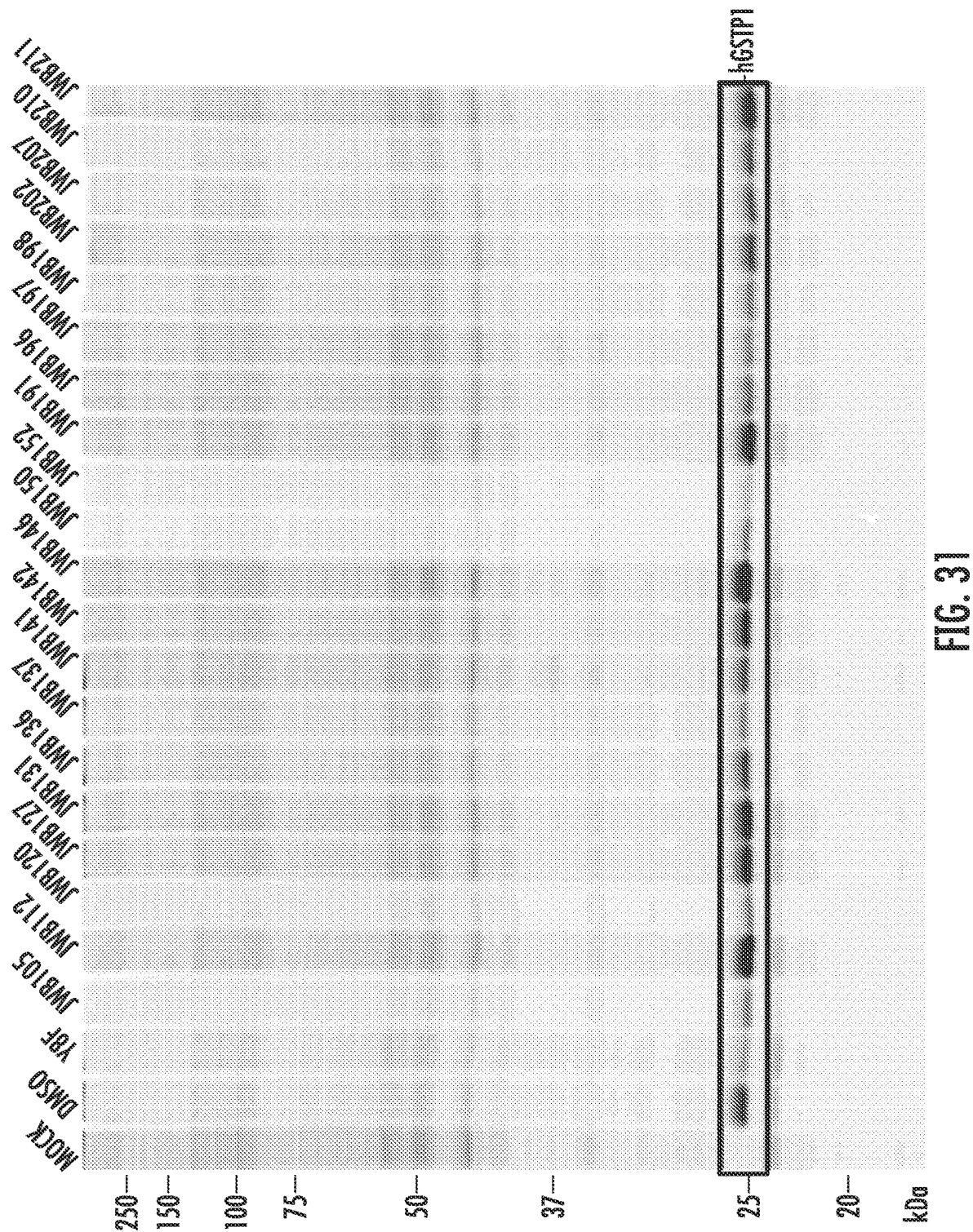

FIG. 31: Gel-based chemical proteomic screen for human GSTP1 (hGSTP1) fragment ligands. Recombinant hGSTP1-HEK293T soluble proteomes (1 mg/mL) were pretreated with indicated fragment (100 μM, 30 min, 37° C.) followed by labeling with HHS-482 (50 μM, 30 min, 37° C.). GSTP1 Y8F mutant showed near-complete loss of HHS-482 labeling, which supports site selective labeling at this tyrosine site. Gel-based chemical proteomics were performed as shown in FIG. 29, top. Data shown are representative of n=3 biologically independent experiments.

Figure 32C:
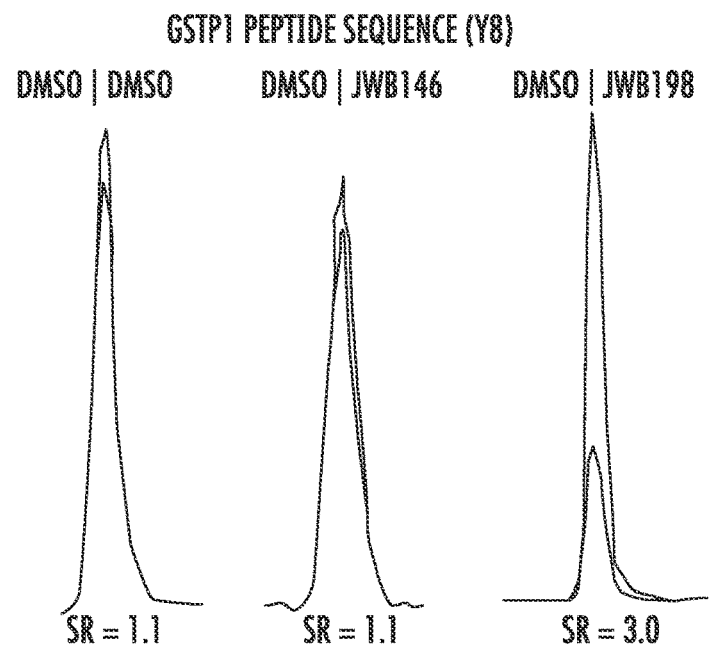
Figure 32D:
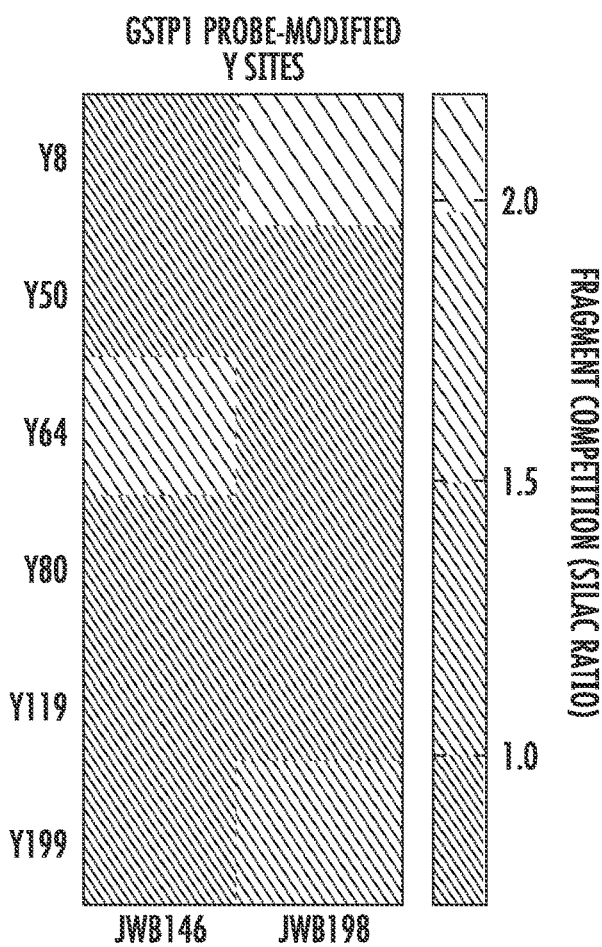

FIGS. 32A-32D: Liganding a hyper-reactive phosphotyrosine site of GSTP1 in live cells. FIG. 32A shows a gel-based chemical proteomic analysis of GSTP1-HEK293T soluble proteomes pretreated with vehicle or fragment electrophiles (50 μM, 30 min, 37° C.) followed by labeling with HHS-482 under the same treatment conditions. GSTP1 Y8F mutant shows >90% reductions in probe labeling compared with wild-type protein. JWB152 and JWB198 but not JWB146 or JWB191 block HHS-482 labeling to levels comparable with Y8F mutant. Bottom panel: gel-based evaluation of soluble proteomes from recombinant GSTP1-HEK293T cells treated with SuTEx fragments (50 μM compounds, 4 hr) show reduced HHS-482 labeling in JWB152 but not JWB146 treatments. Western blot analyses confirm equivalent FLAG-tagged GSTP1 expression across all conditions tested. FIG. 32B shows in vitro potency of JWB152 and JWB198 against recombinant GSTP1 lysates as evaluated by GSH substrate assay (JWB152, $IC_{50}$=23 μM, 95% confidence intervals: 14-39 μM; JWB198, $IC_{50}$=16 μM, 95% confidence intervals: 11-22 μM). The negative control probes JWB146 and JWB191 did not show inhibitory activity even at the highest concentration tested (100 μM). The SuFEx analog (SuFEx-2) showed moderate inhibition of GSTP1 activity at the highest concentration tested (250 μM). Data are shown as mean±s.e.m; n=3 biologically independent experiments. FIG. 32C shows that GSTP1 Y8 site is liganded (~70% blockade) by JWB198 but not JWB146 in live DM93 cells treated with SuTEx fragments followed by quantitative chemical proteomic analysis. FIG. 32D shows a heat map showing quantified tyrosine sites on GSTP1 and the ability of JWB198 to ligand Y8 with site specificity in live cells. All data shown are representative of n=2 biologically independent experiments.

Figure 33:
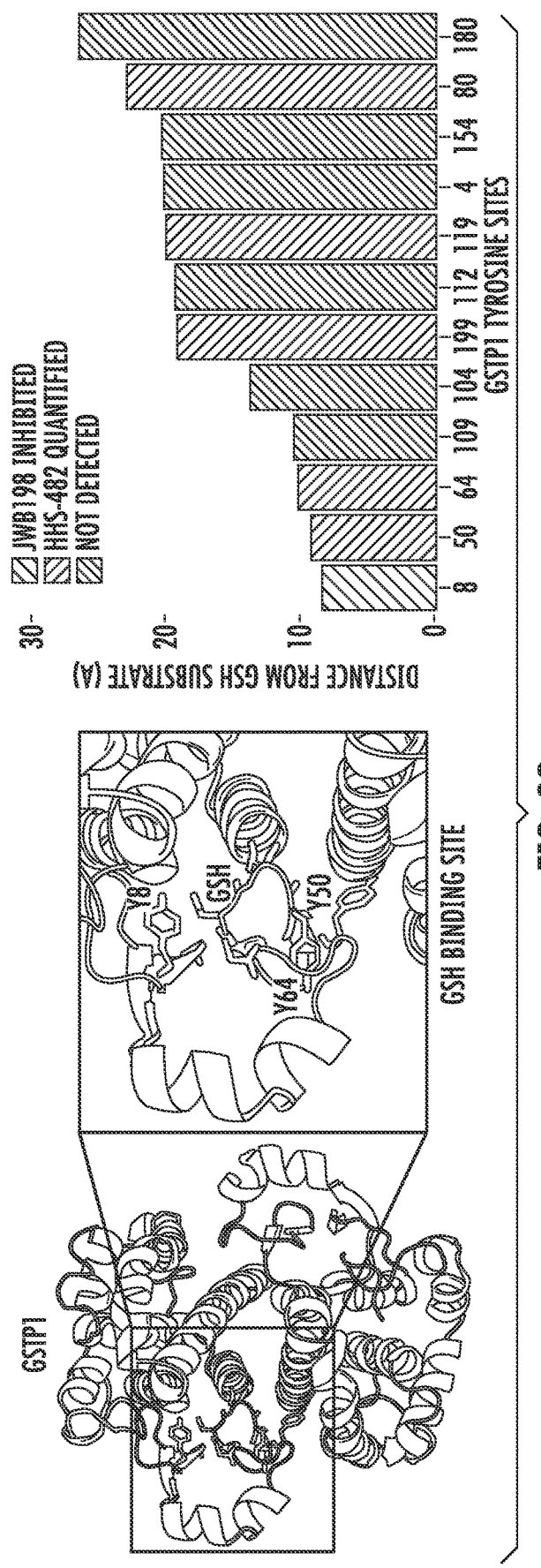

FIG. 33: Crystal structure (left) of GSTP1 with GSH ligand (PDB ID: 5GSS). Inset shows the GSH binding site and tyrosines in proximity to GSH that are liganded by JWB198, non-liganded but quantified by HHS-482 probe labeling, or not detected by chemical proteomics. Bar graph (right) shows tyrosine sites organized by their Euclidean distance from GSH substrate.

Figure 34:
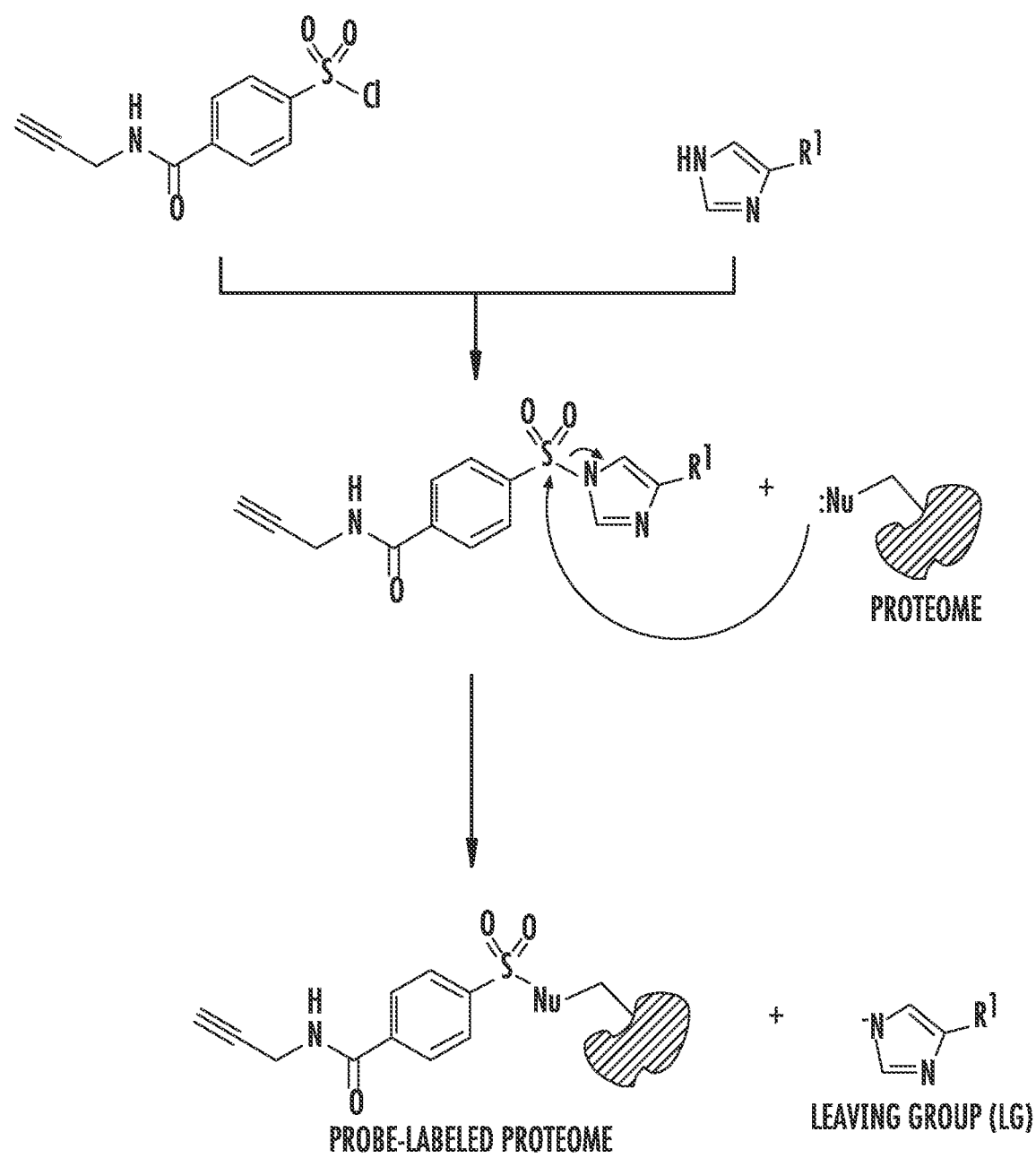

FIG. 34 is a schematic diagram showing probe synthesis and the mechanism of proteomic modification of an exemplary sulfonyl-imidazole probe.

Figure 35A:
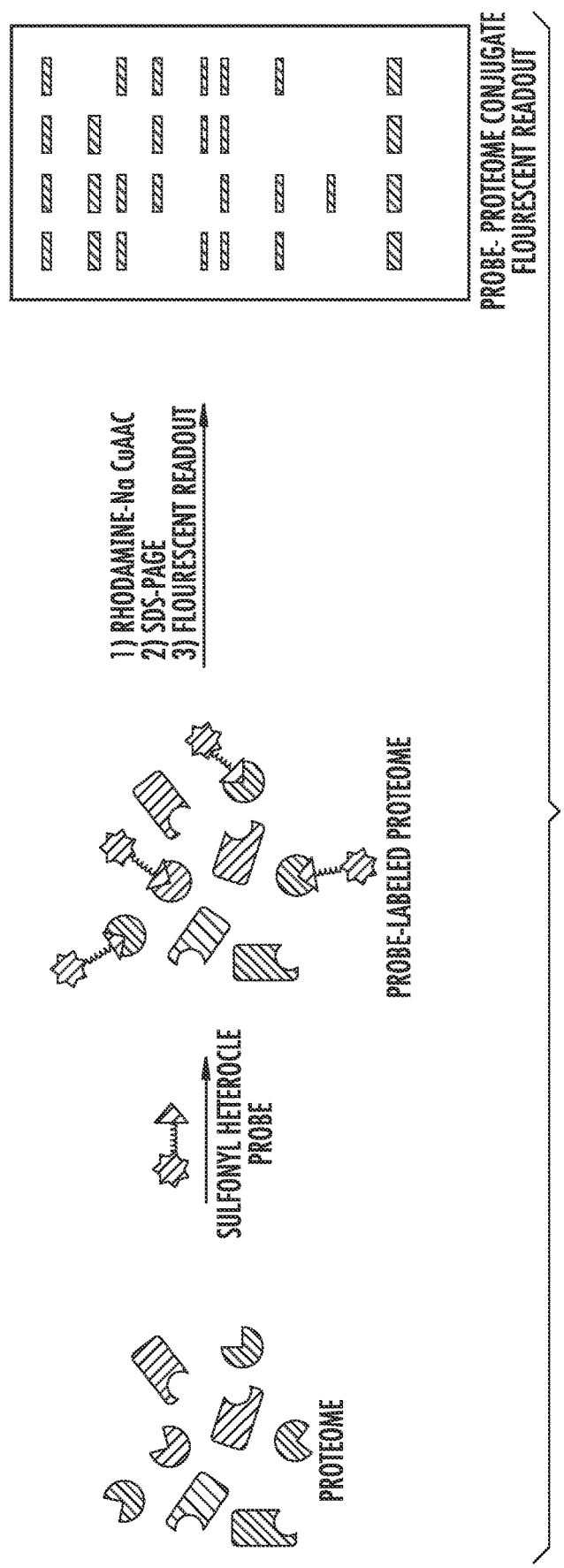
Figure 35B:
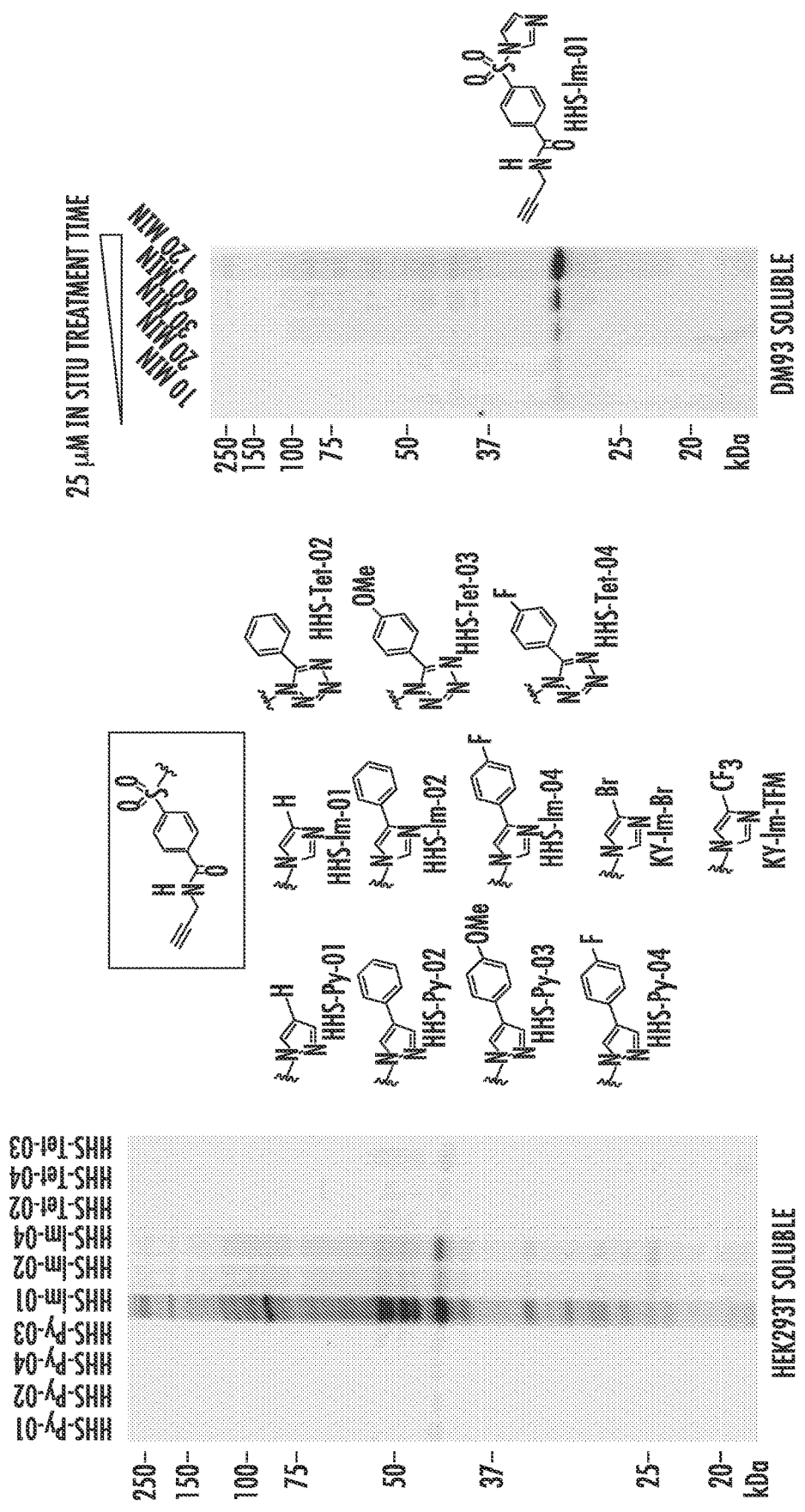

FIGS. 35A-35B: SDS-PAGE in gel chemical proteomic probe validation. FIG. 35A is a schematic diagram showing general workflow of activity-based probes in gel validation. FIG. 35B is (left) SDS-PAGE showing in vitro modified proteome by the sulfonyl-heterocycle probes (100 µM, 30 min, 37° C.); (middle) structures of exemplary probes; and (right) SDS-PAGE showing in situ (live cell) treated proteome by HHS-Im-01 probe at 25 µM concentration for an increasing time period of 10, 20, 30, 60, and 120 min.

Figure 36:
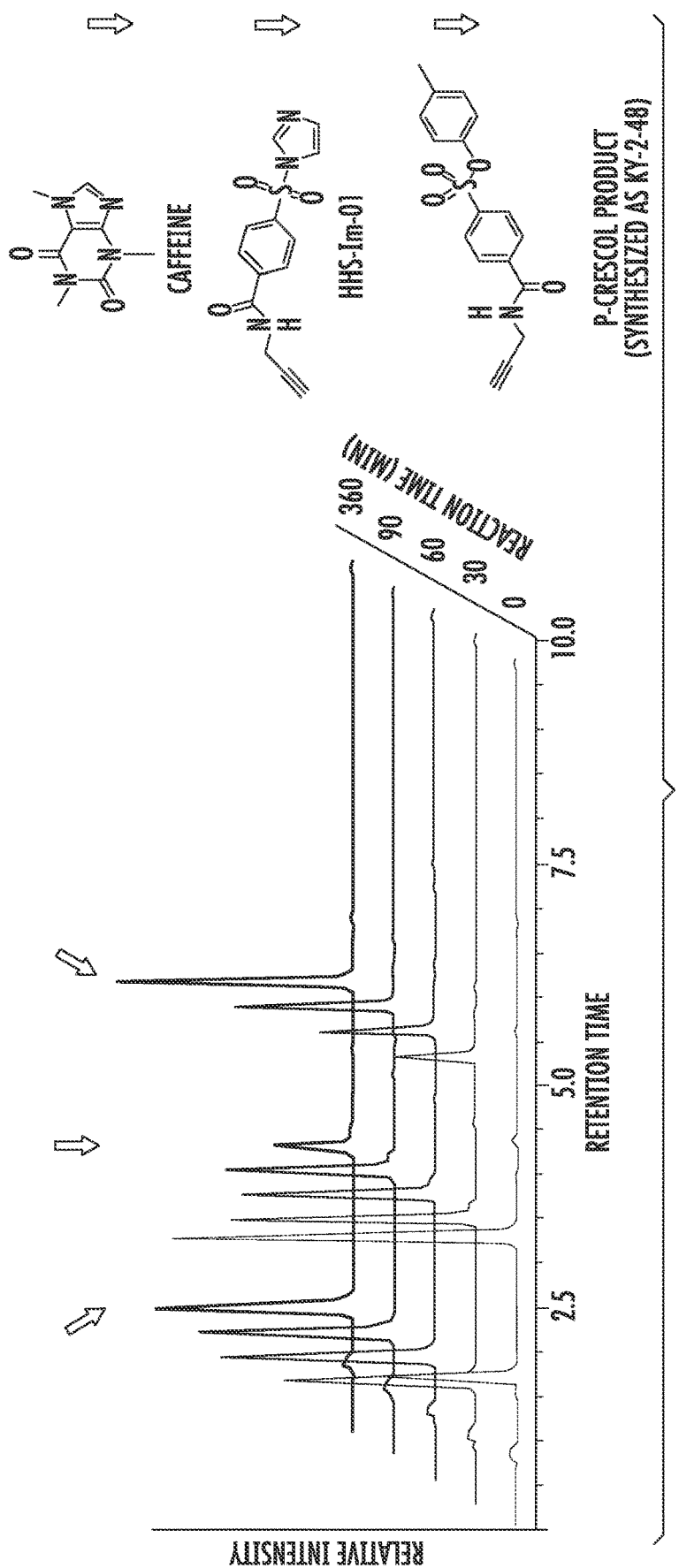

FIG. 36: HPLC reactivity assay of HHS-Im-01. The assay entails having the probe react with 1.1 eq. p-cresol (tyrosine mimetic) or 1.1 eq. n-butylamine (lysine mimetic) under basic conditions (1.1 eq. TMG). The reaction progress is monitored by quantifying the area under the curve ratio to caffeine standard (8.3 µM). The peaks from left to right correspond to the caffeine standard, the probe, and the product formed by reaction of the probe with p-cresol. The formation of product is verified by synthesizing the p-cresol product and the n-butylamine product. While the figure shows the assay results for exemplary probe HHS-Im-01, the assay was also performed on additional sulfonyl-heterocycle probes and the reactivity of various sulfonyl-heterocycle probes comprising phenyl substituted heterocycles are as follows: triazole>imidazole>tetrazole>pyrazole. Within the imidazole analogs, the solution reactivity increases as the phenyl-substituents are as follows: H<phenyl<4-fluorophenyl<bromo<trifluoromethyl.

Figure 37A:
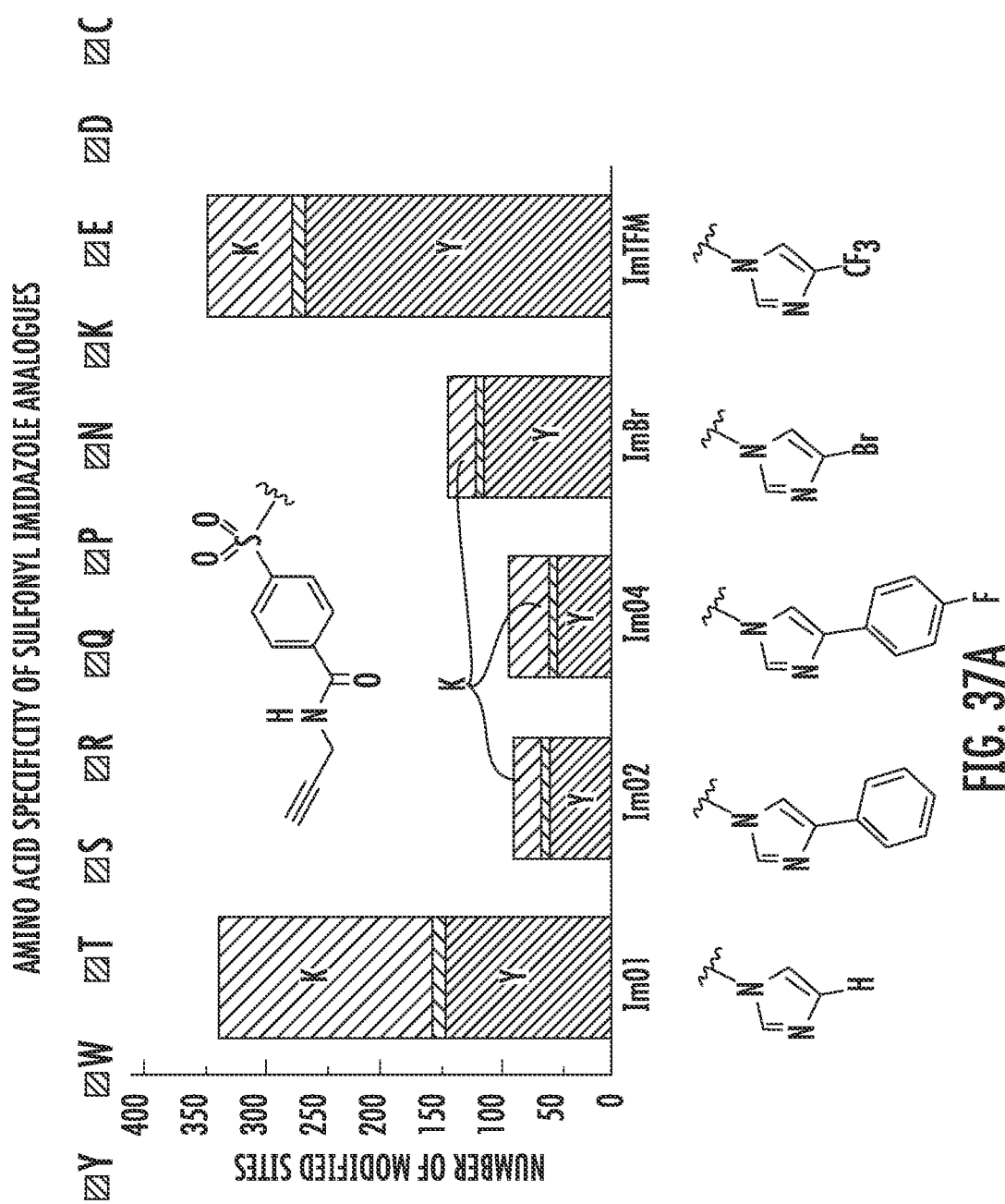
Figure 37B:
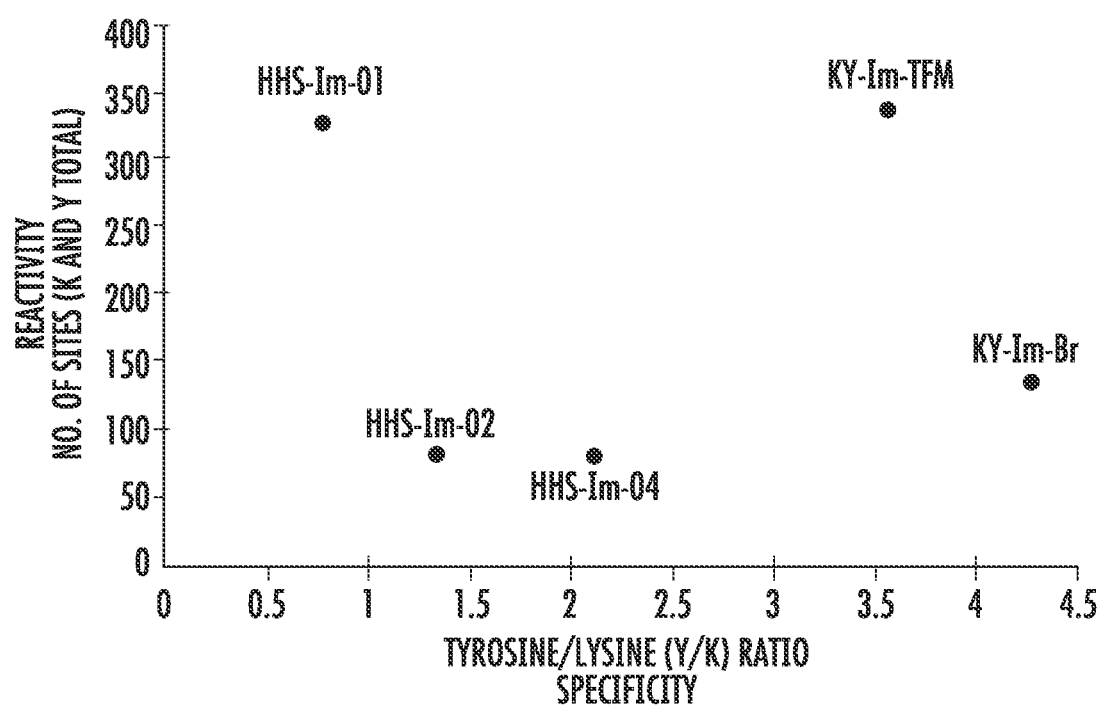
Figure 37C:
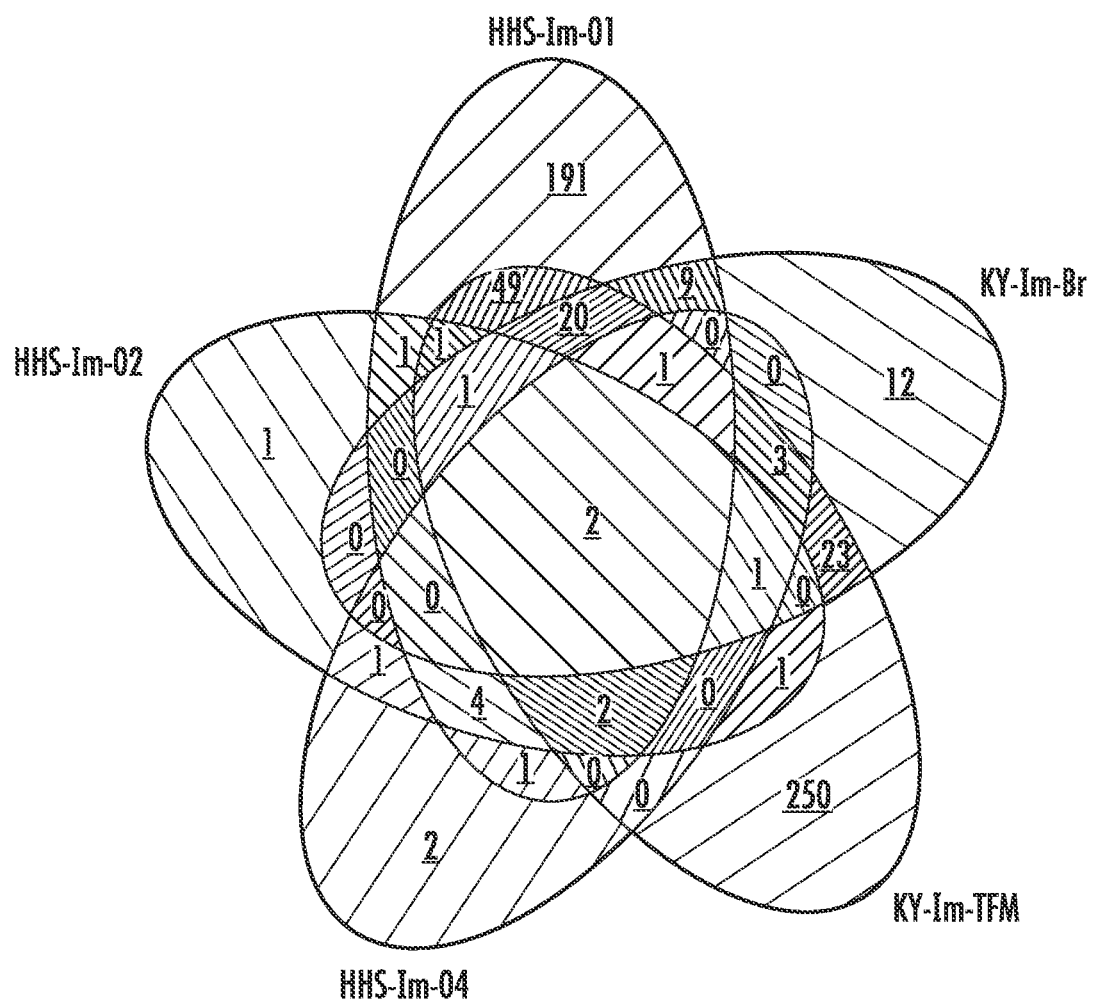

FIGS. 37A-37C: Proteome-wide structural activity and selectivity investigation of sulfonyl imidazole analogs. FIG. 37A shows an inclusive proteome-wide probe-modified peptide search of all sulfonyl imidazole analogs. Modified peptides are filtered with a data confidence control criteria of ≥300 Byonic score, ≥3 log probability and ≤5 ppm mass accuracy (amino acid residues modifications of Y, W, T, S, R, Q, P, N, K, E, D, and C have been processed). FIG. 37B is a graph showing sulfonyl imidazole analogs' overall reactivity and specificity towards lysine and tyrosine. FIG. 37C is a schematic diagram showing the protein binding site characterization of sulfonyl imidazole analogs and shows that individual sulfonyl imidazole probes generally modify unique sites.

Figure 38:
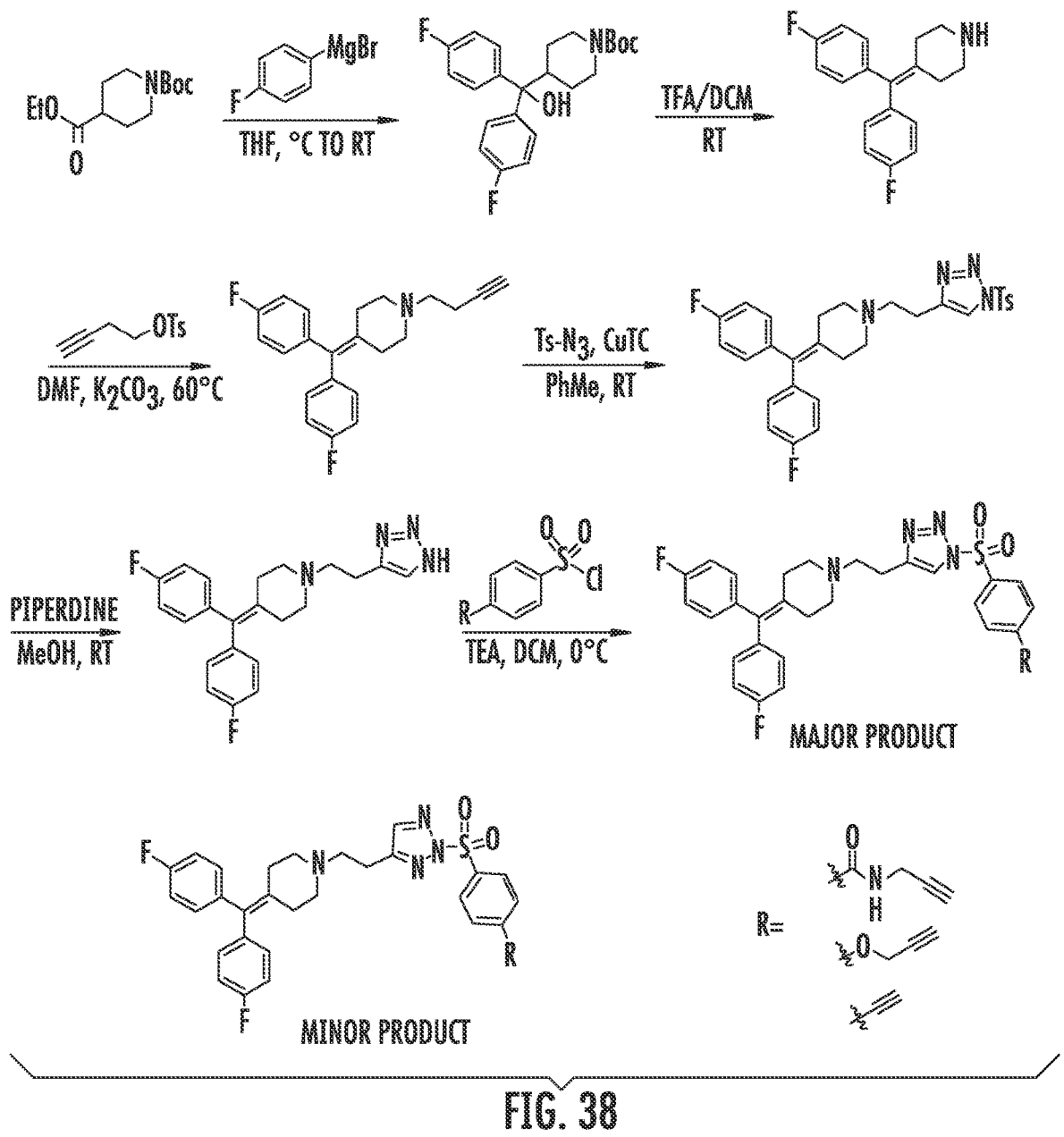

FIG. 38 is a schematic drawing showing a synthetic route to sulfonyl-triazole probes (referred to herein as "TH SuTEx probes") where the triazole is substituted with a 4-(bis(4-fluorophenyl)methylene)piperidine recognition moiety for human diacylglycerol kinase-alpha (DGKA).

Figure 39A:
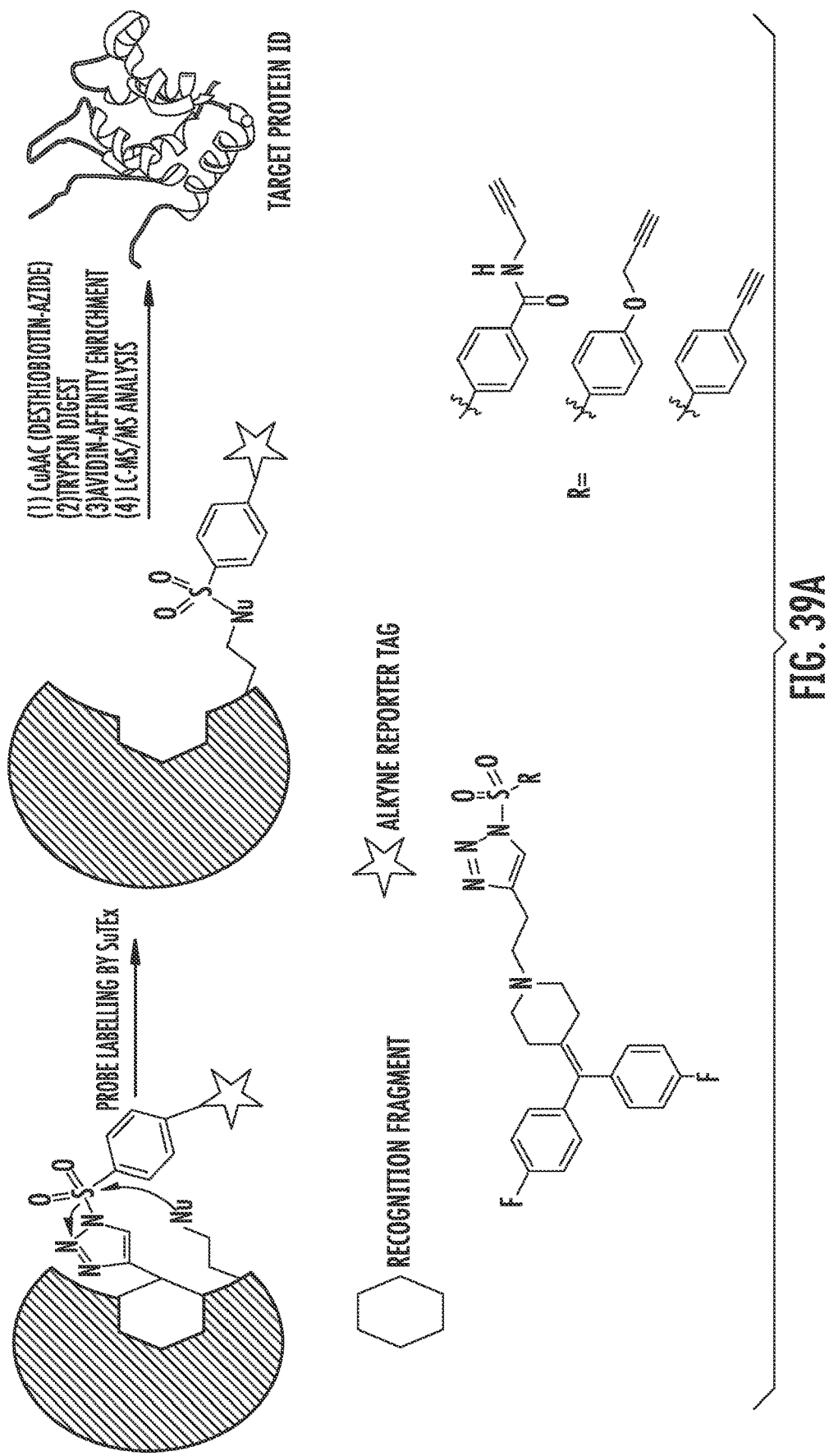
Figure 39D:
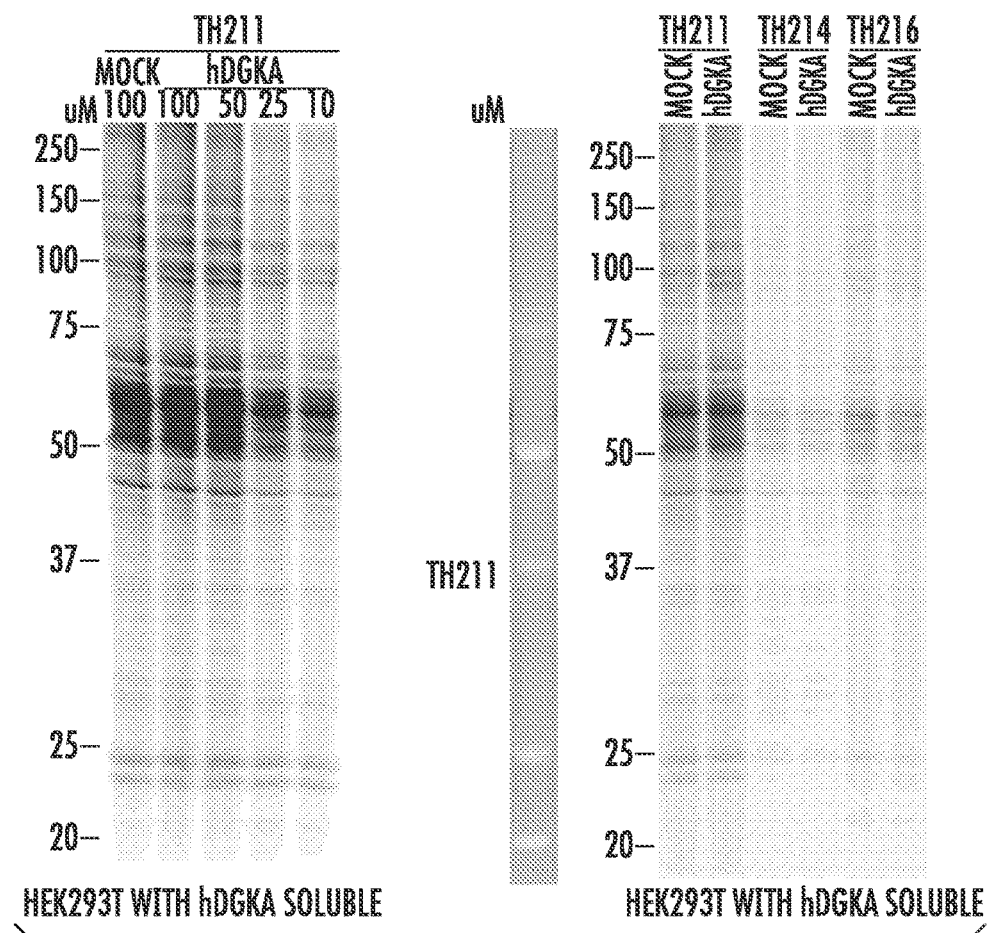
Figure 39E:
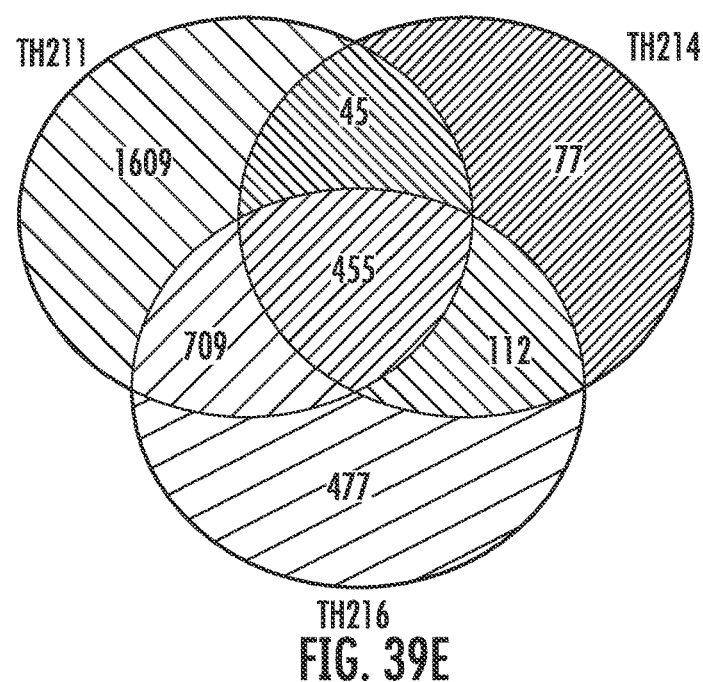

FIGS. 39A-39E: Biological activity of the TH SuTEx probes. FIG. 39A is a schematic drawing showing (top) the reaction mechanism of TH SuTEx probes with nucleophiles on proteins (tyrosine and lysine) and methods of identifying the binding sites; and (bottom) the core structures of exemplary TH SuTEx probes. FIG. 39B is a series of schematic diagrams showing probe-modified tyrosine binding sites detected using TH SuTEx probes (from top to bottom: TH211 (100 µM), TH214 (100 µM), TH216 (100 µM) and TH211 (5 µM)) on recombinant human diacylglycerol kinase-alpha (DGKA) from labeling studies performed on lysates. The site of binding (Y followed by amino acid position) are shown across the different domains of human DGKA. FIG. 39C is a schematic diagram showing the probe-modified tyrosine binding sites detected using TH SuTEx probes (TH211 50 µM) on native human DGKA from labeling studies performed on live Jurkat T cells. The site of binding (Y followed by amino acid position) are shown across the different domains of human DGKA. FIG. 39D is a series of images from gel-based probe labeling studies with TH SuTEx probes. The left panel depicts the ability of TH211 to fluorescently label recombinant human DGKA in a concentration dependent manner. DGKA has a molecular weight of ~80-90 kDa. Mock (lysates not overexpressing recombinant DGKA) is used to establish baseline labeling profiles of HEK293T cells, which were used for recombinant protein production. Right panel compares the ability of different TH probes (TH211, TH214, and TH216) to detect recombinant human DGKA in gel-based studies. FIG. 39E is a schematic diagram of the comparison of overlapping and unique binding sites modified by TH SuTEx probes from LC-MS quantitative chemical proteomic studies in recombinant DGKA-HEK293T lysates. These studies were performed to evaluate the reactivity of TH SuTEx probes as determined by the number of tyrosine and lysine sites modified in proteomes.

FIG. 40 shows in vitro potency of JWB179, JWB183, and JWB198 against recombinant GSTP1 lysates as evaluated by GSH substrate assay. Structural modifications to JWB198 (represented in the structures of JWB179 and JWB183) provide increased potency (i.e., lower $IC_{50}$). Data are shown as mean 1 s.e.m.

FIG. 41: GSH stability of SuTEx molecules. FIG. 41 (right panel) is a schematic drawing showing the chemistry of an HPLC reactivity assay performed to evaluate whether sulfonyl-triazoles (using exemplary SuTEx probe HHS-475) react with glutathione (GSH). FIG. 41 (left panel) is a graph showing the results of the HPLC assay. Briefly, HHS-475 reacts rapidly with p-cresol (a tyrosine side chain mimic) under basic conditions (TMG). HHS-475 exposed to 5×GSH under basic conditions showed negligible reaction. HHS-475 can react with another electrophile (cysteine-reactive compound) in the presence of GSH.

Figure 42A:
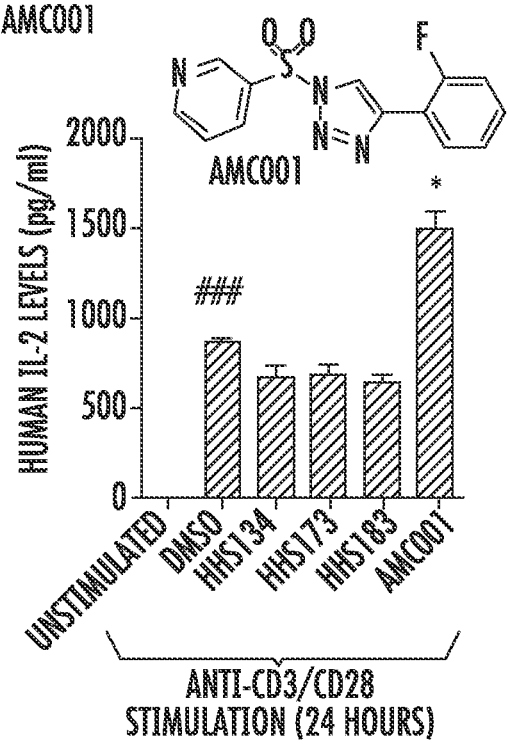
Figure 42B:
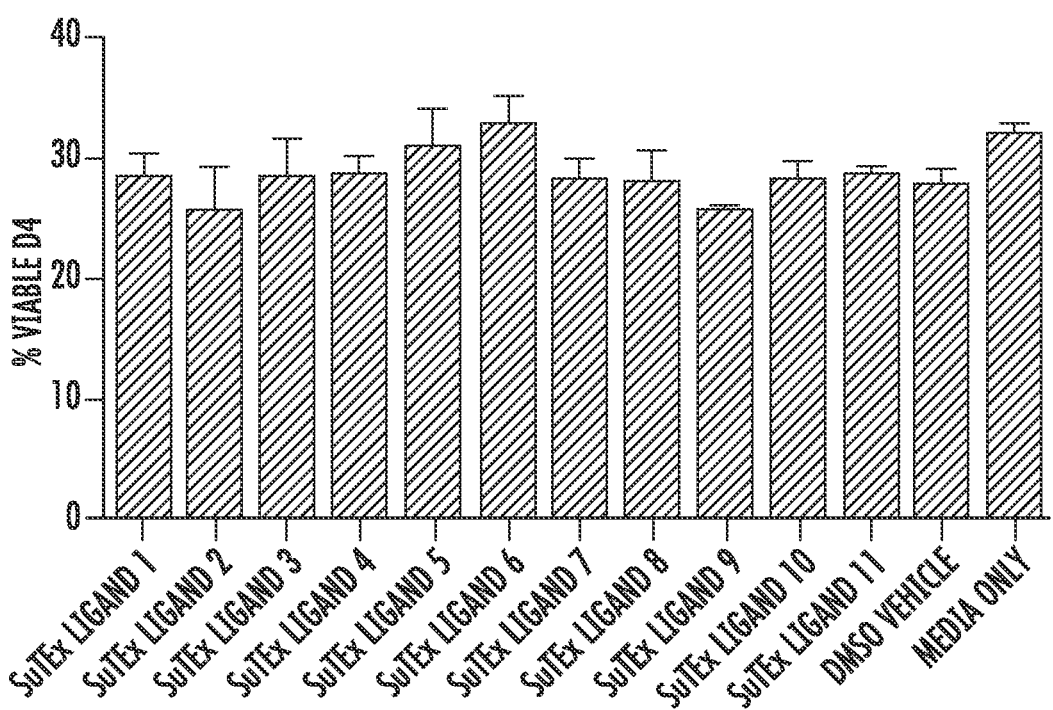

FIGS. 42A and 42B: PBMC Toxicity of SuTEx Fragments. FIG. 42A is a graph showing the ability of various SuTEx fragments to enhance T cell activation. FIG. 42B is a graph showing the toxicity of various SuTEx fragments (25 µM concentration) against human peripheral blood mononuclear cells (PBMCs) from de-identified healthy donors. For comparison, cell viability After isolation of PBMCs, cells were stimulated with anti-CD3 and anti-CD28 antibodies for 4 days in the presence of SuTEx ligands (25 µM final concentration), dimethylsulfoxide (DMSO) vehicle, or no treatment (media only).

Figure 43:
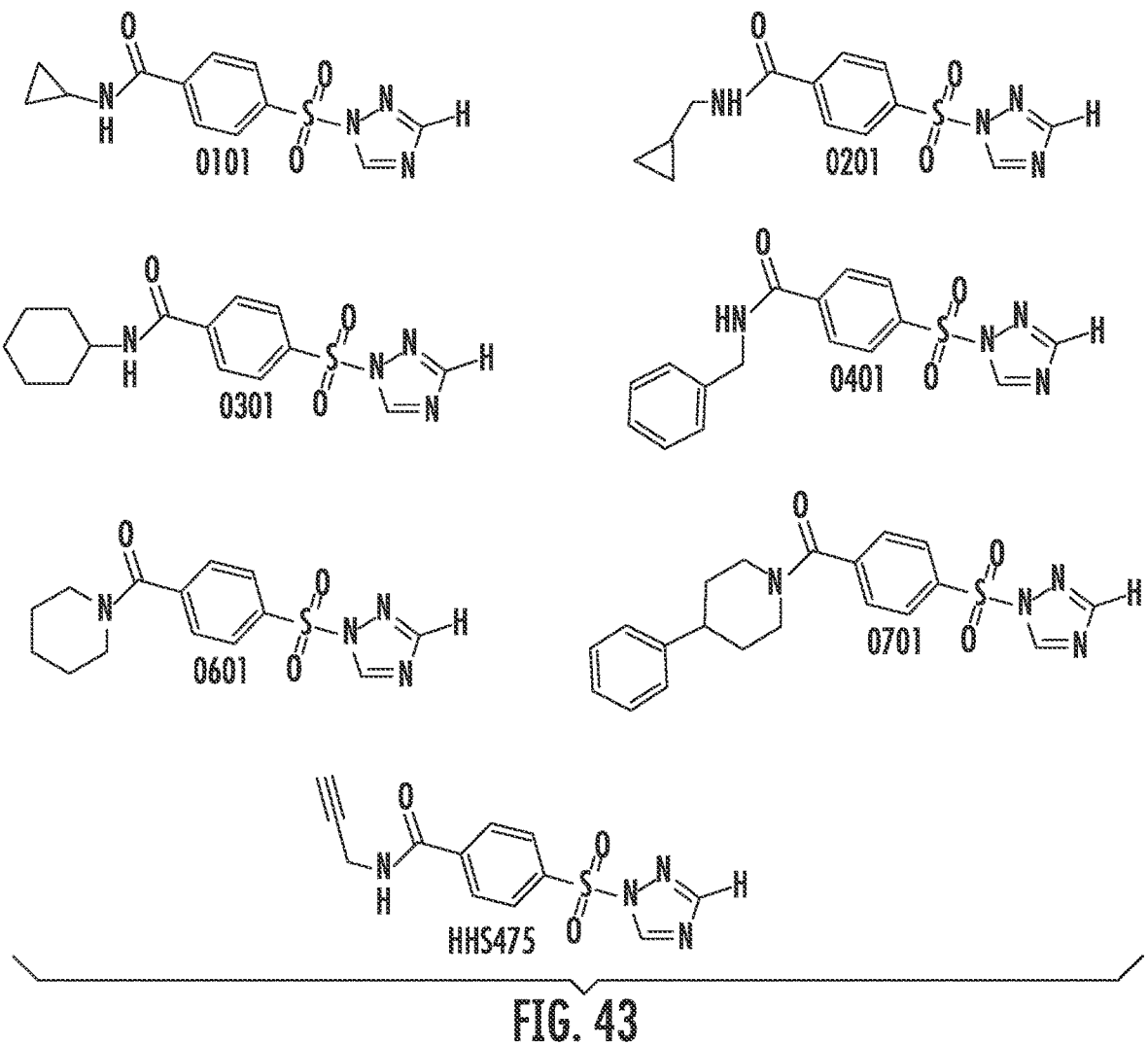

FIG. 43 is a schematic drawing showing additional "HHS" SuTEx ligands, i.e., HHS0101, HHS0201, HHS0301, HHS0401, HHS0601, and HHS0701. For comparison, a related SuTEx probe structure, i.e., HHS475 is also shown. Ligand structures in the figure are denoted only by number, without the initial HHS designation.

Figure 44A:
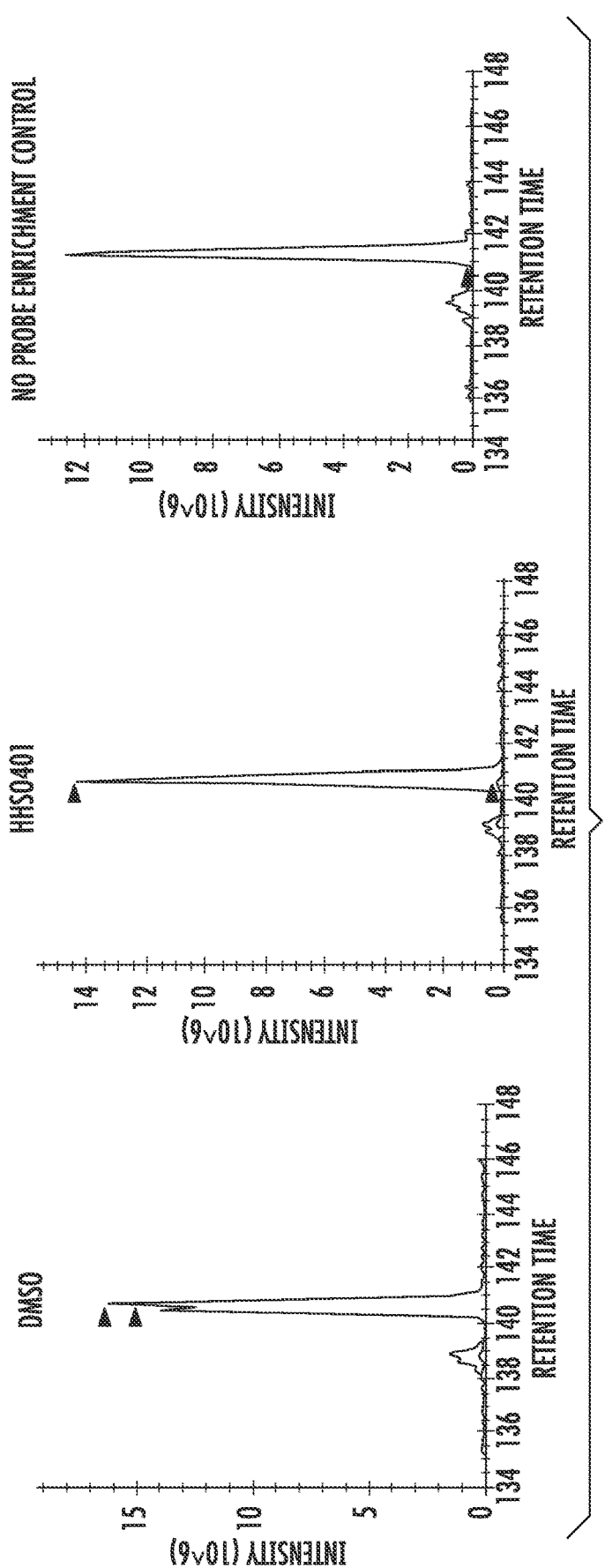
Figure 44B:
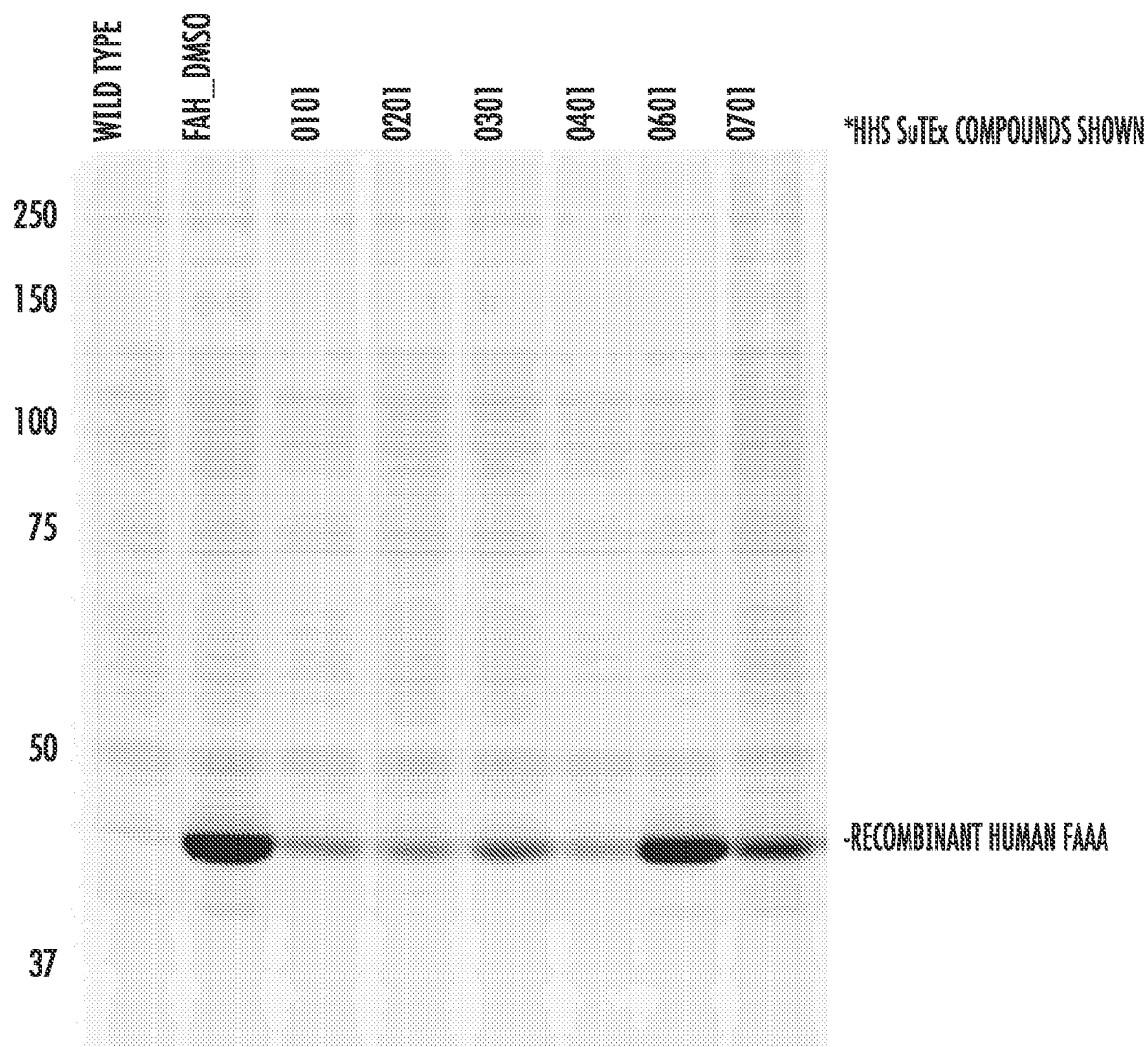
Figure 44C:
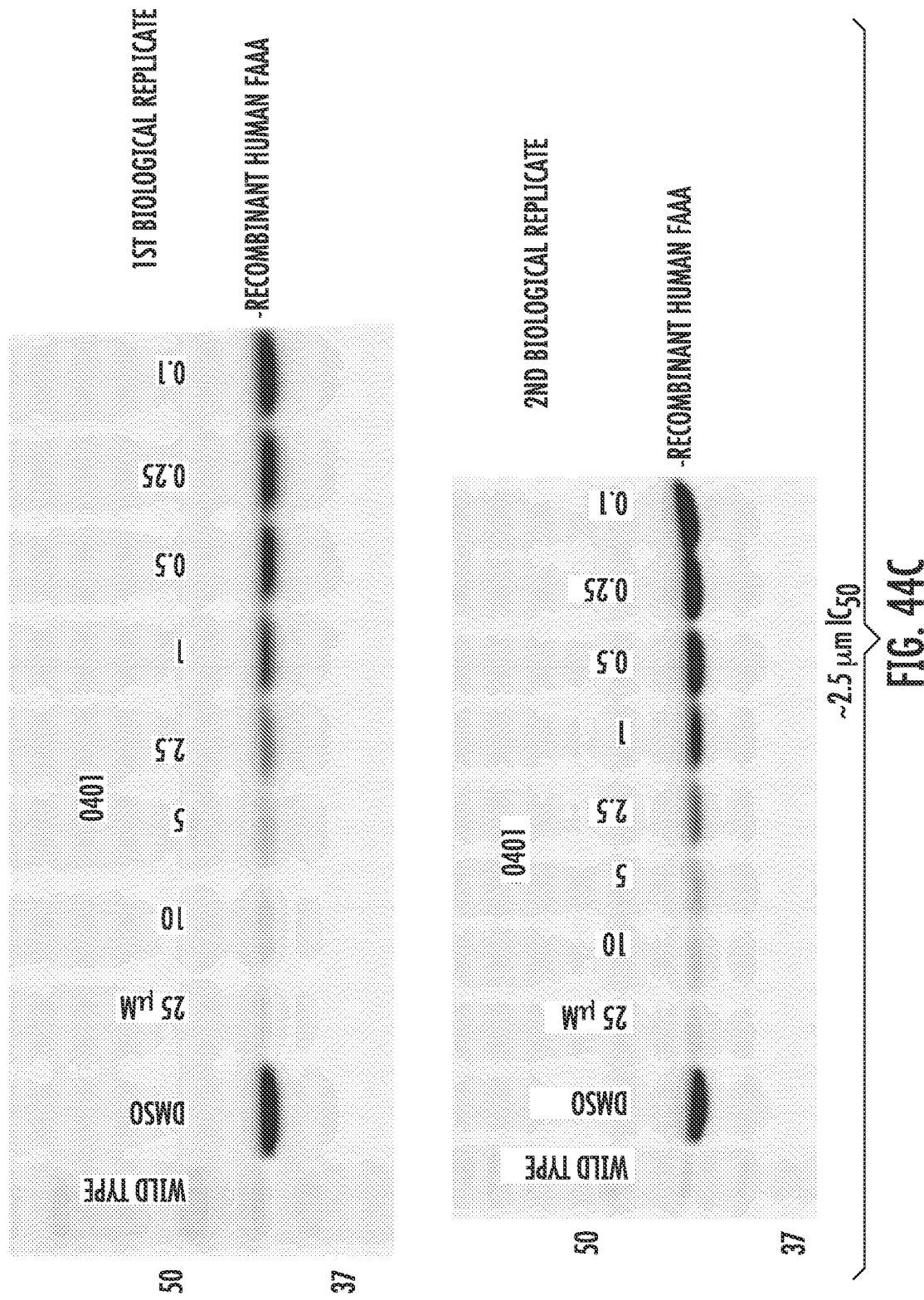

FIGS. 44A-44C. Modification of human fumarylacetoacetase (FAAA) with HHS SuTEx ligands. FIG. 44A is a series of graphs showing the chemical proteomics analysis of human FAAA using an HHS SuTEx ligand, HHS0401 (25 µM) shown in FIG. 43. HHS0401 modifies the tyrosine at residue 244. FIG. 44B is an image of a gel-based chemical proteomic screen for human FAAA fragment ligands. Recombinant hFAAA-HEK293T soluble proteomes pretreated with indicated fragment (25 μM, 120 min) followed by labeling with HHS-475 (100 μM, 120 min). FIG. 44C is a pair of images of the gel-based chemical proteomic analysis of the dose-dependent inhibition of FAAA by HHS0401.

Figure 45A:
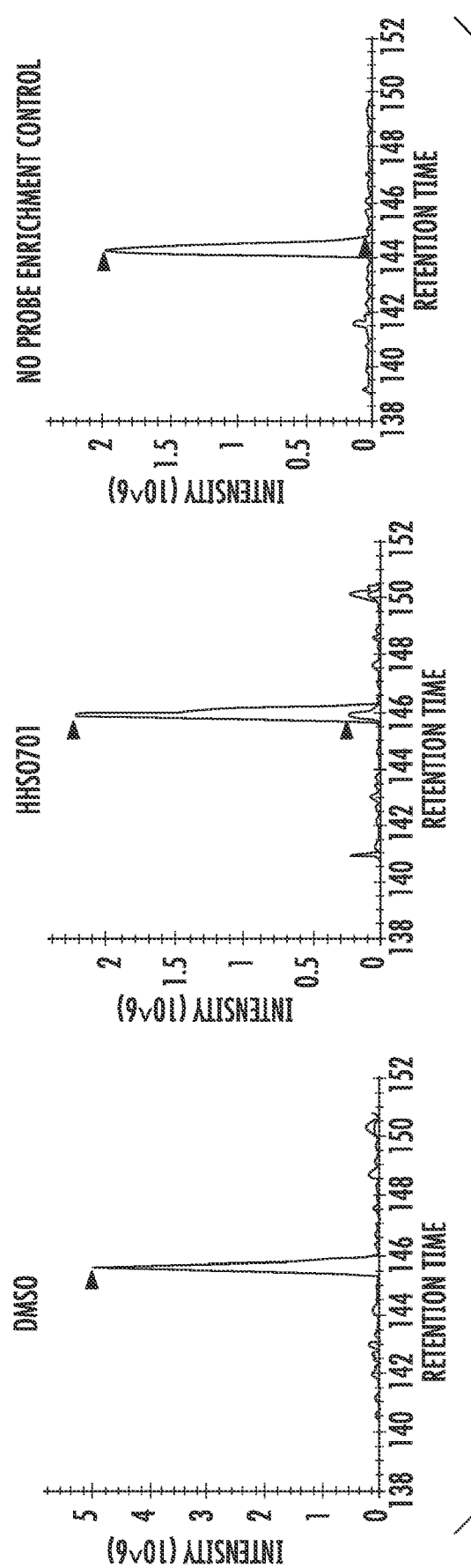
Figure 45B:
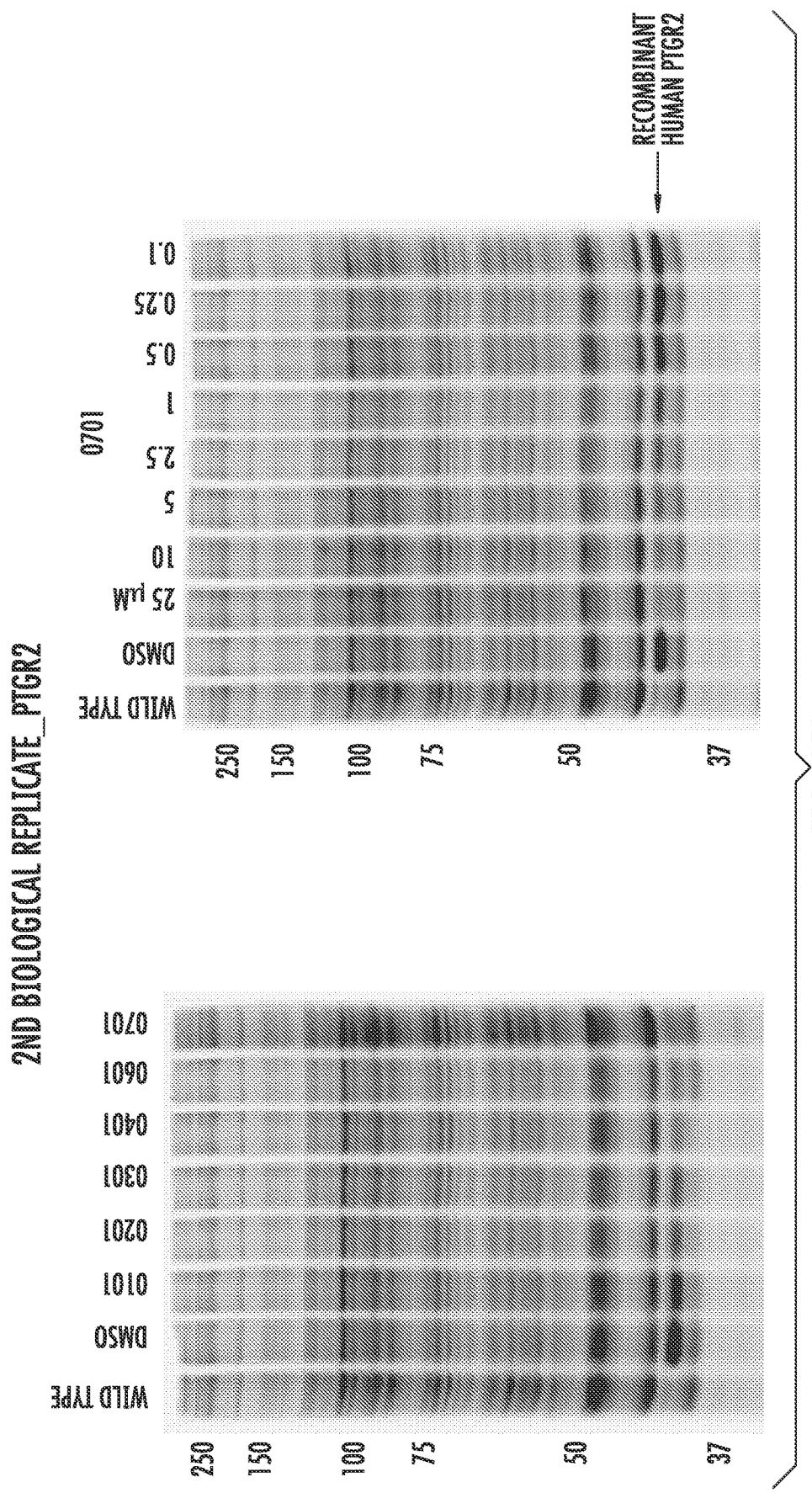

FIGS. 45A and 45B: Modification of human prostaglandin reductase 2 (PTGR2) with HHS SuTEx ligands. FIG. 45A is a series of graphs showing the chemical proteomics analysis of human PTGR2 using HHS0701 (25 μM) shown in FIG. 43. HHS0701 modifies the tyrosine at residue 100. FIG. 45B is a pair of images of gel-based chemical proteomic screens for human PTGR2 fragment ligands (left) and the dose-dependent inhibition of PTGR2 by HHS0701 (right).

FIGS. 46A and 46B: Inhibition of mRNA decapping protein 3 (EDC3) Y475 by EKT-231. FIG. 46A is a schematic drawing of the chemical structure of EKT-231. FIG. 46B is a series of graphs showing the chemical proteomics analysis of EDC3 using EKT-231 and HHS-465.

Figure 47A:
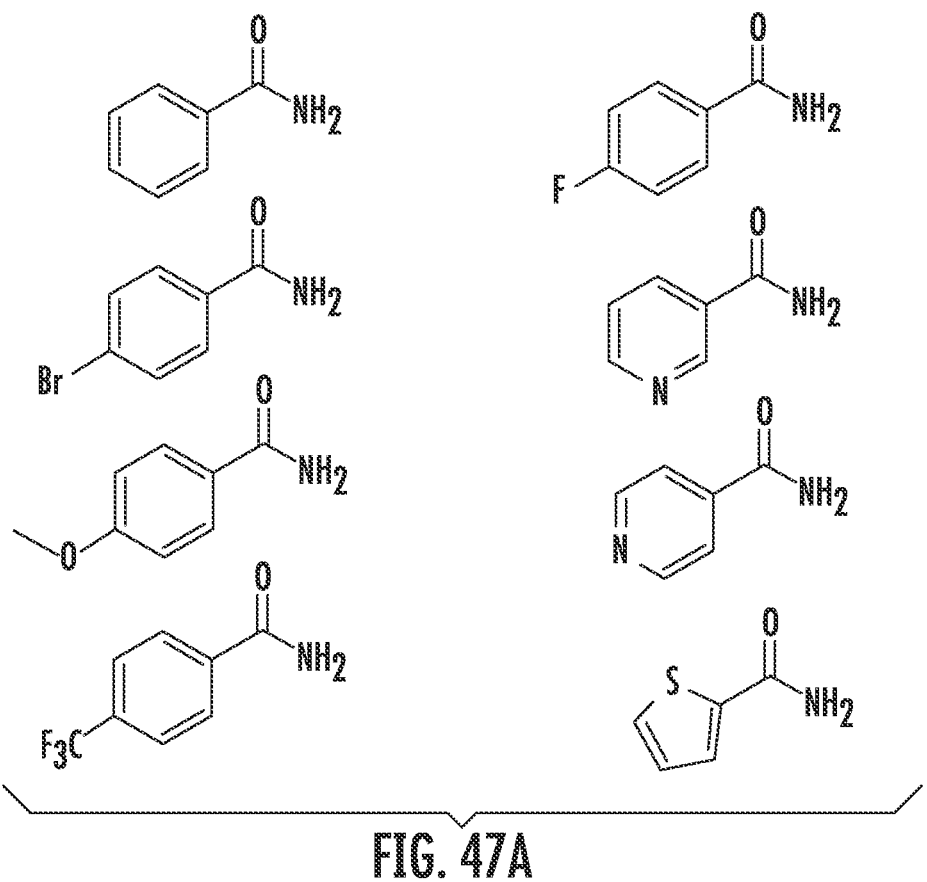
Figure 47B:
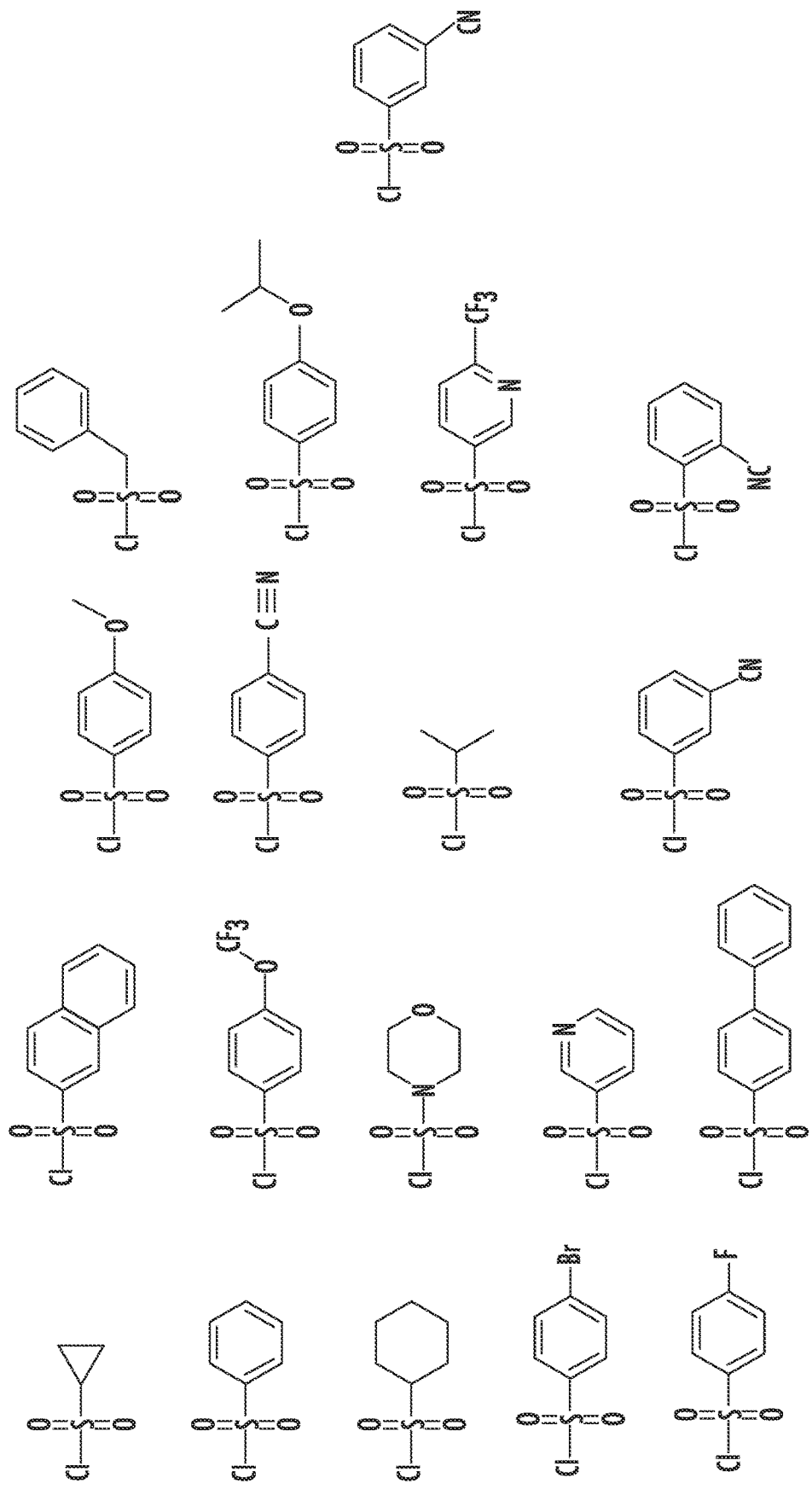

FIGS. 47A and 47B: Exemplary starting materials for the synthesis of 1,2,4-triazole SuTEx compounds. FIG. 47A is a schematic drawing showing the structures of exemplary aryl amide compounds that can be used in the synthesis of 1,2,4-triazole-containing SuTEx compounds. FIG. 47B is a schematic drawing showing the structures of exemplary sulfonyl chlorides that can be used in the synthesis of 1,2,4-trizaole-containing SuTEx compounds.

Figure 48A:
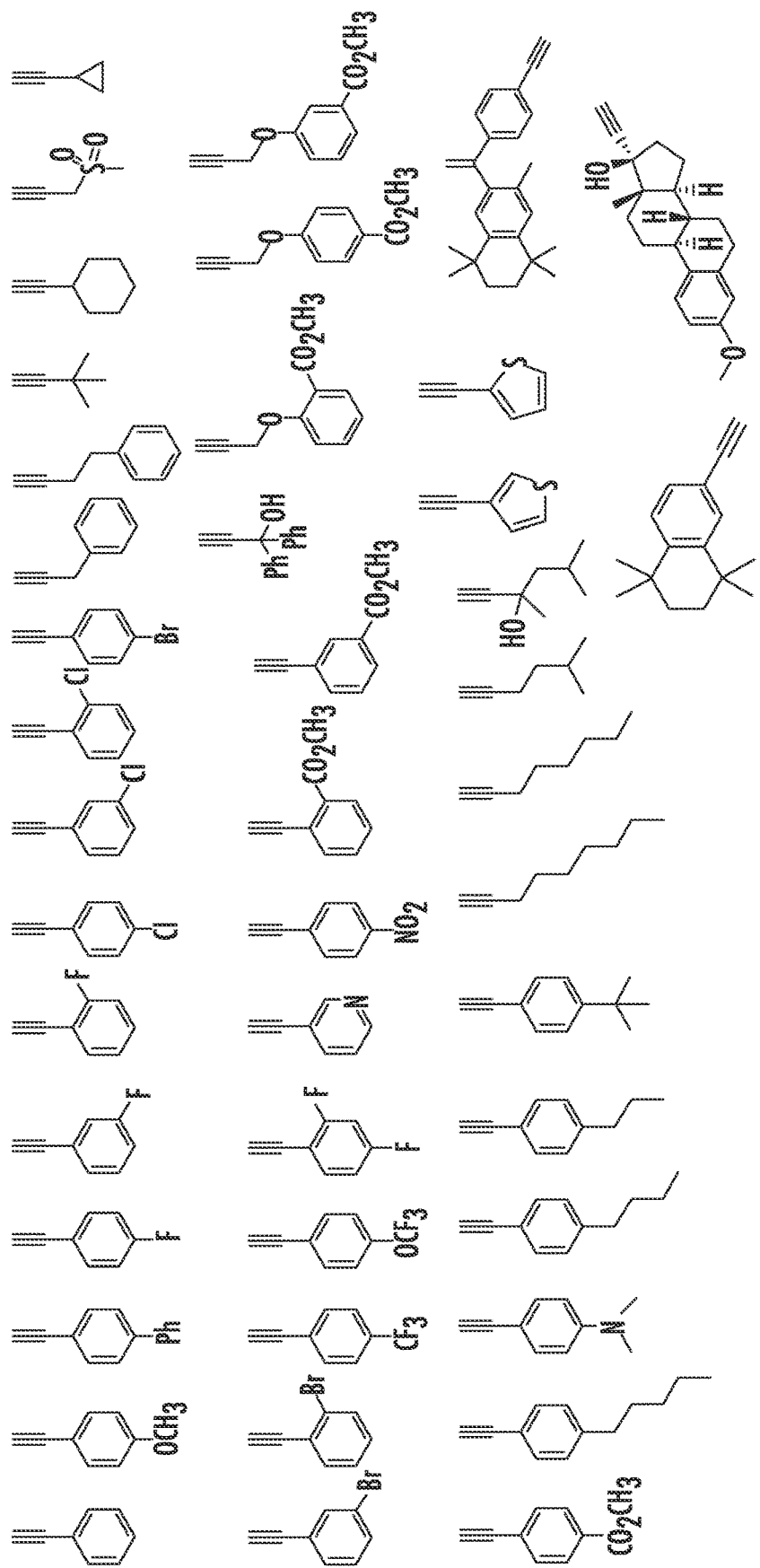
Figure 48B:
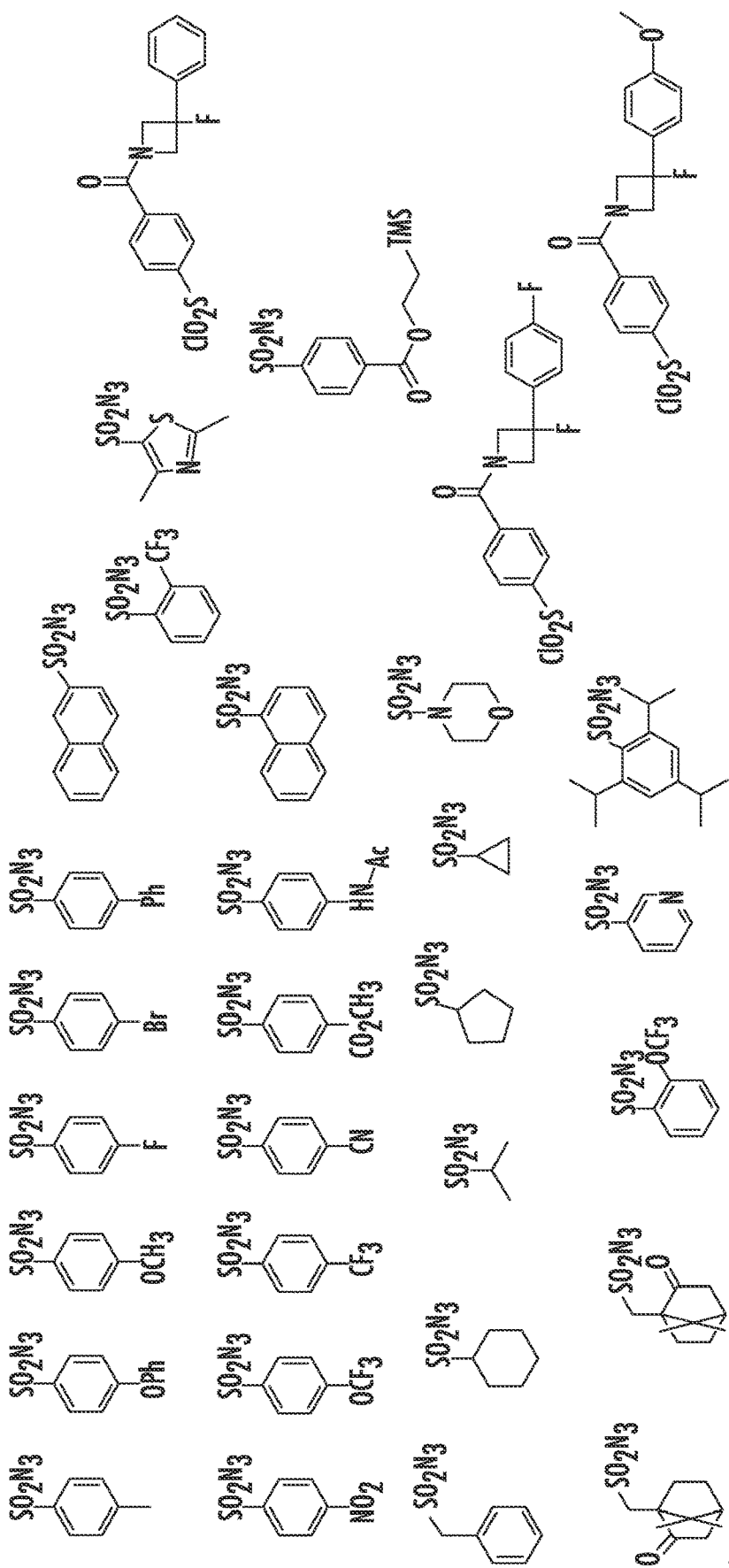

FIGS. 48A and 48B: Exemplary starting materials for the synthesis of 1,2,3-triazole SuTEx compounds. FIG. 48A is a schematic drawing showing the structures of exemplary alkynes that can be used in the synthesis of 1,2,3-triazole-containing SuTEx compounds. FIG. 48B is a schematic drawing showing the structures of exemplary sulfonyl azides that can be used in the synthesis of 1,2,3-triazole-containing SuTEx compounds.

DETAILED DESCRIPTION

The presently disclosed subject matter provides sulfur-heterocycle exchange chemistry for use in investigating tyrosine and/or lysine reactivity, function and post-translational modification state in proteomes and live cells. For instance, according to one aspect of the presently disclosed subject matter, sulfur-triazole exchange chemistry (dubbed SuTEx) is provided for development of phenol-reactive probes that can be tuned for tyrosine chemoselectivity in proteomes (>10,000 distinct sites in ~3,700 proteins) through modifications to the triazole LG. These probes can be used to identify a subset of tyrosines with enhanced reactivity that are localized to functional protein domains and to apply SuTEx for global phosphotyrosine profiling of pervanadate-activated cells. The findings described herein illustrate the broad potential for deploying SuTEx and related sulfur-heterocycle compounds to globally investigate tyrosine and/or lysine reactivity, function, and post-translational modification state in proteomes and live cells.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the presently disclosed and claimed subject matter.

Following long-standing patent law convention, the terms "a", "an", and "the" refer to "one or more" when used in this application, including in the claims. For example, the phrase "an antibody" refers to one or more antibodies, including a plurality of the same antibody. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

A disease or disorder is "alleviated" if the severity of a symptom of the disease, condition, or disorder, or the frequency at which such a symptom is experienced by a subject, or both, are reduced.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

The terms "additional therapeutically active compound" and "additional therapeutic agent", as used in the context of the presently disclosed subject matter, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease, or disorder being treated.

As used herein, the term "adjuvant" refers to a substance that elicits an enhanced immune response when used in combination with a specific antigen.

As use herein, the terms "administration of" and/or "administering" a compound should be understood to refer to providing a compound of the presently disclosed subject matter to a subject in need of treatment.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition, and are encompassed within the nature of the phrase "consisting essentially of".

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

With respect to the terms "comprising", "consisting of", and "consisting essentially of", where one of these three terms is used herein, the presently disclosed and claimed subject matter can include the use of either of the other two terms. For example, a composition that in some embodiments comprises a given active agent also in some embodiments can consist essentially of that same active agent, and indeed can in some embodiments consist of that same active agent.

The term "aqueous solution" as used herein can include other ingredients commonly used, such as sodium bicarbonate described herein, and further includes any acid or base solution used to adjust the pH of the aqueous solution while solubilizing a peptide.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner", as used herein, refers to a molecule capable of binding to another molecule.

The term "biocompatible", as used herein, refers to a material that does not elicit a substantial detrimental response in the host.

As used herein, the terms "biologically active fragment" and "bioactive fragment" of a peptide encompass natural and synthetic portions of a longer peptide or protein that are capable of specific binding to their natural ligand and/or of performing a desired function of a protein, for example, a fragment of a protein of larger peptide which still contains the epitope of interest and is immunogenic.

The term "biological sample", as used herein, refers to samples obtained from a subject, including but not limited to skin, hair, tissue, blood, plasma, cells, sweat, and urine.

A "coding region" of a gene comprises the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids (e.g., two DNA molecules). When a nucleotide position in both of the molecules is occupied by nucleotides normally capable of base pairing with each other at a given position, the nucleic acids are considered to be complementary to each other at this position. Thus, two nucleic acids are complementary to each other when a substantial number (in some embodiments at least 50%) of corresponding positions in each of the molecules are occupied by nucleotides that can base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. By way of example and not limitation, the first region comprises a first portion and the second region comprises a second portion, whereby, when the first and second portions are arranged in an antiparallel fashion, in some embodiments at least about 50%, in some embodiments at least about 75%, in some embodiments at least about 90%, and in some embodiments at least about 95% of the nucleotide residues of the first portion are capable of base pairing with nucleotide residues in the second portion. In some embodiments, all nucleotide residues of the first portion are capable of base pairing with nucleotide residues in the second portion.

A "compound", as used herein, refers to a polypeptide, an isolated nucleic acid, or other agent used in the method of the presently disclosed subject matter.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a condition, disease, or disorder for which the test is being performed.

A "test" cell is a cell being examined.

A "pathogenic" cell is a cell that, when present in a tissue, causes or contributes to a condition, disease, or disorder in the animal in which the tissue is located (or from which the tissue was obtained).

A tissue "normally comprises" a cell if one or more of the cell are present in the tissue in an animal not afflicted with a condition, disease, or disorder.

As used herein, the terms "condition", "disease condition", "disease", "disease state", and "disorder" refer to physiological states in which diseased cells or cells of interest can be targeted with the compositions of the presently disclosed subject matter. In some embodiments, a disease is leukemia, which in some embodiments is Acute Myeloid Leukemia (AML).

As used herein, the term "diagnosis" refers to detecting a risk or propensity to a condition, disease, or disorder. In any method of diagnosis exist false positives and false negatives. Any one method of diagnosis does not provide 100% accuracy.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" refers to an amount of a compound or composition sufficient to produce a selected effect, such as but not limited to alleviating symptoms of a condition, disease, or disorder. In the context of administering compounds in the form of a combination, such as multiple compounds, the amount of each compound, when administered in combination with one or more other compounds, may be different from when that compound is administered alone. Thus, an effective amount of a combination of compounds refers collectively to the combination as a whole, although the actual amounts of each compound may vary. The term "more effective" means that the selected effect occurs to a greater extent by one treatment relative to the second treatment to which it is being compared.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA, and mRNA) or a defined sequence of amino acids and the biological properties resulting therefrom. Thus, a gene encodes a protein if transcription and translation of an mRNA corresponding to or derived from that gene produces the protein in a cell or other biological system and/or an in vitro or ex vivo system. Both the coding strand, the nucleotide sequence of which is identical to the mRNA sequence (with the exception of uracil bases presented in the latter) and is usually provided in Sequence Listing, and the non-coding strand, used as the template for transcription of a gene or cDNA, can be referred to as encoding the protein or other product of that gene or cDNA.

As used herein, an "essentially pure" preparation of a particular protein or peptide is a preparation wherein in some embodiments at least about 95% and in some embodiments at least about 99%, by weight, of the protein or peptide in the preparation is the particular protein or peptide.

In some embodiments, the terms "fragment", "segment", or "subsequence" as used herein refers to a portion of an amino acid sequence, comprising at least one amino acid, or a portion of a nucleic acid sequence comprising at least one nucleotide. Thus, in some embodiments, the terms "fragment", "segment", and "subsequence" are used interchangeably herein. In some embodiments, the term "fragment" refers to a compound (e.g., a small molecule compound) that can react with a reactive amino acid residue (e.g., a reactive tyrosine or a reactive lysine) to form an adduct comprising a modified amino acid residue. Thus, in some embodiments, the terms "fragment" and "ligand" are used interchangeably. In some embodiments, the term "fragment" refers to that portion of a ligand that remains covalently attached to the reactive amino acid residue.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, a "functional" biological molecule is a biological molecule in a form in which it exhibits a property by which it can be characterized. A functional enzyme, for example, is one that exhibits the characteristic catalytic activity by which the enzyme can be characterized.

As used herein "injecting", "applying", and administering" include administration of a compound of the presently disclosed subject matter by any number of routes and modes including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, vaginal, and rectal approaches.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, such as but not limited to through ionic or hydrogen bonds or van der Waals interactions.

The terms "measuring the level of expression" and "determining the level of expression" as used herein refer to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "pharmaceutical composition" refers to a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

"Pharmaceutically acceptable" means physiologically tolerable, for either human or veterinary application. Similarly, "pharmaceutical compositions" include formulations for human and veterinary use.

As used herein, the term "pharmaceutically acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" refers to non-naturally occurring peptides or polypeptides. Synthetic peptides or polypeptides can be synthesized, for example, using an automated polypeptide synthesizer. Various solid phase peptide synthesis methods are known to those of skill in the art.

As used herein, the term "mass spectrometry" (MS) refers to a technique for the identification and/or quantitation of molecules in a sample. MS includes ionizing the molecules in a sample, forming charged molecules; separating the charged molecules according to their mass-to-charge ratio; and detecting the charged molecules. MS allows for both the qualitative and quantitative detection of molecules in a sample. The molecules can be ionized and detected by any suitable means known to one of skill in the art. Some examples of mass spectrometry are "tandem mass spectrometry" or "MS/MS," which are the techniques wherein multiple rounds of mass spectrometry occur, either simultaneously using more than one mass analyzer or sequentially using a single mass analyzer. The term "mass spectrometry" can refer to the application of mass spectrometry to protein analysis. In some embodiments, electrospray ionization (ESI) and matrix-assisted laser desorption/ionization (MALDI) can be used in this context. In some embodiments, intact protein molecules can be ionized by the above techniques, and then introduced to a mass analyzer. Alternatively, protein molecules can be broken down into smaller peptides, for example, by enzymatic digestion by a protease, such as trypsin. Subsequently, the peptides are introduced into the mass spectrometer and identified by peptide mass fingerprinting or tandem mass spectrometry.

As used herein, the term "mass spectrometer" is used to refer an apparatus for performing mass spectrometry that includes a component for ionizing molecules and detecting charged molecules. Various types of mass spectrometers can be employed in the methods of the presently disclosed subject matter. For example, whole protein mass spectroscopy analysis can be conducted using time-of-flight (TOF) or Fourier transform ion cyclotron resonance (FT-ICR) instruments. For peptide mass analysis, MALDI time-of-flight instruments can be employed, as they permit the acquisition of peptide mass fingerprints (PMFs) at high pace. Multiple stage quadrupole-time-of-flight and the quadrupole ion trap instruments can also be used.

The terms "high throughput protein identification," "proteomics" and other related terms are used herein to refer to the processes of identification of a large number or (in some cases, all) proteins in a certain protein complement. Post-translational protein modifications and quantitative information can also be assessed by such methods. One example of "high throughput protein identification" is a gel-based process that includes the pre-fractionation and purification of proteins by one-dimensional protein gel electrophoresis. The gel can then be fractionated into several molecular weight fractions to reduce sample complexity, and proteins can be in-gel digested with trypsin. The tryptic peptides are extracted from the gel, further fractionated by liquid chromatography and analyzed by mass spectrometry. In another approach, a sample can be fractionated without using the gels, for example, by protein extraction followed by liquid chromatography. The proteins can then be digested in-solution, and the proteolytic fragments further fractionated by liquid chromatography and analyzed by mass spectrometry.

As used herein, the term "Western blot," which can be also referred to as "immunoblot", and related terms refer to an analytical technique used to detect specific proteins in a sample. The technique uses gel electrophoresis to separate the proteins, which are then transferred from the gel to a membrane (typically nitrocellulose or PVDF) and stained, in membrane, with antibodies specific to the target protein.

The expression "stable isotope labeling by amino acids in cell culture" (SILAC) is used herein to refer to an approach for incorporation of a label into proteins for mass spectrometry (MS)-based quantitative proteomics. SILAC comprises metabolic incorporation of a given "light" or "heavy" form of the amino acid into the proteins. For example, SILAC comprises the incorporation of amino acids with substituted stable isotopic nuclei (e.g. deuterium, $^{13}C$, $^{15}N$). In an illustrative SILAC experiment, two cell populations are grown in culture media that are identical, except that one of them contains a "light" and the other a "heavy" form of a particular amino acid (for example, $^{12}C$ and $^{13}C$ labeled L-lysine, respectively). When the labeled analog of an amino acid is supplied to cells in culture instead of the natural amino acid, it is incorporated into all newly synthesized proteins. After a number of cell divisions, each instance of the amino acid is replaced by its isotope-labeled analog. Since there is little chemical difference between the labeled amino acid and the natural amino acid isotopes, the cells behave substantially similar to the control cell population grown in the presence of a normal amino acid.

The term "prevent", as used herein, means to stop something from happening, or taking advance measures against something possible or probable from happening. In the context of medicine, "prevention" generally refers to action taken to decrease the chance of getting a disease or condition. It is noted that "prevention" need not be absolute, and thus can occur as a matter of degree.

A "preventive" or "prophylactic" treatment is a treatment administered to a subject who does not exhibit signs, or exhibits only early signs, of a condition, disease, or disorder. A prophylactic or preventative treatment is administered for the purpose of decreasing the risk of developing pathology associated with developing the condition, disease, or disorder.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process.

A "highly purified" compound as used herein refers to a compound that is in some embodiments greater than 90% pure, that is in some embodiments greater than 95% pure, and that is in some embodiments greater than 98% pure.

As used herein, the term "mammal" refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

The term "subject" as used herein refers to a member of species for which treatment and/or prevention of a disease or disorder using the compositions and methods of the presently disclosed subject matter might be desirable. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Aves (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

A "sample", as used herein, refers in some embodiments to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, in some embodiments, humans.

As used herein, a "subject in need thereof" is a patient, animal, mammal, or human, who will benefit from the method of this presently disclosed subject matter.

The term "substantially pure" describes a compound, e.g., a protein or polypeptide, which has been separated from components which naturally accompany it. Typically, a compound is substantially pure when in some embodiments at least 10%, in some embodiments at least 20%, in some embodiments at least 50%, in some embodiments at least 60%, in some embodiments at least 75%, in some embodiments at least 90%, and in some embodiments at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse, and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the phrase "therapeutic agent" refers to an agent that is used to, for example, treat, inhibit, prevent, mitigate the effects of, reduce the severity of, reduce the likelihood of developing, slow the progression of, and/or cure, a disease or disorder.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented.

As used herein, the terms "vector", "cloning vector", and "expression vector" refer to a vehicle by which a polynucleotide sequence (e.g., a foreign gene) can be introduced into a host cell, so as to transduce and/or transform the host cell in order to promote expression (e.g., transcription and translation) of the introduced sequence. Vectors include plasmids, phages, viruses, etc.

All genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. In some embodiments, the alkyl group is "lower alkyl." "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In some embodiments, the alkyl is "higher alkyl." "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic moiety that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, carbonyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "heteroaryl" refers to aryl groups wherein at least one atom of the backbone of the aromatic ring or rings is an atom other than carbon. Thus, heteroaryl groups have one or more non-carbon atoms selected from the group including, but not limited to, nitrogen, oxygen, and sulfur.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

The terms "heterocycle" or "heterocyclic" refer to cycloalkyl groups (i.e., non-aromatic, cyclic groups as described hereinabove) wherein one or more of the backbone carbon atoms of a cyclic ring is replaced by a heteroatom (e.g., nitrogen, sulfur, or oxygen). Examples of heterocycles include, but are not limited to, tetrahydrofuran, tetrahydropyran, morpholine, dioxane, piperidine, piperazine, and pyrrolidine.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Alkoxyl" or "alkoxy" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

The term "amino" refers to the —NR'R" group, wherein R' and R" are each independently selected from the group including H and substituted and unsubstituted alkyl, cycloalkyl, heterocycle, aralkyl, aryl, and heteroaryl. In some embodiments, the amino group is —$NH_2$.

The term "carbonyl" refers to the —(C=O)— or a double bonded oxygen substituent attached to a carbon atom of a previously named parent group.

The term "carboxyl" refers to the —COOH group.

The terms "halo", "halide", or "halogen" as used herein refer to fluoro, chloro, bromo, and iodo groups.

The term "perhaloalkyl" refers to an alkyl group wherein all of the hydrogen atoms are replaced by halo. Thus, for example, perhaloalkyl can refer to a "perfluroalkyl" group wherein all of the hydrogen atoms of the alkyl group are replaced by fluoro. Perhaloalkyl groups include, but are not limited to, —$CF_3$.

The terms "hydroxyl" and "hydroxy" refer to the —OH group.

The term "oxo" refers to a compound described previously herein wherein a carbon atom is replaced by an oxygen atom.

The term "cyano" refers to the —CN group.
The term "nitro" refers to the —$NO_2$ group.

II. Methods of Identifying Reactive Amino Acid Residues

Covalent probes can serve as valuable tools for the global investigation of protein function and ligand binding capacity. Despite efforts to expand coverage of residues available for chemical proteomics (e.g. cysteine and lysine), a large fraction of the proteome remains inaccessible with current activity-based probes. According to one aspect of the presently disclosed subject matter is described sulfur-heterocycle exchange chemistry (e.g., sulfur-triazole exchange (SuTEx) chemistry) as a tunable platform for developing covalent probes with broad applications for chemical proteomics. Sulfur-heterocycle probes can act as electrophiles for reactive nucleophilic amino acid side chains of proteins, where reaction of the nucleophilic group of the nucleophilic amino acid side chain with the sulfur-heterocycle probe results in formation of a covalent bond between the nucleophilic group and the sulfur atom of a sulfonyl group in the probe and the breaking of a bond between the sulfonyl group and the heterocycle.

As example of the tunability of this platform, in SuTEx probes, modifications to the triazole leaving group can furnish sulfonyl probes with ~5-fold enhanced chemoselectivity for tyrosines over other nucleophilic amino acids to investigate, for the first time, more than 10,000 tyrosine sites in lysates and live cells. Using the SuTEx chemistry described hereinbelow, it has been found that tyrosines with enhanced nucleophilicity are enriched in enzymatic, protein-protein interaction, and nucleotide recognition domains. In addition, SuTEx can be used as a chemical phosphoproteomics strategy to monitor activation of phosphotyrosine sites. Collectively, SuTEx and related sulfur-heterocycle exchange is described herein as a biocompatible chemistry for chemical biology investigations of the human proteome.

In some embodiments, the presently disclosed subject matter provides small molecule probes that interact with reactive nucleophilic residues on proteins or peptides, such as a reactive tyrosine residue of a tyrosine-containing protein and/or a reactive lysine residue of a lysine-containing protein, as well as methods of identifying a protein or peptide that contains such a reactive residue (e.g., a druggable tyrosine residue and/or a druggable lysine residue). In some instances, also described herein are methods of profiling a ligand that interacts with one or more tyrosine- and/or lysine-containing protein comprising one or more reactive tyrosines or lysines.

In some embodiments, the presently disclosed subject matter provides a method of identifying a reactive tyrosine of a protein, the method comprising: (a) providing a protein sample comprising isolated proteins, living cells, or a cell lysate; (b) contacting the protein sample with a probe compound (e.g., a compound of Formula (I)) for a period of time sufficient for the probe compound to react with at least one reactive tyrosine in a protein in the protein sample, thereby forming at least one modified reactive tyrosine residue; and (c) analyzing proteins in the protein sample to identify at least one modified tyrosine residue, thereby identifying at least one reactive tyrosine of a protein. In some embodiments, the probe compound has a structure of Formula (I):

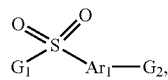

wherein: $G_1$ is a monovalent moiety comprising an alkyne moiety, a fluorophore moiety, a detectable labeling group, or a combination thereof, $Ar_1$ is heteroaryl; and $G_2$ is H or an aryl group substituent; and the at least one modified reactive tyrosine residue comprises a modified tyrosine residue comprising a structure of Formula (II):

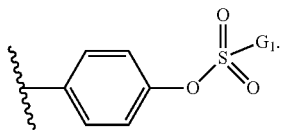

In some embodiments, $Ar_1$ is a five-membered heteroaryl and/or a nitrogen-containing heteroaryl group. In some embodiments, $G_2$ is selected from the group consisting of H, halo, —$CF_3$, alkyl, substituted alkyl, aralkyl, substituted aralkyl, aryl, heteroaryl, substituted aryl, and substituted heteroaryl. In some embodiments, $G_2$ includes a recognition moiety for a particular protein or group of proteins. For example, the recognition moiety can comprise a tetramethyltetrahydronaphthyl group, a hormone derivative (e.g., an estrogen steroid derivative, such as a mestranol), or a bis(4-fluorophenyl)methylene group, such as a bis(4-fluorophenyl)methylene)piperadinyl group or a bis(4-flurophenyl)methylene)piperazinyl group.

In some embodiments, $G_1$ comprises a fluorophore or detectable labeling moiety as described hereinbelow. In some embodiments, $G_1$ comprises an aryl group substituted by an alkyne-substituted alkyl group, an alkyne-substituted alkoxy group, or a group having the formula —C(=O)—NH-alkylene-C≡CH.

In some embodiments, $G_1$ is a group having the formula —$Ar_2$-$G_3$ and the probe compound having a structure of Formula (I) has a structure of Formula (Ia):

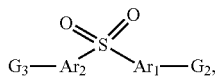

wherein $Ar_2$ is aryl; $G_3$ is a monovalent moiety comprising an alkyne moiety, a fluorophore moiety, a detectable labeling group, or a combination thereof; and $Ar_1$ and $G_2$ are as defined for Formula (I). In some embodiments, $Ar_2$ is phenyl, naphthyl, or pyridyl. In some embodiments, $Ar_2$ is phenyl. In some embodiments, $G_3$ comprises or consists of —C≡CH, -alkylene-C≡CH, —O-alkylene-C≡CH (e.g., —O—$CH_2$—C≡CH), or —C(=O)—NH-alkylene-C≡CH (e.g., C(=O)—NH—$CH_2$—C≡CH). In some embodiments, the alkylene group is a $C_1$-$C_5$ alkylene group. In some embodiments, the alkylene group is methylene.

In some embodiments, $Ar_1$ is a five-membered heteroaryl group. In some embodiments, $Ar_1$ is a nitrogen-containing heteroaryl group. In some embodiments, $Ar_1$ is a five-membered, nitrogen-containing heteroaryl group. In some embodiments, $Ar_1$ selected from the group comprising triazole, imidazole, pyrazole, and tetrazole.

In some embodiments, $Ar_1$ is triazole, and the probe compound of Formula (Ia) has a structure of:

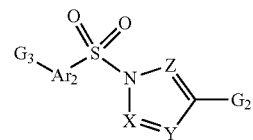

wherein X, Y, and Z are each selected from C and N, subject to the proviso that two of X, Y, and Z are N; $G_2$ is H or an aryl group substituent (e.g. wherein $G_2$ is selected from H, halo, perhaloalkyl, alkyl, substituted alkyl, aryl, heteroaryl, substituted aryl, and substituted heteroaryl), and wherein $Ar_2$ and $G_3$ are the same as in Formula (Ia). Thus, the probe compound can include a 1,2,3, -triazole or a 1,2,4-triazole, and 1,2,3-triazole probes can be a 1,4- or a 2,4-regioisomer.

In some embodiments, the probe compound of Formula (Ia) has a structure of Formula (Ib):

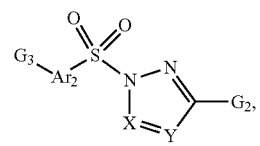

wherein: X and Y are each selected from C and N, subject to the proviso that one of X and Y is N and one of X and Y is C; $G_2$ is H or an aryl group substituent (e.g., wherein $G_2$ is selected from H, halo, perhaloalkyl, alkyl, substituted alkyl, aryl, heteroaryl, substituted aryl, and substituted heteroaryl); $Ar_2$ is aryl (e.g., phenyl, naphthyl, or pyridinyl); and $G_3$ is a monovalent moiety comprising an alkyne moiety, a fluorophore moiety, a detectable labeling group, or a combination thereof. In some embodiments, $Ar_2$ is phenyl.

In some embodiments, the probe compound of Formula (Ib) has a structure of Formula (Ic):

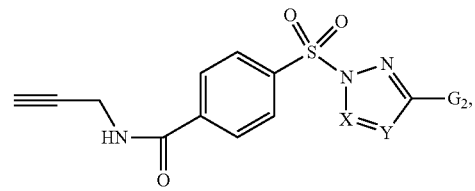

wherein X, Y, and $G_2$ are as defined for the probe compound of Formula (Ib). In some embodiments, $G_2$ is selected from halo (i.e., F, Cl, Br, or I), alkyl, substituted alkyl, or perhaloalkyl (e.g., —$CF_3$). In some embodiments, $G_2$ is selected from H, phenyl, and substituted phenyl, optionally wherein the substituted phenyl is phenyl substituted with one or more substituent (e.g. one, two or three substituents) selected from the group comprising halo, alkoxy, alkyl, and perfluoralkyl. In some embodiments, $G_2$ is selected from H, phenyl and substituted phenyl. In some embodiments, the substituted phenyl is phenyl substituted with one or more substituent selected from the group comprising halo, methoxy, and —$CF_3$.

In some embodiments, the probe is selected from the group comprising HHS-475, HHS-465, HHS-481, HHS-482, and HHS-483, the structures of which are provided hereinbelow, in Example 1. In some embodiments, the probe is selected from the group comprising HHS-Py-01, HHS-Py-02, HHS-Py-03, HHS-Py-04, HHS-Im-01, HHS-Im-02, HHS-Im-04, Ky-Im-Br, HHS-Tet-02, HHS-Tet-03, and HHS-Tet-04, the structures of which are provided hereinbelow, in Example 8. In some embodiments, the probe is selected from the group comprising TH211, TH214, TH216, TH213, TH217, TH312, TH313, TH314, TH315, TH316, and TH317, the structures of which are provided hereinbelow, in Example 10. In some embodiments, the probe is KY-26, the structure of which is provided hereinbelow, in Example 11.

In some embodiments, e.g., when $G_1$ comprises an alkyne group, the analyzing of step (c) further comprises tagging the at least one modified reactive tyrosine residue with a compound comprising detectable labeling group, thereby forming at least one tagged reactive tyrosine residue comprising said detectable labeling group. In some embodiments, the detectable labeling group comprises biotin or a biotin derivative. In some embodiments, the biotin derivative is desthiobiotin.

In some embodiments, the tagging comprises reacting an alkyne group in a $G_1$ moiety of at least one tagged reactive tyrosine residue with a compound comprising both an azide moiety (or other alkyne-reactive group) and a detectable labeling group (e.g., biotin or a biotin derivative. In some embodiments, the compound comprising the azide moiety and the detectable labeling group further comprises an alkylene linker, which in some embodiments, can comprise a polyether group, such as an oligomer of methylene glycol, ethylene glycol or propylene glycol (e.g., a group having the formula —(O—C$_2$H$_4$—)$_x$-). In some embodiments, the tagging comprises performing a copper-catalyzed azide-alkyne cycloaddition (CuAAC) coupling reaction.

In some embodiments, the analyzing further comprises digesting the protein sample to provide a digested protein sample comprising a protein fragment comprising the at least one tagged reactive tyrosine moiety comprising the detectable group. In some embodiments, the digesting is performed with a peptidase. In some embodiments, the digesting is performed with trypsin.

In some embodiments, the analyzing further comprises enriching the digested protein sample for the detectable labeling group. For example, in some embodiments, the enriching comprises contacting the digested protein sample with a solid support comprising a binding partner of the detectable labeling group. In some embodiments, when the detectable labeling group comprises biotin or a derivative thereof, the solid support comprises streptavidin. In some embodiments, the analyzing further comprises analyzing the digested protein sample (e.g., the enriched digested sample) via liquid chromatography-mass spectrometry or via a gel-based assay.

In some embodiments, providing the protein sample further comprises separating the protein sample into a first protein sample and a second protein sample. Then, in the contacting step, the first protein sample can be contacted with a first probe compound of Formula (I) at a first probe concentration for a first period of time and the second protein sample can be contacted with a second probe compound of Formula (I) (i.e., a probe compound of Formula (I) having a different structure than that of the first probe compound of Formula (I)) at the same probe concentration (i.e., at the first probe concentration) for the same time period (i.e., for the first period of time. Alternatively, the second protein sample can be contacted with the same probe compound as the first protein sample, but at a different probe concentration (i.e., a second probe concentration) or for a different period of time. In some embodiments, analyzing proteins comprises analyzing the first and second protein samples to determine the presence and/or identity of a modified reactive tyrosine residue in the first sample and the presence and/or identity of a modified reactive tyrosine residue in the second sample. In some embodiments, the identities and/or amounts of identified modified reactive tyrosine residues from the first and second protein samples are compared.

In some embodiments, the protein sample comprises living cells. In some embodiments, providing the protein sample further comprises separating the protein sample into a first protein sample and a second protein sample and culturing the first protein sample in a first cell culture medium comprising heavy isotopes prior to the contacting of step (b) and culturing the second protein sample in a second cell culture medium, wherein the second culture medium comprises a naturally occurring isotope distribution prior to the contacting of step (b). In some embodiments, the first cell culture medium comprises $^{13}$C- and/or $^{15}$N-labeled amino acids. In some embodiments, the first cell culture medium comprises $^{13}$C-,$^{15}$N-labeled lysine and arginine.

In some embodiments, e.g., if the protein sample does not comprise living cells, the probe compound of Formula (I) can comprise a detectable labeling group comprising a heavy isotope (e.g., a $^{13}$C label) or the method can comprise tagging the at least one modified tyrosine residue with a detectable labeling group comprising a heavy isotope. An exemplary "heavy" detectable labeling group is described hereinbelow in Example 15.

In some embodiments, the protein sample is separated into a first and a second protein sample and one of the first and the second protein sample is cultured in the presences of a tyrosine phosphatase inhibitor (e.g., pervanadate). Thus, in some embodiments, the presently disclosed methods can be used in phosphoproteomics.

While many of the probes of Formula (I) have selectivity for covalent labeling of tyrosine residues compared to lysine residues (see e.g., FIGS. 4A and 4B), they can, in several cases, also react with reactive lysine residues. For example, TH211 (see Example 10, below) and KY-26 (see Example 11, below) have shown reactivity for lysine residues. In particular, TH211 has shown an ability to modify lysine sites on membrane proteins in human cell proteomes. Table 1, below, provides a list of membrane protein lysine sites modified by TH211. KY-26 can bind to the catalytic lysine residues of kinases. The addition of KY-26 to a tyrosine or lysine residue can be dependent upon the location of the probe in various binding sites. When a tyrosine is modified in a kinase, it usually within the nucleotide binding region. If a surface residue of a protein is modified, it is usually a tyrosine. Table 2, below, provides a list of lysine and tyrosine sites targeted by KY-26 in various kinases. In addition, some of the probes of Formula (I) (e.g., HHS-Im-01) are selective for lysine. See FIGS. 37A and 37B.

TABLE 1

Membrane protein lysine sites modified by TH211.

| Uniprot ID | Modified Amino Acid Number | Protein Name | Amino Acid Modified |
|---|---|---|---|
| O42676 | 39 | NDUB3 human | K |
| Q9P032 | 24 | NDUF4 human | K |
| P51970 | 172 | NDUA8 human | K |
| Q16718 | 30 | NDUA5 human | K |
| O95168 | 114 | NDUB4 human | K |
| O95168 | 7 | NDUB4 human | K |
| O95168 | 85 | NDUB4 human | K |

TABLE 1-continued

Membrane protein lysine sites modified by TH211.

| Uniprot ID | Modified Amino Acid Number | Protein Name | Amino Acid Modified |
|---|---|---|---|
| P03915 | 455 | NU5M human | K |
| Q02127 | 166 | PYRD human | K |
| Q9BQB6 | 152 | VKOR1 human | K |
| Q9BQB6 | 159 | VKOR1 human | K |
| Q02750 | 97 | MP2K1 human | K |

TABLE 2

Kinase lysine and tyrosine sites modified by KY-26.

| Protein (human) | Modification Site |
|---|---|
| Tyrosine-protein kinase Lck | K273 |
| Serine/threonine-protein kinase tousled-like 2 | K491 |
| Cyclin-dependent kinase 1 | K33 |
| Phosphatidylinositol 4,5-bisphosphate 3-kinase catalytic subunit delta isoform | K708 |
| Cyclin-dependent kinase 1 OS = *Homo sapiens* | K33 |
| Cyclin-dependent-like kinase 5 OS = *Homo sapiens* | K33 |
| Cyclin-dependent kinase 2 OS = *Homo sapiens* | K33 |
| Phosphoglycerate kinase 1 | K323 |
| Tyrosine-protein kinase Fer | K591 |
| Mitogen-activated protein kinase kinase kinase kinase 1 | K46 |
| GTP binding nuclear protein | Y147 |
| Serine/threonine-protein kinase MARK2 | K82 |
| dlF-2-alpha kinase GCN2 | K619 |
| Protein-tyrosine kinase 2-beta | K457 |
| Serine/threonine-protein kinase 4 | Y41 |
| Receptor-interacting serine/threonine-protein kinase 1 | Y308 |
| Dual specificity mitogen-activated protein kinase kinase 1 | K97 |
| Interleukin-1 receptor-associated kinase 4 | K213 |
| MAP/microtubule affinity-regulating kinase 4 | K87 |
| Protein-tyrosine kinase 2-beta OS = *Homo sapiens* | K457 |
| Mitogen-activated protein kinase kinase kinase kinase 2 | Y27 |
| Mitogen-activated protein kinase kinase kinase kinase 5 | Y31 |
| Septin-7 | Y319 |
| T-complex protein 1 subunit eta | K157 |
| Proteasome subunit beta type-5 | K150 |
| ATP-citrate synthase | Y384 |
| Pyruvate kinase PKM | Y370 |
| Stress-induced-phosphoprotein 1 | Y451 |
| Stress-induced-phosphoprotein 1 | K442 |
| Alpha-enolase | K60 |
| Heat shock protein HSP 90-beta | Y56 |
| Stress-induced-phosphoprotein 1 | Y404 |
| Phosphoglycerate kinase 1 | Y76 |
| Phosphoglycerate kinase 1 | Y324 |
| Fructose-bisphosphate aldolase A | Y328 |
| Fructose-bisphosphate aldolase A | Y5 |
| Fructose-bisphosphate aldolase A | Y3 |
| Fructose-bisphosphate aldolase A | Y328 |
| Tyrosine-protein kinase Fer | Y714 |
| Phosphatidylinositol 4,5-bisphosphate 3-kinase catalytic subunit delta | K708 |
| Thymidylate kinase | Y151 |

Thus, in some embodiments, the presently disclosed methods can also provide for identifying reactive lysine residues in a protein. For example, during the contacting step (b) of the method described hereinabove, the probe compound of Formula (I) can react with at least one reactive lysine in a protein in the protein sample, thereby forming at least one modified reactive lysine residue, and during the analyzing step (c), the method can further comprise analyzing the proteins in the protein sample to identify the at least one modified lysine residue, thereby identifying at least one reactive lysine of a protein. In some embodiments, the probe compound of Formula (I) is TH211, HHS-Im-01, or KIY-26.

In some embodiments, the presently disclosed subject matter provides a method of identifying a reactive lysine of a protein, the method comprising: (a) providing a protein sample comprising isolated proteins, living cells, or a cell lysate; (b) contacting the protein sample with a probe compound of Formula (I) for a period of time sufficient for the probe compound to react with at least one reactive lysine in a protein in the protein sample, thereby forming at least one modified reactive lysine residue; and (c) analyzing proteins in the protein sample to identify at least one modified lysine residue, thereby identifying at least one reactive lysine of a protein; wherein the probe compound has a structure of Formula (I):

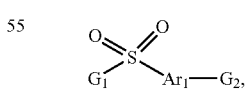

wherein: $G_1$ is a monovalent moiety comprising an alkyne moiety, a fluorophore moiety, a detectable labeling group, or a combination thereof; $Ar_1$ is heteroaryl; (e.g., a five-membered heteroaryl and/or nitrogen-containing heteroaryl); and $G_2$ is H or an aryl group substituent. In some embodiments, $G_2$ is selected from the group comprising H, alkyl, substituted alkyl, aralkyl, substituted aralkyl, aryl, heteroaryl, substituted aryl, and substituted heteroaryl. In some embodiments, the at least one modified reactive lysine residue comprises a modified mine residue comprising a structure of Formula (II'):

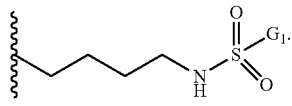

In some embodiments, the probe compound is TH211, HHS-Im-01, or KY-26. In some embodiments, the at least one modified reactive lysine residue is in a kinase.

III. Probes

In some embodiments, the presently disclosed subject matter provides a probe compound (e.g., a small molecule probe compound) that comprises a reactive moiety (i.e., a reactive electrophilic moiety) which can interact with the phenol group of a tyrosine residue of a tyrosine-containing protein (and/or a nucleophilic group of the side chain of another amino acid residue, such as the primary amino group of a lysine residue of a lysine-containing protein). In some instances, the probe reacts with a tyrosine and/or lysine residue to form a covalent bond. Typically, the probe is a non-naturally occurring molecule, or forms a non-naturally occurring product (i.e., a "modified" protein or adduct) after reaction with the phenol group of a tyrosine residue of a tyrosine containing protein or other nucleophilic group of an amino acid, e.g., the primary amino group of a lysine residue. In some instances, the phenol group of a reactive tyrosine in the tyrosine-containing protein is connected to the small molecule fragment moiety via an —O—S(=O)$_2$— bond. In some instances, the primary amino group of a reactive lysine in a lysine-containing protein is connected to a small molecule fragment moiety via an —NH—S(=O)$_2$— bond.

For example, in some embodiments, the presently disclosed subject matter provides a probe compound that has a structure of Formula (I)

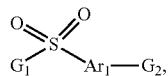

wherein: $G_1$ is a monovalent moiety comprising an alkyne moiety, a fluorophore moiety, a detectable labeling group, or a combination thereof; $Ar_1$ is heteroaryl; and $G_2$ is H or an aryl group substituent. In some embodiments, $G_2$ is selected from H, halo, —CF$_3$, aryl, alkyl, substituted alkyl, aralkyl, substituted aralkyl, aryl, heteroaryl, substituted aryl, and substituted heteroaryl. Thus, in some embodiments, the probe compound of Formula (I) can form a protein or peptide comprising at least one modified reactive tyrosine residue, wherein the modified reactive tyrosine comprises a structure of Formula (II):

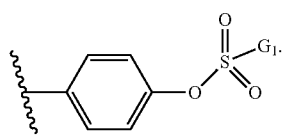

In some embodiments, the probe compound of Formula (I) can form a protein or peptide comprising at least one modified reactive lysine residue, wherein the modified reactive lysine residue comprises a structure of Formula (II'):

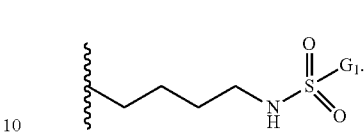

The fluorophore of $G_1$ can be any suitable fluorophore. In some embodiments, the fluorophore is selected from the group including, but not limited to, rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, and TAMRA.

In some embodiments, $G_1$ comprises a fluorophore moiety. In some cases, $G_1$ is obtained from a compound library. In some cases, the compound library comprises ChemBridge fragment library, Pyramid Platform Fragment-Based Drug Discovery, Maybridge fragment library, FRGx from AnalytiCon, TCI-Frag from AnCoreX, Bio Building Blocks from ASINEX, BioFocus 3D from Charles River, Fragments of Life (FOL) from Emerald Bio, Enamine Fragment Library, IOTA Diverse 1500, BIONET fragments library, Life Chemicals Fragments Collection, OTAVA fragment library, Prestwick fragment library, Selcia fragment library, TimTec fragment-based library, Allium from Vitas-M Laboratory, or Zenobia fragment library.

In some embodiments, the detectable labeling moiety is selected from the group comprising a member of a specific binding pair (e.g., biotin:streptavidin, antigen-antibody, nucleic acid:nucleic acid), a bead, a resin, a solid support, or a combination thereof. In some embodiments, the detectable labeling group is a biotin moiety, a streptavidin moiety, bead, resin, a solid support, or a combination thereof. In some embodiments, the detectable labeling moiety comprises biotin or a derivative thereof (e.g., desthiobiotin). In some embodiments, the detectable labeling moiety comprises a heavy isotope (i.e., $^{13}$C).

In some embodiments, $G_1$ comprises an aryl group $Ar_2$ directly attached to the sulfur atom of the sulfonyl group. Thus, in some embodiments, $G_1$ has a structure —$Ar_2$-$G_3$, wherein $Ar_2$ is aryl and $G_3$ is a monovalent moiety comprising an alkyne moiety, a fluorophore moiety, a detectable labeling group, or a combination thereof. In some embodiments, $Ar_2$ is selected from the group comprising phenyl, naphthyl, and pyridyl.

In some embodiments, $Ar_1$ is a five-membered heteroaryl and/or a nitrogen-containing heteroaryl group, such as, but not limited to triazole, tetrazole, imidazole, and pyrazole. In some embodiments, $G_2$ is selected from H, halo, —$CF_3$, alkyl, substituted alkyl, aralkyl, substituted aralkyl, aryl, heteroaryl, substituted aryl, and substituted heteroaryl. In some embodiments, $G_2$ is selected from the group consisting of H, alkyl, substituted alkyl, aralkyl, substituted aralkyl, aryl, heteroaryl, substituted aryl, and substituted heteroaryl. In some embodiments, $G_2$ includes a recognition moiety for a particular protein or group of proteins. For example, the recognition moeity can comprise a tetramethyl-tetrahydronaphthyl group, a hormone derivative (e.g., an estrogen steroid derivative, such as a mestranol), or a bis(4-fluorophenyl)methylene group, such as a bis(4-fluorophenyl)methylene)piperadinyl group or a bis(4-flurophenyl)methylene)piperazinyl group.

In some embodiments, $G_1$ comprises a fluorophore or detectable labeling moiety as described hereinbelow. In some embodiments, $G_1$ comprises an aryl group substituted by an alkyne-substituted alkyl group, an alkyne-substituted alkoxy group, or a group having the formula —C(=O)—NH-alkylene-C≡CH.

In some embodiments, $G_1$ is a group having the formula —$Ar_2$-$G_3$ and the probe compound having a structure of Formula (I) has a structure of Formula (Ia):

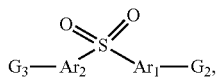

wherein $Ar_2$ is aryl. $G_3$ is a monovalent moiety comprising an alkyne moiety, a fluorophore moiety, a detectable labeling group, or a combination thereof; and $Ar_1$ and $G_2$ are as defined for Formula (I). In some embodiments, $Ar_2$ is phenyl, naphthyl, or pyridyl. In some embodiments, $Ar_2$ is phenyl. In some embodiments, $G_3$ comprises or consists of —C≡CH, -alkylene-C≡CH, —O-alkylene-C≡CH (e.g., —$CH_2$—C≡CH), or —C(=O)—NH-alkylene-C≡CH (e.g., C(=O)—NH—$CH_2$—C≡CH). In some embodiments, the alkylene group is a $C_1$-$C_5$ alkylene group. In some embodiments, the alkylene group is methylene.

In some embodiments, $Ar_1$ is a five-membered heteroaryl group. In some embodiments, $Ar_1$ is a nitrogen-containing heteroaryl group. In some embodiments, $Ar_1$ is a five-membered, nitrogen-containing heteroaryl group. In some embodiments, $Ar_1$ is selected from the group comprising triazole, imidazole, pyrazole, and tetrazole.

In some embodiments, $Ar_1$ is triazole, and the probe compound of Formula (Ia) has a structure of

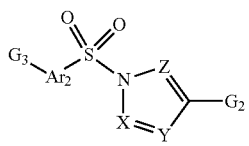

wherein X, Y, and Z are each selected from C and N, subject to the proviso that two of X, Y, and Z is N; $G_2$ is H or an aryl group substituent (e.g. wherein $G_2$ is selected from H, alkyl, substituted alkyl, aryl, heteroaryl, substituted aryl, and substituted heteroaryl), and wherein $Ar_2$ and $G_3$ are the same as in Formula (Ia). Thus, the probe compound can include a 1,2,3, -triazole or a 1,2,4-triazole, and 1,2,3-triazole probes can include 1,4- and 2,4-regioisomers.

In some embodiments, the probe compound of Formula (Ia) has a structure of Formula (Ib):

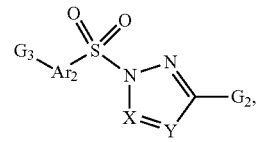

wherein: X and Y are each selected from C and N, subject to the proviso that one of X and Y is N and one of X and Y is C; $G_2$ is H or an aryl group substituent (e.g., wherein $G_2$ is selected from H, halo, —$CF_3$, alkyl, substituted alkyl, aryl, heteroaryl, substituted aryl, and substituted heteroaryl); $Ar_2$ is aryl (e.g., phenyl, naphthyl, or pyridinyl); and $G_3$ is a monovalent moiety comprising an alkyne moiety, a fluorophore moiety, a detectable labeling group, or a combination thereof. In some embodiments, $Ar_2$ is phenyl.

In some embodiments, the probe compound of Formula (Ib) has a structure of Formula (Ic):

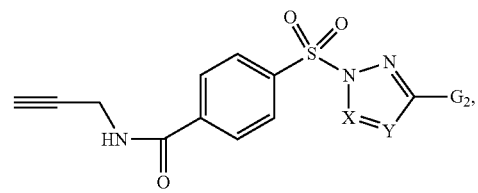

wherein X, Y, and $G_2$ are as defined for the probe compound of Formula (Ib). In some embodiments, $G_2$ is selected from halo (i.e., F, Cl, Br, or I), alkyl, substituted alkyl, or perhaloalkyl (e.g., —$CF_3$). In some embodiments, $G_2$ is selected from H, phenyl, and substituted phenyl, optionally wherein the substituted phenyl is phenyl substituted with one or more substituent (e.g., one, two or three substituents) selected from the group comprising halo, alkoxy, alkyl, and perfluoralkyl. In some embodiments, $G_2$ is selected from H, phenyl and substituted phenyl. In some embodiments, the substituted phenyl is phenyl substituted with one or more substituent (e.g., one, two, or three substituents) selected from the group comprising halo, methoxy, and —$CF_3$.

In some embodiments, the probe is selected from the group comprising HHS-475, HHS-465, HHS-481, HHS-482, and HHS-483, the structures of which are provided hereinbelow, in Example 1. In some embodiments, the probe is selected from the group comprising HHS-Py-01, HHS-Py-02, HHS-Py-03, HHS-Py-04, HHS-Im-01, HHS-Im-02, HHS-Im-04, Ky-Im-Br, HHS-Tet-02, HHS-Tet-03, and HHS-Tet-04, the structures of which are provided hereinbelow, in Example 8. In some embodiments, the probe is selected from the group comprising TH211, TH214, TH216, TH213, TH217, TH312, TH313, TH314, TH315, TH316, and TH317, the structures of which are provided hereinbelow, in Example 10. In some embodiments, the probe is KY-26, the structure of which is provided hereinbelow, in Example 11.

IV. Ligands

Small molecules can serve as versatile probes for perturbing the functions of proteins in biological systems. In some instances, a plurality of human proteins lack selective chemical ligands. In some cases, several classes of proteins are further considered as undruggable. Covalent ligands (also referred to herein as "fragments) offer a strategy to expand the landscape of proteins amenable to targeting by small molecules. In some instances, covalent ligands combine features of recognition and reactivity, thereby providing for the targeting of sites on proteins that are difficult to address by reversible binding interactions alone.

In some embodiments, a ligand of the presently disclosed subject matter can compete with a probe compound described herein for binding with a reactive tyrosine and/or lysine residue. In some instances, a ligand comprises a small molecule compound, a polynucleotide, a polypeptide or its fragments thereof, or a peptidomimetic. In some embodiments, the ligand comprises a small molecule compound. In some instances, a small molecule compound comprises a fragment moiety that facilitates interaction of the compound with a reactive tyrosine and/or lysine residue. In some cases, a small molecule compound comprises a small molecule fragment that facilitates hydrophobic interaction, hydrogen bonding, or a combination thereof. Often, ligands are non-naturally occurring, or form non-naturally occurring products after reaction with the phenol group of a tyrosine residue of a tyrosine-containing protein or an amino group of a lysine residue of a lysine containing protein.

In some embodiments, the presently disclosed subject matter provides a ligand (i.e., a tyrosine-reactive and/or lysine-reactive compound) having a structure of Formula (III):

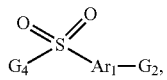

wherein $Ar_1$ is selected from the group consisting of triazole, imidazole, pyrazole, and tetrazole; $G_2$ is H or an aryl group substituent; and $G_4$ is selected from the group consisting of alkyl, substituted alkyl, cycloalkyl, substituted cycloalkyl, heterocycyl, aralkyl, substituted aralkyl, aryl, substituted aryl, heteroaryl, and substituted heteroaryl. For example, $G_4$ can be selected from the group comprising alkyl (e.g., isopropyl); substituted alkyl, including alkyl substituted with a cycloalkyl (e.g., cyclopropyl) or bicyclic moiety, such as norbornene or dimethylnorbornene; cycloalkyl (e.g., cyclopropyl, cyclopentyl, and cyclohexyl); non-aromatic heterocyclic (e.g., morpholinyl), and aralkyl (e.g., benzyl). In some embodiments, $G_4$ is —$Ar_2$-$(G_5)_y$, wherein y is an integer from 1 to 3 (i.e., 1, 2, or 3); $Ar_2$ is an aryl or heteroaryl group; and each $G_5$ is an aryl group substituent, such as, but not limited to, halo, alkyl (e.g., $C_1$-$C_5$ alkyl, such as methyl or isopropyl), alkoxy (e.g., methoxy), aryloxy (e.g., phenoxy), aryl (e.g., phenyl), nitro, —$OCF_3$, perfluoroalkyl (e.g., —$CF_3$), cyano, —C(=O)—O-alkyl, —NHC(=O)-alkyl, and —C(=O)—NRR', wherein R and R' are each selected from H, alkyl, aralkyl, and aryl or wherein R and R' together form an alkylene or substituted alkylene group. In some embodiments, ligands wherein $G_4$ is alkyl or cycloalkyl can be less reactive than ligands wherein $G_4$ is aryl, substituted aryl, heteroaryl, or substituted heteroaryl; however, this reduced reactivity can provide enhanced selectivity.

In some embodiments, $Ar_2$ is selected from the group comprising phenyl, naphthyl, pyridyl, and thiazolidinyl. In some embodiments, $G_4$ is —$Ar_2$-$G_5$. In some embodiments, $Ar_2$ is phenyl. In some embodiments, the phenyl is para-substituted with $G_5$. In some embodiments, $G_5$ is selected from the group comprising halo, alkoxy, cyano, perfluoralkoxy, aryl, —C(=O)—NH(alkyl), —C(=O)—NH(cycloalkyl), and —C(=O)—NH(aralkyl).

In some embodiments, $Ar_1$ is triazole. In some embodiments, $Ar_1$ is 1,2,4-triazole. In some embodiments, $Ar_1$ is 1,2,3-triazole. In some embodiments, the compound comprises a 1,4-regioisomer of 1,2,3-triazole. In some embodiments, the compound comprises a 2,4-regioisomer of 1,2,3-triazole.

In some embodiments, $G_2$ is selected from the group comprising H, alkyl, substituted alkyl (e.g., aryloxy-substituted alkyl), cycloalkyl (e.g., cyclopropyl or cyclohexyl), aralkyl (e.g., benzyl) phenyl, pyridyl, thiophenyl, and substituted phenyl. In some embodiments, $G_2$ is phenyl substituted with one, two or three aryl group substituents selected from halo, alkoxy, nitro, amino, perfluoroalkyl (—$CF_3$), perfluoroalkoxy (—$OCF_3$), and —C(=O)—O-alkyl (e.g., —$CO_2CH_3$).

In some embodiments, the ligand (e.g., the tyrosine-reactive and/or lysine-reactive compound) comprises 1,2,4-triazole and has a structure of Formula (IV):

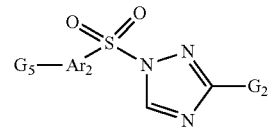

wherein $Ar_2$ is selected from the group consisting of phenyl, naphthyl, and pyridyl; $G_2$ is selected from H and an aryl group substituent; and $G_5$ is selected from the group consisting of H, halo, alkoxy, cyano, perfluoralkoxy, aryl, —C(=O)—NH(alkyl), —C(=O)—NH(cycloalkyl), and —C(=O)—NH(aralkyl). In some embodiments, $G_2$ is selected from H, aryl, and substituted aryl. In some embodiments, $G_2$ is —$Ar_3$-$G_6$, wherein $Ar_3$ is selected from phenyl, pyridyl, and thiophenyl; and wherein $G_6$ is selected from H, alkoxy (e.g., methoxy), perfluoroalkyl (e.g., —$CF_3$), perfluoroalkoxy (e.g., —$OCF_3$), —C(=O)—O-alkyl (e.g., —C(=O)—$OCH_3$), halo, aryl, alkyl, and amino (e.g., dialkylamino).

In some embodiments, the ligand is selected from the group comprising JWB105, JWB112, JWB120, JWB127, JWB131, JWB135, JWB136, JWB137, JWB141, JWB142, JWB146, JWB150, JWB151, JWB152, JWB157, JWB179, JWB183, JWB191, JWB196, JWB197, JWB198, JWB202, JWB206, JWB207, JWB210, JWB211, JWB212, JWB217, JWB232, JWB233, and JWB234, the structures of which are shown in Example 5, hereinbelow and/or in FIG. 40. In some embodiments, the ligand is selected from the group comprising JWB105, JWB112, JWB120, JWB127, JWB135, JWB136, JWB137, JWB141, JWB142, JWB150, JWB151, JWB152, JWB157, JWB196, JWB197, JWB198, JWB202, JWB207, JWB210, JWB211, JWB212, JWB217, JWB232, JWB233, JWB234, and JWB 243.

In some embodiments, the ligand is KY-239, the structure of which is shown in Example 11, hereinbelow. In some embodiments, the ligand is EKT 055, either the 1,4-regioisomer or the 2,4-regioisomer, the structures of which are shown in Example 12. In some embodiments, the ligand is selected from EKT151, EKT165, EKT197, EKT225, HHS134, and HHS183. The structures of the 1,4-regioisomers of these ligands are shown in Example 16, hereinbelow. In some embodiments, the ligand is selected from the group comprising HHS0101, HHS0201, HHS0301, HHS0401, HHS0601, and HHS0701, the structures of which are shown in FIG. 43. In some embodiments, the ligand is EKT231, the structure of which is shown in FIG. 46A.

The presently disclosed subject matter encompasses the preparation and use of pharmaceutical compositions comprising a ligand compound as described herein useful for treatment of diseases and disorders as would be apparent upon review of the instant disclosure as an active ingredient. Such a pharmaceutical composition can comprise, consist essentially of, or consist of the active ingredient alone, in a form suitable for administration to a subject, or the pharmaceutical composition can comprise the active ingredient and one or more pharmaceutically acceptable carriers, one or more additional ingredients, or some combination of these. The active ingredient can be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The compositions of the presently disclosed subject matter can comprise at least one active ingredient, one or more acceptable carriers, and optionally other active ingredients or therapeutic agents.

Pharmaceutically acceptable carriers include physiologically tolerable or acceptable diluents, excipients, solvents, or adjuvants. The compositions are in some embodiments sterile and nonpyrogenic. Examples of suitable carriers include, but are not limited to, water, normal saline, dextrose, mannitol, lactose or other sugars, lecithin, albumin, sodium glutamate, cysteine hydrochloride, ethanol, polyols (propylene glycol, polyethylene glycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, kaolin, agar-agar and tragacanth, or mixtures of these substances, and the like.

The pharmaceutical compositions can also contain minor amounts of nontoxic auxiliary pharmaceutical substances or excipients and/or additives, such as wetting agents, emulsifying agents, pH buffering agents, antibacterial and antifungal agents (such as parabens, chlorobutanol, phenol, sorbic acid, and the like). Suitable additives include, but are not limited to, physiologically biocompatible buffers (e.g., tromethamine hydrochloride), additions (e.g., 0.01 to 10 mole percent) of chelants (such as, for example, DTPA or DTPA-bisamide) or calcium chelate complexes (as for example calcium DTPA or CaNaDTPA-bisamide), or, optionally, additions (e.g., 1 to 50 mole percent) of calcium or sodium salts (for example, calcium chloride, calcium ascorbate, calcium gluconate or calcium lactate). If desired, absorption enhancing or delaying agents (such as liposomes, aluminum monostearate, or gelatin) can be used. The compositions can be prepared in conventional forms, either as liquid solutions or suspensions, solid forms suitable for solution or suspension in liquid prior to injection, or as emulsions. Pharmaceutical compositions according to the presently disclosed subject matter can be prepared in a manner fully within the skill of the art.

The compositions of the presently disclosed subject matter or pharmaceutical compositions comprising these compositions can be administered so that the compositions may have a physiological effect. Administration can occur enterally or parenterally; for example, orally, rectally, intracisternally, intravaginally, intraperitoneally, locally (e.g., with powders, ointments or drops), or as a buccal or nasal spray or aerosol. Parenteral administration is an approach. Particular parenteral administration methods include intravascular administration (e.g., intravenous bolus injection, intravenous infusion, intra-arterial bolus injection, intra-arterial infusion and catheter instillation into the vasculature), peri- and intra-target tissue injection, subcutaneous injection or deposition including subcutaneous infusion (such as by osmotic pumps), intramuscular injection, and direct application to the target area, e.g., intratumoral injection, for example by a catheter or other placement device.

Where the administration of the composition is by injection or direct application, the injection or direct application can be in a single dose or in multiple doses. Where the administration of the compound is by infusion, the infusion can be a single sustained dose over a prolonged period of time or multiple infusions.

The formulations of the pharmaceutical compositions described herein can be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the presently disclosed subject matter is contemplated include, but are not limited to, humans and other primates, mammals including commercially and/or socially relevant mammals such as cattle, pigs, horses, sheep, cats, and dogs, birds including commercially and/or socially relevant birds such as chickens, ducks, geese, parrots, and turkeys.

A pharmaceutical composition of the presently disclosed subject matter can be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the presently disclosed subject matter will vary, depending upon the identity, size, and condition of the subject treated and further depending upon the route by which the composition is to be administered. By way of example, the composition can comprise between 0.1% and 100% (w/w) active ingredient.

In addition to the active ingredient, a pharmaceutical composition of the presently disclosed subject matter can further comprise one or more additional pharmaceutically active agents.

Controlled- or sustained-release formulations of a pharmaceutical composition of the presently disclosed subject matter can be made using conventional technology.

As used herein, "additional ingredients" include, but are not limited to, one or more of the following: excipients; surface active agents; dispersing agents; inert diluents;

granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the presently disclosed subject matter are known in the art and described, for example in Gennaro (1990) *Remington's Pharmaceutical Sciences,* 18th ed., Mack Pub. Co., Easton, Pennsylvania, United States of America and/or Gennaro (ed.) (2003) *Remington: The Science and Practice of Pharmacy,* 20*th edition* Lippincott, Williams & Wilkins, Philadelphia, Pennsylvania, United States of America, each of which is incorporated herein by reference.

The compositions may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Other approaches include but are not limited to nanosizing the composition comprising a ligand compound as described herein to be delivered as a nanoparticle intravenously, intraperitoneal injection, or implanted beads with time release of a ligand compound as described herein.

Suitable preparations include injectables, either as liquid solutions or suspensions, however, solid forms suitable for solution in, suspension in, liquid prior to injection, may also be prepared. The preparation may also be emulsified, or the compositions encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the preparation may also include minor amounts of auxiliary substances such as wetting or emulsifying agents, pH buffering agents, and/or adjuvants.

The presently disclosed subject matter also includes a kit comprising the composition of the presently disclosed subject matter and an instructional material which describes administering the composition to a cell or a tissue of a subject. In some embodiments, this kit comprises a (in some embodiments sterile) solvent suitable for dissolving or suspending the composition of the presently disclosed subject matter prior to administering the compound to the subject and/or a device suitable for administering the composition such as a syringe, injector, or the like or other device as would be apparent to one of ordinary skill in the art upon a review of the instant disclosure.

As used herein, an "instructional material" includes a publication, a recording, a diagram, or any other medium of expression which can be used to communicate the usefulness of the composition of the presently disclosed subject matter in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the presently disclosed subject matter can, for example, be affixed to a container which contains a composition of the presently disclosed subject matter or be shipped together with a container which contains the composition. Alternatively, the instructional material can be shipped separately from the container with the intention that the instructional material and the composition be used cooperatively by the recipient.

V. Synthesis

The probes and ligands of the presently disclosed subject matter can be prepared using organic group transformations known in the art of organic synthesis and as further described in the Examples below.

Figure 20:
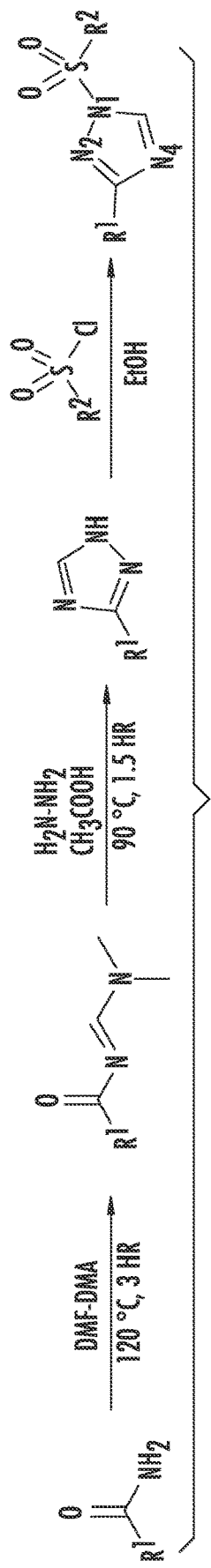
FIG. 20 is a schematic diagram showing general strategy for synthesis of a 1,2,4-sulfonyl triazole ligand library.

By way of example, SuTEx probes and ligands comprising a 1,2,4-triazole group can be prepared as shown in FIG. 20. As shown in FIG. 20, an amide starting material (e.g., a phenyl amide) can be coupled with DMF-DMA to produce an amidine intermediate. The amidine intermediate can undergo cyclization in acetic acid with hydrazine hydrate to form the corresponding 1,2,4-triazole[58]. The 1,2,4-triazole can then be reacted with a suitable sulfonyl chloride to provide the final SuTEx probe or ligand. Structures of exemplary phenyl amide starting materials that can provide diversity to the leaving group of these 1,2,4-SuTEx probes and ligands are shown in FIG. 47A. Structures of exemplary sulfonyl chlorides that can provide diversity to the adduct group of the 1,2,4-SuTEx probes are shown in FIG. 47B. Additional compounds for sulfur heterocycle exchange chemistry can be prepared by reacting the sulfonyl chlorides of FIG. 47B with other N-heteroaryl compounds, e.g., imidazole, a substituted imidazole, pyrazole, a substituted pyrazole, tetrazole, or a substituted pyrazole. See, e.g., Example 8.

SuTEx probes comprising a 1,2,3-triazole group can be prepared as using a previously reported procedure[101], involving a copper catalyzed azide-alkyne cycloaddition, as described in Scheme 3 of Example 12, below. This initial cycloaddition provides a 1,4-regioisomer of the 1,2,3-triazole, which can be converted to the 2,4-regioisomer as shown in Scheme 4 of Example 12. FIG. 48B shows the structure of exemplary sulfonyl azides that can be used in the cycloaddition to provide diversity to the adduct group of the 1,2,3-triazole-based SuTEx compounds, while FIG. 48A shows the structures of exemplary alkynes that can be used in the cycloaddition to provide diversity to the LG of the 1,2,3-triazole-based SuTEx compounds.

VI. Modified Proteins

In some embodiments, the presently disclosed subject matter provides a modified tyrosine- and/or lysine-containing protein. The modified protein can be a protein comprising the adduct formed between a tyrosine phenol group or a lysine primary amino group and a probe or ligand of the presently disclosed subject matter. The modified protein can have a different biological activity than the unmodified protein.

In some embodiments, the presently disclosed subject matter provides a modified tyrosine-containing protein comprising modified tyrosine residue comprising a structure of Formula (II):

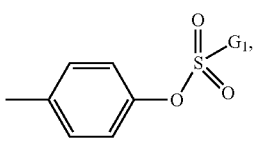

wherein $G_1$ is a monovalent moiety comprising an alkyne moiety, a fluorophore moiety, a detectable labeling group, or a combination thereof, and wherein the —S(=O)$_2$-$G_1$ group is the fragment of a non-naturally occurring synthetic molecule. In some embodiments, $G_1$ has a structure of the formula: —Ar$_2$-$G_3$, wherein Ar$_2$ is an aryl group, optionally a phenyl, naphthyl, or pyridyl group; and $G_3$ is a monovalent moiety comprising an alkylene moiety, a fluorophore moiety, a detectable labeling group, or a combination thereof.

In some embodiments, the presently disclosed subject matter provides a modified tyrosine-containing protein comprising a modified tyrosine residue wherein the modified tyrosine residue is formed by the reaction of a tyrosine residue with a non-naturally occurring compound having a structure of Formula (III):

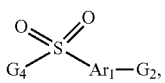

wherein Ar$_1$ is selected from the group consisting of 1,2,4-triazole, imidazole, pyrazole, and tetrazole; $G_2$ is H or an aryl group substituent (e.g., wherein $G_2$ is selected from H, aryl, and substituted aryl); and $G_4$ is selected from the group consisting of alkyl, substituted alkyl, cycloalkyl, substituted cycloalkyl, heterocycyl, aralkyl, substituted aralkyl, aryl, substituted aryl, heteroaryl, and substituted heteroaryl. Thus, in some embodiments, the modified tyrosine residue comprises a structure of Formula (II"):

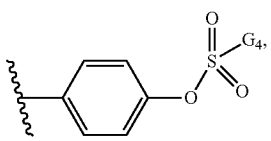

wherein $G_4$ is selected from the group consisting of alkyl, substituted alkyl, cycloalkyl, substituted cycloalkyl, heterocycyl, aralkyl, substituted aralkyl, aryl, substituted aryl, heteroaryl, and substituted heteroaryl.

The modified tyrosine-containing protein can be a protein that comprises a tyrosine residue as denoted in Table 2 or Table 3. In some embodiments, the modified tyrosine-containing protein is modified at a tyrosine residue in a RNA-recognition motif (RRM) or at a domain mediating protein-protein interactions, such as a proteasome/COP9/IF3 (PCI/PINT) or SRC homology 3 (SH3) domain. In some embodiments, the modified tyrosine-containing protein is an enzyme. In some embodiment, the modified tyrosine-containing protein is a kinase and the site of modification is in a nucleotide-binding region or wherein the site of modification is a surface residue.

In some embodiments, the modified tyrosine-containing protein is selected from the group comprising glutathione-S-transferase Pi (GSTP1), phosphoglycerate mutase 1 (PGAM1), enhancer of mRNA-decapping protein 3 (EDC3), dipeptidyl peptidase 3 (DPP3), fumarylacetoacetase (FAAA), and prostaglandin reductase 2 (PTGR2). In some embodiments, the modified tyrosine-containing protein is DPP3 modified at tyrosine position 417. In some embodiments, the modified tyrosine residue at position 417 of DPP3 is a tyrosine modified by JWB142 (i.e., a modified tyrosine residue where $G_4$ in the structure of Formula (II") is biphenyl). In some embodiments, the modified tyrosine-containing protein is PGAM1 modified at tyrosine position 92. In some embodiments, the modified tyrosine-containing protein is GSTP1 modified at tyrosine position 8. In some embodiments, the modified tyrosine residue at position 8 of GSTP1 is a tyrosine modified by JWB198, JWB183, or JWB179 (i.e., a modified tyrosine residue where $G_4$ in the structure of Formula (II") is naphthyl or p-bromophenyl). In some embodiments, the modified tyrosine-containing protein is EDC3 modified at tyrosine position 475. In some embodiments, the modified tyrosine residue at position 475 of EDC3 is a tyrosine modified by EKT231 (i.e., a modified tyrosine residue where $G_4$ in the structure of Formula (II") is p-cyanophenyl). In some embodiments, the modified tyrosine-containing protein is FAAA modified at tyrosine position 244. In some embodiments, the modified tyrosine residue at position 244 of FAAA is a tyrosine modified by HHS0401 (i.e., a modified tyrosine residue where $G_4$ in the structure of Formula (II") is -phenyl-C(=O)—NH-benzyl). In some embodiments, the modified tyrosine-containing protein is PTGR2 modified at tyrosine position 100. In some embodiments, the modified tyrosine residue at position 100 of PTGR2 is a tyrosine modified by HHS0701 (i.e., a modified tyrosine residue where $G_4$ in the structure of Formula (II") is -phenyl-C(=O)—NH-piperidinyl-phenyl).

In some embodiments, the presently disclosed subject matter provides a modified lysine-containing protein, wherein the modified lysine-containing protein comprises an adduct formed between a primary amino group of a lysine residue and a non-naturally molecule, such as a probe or ligand of the presently disclosed subject matter. Thus, in some embodiments, the modified lysine-containing protein comprises a modified lysine residue having the structure:

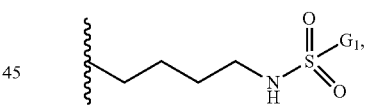

wherein $G_1$ is a monovalent moiety comprising an alkyne moiety, a fluorophore moiety, a detectable labeling group, or a combination thereof, and wherein the —S(=O)$_2$-$G_1$ group is the fragment of a non-naturally occurring synthetic molecule. In some embodiments, $G_1$ has a structure of the formula: —Ar$_2$-$G_3$, wherein Ar$_2$ is an aryl group, optionally a phenyl, naphthyl, or pyridyl group; and $G_3$ is a monovalent moiety comprising an alkylene moiety, a fluorophore moiety, a detectable labeling group, or a combination thereof.

In some embodiments, the modified lysine-containing protein comprises a modified lysine residue having the structure:

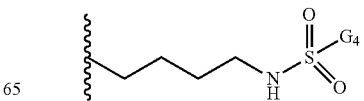

wherein $G_4$ is selected from the group consisting of alkyl, substituted alkyl, cycloalkyl, substituted cycloalkyl, heterocycyl, aralkyl, substituted aralkyl, aryl, substituted aryl, heteroaryl, and substituted heteroaryl.

In some embodiments, the modified lysine-containing protein is a protein that comprises a lysine residue as denoted in Table 1 or Table 2. In some embodiments, the modified lysine-containing protein is a kinase.

VII. Cells, Analytical Techniques and Instrumentation

In some embodiments, one or more of the methods disclosed herein comprise a sample (e.g., a cell sample, or a cell lysate sample). In some embodiments, the sample for use with the methods described herein is obtained from cells of an animal. In some instances, the animal cell includes a cell from a marine invertebrate, fish, insects, amphibian, reptile, or mammal. In some instances, the mammalian cell is a primate, ape, equine, bovine, porcine, canine, feline, or rodent. In some instances, the mammal is a primate, ape, dog, cat, rabbit, ferret, or the like. In some cases, the rodent is a mouse, rat, hamster, gerbil, hamster, chinchilla, or guinea pig. In some embodiments, the bird cell is from a canary, parakeet or parrots. In some embodiments, the reptile cell is from a turtles, lizard or snake. In some cases, the fish cell is from a tropical fish. In some cases, the fish cell is from a zebrafish (e.g. *Danio rerio*). In some cases, the worm cell is from a nematode (e.g. *C. elegans*). In some cases, the amphibian cell is from a frog. In some embodiments, the arthropod cell is from a tarantula or hermit crab.

In some embodiments, the sample for use with the methods described herein is obtained from a mammalian cell. In some instances, the mammalian cell is an epithelial cell, connective tissue cell, hormone secreting cell, a nerve cell, a skeletal muscle cell, a blood cell, or an immune system cell. Exemplary mammalian cell lines include, but are not limited to, 293A cells, 293FT cells, 293F cells, 293H cells, HEK 293 cells, CHO DG44 cells, CHO-S cells, CHO-K1 cells, and PC12 cells.

In some embodiments, the sample for use with the methods described herein is obtained from cells of a tumor cell line. In some instances, the sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the sample for use with the methods described herein is obtained from a tumor cell line. Exemplary tumor cell lines include, but are not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, $H_{1299}$, NCI-$H_{460}$, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the sample for use in the methods is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the sample is a tissue sample, such as a sample obtained from a biopsy or a tumor tissue sample. In some embodiments, the sample is a blood serum sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the samples are obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

VIII. Sample Preparation and Analysis

In some embodiments, the sample (e.g., cell sample, cell lysate sample, or comprising isolated proteins) is a sample solution. In some instances, the sample solution comprises a solution such as a buffer (e.g. phosphate buffered saline) or a media. In some embodiments, the media is an isotopically labeled media. In some instances, the sample solution is a cell solution.

In some embodiments, the sample (e.g., cell sample, cell lysate sample, or comprising isolated proteins) is incubated with one or more compound probes for analysis of protein-probe interactions. In some instances, the sample (e.g., cell sample, cell lysate sample, or comprising isolated proteins) is further incubated in the presence of an additional compound probe prior to addition of the one or more probes. In other instances, the sample (e.g., cell sample, cell lysate sample, or comprising isolated proteins) is further incubated with a non-probe small molecule ligand, in which the non-probe small molecule ligand does not contain a photoreactive moiety and/or an alkyne group. In such instances, the sample is incubated with a probe and non-probe small molecule ligand for competitive protein profiling analysis.

In some cases, the sample is compared with a control. In some cases, a difference is observed between a set of probe protein interactions between the sample and the control. In some instances, the difference correlates to the interaction between the small molecule fragment and the proteins.

In some embodiments, one or more methods are utilized for labeling a sample (e.g. cell sample, cell lysate sample, or comprising isolated proteins) for analysis of probe protein interactions. In some instances, a method comprises labeling the sample (e.g. cell sample, cell lysate sample, or comprising isolated proteins) with an enriched media. In some cases, the sample (e.g. cell sample, cell lysate sample, or comprising isolated proteins) is labeled with isotope-labeled amino acids, such as $^{13}C$ or $^{15}N$-labeled amino acids. In some cases, the labeled sample is further compared with a non-labeled sample to detect differences in probe protein interactions between the two samples. In some instances, this difference is a difference of a target protein and its interaction with a small molecule ligand in the labeled sample versus the non-labeled sample. In some instances, the difference is an increase, decrease or a lack of protein-probe interaction in the two samples. In some instances, the isotope-labeled method is termed SILAC, stable isotope labeling using amino acids in cell culture.

In some embodiments, a method comprises incubating a sample (e.g. cell sample, cell lysate sample, or comprising isolated proteins) with a labeling group (e.g., an isotopically labeled labeling group) to tag one or more proteins of interest for further analysis. In such cases, the detectable labeling group comprises a biotin, a streptavidin, bead, resin, a solid support, or a combination thereof, and further comprises a linker that is optionally isotopically labeled. As described above, the linker can be about 5, 6, 7, 8, 9, 10, 11, 12, 13, 14, 15 or more residues in length and might further comprise a cleavage site, such as a protease cleavage site (e.g., TEV cleavage site). In some cases, the labeling group is a biotin-linker moiety, which is optionally isotopically labeled with $^{13}C$ and $^{15}N$ atoms at one or more amino acid residue positions within the linker. In some cases, the biotin-linker moiety is a isotopically-labeled TEV-tag as previously described.[10]

In some embodiments, an isotopic reductive dimethylation (ReDi) method is utilized for processing a sample. In some cases, the ReDi labeling method involves reacting peptides with formaldehyde to form a Schiff base, which is then reduced by cyanoborohydride. This reaction dimethylates free amino groups on N-termini and lysine side chains and monomethylates N-terminal prolines. In some cases, the ReDi labeling method comprises methylating peptides from a first processed sample with a "light" label using reagents with hydrogen atoms in their natural isotopic distribution and peptides from a second processed sample with a "heavy" label using deuterated formaldehyde and cyanoborohydride. Subsequent proteomic analysis (e.g., mass spectrometry analysis) based on a relative peptide abundance between the heavy and light peptide version might be used for analysis of probe-protein interactions.

In some embodiments, isobaric tags for relative and absolute quantitation (iTRAQ) method is utilized for processing a sample. In some cases, the iTRAQ method is based on the covalent labeling of the N-terminus and side chain amines of peptides from a processed sample. In some cases, reagent such as 4-plex or 8-plex is used for labeling the peptides.

In some embodiments, the probe-protein complex is further conjugated to a chromophore, such as a fluorophore. In some instances, the probe-protein complex is separated and visualized utilizing an electrophoresis system, such as through a gel electrophoresis, or a capillary electrophoresis. Exemplary gel electrophoresis includes agarose based gels, polyacrylamide based gels, or starch based gels. In some instances, the probe-protein is subjected to a native electrophoresis condition. In some instances, the probe-protein is subjected to a denaturing electrophoresis condition.

In some instances, the probe-protein after harvesting is further fragmentized to generate protein fragments. In some instances, fragmentation is generated through mechanical stress, pressure, or chemical means. In some instances, the protein from the probe-protein complexes is fragmented by a chemical means. In some embodiments, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage KIF endosialidase CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), matrix-assisted laser desorption/ionization (MALDI-TOF), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electro spray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ER-LIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC*GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI-QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more cysteine binding proteins or protein fragments disclosed herein. In some embodiments, the NMR method includes one dimensional (1D) NMR methods, two dimensional (2D) NMR methods, solid state NMR methods and NMR chromatography. Exemplary 1D NMR methods include $^{1}$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (INADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state .sup.13Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as previously described.[10]

In some embodiments, the results from the mass spectroscopy method are analyzed by an algorithm for protein identification. In some embodiments, the algorithm combines the results from the mass spectroscopy method with a protein sequence database for protein identification. In some embodiments, the algorithm comprises ProLuCID algorithm, Probity, Scaffold, SEQUEST, or Mascot.

In accordance with the presently disclosed subject matter, as described above or as discussed in the EXAMPLES below, there can be employed conventional chemical, cellular, histochemical, biochemical, molecular biology, microbiology, recombinant DNA, and clinical techniques which are known to those of skill in the art. Such techniques are explained fully in the literature. See for example, Sambrook et al. (1989) *Molecular Cloning: A Laboratory Manual*, Cold Spring Harbor Laboratory Publications, Cold Spring Harbor, New York, United States of America; Glover (1985) DNA Cloning: A Practical Approach. Oxford Press, Oxford; Gait (1984) Oligonucleotide Synthesis: A Practical Approach, IRL Press, Oxford, England; Harlow & Lane, 1988, Antibodies, A Laboratory Manual, Cold Spring Harbor Publications, New York; Roe et al. (1996) *DNA Isolation and Sequencing: Essential Techniques*, John Wiley, New York, New York, United States of America; and Ausubel et al. (1995) Current Protocols in Molecular Biology, Greene Publishing.

IX. Therapeutic Uses and Pharmaceutical Compositions

Small molecules, such as the presently disclosed ligands and probes, present an alternative method to selectively modulate proteins and to serve as leads for the development of novel therapeutics.

Dysregulated expression of a tyrosine-containing protein, in many cases, is associated with or modulates a disease, such as an inflammatory related disease, a neurodegenerative disease, or cancer. As such, identification of a potential agonist/antagonist to a tyrosine-containing protein aids in improving the disease condition in a patient.

Thus, in some embodiments, disclosed herein are tyrosine-containing proteins that comprise one or more ligandable tyrosines. In some instances, the tyrosine-containing protein is a soluble protein or a membrane protein. In some instances, the tyrosine-containing protein is involved in one or more of a biological process such as protein transport, lipid metabolism, apoptosis, transcription, electron transport, mRNA processing, or host-virus interaction. In some instances, the tyrosine-containing protein is associated with one or more of diseases such as cancer or one or more disorders or conditions such as immune, metabolic, developmental, reproductive, neurological, psychiatric, renal, cardiovascular, or hematological disorders or conditions.

In some embodiments, disclosed herein are lysine-containing proteins that comprise one or more ligandable lysines. In some instances, the lysine-containing protein is a soluble protein. In other instances, the lysine-containing protein is a membrane protein. In some cases, the lysine-containing protein is involved in one or more of a biological process such as protein transport, lipid metabolism, apoptosis, transcription, electron transport, mRNA processing, or host-virus interaction. In additional cases, the lysine-containing protein is associated with one or more of diseases such as cancer or one or more disorders or conditions such as immune, metabolic, developmental, reproductive, neurological, psychiatric, renal, cardiovascular, or hematological disorders or conditions.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the presently disclosed subject matter provides pharmaceutical compositions comprising one or more of the presently disclosed ligands or probes. The pharmaceutical compositions comprise at least one disclosed compound, e.g. selected from compounds of Formula (I), (Ia), (Ib), (Ic), (III), and (IV) and related formulas described herein in combination with a pharmaceutically acceptable carrier, vehicle, or diluent, such as an aqueous buffer at a physiologically acceptable pH (e.g., pH 7 to 8.5), a non-aqueous liquid, a polymer-based nanoparticle vehicle, a liposome, and the like. The pharmaceutical compositions can be delivered in any suitable dosage form, such as a liquid, gel, solid, cream, or paste dosage form. In one embodiment, the compositions can be adapted to give sustained release of the probe.

In some embodiments, the pharmaceutical compositions include, but are not limited to, those forms suitable for oral, rectal, nasal, topical, (including buccal and sublingual), transdermal, vaginal, parenteral (including intramuscular, subcutaneous, and intravenous), spinal (epidural, intrathecal), central (intracerebroventricular) administration, in a form suitable for administration by inhalation or insufflation. The compositions can, where appropriate, be provided in discrete dosage units. The pharmaceutical compositions of the invention can be prepared by any of the methods well known in the pharmaceutical arts. Some preferred modes of administration include intravenous (i.v.), intraperitoneal (i.p.), topical, subcutaneous, and oral.

Pharmaceutical formulations suitable for oral administration include capsules, cachets, or tablets, each containing a predetermined amount of one or more of the ligands, as a powder or granules. In another embodiment, the oral composition is a solution, a suspension, or an emulsion. Alternatively, the ligands can be provided as a bolus, electuary, or paste. Tablets and capsules for oral administration can contain conventional excipients such as binding agents, fillers, lubricants, disintegrants, colorants, flavoring agents, preservatives, or wetting agents. The tablets can be coated according to methods well known in the art, if desired. Oral liquid preparations include, for example, aqueous or oily suspensions, solutions, emulsions, syrups, or elixirs. Alternatively, the compositions can be provided as a dry product for constitution with water or another suitable vehicle before use. Such liquid preparations can contain conventional additives such as suspending agents, emulsifying agents, non-aqueous vehicles (which may include edible oils), preservatives, and the like. The additives, excipients, and the like typically will be included in the compositions for oral administration within a range of concentrations suitable for their intended use or function in the composition, and which are well known in the pharmaceutical formulation art. The presently disclosed ligands will be included in the compositions within a therapeutically useful and effective concentration range, as determined by routine methods that are well known in the medical and pharmaceutical arts. For example, a typical composition can include one or more of the ligands at a concentration in the range of at least about 0.01 nanomolar to about 1 molar, preferably at least about 1 nanomolar to about 100 millimolar.

Pharmaceutical compositions for parenteral, spinal, or central administration (e.g. by bolus injection or continuous infusion) or injection into amniotic fluid can be provided in unit dose form in ampoules, pre-filled syringes, small volume infusion, or in multi-dose containers, and preferably include an added preservative. The compositions for parenteral administration can be suspensions, solutions, or emulsions, and can contain excipients such as suspending agents, stabilizing agents, and dispersing agents. Alternatively, the ligands can be provided in powder form, obtained by aseptic isolation of sterile solid or by lyophilization from solution, for constitution with a suitable vehicle, e.g. sterile, pyrogen-free water, before use. The additives, excipients, and the like typically will be included in the compositions for parenteral administration within a range of concentrations suitable for their intended use or function in the composition, and which are well known in the pharmaceutical formulation art. The ligands of the presently disclosed subject matter can be included in the compositions within a therapeutically useful and effective concentration range, as determined by routine methods that are well known in the medical and pharmaceutical arts. For example, a typical composition can include one or more of the ligands at a concentration in the range of at least about 0.01 nanomolar to about 100 millimolar, preferably at least about 1 nanomolar to about 10 millimolar.

Pharmaceutical compositions for topical administration of the ligands to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like. The additives, excipients, and the like typically will be included in the compositions for topical administration to the epidermis within a range of concentrations suitable for their intended use or function in the composition, and which are well known in the pharmaceutical formulation art. The ligands of the presently disclosed subject matter can be included in the compositions within a therapeutically useful and effective concentration range, as determined by routine methods that are well known in the medical and pharmaceutical arts. For example, a typical composition can include one or more of the ligands at a concentration in the range of at least about 0.01 nanomolar to about 1 molar, preferably at least about 1 nanomolar to about 100 millimolar.

Pharmaceutical compositions suitable for topical administration in the mouth (e.g., buccal or sublingual administration) include lozenges comprising the ligand in a flavored base, such as sucrose, acacia, or tragacanth; pastilles comprising the ligand in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired. The additives, excipients, and the like typically will be included in the compositions of topical oral administration within a range of concentrations suitable for their intended use or function in the composition, and which are well known in the pharmaceutical formulation art. The ligands of the presently disclosed subject matter invention can be included in the compositions within a therapeutically useful and effective concentration range, as determined by routine methods that are well known in the medical and pharmaceutical arts. For example, a typical composition can include one or more of the ligands at a concentration in the range of at least about 0.01 nanomolar to about 1 molar, preferably at least about 1 nanomolar to about 100 millimolar.

A pharmaceutical composition suitable for rectal administration comprises a ligand of the presently disclosed subject matter in combination with a solid or semisolid (e.g., cream or paste) carrier or vehicle. For example, such rectal compositions can be provided as unit dose suppositories. Suitable carriers or vehicles include cocoa butter and other materials commonly used in the art. The additives, excipients, and the like typically will be included in the compositions of rectal administration within a range of concentrations suitable for their intended use or function in the composition, and which are well known in the pharmaceutical formulation art. The ligands of the presently disclosed subject matter can be included in the compositions within a therapeutically useful and effective concentration range, as determined by routine methods that are well known in the medical and pharmaceutical arts. For example, a typical composition can include one or more of the ligands at a concentration in the range of at least about 0.01 nanomolar to about 1 molar, preferably at least about 1 nanomolar to about 100 millimolar.

According to one embodiment, pharmaceutical compositions of the present invention suitable for vaginal administration are provided as pessaries, tampons, creams, gels, pastes, foams, or sprays containing a ligand of the presently disclosed subject matter in combination with a carriers as are known in the art. Alternatively, compositions suitable for vaginal administration can be delivered in a liquid or solid dosage form. The additives, excipients, and the like typically will be included in the compositions of vaginal administration within a range of concentrations suitable for their intended use or function in the composition, and which are well known in the pharmaceutical formulation art. The ligands of the presently disclosed subject matter will be included in the compositions within a therapeutically useful and effective concentration range, as determined by routine methods that are well known in the medical and pharmaceutical arts. For example, a typical composition can include one or more of the presently disclosed ligands at a concentration in the range of at least about 0.01 nanomolar to about 1 molar, preferably at least about 1 nanomolar to about 100 millimolar.

Pharmaceutical compositions suitable for intra-nasal administration are also encompassed by the present invention. Such intra-nasal compositions comprise a ligand of the presently disclosed subject matter in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising the ligand. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of the ligand. Alternatively, pharmaceutical compositions for administration by inhalation or insufflation can be provided in the form of a dry powder composition, for example, a powder mix of the ligand and a suitable powder base such as lactose or starch. Such powder composition can be provided in unit dosage form, for example, in capsules, cartridges, gelatin packs, or blister packs, from which the powder can be administered with the aid of an inhalator or insufflator. The additives, excipients, and the like typically will be included in the compositions of intra-nasal administration within a range of concentrations suitable for their intended use or function in the composition, and which are well known in the pharmaceutical formulation art. The ligand of the presently disclosed subject matter will be included in the compositions within a therapeutically useful and effective concentration range, as determined by routine methods that are well known in the medical and pharmaceutical arts. For example, a typical composition can include one or more ligand at a concentration in the range of at least about 0.01 nanomolar to about 1 molar, preferably at least about 1 nanomolar to about 100 millimolar.

Optionally, the pharmaceutical compositions of the presently disclosed subject matter can include one or more other therapeutic agent, e.g., as a combination therapy. The additional therapeutic agent will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration can be lower than a typical monotherapy concentration if there is a synergy when combined with a ligand of the presently disclosed subject matter.

X. Kits/Articles of Manufacture

Disclosed herein, in certain embodiments, are kits and articles of manufacture for use with one or more methods described herein. In some embodiments, described herein is a kit for generating a protein comprising a detectable group and/or a fragment of a ligand compound described herein. In some embodiments, such kit includes a probe or ligand as described herein, small molecule fragments or libraries, and/or controls, and reagents suitable for carrying out one or more of the methods described herein. In some instances, the kit further comprises samples, such as a cell sample, and suitable solutions such as buffers or media. In some embodiments, the kit further comprises recombinant proteins for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use. For example, the container(s) include probes, ligands, control compounds, and one or more reagents for use in a method disclosed herein.

The presently disclosed kits and articles of manufacture optionally include an identifying description or label or instructions relating to its use in the methods described herein. For example, a kit typically includes labels listing contents and/or instructions for use, and package inserts with instructions for use. A set of instructions will also typically be included. In some embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. The label also indicates directions for use of the contents, such as in the methods described herein.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Without further description, it is believed that one of ordinary skill in the art can, using the preceding description and the following illustrative EXAMPLES, make and utilize the compounds of the presently disclosed subject matter and practice the methods of the presently disclosed subject matter. The following EXAMPLES therefore particularly point out embodiments of the presently disclosed subject matter and are not to be construed as limiting in any way the remainder of the disclosure.

Example 1

SuTEx Probe Synthesis
General Methods and Materials

All chemicals used were reagent grade and used as supplied, except where noted. N,N-Dimethylformamide (DMF), dichloromethane (DCM), toluene and tetrahydrofuran (THF) were used without any further purification steps. Analytical thin layer chromatography (TLC) was performed on Merck silica gel 60 F254 plates (0.25 mm). Flash column chromatography was carried out using forced flow of the indicated solvent on Silica Gel 60 (230-400 mesh) purchased from Fisher Scientific (Hampton, New Hampshire, United States of America). Compounds were visualized by UV-irradiation and iodine chamber. Analytical HPLC chromatograms were recorded on a Shimadzu 1100 Series spectrometer (Shimadzu, Kyoto, Japan). $^1$H and $^{13}$C NMR spectra were recorded on a Varian Inova 500 (500 MHz) or 600 (600 MHz) spectrometers (Varian, Inc., Palo Alto, California, United States of America), or Bruker Avance III 800 (800 MHz) spectrometers (Bruker, Billerica, Massachusetts, United States of America) in CDCl$_3$, Acetone-d6, or DMSO-d6 with chemical shifts referenced to internal standards (CDCl$_3$: 7.26 ppm $^1$H, 77.16 ppm $^{13}$C; (CD$_3$)$_2$CO: 2.05 ppm $^1$H, 29.84 and 206.26 ppm $^{13}$C;

(CD₃)₂SO: 2.50 ppm ¹H, 39.52 ppm ¹³C) unless stated otherwise. Splitting patterns are indicated as s, singlet; d, doublet; t, triplet; q, quartet; m, multiplet; br, broad singlet for 1H-NMR data. NMR chemical shifts (δ) are reported in ppm and coupling constants (J) are reported in Hz. NMR studies were performed once per compound stock following standard synthetic protocols. High resolution mass spectral (HRMS) data were obtained by an Agilent 6545B LC/Q-TOF (Agilent Technologies, Santa Clara, California, United States of America). 3-(4-(Trifluoromethyl)phenyl)-1H-1,2,4-triazole, 3-Thiophen-2-yl-1H-1,2,4-triazole, 2-(1H-1,2,4-Triazol-3-yl)pyridine were synthesized according to literature procedures[57, 58].

Solvents purchased commercially were LC-MS grade. The following chemicals were purchased commercially and showed ≥95% purity: from Enamine (Kyiv, Ukraine) 1H-1,2,3-Triazole; from Fisher Scientific (Hampton, New Hampshire, United States of America) 1H-1,2,4-triazole, N,N-diisopropylethylamine, propargylamine, Hydrazine hydrate, N,N-Dimethylformamide dimethyl acetal, Acetic acid (optima LC/MS grade), Water (HPLC grade grade), and Acetonitrile (optima LC/MS grade); from Combi-Blocks (San Diego, California, United States of America) 4-(Chlorosulfonyl)benzoic acid, 3-Phenyl-1H-1,2,4-triazole, 3-(4-Methoxyphenyl)-1H-1,2,4-triazole, 3-(4-Fluorophenyl)-1H-1,2,4-triazole, 4-(Fluorosulfonyl)benzoic acid, and p-Cresol, n-Butylamine; from Acros Organics (Thermo Fisher Scientific, Waltham, Massachusetts, United States of America) 1,1,3,3-tetramethylguanidine, 99% (TMG); from Alfa Aesar (Haverhill, Massachusetts, United States of America) Caffeine.

Probe Synthesis

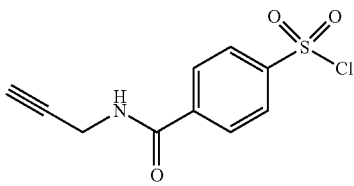 [SMILES: C#CCNC(=O)c1ccc(S(=O)(=O)Cl)cc1]

4-(Prop-2-yn-1-ylcarbamoyl)benzenesulfonyl chloride, S1 (1)

To a solution of 4-(chlorosulfonyl)benzoic acid (1.8 g, 8.2 mmol, 1.0 eq.) in DCM (41 mL) was added 1-ethyl-3-(3-dimethylaminopropyl)carbodiimide (EDCI) (1.7 g, 8.98 mmol, 1.1 eq.), and propargylamine (624 µL, 8.2 mmol, 1.0 eq.) at 0° C. and the reaction mixture was stirred for 1 h. The reaction was quenched with 1 M aqueous HCl, diluted with DCM, and the organic layer was separated. The aqueous layer was extracted with DCM. The organic layers were combined, washed with saturated aqueous NaHCO₃, dried over MgSO₄ and concentrated in vacuo. The crude product was purified by silica gel column chromatography (hexane: ethyl acetate:DCM=7:2:1 to 7:3:1, v/v/v) to give S1 (1.11 g, 53%). 1H NMR (600 MHz, CDCl₃) 8.13-8.11 (m, 2H), 8.03-8.01 (m, 2H), 6.51 (s, 1H), 4.28 (dd, J=5.2, 2.6 Hz, 2H), 2.32 (t, J=2.6 Hz, 1H). ¹³C NMR (150 MHz, CDCl₃) δ 165.02, 146.73, 139.98, 128.62, 127.55, 78.76, 72.72, 30.30. ESI-TOF (HRMS) m/z [M+H]⁺ calculated for C₁₀H₉ClNO₃S 257.9986, found 257.9990.

General Protocol to Synthesize HHS-465 (2) and HHS-475 (3)

Figure 7:
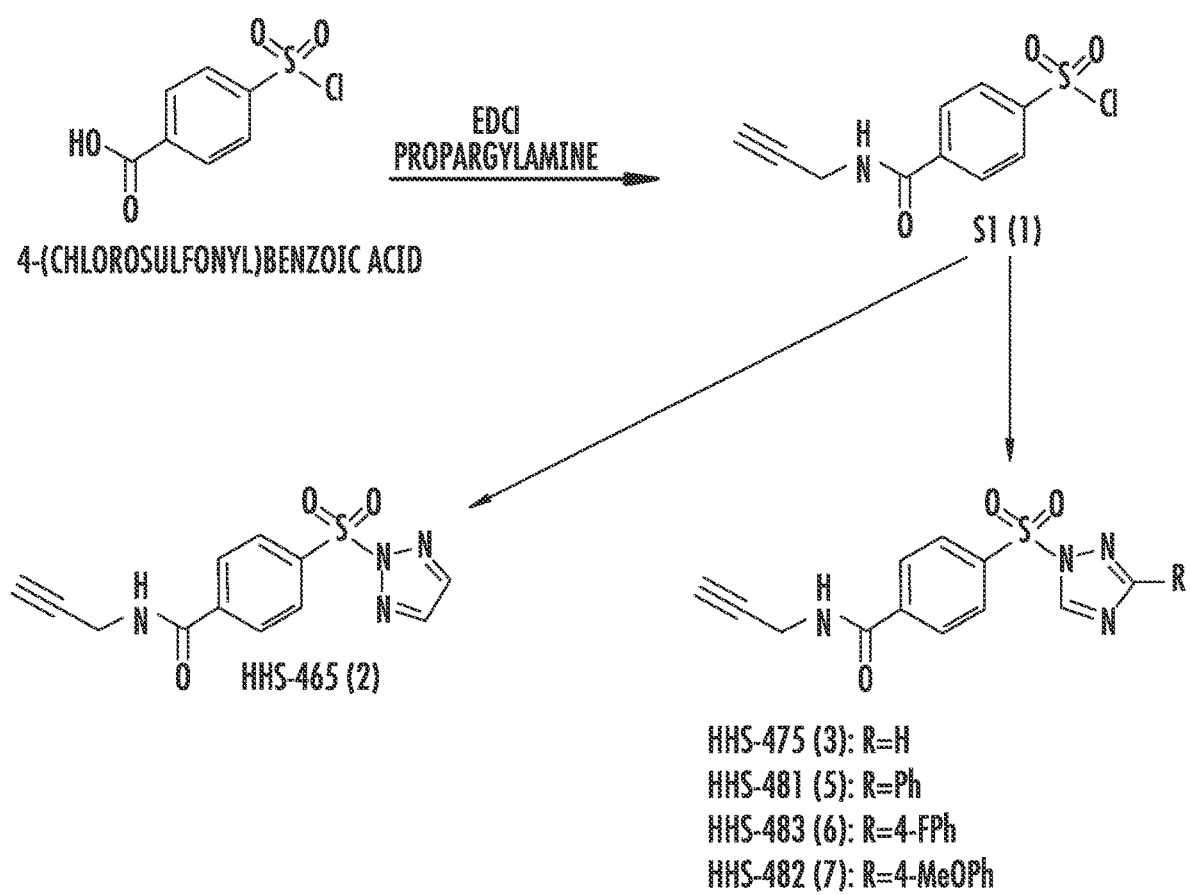

As shown in FIG. 7, to a solution of compound S1 (0.1 g, 0.39 mmol, 1.0 eq.) in anhydrous DCM (1.9 mL, 0.2 M) was added the corresponding triazole (1.94 mmol, 5.0 eq.) and N,N-diisopropylethylamine (DIPEA) (124 µL, 0.78 mmol, 2.0 eq.) at 0° C. Then the reaction mixture was stirred at room temperature for overnight. The crude product was directly loaded and purified using silica gel flash column chromatography (acetone/DCM=5:100 to 10:100) to afford HHS-465 and HHS-475, respectively.

General Protocol to Synthesize HHS-481 (5), HHS-482 (7), and HHS-483 (6)

To a solution of compound S1 (0.1 g, 0.39 mmol, 1.0 eq.) in anhydrous DCM (1.9 mL, 0.2 M) was added the corresponding triazole (0.47 mmol, 1.2 eq.) and DIPEA (124 µL, 0.47 mmol, 1.2 eq.) at 0° C. Then the reaction mixture was stirred at room temperature for overnight. The crude product was directly loaded and purified using silica gel flash column chromatography (acetone/DCM=3:100 to 7:100) to afford HHS-481, HHS-482, and HHS-483, respectively.

4-((2H-1,2,3-Triazol-2-yl)sulfonyl)-N-(prop-2-yn-1-yl)benzamide, HHS-465

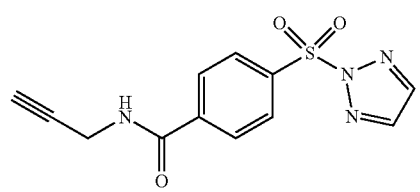

Yield: 35%, ¹H NMR (600 MHz, (CD₃)₂CO) δ 8.40 (s, 1H, NH), 8.21-8.06 (m, 6H), 4.20 (dd, J=5.5, 2.6 Hz, 2H), 2.69 (d, J=2.3 Hz, 1H). ¹³C NMR (150 MHz, (CD₃)₂CO) δ 165.34, 141.50, 140.48, 139.06, 129.61, 129.49, 80.80, 72.35, 29.78 ESI-TOF (HRMS) m/z [M+H]⁺ calculated for C₁₂H₁₁N₄O₃S 291.0546, found 291.0546.

4-((1H-1,2,4-Triazol-1-yl)sulfonyl)-N-(prop-2-yn-1-yl)benzamide, HHS-475

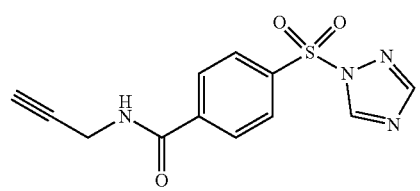

Yield: 66%, ¹H NMR (600 MHz, (CD₃)₂CO) δ 9.15 (s, 1H), 8.46 (d, J=5.7 Hz, 1H), 8.25-8.22 (m, 2H), 8.21 (s, 1H), 8.20-8.17 (m, 2H), 4.22 (dd, J=5.5, 2.6 Hz, 2H), 2.70 (t, J=2.6 Hz, 1H). ¹³C NMR (150 MHz, (CD₃)₂CO) δ 165.35, 155.46, 146.70, 141.55, 139.00, 129.62, 129.57, 80.72, 72.37, 29.75. ESI-TOF (HRMS) m/z [M+H]⁺ calculated for C₁₂H₁₁N₄O₃S 291.0546, found 291.0546.

4-((3-Phenyl-1H-1,2,4-triazol-1-yl)sulfonyl)-N-(prop-2-yn-1-yl)benzamide, HHS-481

HHS-481

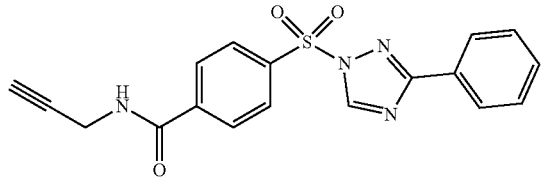

Yield: 72%, $^1$H NMR (600 MHz, (CD$_3$)$_2$CO) δ 9.18 (s, 1H), 8.38 (br, 1H, NH), 8.31-8.28 (m, 2H), 8.21-8.16 (m, 2H), 8.10-8.04 (m, 2H), 7.53-7.44 (m, 3H), 4.20 (dd, J=5.6, 2.6 Hz, 2H), 2.69 (t, J=2.6 Hz, 1H). $^{13}$C NMR (150 MHz, (CD$_3$)$_2$CO) δ 165.79, 165.33, 147.76, 141.61, 139.20, 131.45, 130.15, 129.67, 129.64, 129.62, 127.61, 80.76, 72.34, 29.72. ESI-TOF (HRMS) m/z [M+Na]$^+$ calculated for C$_{18}$H$_{14}$N$_4$NaO$_3$S 389.0679, found 389.0681.

4-((3-(4-Methoxyphenyl)-1H-1,2,4-triazol-1-yl)sulfonyl)-N-(prop-2-yn-1-yl)benzamide, HHS-482

HHS-482

Yield: 82%, $^1$H NMR (600 MHz, (CD$_3$)$_2$CO) δ 9.12 (s, 1H), 8.38 (br, 1H, NH), 8.30-8.25 (m, 2H), 8.19-8.16 (m, 2H), 8.03-7.98 (m, 2H), 7.06-7.00 (m, 2H), 4.20 (dd, J=5.6, 2.5 Hz, 2H), 3.85 (s, 3H), 2.69 (t, J=2.6 Hz, 1H). $^{13}$C NMR (150 MHz, (CD$_3$)$_2$CO) δ 165.79, 165.35, 162.68, 147.65, 141.60, 139.39, 129.67, 129.58, 129.26, 122.63, 115.05, 80.80, 72.33, 55.77, 29.75. ESI-TOF (HRMS) m/z [M+Na]$^+$ calculated for C$_{19}$H$_{16}$N$_4$NaO$_4$S 419.0784, found 419.0788.

4-((3-(4-Fluorophenyl)-1H-1,2,4-triazol-1-yl)sulfonyl)-N-(prop-2-yn-1-yl)benzamide, HHS-483

HHS-483

Yield: 77%, $^1$H NMR (600 MHz, (CD$_3$)$_2$CO) δ 9.19 (s, 1H), 8.40 (s, 1H), 8.31-8.26 (m, 2H), 8.21-8.17 (m, 2H), 8.14-8.09 (m, 2H), 7.29-7.23 (m, 2H), 4.20 (dd, J=5.5, 2.6 Hz, 2H), 2.69 (t, J=2.6 Hz, 1H). $^{13}$C NMR (150 MHz, (CD$_3$)$_2$CO) δ 165.84, 165.33, 164.92, 164.19, 147.85, 141.62, 139.13, 129.95 (d, J=8.7 Hz), 129.66 (d, J=5.7 Hz), 126.63 (d, J=3.0 Hz), 116.63 (d, J=22.1 Hz), 80.75, 72.36, 29.75. $^{19}$F NMR (564 MHz, (CD$_3$)$_2$CO) δ −111.48. ESI-TOF (HRMS) m/z [M+H]$^+$ calculated for C$_{18}$H$_{14}$FN$_4$O$_3$S 385.0765, found 385.0755.

4-(Prop-2-yn-1-ylcarbamoyl)benzenesulfonyl fluoride, HHS-SF-1 (4)

HHS-SF-1

To a solution of 4-(Fluorosulfonyl)benzoic acid (0.2 g, 0.98 mmol, 1.0 eq.) in DCM was added Ethyl-3-(3-dimethylaminopropyl)carbodiimide (EDCI) (206 mg, 1.08 mmol, 1.1 eq.), and propargylamine (68 µL, 0.98 mmol, 1.0 eq.) at 0° C. and the reaction mixture was stirred for 1 h. The reaction was quenched with 1 M aqueous HCl, diluted with DCM, and the organic layer was separated. The aqueous layer was extracted with DCM. The organic layers were combined, washed with saturated aqueous NaHCO$_3$, dried over MgSO$_4$ and concentrated in vacuo. The crude product was purified by silica gel column chromatography (hexane-ethyl acetate-DCM=7:2:1 to 7:3:1, v/v/v) to give HHS-SF-1 (145.5 mg, 62%). $^1$H NMR (600 MHz, CDCl$_3$) δ 8.08 (d, J=8.5 Hz, 2H), 8.03 (d, J=8.2 Hz, 2H), 6.69 (s, 1H), 4.27 (dd, J=5.3, 2.5 Hz, 2H), 2.31 (t, J=2.6 Hz, 1H). $^{13}$C NMR (150 MHz, CDCl$_3$) δ 165.06, 140.40, 135.84 (d, J=25.5 Hz), 128.96, 128.54, 78.77, 72.61, 30.24. $^{19}$F NMR (564 MHz, CDCl$_3$) δ +65.91. ESI-TOF (HRMS) m/z [M+H]$^+$ calculated for C$_{10}$H$_9$FNO$_3$S 242.0282, found 242.0281.

Synthesis of n-Butylamine-Probe and p-Cresol-Probe HPLC Standards

4-(N-Butylsulfamoyl)-N-(prop-2-yn-1-yl)benzamide, KY-2-42 (9)

To a solution of compound S1 (0.099 g, 0.38 mmol, 1.0 eq) in anhydrous DCM (3.8 mL, 100 mM) was added the n-butylamine (41.5 µL, 0.43 mmol, 1.1 eq) and DIPEA (73.3 µL, 0.42 mmol, 1.1 eq). The reaction was stirred at room temperature for 1.5 hours. The reaction mixture was poured into 1 M HCl aqueous solution (3.8 mL) and extracted with DCM (3.8 mL) 3 times. The organic phase was combined and washed with saturated NaHCO$_3$ (10.0 mL) and brine (10.0 mL). The solution was dried over MgSO$_4$ and evaporated under reduced pressure. The product was purified using silica gel flash column chromatography (ethyl acetate/hexane=1:2 to 1:1) to afford KY-2-42, a white powder. Yield: 86%, $^1$H NMR (600 MHz, (CD$_3$)$_2$CO) δ 8.37-8.29 (m, 1H), 8.12-8.06 (m, 2H), 7.96-7.91 (m, 2H), 6.55 (t, J=6.0 Hz, 1H), 4.22 (dd, J=5.6, 2.5 Hz, 2H), 2.93 (td, J=7.1, 6.1 Hz, 2H), 2.70 (t, J=2.5 Hz, 1H), 1.49-1.41 (m, 2H), 1.34-1.25 (m, 2H), 0.83 (t, J=7.4 Hz, 3H). $^{13}$C NMR (151 MHz, (CD$_3$)$_2$CO) δ 166.04, 144.63, 138.52, 128.94, 127.87, 81.11, 72.25, 43.66, 32.42, 29.71, 20.36, 13.87. ESI-TOF (HRMS) m/z [M+Na]$^+$ calculated for C$_{14}$H$_{18}$N$_2$NaO$_3$S 317.0930 found 317.0930.

p-Tolyl 4-(prop-2-yn-1-ylcarbamoyl)benzene-sulfonate, KY-2-48 (8)

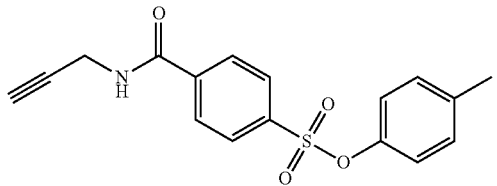 [SMILES: C#CCNC(=O)c1ccc(S(=O)(=O)Oc2ccc(C)cc2)cc1]

To a solution of compound S1 (0.041 g, 0.14 mmol, 1.0 eq.) in anhydrous DCM (1.4 mL, 100 mM) was added the p-cresol (15.7 μL, 0.15 mmol, 1.1 eq.), DIPEA (19.1 μL, 0.15 mmol, 1.1 eq) and DMAP (3.4 mg, 0.03 mmol, 0.2 eq). The reaction was stirred at room temperature for 1 hour. The reaction mixture was poured into 1 M HCl aqueous solution (1.4 mL) and extracted with DCM (1.4 mL) 3 times. The organic phase was combined and washed with saturated NaHCO$_3$ (1.4 mL) and brine (1.4 mL). The solution was dried over MgSO$_4$ and evaporated under reduced pressure. The purification was carried out using silica gel flash column chromatography (ethyl acetate/hexane=1:3 to 1:1) to afford KY-2-48, a colorless oil. Yield: 70%, $^1$H NMR (600 MHz, CDCl$_3$) δ 7.92-7.88 (m, 2H), 7.88-7.84 (m, 2H), 7.07-7.03 (m, 2H), 6.84-6.80 (m, 2H), 6.55 (t, J=5.3 Hz, 1H), 4.25 (dd, J=5.2, 2.5 Hz, 2H), 2.31-2.26 (m, 4H). $^{13}$C NMR (151 MHz, CDCl$_3$) δ 165.31, 147.19, 138.88, 138.23, 137.39, 130.26, 128.87, 127.83, 121.84, 78.79, 72.35, 30.02, 20.84. ESI-TOF (HRMS) m/z [M+Na]$^+$ calculated for C$_{17}$H$_{15}$NNaO$_4$S 352.0614 found 352.0620.

Data Availability

Crystallographic data for small molecules has been deposited in the Cambridge Crystallographic Data Centre (Cambridge, United Kingdom) and have been assigned the following deposition numbers HHS-465 (CCDC 1954297), HHS-475 (CCDC 1954298), HHS-483 (CCDC 1954299).

HPLC Analysis of Compound Purity

The purity of compounds was determined by HPLC on a Shimadzu Prominence series HPLC instrument with UV detection at 254 nm (Shimadzu, Kyoto, Japan). Chromatographic separation was performed using a Phenomenex Kinetex C18 column (2.6 μm, 50 mm×4.6 mm; Phenomenex, Torrence, California, United States of America). Mobile phases A and B were composed of H$_2$O and CH$_3$CN, respectively. Using a constant flow rate of 0.4 mL/min, the mobile phase was as follows: 0-1 min, 25% B; 1-6 min 25-100% B (linear gradient); 6-8 min 100% B; 8-9 min 100-25% B; 9-10 min 25% B. All final compounds were determined to be >95% pure by this method. HPLC analysis of compound purity was performed once per compound stock following standard synthetic protocols Example 2

Probe Reactivity and Stability
HPLC Assay for Profiling Solution Reactivity and Stability of Sulfonyl Probes The following reagents were prepared and kept at 0° C. prior to use: 0.1 M solution of caffeine in acetonitrile (ACN), 1.0 M solution of n-butylamine, p-cresol, tetramethylguanidine (TMG), acetic acid in ACN, and 10 mM solution of the probes in a mixture of DMF-ACN (v/v=10:90) are made.

(i) p-Cresol reactivity against a probe mixture: A solution of p-cresol (16.5 μmol, 3.3 eq) was premixed with 1.1, 2.2, or 3.3 eq of TMG. To initiate the reaction, the p-cresol/TMG solution was added to a sulfonyl probe mixture of HHS-475/HHS-482/HHS-SF-1 (500 μL, 5 μmol, 1.0 eq each) and the reaction was kept at 0° C. The reaction progress was monitored by taking out a 50.0 μL aliquot of the reaction mixture at various time points followed by addition of a 10 μL quenching solution of acetic acid (0.5 M final, 5.0 μmol) and the internal caffeine standard (0.05 M final, 0.5 μmol). Sample (1.0 μL) was injected and analyzed by reverse-phase HPLC on a Shimadzu 1100 Series spectrometer (Shimadzu, Kyoto, Japan) with UV detection at 254 nm. Reaction progress was evaluated by monitoring consumption of sulfonyl probes because all probes generate a shared p-cresol and n-butylamine product. Chromatographic separation was performed using a Phenomenex Kinetex C18 column (2.6 μm, 50 mm×4.6 mm, Phemonenex, Torrance, California, United States of America). Mobile phases A and B were composed of H$_2$O (with 0.1% AcOH) and CH$_3$CN (with 0.1% AcOH), respectively. Using a constant flow rate of 0.8 mL/min, the gradient was as follows: 0-0.5 min, 15% B; 0.5-6.5 min 15-85% B (linear gradient); 6.5-7 min 85-100% B (linear gradient); 7-8.5 min 100% B; 8.5-9 min 100-15% B (linear gradient); 9-9.8 min 15% B.

(ii) n-Butylamine reactivity against a probe mixture: Reactivity of sulfonyl probes against n-butylamine (3.3 eq) was performed as described above except the amount of TMG was fixed at 3.3 eq.

(iii) Probe reactivity against a p-cresol/n-butylamine mixture: A solution of n-Butylamine (50.0 μL, 50.0 μmol, 5.0 eq), p-cresol (10.0 μL, 10.0 μmol, 1.0 eq), and TMG (5.0 μL, 5 μmol, 0.5 eq) were prepared. Probe reaction was initiated by addition of this solution to HHS-475, HHS-482, or HHS-SF-1 (10 μmol, 1.0 eq) at 0° C. Reaction progress was monitored as described above. A control experiment was also performed where equal amounts of n-butylamine (1.0 eq) and p-cresol (1.0 eq) were mixed.

(iv) Probe stability studies: Each probe was dissolved in DMSO or a solution of DMF:ACN:PBS (4:6:1 (v/v)) at the following concentrations: 20 mM of HHS-475, 20 mM HHS-SF-1, and 10 mM of HHS-482 in a final volume of 50 μL. The internal caffeine standard (0.5 μmol) was spiked into each probe sample. Probe stability was monitored at room temperature by taking 1.0 μL of sample at three time points (0, 24, and 48 hours) and analyzing probe degradation by HPLC as described above.

Example 3

Proteomics Methods
Cell Culture

Cell lines were cultured at 37° C. with 5% $CO_2$ with manufacturer recommended media supplemented with 10% fetal bovine serum (FBS, U.S. Source, Omega Scientific, Tarzana, California, United States of America) and 1% L-glutamine (Fisher Scientific, Hampton, New Hampshire, United States of America): HEK293T: DMEM; DM93, A549, Jurkat, H82: RPMI. Cells were harvested for experimental use when they reached ~90% confluency. The media was aspirated, cells washed with cold PBS (2×) and scraped from plates. The cells were pelleted by centrifugation at 400×g for 5 min, snap-frozen using liquid nitrogen and stored at −80° C. until further use.

SILAC Cell Culture

SILAC HEK293T cells were cultured at 37° C. with 5% $CO_2$ in either 'light' or 'heavy' media consisting of DMEM (Fisher Scientific, Hampton, New Hampshire, United States of America) supplemented with 10% dialyzed FBS (Omega Scientific, Tarzana, California, United States of America), 1% L-glutamine (Fisher Scientific, Hampton, New Hampshire, United States of America), penicillin/streptomycin, and isotopically-labeled amino acids. Light media was supplemented with 100 µg/mL L-arginine and 100 µg/mL L-lysine. Heavy media was supplemented with 100 µg/mL [$^{13}C_6^{15}N_4$]L-arginine and 100 µg/mL [$^{13}C_6^{15}N_2$]L-lysine. The cells were grown for 6 passages before use in proteomics experiments. Cells were washed with PBS (2×), harvested, snap-frozen using liquid nitrogen and stored at −80° C. until further use.

Transient Transfection

Recombinant protein production by transient transfection of HEK293T cells was performed as previously described[51]. The following plasmid constructs (human proteins) were purchased from GenScript: pcDNA3.1-GSTP1-FLAG, pcDNA3.1-DPP3-FLAG, pcDNA3.1-PGAM1-FLAG, pcDNA3.1-EDC3-FLAG. Site-directed mutagenesis of wild-type constructs was used to generate mutant plasmids: pcDNA3.1-GSTP1 (Y8F)-FLAG, pcDNA3.1-DPP3 (Y417F)-FLAG, pcDNA3.1-PGAM1 (Y92F)-FLAG, pcDNA3.1-EDC3 (Y475F)-FLAG.

Pervanadate Activation

Pervanadate (100 mM) was prepared as previously described[41] by mixing 100 µL of sodium orthovanadate (100 mM $Na_3VO_4$, New England BioLabs #P0758S, Ipswich, Massachusetts, United States of America) with 1 µL of hydrogen peroxide ($H_2O_2$, 30% v/v in water) on ice. The mixture was incubated on ice for 15 min followed by immediate addition to cells (1:1000, 100 µM final) and incubation for 30 min at 37° C. with 5% $CO_2$ for general inhibition of protein tyrosine phosphatases. After pervanadate treatment, cells were washed twice with cold PBS followed by harvest. Cell pellets were resuspended in PBS supplemented with protease and phosphatase inhibitor mini tablets (Thermo Scientific #A32959; ThermoFisher Scientific, Waltham, Massachusetts, United States of America) and then lysed by sonication (3×1 sec pulse, 20% amplitude). For CTNND1 western blot studies, cell pellets were lysed in NP40 Cell Lysis Buffer (#FNN0021, Invitrogen, Carlsbad, California, United States of America) supplemented with protease/phosphatase inhibitor tablets. Cell lysates were separated via centrifugation at 100,000×g for 45 min at 4° C. for western blot or chemical proteomic studies. Note: pervanadate treatments are performed on live cells but SuTEx probe labeling occurs in proteomes in vitro.

Western Blot Analysis

Western blot analysis of recombinant protein expression was performed as previously described[51]. For analysis of tyrosine phosphorylation, the protocol used was the same except the nitrocellulose blot was blocked with 3% BSA instead of 5% milk in TBS-T. The following antibodies were purchased from Cell Signaling Technology (CST, Danvers, Massachusetts, United States of America) for phosphotyrosine studies: Phospho-tyrosine (pY): P-Tyr-100 biotinylated, CST #9417S; pPKM: Phospho-PKM (Y105) Rabbit Ab, CST #3827S; PKM: PKM Rabbit Ab, CST #3198S; pSTAT3: Phospho-STAT3 (Y705) Rabbit mAb, CST #9145S; STAT3: STAT3 Mouse mAb, CST #9139S; pCTNND1: Phospho-Catenin δ-1 (Tyr228) Rabbit Ab, CST #2911; CTNND1: Catenin δ-1 Rabbit Ab, CST #4989; GAPDH: GAPDH Rabbit mAb, CST #2118S. The following secondary antibodies were used for fluorescence detection: Goat Anti-Rabbit IgG DyLight 550 Conjugated, Thermo Scientific, #84541 ThermoFisher Scientific, Waltham, Massachusetts, United States of America); Goat Anti-Mouse IgG DyLight 650 Conjugated, Invitrogen, #84545 (Invitrogen, Carlsbad, California, United States of America); Streptavidin DyLight 550 Conjugated, Thermo Scientific, #84542 (ThermoFisher Scientific, Waltham, Massachusetts, United States of America).

Gel-Based Chemical Proteomic Assay

Cell pellets were lysed in PBS by sonication and fractionated (100,000×g, 45 min, 4° C.) to generate soluble and membrane fractions. Protein concentrations were determined using the Bio-Rad DC protein assay (Bio-Rad Laboratories, Inc., Hercules, California, United States of America) and adjusted to 1 mg/mL in PBS. Proteome samples (49 µL aliquots) were treated with sulfonyl-triazole or -fluoride probes at the indicated concentrations (1 µL, 50× stock in DMSO) for 1 hr at room temperature. Probe-labeled samples were conjugated by copper-catalyzed azide-alkyne cycloaddition (CuAAC) to rhodamine-azide (1 µL of 1.25 mM stock; final concentration of 25 µM) using tris(2-carboxyethyl)phosphine (TCEP; 1 µL of fresh 50 mM stock in water; final concentration of 1 mM), tris[(1-benzyl-1H-1,2,3-triazol-4-yl)methyl]amine (TBTA, 3 µL of a 1.7 mM 4:1 t-butanol/DMSO stock, final concentration of 100 µM), and copper sulfate ($CuSO_4$, 1 µL of 50 mM stock, final concentration of 1 mM). Samples were reacted for 1 hr at room temperature, quenched with 17 µL of 4×SDS-PAGE loading buffer and beta-mercaptoethanol (βME), and quenched samples (30 µL) analyzed by SDS-PAGE gel and in-gel fluorescence scanning.

Live Cell Evaluation of Sulfonyl-Triazole Probes

Cells grown to ~90% confluency in 10 cm plates were treated with DMSO vehicle or sulfonyl-triazole probe (10 µL of 1000×DMSO stock) in serum-free media for the indicated concentrations and times at 37° C. with 5% $CO_2$. After treatment, cells were washed with cold PBS twice before harvesting and preparation for gel-based chemical proteomic evaluation as described above. For LC-MS studies, protein concentrations were normalized to 2.3 mg/mL and 432 µL (for 1 mg final protein amount) were used for sample preparation as detailed below.

Preparation of Proteomes for LC-MS/MS Analysis

Proteomes were diluted to 2.3 mg/mL in PBS and sample aliquots (432 µL) were treated with sulfonyl-triazole or -fluoride probes at the indicated concentrations (5 µL, 100× stock in DMSO), mixed gently and incubated for 1 h at room temperature. Probe-modified proteomes were subjected to CuAAC conjugation to desthiobiotin-PEG3-azide (10 µL of 10 mM stock in DMSO; final concentration of 200 µM) using TCEP (10 µL of fresh 50 mM stock in water; 1 mM final concentration), TBTA ligand (33 µL of a 1.7 mM 4:1 t-butanol/DMSO stock, 100 µM final concentration), and $CuSO_4$ (10 µL of 50 mM stock, 1 mM final concentration).

Samples were mixed by vortexing and then incubated for 1 h at room temperature. Excess reagents were removed by chloroform-methanol extraction as previously described[51]. Protein pellets were re-suspended in 500 µL of 6M urea/25 mM ammonium bicarbonate followed by DTT reduction and IAA alkylation as previously described[5]. Excess reagents were removed by chloroform/methanol extraction as described above, and the protein pellet was re-suspended in 500 µL of 25 mM ammonium bicarbonate and then digested to peptides using trypsin/Lys-C (7.5 µg in 15 µL of ammonium bicarbonate, sequencing grade from Promega, Madison, Wisconsin, United States of America) was added to the mixture and incubated for 3 hrs at 37° C. Probe-modified peptides were enriched by avidin affinity chromatography, eluted, and prepared for LC-MS analysis as previously described[51].

Preparation of SILAC Proteomes for LC-MS/MS Analysis

Heavy and light proteomes (432 µL of each) were diluted to 2.3 mg/mL in PBS. For 10:1 comparisons, heavy and light proteomes were treated with 250 µM and 25 µM of HHS465, respectively (5 µL, 100× stock in DMSO). In a control 1:1 comparison experiment both heavy and light proteome were treated with 25 µM of HHS465. Samples were mixed gently and incubated for 1 h at room temperature. Light and heavy samples were separately conjugated to desthiobiotin-PEG3-azide as described above. Light and heavy samples were mixed during the chloroform-methanol extraction step. Probe-modified peptides were prepared for LC-MS/MS analysis as described above.

LC-MS/MS Analysis of Samples

Nano-electrospray ionization-liquid chromatography-mass spectrometry analyses (LC-MS/MS) were performed using an Ultimate 3000 RSLC nanoSystem-Orbitrap Q Exactive Plus mass spectrometer (Thermo Scientific, Waltham, Massachusetts, United States of America) as previously described[51] except LC conditions were modified to use the following gradient (A: 0.1% formic acid/H$_2$O; B: 80% ACN, 0.1% formic acid in H$_2$O): 0-1:48 min 1% B, 400 nL/min; 1:48-2:00 min 1% B, 300 nL/min; 2-90 min 16% B; 90-146 25% B; 146-147 min 95% B; 147-153 min 95% B; 153-154 min 1% B; 154.0-154.1 min 1% B, 400 nL/min; 154.1-180 min 1% B, 400 nL/min. A top 10 data-dependent acquisition MS method was used.

LC-MS/MS Data Analysis

Identification of peptides and proteins from tandem mass spectrometry analyses was accomplished using the MS/MS protein and peptide search engine software package BYONIC™ (Protein Metrics Inc., Cupertino, California, United States of America).[31] Data were searched against a modified human protein database (UniProt human protein database, angiotensin I and vasoactive intestinal peptide standards; 40,660 proteins) with the following parameters: up to 3 missed cleavages to account for a lysine probe modification, 10 ppm precursor mass tolerance, 20 ppm fragment mass tolerance, too high (narrow) "precursor isotope off by x", precursor and charge assignment computed from MS1, maximum of 1 precursor per MS2, 0.01 smoothing width, 1% protein false discovery rate, variable (common) methionine oxidation (+15.9949 Da) and fixed cysteine carbamidomethylation (+57.021464 Da). Sulfonyl-probe modifications of tyrosine, lysine, and other amino acids were included as a variable (common) modification of +635.27374 Da. Search results were imported into R and filtered for fully tryptic peptides (except N- and C-terminally modified), a Byonic score of ≥300 (unless otherwise specified), and a precursor mass error between −5 ppm and +5 ppm. A Byonic score of 300 was applied for a more inclusive initial evaluation of the search results and thereby consider more possible probe-modified sites. MS1 and MS2 spectra corresponding to the highest-scoring tyrosine- and lysine (internal or non-C terminal)-modified sequences (~50-100 peptides) were manually verified. The next most frequently matched and high-scored probe-modified amino acid residues were C-terminal lysines or arginines, which were determined to be false positive matches based on manual analysis of MS2 spectra (top ~50 highest Byonic scored-matches). These findings are consistent with the observation from previous studies with other probes[11, 51] that trypsin does not cleave after a modified lysine or arginine. Distinct peptides containing probe-modified amino acid residues (termed sites) were determined by identifying all unique razor protein and site combinations across all of the proteomes tested.

Analysis and Comparison of Sulfonyl Probe Modified Amino Acid Sites

To compare amino acid residues modified by sulfonyl probes, protein and peptide identifications were accomplished as described above with variable (common) modification of +635.27374 Da on the following amino acid residues: cysteine, aspartic acid, glutamic acid, histidine, lysine, methionine, asparagine, glutamine, arginine, serine, threonine, tryptophan, and tyrosine. For these amino acid comparisons, carbamidomethylation (+57.021464 Da) of cysteines was searched as a variable/common modification to allow for the potential of probe modification on cysteines. Comparisons of probe-modified sites across all probes and cell lines tested were performed using the R package ggplot2 (online at tidyverse.org). Venn diagrams for comparisons were generated using the VennDiagram R package[52]. For amino acid comparisons, a Byonic score cutoff of 600 was used to minimize false positive identifications of modified residues, which were confirmed by manual evaluation to be incorrect assignments.

Domain Enrichment Analysis

Probe-modified sites were compared to ProRule domain annotations (available on PROSITE, release 20.8553, online at prosite.expasy.org) using the annotated human UniProt proteome (online at uniprot.org) as a database for identifying amino acid sequences that match ProRule domains. A probe-modified site that is within a ProRule domain is considered a "hit" and is counted as enrichment of a domain by the sulfonyl probe. Several sites within the same ProRule domain annotation are a considered a single hit. If a site had several annotations each one was considered a hit; for example, a modified site within the proton acceptor region of a kinase domain would be annotated as a hit for ProRules PRU10027 and PRU00159, respectively. The database count is determined by the number of non-overlapping occurrences of the domain such that calmodulin would account for 4 EF-hand domains (PRU00448). The probability of the domains P(D) in the reference UniProt human database was found to determine how frequently they exist in nature:

$$P(D) = n(D)/N$$

Where n(D) is the number of domain occurrences in the database and N is the total number of domains in the reference database. The p-values were calculated using a binomial test previously reported for GO statistical overrepresentation test[54].

$$Pvalue = \sum \binom{K}{k} P(D)^k (1 - P(D))^{K-k}$$

Binomial Test

Where K is number of domain annotation hits in the experimental data (sulfonyl probe). The p-value was then corrected for a 1% false discovery rate (FDR) using Benjamini-Hochberg correction for multiple hypothesis testing. From these statistical analyses, ProRule domains that show statistically significant overrepresentation (Q value <0.01) are used to generate bar graphs and pie charts shown in figures. Note that a −log (Q value) is used so that positive values are shown for simplicity. In order to verify that the binomial approximation to hypergeometric probability we ensured sum of all n(D) was less than 5 percent of N and verified that using a hypergeometric test did not alter the enriched domains. The enriched domains were grouped according to their function into four categories; nucleotide binding, enzyme, protein-protein interaction and undefined based on gene ontology molecular function annotation of the respective ProRule domain. Pie charts and bar graphs were generated using the ggplot2 package in R.

Classification of Protein Domains

The distinction between protein-protein interaction (PPI) and nucleotide binding domains was determined by whether the interacting partner of the domain is annotated as a peptide or a nucleotide sequence. The SH2 domain (PRU00191) which interacts with proteins featuring phosphorylated tyrosines is classified as a PPI domain, and a Homeobox DNA-binding domain (PRU00108) is classified as a nucleotide binding domain. An enzyme domain is the protein subunit that has been shown to catalyze the conversion of a substrate to a product. The Ribonuclease H domain (PRU00408) functions as an endonuclease which will interact with RNA but is classified as an enzyme domain because of its nuclease activity. Gene ontology (GO) molecular function annotations associated with the ProRule domains that inherit the annotation for catalytic activity (GO: 0003824) were applied to determine if proteins belong to the enzyme domain group. For example, the term Ribonuclease H domain (PRU00408) has the GO annotation for endonuclease activity (GO:0004519) which has catalytic activity (GO:0003824) in its ancestor chart and is therefore classified as an enzyme.

DrugBank Analysis

Proteins labeled by sulfonyl probes in live cells were compared against protein targets of FDA approved and all drugs in the DrugBank databases[33] (version 5.1.1).

Phosphosite Plus Analysis

Probe-labeled sites were searched for in the PhosphoSitePlus database[32] either unfiltered or filtered by a high-throughput reference score of 10 or greater where specified.

Nucleophilicity Data Analysis (SILAC)

Peptide and protein identification was accomplished using Byonic as previously described above. SILAC samples were searched with added masses for heavy-labeled amino acids (+10.0083 Da for R, +8.0142 Da for K) and converted into mzXML (from raw data file) and mzid (exported from Byonic) format for export into Skyline-daily[55] to determine SILAC ratios (SR) of light/heavy peptides as previously described[51]. SILAC ratios from peptides with the same probe-modified site were averaged. The SILAC ratios were then plotted using the ggplot2 package in R[56]. Nucleophilicity was defined as follows: hyper-reactive, SR≤2; mild reactivity, 2<SR≤5; low reactivity, SR>5.

GSTP1 Biochemical Substrate Assay

Recombinant GSTP1-HEK293T soluble cell proteomes were diluted to 1 mg/ml in assay buffer (100 mM $NaH_2PO_4$, pH 7.0). GSH stock solution (250 mM in water) was diluted to 4 mM in assay buffer and 25 μL of diluted GSH solution was added to each sample. A substrate stock solution of 75 mM 1-bromo-2,4-dinitrobenzene (DBNB) in ethanol was diluted to 2 mM in assay buffer. Samples (25 μL) were aliquoted into a 96 well plate and spun briefly via centrifuge. 50 μl of 2 mM BDNB was added to each well and the reaction was monitored in kinetic mode by measuring absorbance at 340 nm for 10 min on a BMG Labtech CLARIOstar® plate reader (BMG Labtech, Cary, North Carolina, United States of America).

DPP3 Biochemical Substrate Assay

Substrate assays were performed on recombinant DPP3-HEK293T soluble proteomes diluted to 1 mg/mL in assay. DPP3 sample (10 μL) was diluted to 85 μL with assay buffer and transferred to a black 96-well plate. A stock solution of DPP3 substrate (Arg-Arg β-naphthylamide trihydrochloride, 0.5 mM; Sigma-Aldrich, St. Louis, Missouri, United States of America) was diluted to 100 μM in assay buffer. Substrate solution (5 μL) was added to each sample. Samples were mixed briefly by shaking and reaction monitored in kinetic mode by measuring fluorescence at 450 nm for 10 min on a BMG Labtech CLARIOstar® plate reader (BMG Labtech, Cary, North Carolina, United States of America).

Example 4

Discussion of Examples 1-3

Discussion of Design and Synthesis of Sulfonyl-Triazole Probes

Figure 1A:
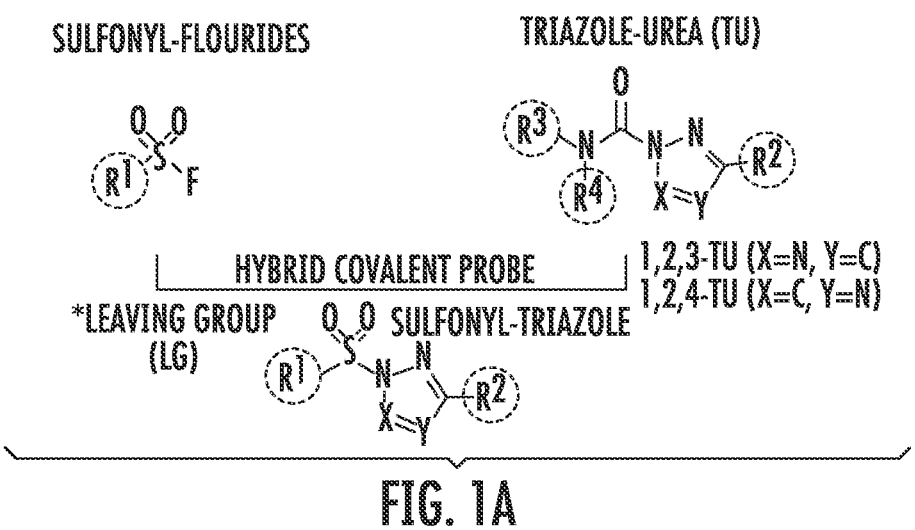

In some embodiments of the presently disclosed subject matter triazoles are used as a replacement for the fluorine LG used to promote SuFEx[24]. Previous studies have demonstrated that triazoles activate ureas for covalent protein modification with a significant advantage of tunability[29], which is not possible with fluorine as a LG by comparison. Thus, according to the presently disclosed subject matter, a sulfonyl-triazole scaffold is developed to permit evaluation, and potentially control, of reactivity and specificity of the sulfur electrophile through structural modifications to the triazole LG. See FIG. 1A. This hybrid probe strategy is further bolstered by the broad functional group tolerance of 1,2,3- and 1,2,4-triazoles as a LG for development of covalent serine hydrolase inhibitors[29, 30].

Figure 1B:
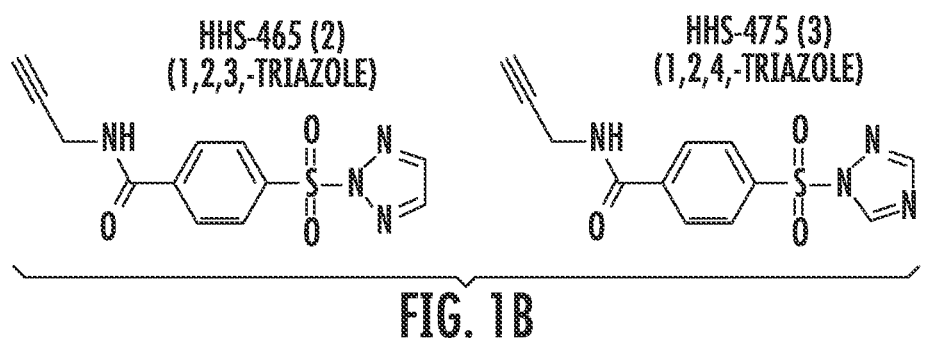

A general strategy for synthesizing sulfonyl-triazole probes for testing in chemical proteomic assays was developed. To add an alkyne reporter tag for downstream detection, a propargyl-amine was coupled to 4-(chlorosulfonyl) benzoic acid to produce an alkyne-modified sulfonyl chloride intermediate (S1) that could be further coupled to either unsubstituted or substituted triazoles. See FIG. 7. An unsubstituted triazole analog HHS-465 was synthesized as a starting point for testing LG effects on proteome reactivity. See FIG. 1B. The N2 isomeric state of HHS-465 was confirmed by NMR and x-ray crystallography. Purity of the N2-isomer was confirmed to be >95% as measured by HPLC.

Chemical Proteomic Evaluation of SuTEx Chemistry

Figure 1C:
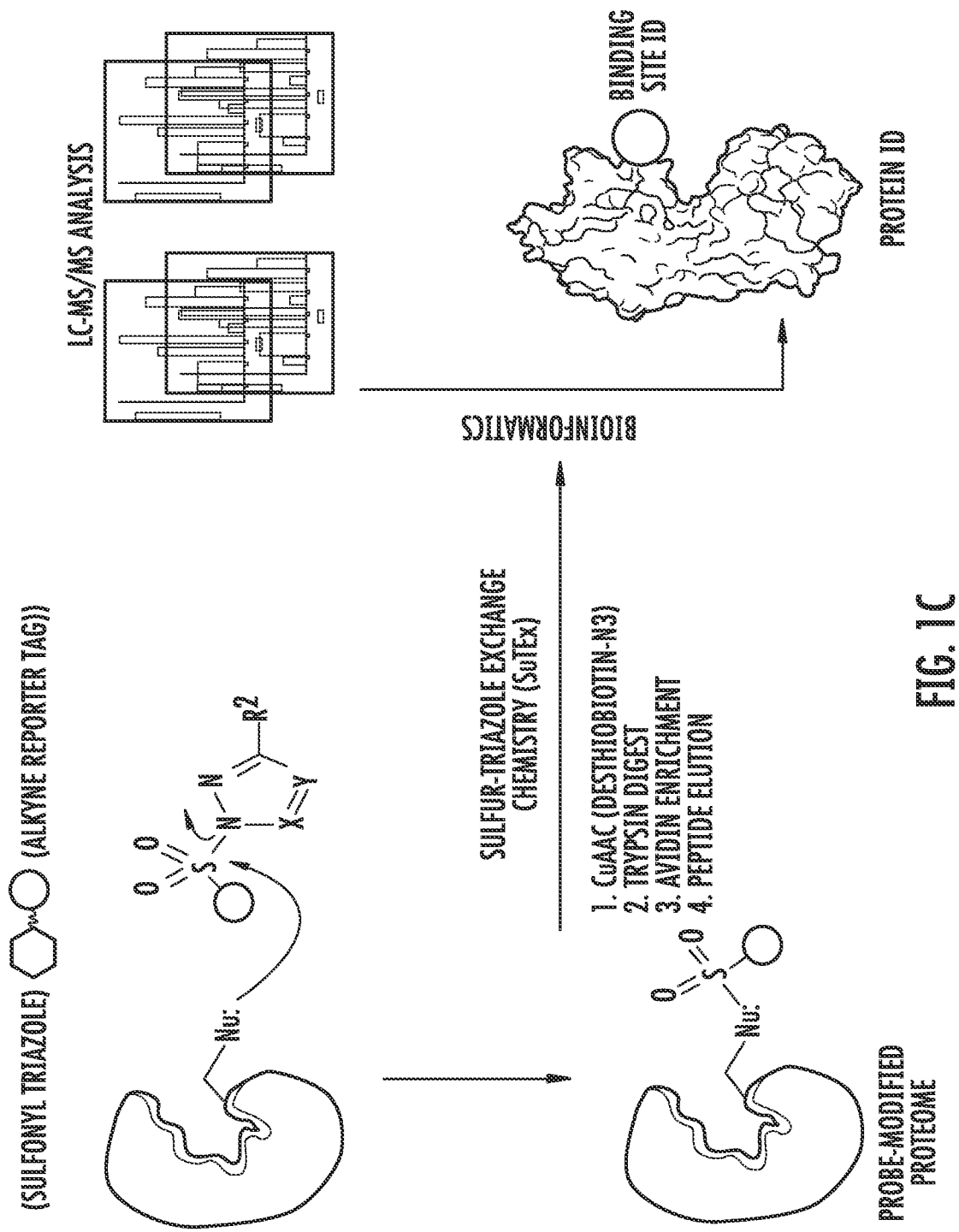

A chemical proteomic method was established to assess the reactivity of HHS-465 with amino acid residues in proteomes. HEK293T cell proteomes were treated with HHS-465 (100 μM, 1 hr, 25° C.) followed by copper-catalyzed azide-alkyne cycloaddition (CuAAC) coupling with a desthiobiotin-azide tag. Proteomes were digested with trypsin protease and desthiobiotin-modified peptides enriched by avidin affinity chromatography, released, and analyzed by high-resolution liquid chromatography-mass spectrometry (LC-MS). See FIG. 1C. Probe-modified peptide-spectrum matches (PSMs) that met a quality control confidence criteria of ≥300 Byonic score[31] and ≤5 ppm mass accuracy were selected for further manual evaluation.

Figure 1D:
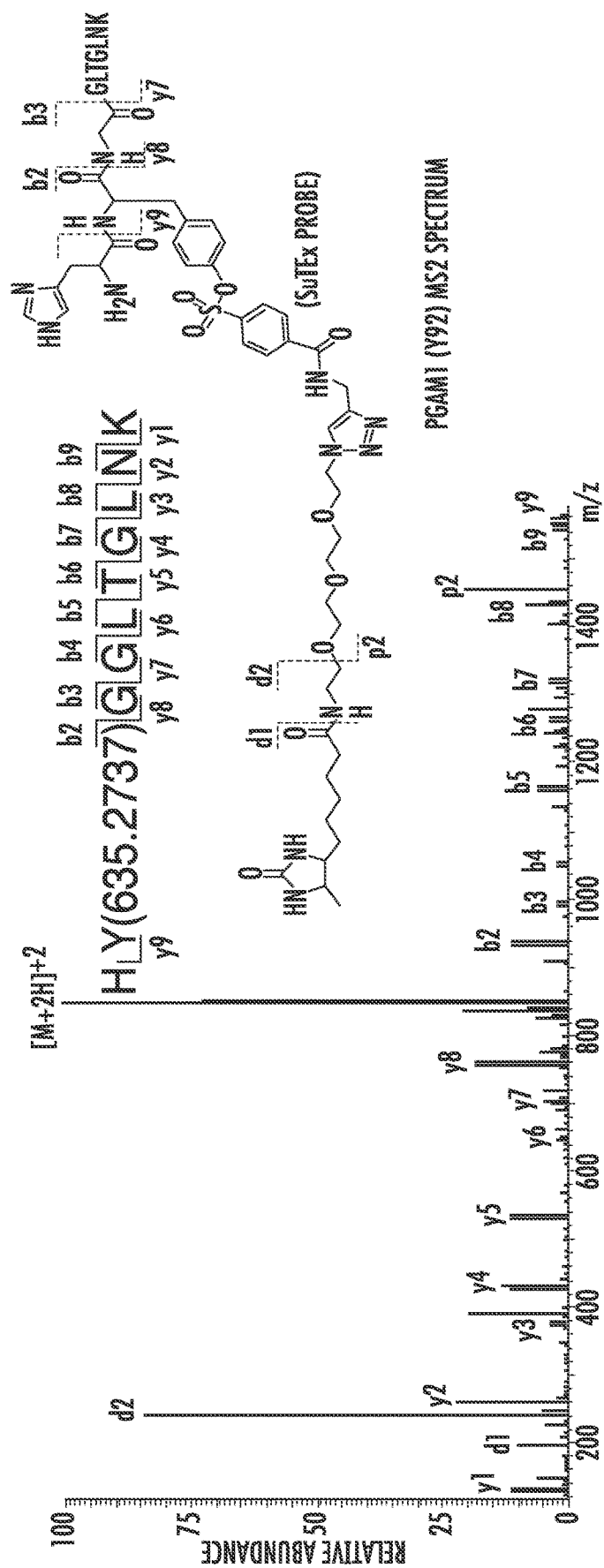
Figure 2A:
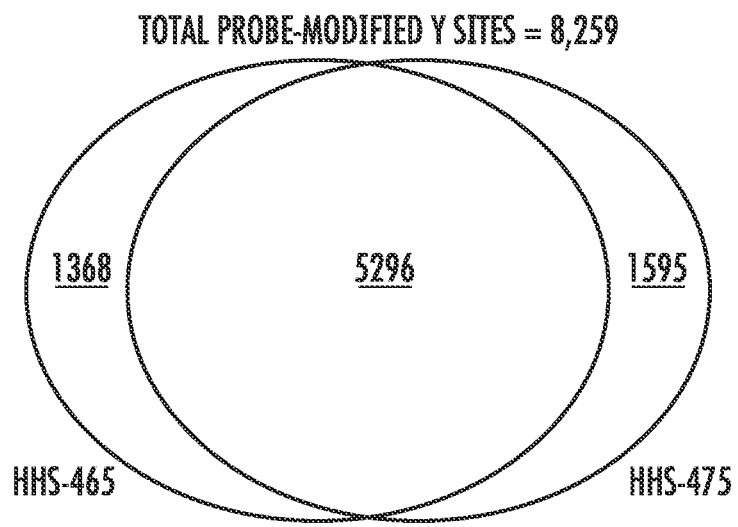
Figure 2B:
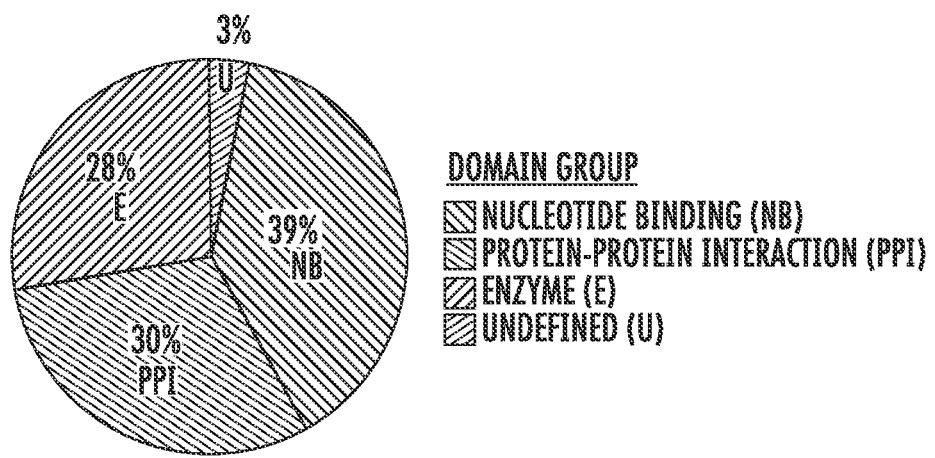
Figure 8:
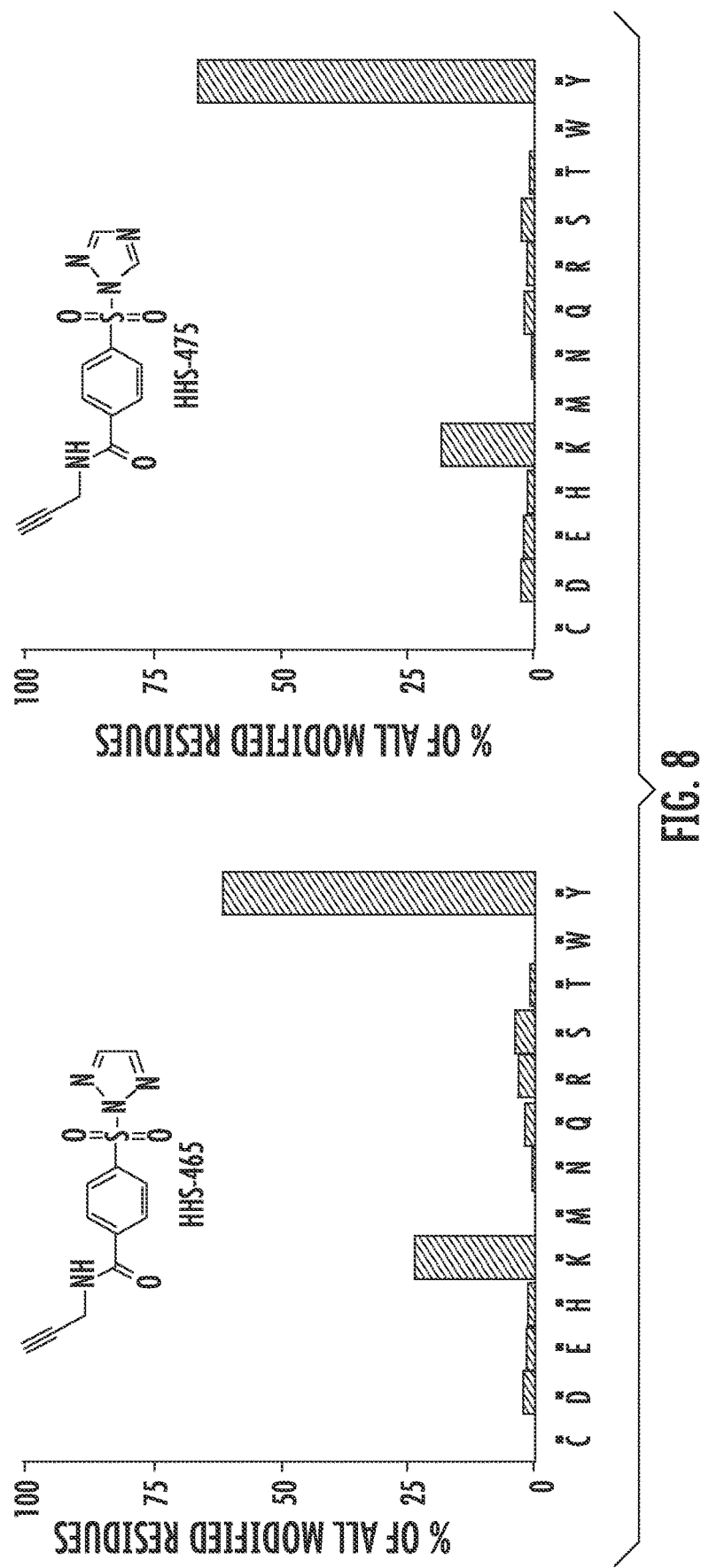

Based on the proposed reaction mechanism, amino acid residues modified by HHS-465 can be identified by differential modification with a sulfonyl-desthiobiotin adduct that is the product of SuTEx reaction. See FIG. 1C. A 1,2,4-triazole counterpart, HHS-475, was synthesized for testing to demonstrate SuTEx as a common mechanism among triazole regioisomers. See FIG. 1B. Initial evaluation of the data assigned >60% of HHS-465- and HHS-475-labeled peptides as uniquely modified tyrosines. See FIG. 8. Evaluation of MS2 spectra showed confident identification of all major y-ions and a large fraction of b-ions, including fragment ions (y and b) that allowed identification of the tyrosine site of HHS-465 and HHS-475 binding (mass adduct of 635.2737 Da). See FIG. 1D. The remaining probe-modified peptides were assigned largely to lysines, which after removal of incorrect search algorithm matches to C-terminal modified peptides represented a minor fraction of total modified residues (<25%). Additional human cell proteomes were evaluated to determine the number and type of tyrosines amenable to SuTEx reaction. On average, >2,800 tyrosines per data set and in aggregate, ~8,000 tyrosine sites from ~3,000 proteins with diverse enzymatic and non-catalytic functions were identified across 5 cell proteomes evaluated with HHS-465- and -475. See FIGS. 2A and 2B. A large fraction of HHS-465/475-modified sites were also annotated as phosphorylation sites as reported in the PhosphoSitePlus database.[32] See FIG. 2C.

Figure 9:
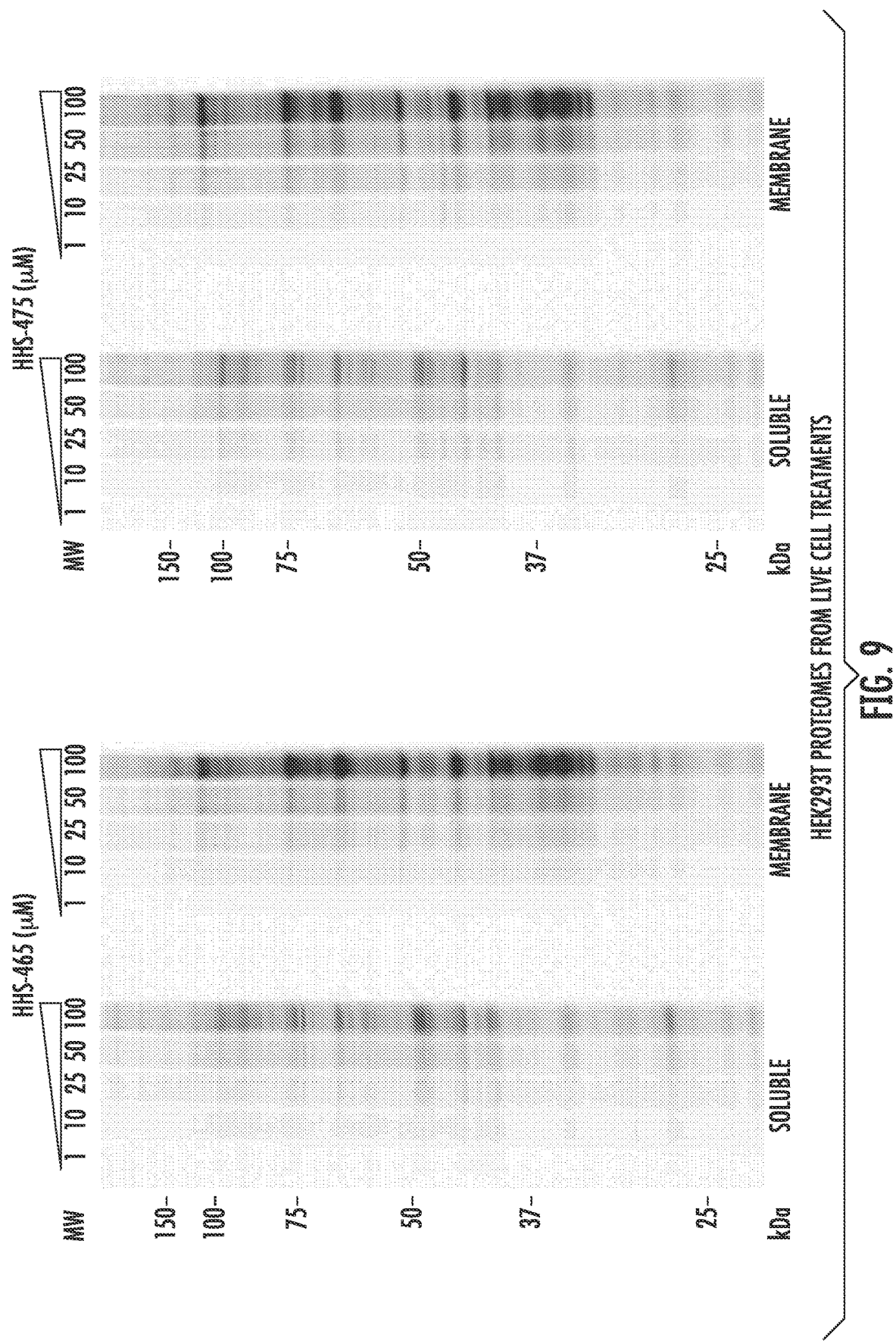
Figure 10:
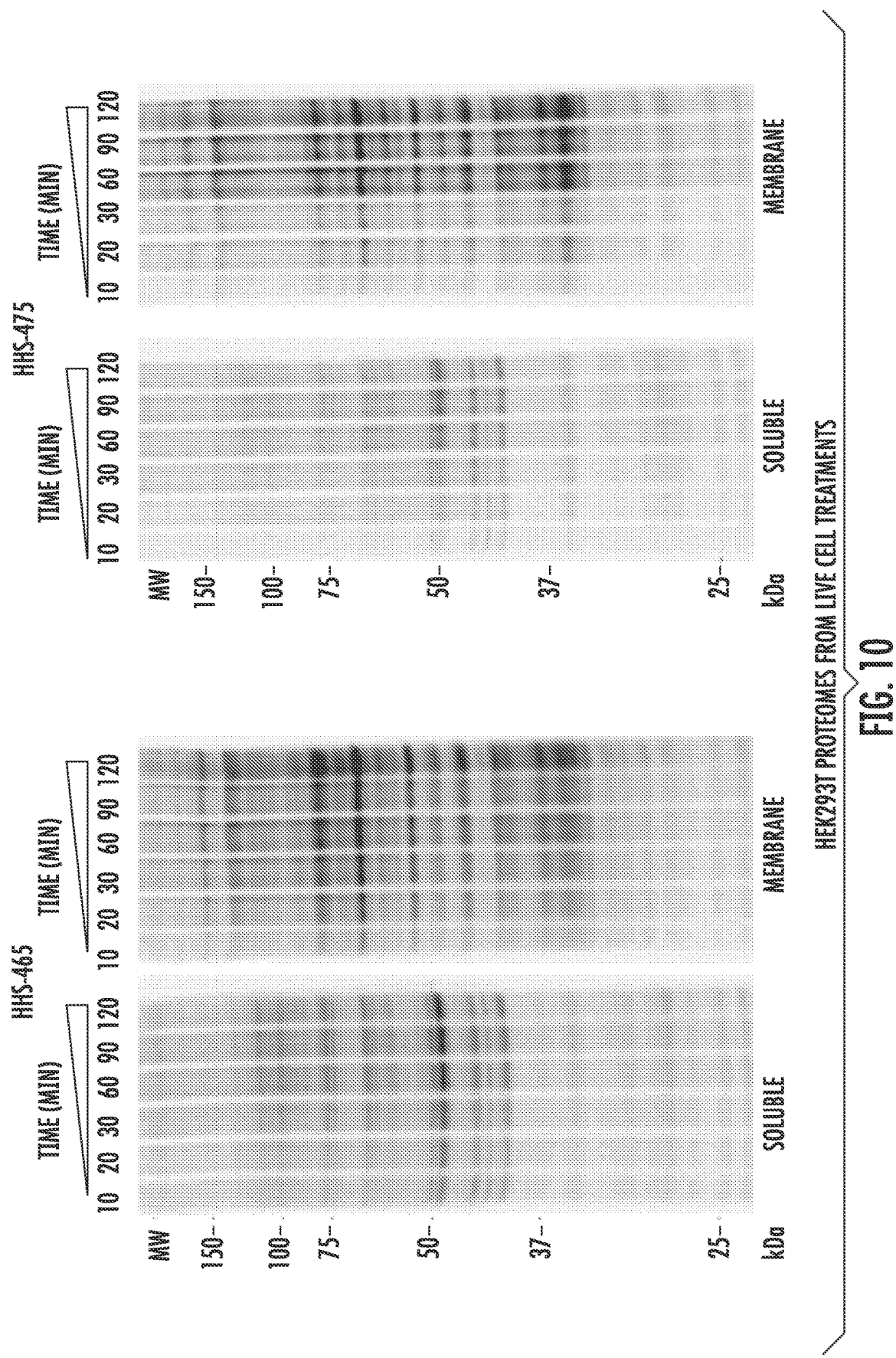

The SuTEx probes were tested to determine if they exhibit sufficient stability and cell permeability to permit global tyrosine profiling in living systems. Robust proteome labeling was observed that was concentration- and time-dependent in fluorescence gel-based analyses of proteomes from HEK293T cells treated with HHS-465 or HHS-475. See FIGS. 9 and 10. Using a saturating probe labeling condition (100 μM, 2 hr, 37° C.) for live cell studies, ~3,500 distinct tyrosine sites (corresponding to ~1,700 proteins), in total, were consistently measured across membrane and soluble fractions in each cell line tested (HEK293T, Jurkat). For comparison, recent reports using sulfonyl-fluorides showed probe modifications of ~70-130 protein targets in live cell studies[21, 25]. HHS-465- and HHS-475-labeled proteins from live cell profiling were largely absent from the DrugBank database[33] (77%). See FIG. 2D. Evaluation of probe-enriched domains (Q-values <0.01) from the non-DrugBank protein (non-DBP) group revealed highly enriched functions that include proteins involved in RNA recognition (RRM domain[34]) and protein-protein interactions (PCI/PINT and SH3 domains[35]). See FIG. 2D. By comparison, the DrugBank protein group (DBP) was largely overrepresented with domains found in enzymes (kinases and redox enzymes). See FIG. 2D.

Discovery of Hyper-Reactive Tyrosines in Human Proteomes

Figure 12:
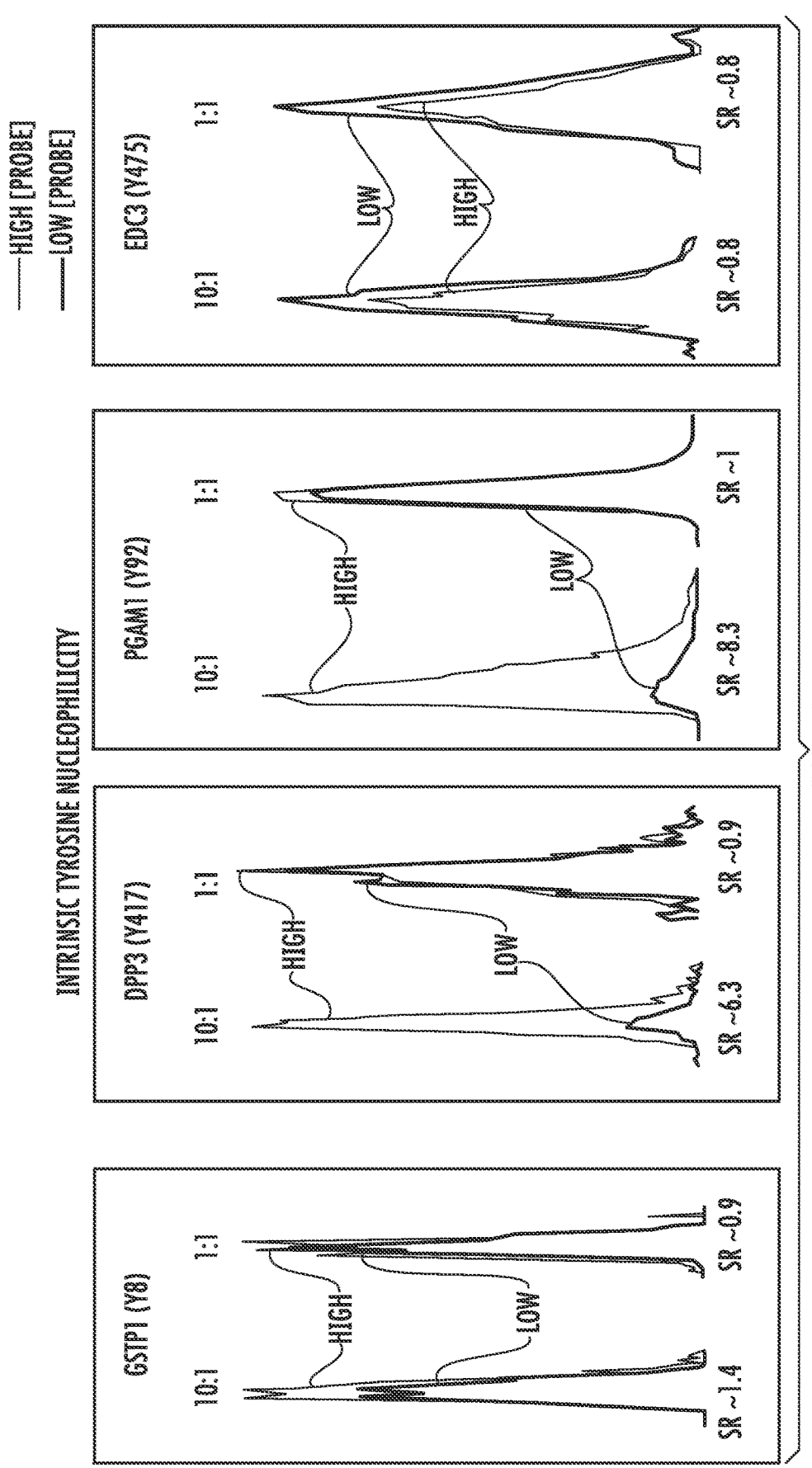

Previous studies identified a subset of hyper-reactive cysteine and lysine residues that specify function and are susceptible to binding with electrophilic ligands[10, 11]. Whether tyrosines differ in intrinsic reactivity and the functional implications of heightened nucleophilicity remain largely underexplored on a proteome-wide scale. Here, HHS-465 and quantitative chemical proteomics were used to evaluate tyrosine reactivity directly in human cell proteomes derived from isotopically light and heavy amino acid-labeled HEK293T cells (i.e. stable isotope labeling with amino acids in cell culture; SILAC[36]) Concentration-dependent HHS-465 labeling was measured where nucleophilic tyrosines are expected to exhibit comparable labeling intensity at low and high concentrations of HHS-465 while less nucleophilic tyrosines show concentration-dependent increases in probe labeling. HEK293T proteomes were treated with high versus low concentrations of HHS-465 (250 versus 25 μM; 10:1 comparison) for 1 hr (25° C.) and then samples were analyzed by quantitative LC-MS. See FIG. 11. Tyrosine nucleophilicity was segregated into low, medium, and high groups based on their respective SILAC ratios (SR>5, 2<SR<5, SR≤2, respectively). See FIG. 3A. A control experiment (25 vs 25 μM) verified that SR values were ~1 in a 1:1 comparison. See FIG. 12.

Figure 13:
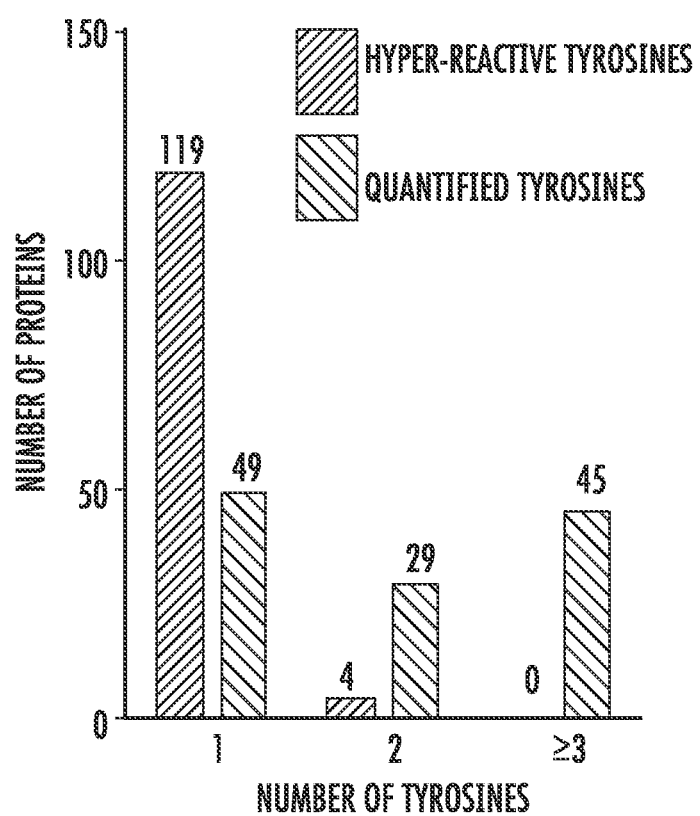

In total, ~2,400 tyrosine residues from >1,100 proteins were quantified in soluble proteomes from HEK293T cells that showed consistent SILAC ratios across replicate experiments (n=4). See FIG. 3A. The majority of quantified tyrosines showed concentration-dependent increases in HHS-465 labeling, which is indicative of low intrinsic nucleophilicity. See FIG. 3A. Similar to cysteines and lysine residues, a subset of tyrosines (~5%, 127 sites in total) demonstrated enhanced nucleophilicity (i.e. hyper-reactivity[10, 11]) as evidenced by SR<2 for 10:1 conditions. See FIG. 3A. The majority of proteins contained a single hyper-reactive tyrosine among several tyrosines quantified. See FIG. 13. Reactive tyrosines (SR<5) were enriched in domains of enzymes while tyrosines with lower reactivity (SR>5) were localized at small molecule binding sites. See FIG. 3B. Comparison of tyrosine reactivity and evidence of phosphorylation revealed an inverse correlation. For example, tyrosines with low reactivity (SR>5) were significantly overrepresented for phosphotyrosine sites compared with medium- and hyper-reactive groups (SR≤5). See FIG. 3C.

Tyrosine reactivity annotations were verified by comparing SuTEx probe labeling of recombinant wild-type (WT) and tyrosine-to-phenylalanine mutants of human proteins with tyrosine sites identified as high (Y8, GSTP1; Y475, EDC3), low/medium (Y417, DPP3), or low hyper-reactivity (Y92, PGAM1). Proteins like glutathione S-transferase Pi (GSTP1) with a single hyper-reactive tyrosine, among several modified tyrosines, showed robust HHS-475 labeling that was largely abolished in recombinant Y8F mutant. See FIG. 3D. Mutation of the hyper-reactive tyrosine in the Yjef-N domain of enhancer of mRNA decapping protein 3 (EDC3) also resulted in near-complete loss of probe labeling (Y475F). See FIG. 3D. In contrast, mutation of a tyrosine with low nucleophilicity in PGAM1 resulted in negligible alterations in probe labeling (Y92F). See FIG. 3D. A notable exception was dipeptidyl peptidase 3 (DPP3), which contains a single modified tyrosine (Y417) that, despite a low/medium nucleophilicity ratio (SR~6), showed near-complete blockade of probe labeling in corresponding tyrosine mutants (Y417F). See FIG. 3D.

Figure 14C:
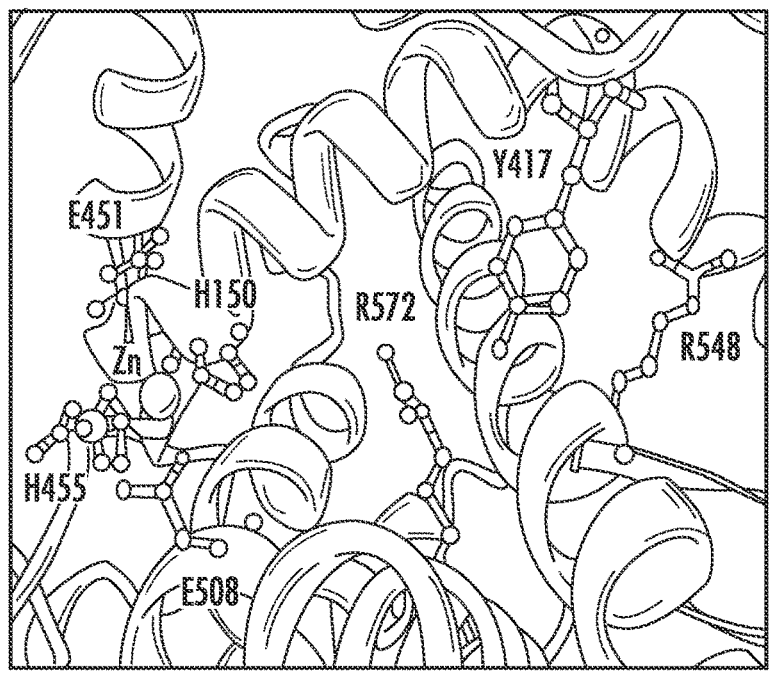
Figure 14D:
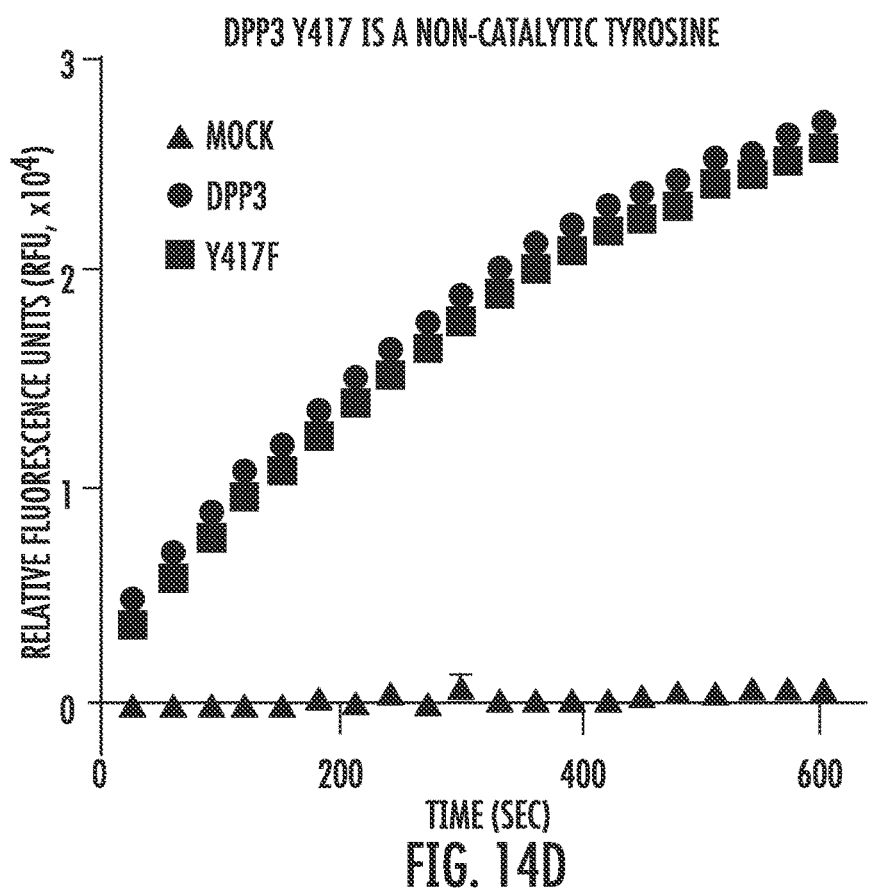
Figure 15:
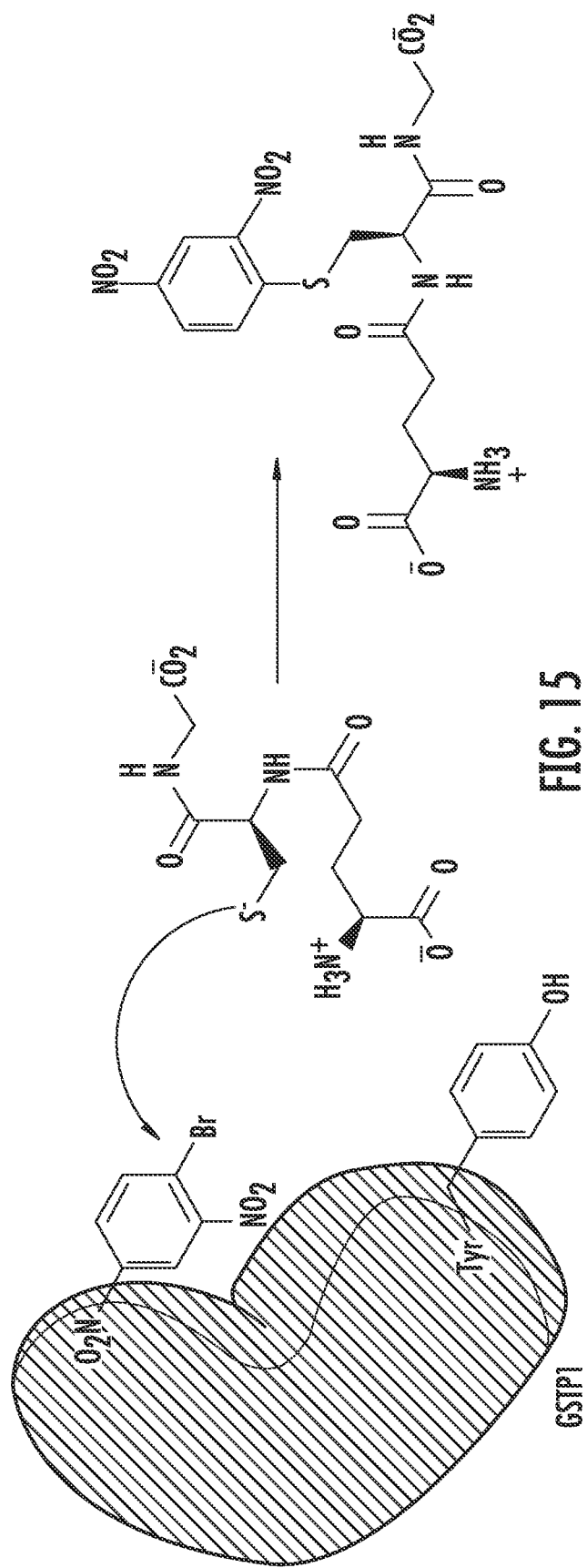

Finally, the catalytic role of GSTP1 tyrosine 8, located in the GSH binding site (G-site), was confirmed by mutating this residue (Y8F) and demonstrating abolished biochemical activity. See FIGS. 14A, 14B, and 15. In comparison, recombinant DPP3 WT- and Y417F mutant-overexpressed cell lysates showed comparable catalytic activity in a peptidase substrate assay, supporting a non-catalytic role for Y417. See FIGS. 14C, 14D, 16A, and 16B. Without being bound to any one theory, it is believed that the moderate reactivity of the non-catalytic Y417 can be exploited for DPP3 inhibitor development.

Tuning the Triazole LG for Tyrosine Chemoselectivity

An advantage of SuTEx technology is the capacity for modifying the triazole LG to tune chemoselectivity of resulting probes. Here, the ability to enhance the specificity of HHS-465/475 for tyrosine modification through addition of functional groups to the triazole was studied. See FIG. 4A. To globally evaluate probe reactivity and specificity in parallel, the total number of probe-modified sites (Y and K combined) as a function of the ratio of modified tyrosines to lysines (Y/K ratio), respectively, was compared for each SuTEx analog. First, a sulfonyl-fluoride counterpart to HHS-465/475, termed HHS-SF-1 was synthesized to directly compare fluoro- and triazole-LGs with respect to proteome specificity and reactivity. HHS-SF-1 exhibited a ~4-fold reduction in the total number of modified sites and lower specificity for tyrosine compared with HHS-465 and HHS-475 (Y/K of 2.3 versus 2.5 and 2.8, respectively). See FIG. 4A.

Figure 4A:
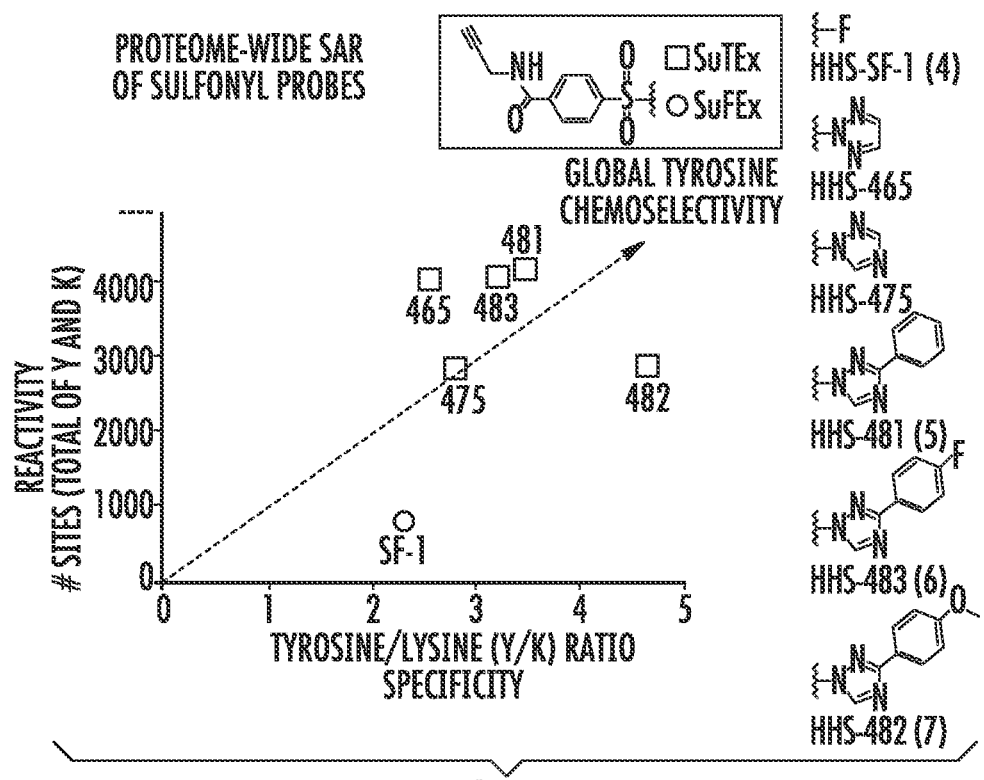
Figure 4B:
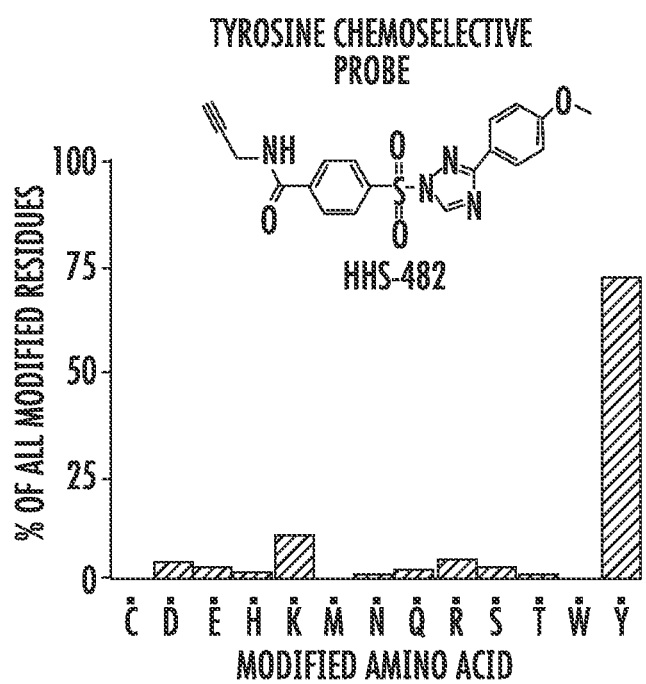

In light of the improved tyrosine specificity of HHS-475, a series of 1,2,4-triazole analogs bearing different substituents at the R2 position were synthesized and evaluated. See FIGS. 1A and 4A. Addition of a phenyl group improved both tyrosine specificity (Y/K=3.5) and overall proteome reactivity of the resulting HHS-481 probe (~4,000 total sites). FIG. 4A. Modification of the phenyl-triazole resulted in further alterations in proteome activity of SuTEx probes. Addition of a para-fluoro substituent (HHS-483) resulted in comparable reactivity and slightly lowered tyrosine specificity compared with HHS-481. See FIG. 4A. In contrast, the para-methoxy probe HHS-482 showed the highest tyrosine specificity (Y/K ratio of ~5) while maintaining good overall proteome reactivity (~3,000 probe-modified sites, HHS-482). See FIG. 4A. Evaluation of HHS-482 reactivity against other amino acids revealed high tyrosine specificity with ~75% of probe-modified residues assigned to tyrosines. See FIG. 4B.

Figure 4C:
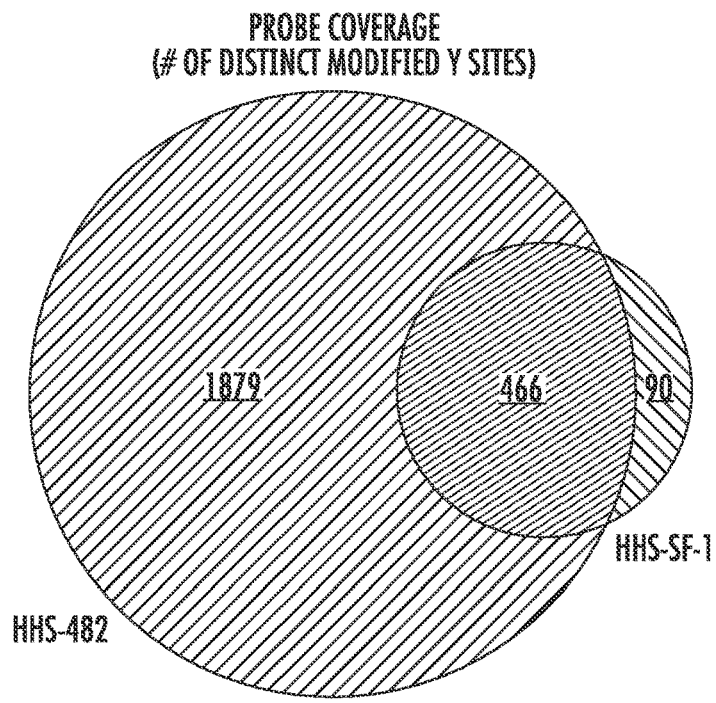
Figure 4D:
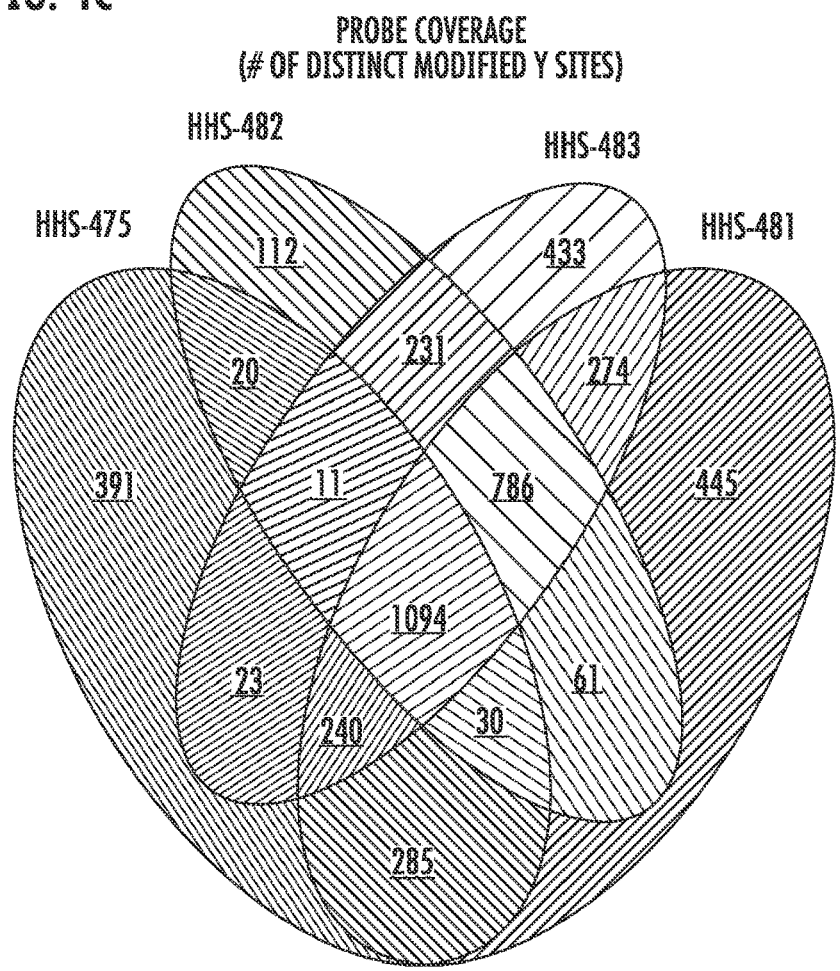

Comparison of tyrosine sites modified by HHS-SF-1 and HHS-482 revealed high overlap (>90%) indicating that substitution of fluorine for a triazole LG did not result in loss of tyrosine coverage. See FIG. 4C. In contrast, LG modifications to 1,2,4-SuTEx probes furnished analogs that each expanded tyrosine coverage via detection of unique-modified sites (HHS-475, 391 sites; HHS-482, 112 sites; HHS-483, 433 sites; HHS-481, 445 sites). See FIG. 4D. In summary, the present studies highlight a difference between sulfonyl-fluoride compared with -triazole chemistry; the latter reaction enhances overall reactivity and through LG modifications can be tuned for enhanced tyrosine chemoselectivity and coverage in proteomes. See FIGS. 4B and 4D.

Triazole LG Enhances Phenol Reactivity of Probes

Next, solution reactivity of sulfonyl probes was compared to evaluate whether the enhanced tyrosine reactivity of SuTEx is a function of the LG or protein microenvironment. An HPLC assay was developed to test reactivity of SuTEx and SuFEx probes with nucleophiles that model side chain groups of tyrosine (p-cresol) and lysine (n-butylamine). The predicted products from p-cresol (KY-2-48) and n-butylamine (KY-2-42) reaction with sulfonyl probes were synthesized to establish HPLC conditions for monitoring this covalent reaction in solution. P-cresol was incubated with a mixture of all three sulfonyl probes and the time-dependent reaction by depletion of respective SuTEx (HHS-475, HHS-482) and SuFEx (HHS-SF-1) probe signal was monitored. The probe competition studies were performed with increasing tetramethylguanidine (TMG[37]) base to compare probe reactivity as a function of increasing phenol nucleophilicity. Probe stability was also determined and all three sulfonyl probes showed negligible hydrolysis in aqueous and organic solvents even after incubation for 48 hours at room temperature.

Figure 5A:
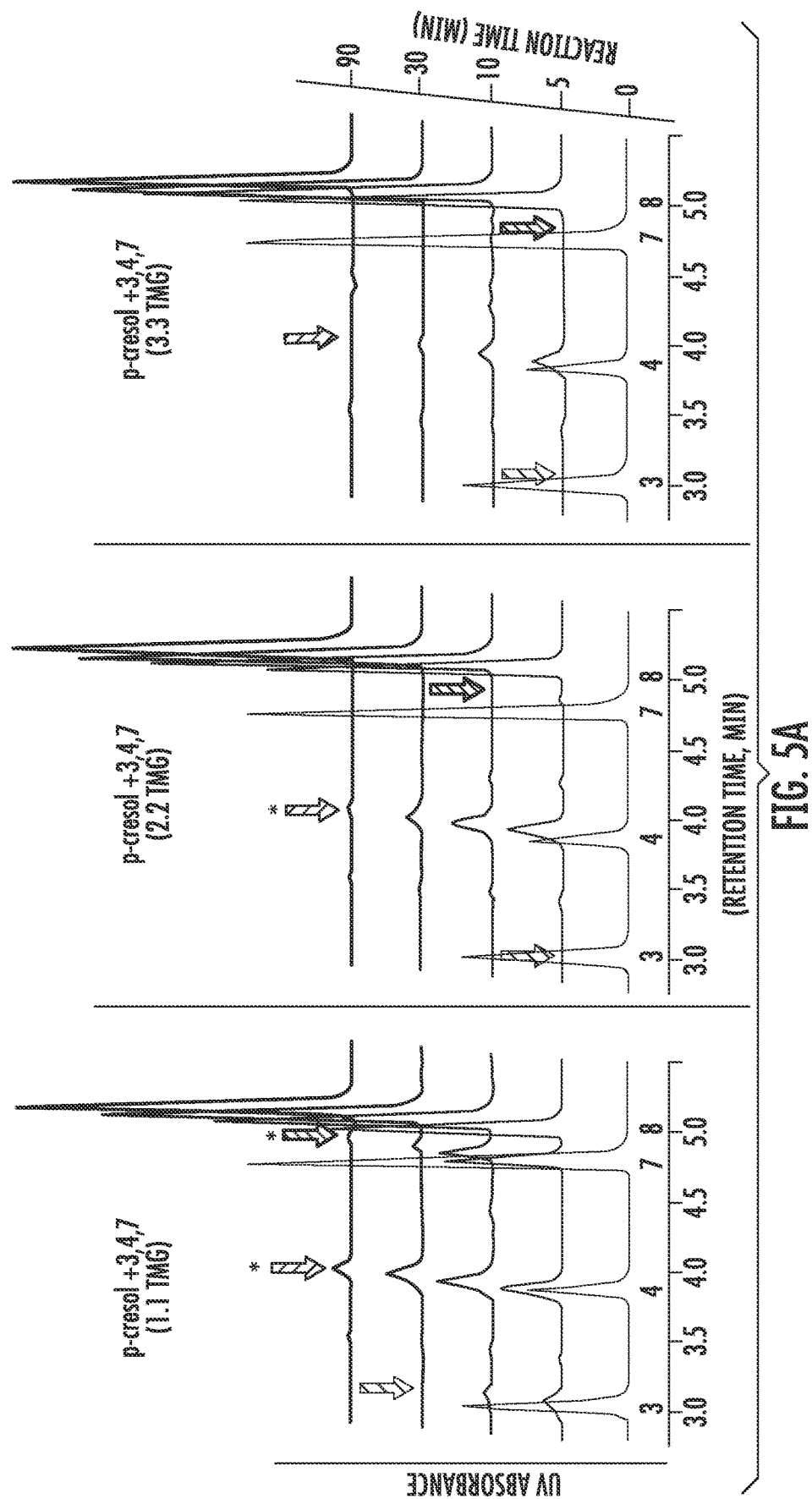
Figure 5B:
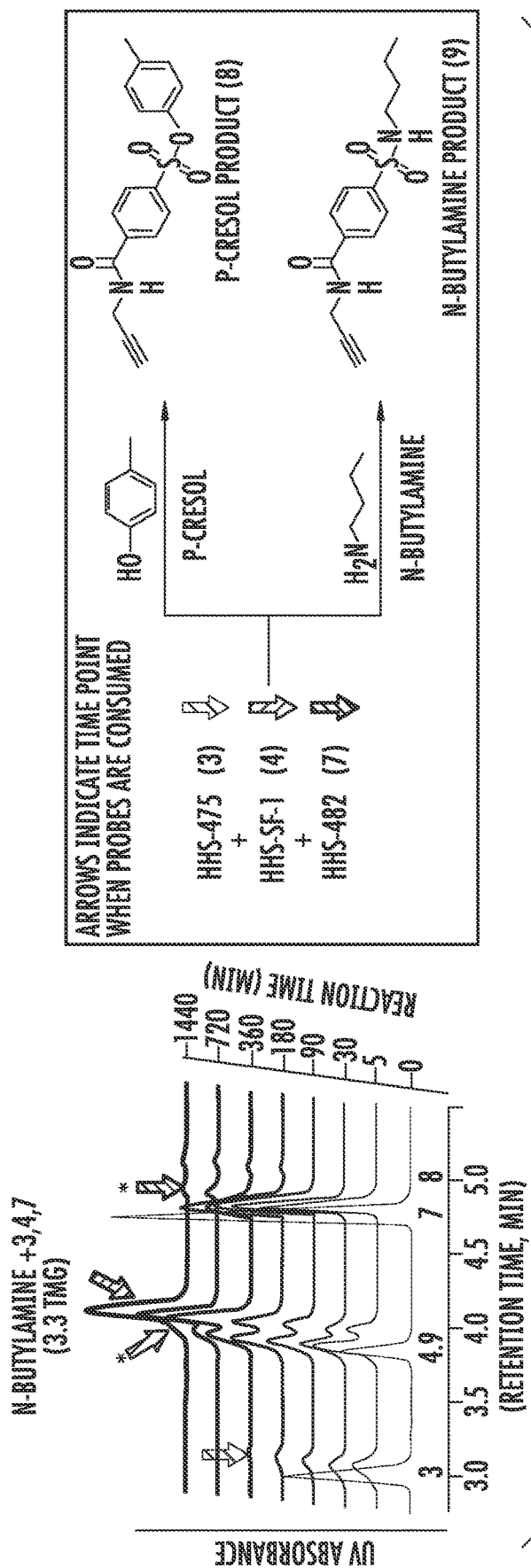

At lower TMG (1.1 equivalents), HHS-475 (peak 3) was the most reactive probe as evidenced by consumption by 30 minutes while unreacted HHS-SF-1 (peak 4) and HHS-482 (peak 7) was still detectable. See FIG. 5A. The difference in reactivity between SuTEx and SuFEx was apparent at higher TMG (2.2 equivalents) conditions. Both SuTEx probes (HHS-475 and HHS-482) were consumed in 10 minutes, while HHS-SF-1 was still detectable even after 90 minutes of reaction. See FIG. 5A. Depletion of HHS-SF-1 signal was only observed at the highest TMG tested (3.3 equivalents). See FIG. 5A. A similar trend in reactivity was observed when p-cresol was incubated with individual sulfonyl probes. The reactivity of all three sulfonyl probes for n-butylamine was substantially reduced compared with p-cresol even at high TMG (3.3 equivalents) conditions. See FIG. 5B. Reaction of HHS-475 with n-butylamine required 6 hours to complete and HHS-482 and HHS-SF-1 were not consumed even after 24 hours. See FIG. 5B. To investigate selectivity further, sulfonyl probes were incubated with n-butylamine and p-cresol mixed in a 5:1 ratio and demonstrated minimal n-butylamine- compared with p-cresol-probe adduct formation for HHS-475 as well as HHS-482 and HHS-SF-1.

Collectively, it appears that the triazole LG enhances intrinsic reactivity of sulfonyl probes for phenol without compromising stability in solvents commonly used for biological experiments (i.e. DMSO). While the solution findings agree with the enhanced reactivity of SuTEx compared with SuFEx observed by proteomics, the differences in tyrosine chemoselectivity between HHS-482 and HHS-475 are likely a function of the protein microenvironment and a feature of probe reactivity that has been reported for other electrophiles[38].

Chemoproteomic Profiling of Phosphotyrosine Activation

Figure 17:
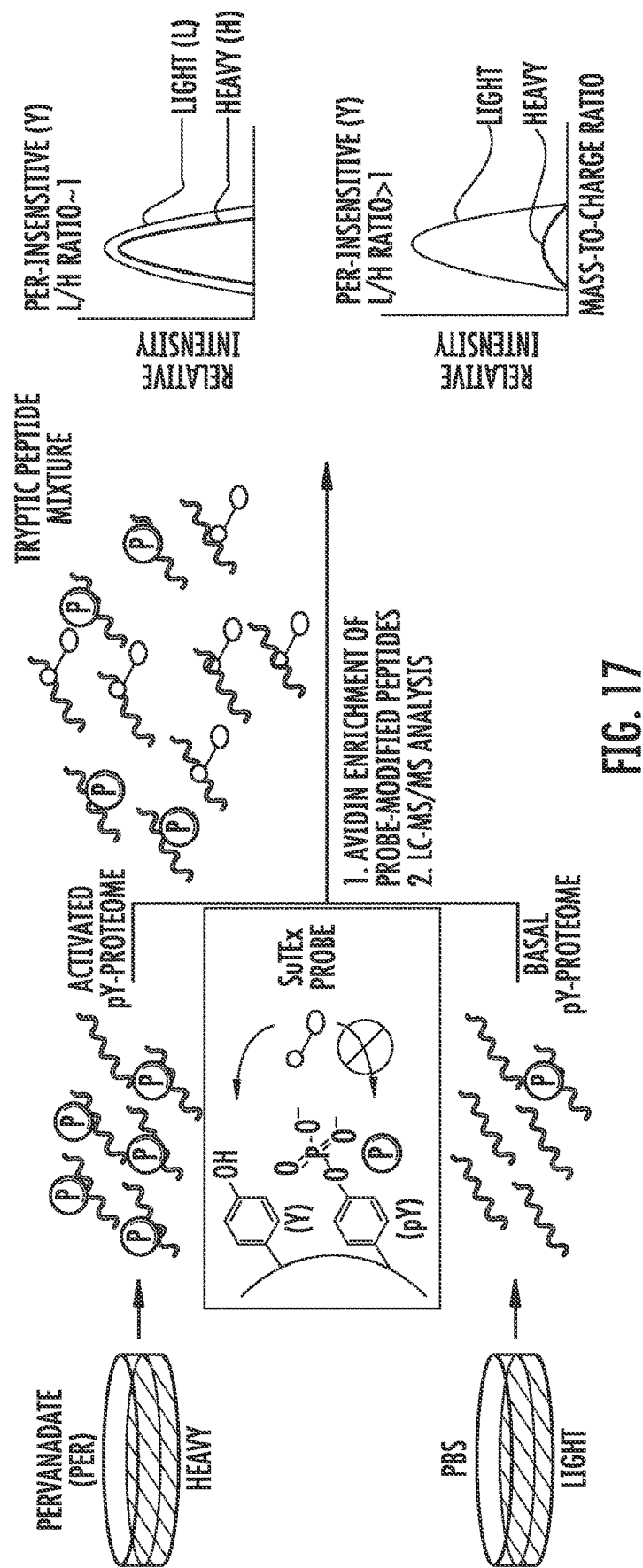

Considering the overlap of SuTEx-modified tyrosines with reported phosphotyrosine sites (pY, see FIG. 2C), a "chemical" phosphoproteomics approach using SuTEx methodology was investigated. It was hypothesized that tyrosine accessibility by SuTEx probes would be inversely correlated with modification status and could be used to identify changes in pY sites. See FIG. 17. Given the low abundance of phospho-tyrosine (1%) compared with -serine (88%) and -threonine (11%) detected in cell[39] and tissue proteomes[40], global phosphorylation was activated using cell permeable tyrosine phosphatase inhibitors to increase pY signals for our LC-MS studies. Previous live cell studies demonstrated the high efficiency of pervanadate for global inhibition of tyrosine phosphatase activity[41]. Accordingly, live A549 cells were treated with pervanadate at varying concentrations (0-500 µM) and time (0-30 min) and global changes were measured in tyrosine phosphorylation by western blot using a pY-specific antibody (P-Tyr-100[42]). Robust increases in global tyrosine phosphorylation were observed as judged by a significant increase in pY-antibody signals that appeared to saturate at 100 µM and 30 min of pervanadate treatment.

Figure 18:
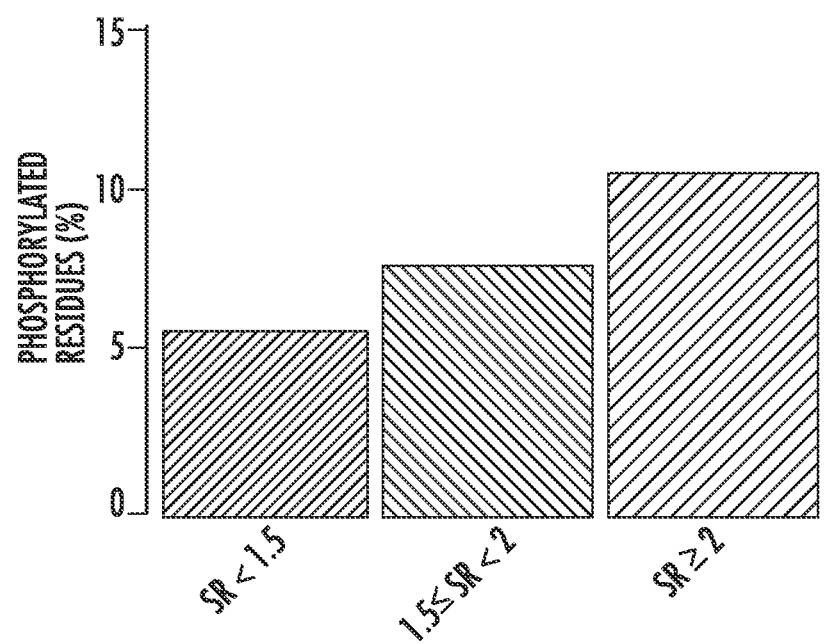

Proteomes from cells treated with pervanadate activation conditions (100 µM, 30 min) were labeled with HHS-475 or HHS-482 (100 µM, 30 min) followed by CuAAC with desthiobiotin and quantitative LC-MS to evaluate how phosphorylation status affected SuTEx probe labeling. Pervanadate blockade of tyrosine phosphatases should activate endogenous phosphorylation and compete for SuTEx probe labeling at phosphorylated- but not unmodified-tyrosine sites that can be differentiated by SILAC ratios of vehicle- (light) versus pervanadate (heavy)-treated cells. See FIG. 6A. In total ~2,200 probe-modified tyrosine sites were detected across ~1,000 proteins using both HHS-475 and HHS-482 that were further separated into pervanadate-sensitive (PerS, SR≥2) and -insensitive groups (PerI, SR<2). See FIG. 6B. The probe-modified tyrosines found in the PerS group appeared to be enriched for annotated phospho-tyrosine sites (HTP≥10 in PhosphoSitePlus, see FIGS. 6C and 18) and represented only a small fraction of all unique HHS-475- and HHS-482-modified tyrosines detected by chemical proteomics (~3%, 67 sites). The overall median SR of all probe-modified tyrosines was ~1 for both HHS-475 and HHS-482 datasets, which supports tyrosine phosphorylation as a rare post-translational event and the ability of the presently disclosed platform to capture subtle changes in the tyrosine phosphoproteome.

To further validate the present chemical phosphoproteomics strategy, tyrosine sites identified as pervanadate sensitive were also tested to see if they were directly phosphorylated under the same treatment conditions. For these studies, several proteins were chosen from the PerS group based on a high phosphotyrosine annotation score (HTP>100, PhosphoSitePlus) and evidence for a role in signaling in human cancer cells like A549. Signal transducer and activator of transcription 3 (STAT3) was identified as a target protein with reduced SuTEx probe labeling at Y705 (SR=2.3, see FIG. 6D) that corresponded with enhanced phosphorylation at this site upon pervanadate activation. See FIG. 6E. The data are in agreement with previous findings reporting STAT3 Y705 as a phosphorylation site for activation by tyrosine kinases in human non-small cell lung cancer lines including A549[43]. Another tyrosine kinase-targeted site (Y228) on catenin 6-1 (CTNND1[44]) was validated and showed blockade of SuTEx probe labeling (SR=3.3, see FIG. 6D) coincided with direct phosphorylation at this tyrosine site by western blot analysis. See FIG. 6E.

In contrast, Y105 was identified as a pervanadate insensitive site (SR=1.1, see FIG. 6D) on pyruvate kinase (PKM) that showed negligble changes in phosphorylation at this tyrosine upon pervanadate activation. See FIG. 6E. Proteomic findings support previous reports of substantial basal levels of phosphorylated-Y105 on PKM in A549 cells[45], which could explain why pervanadate activation did not further enhance pY levels. As a control, SuTEx probe treatment of pervanadate-activated cell proteomes was shown not to result in non-specific displacement of phosphates from tyrosines. In summary, SuTEx technology was applied as a chemical strategy that exploits probe labeling as a site-specific readout of changes in pY levels upon global activation of the phosphoproteome.

Summary of Results from Examples 1-3

Accordingly, sulfur-triazole exchange chemistry is described for development of covalent probes that are compatible with biological systems, easily accessible via modern synthetic chemistry, and can be adapted for diverse chemical proteomic applications. It is demonstrated, on a proteomic scale, that addition of a triazole LG introduces capabilities to the sulfur electrophile including tunability for protein reaction, robust cellular activity, and capacity for directing amino acid specificity. Compared with more widely used sulfonyl-fluorides, the triazole LG dramatically enhanced overall reactivity of sulfonyl probes in solution (see FIGS. 5A and 5B) that can, through modest structural modifications, be optimized for high tyrosine chemoselectivity in proteomes. See FIGS. 4A and 4B. A general synthetic strategy for introducing a common mass spectrometry-stable enrichment tag (see FIG. 1D) and incorporating diverse triazole LGs to provide global structure-activity relationship (SAR) studies of SuTEx probes directly in lysates and live cells is described. See FIGS. 2A-2D.

These features of SuTEx were exploited for functional studies of >10,000 unique tyrosine sites from ~3,700 protein targets detected in human cell proteomes. While previous chemical proteomic studies have shown promise for functional tyrosine profiling[20, 25, 26, 46], the broad coverage of SuTEx permitted global tyrosine quantitation with unprecedented depth and breadth. One discovery from the presently disclosed studies was enrichment of tyrosine sites in nucleotide-binding domains from in vitro and in situ probe-labeling experiments using HHS-465 and HHS-475. See FIGS. 2B and 2D. Labeling of tyrosines localized in RNA-recognition motifs (RRMs) of serine/arginine-rich protein splice factors (SRSF1-12, ~70% coverage of members by SuTEx) involved in regulation of mRNA splicing, export, and translation[47] was observed. Several probe-labeled tyrosines including Y13 of SRSF3 RRM have been shown through structural studies to directly mediate RNA binding[48]. Combined with prominent in situ labeling at domains mediating protein-protein interactions (e.g. PCI/PINT and SH3[35]), SuTEx offers a resource for developing chemical probes against proteins that have been historically challenging to target with small molecules. See FIG. 2D.

The present functional profiling studies led to the discovery of intrinsically nucleophilic tyrosines that are enriched in enzyme sites but also prominent in domains mediating protein-small molecule and protein-protein interactions (SR<5). See FIG. 3B. The rare nature of hyper-reactive tyrosines (~5% of all quantified sites) are in agreement with previous chemical proteomic studies that identified minor subsets of cysteine and lysine residues that demonstrate enhanced reactivity.[10, 11] The presently disclosed studies demonstrated that hyper-reactive residues like Y8 of GSTP1 are important for catalytic function and mutation of this site (Y8F) abolished biochemical activity. See FIGS. 14A and 14B. The present studies also identified a non-catalytic tyrosine near the zinc-binding region of DPP3 (Y417) that exhibited moderate nucleophilicity (SR~6), which offers an ability to develop site-specific ligands. See FIGS. 3D and 14D. Of note, several arginines (R548 and R572, see FIG. 14C) are in close proximity to Y417 and it is possible that these positively-charged residues can play a role in perturbing the pKa of neighboring tyrosine residues as previously reported for alanine racemase[49]. In contrast with GSTP1 and DPP3 enzymes, the discovery of a hyper-reactive tyrosine (Y475, see FIG. 3D) in the Yjef-N domain of the scaffolding protein EDC3 is intriguing given the role of this domain in assembly of cytoplasmic RNA-protein (RNP) granules known as P-bodies involved in post-transcriptional regulation[50]. It is possible that the hyper-reactive nature of the Y475 site can be exploited for developing ligands to modulate EDC3 function.

SuTEx was applied for development of a chemical phosphoproteomics platform to identify and quantitatively measure tyrosine sites whose probe modification status is competed by activation of phosphorylation. As proof of concept, global changes in the tyrosine phosphoproteome were studied under pervanadate activation of A549 cells to identify pervanadate-sensitive (PerS) sites that represented putative phosphotyrosines. See FIGS. 6A-6E and FIG. 18. Across >2,000 quantified sites, a small subset of PerS sites (67 sites) were identified, which is in agreement with the low frequency of tyrosine phosphorylation (1%) compared with more abundant phospho-serines and -threonines[39, 40] SuTEx probe labeling is anticorrelated with phosphorylation at Y705 and Y228 of STAT3 and CTNND1, respectively. See FIGS. 6D and 6E. Both sites are highly annotated phosphotyrosines and reported substrates for tyrosine kinases in cancer cell signaling[43, 44]. In contrast, the pervanadate-insensitive Y105 site of PKM did not show changes in phosphotyrosine signals with pervanadate activation and further supports the ability of SuTEx to differentiate probe labeling of tyrosines based on phosphorylation state. See FIGS. 6D and 6E. It is expected that further refinement, e.g. improvements to LC-MS method and use of SuTEx probe cocktails, can expand the number and type of phosphotyrosine sites quantified.

In summary, SuTEx was deployed for development of a quantitative chemical proteomics platform to globally profile tyrosine nucleophilicity and post-translational modification state in human cell proteomes. Without being bound to any one theory, it is believed that the presently disclosed studies serve as a blueprint for design of activity-based probes that can be synthetically modulated to meet the proteomic demands of chemical biology applications. Expansion of the chemical phosphoproteomics to other activation paradigms can afford additional opportunities for studying and potentially targeting tyrosine post-translational modifications. See FIG. 2C. This latter effort can be expedited by conversion of SuTEx probes into inhibitors or ligands to reveal the inventory of tyrosine (and potentially phospho-tyrosine) sites that are "druggable" in proteomes.

Example 5

Synthesis of Ligands and Related Adducts

Chemicals used were all reagent grade and used as supplied, except where noted. Analytical thin layer chromatography (TLC) was performed on Merck silica gel 60 F254 plates (0.25 mm). Compounds were visualized by UV-irradiation. Analytical HPLC chromatograms were recorded on a Shimadzu 1100 Series spectrometer (Shimadzu, Kyoto, Japan). $^1$H and $^{13}$C NMR spectra were recorded on a Varian Inova 600 (600 MHZ) spectrometer (Varian, Inc., Palo Alto, California, United States of America) or a Bruker Avance III (800 MHz) spectrometer (Bruker, Billerica, Massachusetts, United States of America) in CDCl$_3$, Acetone-d6, or DMSO-d6 with chemical shifts referenced to internal standards (CDCl$_3$: 7.26 ppm $^1$H, 77.16 ppm $^{13}$C; (CD$_3$)$_2$CO: 2.05 ppm $^1$H, 29.84 and 206.26 ppm $^{13}$C; (CD$_3$)$_2$SO: 2.50 ppm $^1$H, 39.52 ppm $^{13}$C) unless stated otherwise. Splitting patterns are indicated as follows: s, singlet; d, doublet; t, triplet; q, quartet; m, multiplet; br, broad singlet for 1H-NMR data. NMR chemical shifts (δ) are reported in ppm and coupling constants (J) are reported in Hz. High resolution mass spectral (HRMS) data were obtained using an Agilent 6545B LC/Q-TOF (Agilent Technologies, Santa Clara, California, United States of America).

Solvents purchased commercially were LC-MS grade. The following chemicals were purchased commercially and showed ≥95% purity: from Fisher Scientific (Hampton, New Hampshire, United States of America) N,N-diisopropylethylamine, hydrazine hydrate, N,N-dimethylformamide dimethyl acetal, acetic acid (HOAc, Optima LC/MS grade), water (HPLC grade grade), and acetonitrile (ACN, Optima LC/MS grade); from Combi-Blocks (San Diego, California, United States of America) 4-methoxybenzenesulfonyl chloride, p-cresol, n-butylamine; from Acros Organics (ThermoFisher Scientific, Waltham, Massachusetts, United States of America) 1,1,3,3-tetramethylguanidine (99%), 2-naphthalenesulfonyl chloride, 4-fluorobenzenesulfonyl chloride, 4-biphenylsulfonyl chloride, 4-methoxyphenyl sulfonyl chloride, benzenesulfonyl chloride, 4-bromobenzenesulfonyl chloride, 4-cyanobenzenesulfonyl chloride, 4-bromobenzamide, 4-methoxybenzamide,4-(trifluoromethyl) benzamide, pyridine-3-sulfonyl chloride; from Alfa Aesar (Haverhill, Massachusetts, United States of America) caffeine, benzamide; from Oakwood Products, Inc. (Estill, South Carolina, United States of America) cyclopropanesulfonyl chloride, thiophene-2-carboxamide; from Decon Laboratories (Decon Labs Inc., King of Prussia, Pennsylvania, United States of America) 200 proof ethanol; from AK Scientific (Union City, California, United States of America) isonicotinamide.

HPLC Assay for Profiling Solution Reactivity and Stability of Sulfonyl Triazole Fragments The following reagents were prepared and stored on ice prior to use. 0.1 M solution of caffeine in acetonitrile, 1.0 M solution of n-butylamine, p-cresol, tetramethylguanidine (TMF), 1 M HOAc in ACN and 10 mM solution of SuTEx fragment in DMF-ACN mixture (10:90, v/v). 500 μL of fragment solution was transferred to a dram vial on ice. To the mixture, 5.5 μL of TMG and 5.5 μL of p-cresol or n-butylamine was added and solutions were stirred on ice for 6 h. To monitor reactivity, 50 μL aliquots were removed at indicated time points and quenched with 10 μL of a 1:1 mixture of caffeine and HOAc. Samples were injected (1 μL) and analyzed by reverse-phase HPLC on a Shimadzu 1100 Series spectrometer (Shimadzu, Kyoto, Japan) with UV detection at 254 nm. Reaction progress was evaluated by monitoring consumption of starting material (SuTEx fragment) normalized to caffeine standard. Chromatographic separation was performed using a Phenomenex Kinetex C18 column (2.6 μm, 50×4.6 mm) (Phenomenex, Torrance, California, United States of America). Mobile phases A and B were composed of H$_2$O+0.1% HOAc and ACN+0.1% HOAc, respectively. Samples were analyzed using the following analytical conditions: using a flow rate of 0.8 ml min$^{-1}$, the gradient was as follows: 0-0.5 min, 15% B; 0.5-6.5 min 85% B; 6.5-7 min 100% B: 7-8.5 min 100% B; 8.5-9 min 15% B; 9-9.8 min 15% B.

General protocol for synthesis of
1,2,4-sulfonyl-triazole fragment library

To a solution of sulfonyl chloride (1.0 mmol, 1.0 eq.) in anhydrous ethanol (1.9 mL, 0.2 M) was added the corresponding triazole (1.0 mmol, 1.0 eq.) and triethylamine (124 μL, 1.1 mmol, 1.1 eq.) at room temperature. The reaction mixture was stirred at room temperature for 2 h until product precipitated out of solution. Filtrate was removed and product was washed several times with cold ethanol. Product was dried under high-vacuum.

(E)-N-((Dimethylamino)methylene)thiophene-2-carboxamide

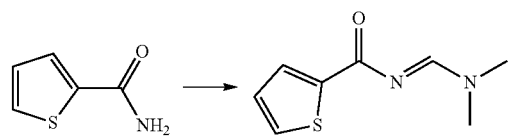

Thiophene-2-carboxamide (10.0 g, 78.6 mmol) was dissolved in 25 mL of DMF-DMA in a 100 mL round bottom flask. The reaction was allowed to stir at 120° C. for 30 min. Reaction was allowed to cool back to room temperature and 25 mL of anhydrous ether was added to reaction flask and the flask was placed on ice. Reaction was filtered and product was washed with 1:1 ether/hexanes. Yield: 68.8%, $^1$H NMR (800 MHz, (CD$_3$)$_2$CO) δ 8.63 (s, 1H), 7.87 (d, J=4.8 Hz, 1H), 7.72 (d, J=4.9 Hz, 1H), 7.22-7.16 (m, 1H), 3.34 (s, 3H), 3.25 (s, 3H). $^{13}$C NMR (201 MHz, (CD$_3$)$_2$CO) δ 172.17, 161.39, 161.22, 144.74, 132.11, 131.98, 131.90, 128.50, 128.33, 41.55, 41.43, 41.31, 35.33. ESI-TOF (HRMS) m/z [M+H]$^+$ calculated for C$_8$H$_{11}$N$_2$OS$^+$ 183.0587, found 183.0582.

3-(Thiophen-2-yl)-1H-1,2,4-triazole

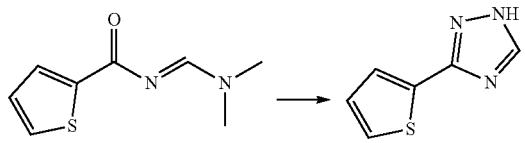

11.84 g (64.9 mmoL) of (E)-N-((dimethylamino)methylene)thiophen-2-carboxamide was dissolved in 50 mL of acetic acid. The solution was heated to 90° C. and hydrazine hydrate monohydrate (1.1 eq.) was added dropwise to reaction and allowed to stir for 90 min. The reaction was cooled to room temperature and concentrated via roto-evaporator. The reaction was diluted in ether and the pH was neutralized with saturated NaHCO$_3$. The aqueous and organic layers were separated and extracted with ethyl acetate. The organic layer was washed with brine and dried over anhydrous MgSO$_4$. The organic fraction was dried via roto-evaporator to provide the product. Yield: 78:4%, 1H NMR (800 MHz, (CD$_3$)$_2$CO) δ 8.40 (s, 1H), 7.70 (dd, J=3.6, 1.2 Hz, 1H), 7.52 (dd, J=5.0, 1.2 Hz, 1H), 7.14 (dd, J=5.0, 3.6 Hz, 1H). $^{13}$C NMR (201 MHz, (CD$_3$)$_2$CO) δ 127.76, 127.59, 126.68, 126.55, 125.91, 125.82. ESI-TOF (HRMS) m/z [M+H]$^+$ calculated for C$_6$H$_6$N$_3$S$^+$ 152.0277, found 152.0281.

1-((4-Fluorophenyl)sulfonyl)-3-phenyl-1H-1,2,4-triazole, JWB105

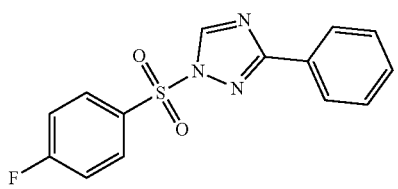 [SMILES: O=S(=O)(c1ccc(F)cc1)n1cnc(-c2ccccc2)n1]

Yield: 56.4%, 1H NMR (600 MHz, (CD$_3$)$_2$SO) δ 9.47 (s, 1H), 8.26 (dd, J=9.0, 4.9 Hz, 2H), 7.99 (d, J=7.8 Hz, 2H), 7.60 (t, J=8.8 Hz, 2H), 7.53-7.48 (m, 3H). $^{13}$C NMR (201 MHz, (CD$_3$)$_2$SO) δ 162.96, 161.74, 145.42, 130.07, 129.35, 128.31, 128.27, 126.46, 114.85, 114.75. $^{19}$F NMR (564 MHz, (CD$_3$)$_2$SO) δ -100.45. ESI-TOF (HRMS) m/z [M+H]$^+$ calculated for C$_{14}$H$_{11}$FN$_3$O$_2$S$^+$ 304.0551, found 304.0539.

1-([1,1'-Biphenyl]-4-ylsulfonyl)-3-phenyl-1H-1,2,4-triazole, JWB112

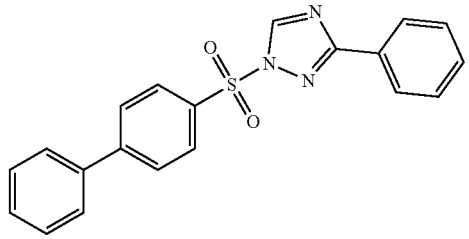 [SMILES: O=S(=O)(c1ccc(-c2ccccc2)cc1)n1cnc(-c2ccccc2)n1]

Yield: 47.5%, 1H NMR (800 MHz, CDCl$_3$) δ 8.77 (s, 1H), 8.19-8.16 (m, 2H), 8.01-7.97 (m, 2H), 7.79 (d, J=8.7 Hz, 2H), 7.60-7.55 (m, 5H), 7.48 (t, J=7.4 Hz, 2H), 7.44 (t, J=7.3 Hz, 1H). $^{13}$C NMR (201 MHz, CDCl$_3$) δ 165.22, 148.48, 145.35, 138.59, 134.47, 130.47, 129.24, 129.16, 129.15, 129.08, 128.61, 128.22, 127.42, 127.11. ESI-TOF (HRMS) m/z [M+H]$^+$ calculated for C$_{20}$H$_{16}$N$_3$O$_2$S$^+$ 362.0958, found 362.0979.

3-(4-Bromophenyl)-1-((4-fluorophenyl)sulfonyl)-1H-1,2,4-triazole, JWB120

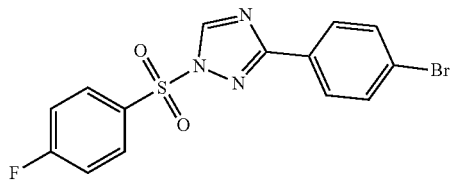 [SMILES: O=S(=O)(c1ccc(F)cc1)n1cnc(-c2ccc(Br)cc2)n1]

Yield: 72.2%, $^1$H NMR (600 MHz, (CD$_3$)$_2$SO) δ 9.49 (s, 1H), 8.26 (dd, J=9.0, 4.9 Hz, 2H), 7.95-7.91 (m, 2H), 7.73-7.68 (m, 2H), 7.60 (t, J=8.8 Hz, 2H). $^{13}$C NMR (201 MHz, (CD$_3$)$_2$SO) δ 162.97, 161.76, 145.38, 132.34, 128.37, 128.32, 128.28, 123.13, 114.87, 114.76. $^{19}$F NMR (564 MHz, (CD$_3$)$_2$SO) δ -100.30. ESI-TOF (HRMS) m/z [M+H]$^+$ calculated for C$_{14}$H$_{10}$BrFN$_3$O$_2$S$^+$ 381.9656, found 381.9659.

1-([1,1'-Biphenyl]-4-ylsulfonyl)-3-(4-bromophenyl)-1H-1,2,4-triazole, JWB127

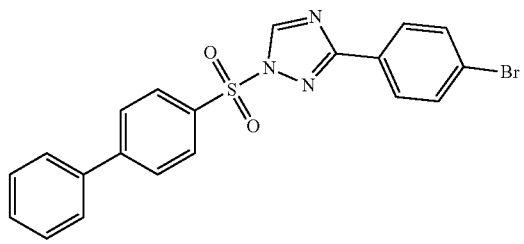 [SMILES: O=S(=O)(c1ccc(-c2ccccc2)cc1)n1cnc(-c2ccc(Br)cc2)n1]

Yield: 63.8%. 1H NMR (600 MHz, (CD$_3$)$_2$SO) δ 9.54 (s, 1H), 8.22 (d, J=8.7 Hz, 2H), 8.02 (d, J=8.7 Hz, 2H), 7.93 (d, J=8.5 Hz, 2H), 7.75 (d, J=7.2 Hz, 2H), 7.70 (d, J=8.5 Hz, 2H), 7.51 (d, J=7.7 Hz, 2H), 7.48-7.43 (m, 1H). $^{13}$C NMR (151 MHz, (CD$_3$)$_2$SO) δ 183.25, 163.63, 148.35, 147.86, 138.08, 134.05, 132.56, 129.65, 129.46, 128.95, 128.83, 128.31, 127.81, 124.71. ESI-TOF (HRMS) m/z [M+H]+ calculated for $C_{20}H_{15}BrN_3O_2S^+$ 440.0063, found 440.0061.

1-(Cyclopropylsulfonyl)-3-(4-methoxyphenyl)-1H-1,2,4-triazole, JWB131

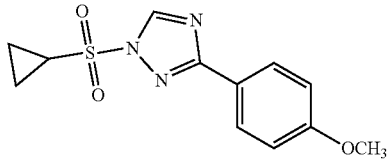 [SMILES: COc1ccc(-c2ncn(S(=O)(=O)C3CC3)n2)cc1]

Yield: 17.3%, 1H NMR (800 MHz, $(CD_3)_2CO$) δ 8.90 (s, 1H), 8.12-8.08 (m, 2H), 7.09-7.06 (m, 2H), 3.88 (s, 3H), 3.19 (m, 1H), 1.50-1.47 (m, 2H), 1.36 (dd, J=7.9, 2.7 Hz, 2H). $^{13}$C NMR (201 MHz, $(CD_3)_2CO$) δ 165.16, 162.53, 147.21, 129.19, 123.08, 115.05, 55.76, 31.96, 7.73. ESI-TOF (HRMS) m/z [M+H]+ calculated for $C_{12}H_{14}N_3O_3S^+$ 280.0750, found 280.0749.

1-((4-Fluorophenyl)sulfonyl)-3-(4-methoxyphenyl)-1H-1,2,4-triazole, JWB135

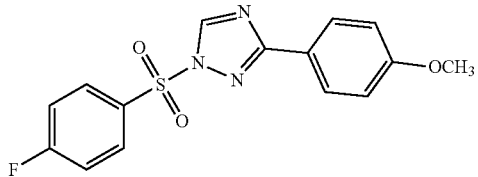 [SMILES: COc1ccc(-c2ncn(S(=O)(=O)c3ccc(F)cc3)n2)cc1]

Yield: 51.0%, 1H NMR (600 MHz, $(CD_3)_2SO$) δ 9.41 (s, 1H), 8.24 (dd, J=9.0, 4.9 Hz, 2H), 7.94-7.91 (m, 2H), 7.59 (t, J=8.8 Hz, 2H), 7.06-7.03 (m, 2H), 3.80 (s, 3H). $^{13}$C NMR (201 MHz, $(CD_3)_2SO$) δ 162.97, 161.75, 161.27, 145.41, 145.39, 128.32, 128.28, 114.93, 114.86, 114.75, 55.83. $^{19}$F NMR (564 MHz, $(CD_3)_2SO$) δ −100.59. ESI-TOF (HRMS) m/z [M+H]+ calculated for $C_{15}H_{13}FN_3O_3S^+$ 334.0656, found 334.0658.

3-(4-Methoxyphenyl)-1-((4-methoxyphenyl)sulfonyl)-1H-1,2,4-triazole, JWB136

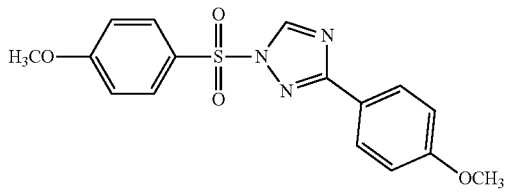 [SMILES: COc1ccc(-c2ncn(S(=O)(=O)c3ccc(OC)cc3)n2)cc1]

Yield: 49.1%, 1H NMR (800 MHz, $(CD_3)_2CO$) δ 9.04 (s, 1H), 8.13-8.09 (m, 2H), 8.02-7.98 (m, 2H), 7.22-7.18 (m, 2H), 7.04-6.99 (m, 2H), 3.92 (s, 3H), 3.84 (s, 3H). $^{13}$C NMR (201 MHz, $(CD_3)_2CO$) δ 166.25, 165.36, 162.51, 147.03, 131.92, 129.13, 128.05, 122.91, 116.04, 114.99, 56.52, 55.73. ESI-TOF (HRMS) m/z [M+H]+ calculated for $C_{16}H_{16}N_3O_4S^+$ 346.0856, found 346.0858.

4-((3-(4-Methoxyphenyl)-1H-1,2,4-triazol-1-yl)sulfonyl)benzonitrile, JWB137

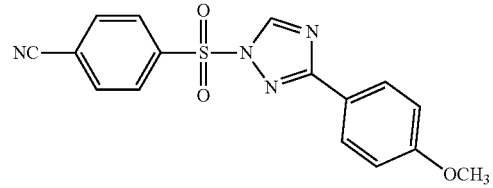 [SMILES: COc1ccc(-c2ncn(S(=O)(=O)c3ccc(C#N)cc3)n2)cc1]

Yield: 60.7%, 1H NMR (800 MHz, $(CD_3)_2CO$) δ 9.15 (s, 1H), 8.40-8.38 (m, 2H), 8.17-8.15 (m, 2H), 8.02-8.00 (m, 2H), 7.04-7.02 (m, 2H), 3.85 (s, 3H). $^{13}$C NMR (201 MHz, $(CD_3)_2CO$) δ 165.98, 162.76, 147.91, 140.94, 134.75, 130.12, 129.32, 122.45, 119.65, 117.64, 115.06, 55.77. ESI-TOF (HRMS) m/z [M+H]+ calculated for $C_{16}H_{13}N_4O_3S^+$ 341.0703, found 341.0718.

3-((3-(4-Methoxyphenyl)-1H-1,2,4-triazol-1-yl)sulfonyl)pyridine, JWB141

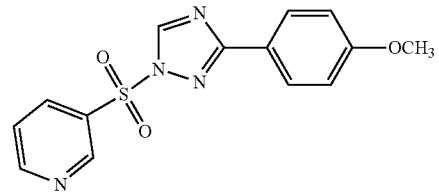 [SMILES: COc1ccc(-c2ncn(S(=O)(=O)c3cccnc3)n2)cc1]

Yield: 44.9%, 1H NMR (800 MHz, $CDCl_3$) δ 9.32 (d, J=2.4 Hz, 1H), 8.92 (dd, J=4.8, 1.6 Hz, 1H), 8.73 (s, 1H), 8.40 (m, 1H), 8.06-8.01 (m, 2H), 7.54 (dd, J=8.9, 4.8 Hz, 1H), 6.96-6.93 (m, 2H), 3.85 (s, 3H). $^{13}$C NMR (201 MHz, $CDCl_3$) δ 165.58, 161.73, 155.48, 149.19, 145.35, 136.17, 133.36, 128.75, 123.99, 121.45, 114.12, 55.34. ESI-TOF (HRMS) m/z [M+H]+ calculated for $C_{14}H_{13}N_4O_3S^+$ 317.0703, found 317.0702.

1-([1,1'-Biphenyl]-4-ylsulfonyl)-3-(4-methoxyphenyl)-1H-1,2,4-triazole, JWB142

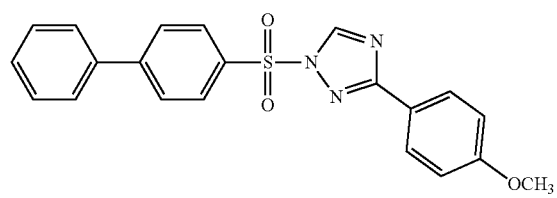 [SMILES: COc1ccc(-c2ncn(S(=O)(=O)c3ccc(-c4ccccc4)cc3)n2)cc1]

Yield: 60.4%, 1H NMR (800 MHz, $(CD_3)_2CO$) δ 9.13 (s, 1H), 8.25 (d, J=8.7 Hz, 2H), 8.01 (dd, J=17.9, 8.8 Hz, 4H), 7.75 (d, J=7.2 Hz, 2H), 7.52 (t, J=7.6 Hz, 2H), 7.47 (t, J=7.4 Hz, 1H), 7.03 (d, J=8.9 Hz, 2H), 3.85 (s, 3H). $^{13}$C NMR (201 MHz, $(CD_3)_2CO$) δ 165.62, 162.61, 148.94, 147.46, 139.34, 135.66, 130.06, 130.00, 129.96, 129.22, 129.18, 128.33, 122.77, 115.03, 55.75. ESI-TOF (HRMS) m/z [M+H]+ calculated for $C_{21}H_{18}N_3O_3S^+$ 392.1063, found 392.1072.

1-(Cyclopropylsulfonyl)-3-(4-(trifluoromethyl)phenyl)-1H-1,2,4-triazole, JWB146

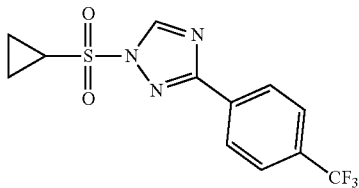 [SMILES: O=S(=O)(C1CC1)n1cnc(-c2ccc(C(F)(F)F)cc2)n1]

Yield: 14.6%, 1H NMR (800 MHz, (CD$_3$)$_2$CO) δ 9.04 (s, 1H), 8.37 (d, J=8.6 Hz, 2H), 7.89 (d, J=8.6 Hz, 2H), 3.26 (m, 1H), 1.55-1.52 (m, 2H), 1.42-1.39 (m, 2H). $^{13}$C NMR (201 MHz, (CD$_3$)$_2$CO) δ 162.97, 146.87, 133.44, 131.65, 131.49, 131.33, 131.17, 31.17, 7.06. $^{19}$F NMR (201 MHz, (CD$_3$)$_2$CO) δ -63.38. ESI-TOF (HRMS) m/z [M+H]$^+$ calculated for C$_{12}$H$_{11}$F3N$_3$O$_2$S$^+$ 318.0519, found 318.0533.

1-((4-Fluorophenyl)sulfonyl)-3-(4-(trifluoromethyl)phenyl)-1H-1,2,4-triazole, JWB150

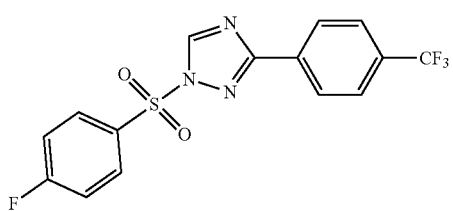 [SMILES: O=S(=O)(c1ccc(F)cc1)n1cnc(-c2ccc(C(F)(F)F)cc2)n1]

Yield: 51.6%, 1H NMR (800 MHz, CDCl$_3$) δ 8.86 (s, 1H), 8.31 (m, 2H), 8.29-8.25 (m, 2H), 7.79-7.77 (m, 2H), 7.41-7.37 (m, 2H). $^{13}$C NMR (201 MHz, CDCl$_3$) δ 167.52, 166.23, 164.08, 145.47, 131.88, 131.83, 127.39, 125.65, 125.63, 117.36, 117.25. $^{19}$F NMR (564 MHz, (CD$_3$)$_2$SO) δ -61.47, -85.01. ESI-TOF (HRMS) m/z [M+H]$^+$ calculated for C$_{15}$H$_{10}$F$_4$N$_3$O$_2$S$^+$ 372.0424, found 372.0426.

1((4-Methoxyphenyl)sulfonyl)-3-(4-(trifluoromethyl)phenyl)-1H-1,2,4-triazole, JWB151

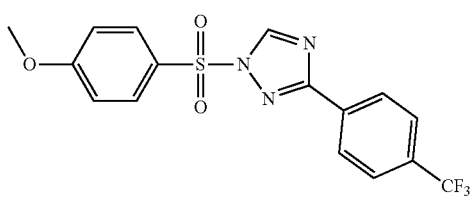

Yield: 75.4%, 1H NMR (800 MHz, DMSO-d6) δ 9.62 (s, 1H), 8.74-8.71 (m, 2H), 8.63-8.54 (m, 2H), 8.31-8.26 (m, 2H), 7.71-7.65 (m, 2H), 4.39 (s, 3H). $^{13}$C NMR (201 MHz, DMSO-d6) δ 176.17, 173.73, 157.19, 143.87, 142.04, 141.88, 141.82, 137.85, 137.27, 136.36 (q, J=3.9 Hz), 125.84, 66.26. $^{19}$F NMR (564 MHz, DMSO-d6) δ -63.41. ESI-TOF (HRMS) m/z [M+H]$^+$ calculated for C$_{16}$H$_{13}$F$_3$N$_3$O$_3$S 384.0624, found 384.0626.

4-((3-(4-(Trifluoromethyl)phenyl)-1H-1,2,4-triazol-1-yl)sulfonyl)benzonitrile, JWB152

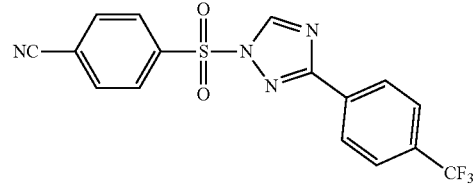 [SMILES: N#Cc1ccc(S(=O)(=O)n2cnc(-c3ccc(C(F)(F)F)cc3)n2)cc1]

Yield: 57.2%, 1H NMR (800 MHz, (CD$_3$)$_2$CO) δ 9.29 (s, 1H), 8.44-8.42 (m, 2H), 8.30-8.28 (m, 2H), 8.20-8.18 (m, 2H), 7.86 (d, J=8.7 Hz, 2H). $^{13}$C NMR (201 MHz, (CD$_3$)$_2$CO) δ 164.68, 148.40, 140.60, 134.83, 133.79, 132.63, 132.47, 130.31, 128.35, 126.75, 119.89, 117.59. $^{19}$F NMR (564 MHz, (CD$_3$)$_2$CO) δ -63.47. ESI-TOF (HRMS) m/z [M+H]$^+$ calculated for C$_{16}$H$_{10}$F$_3$N$_4$O$_2$S$^+$ 379.0471, found 379.0484.

1-([1,1'-Biphenyl]-4-ylsulfonyl)-3-(4-(trifluromethyl)phenyl)-1H-1,2,4-triazole, JWB157

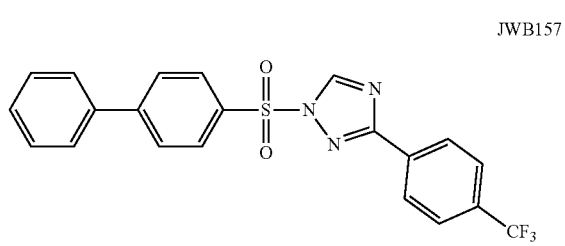 [SMILES: O=S(=O)(c1ccc(-c2ccccc2)cc1)n1cnc(-c2ccc(C(F)(F)F)cc2)n1]

Yield: 70.2% 1H NMR (800 MHz, (CDCl$_3$) δ 8.81 (s, 1H), 8.24 (d, J=8.1 Hz, 2H), 8.21-8.17 (m, 2H), 7.82-7.79 (m, 2H), 7.69 (d, J=8.2 Hz, 2H), 7.60-7.57 (m, 2H), 7.50-7.47 (m, 2H), 7.46-7.43 (m, 1H). $^{13}$C NMR (201 MHz, (CDCl$_3$) δ 164.05, 148.85, 145.69 (d, J=35.3 Hz), 138.57, 134.17, 132.68, 132.32 (q, J=32.9 Hz), 129.40, 129.29, 128.50, 128.43, 127.62, 127.53, 125.78 (d, J=16.4 Hz), 124.01 (d, J=272.2 Hz). $^{19}$F NMR (564 MHz, (CD$_3$)$_2$CO) δ -63.42. ESI-TOF (HRMS) m/z [M+H]$^+$ calculated for C$_{21}$H$_{15}$F$_3$N$_3$O$_2$S 430.0832, found 430.0850.

4-(1-(Cyclopropylsulfonyl)-1H-1,2,4-triazol-3-yl)pyridine, JWB191

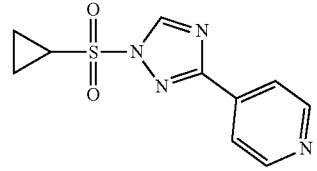 [SMILES: O=S(=O)(C1CC1)n1cnc(-c2ccncc2)n1]

Yield 13.1%, $^1$H NMR (800 MHz, (CD$_3$)$_2$CO) δ 9.06 (s, 1H), 8.78-8.74 (m, 2H), 8.05-8.02 (m, 2H), 3.26 (m, 1H), 1.55-1.52 (m, 2H), 1.42-1.39 (m, 2H). $^{13}$C NMR (201 MHz, (CD$_3$)$_2$CO) δ 163.26, 151.56, 147.89, 137.63, 121.44, 32.07, 8.00. ESI-TOF (HRMS) m/z [M+H]+ calculated for C10H11N4O2S+ 251.0597, found 251.0606.

4-(1-((4-Methoxyphenyl)sulfonyl)-1H-1,2,4-triazol-3-yl)pyridine, JWB196

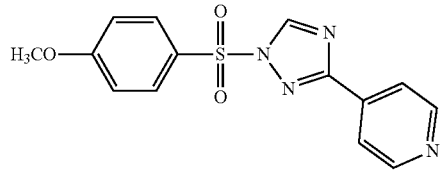 [SMILES: COc1ccc(S(=O)(=O)n2cnc(-c3ccncc3)n2)cc1]

Yield: 22.6%, $^1$H NMR (800 MHz, (CD$_3$)$_2$SO) δ 9.54 (d, J=2.1 Hz, 1H), 8.76-8.71 (m, 2H), 8.15-8.07 (m, 2H), 7.95-7.90 (m, 2H), 7.24 (dd, J=9.0, 1.9 Hz, 2H), 3.87 (d, J=1.7 Hz, 3H). $^{13}$C NMR (201 MHz, (CD$_3$)$_2$SO) δ 165.17, 161.72, 150.14, 147.80, 136.48, 131.14, 125.63, 120.69, 115.63, 56.18. ESI-TOF (HRMS) m/z [M+H]+ calculated for C$_{14}$H$_{13}$N$_4$O$_3$S+ 317.0703, found 317.0709.

4-((3-(Pyridin-4-yl)-1H-1,2,4-triazol-1-yl)sulfonyl)benzonitrile, JWB197

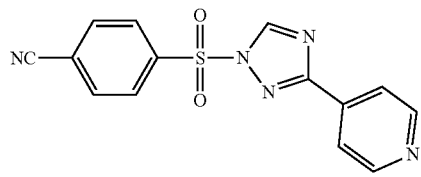 [SMILES: N#Cc1ccc(S(=O)(=O)n2cnc(-c3ccncc3)n2)cc1]

Yield: 34.8%, $^1$H NMR (800 MHz, CDCl$_3$) δ 8.82 (s, 1H), 8.74-8.72 (m, 2H), 8.28-8.26 (m, 2H), 7.97-7.95 (m, 2H), 7.94-7.92 (m, 2H). $^{13}$C NMR (201 MHz, CDCl$_3$) δ 163.84, 150.55, 146.09, 139.73, 136.36, 133.64, 129.54, 121.14, 119.59, 116.56. ESI-TOF (HRMS) m/z [M+H]+ calculated for C$_{14}$H$_{10}$N$_5$O$_2$S+ 312.0550, found 312.0551.

4-(1-(Naphthalen-2-ylsulfonyl)-1H-1,2,4-triazol-3-yl)pyridine, JWB198

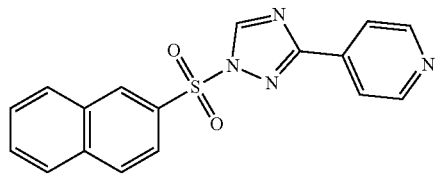 [SMILES: O=S(=O)(c1ccc2ccccc2c1)n1cnc(-c2ccncc2)n1]

Yield: 52.6%, 1H NMR (600 MHz, (CD$_3$)$_2$SO) δ 9.63 (s, 1H), 9.01-8.98 (m, 1H), 8.71-8.67 (m, 2H), 8.32 (d, J=8.2 Hz, 1H), 8.25 (d, J=8.9 Hz, 1H), 8.10 (d, J=8.1 Hz, 1H), 8.06 (dd, J=8.8, 2.1 Hz, 1H), 7.90-7.87 (m, 2H), 7.82 (m, 1H), 7.76 (m, 1H). $^{13}$C NMR (201 MHz, (CD$_3$)$_2$SO) δ 147.04, 146.02, 145.51, 144.19, 133.18, 132.61, 128.91, 127.91, 127.78, 126.89, 126.76, 124.51, 124.43, 122.93, 99.98. ESI-TOF (HRMS) m/z [M+H]+ calculated for C$_{17}$H$_{13}$N$_4$O$_2$S+ 337.0754, found 337.077.

4-(1-([1,1'-Biphenyl]-4-ylsulfonyl)-1H-1,2,4-triazol-3-yl)pyridine, JWB202

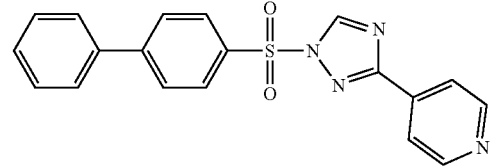 [SMILES: O=S(=O)(c1ccc(-c2ccccc2)cc1)n1cnc(-c2ccncc2)n1]

Yield: 31.8%, $^1$H NMR (800 MHz, (CD$_3$)$_2$SO) δ 9.63 (s, 1H), 8.72 (d, J=5.2 Hz, 2H), 8.24 (d, J=8.2 Hz, 2H), 8.03 (d, J=8.3 Hz, 2H), 7.91 (d, J=5.2 Hz, 2H), 7.75 (d, J=7.7 Hz, 2H), 7.51 (t, J=7.6 Hz, 2H), 7.46 (t, J=7.3 Hz, 1H). $^{13}$C NMR (201 MHz, (CD$_3$)$_2$SO) δ 163.64, 152.13, 149.73, 149.07, 139.12, 137.40, 134.93, 130.78, 130.74, 130.64, 129.95, 128.90, 122.07. ESI-TOF (HRMS) m/z [M+H]+ calculated for C$_{19}$H$_{15}$N$_4$O$_2$S+ 363.0910, found 363.0925.

1-(Cyclopropylsulfonyl)-3-(thiophen-2-yl)-1H-1,2,4-triazole, JWB206

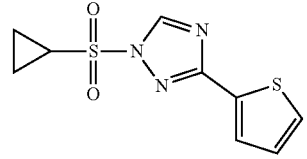 [SMILES: O=S(=O)(C1CC1)n1cnc(-c2cccs2)n1]

Yield: 20.3%, 1H NMR (800 MHz, (CD$_3$)$_2$C$_0$) δ 8.93 (s, 1H), 7.80 (dd, J=3.6, 1.2 Hz, 1H), 7.67 (dd, J=5.0, 1.2 Hz, 1H), 7.21 (dd, J=5.0, 3.6 Hz, 1H), 3.21 (tt, J=7.9, 4.6 Hz, 1H), 1.51-1.48 (m, 3H), 1.41-1.36 (m, 3H). $^{13}$C NMR (201 MHz, (CD$_3$)$_2$CO) δ 161.40, 147.40, 133.01, 129.43, 129.00, 128.89, 32.02, 7.85. ESI-TOF (HRMS) m/z [M+H]+ calculated for C$_9$H$_{10}$N$_3$O$_2$S$_2$ 256.0209, found 256.0207.

1-(Phenylsulfonyl)-3-(thiophen-2-yl)-1H-1,2,4-triazole, JWB207

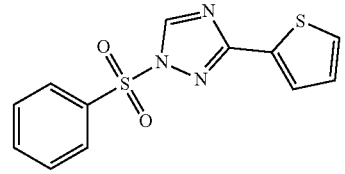 [SMILES: O=S(=O)(c1ccccc1)n1cnc(-c2cccs2)n1]

Yield: 66.3%, 1H NMR (600 MHz, CDCl$_3$) δ 8.70 (s, 1H), 8.12 (dd, J=8.5, 1.1 Hz, 2H), 7.77-7.69 (m, 2H), 7.64-7.58 (m, 2H), 7.41 (dd, J=5.0, 1.1 Hz, 1H), 7.09 (dd, J=5.0, 3.7 Hz, 1H). $^{13}$C NMR (201 MHz, CDCl$_3$) δ 161.24, 145.36, 136.13, 135.37, 131.76, 129.68, 128.61, 128.38, 128.34, 127.82. ESI-TOF (HRMS) m/z [M+H]+ calculated for C$_{12}$H$_{10}$N$_3$O$_2$S$_2$+ 292.0209, found 292.0211.

101

1-((4-Fluorophenyl)sulfonyl)-3-(thiophen-2-yl)-1H-1,2,4-triazole, JWB210

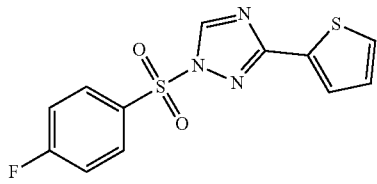 [SMILES: O=S(=O)(c1ccc(F)cc1)n1cnc(-c2cccs2)n1]

Yield: 35.5%, 1H NMR (800 MHz, CDCl$_3$) δ 8.78 (s, 1H), 8.26-8.23 (m, 2H), 7.84 (dd, J=3.7, 1.2 Hz, 1H), 7.50 (dd, J=5.0, 1.2 Hz, 1H), 7.38-7.35 (m, 2H), 7.18 (dd, J=5.0, 3.7 Hz, 1H). $^{13}$C NMR (201 MHz, CDCl$_3$) δ 167.43, 166.13, 161.38, 145.27, 131.81, 131.76, 128.48, 127.86, 117.27, 117.16. $^{19}$F NMR (564 MHz, (CD$_3$)$_2$SO) δ −100.34. ESI-TOF (HRMS) m/z [M+H]$^+$ calculated for C$_{12}$H$_9$FN$_3$O$_2$S$_2^+$ 310.0115, found 310.0114.

1-((4-Methoxyphenyl)sulfonyl)-3-(thiophen-2-yl)-1H-1,2,4-triazole, JWB211

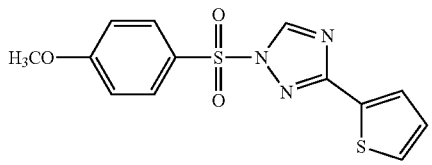 [SMILES: COc1ccc(S(=O)(=O)n2cnc(-c3cccs3)n2)cc1]

Yield: 36.2%, 1H NMR (800 MHz, (CD$_3$)$_2$CO) δ 9.06 (s, 1H), 8.10 (d, J=9.1 Hz, 2H), 7.72 (dd, J=3.6, 1.2 Hz, 1H), 7.62 (d, J=1.2 Hz, 1H), 7.23-7.20 (m, 2H), 7.16 (dd, J=5.0, 3.6 Hz, 1H), 3.94 (s, 3H). $^{13}$C NMR (201 MHz, (CD$_3$)$_2$CO) δ 166.37, 161.58, 147.22, 132.85, 132.00, 129.44, 128.99, 128.84, 127.76, 116.11, 56.55. ESI-TOF (HRMS) m/z [M+H]$^+$ calculated for C$_{13}$H$_{12}$N$_3$O$_3$S$_2^+$ 322.0315, found 322.0327.

4-((3-Thiophen-2-yl)-1H-1,2,4-triazol-1-yl)benzonitrile, JWB212

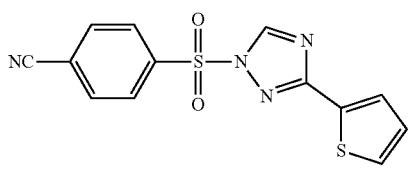

Yield: 81.6%, 1H NMR (800 MHz, (CD$_3$)$_2$CO) δ 9.18 (d, J=1.6 Hz, 2H), 8.41-8.38 (m, 2H), 8.19-8.17 (m, 2H), 7.75 (ddd, J=3.3, 1.9, 1.4 Hz, 1H), 7.67 (dd, J=5.0, 1.2 Hz, 1H), 7.19-7.17 (m, 1H). $^{13}$C NMR (201 MHz, (CD$_3$)$_2$CO) δ 162.15, 148.11, 140.73, 134.80, 132.37, 130.18, 129.95, 129.50, 128.95, 119.78, 117.62. ESI-TOF (HRMS) m/z [M+H]$^+$ calculated for C$_{13}$H$_9$N$_4$O$_2$S$_2$ 317.0161, found 317.0178.

102

1-([1,1'-Biphenyl]-4-ylsulfonyl)-3-thiophen-2-yl)-1H-1,2,4-triazole, JWB217

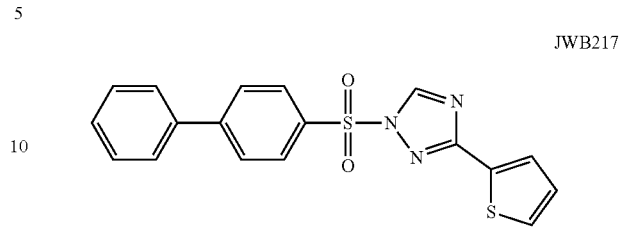

Yield: 68.2%, 1H NMR (800 MHz, (CDCl$_3$) δ 8.73 (s, 1H), 8.17 (d, J=8.6 Hz), 1H, 7.80-7.78 (m, 2H), 7.76 (dd, J=3.7, 1.2 Hz, 1H), 7.60-7.57 (m, 2H), 7.50-7.47 (m, 2H), 7.45-7.43 (m, 1H), 7.41 (dd, J=5.0, 1.2 Hz, 1H), 7.09 (dd, J=5.0, 3.7 Hz, 1H). $^{13}$C NMR (201 MHz, (CDCl$_3$) δ 161.36, 148.69, 145.48, 145.47, 138.68, 134.33, 131.86, 129.33, 129.27, 128.55, 128.53, 128.43, 128.03, 127.59, 127.57. ESI-TOF (HRMS) m/z [M+H]$^+$ calculated for C$_{18}$H$_{14}$N$_3$O$_2$S$_2$ 368.0522, found 368.0535.

3-((3-Pyridin-4-yl)-1H-1,2,4-triazol-1-yl)sulfonyl)benzonitrile, JWB232

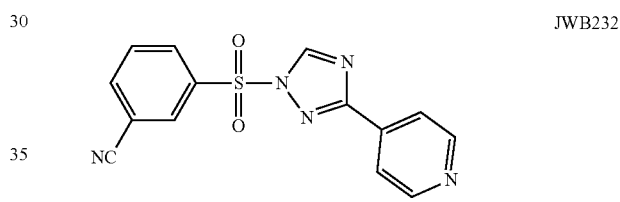

Yield: 65.2%, 1H NMR (800 MHz, DMSO-d6) δ 9.66 (d, J=0.6 Hz, 1H), 8.77-8.72 (m, 2H), 8.50-8.45 (m, 1H), 8.28 (dd, J=7.2, 1.7 Hz, 1H), 8.13-8.05 (m, 2H), 7.93-7.89 (m, 2H). $^{13}$C NMR (201 MHz, DMSO) δ 162.54, 150.60, 149.03, 137.10, 136.80, 135.92, 135.65, 134.92, 131.77, 120.75, 114.66, 110.32. ESI-TOF (HRMS) m/z [M+H]$^+$ calculated for C$_{14}$H$_{10}$N$_5$O$_2$S 312.0550, found 312.0551.

3-((3-(4-(Trifluoromethyl)phenyl)-1H-1,2,4-triazol-1-yl)sulfonyl)benzonitrile, JWB233

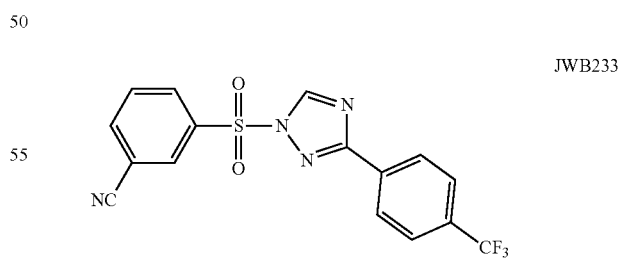

Yield: 28.5%, 1H NMR (800 MHz, (CD$_3$)$_2$CO) δ 9.28 (s, 1H), 8.64 (t, J=1.8 Hz, 1H), 8.55 (ddd, J=8.2, 2.0, 1.0 Hz, 1H), 8.29 (ddt, J=9.1, 7.8, 1.1 Hz, 3H), 8.01 (t, J=8.0 Hz, 1H), 7.87-7.84 (m, 2H). $^{13}$C NMR (201 MHz, (CD$_3$)$_2$CO) δ 164.69, 145.94, 145.90, 138.59, 137.75, 132.78, 132.61 (d, J=2.9 Hz), 132.37 (d, J=2.7 Hz), 132.18, 131.09, 127.70-127.55 (m), 125.90 (q, J=3.9 Hz), 116.37, 114.88. $^{19}$F NMR (565 MHz, (CD$_3$)$_2$CO) δ −62.98. ESI-TOF (HRMS) m/z [M+H]$^+$ calculated for C$_{16}$H$_{10}$F$_3$N$_4$O$_2$S 379.0471, found 379.0488.

3-((3-(4-methoxyphenyl)-1H-1,2,4-triazol-1-yl)sulfonyl)benzonitrile, JWB234

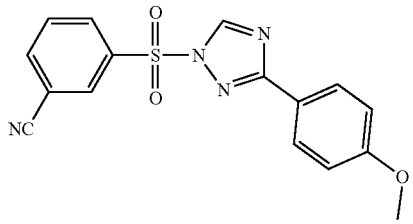

Yield: 53.5%, 1H NMR (800 MHz, (CDCl$_3$) δ 8.72 (s, 1H), 8.42 (t, J=1.7 Hz, 1H), 8.34 (ddd, J=8.1, 1.9, 1.1 Hz, 1H), 8.03 (d, J=8.9 Hz, 2H), 7.98 (dt, J=7.7, 1.3 Hz, 1H), 7.76 (t, J=7.9 Hz, 1H), 6.95 (d, J=8.8 Hz, 2H), 3.85 (s, 3H). $^{13}$C NMR (201 MHz, (CDCl$_3$) δ 165.72, 161.76, 145.50, 138.17, 137.95, 132.35, 132.13, 130.80, 128.80, 121.26, 116.36, 114.46, 114.15, 55.42. ESI-TOF (HRMS) m/z [M+H]$^+$ calculated for C$_{16}$H$_{13}$N$_4$O$_3$S 341.0703, found 341.0701.

3-((3-(Thiophen-2-yl)-1H-1,2,4-triazol-1-yl)sulfonyl)benzonitrile, JWB243

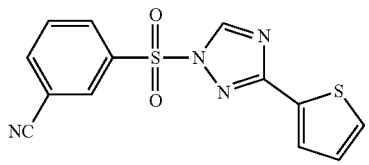 [SMILES: N#Cc1cccc(S(=O)(=O)n2cnc(-c3cccs3)n2)c1]

Yield: 44.6%, 1H NMR (800 MHz, ((CD$_3$)$_2$CO) δ 9.23 (s, 1H), 8.52 dd, J=7.9 Hz, 1H), 8.20 (dd, J=7.5, 1.4 Hz, 1H), 8.14 (td, J=7.9, 1.4 Hz, 1H), 8.10 (td, J=7.6, 1.3 Hz, 1H), 7.74 dd, J=3.6, 1.2 Hz, 1H), 7.66 (dd, J=5.0, 1.2 Hz, 1H), 7.17 (dd, J=5.0, 3.7 Hz, 1H). $^{13}$C NMR (201 MHz, ((CD$_3$)$_2$CO) δ 161.30, 147.75, 136.77, 136.63, 136.22, 134.29, 131.76, 131.39, 129.14, 128.72, 128.06, 114.39, 111.07. ESI-TOF (HRMS) m/z [M+H]$^+$ calculated for C$_{13}$H$_9$N$_4$O$_2$S$_2$ 317.0161, found 317.0160.

General Synthesis of Sulfonamide Adducts

To a solution of sulfonyl chloride (0.50 mmol, 1.0 eq) in anhydrous DCM (5 mL, 100 mM) was added n-butylamine (1.1 eq) and DIPEA (1.1 eq). The reaction was stirred at room temperature for 1.5 hours. The reaction mixture was poured into 1 M HCl aqueous solution (5.0 mL) and extracted with DCM (5.0 mL) 3 times. The organic phase was combined and washed with saturated NaHCO$_3$ (10.0 mL) and brine (10.0 mL). The solution was dried over MgSO$_4$ and evaporated under reduced pressure. The product was purified using silica gel flash column chromatography (ethyl acetate/hexane=1:2 to 1:1).

General Synthesis of Sulfonate Adducts

To a solution of sulfonyl chloride (0.5 mmol, 1.0 eq.) in anhydrous DCM (5.0 mL, 100 mM) was added p-cresol (0.9 eq.), DIPEA (1.0 eq) and DMAP (0.2 eq). The reaction was stirred at room temperature for 1 hour. The reaction mixture was poured into 1 M HCl aqueous solution (5.0 mL) and extracted with DCM (5.0 mL) 3 times. The organic phase was combined and washed with saturated NaHCO$_3$ (5.0 mL) and brine (5.0 mL). The solution was dried over MgSO$_4$ and evaporated under reduced pressure. The purification was carried out using silica gel flash column chromatography (ethyl acetate/hexane=1:3 to 1:1) to afford product.

N-Butyl-4-fluiorobenzenesulfonamide, KY-347-BA

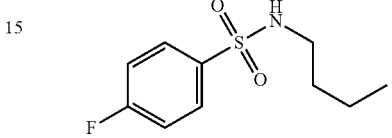

Yield: 66.2%, $^1$H NMR (600 MHz, CDCl$_3$) 7.90-7.85 (m, 2H), 7.21-7.15 (m, 2H), 4.35 (s, 1H), 2.95 (q, 2H), 1.48-1.40 (m, 2H), 1.33-1.23 (m, 2H), 0.85 (t, J=7.4 Hz, 3H). $^{13}$C NMR (151 MHz, CDCl$_3$) δ 165.80, 164.11, 136.04, 136.02, 129.75, 116.30, 116.15, 42.87, 31.45, 19.60, 13.43. $^{19}$F NMR (564 MHz, CDCl$_3$) δ −105.55. ESI-TOF (HRMS) m/z [M+H]$^+$ calculated for C$_{10}$H$_{15}$FNO$_2$S$^+$ 232.0802, found 232.0802.

p-Tolyl 4-fluorobenzenesulfonate, KY-347-CA

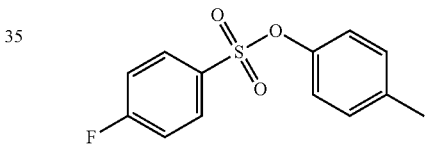

Yield: 82.7%, $^1$H NMR (600 MHz, CDCl$_3$) δ 7.88-7.78 (m, 21H), 7.21-7.15 (m, 2H), 7.09-7.05 (m, 2H), 6.86-6.82 (m, 2H), 2.30 (s, 3H), $^{13}$C NMR (151 MHz, CDCl$_3$) δ 166.79, 165.08, 147.29, 137.21, 131.43, 131.40, 131.34, 130.18, 121.95, 116.53, 116.38, 20.85. $^{19}$F NMR (564 MHz, CDCl$_3$) δ −102.39. ESI-TOF (HRMS) m/z [M+H]$^+$ calculated for C$_{13}$H$_{12}$FO$_3$S$^+$ 267.0486, found 267.0480.

N-Butyl-4-methoxybenzenesulfonamide, KY-348-BA

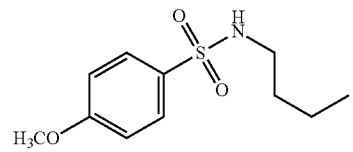 [SMILES: CCCCNS(=O)(=O)c1ccc(OC)cc1]

Yield: 90%, $^1$H NMR (600 MHz, CDCl$_3$) δ 7.81-7.76 (m. 2H), 6.99-6.94 (m, 2H), 3.86 (s, 3H), 2.91 (t, J=7.1 Hz, 2H), 1.46-1.38 (m, 2H), 1.32-1.24 (m, 2H), 0.84 (t, J=7.4 Hz, 3H). $^{13}$C NMR (151 MHz, CDCl$_3$) δ 162.75, 131.53, 129.16, 114.16, 55.55, 42.83, 31.48, 19.65, 13.48. ESI-TOF (HRMS) m/z [M+H]$^+$ calculated for C$_{11}$H$_{18}$NO$_3$S$^+$ 244.1002, found 244.0998.

p-Tolyl 4-methoxy benzenesulfonate, KY-348-CA

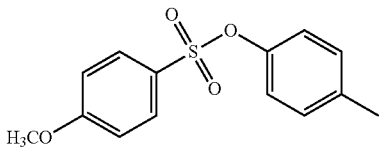 [SMILES: COc1ccc(S(=O)(=O)Oc2ccc(C)cc2)cc1]

Yield: 39.5%, ¹H NMR (600 MHz, CDCl₃) δ 7.75-7.71 (m, 2H), 7.08-7.03 (m, 2H), 6.98-6.92 (m, 2H), 6.87-6.82 (m, 2H), 3.87 (s, 3H), 2.30 (s, 3H). ¹³C NMR (151 MHz, CDCl₃) δ 163.96, 147.45, 136.84, 130.69, 130.00, 126.73, 122.06, 114.20, 55.65, 20.81. ESI-TOF (HRMS) m/z [M+H]⁺ calculated for $C_{14}H_{15}O_4S^+$ 279.0686, found 279.0682.

N-Butyl-4-cyanobenzenesulfonamide, KY-349-BA

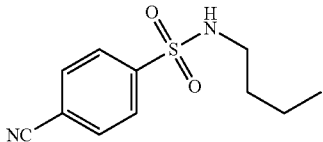 [SMILES: CCCCNS(=O)(=O)c1ccc(C#N)cc1]

Yield: 70.9%, 3H NMR (600 MHz, CDCl₃) δ 8.00-7.94 (m 2H), 7.84-7.78 (m, 2H), 4.43 (s, 1H) 2.99 (td, J=7.1, 6.1 Hz, 2H), 1.49-1.41 (m, 2H), 1.33-1.24 (m, 2H), 0.86 (t, J=7.4 Hz, 3H). ¹³C NMR (151 MHz, CDCl₃) δ 144.43, 132.95, 127.65, 117.33, 43.02, 31.58, 19.58, 13.45. ESI-TOF (HRMS) m/z [M+H]⁺ calculated for $C_{11}H_{15}N_2O_2S^+$ 239.0849, found 239.0849.

p-Tolyl 4-cyanobenzenesulfonate, KY-349-CA

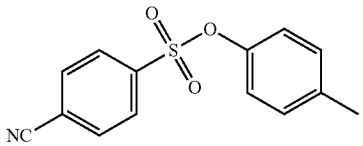 [SMILES: Cc1ccc(OS(=O)(=O)c2ccc(C#N)cc2)cc1]

Yield: 49.4%, ¹H NMR (600 MHz, CDCl₃) δ 7.97-7.90 (m, 2H), 7.84-7.78 (m, 2H), 7.12-7.06 (m, 2H), 6.86-6.80 (m, 2H), 2.31 (s, 3H). ¹³C NMR (151 MHz, CDCl₃) δ 146.99, 139.48, 137.59, 132.79, 130.33, 129.08, 121.68, 117.82, 116.88, 20.80. ESI-TOF (HRMS) m/z [M+H]⁺ calculated for $C_{14}H_{12}NO_3S^+$ 274.0532, found 274.0526.

N-Butylcyclopropanesulfonamide, KY-350-BA

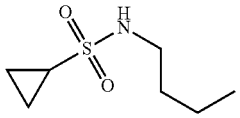

Yield: 78.2%, ¹H NMR (600 MHz, CDCl₃) δ 4.15 (s, 1H), 3.14 (t, J=7.1 Hz, 2H), 2.38 (tt, J=8.0, 4.8 Hz, 1H), 1.57-1.50 (m, 2H), 1.41-1.31 (m, 2H), 1.17-1.13 (m, 2H), 0.99-0.95 (m, 2H), 0.92 (t, J=7.41 Hz, 3H). ¹³C NMR (151 MHz, CDCl₃) δ 43.08, 32.25, 29.89, 19.69, 13.57, 5.20 ESI-TOF (HRMS) m/z [M+H]⁺ calculated for $C_7H_{16}NO_2S^+$ 178.0896, found 178.0895.

p-Tolyl cyclopropanesulfonate, KY-350-CA

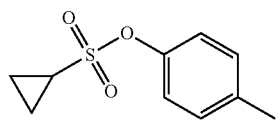

Yield: 51.8%, ¹H NMR (600 MHz, Chloroform-d) δ 7.16 (s, 4H), 2.55 (t, J=8.0, 4.7 Hz, 1H) 2.34 (s, 3H), 1.27-1.19 (m, 2H), 1.12-1.04 (m, 2H). ¹³C NMR (151 MHz, Chloroform-d) δ 147.47, 137.01, 130.23, 121.93, 27.52, 20.83, 6.11. ESI-TOF (HRMS) m/z [M+H]⁺ calculated for $C_{10}H_{13}O_3S^+$ 213.0580, found 213.0576.

N-Butyl-[1,1'-biphenyl]-4-sulfonamide, KY-351-BA

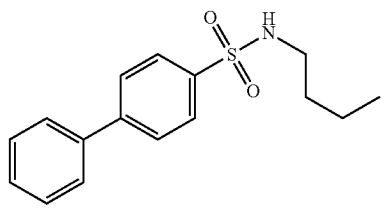 [SMILES: CCCCNS(=O)(=O)c1ccc(-c2ccccc2)cc1]

Yield: 82.9%, ¹H NMR (600 MHz, CDCl₃) δ 7.94 (d, J=8.7 Hz, 2H), 7.72 (d, J=5.2 Hz, 2H), 7.61 (d, J=8.2 Hz, 2H), 7.52-7.45 (m, 2H), 7.45-7.39 (m, 1H), 4.67 (s, 1H), 3.00 (t, J=7.1 Hz, 2H), 1.48 (p, J=7.3 Hz, 2H), 1.31 (m, 2H), 0.86 (t, J=7.3 Hz, 1.0 Hz, 3H). ¹³C NMR (151 MHz, CDCl₃) δ 145.50, 139.32, 138.54, 129.03, 128.44, 127.69, 127.57, 127.29, 42.98, 31.63, 19.68, 13.52. ESI-TOF (HRMS) m/z [M+H]⁺ calculated for $C_{16}H_{20}NO_2S^+$ 290.1209, found 290.1207.

p-Tolyl[1,1'-biphenyl]-4-sulfonate, KY-351-CA

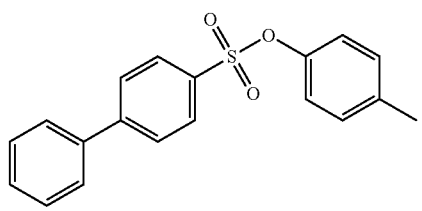 [SMILES: Cc1ccc(OS(=O)(=O)c2ccc(-c3ccccc3)cc2)cc1]

Yield: 34.6%, ¹H NMR (600 MHz, CDCl₃) δ 7.89 (d, J=8.5 Hz, 2H), 7.75-7.70 (m, 2H), 7.65-7.60 (m, 2H) 753-7.47 (m, 2H), 7.47-7.42 (m, 11H), 7.11-7.06 (m, 2H), 6.92-6.87 (m, 2H), 2.31 (s, 3H). ¹³C NMR (151 MHz, CDCl₃) δ 147.44, 146.95, 138.87, 137.03, 133.97, 130.13, 129.11, 129.02, 128.80, 127.57, 127.35, 122.05, 20.87. ESI-TOF (HRMS) m/z [M+H]⁺ calculated for $C_{19}H_{17}O_3S^+$ 325.0893, found 325.0881.

N-Butylbenzenesulfonamide, KY-352-BA

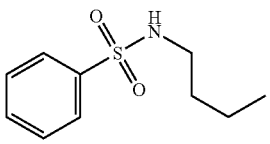

Yield: 81.7%, $^1$H NMR (600 MHz, CDCl$_3$) δ 7.88-7.84 (m, 2H), 7.59-7.55 (m, 1H), 7.54-7.49 (m, 2H), 4.37 (s, 1H), 2.95 (q, J=6.5 Hz, 2H), 1.48-1.39 (m, 2H), 1.34-1.23 (m, 2H), 0.84 (t, J=7.4 Hz, 3H). $^{13}$C NMR (151 MHz, CDCl$_3$) δ 139.96, 132.53, 129.05, 12701, 42.91, 31.54, 31.52, 19.63, 13.48. ESI-TOF (HRMS) m/z [M+H]$^+$ calculated for C$_{10}$H$_{16}$NO$_2$S$^+$ 214.0896, found 214.0895.

p-Tolyl Benzenesulfonate, KY-352-CA

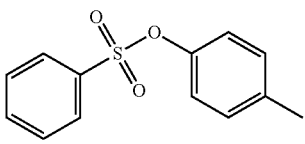 [SMILES: Cc1ccc(OS(=O)(=O)c2ccccc2)cc1]

Yield: 32.9%, $^1$H NMR (600 MHz, CDCl$_3$) δ 7.85-7.80 (m, 2H), 7.67-7.64 (m, 1H), 7.54-7.49 (m, 2H), 7.08-7.04 (m, 2H), 6.86-6.82 (m, 2H), 2.30 (s, 3H). $^{13}$C NMR (151 MHz, CDCl$_3$) δ 147.37, 137.01, 135.42, 134.07, 130.06, 129.03, 128.45, 121.96, 20.81. ESI-TOF (HRMS) m/z [M+H]$^+$ calculated for C$_{13}$H$_{13}$O$_3$S$^+$ 249.0580, found 249.0577.

N-Butylpyridine-3-sulfonamide, KY-353-BA

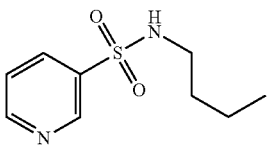

Yield: 34.6%, $^1$H NMR (600 MHz, CDCl$_3$) δ 9.07 (s, 1H), 8.79 (d, J=5.1 Hz, 1H), 8.15 (m, 1H) 747 (dd, J=8.1, 4.8 Hz, 1H), 5.08 (t, J=6.2 Hz, 1H), 2.99 (q, J=6.7, 6.1 Hz, 2H), 1.50-1.41 (m, 2H), 1.28 (dt, J=15.1, 7.4 Hz, 2H), 0.84 (td, J=7.3, 1.1 Hz, 3H). $^{13}$C NMR (151 MHz, CDCl$_3$) δ 152.88, 147.80, 136.93, 134.87, 123.80, 42.94, 31.59, 19.61, 13.44. ESI-TOF (HRMS) m/z [M+H]$^+$ calculated for C$_9$H$_{15}$N$_2$O$_2$S$^+$ 215.0849, found 215.0854.

p-Tolyl pyridine-3-sulfonate, KY-353-CA

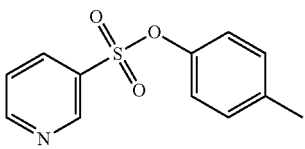 [SMILES: Cc1ccc(OS(=O)(=O)c2cccnc2)cc1]

Yield: 40.8%, $^1$H NMR (600 MHz, CDCl$_3$) δ 8.98 (dd, J=2.3, 0.8 Hz, 1H), 8.86 (dd, J=4.8, 1.6 Hz, 1H), 8.09 (dt, J=8.0, 2.0 Hz, 1H), 7.47 (m, 1H), 7.11-7.05 (m, 2H), 6.88-6.83 (m, 2H), 2.29 (s, 3H). $^{13}$C NMR (151 MHz, CDCl$_3$) δ 154.53, 149.07, 147.02, 137.55, 136.09, 13226, 130.36, 12369, 121.84, 20.83. ESI-TOF (HRMS) m/z [M+H]$^+$ calculated for C$_{12}$H$_{12}$NO$_3$S$^+$ 250.0532, found 250.0538.

N-Butylnaphthalene-2-sulfonamide, JWB-195-BA

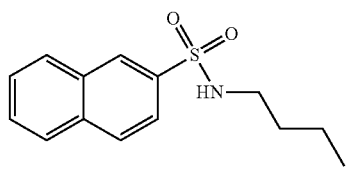 [SMILES: CCCCNS(=O)(=O)c1ccc2ccccc2c1]

Yield: 59.2%. 1H NMR (600 MHz, CDCl$_3$) δ 8.45 (s, 1H), 7.97 (d, J=8.4 Hz, 2H), 7.91 (d, J=7.6 Hz, 1H), 7.85 (dd, J=8.6, 1.8 Hz, 1H), 7.67-7.58 (m, 2H), 4.70 (s, 1H), 2.98 (t, J=7.2 Hz, 2H), 1.49-1.40 (m, 2H), 1.28 (m, 2H), 0.82 (t, J=7.4 Hz, 3H). $^{13}$C NMR (151 MHz, CDCl$_3$) δ 136.75, 134.76, 132.15, 129.45, 129.20, 128.71, 128.40, 127.88, 127.50, 122.32, 42.97, 31.59, 19.65, 13.47. ESI-TOF (HRMS) m/z [M+H]$^+$ calculated for C$_{14}$H$_{18}$NO$_2$S$^+$ 264.1053, found 264.1050.

p-Tolyl naphthalene-2-sulfonate, JWB-195-CA

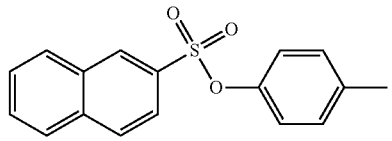 [SMILES: Cc1ccc(OS(=O)(=O)c2ccc3ccccc3c2)cc1]

Yield: 57.1%. 1H NMR (600 MHz, CDCl$_3$) δ 8.37 (d, J=2.1 Hz, 1H), 7.98 (d, J=8.9 Hz, 1H), 7.96-7.90 (m, 2H), 7.84 (dt, J=8.7, 1.8 Hz, 1H), 7.69 (m, 1H), 7.62 (m, 1H), 7.03 (d, J=8.6 Hz, 2H), 6.89-6.83 (m, 2H), 2.28 (s, 3H). $^{13}$C NMR (151 MHz, CDCl$_3$) δ 147.45, 137.00, 135.36, 132.37, 131.77, 130.41, 130.10, 129.49, 129.42, 129.41, 127.97, 127.76, 122.95, 121.99, 20.81. ESI-TOF (HRMS) m/z [M+Na]$^+$ calculated for C$_{17}$H$_{14}$NaO$_3$S$^+$ 321.0556, found 321.0553.

Example 6

Biological Methods

Cell Culture

All cell lines were cultured at 37° C. with 5% CO) using manufacturer recommended media supplemented with 10% fetal bovine serum (US Source, Omega Scientific, Tarzana, California, United States of America) and 1% L-glutamine (Fisher Scientific, Hampton, New Hampshire, United States of America): HEK293T, DMEM; DM93, RPMI Cells were seeded at 440,000 cells per plate and collected for experimental use when they reached 90% confluency. Media was aspirated and cells washed with cold PBS (2×) before scraping from plates. Cells were transferred to microfuge tubes and pelleted by centrifugation at 500×g for 5 min, and snap-frozen using liquid N, and stored −80° C. until further use.

SILAC Cell Culture

SILAC cells were cultured at 37° C. with 5% $CO_2$ in either 'light' or 'heavy' media supplemented with 10% dialyzed fetal bovine serum (Omega Scientific, Tarzana, California, United States of America), 1% L-glutamine (Fisher Scientific, Hampton, New Hampshire), and isotopically labeled amino acids. Light media was supplemented with 100 µg $ml^{-1}$ L-arginine and 100 µg $ml^{-1}$ L-lysine. Heavy media was supplemented with 100 µg $ml^{-1}$ $[^{13}C_6{}^{15}N_4]$ L-arginine and 100 µg $ml^{-1}$ $[^{13}C_6{}^{15}N_2]$ L-lysine. Labelled amino acids were incorporated for at least five passages before utilizing SILAC cells for experiments.

Transient Transfection

Recombinant proteins were produced by transient transfection of HEK293T as previously described[58]. The following plasmid constructs for expressing human proteins were purchased from GenScript: pcDNA3.1-GSTP1-FLAG, pcDNA3.1-DPP3-FLAG. Site-directed mutagenesis was used to generate mutant plasmids as previously described[57]: pcDNA3.1-GSTP1(Y8F)-FLAG, pcDNA3.1-DPP3 (Y417F)-FLAG.

Western Blot Analysis

Western blot analysis of recombinant protein expression was performed as previously described[58].

Gel-Based Chemical Proteomic Assay

Cell pellets were lysed in PBS and fractionated (100,000× g, 45 min, 4° C.) to generate soluble and membrane fractions. Protein concentrations were determined using Bio-Rad DC protein assay (Bio-Rad Laboratories, Inc., Hercules, California, United States of America), and adjusted to 1 $mgml^{-1}$ in PBS. Proteome samples (49 µl aliquots) were treated with DMSO vehicle or indicated concentration of SuTEx fragment (1 µL, 50× stock in DMSO) for 30 min at 37° C. Samples were then treated with HHS-482 probe (1 µL, 2.5 mM stock in DMSO) for 30 min at 37° C. Probe labeled samples were conjugated to rhodamine-azide (1 µL, 1.25 mM stock; final concentration of 25 µM) by copper-catalyzed azide-alkyne cycloadditions (CuAAC) for 1 h at room temperature followed by SDS-PAGE and in-gel fluorescence scanning as previously described[57].

Live Cell Evaluation of Sulfonyl-Triazole Fragments

Cells grown to ~90% confluency in 10 cm plates were treated with DMSO vehicle or SuTEx fragment (10 µl of 1,000× stock) in serum-free media for the indicated concentrations and times at 37° C. with 5% $CO_2$. After treatment, cells were washed with cold PBS twice before collection and preparation for gel-based chemical proteomic evaluation as described above. For LC-MS studies, protein concentrations were normalized to 2.3 mg $ml^{-1}$ and 432 µl (for 1 mg final protein amount) were used for sample preparation as detailed below.

Preparation of SILAC Proteomes for Liquid Chromatography-Tandem Mass Spectrometry (LC-AMS/MS) Analysis Heavy and light proteomes (432 µl of each) were diluted to 2.3 mg $ml^{-1}$ in PBS and sample aliquots (432 µl) were treated with SuTEx fragment at the indicated concentrations (5 µl, 100× stock in DMSO), mixed gently and incubated for 30 min at 37° C. Samples were then treated with HHS-482 (5 µL, 5 mM stock in DMSO) for 30 min at 37° C. Probe-modified proteomes were conjugated to desthiobiotin-PEG3-azide followed by enrichment of probe-modified peptides for nano-electrospray ionization-LC-MS/MS analyses as previously described[57].

LC-MS/MS Data Analysis

Identification of peptides and proteins from tandem mass spectrometry analyses was accomplished using bioinformatics software and quality control criteria as previously described[57].

GSTP1 Biochemical Substrate Assay

Recombinant GSTP1-HEK293T soluble cell proteomes were diluted to 1 mg $ml^{-1}$ in assay buffer (100 mM $NaH_2PO_4$, pH 7.0). Samples were treated with inhibitor at indicated concentrations for 30 min at 37° C. GSH stock solution (250 mM in water) was diluted to 4 mM in assay buffer and 25 µl of diluted GSH solution was added to each sample. A substrate stock solution of 75 mM 1-bromo-2,4-dinitrobenzene (DBNB) in ethanol was diluted to 2 mM in assay buffer. Samples (25 µl) were aliquoted into a 96-well plate and spun briefly via centrifuge. Next, 50 µl of 2 mM BDNB was added to each well and the reaction was monitored in kinetic mode by measuring absorbance at 340 nm for 10 min on a BMG Labtech CLARIOstar plate reader (BMG Labtech, Cary, North Carolina, United States of America).

DPP3 Biochemical Substrate Assay

Substrate assays were performed using purified DPP3 protein diluted to 5 ng/µL in assay buffer. DPP3 samples (10 µl) were diluted to 85 µl with assay buffer and transferred to a black 96-well plate. Samples were treated with a 50× stock of SuTEx-fragment at indication concentration for 30 min at 37° C. A stock solution of DPP3 substrate (Arg-Arg β-naphthylamide trihydrochloride, 0.5 mM: Sigma-Aldrich. St, Louis, Missouri, United States of America) was diluted to 100 µM in assay buffer. Substrate solution (5 µl) was added to each sample. Samples were mixed briefly by shaking and reaction monitored in kinetic mode by measuring fluorescence at 450 nm for 10 min on a BMG Labtech CLARIOstar plate reader (BMG Labtech, Cary, North Carolina, United States of America).

Example 7

Discussion of SuTEx Fragment Results

SuTEx Fragment Design and Synthesis

A fragment library of 1,2,4-sulfonyl triazoles was synthesized. The common SuTEx electrophile core was structurally elaborated with diverse small molecule binding elements on both the adduct group (AG) and LG to create library members with an average molecular weight of 336 Da. See FIG. 19. Fragments were created with structural elements bearing differing electron-withdrawing (EWG) or -donating (EDG) properties to test substituent effects on SuTEx reaction mechanism. Functional groups that are EWG by both resonance and polar interactions (cyano) as well as substituents (fluoro) with opposing effects from resonance (EDG) and polar (EWG) components were represented in the library[79]. Alkyl groups (cyclopropyl) were also included for direct comparison with aryl substituents.

R-substituted phenyl amides were coupled with DMF-DMA to produce amidine intermediates that underwent cyclization in acetic acid with hydrazine hydrate to form the corresponding 1,2,4-triazole[58], as shown in FIG. 20. In general, amidine cyclization reactions proceeded with greater than 75% yields across diverse functional groups and were purified by re-crystallization to complete the entire process in ~6 hrs. AG diversity was introduced by coupling 1,2,4-triazoles with alkyl- or aryl-sulfonyl chlorides modified with respective functional groups. Aryl sulfonyl chlorides reacted rapidly with 1,2,4-triazoles (completion in minutes at room temperature) while alkyl counterparts reacted slowly or not at all under the same conditions.

In summary, an efficient synthetic strategy for installing chemical diversity into SuTEx molecules via both AG and LG modifications is provided. Functional group tolerance to build structurally diverse SuTEx fragments is demonstrated. Compared with SuFEx, the SuTEx scaffold offers opportunities to simultaneously probe features of both the AG and LG that affect covalent reaction of the sulfur electrophile.

Tuning SuTEx Reactivity

Figure 21:
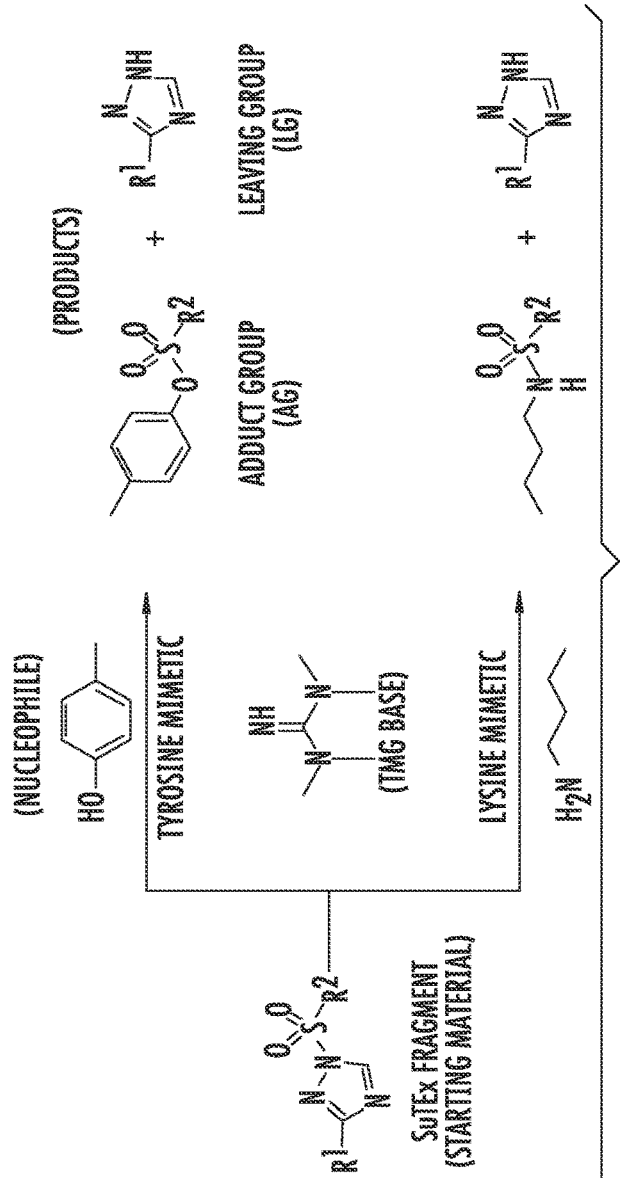
FIG. 21 is a schematic diagram of an HPLC assay for measuring SuTEx ligand (i.e., SuTEx fragment) solution reactivity. SuTEx ligands were incubated with p-cresol or n-butylamine in the presence of TMG and the time-dependent covalent reaction monitored by the reduction of ligand signal.

High-performance liquid chromatography (HPLC) was used to investigate the effects of AG/LG modifications on SuTEx reactivity in solution. Nucleophiles that modeled tyrosine (p-cresol) and lysine (n-butylamine) side chains were used for HPLC studies based on previous reports of SuTEx reaction with these residues[72]. For these studies, SuTEx fragments exposed to p-cresol or n-butylamine, in the presence of TMG base, undergo nucleophilic substitution reactions that are monitored by depletion of SuTEx fragment- and appearance of the respective covalent product-signal. See FIG. 21. Standards of the predicted products from reaction of each SuTEx fragment were synthesized to optimize chromatography and detection in the HPLC assay.

A direct comparison of different AGs revealed differences in reaction of alkyl- compared with aryl-sulfonyl-triazoles. The addition of a cyclopropyl group on the AG eliminated activity of SuTEx fragments towards p-cresol. See FIG. 22A. Closer inspection of aryl-sulfonyl-triazoles revealed trends in reactivity that support electronic effects of substituents to facilitate covalent reaction. For example, modification with the cyano EWG group resulted in completion of reaction in ~5 minutes (JWB137). See FIG. 22A. Substitution with another electron-deficient aromatic system like pyridine also resulted in rapid reaction of the sulfur electrophile with p-cresol (completion in ~30 minutes, JWB141). See FIG. 22A. In contrast, substituents like the fluoro (JWB135) and biphenyl group (JWB142) characterized by mixed polar and resonance interactions[79] showed attenuated reactivity. See FIG. 22A. Addition of a methoxy group reduced SuTEx reactivity as evidenced by incomplete reaction in the time-frame tested (JWB136). See FIG. 22A.

Modifications to the LG altered SuTEx reactivity in a more graded fashion that tracked with the electron withdrawing character of the respective substituent. For example, the addition of a trifluoromethyl group to the phenyl-triazole LG accelerated solution reaction with p-cresol (compare JWB105 and JWB150). See FIG. 22B. In contrast with the AG, modifications to the LG resulted in more subtle alterations in SuTEx reaction as evidenced by comparing half-life of reactions across the fragments tested ($t_{1/2}$). Comparing the range of $t_{1/2}$ values across fragments demonstrated that AG modifications have more impact on SuTEx reaction ($t_{1/2}$ from 1 to >360 min) compared with analogous changes on the LG ($t_{1/2}$ from 3-11 min). Finally, it was determined that SuTEx fragments reacted with p-cresol more rapidly compared with n-butylamine, which matched previous findings that SuTEx chemistry is more phenol reactive[72].

In summary, the solution studies highlighted the merits of modifying the AG and LG for broad- and fine-tuning, respectively, of SuTEx reaction with nucleophiles in solution. The general enhancement of the nucleophilic substitution reaction with EWG substituents is likely due to the increased electrophilic character of the sulfur center. The acceleration in covalent reaction did not compromise chemoselectivity of SuTEx for phenol-over amine-nucleophiles. A cyclopropyl-AG modification was identified that largely eliminated SuTEx reactivity, which provides a means to produce inactive control molecules. Taken together, SuTEx chemistry offers multiple avenues for controlling electrophilicity of the sulfur center, which are enabling features for applications in protein ligand discovery.

Proteome-Wide Structure-Reactivity Relationships of SuTEx Fragments

The chemical proteomic method for functional tyrosine profiling[72] was tailored to investigate AG/LG effects on SuTEx fragment reactivity in complex proteomes. See FIG. 23. In brief, isotopically light and heavy soluble proteomes from DM93 melanoma cells cultured by stable isotopic labeling by amino acids in cell culture (SILAC[80]) media were used for quantitative liquid chromatography-mass spectrometry (LC-MS) studies. Light and heavy DM93 proteomes were treated with dimethyl sulfoxide (DMSO) vehicle or SuTEx fragment (50 µM, 30 min, 37° C.), respectively, followed by labeling with the tyrosine-reactive probe HHS-482 described hereinabove (50 µM, 30 min, 37° C.) and copper-catalyzed azide-alkyne cycloaddition (CuAAC) conjugation of a desthiobiotin-azide enrichment tag. Proteomes were digested with trypsin protease, HHS-482-modified peptides enriched by avidin chromatography and analyzed by high-resolution LC-MS/MS and bioinformatics as described hereinabove.

To evaluate substituent effects on proteome activity, reactivity profiles of each respective SuTEx fragment were compared across >1500 total distinct HHS-482-modified tyrosine sites from >650 detected proteins. Fragments were screened across independent biological replicates (n=2-3) and high-quality tyrosine site annotations were identified by detection in at least a single biological replicate from each fragment dataset, probe-specific enrichment (HHS-482 probe/DMSO SILAC ratio (SR)>5), and quality control confidence criteria of ≥300 Byonic score[31], 1/o protein false discovery rate (FDR), and ≤5 ppm mass accuracy in order to minimize the potential for false positives[72]. SILAC ratios (SR) from competitive studies (Light-DMSO/Heavy-fragment) were used to identify fragment-competed tyrosine residues as sites showing >75% reduction in enrichment by HHS-482 compared with DMSO vehicle control (i.e. liganded tyrosines, SR>4). See FIGS. 24A and 24B. In total, 305 liganded tyrosines on 213 distinct proteins were identified, corresponding to ~30% and ~44% of total quantified tyrosines and proteins, respectively. See FIG. 25A. These percentages are comparable with ligandability measures reported for cysteines[5]. In agreement with previous SuTEx probe studies described above, we observed a high preference for tyrosine compared with lysine sites (Y/K ratio) in our fragment ligand competition studies (average Y/K ratio of 4.5). See FIG. 26.

Liganded tyrosine sites were enriched for functional domains involved in nucleotide binding (PRU00267, PRU1059), protein-protein interactions (PRU00191, PRU00386), enzymatic reactions (PRU00691, PRU00277), and metal binding (PRU01163, PRU00472). See FIG. 25B. A large fraction of liganded tyrosines resided in proteins absent from the Drugbank database[33], which supports SuTEx fragments targeting proteins that lack pharmacological probes. See FIG. 25C. Liganded tyrosines included enzymes like GSTP1, for which a hyper-reactive catalytic tyrosine in the glutathione binding site (Y8) was previously identified, as well as a tyrosine site (Y273) in the first catalytic cysteine half-domain (FCCH81) of the ubiquitin activating enzyme UBA1[82-83]. Non-liganded tyrosines were enriched for domain classes that were distinct from fragments and similar to profiles observed for SuTEx alkyne probes. See FIG. 25B. These data support the importance of molecular recognition for SuTEx fragment-tyrosine interactions at protein binding sites. Differences in reactivity were observed with individual fragment electrophiles that displayed liganded tyrosine frequencies ranging from <0.1% (JWB142) to >25% (JWB150) with a mean liganded frequency of 4.6%. See FIG. 24C.

Liganded tyrosines showed clear structure-activity relationships (SAR) with the SuTEx fragment library. See FIG. 24A. Comparison of JWB150, JWB152, and JWB146 uncovered relative trends in proteomic reactivity that suggest EWGs on the AG as a common feature of SuTEx fragments with higher liganded tyrosine frequencies. See FIGS. 24A and 24C). Despite these proteomic trends, which somewhat matched the HPLC studies, differences were also observed that contrasted with the general reactivity profiles of SuTEx fragments. For example, JWB152 showed a lower liganded tyrosine frequency compared with JWB150 despite exhibiting substantially higher reactivity in the HPLC assay. See FIG. 28. Without being bound to any one theory, these data suggest that, in addition to driving reactivity, structural modifications on the AG can contribute to binding events that enhance fragment-tyrosine interactions of compounds sharing a common LG. The differences in reactivity profiles of JWB198 and JWB202, which are differentiated by AG structure on a common LG scaffold, further support recognition as a contributor of SuTEx fragment interactions on proteins. See FIGS. 19 and 24A. Several fragments including JWB142 and JWB146 were identified with a reduced liganded tyrosine frequency while retaining high activity (SR>6) against tyrosine competed sites on YWHAE[84] (Y49) and PLD3[85] (Y437), respectively. See FIGS. 24A and 24C. Finally, the cyclopropyl-AG-modified fragment JWB131 was largely unreactive against the proteome. See FIGS. 19 and 24A.

In summary, chemical proteomic studies highlight the advantage of modifying the AG and LG on SuTEx fragments for tuning reactivity and specificity at tyrosine sites on proteins. See FIGS. 24A-24C and 25A-25C. In contrast with the above-described efforts to develop globally reactive probes, SuTEx fragments with reduced proteome reactivity were identified that retain high efficiency for competing at tyrosine sites on select proteins (JWB202 and JWB198). See FIGS. 24A-24C. The latter finding supports AG and/or LG modification as a strategy for not only controlling electrophilicity (see FIGS. 22A and 22B) but also to alter molecular recognition at protein binding sites as evidenced by the distinct profile of enriched domains in liganded (fragment activity) compared with non-liganded sites (general probe enrichment; FIG. 25B). Importantly, the chemoselectivity for tyrosine over lysine in proteomes is retained in structurally diverse fragments that, combined with the ability to prioritize tyrosine sites based on hyper-reactivity, positions SuTEx as a suitable strategy for fragment-based ligand discovery[76-78].

Liganding a Non-Catalytic Tyrosine to Disrupt Protein Function

To determine the functional impact of tyrosine-ligand interactions identified by SuTEx, human DPP3 was selected because it contains a single probe-modified tyrosine site (Y417) that is not catalytic but is near the zinc binding region of this metallopeptidase[86] (FIG. 27A). With the goal of testing whether liganding a non-catalytic tyrosine is a viable strategy for developing inhibitors of enzymes like DPP3, the SuTEx fragment library was screened for DPP3 ligands by competitive gel-based chemical proteomic profiling with HHS-482 (50 μM fragment, 37° C., 30 min. See FIG. 29, top. As expected, fragments with broad reactivity (JWB150 and JWB152) showed potent competition against recombinant DPP3 but also substantial proteome cross-reactivity across the entire molecular weight range of proteins detected in HEK293T proteomes. See FIG. 29, bottom. Further analysis of the screening data identified JWB142 and JWB202 as attractive leads because these compounds showed ~50% blockade of DPP3 probe labeling while maintaining reasonable selectivity across the proteome. JWB142 was used for further studies because it showed improved selectivity against a ~23 kDa endogenous probe-labeled band detected in HEK293T proteomes. See FIG. 29, bottom.

Given the proximity of Y417 to the catalytic zinc in the active site (FIG. 27A), it was predicted that liganding Y417 with JWB142 would disrupt DPP3 peptidase function. An established peptidase assay was used to measure inhibitor activity of SuTEx fragments[72]. Pretreatment with JWB142 resulted in concentration-dependent blockade of recombinant DPP3 peptidase activity ($IC_{50}$=17 μM). See FIGS. 27B and 27C. A structurally analogous negative control molecule was included that contained a cyclopropyl-modified AG that rendered JWB131 inactive against DPP3 to determine site specificity of inhibitory activity for Y417. See FIGS. 27B and 27C. The ability of the lead fragment to ligand the Y417 site was verified by LC-MS chemical proteomic analysis of recombinant DPP3-HEK293T proteomes (50 μM fragment, 37° C., 30 min). An ~50% blockade of HHS-482 labeling of DPP3 Y417 was observed with JWB142 but not JWB131 competition (SR=2.4). See FIG. 27D.

A biphenyl sulfonyl-fluoride analog of JWB142 was evaluated to compare potency of SuTEx and SuFEx for development of protein ligands (SuFEx-3). See FIG. 27B. In agreement with reduced activity of sulfonyl-fluoride compared -triazole compounds[72], SuFEx-3 showed >10-fold reduced potency against DPP3 compared with JWB142 ($IC_{50}$=246 μM). See FIG. 27C. The difference in biochemical activity was also reflected by HPLC assays, which showed completion of JWB142 reaction within ~6 hours while SuFEx-3 was largely unreactive over the same time period. See FIG. 30.

Thus, JWB142 was identified as a DPP3 ligand that blocks biochemical function via covalent modification of Y417 located adjacent to the catalytic zinc-binding site. Akin to targeting non-catalytic cysteines for inhibitor development[87], liganding a non-catalytic tyrosine was found to be a viable strategy for blocking protein activity. See FIGS. 27A-27D. A matching inactive control molecule JWB131 was used to demonstrate site specificity for JWB142 blockade of DPP3 biochemical activity. See FIGS. 27C and 27D. It was also demonstrated that SuTEx can enhance potency of sulfur electrophiles (compare JWB142 and SuFEx-3, see FIGS. 27B and 27C) while maintaining reasonable specificity across the proteome (JWB142). See FIG. 24A. DPP3 has been implicated in nociception (via N-terminal cleavage of opioid peptides) and human cancers including ovarian[88] and squamous cell lung carcinomas[89] through increased enzymatic activity or protein-protein interactions, respectively.

Liganding a Phosphotyrosine Site in Live Cells

SuTEx fragments were tested as protein ligands in live cells. Glutathione S-transferase Pi (GSTP1) was selected for proof-of-concept studies because it possesses a single hyper-reactive tyrosine that is catalytic and a reported phosphorylation site (Y8[72, 90]) Consistent with its hyper-reactive character, robust HHS-482-labeling of recombinant WT GSTP1 that was lost in Y8F mutant was demonstrated, validating use of this probe for a gel-based competitive assay screen of potential GSTP1 inhibitors. See FIG. 31.

Recombinant human GSTP1-HEK293T proteomes were screened against the SuTEx library (50 µM, 37° C., 30 min) and several hit fragments were identified that showed >80% blockade of HHS-482-labeling. See FIG. 31. JWB152 and JWB198 were selected for further studies because of the availability of structurally analogous negative control compounds to evaluate specificity in pharmacological experiments (JWB146 and JWB191, respectively). See FIG. 32A.

A biochemical substrate assay[72] was used to test whether the fragment molecules blocked GSTP1 catalytic activity. Pretreatment with JWB152 or JWB198 inactivated GSTP1 in a concentration dependent manner ($IC_{50}$=23 and 16 µM, respectively). See FIG. 32B. Specificity of inhibition against recombinant GSTP1 was confirmed by lack of activity of the negative control fragments JWB146 and JWB191. See FIG. 32B. A sulfonyl-fluoride analog SuFEx-2 was also used to directly compare SuFEx and SuTEx activity against recombinant GSTP1. Consistent with the DPP3 findings, the SuTEx fragment showed a >10-fold increase in potency compared with the SuFEx analog in the GSTP1 activity assay. See FIG. 32B.

Next, SILAC DM93 cells were treated with JWB152 or JWB198 to determine whether these SuTEx fragments could ligand Y8 of endogenous GSTP1 in living systems (50 µM compound, 1.5 hr, 37° C.). Cells were pretreated with DMSO vehicle or SuTEx fragments followed by cells lysis, HHS-482 labeling of proteomes, and quantitative chemical proteomics. See FIG. 23. Proteomes from JWB198-treated cells showed ~70% blockade of HHS-482 labeling of native GSTP1 Y8. See FIG. 32C. Inhibitory activity of JWB198 was site specific as determined by lack of activity against other GSTP1 probe-modified sites (Y50, Y64, Y80, Y119, and Y199, SR~1. See FIG. 32D. Several of these probe-modified tyrosines sites (Y50 and Y64) were in equivalent proximity from the GSH substrate compared with Y8 as determined by co-crystal structures of GSTP1 (5GSS). See FIG. 33. In contrast, mild in situ activity was observed for JWB152 against GSTP1 Y8 (~20% inhibition) despite comparable in vitro potency compared with JWB198. See FIG. 32B. Comparison of proteome-wide activity of JWB198 and JWB152 showed the latter compound broadly reacted against tyrosine sites in DM93 proteomes, suggesting that its cellular activity is diluted by cross-reactivity with additional proteins to reduce overall potency in live cells. See FIG. 24A.

Collectively, JWB198 was identified as a SuTEx fragment that is capable of liganding Y8 of GSTP1 in lysates and live cells. Development of tyrosine-reactive SuTEx fragments presents a unique opportunity to site-specifically perturb tyrosines that are known to be regulated by phosphorylation on protein targets involved in drug resistance in cancer[91].

Conclusions

Here, functional group modifications were systemically evaluated for tuning the sulfur electrophile in nucleophilic substitution reactions. Reactivity findings were applied to demonstrate the versatility of SuTEx chemistry for developing ligands to disrupt functional tyrosine sites on proteins. Although SuTEx can be used as a global tyrosine profiling platform, as described above, these studies also highlight the broad potential for developing protein-targeted ligands using this chemistry. The capability for simultaneous modification on the AG and LG of SuTEx fragments uncovered key insights to functional changes required for tuning sulfur electrophiles in solution and proteomes. See FIGS. 22A, 22B and 24A-24C. The EWG and EDG character of functional groups can affect reactivity of SuTEx fragments with nucleophiles albeit to differing extents depending on the location of modification. More particularly, the sulfur electrophile was generally more sensitive to AG compared with LG modifications. See FIGS. 22A and 22B. One example was installation of a cyclopropyl functional group, which eliminated reactivity of resulting SuTEx fragments both in solution and proteomes (JWB131). See FIGS. 22A and 24A These findings support the concept of "coarse" and "fine" tuning of SuTEx reactivity through AG and LG modifications, respectively.

These findings also revealed the importance of binding recognition in the development of SuTEx protein ligands. Evaluation of probe-enriched domains from the liganded and non-liganded protein groups revealed distinct profiles. These data support SuTEx fragments targeting a different subset of the proteome (liganded group) compared with protein sites generally labeled by HHS-482 probe (non-liganded group). See FIGS. 25A and 25B. This hypothesis is further supported by the overlap of enriched domains identified by HHS-482 in this study compared with a similar domain profile observed for SuTEx alkyne probes (HHS-465 and -475) described hereinabove. Further support for molecular recognition in SuTEx activity in proteomes was provided by the disparity in activity of JWB152 and JWB150 in solution compared with proteomes. Although JWB152 was more reactive in solution, reduced as well as orthogonal tyrosine binding sites were observed compared with JWB150 in LC-MS chemical proteomic studies. See FIGS. 24A, 24C, and 28.

Two examples for developing ligands to perturb functional tyrosine sites on proteins were presented. First, fragment ligands were discovered for a tyrosine site located near the zinc-binding region of DPP3 (Y417). The Y417 binding site of DPP3 was leveraged to develop JWB142 as a first in class covalent DPP3 inhibitor that blocks biochemical activity by liganding a non-catalytic tyrosine site[72]. See FIGS. 27A-27D. Given the lack of ligands and inhibitors for DPP3, these findings support the application of SuTEx for covalent fragment-based ligand discovery[76-78] of challenging protein targets (Non-DBP group). FIG. 25C. Considering the success of covalent ligands targeting non-catalytic cysteine residues of kinases[87] and other protein classes[87,50], it is expected that the SuTEx fragment library can be expanded to determine the full inventory of tyrosines that can liganded for development of protein modulators (inhibitors or activators) for biological investigations.

It was demonstrated that SuTEx fragments can ligand tyrosines sites in live cells. The discovery of JWB152 and JWB198 as ligands of GSTP1 Y8 presented an opportunity to target a hyper-reactive tyrosine that is also a known site for phosphorylation[90]. JWB198 could ligand the Y8 site of GSTP1 in live cells. See FIGS. 32A-32D. Evaluation of proteome-wide reactivity showed that JWB198 was substantially less reactive (liganded tyrosine frequency of 1.3%, see FIGS. 24A-24C) while maintaining ~70% blockade of GSTP1 Y8. See FIGS. 32A-32D. JWB198 showed negligible activity against other quantified tyrosine sites and supports the ability of SuTEx fragments to achieve site specificity on a target protein. See FIGS. 32A-32D and FIG. 33. Taken together, these studies highlight the advantage of tunability afforded by SuTEx when optimizing protein ligands for cellular activity.

In summary, SuTEx is demonstrated as a chemistry for profiling and targeting catalytic and non-catalytic tyrosine sites across the proteome. The ability to simultaneously alter reactivity of the sulfur electrophile and incorporate binding recognition through AG and LG modifications can facilitate development of protein ligands with carefully tuned reactivity and binding affinity. Incorporating more structurally diverse scaffolds (e.g. $sp^3$ enriched carbon centers) is expected to further advance SuTEx electrophiles for perturbing protein function in living systems.

Example 8

Probes with Alternate N-heteroaryl Groups
General Protocol to Synthesize Sulfonyl Heterocycle Probes To a solution of compound S1 (see Example 1, above; 0.2 g, 0.78 mmol, 1.1 eq.) in anhydrous DCM (5 mL, 0.15 M) was added the corresponding heterocycle (0.71 mmol, 1.0 eq.) and N,N-diisopropylethylamine (DIPEA) (136 µL, 0.78 mmol, 1.1 eq.) at room temperature. Then the reaction mixture was stirred at room temperature for 2 hours. The crude product was directly loaded and purified using silica gel flash column chromatography (hexane/ethyl acetate=5:1 to 1:1) to afford the respective sulfonyl heterocycle probe.

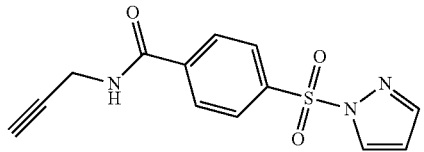 [SMILES: C#CCNC(=O)c1ccc(S(=O)(=O)n2cccn2)cc1]

4-((1H-pyrazol-1-yl)sulfonyl)-N-(prop-2-yn-1-yl)benzamide, HHS-Py-01

$^1$H NMR (600 MHz, Acetone-$d_6$) δ 8.37 (s, 1H), 8.36-8.34 (m, 1H), 8.15-8.09 (m, 4H), 7.83 (dd, J=1.6, 0.6 Hz, 1H), 6.57 (dd, J=2.8, 1.6 Hz, 1H), 4.20 (dd, J=5.5, 2.5 Hz, 2H), 2.70 (t, J=2.6 Hz, 1H). $^{13}$C NMR (151 MHz, Acetone-d6) δ 165.53, 146.74, 140.97, 140.44, 132.96, 129.46, 129.09, 110.41, 80.94, 72.39, 30.67. ESI-TOF (HRMS) m/z [M+H]$^+$ calculated for $C_{13}H_{12}N_3O_3S$ 290.0594, found 290.0595.

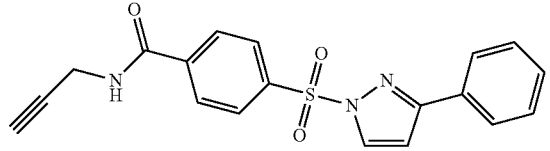 [SMILES: C#CCNC(=O)c1ccc(S(=O)(=O)n2ccc(-c3ccccc3)n2)cc1]

4-((3-phenyl-1H-pyrazol-1-yl)sulfonyl)-N-(prop-2-yn-1-yl)benzamide. HHS-Py-02

$^1$H NMR (600 MHz, Acetone-d6) δ 8.41 (d, J=2.8 Hz, 1H), 8.34 (s, 1H), 8.21-8.16 (m, 2H), 8.15-8.10 (m, 2H), 7.90-7.84 (m, 2H), 7.46-7.37 (m, 3H), 7.05 (d, J=2.9 Hz, 1H), 4.20-4.17 (m, 2H), 2.68 (t, J=2.6 Hz, 1H). $^{13}$C NMR (151 MHz, Acetone-$d_6$) δ 165.57, 158.14, 141.01, 140.44, 134.61, 132.38, 130.32, 129.75, 129.51, 129.13, 127.18, 108.11, 80.92, 72.38, 30.67. ESI-TOF (HRMS) m/z [M+H]$^+$ calculated for $C_{19}H_{16}N_3O_3S$ 366.0907, found 366.0908.

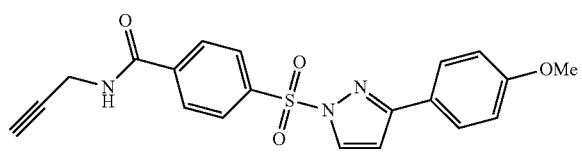 [SMILES: C#CCNC(=O)c1ccc(S(=O)(=O)n2ccc(-c3ccc(OC)cc3)n2)cc1]

4-((3-(4-methoxyphenyl)-1H-pyrazol-1-yl)sulfonyl)-N-(prop-2-yn-1-yl)benzamide, HHS-Py-03

$^1$H NMR (600 MHz, Acetone-$d_6$) δ 8.35 (t, J=3.0 Hz, 1 Hz), 8.32 (s, 1H), 8.15 (ddt, J=8.6, 3.4, 1.9 Hz, 2H), 8.11 (dd, J=8.9, 2.5 Hz, 2H), 7.82-7.77 (m, 2H), 6.99-6.97 (m, 1H), 6.96 (dt, J=4.7, 2.4 Hz, 2H), 4.18 (tt, J=3.5, 2.0 Hz, 2H), 3.82 (ffd, J=2.8 Hz, 3H), 2.70-2.65 (m, 1H). $^{13}$C NMR (151 MHz, Acetone-$d_6$) δ 161.82, 158.10, 140.58, 134.54, 129.47, 129.06, 128.62, 124.88, 115.10, 107.83, 80.93, 72.37, 55.76, 30.43. ESI-TOF (HRMS) m/z [M+H]$^+$ calculated for $C_{20}H_{18}N_3O_4S$ 396.1013, found 396.1014.

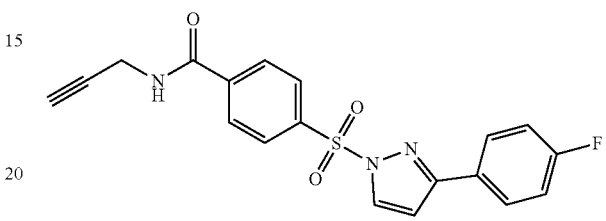

4-((5-(4-fluorophenyl)-1H-pyrazol-1-yl)sulfonyl)-N-(prop-2-yn-1-yl)benzamide, HHS-Py-04

$^1$H NMR (600 MHz, Acetone-$d_6$) δ 8.41 (q, J=2.9, 2.2 Hz, 1H), 8.35 (s, 1H), 8.18 (ddq, J=9.7, 4.0, 2.1 Hz, 2H), 8.13 (ddd, J=8.7, 3.8, 2.0 Hz, 2H), 7.92 (tq, J=5.8, 2.1 Hz, 2H), 7.21 (dddd, J=8.8, 6.7, 3.5, 2.0 Hz, 2H), 7.04 (q, J=2.9, 2.3 Hz, 1H), 4.24-4.13 (m, 2H), 2.69 (dt, J=3.4, 2.4 Hz, 1H). $^{13}$C NMR (151 MHz, Acetone-$d_6$) δ 165.55, 165.48, 165.19, 163.56, 157.18, 141.00, 140.38, 134.73, 129.52, 129.35 (d, J=9.1 Hz), 129.14, 116.61 (d, J=21.1 Hz), 108.02, 72.36, 30.43. $^{19}$F NMR (564 MHz, Acetone-$d_6$) δ −113.54. ESI-TOF (HRMS) m/z [M+H]$^+$ calculated for $C_{19}H_{15}FN_3O_3S$ 384.0813, found 384.0814.

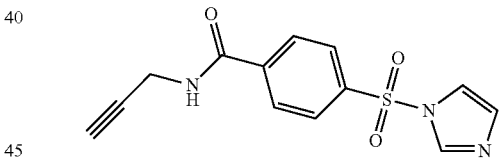

4-((1H-imidazol-1-yl)sulfonyl)-N-(prop-2-yn-1-yl)benzamide, HHS-Im-01

$^1$H NMR (600 MHz, Acetone-$d_6$) δ 8.39 (s, 1H), 8.24-8.18 (m, 3H), 8.18-8.13 (m, 2H), 7.62 (t, J=1.5 Hz, 1H), 7.11 (dd, J=1.7, 0.8 Hz, 1H), 4.24-4.17 (m, 2H), 2.70 (td, J=2.5, 0.7 Hz, 1H). $^{13}$C NMR (151 MHz, Acetone-$d_6$) δ 165.41, 141.22, 141.19, 137.96, 132.61, 129.85, 128.59, 118.86, 80.92, 72.41, 30.67. ESI-TOF (HRMS) m/z [M+H]$^+$ calculated for $C_{13}H_{12}N_3O_3S$ 290.0594, found 290.0602.

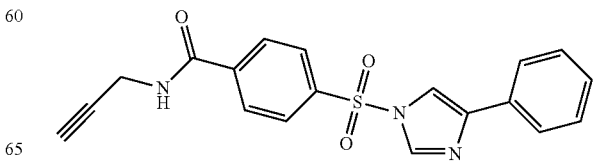

4-((4-phenyl-1H-imidazol-1-yl)sulfonyl)-N-(prop-2-yn-1-yl)benzamide, HHS-Im-02

$^1$H NMR (600 MHz, Acetone-$d_6$) δ 8.35 (s, 1H), 8.29 (d, J=0.7 Hz, 1H), 8.27-8.23 (m, 2H), 8.18-8.14 (m, 2H), 8.07 (dd, J=1.4, 0.6 Hz, 1H), 7.88-7.83 (m, 2H), 7.40-7.35 (m, 2H), 7.31-7.27 (m, 1H), 4.19 (dd, J=4.9, 2.6 Hz, 2H), 2.69 (t, J=2.6 Hz, 1H). $^{13}$C NMR (151 MHz, Acetone-$d_6$) δ 165.42, 142.25, 141.26, 141.17, 138.26, 133.48, 129.87, 129.54, 128.89, 128.67, 126.23, 113.74, 80.89, 72.42, 30.67. ESI-TOF (HRMS) m/z [M+H]$^+$ calculated for $C_{19}H_{16}N_3O_3S$ 366.0907, found 366.0915.

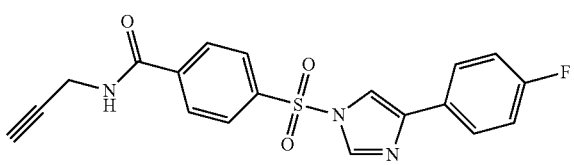 [SMILES: C#CCNC(=O)c1ccc(S(=O)(=O)n2cnc(-c3ccc(F)cc3)c2)cc1]

4-((4-(4-fluorophenyl)-1H-imidazol-1-yl)sulfonyl)-N-(prop-2-yn-1-yl)benzamide, HHS-Im-04

$^1$H NMR (600 MHz, Acetone-$d_6$) δ 8.36 (s, 1H), 8.31-8.28 (m, 1H), 8.25 (dd, J=8.7, 2.3 Hz, 2H), 8.16 (dd, J=8.6, 2.3 Hz, 2H), 8.08-8.06 (m, 1H), 7.90 (ddd, J=8.8, 5.3, 2.4 Hz, 2H), 7.15 (td, J=8.9, 2.4 Hz, 2H), 4.19 (dt, J=5.3, 2.5 Hz, 2H). 2.69 (q, J=2.6 Hz, 1H). $^{13}$C NMR (151 MHz, Acetone-$d_6$) δ 165.41, 164.29, 162.66, 144.30, 141.28, 141.11, 138.32, 129.88, 128.68, 128.22 (d, J=9.1 Hz), 116.34 (d, J=22.6 Hz), 113.60, 80.89, 72.42, 30.43. $^{19}$F NMR (564 MHz, Acetone-$d_6$) δ −115.60 ESI-TOF (HRMS) m/z [M+H]$^+$ calculated for $C_{19}H_{15}FN_3O_3S$ 384.0813, found 384.0821.

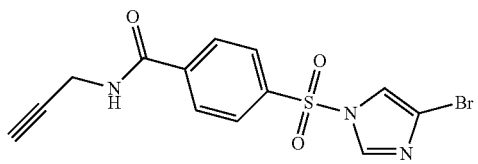 [SMILES: C#CCNC(=O)c1ccc(S(=O)(=O)n2cnc(Br)c2)cc1]

4-((4-bromo-1H-imidazol-1-yl)sulfonyl)-N-(prop-2-yn-1-yl)benzamide, KY-Im-Br $^1$H NMR (600 MHz, Acetone-$d_6$) δ 8.38 (s, 1H), 8.27-8.21 (m, 3H), 8.20-8.16 (m, 2H), 7.80 (dd, J=1.6, 0.4 Hz, 1H), 4.22-4.19 (m, 2H), 2.70 (td, J=2.6, 0.6 Hz, 1H). $^{13}$C NMR (151 MHz, Acetone-$d_6$) δ 165.35, 141.59, 140.46, 138.12, 129.97, 128.95, 119.44, 118.03, 80.87, 72.45, 30.67. ESI-TOF (HRMS) m/z [M+H]$^+$ calculated for $C_{13}H_{11}BrN_3O_3S$ 367.9699, found 367.9698.

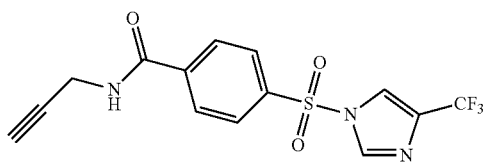 [SMILES: C#CCNC(=O)c1ccc(S(=O)(=O)n2cnc(C(F)(F)F)c2)cc1]

N-(prop-2-yn-1-yl)-4-((4-(trifluoromethyl)-1H-imidazol-1-yl)sulfonyl)benzamide, KY-Im-TFM $^1$H NMR (600 MHz, Acetone-$d_6$) δ 8.47-8.42 (m, 1H), 8.39 (s, 1H), 8.34-8.28 (m, 3H), 8.21-8.17 (m, 2H), 4.22-4.19 (m, 2H), 2.70 (t, J=2.5 Hz, 1H). $^{13}$C NMR (151 MHz, Acetone-$d_6$) δ 164.52, 141.08, 139.40, 138.62, 129.32, 128.50, 122.11, 120.34, 119.03, 80.12, 71.73, 29.95. $^{19}$F NMR (564 MHz, Acetone-$d_6$) δ −64.41. ESI-TOF (HRMS) m/z [M+H]$^+$ calculated for $C_{14}H_{11}F_3N_3O_3S$ 358.0468, found 358.0471.

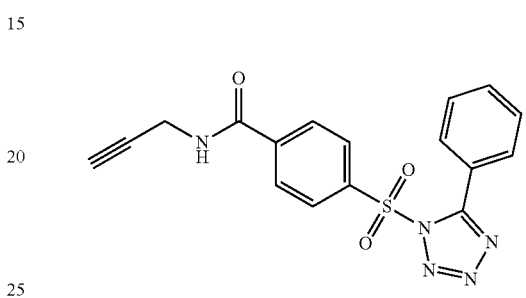

4-((5-phenyl-1H-tetrazol-1-yl)sulfonyl)-N-(prop-2-yn-1-yl)benzamide, HHS-Tet-02

$^1$H NMR (600 MHz, Acetone-$d_6$) δ 8.46 (s, 1H), 8.22-8.17 (m, 2H), 7.99-7.92 (m, 2H), 7.63-7.57 (m, 1H), 7.57-7.52 (m, 2H), 7.51-7.44 (m, 2H), 4.26-4.22 (m, 2H), 2.70 (t, J=2.5 Hz, 1H). $^{13}$C NMR (151 MHz, Acetone-$d_6$) δ 164.58, 154.55, 139.75, 139.52, 131.78, 129.67, 128.82, 128.63, 128.41, 80.00, 71.41, 29.66. ESI-TOF (HRMS) m/z [M+H]$^+$ calculated for $C_{17}H_{14}N_5O_3S$ 367.0739.

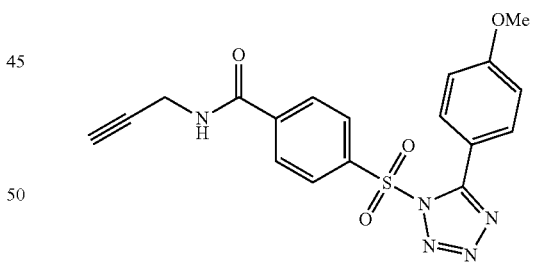

4-((5-(4-methoxyphenyl)-1H-tetrazol-1-yl)sulfonyl)-N-(prop-2-yn-1-yl)benzamide, HHS-Tet-03

$^1$H NMR (600 MHz, Acetone-$d_6$) δ 8.22-8.17 (m, 2H), 8.00-7.95 (m, 2H), 7.55-7.49 (m, 2H), 7.03-6.98 (m, 2H), 4.23 (d, J=2.5 Hz, 2H), 3.88 (s, 3H), 2.70 (t, J=2.6 Hz, 1H), 2.08 (s, 1H). $^{13}$C NMR (151 MHz, Acetone-$d_6$) δ 164.60, 162.80, 155.24, 139.85, 139.59, 130.62, 128.59, 128.36, 121.60, 113.83, 80.02, 71.40, 55.03, 28.72. ESI-TOF (HRMS) m/z [M+H]$^+$ calculated for $C_{18}H_{15}N_5O_4S$ 397.0845.

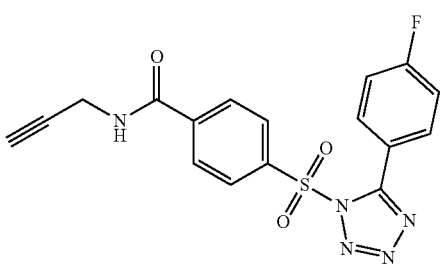 [SMILES: C#CCNC(=O)c1ccc(S(=O)(=O)n2nnnc2-c2ccc(F)cc2)cc1]

4-((5-(4-fluorophenyl)-1H-tetrazol-1-yl)sulfonyl)-N-(prop-2-yn-1-yl)benzamide, HHS-Tet-04

$^1$H NMR (600 MHz, Acetone-d$_6$) δ 8.47 (s, 1H), 8.24-8.18 (m, 2H), 8.00-7.93 (m, 2H), 7.69-7.58 (m, 2H), 7.32-7.23 (m, 2H), 4.25 (dd, J=4.6, 2.5 Hz, 2H), 2.72 (t, J=2.6 Hz, 1H). $^{13}$C NMR (151 MHz, Acetone-d$_6$) δ 166.65, 165.64, 165.57, 164.98, 154.77, 140.88, 140.85, 132.39 (d, J=9.06 Hz), 129.63 (d, J=18.12 Hz), 116.58 (d, J=22.65 Hz), 81.00, 72.43, 30.67. $^{19}$F NMR (564 MHz, Acetone-d$_6$) δ −108.93. ESI-TOF (HRMS) m/z [M+H]$^+$ calculated for C$_{17}$H$_{12}$FN$_5$O$_3$S 385.0645.

Example 9

Studies with Probes with Alternate N-Heteroaryl Groups

Imidiazole, pyrazole, and tetrazole are prevalent structures in chemical synthesis, natural products and drugs. The five-membered heterocycle ring itself is a combination of electron-richness and hydrogen bonding readiness and polarity. Thus, such heterocycles are structures that exist in many bioactive compounds, such as anticancer drugs, antifungal agents and antibacterial agents.[100] Compared with SuFEx molecules' labeling patterns, SuTEx molecules possess cell permeability and also have a higher ratio of selectivity in the labeling of tyrosine to lysine. As imidazole, pyrazole, and tetrazole share a similar 5-membered nitrogen-containing ring structure, these heterocyclic isosteres of triazole were incorporated into SuTEx-related probe structures. A general synthetic scheme and mechanism of action for an imidazole analog of a SuTEx probe is shown in FIG. 34.

Synthesis and Evaluation of Sulfonyl-Heterocyclic Probes for Chemical Proteomics Probes were synthesized via a modular scheme. First, propargyl amine was coupled to 4-(chlorosulfonyl)benzoyl chloride to form a 4-(prop-2-yn-1-ylcarbamoyl)benzenesulfonyl chloride intermediate. Then various substituted heterocycles were attached. Analogs of sulfonyl substituted imidazole, pyrazole, and tetrazole incorporating electron-donating or withdrawing elements were prepared.

The probe analogs were tested in both cell lysate and live cells of HEK293T and DM93 cells to evaluate their proteomic labeling patterns. For the lysate (in vitro) treatment, the probes were dissolved in DMSO and then added to the proteome to yield a 100 μM effective concentration for 30 minutes at 37° C. Similarly, for the live cell (in situ) treatment, the probes were dissolved in DMSO and added to the medium to yield a 100 μM effective concentration for 120 minutes at 37° C. Then the cells were lysed to expose the proteome. Both in vitro and in situ proteome subsequently underwent copper-catalyzed azide-alkyne cycloaddition (CuAAC) conjugation of a rhodamine-azide fluorescent tag and an SDS-PAGE analysis. See FIGS. 35A and 35B. The base variations of sulfonyl imidazole analogs displayed more labeling than the pyrazole and tetrazole analogs.

As a preliminary method of evaluating probes' covalent mode of action, one of the most reactive probes, HHS-IM-01, was treated at a low concentration for increasing duration of time. The result shows the probes labeling increased over 120 minutes and collaborated with the proposed covalent reaction mechanism.

Tuning the Reactivity of the Probe Scaffold

An HPLC assay was used to investigate the leaving group's effect on the overall solution reactivity of different heterocycles. See FIG. 36. In the assay, p-cresol and n-butylamine were used as substrates based on their resemblance to tyrosine and lysine side chains, respectively. The probes undergo nucleophilic substitution with the substrates in the presence of TMG base. Depletion of the probes and formation of the probe-substrate (p-cresol or n-butylamine) adduct were quantified by the AUC of the probes and the adducts.

In the direct comparison of different heterocyclic leaving groups (4-phenyl imidazole, 3-phenyl pyrazole, 5-phenyl tetrazole and 3-phenyl-1,2,4, -triazole) it was found that despite the electron-deficient nature of phenyl, the reactivity decreased as the heterocycle was switched from triazole to imidazole, tetrazole, and pyrazole, in that order.

The modified imidazole probe analogs were validated. With strong electron-withdrawing groups modifying the imidazole LG, it was assumed that the probes' reactivity would increase, whereas electron-donating groups would reduce the scaffold's proteomic labeling ability. This assumption was verified by the solution reactivity measurement, where the rate of probe consumption is more rapid as the electron-withdrawing element is more prominent. In situ and in vitro-based probe labeling for both HEK293T and DM93 cell-lines were performed. The phenyl and 4-fluorophenyl imidazole-modified imidazole showed reduced labeling in the proteome, but the bromo and trifluoromethyl-methyl modified imidazole leaving group displayed augmented proteomic reactivity.

Proteome-Wide Structural-Activity Relationships of Sulfonyl Imidazole Analogs

A chemical proteomic treatment and analysis protocol was established to evaluate the structural-induced effect on the proteomic coverage of the sulfonyl imidazole analogs. Liver Duke Melanoma 93 (DM93) and human embryonic kidney 293T (HEK293T) cells were treated with the probes (100 μM, 2 hours, 37° C.). The cells were harvested, washed and fractionated to expose the proteome. The cytosolic proteome subsequently underwent copper-catalyzed azide-alkyne cycloaddition (CuAAC) with a dethiobiotin PEG-3 azide tag. The tagged proteomes were digested with trypsin lys-C protease mixture, enriched by avidin affinity chromatography, eluted and analyzed by chromatography-tandem high-resolution mass spectrometry (LC-MS). The bioinformatic match of probe modified peptides was filtered with data confidence control criteria of ≥300 Byonic score, ≥3 log probability and ≤5 ppm mass accuracy (amino acid residue modifications of Y, K, N, Q, and W were processed at this point). See FIG. 37A.

The analogs' amino acid specificity was amenable toward tyrosine when various electron-withdrawing elements were added to the leaving group. For example, HHS-Im-01 and KY-IM-TFM had similar overall reactivity towards tyrosine and lysine residues (329 over 338), but KY-Im-TFM changed the analogs' specificity of mildly lysine-specific (Y/K=0.77) to tyrosine selective (Y/K=3.58). See FIG. 37B.

As shown in proteomic target analysis, even if the proteome reactivity can be similar for HHS-Im-02, HHS-Im-04, and KY-Im-Br or HHS-Im-01 and KY-Im-TFM, their proteome coverage can be unique. See FIG. 37C.

In summary, like the highly tunable nature of sulfonyl triazole scaffolds, which are active phosphotyrosine sites, similar principles can be applied to the sulfonyl heterocycle probe analogs. By attaching various heterocyclic leaving groups to the probe scaffold, the overall reactivity and proteomic specificity can be altered. Within each heterocycle analog, the addition of an electron-withdrawing element increases the scaffold's reactivity and tyrosine selectivity. Through heterocycle exchange, sulfonyl-triazole probe scaffold reactivity can be tuned on a macro scale. In contrast, changing the substitution group off the imidazole, for example, can both fine tune the probe's overall reactivity and amino acid specificity toward a specific value. The wide tyrosine/lysine specificity range as well as the proteomic coverage of the sulfonyl imidazole analogs can be further utilized for monitoring particular small-molecule ligand engagement of a particular target protein at a particular domain.

Example 10

Probes with Bis(4-fluorophenyl)methylene)piperidine-Containing LG

All chemical reagents and solvents were obtained from commercial suppliers and used as supplied without further purification unless stated otherwise. Analytical thin layer chromatography (TLC) was performed on Merck Silica gel 60 F254 plates (0.25 mm). Preparative TLC was conducted on Analtech Silica gel GF UV254 (1000 micron; Analtech, Newark, Delaware, United States of America). Flash column chromatography was accomplished with Silica Gel 60 (230-400 mesh) purchased from Fisher Scientific (Hampton, New Hampshire, United States of America). Detection was realized by using UV-light (254 nm) and/or TLC staining reagent such as phosphomolybdic acid (PMA). Nuclear magnetic resonance (NMR) spectra ($^1$H and $^{13}$C) were recorded on a Varian spectrometer at 600 MHz at room temperature. Chemical shifts were provided in parts per million (ppm) with coupling constants in Hz. $^1$H and $^{13}$C spectra were calibrated in relation to deuterated solvents, namely CDCl$_3$ (7.26 ppm for $^1$H and 77.16 ppm for $^{13}$C) and CD$_3$COCD$_3$ (2.05 ppm for $^1$H, 29.84 and 206.26 ppm for $^{13}$C). Splitting patterns for apparent multiplets were indicated as s (singlet), d (doublet), t (triplet), q (quartet), m (multiplet), br (broadened) as well as combinations of them. High resolution mass spectrometry was obtained with an Agilent 6545B LC/Q-TOF (Agilent Technologies, Santa Clara, California, United States of America). Purity of all final products was greater than 97% as determined by analytical high-performance liquid chromatography (HPLC) on a Shimadzu 1100 Series spectrometer (Shimadzu, Kyoto, Japan).

Probes with bis(4-fluorophenyl)methylene)piperidine-containing LGs were prepared as shown in FIG. 38.

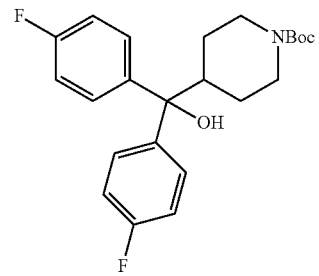 [SMILES: CC(C)(C)OC(=O)N1CCC(C(O)(c2ccc(F)cc2)c2ccc(F)cc2)CC1]

tert-Butyl 4-(bis(4-fluorophenyl)(hydroxy)methyl)piperidine-1-carboxylate (10)[93]

To a cooled solution of 1-Boc-isonipecotic acid ethyl ester (7.7 g, 30 mmol) in anhydrous THF (60 mL) at 0° C. was added 4-fluorophenyl magnesium bromide (2 M in diethyl ether, 36 mL, 72 mmol) over 20 min. The reaction mixture was warmed to room temperature and stirred overnight (14 h) and then quenched with aqueous NH$_4$Cl solution. The aqueous layer was extracted with EtOAc 3 times and the combined organic layer was washed with brine, dried over MgSO$_4$ and concentrated on rotary evaporator. The crude material was dissolved in hot EtOAc/Hexane (1:3) and then cooled to 4° C., and the precipitate was collected to afford compound 1 (10.5 g, 87%) as white solid. $^1$H NMR (600 MHz, CDCl$_3$) δ 7.46-7.34 (m, 4H), 6.95 (t, J=8.7 Hz, 4H), 4.10 (d, J=13.2 Hz, 2H), 2.66 (t, J=12.8 Hz, 2H), 2.54 (broad, 1H), 2.45 (tt, J=11.9, 3.1 Hz, 1H), 1.43 (m, 2H), 1.39 (s, 9H), 1.27 (qd, J=12.6, 4.4 Hz, 2H). $^{13}$C NMR (150 MHz, CDCl$_3$) δ 162.30, 160.67, 154.63, 141.36, 141.34, 127.58, 127.52, 115.05, 114.91, 79.45, 79.00, 44.47, 43.93, 28.37, 26.40.

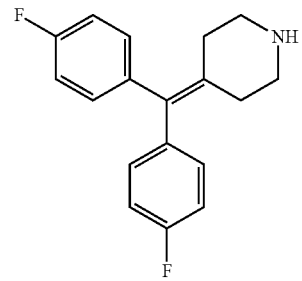 [SMILES: Fc1ccc(C(=C2CCNCC2)c2ccc(F)cc2)cc1]

4-(Bis(4-fluorophenyl)methylene)piperidine (11, RF001)

A mixture of 10 (2.02 g, 5 mmol) and trifluoroacetic acid (10 mL) in CH$_2$Cl$_2$ (10 mL) was stirred at room temperature for overnight (14 h) and then concentrated. The residue was diluted with NaOH (1 N) and extracted with CH$_2$Cl$_2$ several times. The combined organic layers were washed with brine, dried over MgSO$_4$ and concentrated in vacuum to afford compound 11 (1.34 g, 94%) as a white solid. $^1$H NMR (600 MHz, CD$_3$OD) δ 7.18-7.11 (m, 4H), 7.08-7.02 (m, 4H), 3.29 (m, 1H), 3.23 (t, J=6.0 Hz, 4H), 2.56 (t, J=6.0 Hz, 4H). $^{13}$C NMR (150 MHz, CD$_3$OD) δ 162.73, 161.10, 137.75, 137.12, 137.10, 130.86, 130.81, 129.39, 114.87, 114.73, 44.72, 27.80.

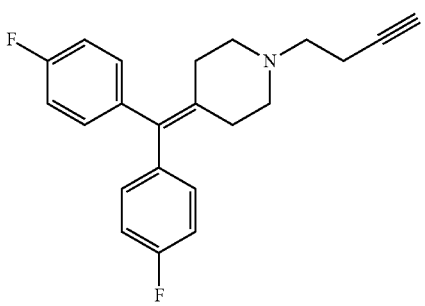 [SMILES: C#CCCN1CCC(=C(c2ccc(F)cc2)c2ccc(F)cc2)CC1]

4-(Bis(4-fluorophenyl)methylene)-1-(but-3-yn-1-yl) piperidine (12)[94]

To a solution of 11 (1.52 g, 5.3 mmol) and 3-butynyl p-toluenesulfonate (1.43 g, 6.36 mmol) in DMF (15 mL) was added K$_2$CO$_3$ powder (3.66 g, 26.5 mmol). The mixture was heated to 60° C. for 6 h and then concentrated when TLC showed most of starting material being consumed. The residue was partitioned between EtOAc and water, and the aqueous layer was extracted with EtOAc. The combined organic layers were washed with sat. Na$_2$CO$_3$, dried over MgSO$_4$ and concentrated on rotary evaporator. The product was purified by silica gel column chromatography (0 to 5% MeOH in DCM) to yield compound 12 (1.52 g, 85%) as a yellowish oil. 1H NMR (600 MHz, CDCl$_3$) δ 7.04 (dd, J=8.8, 5.5 Hz, 4H), 6.95 (t, J=8.8 Hz, 4H), 2.63 (dd, J=8.2, 7.0 Hz, 4H), 2.53 (t, J=5.6 Hz, 4H), 2.42-2.34 (m, 3H), 1.97 (t, J=6 Hz, 1H). $^{13}$C NMR (150 MHz, CDCl$_3$) δ 162.30, 160.67, 138.07, 138.05, 135.82, 133.99, 131.28, 131.22, 115.01, 114.87, 82.70, 69.14, 56.82, 54.77, 31.47, 16.81.

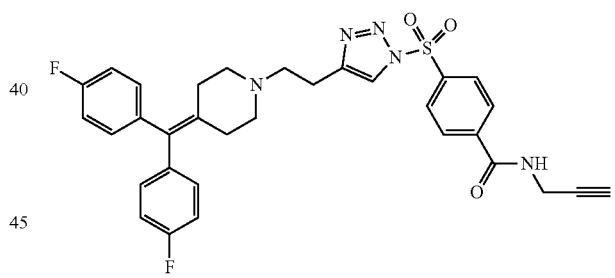

4-(Bis(4-fluorophenyl)methylene)-1-(2-(1-tosyl-1H-1,2,3-triazol-4-yl)ethyl)piperidine (13)[95]

To a solution of 12 (0.82 g, 2.43 mmol) and TsN$_3$ (0.58 g, 2.92 mmol) in toluene (20 mL) was added CuTC (91 mg, 20 mol %) at room temperature and the resulting mixture was stirred for 4 h. Upon completion monitored by TLC, the reaction mixture was concentrated and loaded for column chromatography (0 to 15% acetone in DCM) to afford compound 13 (0.69 g, 50%) as a yellowish syrup, which became solid under vacuum. $^1$H NMR (600 MHz, CDCl$_3$) δ 8.05-7.87 (m, 2H), 7.36 (d, J=8.3 Hz, 2H), 7.11-7.01 (m, 4H), 6.99-6.93 (m, 4H), 2.92 (t, J=7.5 Hz, 2H), 2.67 (t, J=7.5 Hz, 2H), 2.51 (t, J=5.6 Hz, 4H), 2.43 (s, 3H), 2.36 (t, J=5.6 Hz, 4H). $^{13}$C NMR (150 MHz, CDCl$_3$) δ 161.68, 160.05, 146.50, 145.55, 137.48, 135.31, 133.37, 132.62, 130.67, 130.61, 129.74, 127.95, 120.39, 114.39, 114.25, 56.23, 54.28, 30.98, 22.77, 21.17.

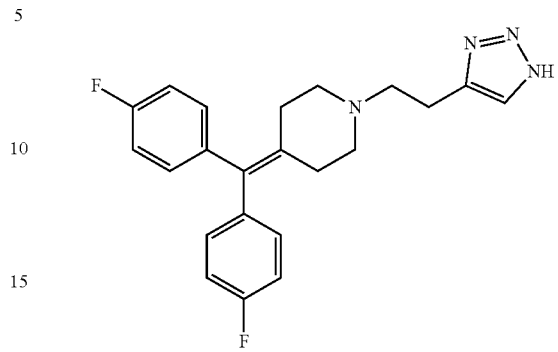

1-(2-(1H-1,2,3-Triazol-4-yl)ethyl)-4-(bis(4-fluorophenyl)methylene)piperidine (14)

To a solution of 13 (0.53 g, 1.0 mmol) in MeOH (5 mL) was added piperidine (0.43 g, 5.0 mmol) and the resulting mixture was stirred at room temperature for 0.5 h, then concentrated and directly loaded for column chromatography (0 to 50% acetone in DCM) to afford compound 14 (0.37 g, 98%) as a yellowish syrup. 1H NMR (600 MHz, CDCl$_3$) δ 7.50 (s, 1H), 7.05 (ddd, J=8.2, 5.4, 2.2 Hz, 4H), 6.97 (td, J=8.7, 2.3 Hz, 4H), 2.96 (td, J=7.1, 2.2 Hz, 2H), 2.75 (td, J=7.1, 2.1 Hz, 2H), 2.61 (td, J=5.7, 2.2 Hz, 4H), 2.48-2.37 (m, 4H). $^{13}$C NMR (150 MHz, CDCl$_3$) δ 162.35, 160.71, 137.93, 137.90, 135.27, 134.41, 131.24, 131.18, 130.90, 115.06, 114.92, 109.99, 56.98, 54.83, 31.40, 21.77.

4-((4-(2-(4-(Bis(4-fluorophenyl)methylene)piperidin-1-yl)ethyl)-1H-1,2,3-triazol-1-yl)sulfonyl)-N-(prop-2-yn-1-yl)benzamide (TH211)

To a solution of compound 14 (100 mg, 0.26 mmol) and triethylamine (TEA, 75 uL, 0.52 mmol) in anhydrous DCM (3 mL) was added a solution of compound S1 (80.2 mg, 0.31 mmol) in DCM (1 mL) at 0° C. The resulting mixture was stirred at room temperature overnight (14 h). The reaction mixture was concentrated and then directly loaded onto preparative TLC plate for purification (10% acetone in DCM) to yield TH211 (55 mg, 35%, after multiple purification) as white oil, which became solid under vacuum. $^1$H NMR (600 MHz, CDCl$_3$) δ 8.11 (d, J=8.5 Hz, 2H), 8.01 (s, 1H), 7.98 (d, J=8.5 Hz, 2H), 7.03 (dd, J=8.5, 5.6 Hz, 4H), 6.95 (dd, J=9.9, 7.5 Hz, 5H), 4.21 (dd, J=5.3, 2.6 Hz, 2H), 2.93 (d, J=7.4 Hz, 2H), 2.69 (t, J=7.4 Hz, 2H), 2.53 (s, 4H), 2.36 (t, J=5.6 Hz, 4H), 2.24 (t, J=2.6 Hz, 1H). $^{13}$C NMR (150 MHz, CDCl₃) δ 187.96, 164.87, 162.32, 160.69, 140.22, 138.72, 137.92, 131.24, 131.18, 128.79, 128.59, 121.36, 115.05, 114.90, 78.79, 72.20, 56.60, 54.82, 31.38, 29.97, 23.17. HRMS (ESI-TOF) m/z [M+H]⁺ calculated for $C_{32}H_{30}F_2N_5O_3S$ 602.2032 found 602.2032.

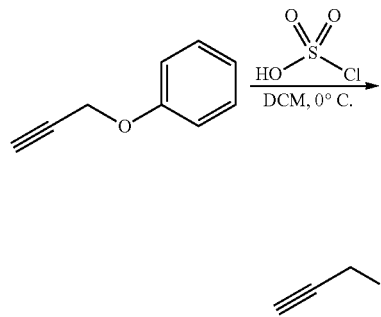

4-(Prop-2-yn-1-yloxy)benzenesulfonyl chloride (15)

The synthesis of compound 15 was adapted from a previously reported method.[96] Briefly, to a solution of phenyl propargyl ether (1.01 g, 7.5 mmol) in DCM (15 mL) was added chlorosulfonic acid (3.46 g, 30 mmol) dropwise using glass syringe at 0° C. ice bath. The black mixture was stirred for 15 min, then poured into ice water to quench the reaction. The aqueous layer was extracted twice with DCM. The combined organic layers were washed with brine, dried over MgSO₄, and concentrated to get a greenish oil, which was purified by column chromatography (20% EtOAc in hexane) to afford compound 15 (1.08 g, 62%) as a yellowish oil. ¹H NMR (600 MHz, CDCl₃) δ 7.98 (d, J=9.1 Hz, 2H), 7.13 (d, J=9.1 Hz, 2H), 4.80 (d, J=2.4 Hz, 2H), 2.60 (t, J=2.4 Hz 1H). ¹³C NMR (150 MHz, CDCl₃) δ 162.62, 136.86, 129.46, 115.62, 77.04, 76.86, 56.30.

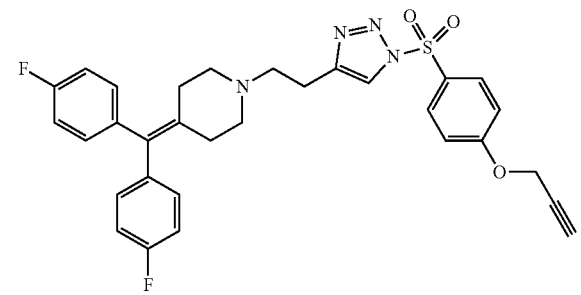 [SMILES: C#CCOc1ccc(S(=O)(=O)n2cc(CCN3CCC(=C(c4ccc(F)cc4)c4ccc(F)cc4)CC3)nn2)cc1]

4-(Bis(4-fluorophenyl)methylene)-1-(2-(1-((4-(prop-2-yn-1-yloxy)phenyl)sulfonyl)-1H-1,2,3-triazol-4-yl)ethyl)piperidine (TH214)

TH214 was synthesized from compound 14 and 15 using the same method as TH211.

¹H NMR (600 MHz, CDCl₃) δ 8.07-8.00 (m, 2H), 7.97 (s, 1H), 7.12-7.07 (m, 2H), 7.06-7.00 (m, 4H), 7.00-6.91 (m, 4H), 4.75 (d, J=2.4 Hz, 2H), 2.98 (d, J=7.5 Hz, 2H), 2.76 (s, 2H), 2.62-2.57 (m, 4H), 2.56 (m, 1H), 2.42 (t, J=5.5 Hz, 4H). ¹³C NMR (150 MHz, CDCl₃) δ 162.96, 162.29, 160.66, 146.09, 138.08, 138.06, 135.93, 133.99, 131.27, 131.22, 131.02, 128.16, 120.88, 115.83, 115.01, 114.87, 77.03, 76.77, 56.86, 56.21, 54.90, 31.61, 23.39. HRMS (ESI-TOF) m/z [M+H]⁺ calculated for $C_{31}H_{29}F_2N_4O_3S$ 545.1818, found 545.1812.

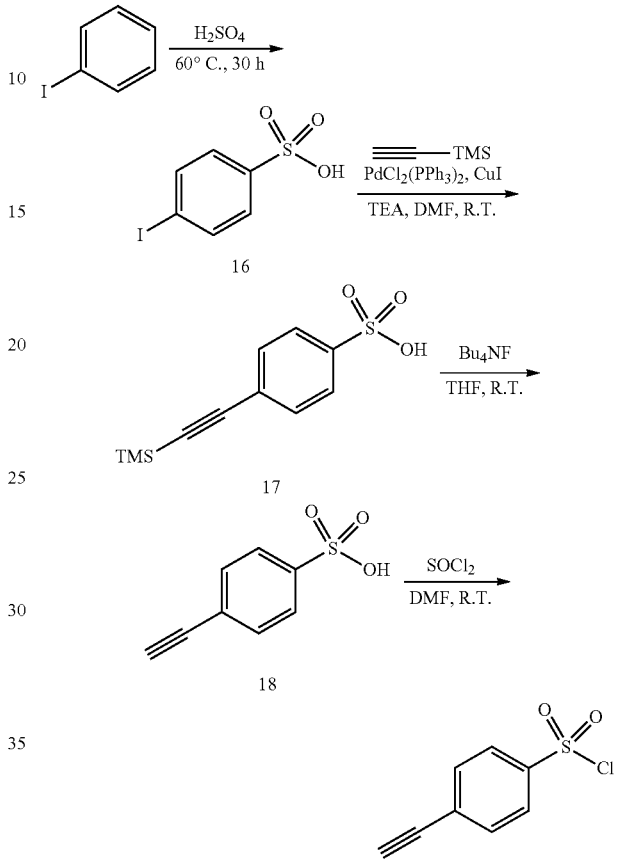

Scheme 1. Synthesis of Intermediate 19.

4-Iodobenzensulfonic Acid (16)[97]

As shown in Scheme 1, above, to iodobenzene (2 mL, 3.64 g, 17.8 mmol) was added concentrated sulfuric acid (5 mL, 8.0 g, 82 mmol) and the reaction mixture was heated to 50° C. for 30 h. Then the reaction mixture was stirred with hexane (5 mL) for 5 min in order to remove unreacted iodobenzene in the hexane layer. The sulfuric acid layer was extracted with small portions of boiling chloroform (total 20 mL) by removing the upper layer (solution of product in CHCl₃) with a pipette. The combined chloroform solution was concentrated to a small volume, and precipitates of the product were collected, washed with hexane, and dried to afford 4-iodobenzensulfonic acid (4.0 g, 80%), which was used for the next step without further purification.

4-((Trimethylsilyl)ethynyl)benzenesulfonic acid (17)[98]

As shown in Scheme 1, above, to a solution of 4-iodobenzensulfonic acid (2.22 g, 7.8 mmol) in anhydrous DMF (20 mL) was added trimethylsilylacetylene (6.6 mL, 47 mmol), triethylamine (10 mL, 78 mmol), PdCl₂(PPh₃)₂ (550 mg, 0.78 mmol) and CuI (75 mg, 0.78 mmol), and the mixture was stirred at room temperature overnight (14 h). After being concentrated under rotary evaporator, the residue was purified on flash silica gel column chromatography (10% MeOH in DCM) to afford the compound 17 (as form of triethylammonium salt, 2.07 g, 74%). $^1$H NMR (600 MHz, CDCl$_3$) δ 7.79-7.63 (m, 2H), 7.38 (d, J=8.2 Hz, 2H), 3.01 (ddd, J=7.4, 4.8, 1.0 Hz, 6H), 1.35-1.04 (m, 9H), 0.16 (d, J=0.8 Hz, 9H). $^{13}$C NMR (150 MHz, CDCl$_3$) δ 145.21, 131.66, 125.74, 124.57, 104.21, 95.66, 46.35, 8.65, −0.17.

4-Ethynylbenzenesulfonic Acid (18)

As shown in Scheme 1, above, to a solution of compound 17 (568 mg, 1.60 mmol) in THF was added tetrabutylammonium fluoride (1.92 mL, 1 M solution in THF), and the mixture was stirred at room temperature for 2 h. After being concentrated under rotary evaporator, the crude product was used for the next step without further purification.

4-Ethynylbenzenesulfonyl Chloride (19)

As shown in Scheme 1, above, a solution of crude 18 (1.6 mmol) in DMF (3 mL) was added thionyl chloride (37 uL, 8 mmol) at 0° C. The mixture was stirred at room temperature for 3 h and then poured into ice water to quench unreacted thionyl chloride. The mixture was extracted with EtOAc for several times and the combined organic layers were washed with brine, dried over MgSO$_4$ and concentrated under rotary evaporator. The residue was purified on flash silica gel column chromatography to afford compound 19 (96 mg, 30% over two steps) as yellowish solid, which was immediately frozen to suppress the hydrolysis of sulfonyl chloride. $^1$H NMR (600 MHz, CDCl$_3$) δ 7.98 (dd, J=8.6, 1.7 Hz, 2H), 7.68 (dd, J=8.6, 1.7 Hz, 2H), 3.37 (s, 1H). $^{13}$C NMR (150 MHz, CDCl$_3$) δ 143.71, 133.13, 129.58, 126.95, 82.81, 81.31.

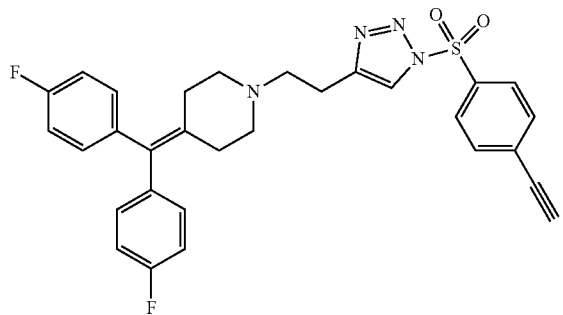 [SMILES: C#Cc1ccc(S(=O)(=O)n2cc(CCN3CCC(=C(c4ccc(F)cc4)c4ccc(F)cc4)CC3)nn2)cc1]

4-(Bis(4-fluorophenyl)methylene)-1-(2-(1-((4-ethynylphenyl)sulfonyl)-1H-1,2,3-triazol-4-yl)ethyl)piperidine (TH216)

TH216 was synthesized from compound 14 and 19 using the same method as TH211.
$^1$H NMR (600 MHz, CDCl$_3$) δ 8.04 (d, J=8.6 Hz, 2H), 7.98 (s, 1H), 7.64 (d, J=8.5 Hz, 2H), 7.04 (dd, J=8.6, 5.6 Hz, 4H), 6.96 (t, J=8.7 Hz, 4H), 3.34 (s, 1H), 3.00 (s, 2H), 2.76 (s, 2H), 2.60 (s, 4H), 2.42 (s, 4H). $^{13}$C NMR (150 MHz, CDCl$_3$) δ 162.35, 160.72, 137.89, 137.87, 135.83, 133.16, 131.22, 131.17, 129.88, 128.46, 121.20, 115.07, 114.93, 82.79, 81.25, 56.64, 54.81, 31.24, 23.10. HRMS (ESI-TOF) m/z [M+H]$^+$ calculated for C$_{30}$H$_{27}$F$_2$N$_4$O$_2$S 575.1923, found 575.1924.

Additional Compounds prepared with S1, 15, or 19 and 14 or with S1, 15, or 19 and the piperazine analog of 14:

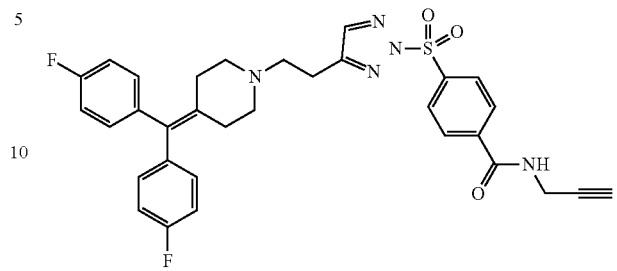

4-((4-(2-(4-(Bis(4-fluorophenyl)methylene)piperidin-1-yl)ethyl)-2H-1,2,3-triazol-2-yl)sulfonyl)-N-(prop-2-yn-1-yl)benzamide (TH213)

$^1$H NMR (600 MHz, CDCl$_3$) δ 8.08 (d, J=8.6 Hz, 2H), 7.95-7.86 (m, 2H), 7.74 (s, 1H), 7.02 (dd, J=8.8, 5.5 Hz, 4H), 6.95 (t, J=8.7 Hz, 4H), 6.67 (s, 1H), 4.21 (dd, J=5.3, 2.6 Hz, 2H), 2.90 (d, J=7.7 Hz, 2H), 2.67 (s, 2H), 2.51 (m, 4H), 2.38-2.29 (m, 4H), 2.25 (t, J=2.6 Hz, 1H). $^{13}$C NMR (150 MHz, CDCl$_3$) δ 165.01, 162.30, 160.67, 152.31, 139.70, 139.15, 138.72, 138.00, 137.98, 131.24, 131.19, 128.84, 128.19, 115.02, 114.88, 78.70, 72.34, 56.23, 54.83, 31.49, 29.99, 23.57. HRMS (ESI-TOF) m/z [M+H]$^+$ calculated for C$_{32}$H$_{30}$F$_2$N$_5$O$_3$S 602.2032, found 602.2033.

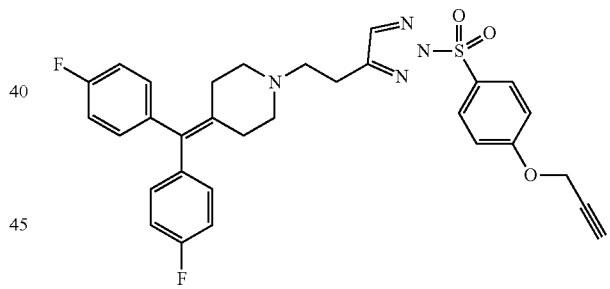

4-(Bis(4-fluorophenyl)methylene)-1-(2-(2-((4-(prop-2-yn-1-yloxy)phenyl)sulfonyl)-2H-1,2,3-triazol-4-yl)ethyl)piperidine (TH215)

$^1$H NMR (600 MHz, CDCl$_3$) δ 8.02-7.97 (m, 2H), 7.70 (s, 1H), 7.07-7.00 (m, 6H), 6.95 (t, J=8.7 Hz, 4H), 4.72 (d, J=2.4 Hz, 2H), 2.89 (t, J=7.4 Hz, 2H), 2.65 (t, J=7.4 Hz, 2H), 2.54 (t, J=2.4 Hz, 1H), 2.48 (t, J=5.6 Hz, 4H), 2.31 (t, J=5.6 Hz, 4H). $^{13}$C NMR (150 MHz, CDCl$_3$) δ 162.57, 162.30, 160.67, 151.47, 138.30, 138.05, 138.03, 135.83, 134.02, 131.26, 131.21, 131.01, 130.96, 128.20, 115.54, 115.01, 114.87, 76.91, 76.85, 56.41, 56.15, 54.85, 31.57, 23.64. HRMS (ESI-TOF) m/z [M+H]$^+$ calculated for C$_{30}$H$_{27}$F$_2$N$_4$O$_2$S 575.1923, found 575.1923.

131

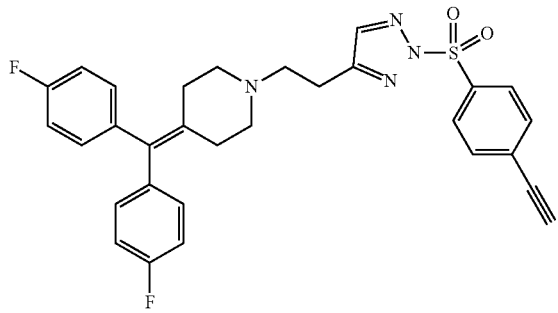 [SMILES: C#Cc1ccc(S(=O)(=O)N/N=C\C(=N)CCN2CCC(=C(c3ccc(F)cc3)c3ccc(F)cc3)CC2)cc1]

4-(Bis(4-fluorophenyl)methylene)-1-(2-(2-((4-ethynylphenyl)sulfonyl)-2H-1,2,3-triazol-4-yl)ethyl)piperidine (TH217)

$^1$H NMR (600 MHz, CDCl$_3$) δ 8.02-7.96 (m, 2H), 7.73 (s, 1H), 7.62-7.56 (m, 2H), 7.07-6.99 (m, 4H), 6.99-6.91 (m, 4H), 3.30 (s, 1H), 2.89 (t, J=7.3 Hz, 2H), 2.64 (t, J=7.4 Hz, 2H), 2.47 (t, J=5.6 Hz, 4H), 2.29 (t, J=5.6 Hz, 4H). $^{13}$C NMR (150 MHz, CDCl$_3$) δ 162.29, 160.66, 152.15, 138.92, 138.05, 138.03, 135.77, 134.04, 132.90, 131.25, 131.20, 129.24, 128.43, 115.01, 114.87, 82.36, 81.40, 56.29, 54.83, 31.56, 23.65. HRMS (ESI-TOF) m/z [M+H]$^+$ calculated for C$_{31}$H$_{29}$F$_2$N$_4$O$_3$S 545.1818, found 545.1819.

132

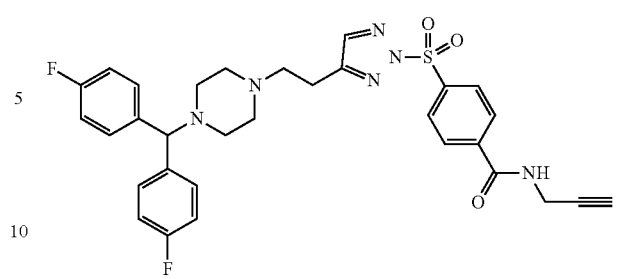

4-((4-(2-(4-(Bis(4-fluorophenyl)methyl)piperazin-1-yl)ethyl)-2H-1,2,3-triazol-2-yl)sulfonyl)-N-(prop-2-yn-1-yl)benzamide (TH313)

$^1$H NMR (600 MHz, CDCl$_3$) δ 8.13-8.05 (m, 2H), 7.94-7.84 (m, 2H), 7.71 (s, 1H), 7.31 (ddd, J=8.7, 5.3, 1.4 Hz, 4H), 6.94 (td, J=8.7, 1.4 Hz, 4H), 6.48 (s, 1H), 4.22 (ddd, J=5.3, 2.6, 1.3 Hz, 2H), 4.17 (s, 1H), 2.85 (t, J=7.4 Hz, 2H), 2.62 (t, J=7.4 Hz, 2H), 2.47 (br, 4H), 2.33 (br, 4H), 2.27 (td, J=2.5, 1.2 Hz, 1H). $^{13}$C NMR (150 MHz, CDCl$_3$) δ 164.99, 162.58, 160.95, 152.24, 139.66, 139.12, 138.77, 138.11, 138.09, 129.20, 129.15, 128.87, 128.15, 115.44, 115.30, 78.66, 74.42, 72.42, 56.23, 53.05, 51.63, 30.02, 23.37. HRMS (ESI-TOF) m/z [M+H]$^+$ calculated for C$_{31}$H$_{31}$F$_2$N$_6$O$_3$S 605.2141, found 605.2143.

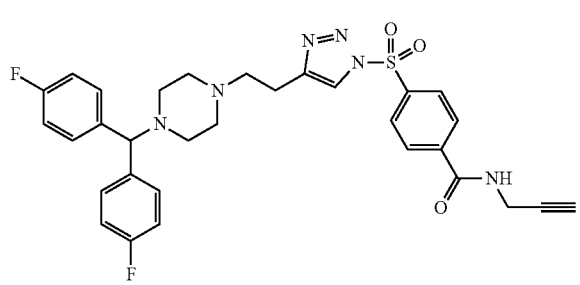 [SMILES: C#CCNC(=O)c1ccc(S(=O)(=O)N/C=C(/CCN2CCN(C(c3ccc(F)cc3)c3ccc(F)cc3)CC2)N=N)cc1]

4-((4-(2-(4-(Bis(4-fluorophenyl)methyl)piperazin-1-yl)ethyl)-1H-1,2,3-triazol-1-yl)sulfonyl)-N-(prop-2-yn-1-yl)benzamide (TH312)

$^1$H NMR (600 MHz, CDCl$_3$) δ 8.11 (d, J=8.6 Hz, 2H), 8.00-7.94 (m, 3H), 7.32 (dd, J=8.7, 5.5 Hz, 4H), 6.94 (t, J=8.7 Hz, 4H), 6.83 (t, J=5.3 Hz, 1H), 4.22 (dd, J=5.3, 2.5 Hz, 2H), 4.19 (s, 1H), 2.89 (t, J=7.4 Hz, 2H), 2.65 (d, J=7.5 Hz, 2H), 2.50 (br, 4H), 2.37 (br, 4H), 2.26 (t, J=2.5 Hz, 1H). $^{13}$C NMR (150 MHz, CDCl$_3$) δ 164.84, 162.58, 160.96, 146.39, 140.19, 138.78, 138.12, 138.10, 129.21, 129.16, 128.81, 128.54, 121.29, 115.46, 115.31, 78.74, 74.43, 72.27, 56.66, 53.09, 51.62, 29.98, 23.04. HRMS (ESI-TOF) m/z [M+H]$^+$ calculated for C$_{31}$H$_{31}$F$_2$N$_6$O$_3$S 605.2141, found 605.2144.

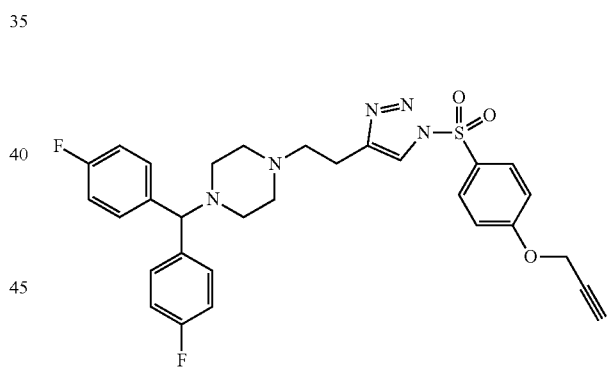

1-(Bis(4-fluorophenyl)methyl)-4-(2-(1-((4-(prop-2-yn-1-yloxy)phenyl)sulfonyl)-1H-1,2,3-triazol-4-yl)ethyl)piperazine (TH314)

$^1$H NMR (600 MHz, CDCl$_3$) δ 8.07-8.00 (m, 2H), 7.96 (s, 1H), 7.37-7.29 (m, 4H), 7.13-7.07 (m, 2H), 7.00-6.90 (m, 4H), 4.75 (dd, J=2.4, 0.7 Hz, 2H), 4.21 (s, 1H), 2.92 (s, 2H), 2.69 (s, 2H), 2.56 (t, J=2.4 Hz, 1H), 2.60-2.29 (m, 8H). $^{13}$C NMR (150 MHz, CDCl$_3$) δ 162.97, 162.60, 160.97, 145.81, 138.13, 138.11, 131.03, 129.21, 129.16, 128.12, 121.03, 115.84, 115.47, 115.33, 77.01, 76.80, 74.42, 56.82, 56.22, 53.09, 51.49, 23.01. HRMS (ESI-TOF) m/z [M+H]$^+$ calculated for C$_{30}$H$_{30}$F$_2$N$_5$O$_3$S 578.2032, found 578.2034.

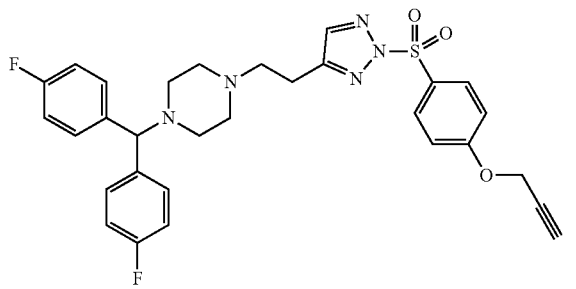 [SMILES: C#CCOc1ccc(S(=O)(=O)n2ncc(CCN3CCN(C(c4ccc(F)cc4)c4ccc(F)cc4)CC3)n2)cc1]

1-(Bis(4-fluorophenyl)methyl)-4-(2-(2-((4-(prop-2-yn-1-yloxy)phenyl)sulfonyl)-2H-1,2,3-triazol-4-yl)ethyl)piperazine (TH315)

$^1$H NMR (600 MHz, CDCl$_3$) δ 8.01-7.98 (m, 2H), 7.67 (s, 1H), 7.34-7.28 (m, 4H), 7.06-7.03 (m, 2H), 6.97-6.93 (m, 4H), 4.73 (d, J=2.4 Hz, 2H), 4.17 (s, 1H), 2.86 (t, J=7.5 Hz, 2H), 2.63 (t, J=7.5 Hz, 2H), 2.55 (t, J=2.4 Hz, 1H), 2.52-2.22 (m, 8H). $^{13}$C NMR (150 MHz, CDCl$_3$) δ 162.58, 162.57, 160.95, 151.35, 138.28, 138.14, 138.12, 130.96, 129.20, 129.15, 128.19, 115.54, 115.44, 115.30, 76.91, 76.86, 74.47, 56.40, 56.15, 53.07, 51.67, 23.42. HRMS (ESI-TOF) m/z [M+H]$^+$ calculated for C$_{30}$H$_{30}$F$_2$N$_5$O$_3$S 578.2032, found 578.2032.

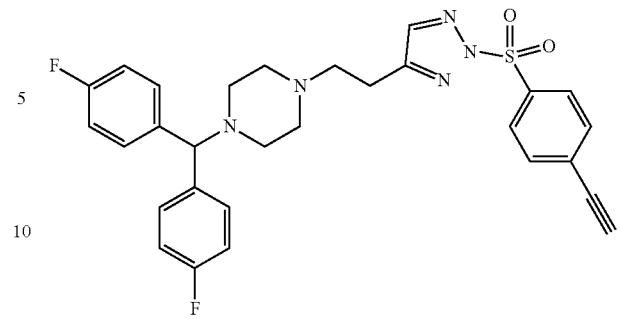

1-(Bis(4-fluorophenyl)methyl)-4-(2-(2-((4-ethynylphenyl)sulfonyl)-2H-1,2,3-triazol-4-yl)ethyl)piperazine (TH317)

$^1$H NMR (600 MHz, CDCl$_3$) δ 8.00-7.97 (m, 2H), 7.70 (s, 1H), 7.62-7.57 (m, 2H), 7.35-7.30 (m, 4H), 6.98-6.92 (m, 4H), 4.17 (s, 1H), 3.31 (s, 1H), 2.86 (t, J=7.4 Hz, 2H), 2.63 (t, J=7.4 Hz, 2H), 2.47 (br, 4H), 2.34 (br, 4H). $^{13}$C NMR (150 MHz, CDCl$_3$) δ 162.59, 160.96, 152.01, 138.89, 138.13, 138.11, 135.78, 133.11, 132.91, 129.20, 129.15, 128.44, 115.45, 115.31, 82.35, 81.42, 74.47, 56.26, 53.06, 51.66, 23.41. HRMS (ESI-TOF) m/z [M+H]$^+$ calculated for C$_{29}$H$_{28}$F$_2$N$_5$O$_3$S 548.1927, found 548.1924.

Cell Culture

Jurkat cells were cultured in RPMI media 1640 (Gibco) and HEK293T cells were in DMEM, both supplemented with 10% fetal bovine serum (FBS, U.S. Source, Omega Scientific, Tarzana, California, United States of America) and 1% L-glutamine (Thermo Fisher Scientific, Waltham, Massachusetts, United States of America). SILAC cells were cultured with corresponding SILAC media supplemented with 10% dialyzed FBS and either $^{12}$C, $^{14}$N-lysine and arginine (100 μg/mL) for "light" or $^{13}$C, $^{15}$N-lysine and arginine (100 μg/mL) for "heavy". All cells were maintained in a humidified incubator at 37° C. with 5% CO$_2$, and used for experiments around 90% confluency (HEK293T) or 1×10$^6$ cells/mL (Jurkat).

Transient Transfection

Recombinant human DGKα protein were produced by transient transfection of HEK293T cells with recombinant DNA plasmid and the protein expression were assayed by Western blot as previously described.[51,99] pGC-FLAG-DGKA (human) was a gift from Dr. Thurl Harris (School of Medicine, University of Virginia).

Live Cell Treatment with Probes and Cell Lysates Preparation

Cells were treated with DMSO or probes (2.5 mM in DMSO, 50×, final concentration at 50 μM) in serum-free media for 2 h at 37° C. with 5% CO$_2$, and then collected, washed with cold PBS for three times. The cell pellets were lysed by sonication (1 sec pulse, 20% amplitude, 3 times) in PBS in the presence of EDTA-free protease inhibitor cocktail tablet (Pierce, Rockford, Illinois, United States of America). The cell lysates were subject to ultracentrifugation (100,000×g, 45 min at 4° C. to separate the cytosolic fraction in the supernatant and the membrane fraction as a pellet. The membrane pellet was re-suspended in the protease inhibitor-containing PBS by sonication. Protein concentration in both fractions were measured by the Bio-Rad DC protein assay and adjusted to levels as needed.

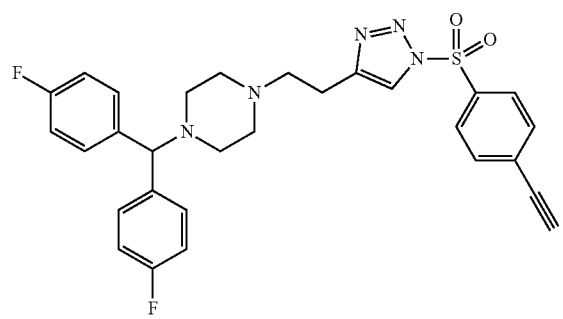 [SMILES: C#Cc1ccc(S(=O)(=O)n2cc(CCN3CCN(C(c4ccc(F)cc4)c4ccc(F)cc4)CC3)nn2)cc1]

1-(Bis(4-fluorophenyl)methyl)-4-(2-(1-((4-ethynylphenyl)sulfonyl)-1H-1,2,3-triazol-4-yl)ethyl)piperazine (TH316)

$^1$H NMR (600 MHz, CDCl$_3$) δ 8.04-8.00 (m, 2H), 7.93 (s, 1H), 7.64-7.61 (m, 2H), 7.32 (dd, J=8.6, 5.5 Hz, 4H), 6.94 (t, J=8.7 Hz, 4H), 4.19 (s, 1H), 3.34 (s, 1H), 2.88 (t, J=7.5 Hz, 2H), 2.64 (dd, J=8.0, 7.0 Hz, 2H), 2.48 (br, 4H), 2.36 (br, 4H). $^{13}$C NMR (150 MHz, CDCl$_3$) δ 162.57, 160.94, 146.30, 138.18, 138.16, 135.86, 133.14, 129.82, 129.21, 129.16, 128.42, 121.11, 115.44, 115.30, 82.81, 81.26, 74.47, 56.73, 53.10, 51.69, 23.12.

HRMS (ESI-TOF) m/z [M+H]$^+$ calculated for C$_{29}$H$_{28}$F$_2$N$_5$O$_3$S 548.1927, found 548.1927.

Gel-Based Chemical Proteomic Assay

Proteome aliquots (2 mg/mL, 49 µL) were treated with probes at indicated concentration (1 µL, 50× stock in DMSO) at 37° C. for 1 h. The subsequent conjugation with fluorophore was accomplished by copper-catalyzed azide-alkyne cycloaddition (CuAAC) with rhodamine-azide (TAMRA-azide, 1.25 mM, 1 µL, final concentration of 25 µM) in the presence of tris(2-carboxyethyl)phosphine (TCEP, 50 mM fresh in water, 1 µL, final concentration of 1 mM), tris[(1-benzyl-1H-1,2,3-triazol-4-yl)methyl]amine (TBTA, 1.7 mM in 4:1 t-butanol/DMSO, 3 µL, final concentration of 100 µM) and $CuSO_4$ (50 mM, 1 µL, final concentration of 1 mM). For samples of live cell treatment, it started with click reaction without the step of the probe treatment in vitro. After 1 h incubation at room temperature, reactions were quenched by adding 4×SDS-PAGE loading buffer and beta-mercaptoethanol (17 µL) and samples were resolved by SDS-PAGE followed by in-gel fluorescence scanning.

SILAC Sample Preparation for MS-Based Chemical Proteomic Assay

The light proteome aliquots (2.3 mg/mL, 432 µL) were treated with the probe (5 µL, 100× fresh stock in DMSO) and the heavy proteome aliquots were treated with either the same probe or DMSO (no probe) at 37° C. for 1 h. Then the samples were subjected to click reaction with the desthiobiotin-PEG3-azide (10 mM in DMSO, 10 µL, final concentration 200 µM) in the presence of TCEP (50 mM, 10 µL), TBTA (1.7 mM, 33 µL) and $CuSO_4$ (50 mM, 10 µL) at room temperature for 1 h. The light and the heavy were mixed in the chloroform-methanol extraction step. The subsequent steps including reduction with dithiothreitol, alkylation with iodoacetamide, digestion with Trypsin/Lys-C, enrichment with avidin beads were conducted as previously described.[72,51]

LC-MS/MS Analysis

Data acquisition: The enriched peptide samples were analyzed by LC-MS/MS on an Easy-nLC 1200 (Thermo Scientific, Waltham, Massachusetts, United States of America) coupled with an Orbitrap Q Exactive Plus mass spectrometer (Thermo Scientific, Waltham, Massachusetts, United States of America). A trap column (Acclaim PEPMAP™, Thermo Scientific, Waltham, Massachusetts, United States of America, 75 µm×2 cm, 3 µm C18) and a homemade nanocapillary analytical column (20 cm, 5 µm C18 packed in 360 µm O.D.×75 µm I.D. fused silica) with in integrated electrospray tip were employed with the following LC gradient (mobile phase A: 0.1% formic acid in $H_2O$; mobile phase B: 80% CAN, 0.1% formic acid in $H_2O$): 0-1.48 min 1% B, 400 nL/min; 1.48-2 min 1% B, to 300 nL/min; 2-10 min to 13% B, 300 nL/min; 10-110 min to 32% B, 300 nL/min; 110-151 min to 60% B, 300 nL/min; 151-152 min to 95% B, 300 nL/min; 152-160 min, 95% B, 300 nL/min; 160-161 min to 1% B, 300 nL/min; 161-161.1 min 1% B, to 400 nL/min; 161.1-180 min 1% B, 400 nL/min. A top 10 data-dependent acquisition method was used, which consisted of one full scan MST scan (m/z 375-1,500) followed by ten MS2 scans of the most abundant ions recorded in the SM1 scan.

Data analysis: Identification of peptides and target proteins from the LC-MS/MS raw data was achieved using the Byonic software package (Protein Metrics Inc., Cupertino, California, United States of America) to search against a modified human protein database (UniProt human protein database, angiotensin I and vasoactive intestinal peptide standards; 40660 proteins) with parameters previously described.[72] Identification of probe-modified peptides was accomplished with variable (common) modification of +635.27374 Da for TH211, +608.26284 for TH214, +578.25228 for TH216 on tyrosine and lysine residues. Other added mass such as variable methionine oxidation (+15.9949 Da), fixed cysteine carbamidomethylation (+57.02146 Da) and the SILAC heavy amino acids (+10.0083 Da for R, +8.0142 Da for K) were included in search. The results from Byonic search were imported into Skyline-daily to determine SILAC ratio (SR) of light/heavy peptides.[51] To account for variations in mixing and sample preparation, SRs of peptide from probe/no-probe (the light was treated with the probe while the heavy was treated with DMSO) were normalized to those from probe/probe (both the light and the heavy were treated with the probe). Unless otherwise stated, the results from Skyline-daily output were filtered in R to keep peptides of high quality that meet the following criteria: Byonic score ≥300; a precursor mass error within 5 ppm; normalized SR≥5, with both isotop dot-product (iDOTP) and ratio dot-product (rDOTP)≥0.8. Comparison of probe-modified sites across all probes and cells were performed using the R package ggplot2 and Venn diagrams were generated with the VennDiagram R package.[72] Other bioinformatics analysis such as the domain enrichment analysis and the DrugBank analysis were performed as previously described.[72]

Discussion: The proposed mechanism of action of the TH SuTEx probes, along with exemplary probe structures, including the bis(4-fluorophenyl)methyl-piperazine recognition moiety attached to the probe LG and the different alkyne-containing labeling groups, are shown in FIG. 39A. Recombinant human diacylglycerol kinase-alpha (DGKA) cells were incubated with probes and probe-modified binding sites were detected from labeling structures performed in the cell lysates according to previously described protocols.[72] See FIG. 39B. Probe-modified tyrosine binding sites were also detected from in native human DGKA in lysates from live Jurkat T cells incubated with TH SuTEx probes. See FIG. 39C. Gel-base probe labeling studies with TH SuTEx probes were also performed using previously described protocols.[72] TH211 was shown to label recombinant human DGKA in a concentration dependent manner. See FIG. 39D, left panel. Comparison of the labeling ability of three different TH SuTEx probes for recombinant DGKA is shown in FIG. 39D, right panel. Comparison of overlapping and unique binding sites modified by TH SuTEx probes in recombinant DGKA-HEK293T cells and detected in the corresponding lysates via LC-MS quantitative chemical proteomic studies is shown in FIG. 39E.

Example 11

Preparation of SuTEx Probes with Kinase Inhibitor-Containing Labeling Group

Scheme 2.

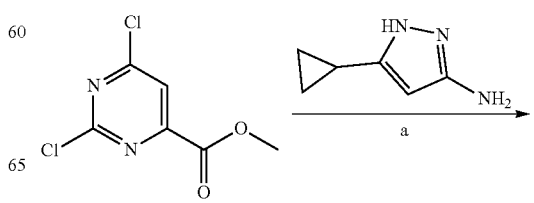

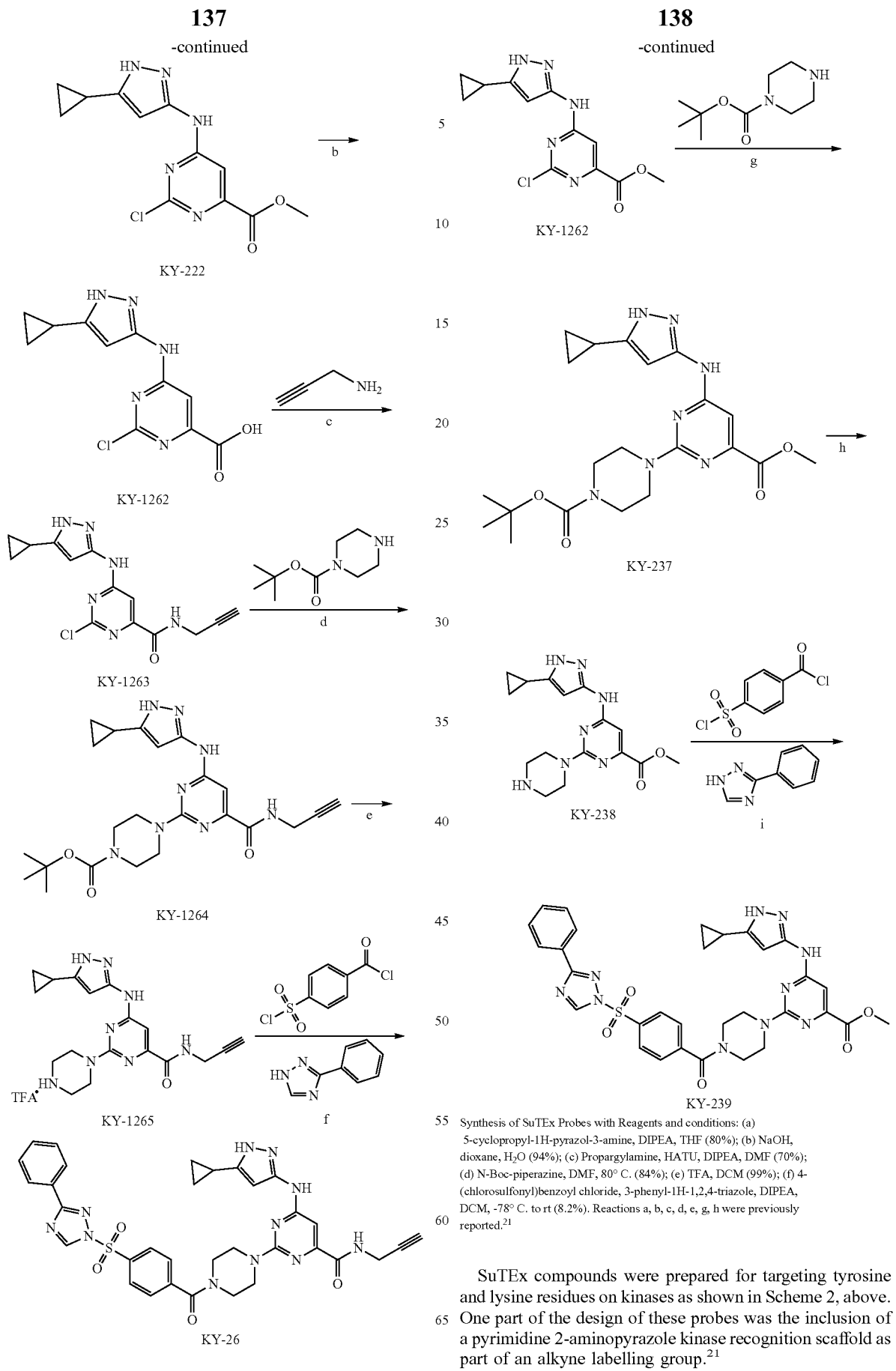

Synthesis of SuTEx Probes with Reagents and conditions: (a) 5-cyclopropyl-1H-pyrazol-3-amine, DIPEA, THF (80%); (b) NaOH, dioxane, H$_2$O (94%); (c) Propargylamine, HATU, DIPEA, DMF (70%); (d) N-Boc-piperazine, DMF, 80° C. (84%); (e) TFA, DCM (99%); (f) 4-(chlorosulfonyl)benzoyl chloride, 3-phenyl-1H-1,2,4-triazole, DIPEA, DCM, -78° C. to rt (8.2%). Reactions a, b, c, d, e, g, h were previously reported.[21]

SuTEx compounds were prepared for targeting tyrosine and lysine residues on kinases as shown in Scheme 2, above. One part of the design of these probes was the inclusion of a pyrimidine 2-aminopyrazole kinase recognition scaffold as part of an alkyne labelling group.[21]

Synthetic Methods:

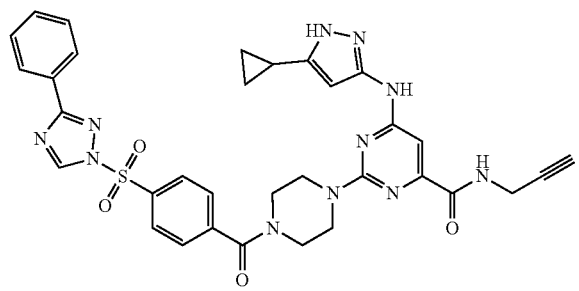 [SMILES: C#CCNC(=O)c1cc(Nc2cc(C3CC3)[nH]n2)nc(N2CCN(C(=O)c3ccc(S(=O)(=O)n4cnc(-c5ccccc5)n4)cc3)CC2)n1]

6-((5-cyclopropyl-1H-pyrazol-3-yl)amino)-2-(4-(4-((3-phenyl-1H-1,2,4-triazol-1-yl)sulfonyl)benzoyl)piperazin-1-yl)-N-(prop-2-yn-1-yl)pyrimidine-4-carboxamide, KY-26

To a solution of 4-(chlorosulfonyl)benzoyl chloride (392 mg, 1.64 mmol) in anhydrous DCM (10 mL) was added DIPEA (789 µL, 4.52 mmol) and KY-1265 (500 mg, 1.37 mmol) in anhydrous DCM (20 mL) over the course of 15 minutes at −78° C. The reaction was kept at −78° C. for 1 hour. 3-phenyl-1H-1,2,4-triazole (198 mg, 1.37 mmol) and DIPEA (263 µL, 1.51 mmol) in anhydrous DCM (10 mL) were added to the reaction mixture and the reaction was stirred at room temperature for 2 hours. The reaction was concentrated in vacuo and the was purified via silica gel flash chromatography (hexanes: ethyl acetate=1:4 to 1:10). KY-26 (76 mg, 0.11 mmol, 8.2%) was obtained as a white solid. $^1$H NMR (600 MHz, DMSO-d6) δ 12.00 (s, 1H), 9.86 (s, 1H), 9.52 (s, 1H), 8.90 (s, 1H), 8.28-8.22 (m, 3H), 8.04-8.01 (m, 2H), 7.84-7.80 (m, 2H), 7.55-7.48 (m, 5H), 4.01-3.65 (m, 10H), 3.08 (t, J=2.5 Hz, 1H), 2.08 (s, 1H), 1.84 (s, 1H), 0.84 (s, 2H), 0.63 (s, 2H). ESI-TOF (HRMS) m/z [M+H]$^+$ calculated for Chemical Formula: $C_{33}H_{32}N_{11}O_4S$ 678.2354, found 678.2352.

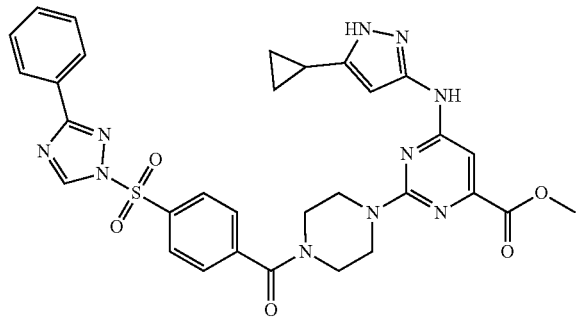 [SMILES: COC(=O)c1cc(Nc2cc(C3CC3)[nH]n2)nc(N2CCN(C(=O)c3ccc(S(=O)(=O)n4cnc(-c5ccccc5)n4)cc3)CC2)n1]

methyl 6-((5-cyclopropyl-1H-pyrazol-3-yl)amino)-2-(4-(4-((3-phenyl-1H-1,2,4-triazol-1-yl)sulfonyl)benzoyl)piperazin-1-yl)pyrimidine-4-carboxylate, KY-239

To a solution of 4-(chlorosulfonyl)benzoyl chloride (313 mg, 1.31 mmol) in anhydrous DCM (8 mL) was added DIPEA (760 µL, 4.36 mmol) and KY-238 (500 mg, 1.09 mmol) in anhydrous DCM (10 mL) over the course of 15 minutes at −78° C. The reaction was kept at −78° C. for 1 hour. 3-phenyl-1H-1,2,4-triazole (157 mg, 1.09 mmol) and DIPEA (189 µL, 1.09 mmol) in anhydrous DCM (8 mL) were added to the reaction mixture and the reaction was stirred at room temperature for 2 hours. The reaction was concentrated in vacuo and the was purified via silica gel flash chromatography (hexanes: ethyl acetate=1:4 to 1:10). KY-239 was obtained as a white solid.

Example 12

General Synthetic Procedure for 1,2,3-Sulfonyl-Triazole (SuTEx) Ligands 1,2,3-sulfonyl-triazole (SuTEx) fragments can be used as ligands and inhibitors of proteins. The present example provides a synthetic route for a 1,4-isomer of an exemplary 1,2,3-SuTEx fragment, EKT-055, having the following structure:

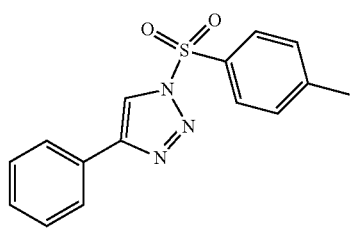 [SMILES: Cc1ccc(S(=O)(=O)n2cc(-c3ccccc3)nn2)cc1]

The initially synthesized 1,4-isomer can be converted to the 2,4-isomer of the 1,2,3-SuTEx molecules as described in the second procedure. The synthesis of EKT-055 is provided as a model example. The procedures can be modified to apply to other 1,2,3-SuTEx molecules by using other azides and/or alkynes in place of the tosyl azide and phenylacetylene in the synthesis of the initial 1,4-isomer. See FIGS. 48A and 48B. For instance, any sulfonyl azide of the structure R—S(=O)$_2$—N$_3$ wherein R is aryl, alkyl, cycloalkyl, and N-heterocycle can be used in place of the tosyl azide.

Preparation of 4-Phenyl-1-tosyl-1H-1,2,3-triazole

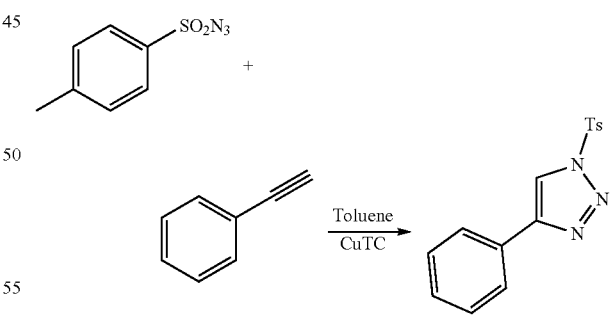

Scheme 3. Preparation of Exemplary Sulfonyl-substituted 1,2,3-Triazole

As shown in Scheme 3, above, and based on a previously described procedure[101] into a 500 mL Erlenmeyer flask was place 250 mL of dry toluene and copper(I) thiophene-2-carboxylate (CuTC). To this mixture was added phenylacetylene and stirred for 10 minutes. The tosyl azide was added as a solution in 50 mL of toluene to the reaction mixture and the flask was stoppered. This was then stirred at ambient temperature for 4 hours. The reaction was quenched with saturated NH$_4$Cl (150 mL) and after vigorously stirring for 30 minutes the layers were separated. The aqueous layer was extracted with ethyl acetate (2×200 mL). The combined organic layer was washed with brine (100 mL) and dried over Na$_2$SO$_4$. This was filtered through a bed of silica gel and celite. The pad was rinsed with ethyl acetate (100 mL) and the filtrate was concentrated on the rotovap and dried on the high vacuum to give 12.14 g of a crystalline solid. This was recrystallized from ethyl acetate/heptane to give 6.36 g of a fine white crystalline solid. The filtrate was concentrated to give a second crop of 1.95 g of a fine white crystalline solid. NMR compared well to literature data.

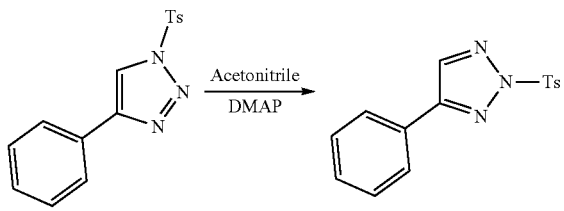 [SMILES: Cc1ccc(S(=O)(=O)n2cc(-c3ccccc3)nn2)cc1 ; Cc1ccc(S(=O)(=O)n2ncc(-c3ccccc3)n2)cc1]

Scheme 4. Preparation of
4-Phenyl-2-tosyl-2H-1,2,3-triazole

As shown in Scheme 4, above, and as previously described[102], into a 250 mL Erlenmeyer flask was place 4-phenyl-1-tosyl-1H-1,2,3-triazole (1.91 g), 4-dimethylaminopyridine (80 mg) and acetonitrile (75 mL). The reaction was stirred at room temperature overnight. The reaction was treated with ethyl acetate (50 mL) and washed with 1N HCl (50 mL) and brine (30 mL) followed by drying over Na$_2$SO$_4$. Concentration on the rotovap gave 2.17 g of a clear oil. This was dissolved in ethyl acetate (15 mL) and treated with heptane (~50 mL). After 5 hours with crystalline product was isolated by filtration and rinsed with 15 mL ethyl acetate/heptane (2/5) and heptane (15 mL). This provided 0.46 g after drying under high vacuum. NMR compared well to literature data.

Example 13

SuTEx GSTP1 Inhibitors

SuTEx ligands can be optimized for increased potency using medicinal chemistry. As described above in Example 7, an initial hit molecule for developing inhibitors was JWB198. Structural modifications to JWB198 can result in increased potency as determined by lower concentrations that provides 50% blockade of GSTP1 biochemical activity (IC$_{50}$ values). From these studies, JWB179 and JWB183 have been identified as new lead GSTP1 inhibitors. See FIG. 40. JWB179 and JWB183 were prepared according to methods analogous to those described in Example 5. GSTP1 biochemical assays were performed as described hereinabove and in Reference 72.

Example 14

GSH Stability of SuTEx Compounds

Glutathione (GSH) adduction to compounds is a mechanism of metabolism for compounds administered to animals and humans. Accordingly, an HPLC reactivity assay[72] was performed to evaluate whether sulfonyl-triazoles (HHS-475) react with GSH. See FIG. 41. HHS-475 (see Example 1) was used as an exemplary SuTEx compound. Initially, the HPLC assay was used to monitor the rapid reaction of HHS-475 with the model nucleophile p-cresol (as a mimic of the tyrosine side chain) under basic conditions (TMG). Then, HHS-475 was exposed to 5×GSH under basic conditions and negligible reaction was observed. The 5×GSH was used because GSH is typically found at high concentrations in vivo. Another electrophile (cysteine-reactive compound) was included to demonstrate that under the experimental conditions GSH reaction can be observed with compounds (positive control). In summary, as shown in FIG. 41, HHS-475 does not show appreciable reaction with excess GSH in conditions that are suitable for nucleophilic substitutions (i.e. basic conditions).

Example 15

Synthesis of "Heavy" Labeling Group

The present example provides an exemplary synthesis of an exemplary "heavy" desthiobiotin linker that can be used in conjunction with the presently disclosed SuTEx and related heteroaryl probes. SILAC methodology, such as that of the SILAC methods described herein, involve the use of isotopically-labeled amino acids (e.g., lysine and arginine) and live cell samples that can be cultured in SILAC media including the isotopically-labeled amino acids. Heavy linkers, such as the $^{13}$C8 labeled desthiobiotin-PEG3-azide presented herein, can provide for the use of sulfur-heterocycle technology of the presently disclosed subject matter for quantitative proteomic analysis of tissues, primary cells, and human-derived materials (e.g. tissue, serum, tumors).

Preparation of 2,2'-((Oxybis(ethane-2,1-diyl)bis (oxy))bis(ethan-1-ol) (x=4)

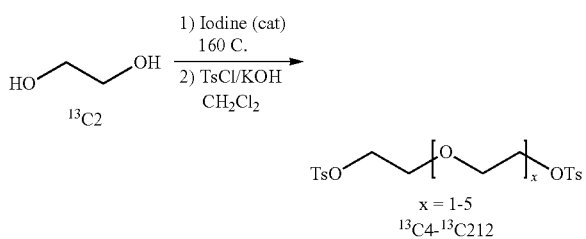

Into a 2 dram vial was placed 1 gram of heavy ethylene glycol and a catalytic amount of iodine. The vial was sealed under a nitrogen atmosphere and stirred in a 160° C. oil bath. The reaction was allowed to run for 7 hours. The reaction was cooled to ambient temperature to give a mixture of glycol compounds. The x=4 isomer was seen by GC to be the major oligomer formed. The mixture was treated with 30 ml of methylene chloride followed by 2.5 grams of tosyl chloride and 2.8 grams of powdered KOH (added in portions). The reaction was stirred for 4 hours followed by treatment with ice-water (50 mL) and extraction with methylene chloride (2×50 mL). The combined organic layer was washed with brine (50 mL) and dried over MgSO$_4$. Concentration on the rotovap provided 2.8 grams of a clear oil. The product was purified by flash chromatography (25% ethyl acetate/hexanes to 50% ethyl acetate/hexanes) to give 1.0 grams of product as an oil.

Preparation of 1-azido-2-(2-(2-azidoethoxy)ethoxy)ethoxy)ethane ($^{13}C8$)

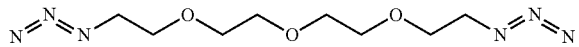

The bis-tosylate (1.0 g) was dissolved in DMF (5 mL) and treated with sodium azide (595 mg) and heated to 65 C under nitrogen overnight. The reaction was cooled and treated with 5 mL of water and extracted with ethyl acetate (3×6 mL). The combined organic layer was washed with water (5 mL) brine (5 mL) and dried over $MgSO_4$. Concentration and drying under high vacuum provided 450 mg of a clear colorless oil. The TLC (ethyl acetate/Iodine stain) indicated a single product. This was used without further purification.

Preparation of 2-(2-(2-(2-azidoethoxy)ethoxy)ethoxy)ethan-1-amine ($^{13}C8$)

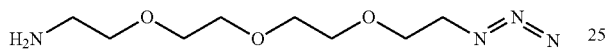

Into a 50 mL round bottom flask was placed the bis-azide and 7 ml of 1N HCl. This was cooled to 0 C in an ice-water bath. To the vigorously stirring mixture was added an ether solution of triphenylphosphine (7 mL of ether). The reaction was allowed to warm up to ambient temperature and stirred overnight. The reaction was then filtered to remove the white solid. The flask was rinsed with ether (5 mL) and 1N HCl (2 mL). The layers were separated, and the aqueous layer was washed with ether (3×10 mL). The aqueous layer was cooled in an ice bath and treated with 3.3 grams of potassium hydroxide. The aqueous layer was extracted with methylene chloride (5×5 mL) and the combined organic layer was dried over $Na_2SO_4$ and concentrated to give 320 mg as a colorless oil.

This compound was used as is in the synthesis of the $^{13}C8$ labeled desthiobiotin-PEG3-azide having a structure as shown hereinbelow using previously reported procedure.[103]

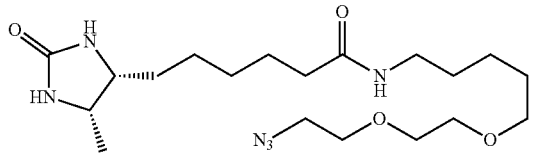 [SMILES: C[C@@H]1NC(=O)N[C@@H]1CCCCCC(=O)NCCCCCOCCOCCN=[N+]=[N-]]

Example 16

PBMC Cell Viability

Studies were performed to evaluate the toxicity of exemplary SuTEx ligands against human peripheral blood mononuclear cells (PBMCs) from de-identified healthy donors. After isolation of PBMCs, cells were stimulated with anti-CD3 and anti-CD28 antibodies for 4 days in the presence of SuTEx ligands (25 µM final concentration), dimethylsulfoxide (DMSO) vehicle, or no treatment (media only). Anti-CD3/anti-CD28 antibodies were used to stimulate the T cell receptor and co-stimulatory pathways, respectively, to activate T cells in the PBMC mixture in order to identify SuTEx ligands that could enhance T cell activation (as determined by measuring IL-2 cytokine production from PBMCs). See FIG. 42A. AMC001 was identified as a SuTEx ligand that showed this positive activity in human PBMCs. After 4 days, the cells were stained with live/dead dyes and analyzed by flow cytometry to determine the percentage of viable cells (live cells/total cells). See FIG. 42B. SuTEx Ligands 1-11 as identified in FIG. 42B correspond AMC 001 (SuTEx ligand 1); EKT 151 (SuTEx ligand 2); EKT 165 (SuTEx ligand 3); EKT 225 (SuTEx ligand 4); EKT 197 (SuTEx ligand 5); HHS 134 (SuTEx ligand 6), HHS 173 (SuTEx ligand 7), HHS 183 (SuTEx ligand 8), TH 211 (SuTEx ligand 9); JWB 150 (SuTEx ligand 10), and JWB 152 (SuTEx ligand 11). The structures of JWB 150 and JWB 152 are shown in Example 5. The structure of TH 211 is shown in Example 10. The structures of the other ligands are as follows:

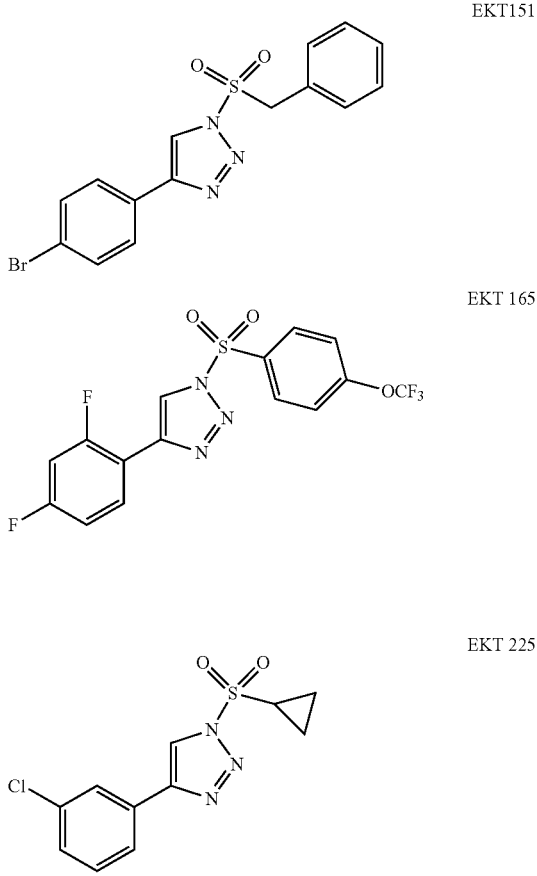

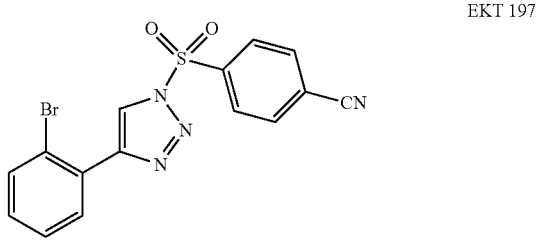

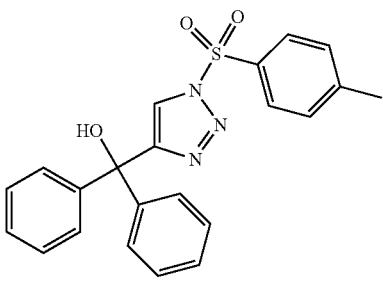

HHS 134

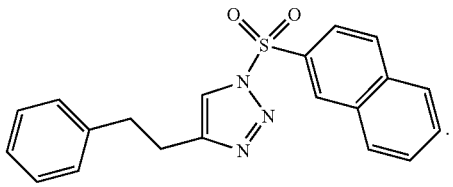

HHS 183

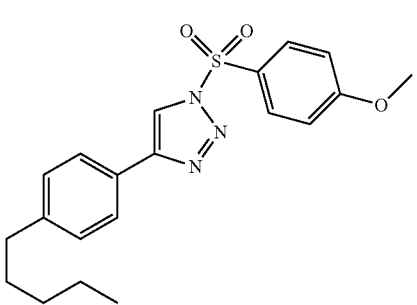

HHS 173

Example 17

Additional Proteins Modified by SuTEx Ligands

The structures of some additional SuTEx fragments are shown in FIG. 43. Chemical proteomics performed as described, for example, in FIG. 23, indicates that SuTEx fragments modify FAAA (Uniprot ID P16930) at tyrosine 244 (see FIGS. 44A-44C) and PTGR2 (Uniprot ID Q8N8N7) at tyrosine 100. See FIGS. 45A-45B. In addition, SuTEx fragment EKT231 (see FIG. 46A) modifies EDC3 at tyrosine 475. See FIG. 46B.

Table 3, below, lists sites of modification targeted by sulfonyl-heterocycle probes and ligands. The format of the table is as follows: protein species, protein Uniprot accession number (see uniprot.org), lysine and/or tyrosine sites (amino acid positions) modified (where if multiple sites are modified in the same protein, the sites are separated by vertical lines).

TABLE 3

Protein Modification Sites Targeted by Sulfonyl-Heterocycle Probes and Ligands.

SUCB2_HUMAN, Q96I99, 123|229|227|
MBOA7_HUMAN, Q96N66, 294|305|456|
TOLIP_HUMAN, Q9H0E2, 83|66|
TCPZ_HUMAN, P40227, 251|109|104|127|159|388|430|377|426|199|10|353|351|
TCTP_HUMAN, P13693, 91|95|18|102|19|
HPBP1_HUMAN, Q9NZL4, 334|
MAT2B_HUMAN, Q9NZL9, 138|
MOGS_HUMAN, Q13724, 738|
EHD1_HUMAN, Q9H4M9, 339|341|468|315|375|
KTHY_HUMAN, P23919, 151|56|
68MP_HUMAN, P56378, 49|
RRBP1_HUMAN, Q9P2E9, 51|56|
MOB1B_HUMAN, Q7L9L4, 95|
RHG01_HUMAN, Q07960, 191|
ATOX1_HUMAN, O00244, 31|
CHMP5_HUMAN, Q9NZZ3, 75|120|
H2AZ_HUMAN, P0C0S5, 61|8|
LMNA_HUMAN, P02545, 259|45|
PBX2_HUMAN, P40425, 264|
IFT27_HUMAN, Q9BW83, 36|
RL13A_HUMAN, P40429, 114|112|137|149|192|48|54|71|125|134|32|91|
DX39B_HUMAN, Q13838, 39|139|265|266|362|371|131|156|163|183|188|268|270|274|384|
TF2B_HUMAN, Q00403, 146|
TXLNA_HUMAN, P40222, 390|
CD97_HUMAN, P48960, 810|
CSTF2_HUMAN, P33240, 189|
GTF2I_HUMAN, P78347, 387|398|373|920|652|
RLA0_HUMAN, P05388, 13|24|257|10|106|146|26|264|77|
RS27A_HUMAN, P62979, 85|11|48|6|59|
FETUA_HUMAN, P02765, 227|225|
RBM12_HUMAN, Q9NTZ6, 526|494|
HNRPM_HUMAN, P52272, 64|100|213|681|126|127|145|214|221|242|381|388|52|651|667|670|685|69|690|692|698|716|
MAN1_HUMAN, Q9Y2U8, 441|
CUL5_HUMAN, Q93034, 221|
ELOC_HUMAN, Q15369, 8|
PCBP2_HUMAN, Q15366, 182|236|349|278|185|23|309|32|322|37|31|
PCBP1_HUMAN, Q15365, 183|270|341|160|314|32|207|
RER1_HUMAN, O15258, 174|29|187|
WASL_HUMAN, O00401, 175|
PHAX_HUMAN, Q9H814, 57|

TABLE 3-continued

Protein Modification Sites Targeted by Sulfonyl-Heterocycle Probes and Ligands.

PSMG2_HUMAN, Q969U7, 127|
PRP19_HUMAN, Q9UMS4, 108|33|179|
DDX47_HUMAN, Q9H0S4, 170|
RFA3_HUMAN, P35244, 33|
MTX2_HUMAN, O75431, 65|166|170|71|
VP26A_HUMAN, O75436, 61|
RADI_HUMAN, P35241, 64|270|55|
MPPB_HUMAN, O75439, 142|202|219|144|
RFC4_HUMAN, P35249, 77|205|84|
LIS1_HUMAN, P43034, 102|394|
RU17_HUMAN, P08621, 126|161|21|219|
DDX18_HUMAN, Q9NVP1, 324|385|500|509|573|583|590|325|507|542|571|584|661|643|
TPD54_HUMAN, O43399, 106|126|154|127|108|
FAF2_HUMAN, Q96CS3, 297|
H2B1C_HUMAN, P62807, 84|
H4_HUMAN, P62805, 73|89|52|13|78|92|
DIAP1_HUMAN, O60610, 209|773|424|59|61|829|830|911|63|
H12_HUMAN, P16403, 97|75|52|
BZW2_HUMAN, Q9Y6E2, 233|64|209|
GPDA_HUMAN, P21695, 63|
C560_HUMAN, Q99643, 141|
ECH1_HUMAN, Q13011, 149|318|77|231|
NCBP1_HUMAN, Q09161, 461|64|98|65|657|
GBRL2_HUMAN, P60520, 25|24|
GPX3_HUMAN, P22352, 149|
DPM1_HUMAN, O60762, 148|149|160|95|
USO1_HUMAN, O60763, 606|655|
RL35A_HUMAN, P18077, 34|106|14|42|51|15|45|52|66|73|8|95|
PP2AB_HUMAN, P62714, 127|267|265|284|248|218|
IL32_HUMAN, P24001, 74|
TEBP_HUMAN, Q15185, 35|48|79|
ATP5H_HUMAN, O75947, 150|152|56|57|149|58|
IPYR_HUMAN, Q15181, 88|17|28|80|87|169|94|176|22|38|90|
DDX5_HUMAN, P17844, 190|418|442|59|76|97|148|244|425|497|518|236|284|
32|340|391|411|80|91|
HMHA1_HUMAN, Q92619, 418|713|
TBG2_HUMAN, Q9NRH3, 82|273|84|
OSGEP_HUMAN, Q9NPF4, 76|78|
PERI_HUMAN, P41219, 288|396|
CHSTB_HUMAN, Q9NPF2, 167|64|
EIF2D_HUMAN, P41214, 418|420|
PRP6_HUMAN, O94906, 732|446|582|
PLPHP_HUMAN, O94903, 252|69|58|254|
SMU1_HUMAN, Q2TAY7, 114|125|132|138|
H1X_HUMAN, Q92522, 48|
PSMD3_HUMAN, O43242, 457|258|
RED_HUMAN, Q13123, 383|
TRI33_HUMAN, Q9UPN9, 524|
CPSF7_HUMAN, Q8N684, 364|317|408|
ACTBL_HUMAN, Q562R1, 189|
SCRB2_HUMAN, Q14108, 284|
HNRPD_HUMAN, Q14103, 244|116|201|110|119|129|161|178|182|197|243|251|
TAF8_HUMAN, Q7Z7C8, 172|
EPN1_HUMAN, Q9Y6I3, 17|
BRI3_HUMAN, O95415, 57|
CERS2_HUMAN, Q96G23, 88|131|93|
RPB2_HUMAN, P30876, 120|1018|814|
CNOT1_HUMAN, A5YKK6, 379|
EF1G_HUMAN, P26641, 147|145|24|416|132|208|212|220|228|401|227|219|
CSRP2_HUMAN, Q16527, 113|73|18|71|
PSMD1_HUMAN, Q99460, 535|
FLNB_HUMAN, O75369, 155|2032|596|142|476|1530|904|
FKBP2_HUMAN, P26885, 45|
COG2_HUMAN, Q14746, 373|
ACTB_HUMAN, P60709, 191|166|169|188|198|218|240|294|306|362|53|91|113|
213|215|238|284|291|315|326|328|373|50|61|
HM13_HUMAN, Q8TCT9, 346|241|352|61|
TNPO2_HUMAN, O14787, 34|
DGKA_HUMAN, P23743, 623|240|477|544|22|543|
GIMA5_HUMAN, Q96F15, 9|
RDH11_HUMAN, Q8TC12, 202|206|
CSK2B_HUMAN, P67870, 113|197|
EIF3I_HUMAN, Q13347, 308|38|300|30|
EFTU_HUMAN, P49411, 115|246|266|92|122|133|357|135|238|256|286|297|311|
342|361|418|447|70|79|88|91|
IF4B_HUMAN, P23588, 224|237|285|298|233|302|321|270|258|
MBB1A_HUMAN, Q9BQG0, 978|889|
FNBP1_HUMAN, Q96RU3, 171|114|

TABLE 3-continued

Protein Modification Sites Targeted by Sulfonyl-Heterocycle Probes and Ligands.

S61A1_HUMAN, P61619, 107|21|29|395|
UGGG1_HUMAN, Q9NYU2, 595|1208|1283|1244|671|
KNTC1_HUMAN, P50748, 1093|
SAC2_HUMAN, Q9Y2H2, 516|
IKZF2_HUMAN, Q9UKS7, 215|
ITPA_HUMAN, Q9BY32, 45|
GDIB_HUMAN, P50395, 197|203|212|224|226|229|245|249|93|115|253|269|39|
RMND1_HUMAN, Q9NWS8, 423|
NCK1_HUMAN, P16333, 55|
NUB1_HUMAN, Q9Y5A7, 239|318|
HINT1_HUMAN, P49773, 109|
FHL1_HUMAN, Q13642, 117|9|207|149|
MCM3_HUMAN, P25205, 188|19|251|312|357|147|435|45|174|
PP1B_HUMAN, P62140, 133|136|113|68|86|149|259|304|306|
SEPT7_HUMAN, Q16181, 306|319|163|223|30|41|80|219|387|43|89|326|429|431|
ANXA3_HUMAN, P12429, 133|
RAGP1_HUMAN, P46060, 585|
YTDC1_HUMAN, Q96MU7, 350|589|
ALKB5_HUMAN, Q6P6C2, 147|139|
AN32B_HUMAN, Q92688, 131|101|137|
HSDL2_HUMAN, Q6YN16, 130|55|409|168|
KAP0_HUMAN, P10644, 323|367|
PSMD8_HUMAN, P48556, 225|315|235|
PRPS1_HUMAN, P60891, 198|94|
OXSR1_HUMAN, O95747, 227|229|295|
MED18_HUMAN, Q9BUE0, 87|
TF3C1_HUMAN, Q12789, 1651|
HBA_HUMAN, P69905, 25|43|41|
MTNA_HUMAN, Q9BV20, 27|
M3K4_HUMAN, Q9Y6R4, 739|
ALDOB_HUMAN, P05062, 138|
BC11B_HUMAN, Q9C0K0, 455|456|
MTNB_HUMAN, Q96GX9, 26|152|
GOSR1_HUMAN, O95249, 204|
SEPT9_HUMAN, Q9UHD8, 389|278|390|506|560|473|271|326|352|476|
ALG6_HUMAN, Q9Y672, 103|
ASH2L_HUMAN, Q9UBL3, 453|455|
WDR82_HUMAN, Q6UXN9, 102|91|
HSP76_HUMAN, P17066, 185|433|
MRE11_HUMAN, P49959, 369|262|
PI42A_HUMAN, P48426, 369|
NU153_HUMAN, P49790, 29|27|
PFKAP_HUMAN, Q01813, 395|298|394|487|645|139|15|567|574|627|659|688|737|753|763|
MYO1G_HUMAN, B0I1T2, 205|350|548|598|72|79|839|86|897|624|193|594|608|815|87|898|
SGT1_HUMAN, Q9Y2Z0, 277|47|95|90|283|317|
CHD5_HUMAN, Q8TDI0, 1328|
USP9X_HUMAN, Q93008, 648|367|2455|
FXR1_HUMAN, P51114, 68|152|
VIGLN_HUMAN, Q00341, 986|241|437|582|40|
CLH1_HUMAN, Q00610, 1438|634|1096|1211|1218|1451|1477|1487|1540|156|184|417|430|479|
510|608|731|754|883|1168|1449|1545|429|619|637|742|279|799|1237|377|
CLPX_HUMAN, O76031, 438|
PAP1L_HUMAN, Q4VXU2, 297|
NU188_HUMAN, Q5SRE5, 1413|
H2B1K_HUMAN, O60814, 44|122|121|84|
GMDS_HUMAN, O60547, 84|323|324|231|69|
TPM1_HUMAN, P09493, 162|
CLIC2_HUMAN, O15247, 123|
DEN4C_HUMAN, Q5VZ89, 1447|
INP5K_HUMAN, Q9BT40, 261|262|
ELOB_HUMAN, Q15370, 45|46|
VAPA_HUMAN, Q9P0L0, 180|205|211|52|
TIA1_HUMAN, P31483, 149|
SERC_HUMAN, Q9Y617, 231|101|131|230|279|289|346|116|71|
WBP2_HUMAN, Q969T9, 231|232|55|91|93|241|
CN37_HUMAN, P09543, 400|397|74|100|110|101|79|
SET_HUMAN, Q01105, 140|189|177|
RFC2_HUMAN, P35250, 213|322|34|
SRSF4_HUMAN, Q08170, 86|
SMC5_HUMAN, Q8IY18, 545|
PRCC_HUMAN, Q92733, 459|
TFG_HUMAN, Q92734, 392|
ATP6_HUMAN, P00846, 36|55|
REEP5_HUMAN, Q00765, 147|25|29|
PGAM1_HUMAN, P18669, 119|133|142|26|92|218|100|113|138|176|222|106|251|
NSUN6_HUMAN, Q8TEA1, 215|
LYRM7_HUMAN, Q5U5X0, 35|
S39A7_HUMAN, Q92504, 320|273|310|

TABLE 3-continued

Protein Modification Sites Targeted by Sulfonyl-Heterocycle Probes and Ligands.

RALY_HUMAN, Q9UKM9, 57|62|13|146|159|17|34|35|
TBL2_HUMAN, Q9Y4P3, 312|313|69|71|
LNP_HUMAN, Q9C0E8, 262|
SRRT_HUMAN, Q9BXP5, 201|
SELK_HUMAN, Q9Y6D0, 60|
BIG2_HUMAN, Q9Y6D5, 97|
RS17_HUMAN, P08708, 20|53|84|19|32|44|49|59|72|
EF1D_HUMAN, P29692, 18|182|238|26|188|185|189|
IF4G2_HUMAN, P78344, 29|642|752|31|
OSB11_HUMAN, Q9BXB4, 500|306|
ERF3B_HUMAN, Q8IYD1, 337|619|
SERC5_HUMAN, Q86VE9, 345|
SPAG7_HUMAN, O75391, 189|167|
CISY_HUMAN, O75390, 382|185|345|381|331|80|246|103|459|
DOCK2_HUMAN, Q92608, 438|437|6|578|520|
SC22B_HUMAN, O75396, 33|179|43|
FERM2_HUMAN, Q96AC1, 395|
JMJD6_HUMAN, Q6NYC1, 32|
NUDC3_HUMAN, Q8IVD9, 312|271|
CRNL1_HUMAN, Q9BZJ0, 223|224|
RL7_HUMAN, P18124, 156|195|139|144|155|182|57|61|82|51|107|127|148|181|
199|202|212|223|53|55|59|77|88|
SCO1_HUMAN, O75880, 297|119|122|
ESYT1_HUMAN, Q9BSJ8, 121|518|803|822|673|681|98|
VRK1_HUMAN, Q99986, 107|113|142|187|194|302|311|317|52|213|147|16|188|
214|314|334|5|92|98|
DEK_HUMAN, P35659, 142|354|100|102|143|150|158|187|
NU214_HUMAN, P35658, 141|
RS4X_HUMAN, P62701, 149|54|103|121|82|106|120|128|16|168|230|233|254|71|
GCP2_HUMAN, Q9BSJ2, 83|423|
PFKAL_HUMAN, P17858, 674|386|395|677|640|694|633|
SDCB1_HUMAN, O00560, 46|
GOGA3_HUMAN, Q08378, 210|
RL29_HUMAN, P47914, 98|
NTPCR_HUMAN, Q9BSD7, 37|
WDR1_HUMAN, O75083, 238|300|336|34|348|398|446|472|72|96|98|216|303|338|390|497|
66|106|21|219|311|317|321|38|511|534|65|7|81|90|569|
PAPS1_HUMAN, O43252, 30|396|
CDN2A_HUMAN, P42771, 44|
RBBP4_HUMAN, Q09028, 22|132|154|181|21|156|215|
AP2A2_HUMAN, O94973, 298|
PARK7_HUMAN, Q99497, 130|
H2B1D_HUMAN, P58876, 38|41|43|84|122|109|117|12|121|21|35|44|47|58|86|
RL1D1_HUMAN, O76021, 114|116|177|
P5CS_HUMAN, P54886, 608|782|288|653|507|
PEMT_HUMAN, Q9UBM1, 191|197|
TBC15_HUMAN, Q8TC07, 243|
CNBP_HUMAN, P62633, 120|159|55|75|99|103|
MAOM_HUMAN, P23368, 175|222|231|347|361|434|82|84|183|224|74|
PFD1_HUMAN, O60925, 97|28|
RS5_HUMAN, P46782, 191|188|38|45|48|167|192|193|201|42|47|63|
RS9_HUMAN, P46781, 13|35|96|11|121|139|155|47|52|
CFDP1_HUMAN, Q9UEE9, 271|
GHC1_HUMAN, Q9H936, 96|
CPNS1_HUMAN, P04632, 87|
GAPR1_HUMAN, Q9H4G4, 114|7|33|
RNH2B_HUMAN, Q5TBB1, 23|262|106|145|25|259|
HUWE1_HUMAN, Q7Z6Z7, 3424|697|1609|223|1148|
PYGB_HUMAN, P11216, 186|197|204|227|234|263|281|298|614|732|733|75|76|821|574|
CKAP5_HUMAN, Q14008, 1808|1860|1394|
BRI3B_HUMAN, Q8WY22, 71|
RFC3_HUMAN, P40938, 18|
ECHA_HUMAN, P40939, 271|283|298|320|343|499|637|639|724|736|740|190|214|249|254|
262|267|284|285|289|326|350|415|505|569|60|625|634|644|728|742|295|
GNL1_HUMAN, P36915, 397|432|441|446|523|384|527|170|
CD99_HUMAN, P14209, 116|
RFC5_HUMAN, P40937, 26|59|16|66|
CND1_HUMAN, Q15021, 1325|1164|
MYH9_HUMAN, P35579, 299|11|1861|193|297|400|573|650|819|9|754|300|721|1460|1775|
185|199|201|202|228|269|373|545|555|560|576|651|678|1445|
1583|1867|938|403|1441|1862|1603|1788|79|1802|1918|395|66|1805|
RBM4_HUMAN, Q9BWF3, 190|325|345|58|37|222|
GMPPB_HUMAN, Q9Y5P6, 144|10|
HNRH3_HUMAN, P31942, 100|262|285|296|85|255|67|76|97|
1433S_HUMAN, P31947, 48|127|128|
NUP93_HUMAN, Q8N1F7, 166|386|801|359|387|764|
STX7_HUMAN, O15400, 230|
S10AB_HUMAN, P31949, 30|32|

TABLE 3-continued

Protein Modification Sites Targeted by Sulfonyl-Heterocycle Probes and Ligands.

STIP1_HUMAN, P31948, 312|50|236|27|310|316|354|376|444|451|468|476|48|58|404|
388|442|453|486|169|434|123|162|383|54|269|261|323|41|296|
TIM14_HUMAN, Q96DA6, 34|
CH10_HUMAN, P61604, 80|76|36|66|28|70|56|40|
PTGR1_HUMAN, Q14914, 16|245|273|
SF3A2_HUMAN, Q15428, 54|57|88|155|
DBNL_HUMAN, Q9UJU6, 140|162|224|144|
NB5R1_HUMAN, Q9UHQ9, 62|
ENOPH_HUMAN, Q9UHY7, 106|
SP16H_HUMAN, Q9Y5B9, 573|666|701|811|764|893|110|626|640|661|741|
P5I11_HUMAN, O14683, 12|
ATPO_HUMAN, P48047, 35|41|46|82|51|60|70|84|98|
TPSN_HUMAN, O15533, 65|342|
SEC62_HUMAN, Q99442, 102|104|19|22|26|398|60|
CHIP_HUMAN, Q9UNE7, 121|
VATA_HUMAN, P38606, 374|525|579|40|
WDR41_HUMAN, Q9HAD4, 377|
ILKAP_HUMAN, Q9H0C8, 265|298|
IQGA2_HUMAN, Q13576, 1480|
ADT4_HUMAN, Q9H0C2, 93|
SAFB1_HUMAN, Q15424, 449|436|714|
CNTP2_HUMAN, Q9UHC6, 1293|
RL3_HUMAN, P39023, 156|228|274|307|323|103|124|136|177|229|250|272|282|286|294|
312|334|341|349|356|366|373|50|66|291|
NFYA_HUMAN, P23511, 298|
HS74L_HUMAN, O95757, 184|454|684|267|
FLNA_HUMAN, P21333, 2505|2571|1938|2501|169|865|1308|2077|
DTL_HUMAN, Q9NZJ0, 320|
PTBP3_HUMAN, O95758, 127|
ACS2L_HUMAN, Q9NUB1, 529|543|623|87|397|523|99|
GSTM5_HUMAN, P46439, 127|197|116|
PUR8_HUMAN, P30566, 294|295|21|432|
FUND2_HUMAN, Q9BWH2, 143|150|68|
KAT3_HUMAN, Q6YP21, 311|97|112|
RBMX_HUMAN, P38159, 285|246|255|272|281|304|206|241|310|234|150|357|
HCFC1_HUMAN, P51610, 268|103|
COF2_HUMAN, Q9Y281, 82|89|117|85|
SOX9_HUMAN, P48436, 172|
UBR4_HUMAN, Q5T4S7, 3474|4622|
ERGI3_HUMAN, Q9Y282, 13|15|337|
SYFA_HUMAN, Q9Y285, 292|305|350|409|469|310|311|406|
SC5A6_HUMAN, Q9Y289, 586|
PGRC1_HUMAN, O00264, 113|164|
RSSA_HUMAN, P08865, 39|156|202|212|40|89|204|
SCYL2_HUMAN, Q6P3W7, 150|
PAWR_HUMAN, Q96IZ0, 213|
XRCC5_HUMAN, P13010, 295|316|333|395|397|444|631|155|291|332|334|399|443|
532|603|606|634|
HACD2_HUMAN, Q6Y1H2, 242|251|252|
PHP14_HUMAN, Q9NRX4, 91|93|52|86|125|57|
LTMD1_HUMAN, Q6P1Q0, 183|71|70|
PNO1_HUMAN, Q9NRX1, 85|
GSTM1_HUMAN, P09488, 127|197|62|69|126|
SMC2_HUMAN, O95347, 850|955|115|930|496|938|
TPIS_HUMAN, P60174, 106|212|105|202|85|186|225|246|
PSD12_HUMAN, O00232, 36|
MPP6_HUMAN, Q9NZW5, 415|387|
NOL12_HUMAN, Q9UGY1, 68|
RTCB_HUMAN, Q9Y3I0, 475|306|316|5|241|349|244|308|357|366|451|
RL23_HUMAN, P62829, 38|13|43|67|69|75|
FXRD1_HUMAN, Q96CU9, 38|458|
RAB1A_HUMAN, P62820, 112|119|140|187|191|198|
RAN_HUMAN, P62826, 152|146|147|155|39|127|134|142|159|23|28|37|60|99|141|
NELFE_HUMAN, P18615, 265|
ZN326_HUMAN, Q5BKZ1, 136|93|372|115|
HDGF_HUMAN, P51858, 23|100|
SON_HUMAN, P18583, 935|942|921|
AFG32_HUMAN, Q9Y4W6, 211|605|689|333|100|117|122|687|97|
STT3B_HUMAN, Q8TCJ2, 588|695|519|688|
MBD3_HUMAN, O95983, 122|52|
SSRB_HUMAN, P43308, 175|33|174|179|
SNAPN_HUMAN, O95295, 115|
UN93B_HUMAN, Q9H1C4, 190|
HMGB3_HUMAN, O15347, 78|153|
NOG1_HUMAN, Q9BZE4, 176|181|
NUP50_HUMAN, Q9UKX7, 193|
GCN1_HUMAN, Q92616, 2001|2611|
LAR4B_HUMAN, Q92615, 332|

TABLE 3-continued

Protein Modification Sites Targeted by Sulfonyl-Heterocycle Probes and Ligands.

KIF2C_HUMAN, Q99661, 347|
UBP15_HUMAN, Q9Y4E8, 761|356|204|
STRN3_HUMAN, Q13033, 123|
PRKRA_HUMAN, O75569, 145|
UBP3_HUMAN, Q9Y6I4, 256|
UGDH_HUMAN, O60701, 108|286|473|53|96|309|
NDKA_HUMAN, P15531, 67|52|
IPO9_HUMAN, Q96P70, 903|889|
LARP1_HUMAN, Q6PKG0, 652|
GPD1L_HUMAN, Q8N335, 65|
ARP8_HUMAN, Q9H981, 394|
HEBP1_HUMAN, Q9NRV9, 138|178|65|64|
AES_HUMAN, Q08117, 95|
ZRAB2_HUMAN, O95218, 102|
THIM_HUMAN, P42765, 182|
UBQL2_HUMAN, Q9UHD9, 265|
RL35_HUMAN, P42766, 78|35|77|79|43|
FBRL_HUMAN, P22087, 134|313|118|121|131|143|318|
CHRD1_HUMAN, Q9UHD1, 178|
INO1_HUMAN, Q9NPH2, 525|
PGTB2_HUMAN, P53611, 30|33|39|
DHB8_HUMAN, Q92506, 173|169|
COPB_HUMAN, P53618, 521|887|
UBP4_HUMAN, Q13107, 192|
UFM1_HUMAN, P61960, 18|19|
TAGL3_HUMAN, Q9UI15, 192|
EI2BD_HUMAN, Q9UI10, 186|
VATH_HUMAN, Q9UI12, 371|466|
UBF1_HUMAN, P17480, 340|
TBA8_HUMAN, Q9NY65, 408|262|357|399|224|103|
IPO4_HUMAN, Q8TEX9, 460|432|445|
TPPP_HUMAN, O94811, 211|
MICA1_HUMAN, Q8TDZ2, 381|
PDLI5_HUMAN, Q96HC4, 247|455|
AHSA1_HUMAN, O95433, 322|333|187|328|
ASNA_HUMAN, O43681, 302|89|93|
DNJC3_HUMAN, Q13217, 262|284|256|
BUB3_HUMAN, O43684, 141|194|42|207|169|
NASP_HUMAN, P49321, 540|600|635|91|636|547|652|93|596|
NDRG3_HUMAN, Q9UGV2, 308|229|
TBCA_HUMAN, O75347, 48|51|52|75|
VATG1_HUMAN, O75348, 87|
DNJB1_HUMAN, P25685, 67|176|256|31|181|35|21|
AP2B1_HUMAN, P63010, 121|6|26|136|
NUP35_HUMAN, Q8NFH5, 300|310|293|
LAP2B_HUMAN, P42167, 394|390|389|401|404|
COTL1_HUMAN, Q14019, 137|
RAC3_HUMAN, P60763, 139|98|
CIRBP_HUMAN, Q14011, 142|
AASS_HUMAN, Q9UDR5, 490|556|578|
COA7_HUMAN, Q96BR5, 72|194|195|73|211|
MDHC_HUMAN, P40925, 192|210|
HAT1_HUMAN, O14929, 15|14|263|348|363|25|20|325|364|
WDR61_HUMAN, Q9GZS3, 120|156|162|129|161|213|
2A5G_HUMAN, Q13362, 375|
CTBP1_HUMAN, Q13363, 140|
DYL2_HUMAN, Q96FJ2, 32|50|
RBM14_HUMAN, Q96PK6, 226|237|25|648|249|285|588|602|645|655|665|261|164|35|593|594|
RACK1_HUMAN, P63244, 194|228|140|246|302|52|130|175|271|38|
UB2Q1_HUMAN, Q7Z7E8, 112|
NSF1C_HUMAN, Q9UNZ2, 167|95|127|172|155|
GMFG_HUMAN, O60234, 75|104|108|119|137|
VAT1_HUMAN, Q99536, 100|273|285|330|59|255|271|277|295|372|377|61|63|
DMD_HUMAN, P11532, 3388|
BNI3L_HUMAN, O60238, 176|
ZN512_HUMAN, Q96ME7, 304|380|
H2A1H_HUMAN, Q96KK5, 120|126|37|
NAA35_HUMAN, Q5VZE5, 412|
IF1AX_HUMAN, P47813, 106|84|95|88|
CMTR1_HUMAN, Q8N1G2, 795|87|258|
WASC5_HUMAN, Q12768, 801|
PUF60_HUMAN, Q9UHX1, 267|
CCHL_HUMAN, P53701, 204|192|51|116|
FSCN1_HUMAN, Q16658, 691|
MIC60_HUMAN, Q16891, 33|636|81|95|101|102|130|640|84|
TPD53_HUMAN, Q16890, 96|
JAM3_HUMAN, Q9BX67, 271|282|293|283|287|
NH2L1_HUMAN, P55769, 11|32|33|86|

TABLE 3-continued

Protein Modification Sites Targeted by Sulfonyl-Heterocycle Probes and Ligands.

UBA3_HUMAN, Q8TBC4, 252|
RN213_HUMAN, Q63HN8, 2792|
CHD4_HUMAN, Q14839, 1091|1093|1322|615|1023|1040|671|892|1063|1092|687|879|1804|
MEPCE_HUMAN, Q7L2J0, 136|
SNX1_HUMAN, Q13596, 463|223|221|226|290|445|429|
TRA2A_HUMAN, Q13595, 142|
USF1_HUMAN, P22415, 188|
ETFA_HUMAN, P13804, 105|149|235|313|84|164|206|321|85|226|
EMD_HUMAN, P50402, 105|161|19|85|37|88|
SMAD3_HUMAN, P84022, 324|
BOD1_HUMAN, Q96IK1, 82|
DHB12_HUMAN, Q53GQ0, 233|238|244|249|261|307|
GDIA_HUMAN, P31150, 226|229|224|249|253|93|339|
RL36A_HUMAN, P83881, 48|
MCM6_HUMAN, Q14566, 276|111|174|418|46|510|567|575|598|783|205|599|95|99|643|
IPO7_HUMAN, O95373, 416|455|977|
COPD_HUMAN, P48444, 164|156|310|
CISD2_HUMAN, Q8N5K1, 19|67|74|
NONO_HUMAN, Q15233, 158|265|267|109|126|190|198|249|336|467|68|99|
RRP12_HUMAN, Q5JTH9, 779|789|833|
VDAC1_HUMAN, P21796, 146|153|173|225|247|62|67|109|161|174|201|252|266|
NUD15_HUMAN, Q9NV35, 92|
EMC10_HUMAN, Q5UCC4, 214|
LZTL1_HUMAN, Q9NQ48, 281|
QCR7_HUMAN, P14927, 110|12|19|78|
KHDR1_HUMAN, Q07666, 103|145|435|440|111|134|175|185|208|432|
ERGI1_HUMAN, Q969X5, 196|219|199|283|
PRAF2_HUMAN, O60831, 159|
DKC1_HUMAN, O60832, 69|
PIPNA_HUMAN, Q00169, 154|62|152|251|67|57|
TPM2_HUMAN, P07951, 162|
SRRM2_HUMAN, Q9UQ35, 967|2323|2390|171|
CHSP1_HUMAN, Q9Y2V2, 109|99|110|120|64|
CNN1_HUMAN, P51911, 189|268|
RTN3_HUMAN, O95197, 1004|1013|1018|1022|1028|897|
PSME2_HUMAN, Q9UL46, 33|239|
AT2A2_HUMAN, P16615, 427|497|753|990|204|431|541|683|
ZN346_HUMAN, Q9UL40, 254|
PYC_HUMAN, P11498, 651|
PDP1_HUMAN, Q9P0J1, 194|
FAKD4_HUMAN, Q969Z0, 468|
UB2D2_HUMAN, P62837, 74|
SUMF2_HUMAN, Q8NBJ7, 107|
GT251_HUMAN, Q8NBJ5, 217|
GLGB_HUMAN, Q04446, 37|560|562|73|41|657|200|554|
PR40A_HUMAN, O75400, 198|
GRP2_HUMAN, Q7LDG7, 127|128|
OCAD2_HUMAN, Q56VL3, 31|
TGT_HUMAN, Q9BXR0, 131|75|
MTX1_HUMAN, Q13505, 415|
RU1C_HUMAN, P09234, 37|22|35|
GORS2_HUMAN, Q9H8Y8, 50|196|
MYDGF_HUMAN, Q969H8, 102|123|125|161|
NUDT5_HUMAN, Q9UKK9, 74|16|
API5_HUMAN, Q9BZZ5, 11|
GNAS1_HUMAN, Q5JWF2, 1003|812|954|961|
PMGE_HUMAN, P07738, 92|
IST1_HUMAN, P53990, 43|48|130|
SC24C_HUMAN, P53992, 668|
ACADS_HUMAN, P16219, 293|
ABRAL_HUMAN, Q9P1F3, 51|
TCPB_HUMAN, P78371, 297|299|456|213|120|135|203|223|230|248|250|272|278|284|40|402|441|
TCPH_HUMAN, Q99832, 222|111|232|275|302|358|438|263|109|145|157|218|277|280|287|366|430|440|463|67|77|55|320|475|
LPXN_HUMAN, O60711, 203|375|116|
EM55_HUMAN, Q00013, 331|329|
CTND1_HUMAN, O60716, 96|257|
RANG_HUMAN, P43487, 103|111|150|68|83|
KLC1_HUMAN, Q07866, 223|307|449|
VPS45_HUMAN, Q9NRW7, 300|
FRG1_HUMAN, Q14331, 116|
ZPR1_HUMAN, O75312, 451|
FUS_HUMAN, P35637, 325|468|
ICAM3_HUMAN, P32942, 519|
TNPO1_HUMAN, Q92973, 150|51|788|197|66|
ADNP_HUMAN, Q9H2P0, 615|764|768|497|
MCMBP_HUMAN, Q9BTE3, 159|59|

TABLE 3-continued

Protein Modification Sites Targeted by Sulfonyl-Heterocycle Probes and Ligands.

RS4Y1_HUMAN, P22090, 54|
MILK1_HUMAN, Q8N3F8, 464|
DCP1A_HUMAN, Q9NPI6, 64|
PABP3_HUMAN, Q9H361, 508|
AP3S1_HUMAN, Q92572, 149|
DUS11_HUMAN, O75319, 321|
NTF2_HUMAN, P61970, 55|
TMX3_HUMAN, Q96JJ7, 99|87|
HNRPK_HUMAN, P61978, 135|138|280|323|380|449|72|225|230|234|236|102|139|168|179|198|207|219|405|456|52|60|63|66|461|
IPO11_HUMAN, Q9UI26, 938|
SRC8_HUMAN, Q14247, 144|181|104|141|154|162|178|199|289|302|310|334|84|545|
IF4A2_HUMAN, Q14240, 71|
CHERP_HUMAN, Q8IWX8, 897|714|
RPB1_HUMAN, P24928, 212|1874|1881|
TOM70_HUMAN, O94826, 450|118|84|237|585|
ZC3HF_HUMAN, Q8WU90, 207|
PSMD2_HUMAN, Q13200, 469|400|751|397|401|
DDX10_HUMAN, Q13206, 675|
DNJB6_HUMAN, O75190, 34|53|
RAC1_HUMAN, P63000, 139|154|98|147|183|
VPS4B_HUMAN, O75351, 47|
CCAR2_HUMAN, Q8N163, 100|231|322|410|198|828|882|54|791|201|
MMAA_HUMAN, Q8IVH4, 323|
DCTD_HUMAN, P32321, 79|
RT34_HUMAN, P82930, 104|34|
IMA1_HUMAN, P52292, 203|
DDX24_HUMAN, Q9GZR7, 662|721|809|671|11|808|
ZN503_HUMAN, Q96F45, 178|602|
RS11_HUMAN, P62280, 58|55|92|10|136|144|147|30|45|59|
YBOX1_HUMAN, P67809, 158|162|72|138|
HMGB2_HUMAN, P26583, 147|16|162|144|
PSMD5_HUMAN, Q16401, 478|440|
PSA2_HUMAN, P25787, 101|167|57|178|6|64|92|76|
PSA3_HUMAN, P25788, 59|
PSA4_HUMAN, P25789, 239|121|
MPH6_HUMAN, Q99547, 45|
TGO1_HUMAN, Q5JRA6, 108|
NTM1A_HUMAN, Q9BV86, 103|
XRN1_HUMAN, Q8IZH2, 93|
ARP3_HUMAN, P61158, 16|184|202|231|245|400|72|191|398|75|18|256|
UCK2_HUMAN, Q9BZX2, 245|
CSN7B_HUMAN, Q9H9Q2, 198|199|
ODBB_HUMAN, P21953, 363|
U5S1_HUMAN, Q15029, 336|482|614|722|832|161|341|
RL6_HUMAN, Q02878, 115|282|216|124|130|131|218|260|285|39|41|
MTA2_HUMAN, O94776, 437|501|504|
MET14_HUMAN, Q9HCE5, 146|169|
TPM4_HUMAN, P67936, 126|
PRS4_HUMAN, P62191, 25|259|24|429|210|225|439|
NHP2_HUMAN, Q9NX24, 24|
PRS8_HUMAN, P62195, 148|189|156|72|
BDH2_HUMAN, Q9BUT1, 49|48|
RS21_HUMAN, P63220, 53|
FOXJ3_HUMAN, Q9UPW0, 83|
MY18A_HUMAN, Q92614, 1324|
ZFR_HUMAN, Q96KR1, 662|
KBP_HUMAN, Q96EK5, 482|
DNM1L_HUMAN, O00429, 449|
ACY1_HUMAN, Q03154, 105|
F10A1_HUMAN, P50502, 153|151|185|213|348|14|5|50|56|364|230|
ARPIN_HUMAN, Q7Z6K5, 5|
THOC5_HUMAN, Q13769, 441|
COQ8A_HUMAN, Q8NI60, 245|
NACA_HUMAN, Q13765, 112|120|113|
TPP1_HUMAN, O14773, 508|
AGK_HUMAN, Q53H12, 220|233|82|
TCRG1_HUMAN, O14776, 1074|148|
UBE2N_HUMAN, P61088, 34|62|76|68|
UBC12_HUMAN, P61081, 172|86|11|177|
HNRL1_HUMAN, Q9BUJ2, 232|302|369|390|450|473|502|510|183|594|667|309|310|375|416|440|448|449|731|729|137|111|
RS23_HUMAN, P62266, 134|108|135|29|37|48|54|76|
FOXK1_HUMAN, P85037, 640|266|463|
RS14_HUMAN, P62263, 72|106|125|61|86|96|
RS18_HUMAN, P62269, 40|77|95|137|88|91|
ATPK_HUMAN, P56134, 55|
ACSL4_HUMAN, O60488, 415|541|59|49|54|

TABLE 3-continued

Protein Modification Sites Targeted by Sulfonyl-Heterocycle Probes and Ligands.

COR1A_HUMAN, P31146, 25|283|294|306|321|364|396|207|214|233|287|313|324|339|355|
DOHH_HUMAN, Q9BU89, 290|
USMG5_HUMAN, Q96IX5, 18|51|56|
AP3B1_HUMAN, O00203, 168|
COR1B_HUMAN, Q9BR76, 396|
CWC27_HUMAN, Q6UX04, 367|139|
RBGPR_HUMAN, Q9H2M9, 355|
SSRP1_HUMAN, Q08945, 166|232|236|311|353|74|219|72|233|36|63|
NAT10_HUMAN, Q9H0A0, 640|708|713|732|
P5CR2_HUMAN, Q96C36, 47|
NENF_HUMAN, Q9UMX5, 137|136|
EWS_HUMAN, Q01844, 278|
NFL_HUMAN, P07196, 389|
TRI26_HUMAN, Q12899, 111|
AN32E_HUMAN, Q9BTT0, 92|101|113|6|65|86|99|
CIP2A_HUMAN, Q8TCG1, 253|
ERG24_HUMAN, O76062, 316|
SEC63_HUMAN, Q9UGP8, 131|149|
DHRS7_HUMAN, Q9Y394, 224|330|263|332|335|
ODPX_HUMAN, O00330, 194|
PGAM2_HUMAN, P15259, 92|
GBRAP_HUMAN, O95166, 25|24|
DCUP_HUMAN, P06132, 164|42|311|
SMC4_HUMAN, Q9NTJ3, 175|1115|1112|870|326|1034|
ELP1_HUMAN, O95163, 1182|1002|806|
IF5A2_HUMAN, Q9GZV4, 69|
MYO1E_HUMAN, Q12965, 974|
PPCS_HUMAN, Q9HAB8, 250|
DNJA3_HUMAN, Q96EY1, 399|120|110|119|157|
CAZA1_HUMAN, P52907, 97|57|
RS15_HUMAN, P62841, 30|97|100|52|65|
RS24_HUMAN, P62847, 83|76|81|97|11|21|32|37|88|
APOC3_HUMAN, P02656, 44|
RS2_HUMAN, P15880, 248|250|266|133|169|223|114|142|183|211|238|257|275|65|71|
NSF_HUMAN, P46459, 294|499|502|611|489|509|
AP1M1_HUMAN, Q9BXS5, 384|134|
NS1BP_HUMAN, Q9Y6Y0, 376|
SCOT1_HUMAN, P55809, 156|161|174|43|407|115|173|176|293|434|473|296|286|421|271|
SNAG_HUMAN, Q99747, 15|28|
ADDA_HUMAN, P35611, 55|
SYLM_HUMAN, Q15031, 79|
FA50B_HUMAN, Q9Y247, 53|
CLC11_HUMAN, Q9Y240, 234|
CPNE1_HUMAN, Q99829, 386|512|
CLN5_HUMAN, O75503, 106|
UBA1_HUMAN, P22314, 273|55|60|618|117|286|388|425|451|471|560|666|873|922|185|
296|304|385|411|526|593|627|671|838|851|882|884|89|923|141|
CCAR1_HUMAN, Q8IX12, 146|192|
CALR_HUMAN, P27797, 286|109|150|285|57|172|182|299|306|308|338|75|128|111|143|
151|153|159|164|185|207|322|41|48|55|62|355|360|43|358|
COPB2_HUMAN, P35606, 761|354|
AMOT_HUMAN, Q4VCS5, 599|832|719|685|420|
REN3B_HUMAN, Q9BZI7, 98|167|
FA50A_HUMAN, Q14320, 53|
TRA2B_HUMAN, P62995, 128|141|
LRC59_HUMAN, Q96AG4, 203|284|138|149|192|215|218|219|226|73|
PRPS2_HUMAN, P11908, 94|
PM34_HUMAN, O43808, 252|
CPSF5_HUMAN, O43809, 24|54|
PRDX4_HUMAN, Q13162, 240|237|54|266|60|
DUS9_HUMAN, Q99956, 122|
SNG1_HUMAN, O43759, 18|
UB2V2_HUMAN, Q15819, 113|
PKP2_HUMAN, Q99959, 626|876|
DSN1_HUMAN, Q9H410, 232|
TR112_HUMAN, Q9UI30, 74|
ARFP1_HUMAN, P53367, 136|146|137|
ARFP2_HUMAN, P53365,
METK2_HUMAN, P31153, 235|377|242|271|92|
GDIR2_HUMAN, P52566, 107|125|130|146|153|172|24|102|114|124|135|138|164|50|96|175|25|
LEGL_HUMAN, Q3ZCW2, 148|
DHR11_HUMAN, Q6UWP2, 166|
TMM33_HUMAN, P57088, 129|148|
1433G_HUMAN, P61981, 133|154|107|123|216|49|110|125|217|50|130|131|
UTP20_HUMAN, O75691, 2768|
TRI25_HUMAN, Q14258, 437|
NU155_HUMAN, O75694, 689|
XRP2_HUMAN, O75695, 10|13|

TABLE 3-continued

Protein Modification Sites Targeted by Sulfonyl-Heterocycle Probes and Ligands.

RCN2_HUMAN, Q14257, 97|64|54|
AP4A_HUMAN, P50583, 82|114|
SMAP2_HUMAN, Q8WU79, 96|
ERO1A_HUMAN, Q96HE7, 120|431|191|188|375|192|373|369|
RL18A_HUMAN, Q02543, 10|110|28|63|94|97|11|128|143|151|2|21|41|76|
ACTN1_HUMAN, P12814, 682|215|582|681|89|
GNPI2_HUMAN, Q8TDQ7, 34|
NIPS2_HUMAN, O75323, 187|53|58|91|
GOGB1_HUMAN, Q14789, 2103|3223|
PGK2_HUMAN, P07205, 161|
CAPG_HUMAN, P40121, 109|116|300|
MPC2_HUMAN, O95563, 32|122|19|27|
FA49B_HUMAN, Q9NUQ9, 317|282|
KINH_HUMAN, P33176, 228|274|277|281|164|649|
1433Z_HUMAN, P63104, 49|118|128|149|19|211|48|212|11|120|68|9|158|75|138|125|126|
SRP09_HUMAN, P49458, 76|
RBM8A_HUMAN, Q9Y5S9, 54|
NOB1_HUMAN, Q9ULX3, 334|
KCAB2_HUMAN, Q13303, 360|270|362|
GPX1_HUMAN, P07203, 98|
ZN363_HUMAN, Q96PM5, 23|
PUM1_HUMAN, Q14671, 784|83|819|
EPN4_HUMAN, Q14677, 21|106|176|27|
STAG2_HUMAN, Q8N3U4, 1074|
COR1C_HUMAN, Q9ULV4, 394|
TPM3_HUMAN, P06753, 163|
H2B1B_HUMAN, P33778, 84|
ARP2_HUMAN, P61160, 72|91|378|7|253|310|
SH3G2_HUMAN, Q99962, 170|
ACTZ_HUMAN, P61163, 38|241|363|242|223|92|
MAGD2_HUMAN, Q9UNF1, 317|
PACN2_HUMAN, Q9UNF0, 390|263|267|388|435|481|55|76|147|157|189|150|164|143|
DDX1_HUMAN, Q92499, 380|96|312|586|65|628|117|69|702|
L2HDH_HUMAN, Q9H9P8, 285|
TSR1_HUMAN, Q2NL82, 779|
DCP2_HUMAN, Q8IU60, 130|
ZCCHV_HUMAN, Q7Z2W4, 108|690|755|775|
41_HUMAN, P11171, 202|
STXB1_HUMAN, P61764, 519|
ODPB_HUMAN, P11177, 336|131|132|334|63|67|68|
MBNL2_HUMAN, Q5VZF2, 233|68|
B2MG_HUMAN, P61769, 111|
CD3Z_HUMAN, P20963, 142|
CHD1L_HUMAN, Q86WJ1, 237|
2AAA_HUMAN, P30153, 261|155|495|255|305|33|542|
COX5B_HUMAN, P10606, 62|
PSMD4_HUMAN, P55036, 74|
SYVM_HUMAN, Q5ST30, 357|
IF2B1_HUMAN, Q9NZI8, 206|321|223|234|269|294|424|566|
TIM10_HUMAN, P62072, 58|39|45|
CH3L2_HUMAN, Q15782, 195|326|377|329|
TOM34_HUMAN, Q15785, 277|
EIF3M_HUMAN, Q7L2H7, 192|177|331|
SNW1_HUMAN, Q13573, 292|260|407|448|179|297|98|46|116|459|
RS13_HUMAN, P62277, 18|38|89|34|39|43|70|93|94|
RS29_HUMAN, P62273, 34|13|
ABCF1_HUMAN, Q8NE71, 710|719|697|724|250|
COQ9_HUMAN, O75208, 175|288|177|
SNUT2_HUMAN, Q53GS9, 430|215|235|433|428|
PSD11_HUMAN, O00231, 417|415|72|
CEBPZ_HUMAN, Q03701, 696|
UBAP2_HUMAN, Q5T6F2, 862|
SRP14_HUMAN, P37108, 27|31|
JAGN1_HUMAN, Q8N5M9, 168|
T106B_HUMAN, Q9NUM4, 84|
ARL11_HUMAN, Q969Q4, 30|
TPD52_HUMAN, P55327, 136|164|108|138|163|169|137|185|102|180|120|
TS101_HUMAN, Q99816, 63|
TCPD_HUMAN, P50991, 179|24|269|282|449|126|319|375|384|489|21|29|55|
TCPQ_HUMAN, P50990, 30|304|426|436|468|47|173|308|242|138|16|225|235|260|307|37|439|459|318|20|351|
ANX11_HUMAN, P50995, 279|365|398|493|264|282|450|442|495|482|
YMEL1_HUMAN, Q96TA2, 455|
SUCB1_HUMAN, Q9P2R7, 84|88|143|148|
SDHA_HUMAN, P31040, 124|141|156|259|263|330|55|604|606|641|169|182|608|167|
ENOG_HUMAN, P09104, 189|25|257|407|270|193|44|
P4K2A_HUMAN, Q9BTU6, 131|362|465|159|
CD5_HUMAN, P06127, 453|

TABLE 3-continued

Protein Modification Sites Targeted by Sulfonyl-Heterocycle Probes and Ligands.

FUBP3_HUMAN, Q96I24, 278|523|
TFIP8_HUMAN, O95379, 55|
EIF3F_HUMAN, O00303, 289|106|157|297|
DYH1_HUMAN, Q9P2D7, 605|
TFR1_HUMAN, P02786, 503|20|58|60|
WWP2_HUMAN, O00308, 347|
ARI2_HUMAN, O95376, 467|337|
UBQL1_HUMAN, Q9UMX0, 269|42|
ANKL2_HUMAN, Q86XL3, 301|
COPE_HUMAN, O14579, 202|203|90|
SNX2_HUMAN, O60749, 203|218|426|433|439|442|223|220|294|287|
RAB21_HUMAN, Q9UL25, 159|88|164|191|
DJB12_HUMAN, Q9NXW2, 345|
RSMB_HUMAN, P14678, 57|8|
MTPN_HUMAN, P58546, 21|19|
SOX10_HUMAN, P56693, 171|83|
RS25_HUMAN, P62851, 66|109|102|57|94|98|
RL17_HUMAN, P18621, 47|139|4|63|27|37|49|55|74|86|
RS26_HUMAN, P62854, 66|62|73|
SEP11_HUMAN, Q9NVA2, 323|297|
RAE1L_HUMAN, P78406, 174|244|345|
HNRPF_HUMAN, P52597, 194|210|219|236|240|243|246|253|266|272|276|298|306|82|180|167|171|185|224|87|
CF298_HUMAN, P57076, 207|245|246|
PIGT_HUMAN, Q969N2, 378|
RTN4_HUMAN, Q9NQC3, 1076|1091|1165|1057|1171|1174|1179|1183|1188|1066|1058|
GSTA2_HUMAN, P09210, 147|
ARHG1_HUMAN, Q92888, 616|
CALU_HUMAN, O43852, 106|263|275|47|281|75|161|294|
EIF3H_HUMAN, O15372, 277|274|269|
EIF3D_HUMAN, O15371, 263|335|215|
ACAP1_HUMAN, Q15027, 456|
PESC_HUMAN, O00541, 265|
MORC2_HUMAN, Q9Y6X9, 418|
SART3_HUMAN, Q15020, 507|
SUZ12_HUMAN, Q15022, 557|
MANF_HUMAN, P55145, 160|76|104|108|111|157|174|94|112|
THOC4_HUMAN, Q86V81, 77|156|81|166|
PGRC2_HUMAN, O15173, 143|135|
VDAC3_HUMAN, Q9Y277, 173|225|67|174|90|
IGBP1_HUMAN, P78318, 277|271|
GLCNE_HUMAN, Q9Y223, 188|
CYTB_HUMAN, P04080, 56|53|85|97|
THOC2_HUMAN, Q8NI27, 1067|532|830|
VAV3_HUMAN, Q9UKW4, 767|
WDR12_HUMAN, Q9GZL7, 89|
ANFY1_HUMAN, Q9P2R3, 1016|
RN114_HUMAN, Q9Y508, 186|139|113|116|
BASI_HUMAN, P35613, 375|
EIF1B_HUMAN, O60739, 79|54|30|
SRP72_HUMAN, O76094, 529|352|
PYRG1_HUMAN, P17812, 354|468|554|265|106|96|360|84|103|473|
FKBP8_HUMAN, Q14318, 232|364|334|340|352|366|377|
RL40_HUMAN, P62987, 114|48|6|59|
FLNC_HUMAN, Q14315, 926|2185|
STRN_HUMAN, O43815, 107|110|
VIME_HUMAN, P08670, 292|117|276|291|30|400|53|61|120|139|313|402|373|294|
RL9_HUMAN, P32969, 180|96|170|174|184|21|28|59|65|
LANC1_HUMAN, O43813, 21|15|
SCPDL_HUMAN, Q8NBX0, 105|102|147|202|237|244|371|165|228|355|359|
T0IP1_HUMAN, Q5JTV8, 379|203|334|556|
SCO2_HUMAN, O43819, 205|
ELMO1_HUMAN, Q92556, 18|20|485|
AP1G1_HUMAN, O43747, 231|
CUED2_HUMAN, Q9H467, 275|247|
MSMO1_HUMAN, Q15800, 39|
DLG3_HUMAN, Q92796, 673|
PUR6_HUMAN, P22234, 22|47|226|116|228|14|231|
NNRE_HUMAN, Q8NCW5, 255|
BCCIP_HUMAN, Q9P287, 217|
SF3B6_HUMAN, Q9Y3B4, 117|36|41|
FKBP3_HUMAN, Q00688, 198|200|
KDM3B_HUMAN, Q7LBC6, 196|
TYY1_HUMAN, P25490, 315|
T126A_HUMAN, Q9H061, 133|62|
NAA16_HUMAN, Q6N069, 86|
CISD3_HUMAN, P0C7P0, 108|57|88|86|67|55|
TKFC_HUMAN, Q3LXA3, 546|

TABLE 3-continued

Protein Modification Sites Targeted by Sulfonyl-Heterocycle Probes and Ligands.

ETHE1_HUMAN, O95571, 175|192|197|
ACSL3_HUMAN, O95573, 96|59|194|68|516|51|58|63|
SYNE2_HUMAN, Q8WXH0, 5390|5402|
MYPT1_HUMAN, O14974, 549|91|446|
PDC6I_HUMAN, Q8WUM4, 223|29|39|233|229|291|
HNRDL_HUMAN, O14979, 167|252|281|314|142|250|288|
PDIA1_HUMAN, P07237, 65|196|327|457|63|99|268|414|116|271|309|326|328|415|103|207|254|276|375|467|71|385|114|436|31|444|283|
DERL2_HUMAN, Q9GZP9, 218|
ABCB7_HUMAN, O75027, 113|
MED15_HUMAN, Q96RN5, 542|
PABP4_HUMAN, Q13310, 291|364|116|196|361|297|
OSBP1_HUMAN, P22059, 296|415|411|
UBP16_HUMAN, Q9Y5T5, 339|
PREB_HUMAN, Q9HCU5, 281|119|
ABCF2_HUMAN, Q9UG63, 503|359|456|310|
RRP1B_HUMAN, Q14684, 34|
SMC1A_HUMAN, Q14683, 186|714|
GNAI2_HUMAN, P04899, 147|155|168|291|297|303|321|74|17|21|296|307|313|51|
OTU7B_HUMAN, Q6GQQ9, 623|
AFG2H_HUMAN, Q8NB90, 393|
OCAD1_HUMAN, Q9NX40, 128|129|73|87|64|91|210|
MARH5_HUMAN, Q9NX47, 84|
RPC1_HUMAN, O14802, 714|
ZDH17_HUMAN, Q8IUH5, 286|
IDH3A_HUMAN, P50213, 137|133|153|186|134|200|214|58|77|90|
DC1I2_HUMAN, Q13409, 291|
NFH_HUMAN, P12036, 402|
SKP1_HUMAN, P63208, 130|
CX7A2_HUMAN, P14406, 44|27|46|
NBN_HUMAN, O60934, 74|
ACADM_HUMAN, P11310, 183|353|397|400|158|385|419|67|73|352|236|389|418|420|69|
P66B_HUMAN, Q8WXI9, 454|
VPS4A_HUMAN, Q9UN37, 290|348|45|
GRHPR_HUMAN, Q9UBQ7, 255|182|
RL37A_HUMAN, P61513, 18|37|71|28|80|87|
EIF3K_HUMAN, Q9UBQ5, 21|32|42|
VPS29_HUMAN, Q9UBQ0, 46|
SMAD2_HUMAN, Q15796, 366|
RS8_HUMAN, P62241, 113|117|198|27|83|109|149|188|148|170|193|94|
RS15A_HUMAN, P62244, 46|119|12|71|84|
P3H1_HUMAN, Q32P28, 500|512|
EDC3_HUMAN, Q96F86, 475|258|
SERPH_HUMAN, P50454, 135|151|
RS16_HUMAN, P62249, 115|99|106|109|130|131|17|26|33|50|60|
GGA2_HUMAN, Q9UJY4, 118|
CCD47_HUMAN, Q96A33, 293|372|388|374|392|
SPB8_HUMAN, P50452, 139|
ADT3_HUMAN, P12236, 112|251|105|147|163|166|23|245|260|268|43|33|63|81|
ADT1_HUMAN, P12235, 147|260|263|268|63|166|81|
THOC3_HUMAN, Q96J01, 34|133|47|
ITCH_HUMAN, Q96J02, 56|343|375|455|
ATX2L_HUMAN, Q8WWM7, 349|
KLC2_HUMAN, Q9H0B6, 208|292|
EP15R_HUMAN, Q9UBC2, 30|151|
GNAQ_HUMAN, P50148, 151|192|145|
ARF3_HUMAN, P61204, 36|35|58|81|
CO3_HUMAN, P01024, 1053|
CSN2_HUMAN, P61201, 118|123|
TCP4_HUMAN, P53999, 88|
CSN5_HUMAN, Q92905, 114|
RL19_HUMAN, P84098, 133|146|53|82|
HS71L_HUMAN, P34931, 117|547|527|433|373|
MCTS1_HUMAN, Q9ULC4, 124|169|88|87|
HSP74_HUMAN, P34932, 181|184|30|336|400|435|445|624|723|148|446|454|89|185|272|388|437|466|674|53|626|
RAB7A_HUMAN, P51149, 144|151|183|28|37|137|146|157|194|31|32|38|
RAB5C_HUMAN, P51148, 184|
UNG_HUMAN, P13051, 8|
THIK_HUMAN, P09110, 323|331|395|237|
DSRAD_HUMAN, P55265, 1112|1208|483|493|722|989|587|494|591|637|
H14_HUMAN, P10412, 71|110|119|197|52|63|75|85|90|97|
ERH_HUMAN, P84090, 19|36|79|82|84|41|
LAMB2_HUMAN, P55268, 48|
RL12_HUMAN, P30050, 40|41|
ATAD1_HUMAN, Q8NBU5, 48|53|57|
PABP1_HUMAN, P11940, 299|512|140|291|297|364|382|513|116|54|56|333|361|
PRS7_HUMAN, P35998, 36|

TABLE 3-continued

Protein Modification Sites Targeted by Sulfonyl-Heterocycle Probes and Ligands.

HNRH2_HUMAN, P55795, 276|306|14|195|
PDLI1_HUMAN, O00151, 144|321|
LYRIC_HUMAN, Q86UE4, 364|
WDR6_HUMAN, Q9NNW5, 581|
ARFG3_HUMAN, Q9NP61, 396|
AATM_HUMAN, P00505, 363|58|82|338|
GLRX1_HUMAN, P35754, 25|20|
UFD1_HUMAN, Q92890, 63|
GSLG1_HUMAN, Q92896, 1048|756|
UBE2F_HUMAN, Q969M7, 75|
YIPF5_HUMAN, Q969M3, 42|
SEPT2_HUMAN, Q15019, 105|17|121|63|258|
RANB9_HUMAN, Q96S59, 526|
AP1B1_HUMAN, Q10567, 26|136|121|
PPM1G_HUMAN, O15355, 211|364|74|160|27|405|367|406|383|
TM10C_HUMAN, Q7L0Y3, 214|216|
WRIP1_HUMAN, Q96S55, 469|534|
TMM43_HUMAN, Q9BTV4, 16|397|
NUP88_HUMAN, Q99567, 688|
ARPC2_HUMAN, O15144, 295|261|
ARPC3_HUMAN, O15145, 132|
CBX5_HUMAN, P45973, 177|186|74|
NUDC_HUMAN, Q9Y266, 292|172|314|297|309|308|
RUVB1_HUMAN, Q9Y265, 454|453|274|168|
EIF3L_HUMAN, Q9Y262, 247|357|95|36|394|89|393|549|40|
ARI1A_HUMAN, O14497, 1226|1523|1281|1285|1506|
DHX9_HUMAN, Q08211, 1155|902|1038|1167|200|274|370|568|616|68|681|748|9|148|21|
259|573|1037|1073|1163|146|235|264|275|29|55|755|
AXA81_HUMAN, Q5VT79, 264|263|
SAM50_HUMAN, Q9Y512, 172|215|407|444|168|221|248|412|59|
CAP1_HUMAN, Q01518, 164|31|419|43|395|422|63|327|282|37|
ECI2_HUMAN, O75521, 111|285|66|69|169|177|289|62|70|54|92|55|
RU2A_HUMAN, P09661, 117|15|29|30|
NPL4_HUMAN, Q8TAT6, 113|116|
COX6C_HUMAN, P09669, 56|47|
S4A7_HUMAN, Q9Y6M7, 1152|
PSD13_HUMAN, Q9UNM6, 162|172|238|
COX3_HUMAN, P00414, 67|77|
UBQL4_HUMAN, Q9NRR5, 279|286|
FUBP1_HUMAN, Q96AE4, 243|242|58|60|248|400|590|589|
BAG3_HUMAN, O95817, 114|
FUBP2_HUMAN, Q92945, 291|627|290|317|625|626|644|674|646|347|
RTF1_HUMAN, Q92541, 562|624|
ACON_HUMAN, Q99798, 151|390|42|432|472|665|71|715|513|160|409|50|700|701|717|520|
TADBP_HUMAN, Q13148, 123|214|77|121|140|192|263|79|
TM9S4_HUMAN, Q92544, 477|58|46|
MIPEP_HUMAN, Q99797, 273|510|
SYNC_HUMAN, O43776, 265|266|489|499|500|502|393|413|448|508|539|407|490|507|123|
STAM1_HUMAN, Q92783, 103|381|
NOP2_HUMAN, P46087, 442|
HNRPU_HUMAN, Q00839, 265|257|260|266|525|669|327|350|466|473|613|238|331|352|464|
489|495|516|524|536|543|544|551|565|592|602|614|620|626|670|682|688|
RBM22_HUMAN, Q9NW64, 156|158|157|181|
GDE_HUMAN, P35573, 584|391|
GRPE1_HUMAN, Q9HAV7, 102|
RL30_HUMAN, P62888, 63|74|27|68|
COQ7_HUMAN, Q99807, 61|
FAAA_HUMAN, P16930, 244|
SMC6_HUMAN, Q96SB8, 818|461|
RB11B_HUMAN, Q15907, 91|95|
SERA_HUMAN, O43175, 146|308|330|384|394|69|
BECN1_HUMAN, Q14457, 413|416|
PAIP1_HUMAN, Q9H074, 386|
CLPB_HUMAN, Q9H078, 430|
CSN1_HUMAN, Q13098, 381|
PTBP1_HUMAN, P26599, 127|430|267|271|402|410|439|440|482|485|489|48|
HGS_HUMAN, O14964, 289|286|
TXNL1_HUMAN, O43396, 123|
HNRPR_HUMAN, O43390, 431|434|435|436|136|147|156|177|208|229|279|296|376|578|110|
120|126|187|224|235|259|285|300|313|359|374|584|
XRCC6_HUMAN, P12956, 103|409|530|534|559|88|114|129|189|297|351|443|
463|468|516|526|539|544|553|570|582|92|
IAH1_HUMAN, Q2TAA2, 229|
TLN2_HUMAN, Q9Y4G6, 201|
COF1_HUMAN, P23528, 92|117|140|68|82|85|89|112|114|121|127|132|144|
152|19|22|30|31|34|44|53|73|78|95|96|
IR3IP_HUMAN, Q9Y5U9, 49|
PIMT_HUMAN, P22061, 153|213|147|

TABLE 3-continued

Protein Modification Sites Targeted by Sulfonyl-Heterocycle Probes and Ligands.

CD53_HUMAN, P19397, 173|
RT22_HUMAN, P82650, 163|
MESD_HUMAN, Q14696, 166|190|58|222|193|
RRP5_HUMAN, Q14690, 1103|1353|1363|
BMS1_HUMAN, Q14692, 847|
HECD1_HUMAN, Q9ULT8, 2008|
MIRO2_HUMAN, Q8IXI1, 409|
RGN_HUMAN, Q15493, 113|219|
PSA7_HUMAN, O14818, 110|118|145|153|21|106|
PGM1_HUMAN, P36871, 12|232|353|430|234|
SF3B2_HUMAN, Q13435, 844|568|547|570|
UBP22_HUMAN, Q9UPT9, 389|450|
ARHG2_HUMAN, Q92974, 125|434|446|356|438|
LSM12_HUMAN, Q3MHD2, 34|37|
UBC9_HUMAN, P63279, 68|65|
GPSM2_HUMAN, P81274, 146|
SPT4H_HUMAN, P63272, 85|81|
ATLA3_HUMAN, Q6DD88, 377|413|364|315|375|422|430|538|
CELF1_HUMAN, Q92879, 190|192|
TXD17_HUMAN, Q9BRA2, 30|4|99|
PSPC1_HUMAN, Q8WXF1, 105|255|383|198|380|257|
SNP29_HUMAN, O95721, 122|160|124|107|
ATPB_HUMAN, P06576, 198|432|395|418|431|196|230|247|269|292|331|361|499|508|
124|133|159|201|212|225|259|264|350|351|426|451|480|
485|489|519|522|
PSA6_HUMAN, P60900, 164|105|107|159|23|96|103|104|
FUCT1_HUMAN, Q96A29, 347|
CLPP_HUMAN, Q16740, 229|73|
1433E_HUMAN, P62258, 153|50|122|131|152|20|49|214|215|128|
F162A_HUMAN, Q96A26, 55|124|139|144|150|62|69|79|96|
CTR9_HUMAN, Q6PD62, 473|826|
SP4_HUMAN, Q02446, 660|
CYBP_HUMAN, Q9HB71, 181|199|71|125|78|90|197|74|212|178|165|
DX39A_HUMAN, O00148, 138|264|265|38|132|155|162|187|267|
MBNL3_HUMAN, Q9NUK0, 69|
ARF5_HUMAN, P84085, 36|35|58|81|
TCPE_HUMAN, P48643, 275|274|446|137|280|420|176|242|282|35|352|42|535|
ABLM1_HUMAN, O14639, 688|
TIGAR_HUMAN, Q9NQ88, 92|208|
QSOX2_HUMAN, Q6ZRP7, 692|
IF5_HUMAN, P55010, 52|74|55|313|
EXOC1_HUMAN, Q9NV70, 766|769|
SPS1_HUMAN, P49903, 345|
PAPOA_HUMAN, P51003, 327|20|
UB2V1_HUMAN, Q13404, 115|
RT07_HUMAN, Q9Y2R9, 126|239|
ACTA_HUMAN, P62736, 190|55|
PRDX3_HUMAN, P30048, 221|
ENAH_HUMAN, Q8N8S7, 16|529|87|38|70|
PRDX6_HUMAN, P30041, 209|89|
ERP29_HUMAN, P30040, 69|64|66|96|230|
PRDX5_HUMAN, P30044, 142|159|75|86|
ZFPL1_HUMAN, O95159, 235|234|
COPG1_HUMAN, Q9Y678, 531|546|
RT18B_HUMAN, Q9Y676, 203|206|
TALDO_HUMAN, P37837, 206|307|
ALG5_HUMAN, Q9Y673, 74|127|139|202|78|
ATX10_HUMAN, Q9UBB4, 176|
COG5_HUMAN, Q9UP83, 342|
VTA1_HUMAN, Q9NP79, 285|151|
PDIA4_HUMAN, P13667, 252|273|392|367|565|509|521|528|576|637|221|573|407|
401|437|570|524|366|515|
CLIC4_HUMAN, Q9Y696, 130|128|220|225|244|
GBB2_HUMAN, P62879, 145|239|289|59|
GBB1_HUMAN, P62873, 111|145|289|59|85|127|89|
URP2_HUMAN, Q86UX7, 162|436|11|
KCD12_HUMAN, Q96CX2, 161|119|106|
FL2D_HUMAN, Q15007, 96|98|
NOP56_HUMAN, O00567, 152|210|277|284|321|348|371|408|110|240|375|90|
CND2_HUMAN, Q15003, 635|428|
XRCC1_HUMAN, P18887, 370|
DP13A_HUMAN, Q9UKG1, 289|
PSMD6_HUMAN, Q15008, 366|
PDXK_HUMAN, O00764, 77|84|127|
UBE2C_HUMAN, O00762, 91|165|
PRPK_HUMAN, Q96S44, 67|60|
GRSF1_HUMAN, Q12849, 337|125|
TBCD_HUMAN, Q9BTW9, 272|663|

TABLE 3-continued

Protein Modification Sites Targeted by Sulfonyl-Heterocycle Probes and Ligands.

TITIN_HUMAN, Q8WZ42, 3196|
ARF4_HUMAN, P18085, 35|58|81|
CBR3_HUMAN, O75828, 198|194|
SF3B1_HUMAN, O75533, 1288|587|805|623|1083|807|943|1086|570|
EIF3G_HUMAN, O75821, 70|274|280|171|
CSDE1_HUMAN, O75534, 37|573|
RL10_HUMAN, P27635, 57|141|156|158|164|169|170|188|30|82|
OXA1L_HUMAN, Q15070, 195|197|
DYN3_HUMAN, Q9UQ16, 390|603|265|125|
HBS1L_HUMAN, Q9Y450, 656|282|
NHLC2_HUMAN, Q8NBF2, 403|
TMX2_HUMAN, Q9Y320, 184|199|140|261|
IDH3B_HUMAN, O43837, 171|121|240|366|122|212|218|242|
RAB8B_HUMAN, Q92930, 5|176|198|
TTC4_HUMAN, O95801, 129|128|
ROA0_HUMAN, Q13151, 180|145|133|137|176|96|
AIMP2_HUMAN, Q13155, 35|
DPYL3_HUMAN, Q14195, 32|
HXK3_HUMAN, P52790, 755|
DCTN1_HUMAN, Q14203, 1149|1235|567|563|513|1244|
DYHC1_HUMAN, Q14204, 1990|2426|2792|2881|2892|4196|4205|2022|3371|3641|1630|170|
1992|4418|4252|2350|775|
ATIF1_HUMAN, Q9UII2, 58|82|49|72|
RL31_HUMAN, P62899, 103|108|25|115|31|91|
DDX17_HUMAN, Q92841, 135|147|238|267|279|321|493|495|502|519|75|269|284|
313|341|361|428|468|488|592|602|
2AAB_HUMAN, P30154, 507|317|
UB2L3_HUMAN, P68036, 73|
ACTC_HUMAN, P68032, 71|93|70|86|190|55|
ANXA7_HUMAN, P20073, 350|427|231|233|426|
CYB5B_HUMAN, O43169, 138|111|107|
PUM2_HUMAN, Q8TB72, 595|
AMRP_HUMAN, P30533, 294|296|290|39|
U520_HUMAN, O75643, 1770|102|1154|1177|1295|1771|470|658|861|87|103|1294|
1603|1874|255|256|
ARFG1_HUMAN, Q8N6T3, 183|226|
CATA_HUMAN, P04040, 358|84|106|
PNPT1_HUMAN, Q8TCS8, 626|539|629|
CHM4B_HUMAN, Q9H444, 111|14|17|
SGTA_HUMAN, O43765, 114|127|135|141|181|182|116|160|183|
M2OM_HUMAN, Q02978, 102|202|61|206|21|57|62|73|94|
RNH2A_HUMAN, O75792, 172|210|206|215|271|
GRAP2_HUMAN, O75791, 324|48|
IRS4_HUMAN, O14654, 808|656|
ML12B_HUMAN, O14950, 122|156|143|150|151|
2A5D_HUMAN, Q14738, 451|589|
LBR_HUMAN, Q14739, 366|589|595|132|187|147|186|350|513|519|524|
XPF_HUMAN, Q92889, 344|627|
DEST_HUMAN, P60981, 16|82|85|22|19|117|
MAGD1_HUMAN, Q9Y5V3, 509|
CPIN1_HUMAN, Q6FI81, 290|
SPE39_HUMAN, Q9H9C1, 11|137|398|400|
MYL6_HUMAN, P60660, 86|89|29|63|
IQGA1_HUMAN, P46940, 1528|1193|172|385|654|977|133|140|143|174|1546|
1437|959|953|
VP13A_HUMAN, Q96RL7, 98|1341|
AEBP1_HUMAN, Q8IUX7, 733|771|
E41L2_HUMAN, O43491, 456|88|216|277|280|210|206|505|
P4R3A_HUMAN, Q6IN85, 391|
SC61B_HUMAN, P60468, 59|35|
C1TC_HUMAN, P11586, 56|240|258|348|52|816|834|852|307|371|402|429|723|262|292|
352|364|543|595|71|740|784|819|327|
RL27_HUMAN, P61353, 75|77|85|
IF4A3_HUMAN, P38919, 155|132|202|205|207|361|396|152|182|374|382|
SDHB_HUMAN, P21912, 128|150|156|170|241|273|134|123|126|151|158|261|
267|268|274|55|41|137|
1A03_HUMAN, P04439, 147|
MIC19_HUMAN, Q9NX63, 177|49|53|37|45|
AINX_HUMAN, Q16352, 396|
CRIP1_HUMAN, P50238, 12|
SMD3_HUMAN, P62318, 28|78|
SMD1_HUMAN, P62314, 67|
NNTM_HUMAN, Q13423, 106|1084|373|388|407|942|933|394|403|462|288|
SC24B_HUMAN, O95487, 883|
PFD3_HUMAN, P61758, 180|57|60|59|61|70|
ACTG_HUMAN, P63261, 188|218|169|198|362|294|53|306|
TCAB1_HUMAN, Q9BUR4, 271|
ACTH_HUMAN, P63267, 189|54|

TABLE 3-continued

Protein Modification Sites Targeted by Sulfonyl-Heterocycle Probes and Ligands.

TM9S3_HUMAN, Q9HD45, 122|272|60|76|583|125|275|581|
LASP1_HUMAN, Q14847, 122|86|13|112|
PDIA3_HUMAN, P30101, 104|100|222|67|95|196|265|269|356|402|445|454|479|467|416|
152|214|218|226|231|234|271|288|289|305|332|335|362|410|
460|466|129|296|417|494|497|347|496|425|
PEX16_HUMAN, Q9Y5Y5, 166|169|
PDCD5_HUMAN, O14737, 73|80|20|33|66|105|
DERL1_HUMAN, Q9BUN8, 207|
GLTP_HUMAN, Q9NZD2, 55|
RS7_HUMAN, P62081, 177|142|147|155|160|178|183|
DJB11_HUMAN, Q9UBS4, 89|42|
PIPNB_HUMAN, P48739, 67|65|215|104|57|24|
KGUA_HUMAN, Q16774, 53|81|
GLO2_HUMAN, Q16775, 193|
H2A2C_HUMAN, Q16777, 58|
H2B2E_HUMAN, Q16778, 41|35|44|84|
ATG3_HUMAN, Q9NT62, 18|209|210|
SIAS_HUMAN, Q9NR45, 188|71|81|74|61|85|
SHLB2_HUMAN, Q9NR46, 50|200|
ESTD_HUMAN, P10768, 191|202|121|123|211|49|67|185|186|224|
PTPRK_HUMAN, Q15262, 831|
PTSS1_HUMAN, P48651, 245|274|445|463|
ABHDA_HUMAN, Q9NUJ1, 215|84|87|68|69|92|
BACH_HUMAN, O00154, 168|162|194|181|286|
RAP1B_HUMAN, P61224, 151|174|42|
RHOG_HUMAN, P84095, 32|40|64|183|
ABCE1_HUMAN, P61221, 172|246|491|134|155|316|350|411|573|133|158|169|343|
412|431|447|121|126|191|
ITIH2_HUMAN, P19823, 490|
CNDP2_HUMAN, Q96KP4, 302|
COG1_HUMAN, Q8WTW3, 56|
PSME4_HUMAN, Q14997, 636|
FCL_HUMAN, Q13630, 292|282|
UBP11_HUMAN, P51784, 195|764|766|245|
XPO2_HUMAN, P55060, 369|282|408|416|42|682|861|158|418|425|52|839|863|912|782|
BI1_HUMAN, P55061, 29|
XPO7_HUMAN, Q9UIA9, 19|393|395|
T2FB_HUMAN, P13984, 153|161|47|
PSDE_HUMAN, O00487, 43|
ADT2_HUMAN, P05141, 165|251|291|297|51|81|95|105|147|163|166|23|245|260|268|272|
295|296|33|43|52|63|92|94|96|49|
PA2G4_HUMAN, Q9UQ80, 247|309|343|98|101|139|158|211|248|287|311|344|68|
NP1L1_HUMAN, P55209, 106|66|96|110|223|231|271|87|105|
TAGL2_HUMAN, P37802, 103|192|8|22|70|40|88|
COX7B_HUMAN, P24311, 28|
NIT2_HUMAN, Q9NQR4, 145|216|49|53|94|
SEH1_HUMAN, Q96EE3, 309|
NUP98_HUMAN, P52948, 1337|1341|550|
UQCC2_HUMAN, Q9BRT2, 114|118|
MIEN1_HUMAN, Q9BRT3, 87|
SSBP_HUMAN, Q04837, 103|122|101|119|73|99|109|51|
SAE1_HUMAN, Q9UBE0, 294|148|161|
CYGB_HUMAN, Q8WWM9, 125|123|159|
SYSM_HUMAN, Q9NP81, 52|
GDS1_HUMAN, P52306, 118|
YBOX3_HUMAN, P16989, 104|
HNRPL_HUMAN, P14866, 130|163|257|267|285|359|363|375|387|406|430|465|47|474|
565|574|576|48|136|178|264|269|393|411|418|475|493|
533|538|568|579|
EEA1_HUMAN, Q15075, 1396|
MRT4_HUMAN, Q9UKD2, 173|85|177|61|86|
SYDC_HUMAN, P14868, 239|245|253|143|24|29|384|389|394|402|455|241|
254|26|393|9|
PRP31_HUMAN, Q8WWY3, 135|
TMCO1_HUMAN, Q9UM00, 124|40|53|75|77|
LC7L3_HUMAN, O95232, 37|
COX41_HUMAN, P13073, 162|38|159|53|60|
PDE12_HUMAN, Q6L8Q7, 172|235|88|307|
NDC1_HUMAN, Q9BTX1, 519|
ISCU_HUMAN, Q9H1K1, 43|
POP7_HUMAN, O75817, 20|
OSTC_HUMAN, Q9NRP0, 18|
COXM2_HUMAN, Q9NRP2, 36|
SEP10_HUMAN, Q9P0V9, 322|
NSUN2_HUMAN, Q08J23, 646|121|262|38|556|640|43|
PROF2_HUMAN, P35080, 99|
PA1B3_HUMAN, Q15102, 201|
ACTS_HUMAN, P68133, 71|93|190|55|

TABLE 3-continued

Protein Modification Sites Targeted by Sulfonyl-Heterocycle Probes and Ligands.

AT5F1_HUMAN, P24539, 116|56|115|162|
RT12_HUMAN, O15235, 130|
CPSF2_HUMAN, Q9P2I0, 461|455|
LSM2_HUMAN, Q9Y333, 35|4|
DHX36_HUMAN, Q9H2U1, 22|883|
AIFM1_HUMAN, O95831, 211|347|109|89|93|199|
IPYR2_HUMAN, Q9H2U2, 136|135|142|230|59|88|128|
EF1B_HUMAN, P24534, 129|133|185|126|18|182|62|56|28|
KAD2_HUMAN, P54819, 147|181|62|65|
DAXX_HUMAN, Q9UER7, 295|
SRS10_HUMAN, O75494, 33|40|46|
TPPC9_HUMAN, Q96Q05, 469|
PTGR3_HUMAN, Q8N4Q0, 224|
ANXA6_HUMAN, P08133, 30|609|10|218|255|302|313|439|477|481|556|572|62|76|95|
645|102|240|262|265|314|34|377|40|418|442|446|478|483|
579|613|63|75|99|610|81|620|406|299|
SMRC1_HUMAN, Q92922, 683|606|66|740|454|
KAD3_HUMAN, Q9UIJ7, 85|
SBDS_HUMAN, Q9Y3A5, 202|
TCEA1_HUMAN, P23193, 273|126|
UTP11_HUMAN, Q9Y3A2, 114|
ERG28_HUMAN, Q9UKR5, 127|
BOLA2_HUMAN, Q9H3K6, 43|
PGAM4_HUMAN, Q8N0Y7, 133|119|92|
GHITM_HUMAN, Q9H3K2, 308|
CACP_HUMAN, P43155, 606|
RBM3_HUMAN, P98179, 125|127|143|151|146|
SH3L3_HUMAN, Q9H299, 18|
RRP8_HUMAN, O43159, 280|
RHG04_HUMAN, P98171, 460|
RBM10_HUMAN, P98175, 165|838|
SUV3_HUMAN, Q8IYB8, 215|409|
HP1B3_HUMAN, Q5SSJ5, 278|284|288|344|367|415|416|289|379|149|291|334|385|390|425|
TIAR_HUMAN, Q01085, 140|146|
SPTB2_HUMAN, Q01082, 1805|2249|2268|1983|1874|2258|2269|2215|1981|1809|997|2207|
U2AF1_HUMAN, Q01081, 158|
ORML3_HUMAN, Q8N138, 152|
RL13_HUMAN, P26373, 130|135|174|200|69|88|
LPPRC_HUMAN, P42704, 1215|1220|1321|1328|1341|160|165|317|320|441|480|570|583|586|
607|277|477|1251|1252|1317|1332|170|280|760|428|
RB15B_HUMAN, Q8NDT2, 517|510|
HTSF1_HUMAN, O43719, 173|217|
TOM1_HUMAN, O60784, 106|
QCR8_HUMAN, O14949, 27|78|82|
YKT6_HUMAN, O15498, 186|
TSNAX_HUMAN, Q99598, 187|
ODO1_HUMAN, Q02218, 966|1000|
KPRB_HUMAN, O60256, 113|115|
CBX3_HUMAN, Q13185, 143|
STT3A_HUMAN, P46977, 331|338|66|340|440|67|
PI51A_HUMAN, Q99755, 77|78|
SFXN1_HUMAN, Q9H9B4, 151|54|73|75|170|202|223|254|
GEMI_HUMAN, O75496, 111|
UFL1_HUMAN, O94874, 146|266|548|249|386|
MZB1_HUMAN, Q8WU39, 70|111|
CSRP1_HUMAN, P21291, 18|71|73|
S30BP_HUMAN, Q9UHR5, 134|151|181|
PPIH_HUMAN, O43447, 153|
CKLF6_HUMAN, Q9NX76, 167|
TUSC3_HUMAN, Q13454, 118|
GNAI1_HUMAN, P63096, 17|
GNAS2_HUMAN, P63092, 190|311|318|360|17|28|305|32|34|58|24|
WDR36_HUMAN, Q8NI36, 801|
KAP2_HUMAN, P13861, 385|
VATE2_HUMAN, Q96A05, 56|
ICLN_HUMAN, P54105, 200|
STML2_HUMAN, Q9UJZ1, 316|321|
3HIDH_HUMAN, P31937, 63|
QCR1_HUMAN, P31930, 132|134|
RPN2_HUMAN, P04844, 627|
CLP1L_HUMAN, Q96KA5, 209|530|
UBE2S_HUMAN, Q16763, 78|
RPN1_HUMAN, P04843, 387|341|400|379|488|517|576|579|264|
ATG9A_HUMAN, Q7Z3C6, 785|
BRAP_HUMAN, Q7Z569, 373|
MBNL1_HUMAN, Q9NR56, 236|68|
MIC27_HUMAN, Q6UXV4, 188|
EI2BG_HUMAN, Q9NR50, 264|278|

TABLE 3-continued

Protein Modification Sites Targeted by Sulfonyl-Heterocycle Probes and Ligands.

IF2P_HUMAN, O60841, 812|446|1100|762|
CNPY2_HUMAN, Q9Y2B0, 92|90|
NOC3L_HUMAN, Q8WTT2, 700|
TPPP3_HUMAN, Q9BW30, 131|
RCN1_HUMAN, Q15293, 115|290|
RL26_HUMAN, P61254, 74|135|42|110|41|69|62|
H31_HUMAN, P68431, 123|15|19|37|80|
AP3D1_HUMAN, O14617, 682|
NUMA1_HUMAN, Q14980, 1774|1610|1611|1433|
CUL4B_HUMAN, Q13620, 634|
NIPS1_HUMAN, Q9BPW8, 104|116|132|148|185|261|262|72|83|87|193|51|56|65|66|73|80|
DJB14_HUMAN, Q8TBM8, 225|
SSRG_HUMAN, Q9UNL2, 103|115|117|87|91|
GALK1_HUMAN, P51570, 109|318|339|236|
SSRD_HUMAN, P51571, 102|117|95|
BAP31_HUMAN, P51572, 73|72|
THOP1_HUMAN, P52888, 221|422|416|
TB10A_HUMAN, Q9BXI6, 258|429|
RM13_HUMAN, Q9BYD1, 132|
SNX12_HUMAN, Q9UMY4, 23|
GAMT_HUMAN, Q14353, 222|
RL18_HUMAN, Q07020, 166|119|154|164|49|9|99|
C1QBP_HUMAN, Q07021, 188|224|268|123|174|180|276|100|91|280|179|
ORC3_HUMAN, Q9UBD5, 527|
SRG2C_HUMAN, P0DJJ0, 170|
SYIM_HUMAN, Q9NSE4, 260|463|465|543|60|993|240|241|664|
DLRB1_HUMAN, Q9NP97, 42|
RT30_HUMAN, Q9NP92, 265|
ARI1_HUMAN, Q9Y4X5, 197|
MOB1A_HUMAN, Q9H8S9, 93|26|11|16|17|95|
OSBL9_HUMAN, Q96SU4, 688|
ACOX1_HUMAN, Q15067, 256|260|
LMNB2_HUMAN, Q03252, 186|
RPR1B_HUMAN, Q9NQG5, 117|61|279|
ACTN3_HUMAN, Q08043, 229|
PPP6_HUMAN, O00743, 123|
RUVB2_HUMAN, Q9Y230, 215|442|365|201|
DOCK5_HUMAN, Q9H7D0, 1071|
ODP2_HUMAN, P10515, 466|363|
ELMD2_HUMAN, Q8IZ81, 55|
APT_HUMAN, P07741, 105|60|101|107|114|167|34|51|
BCLF1_HUMAN, Q9NYF8, 637|
ETFB_HUMAN, P38117, 192|114|
CRYAB_HUMAN, P02511, 48|
PFKAM_HUMAN, P08237, 103|
RCC1_HUMAN, P18754, 362|
DDX46_HUMAN, Q7L014, 328|392|718|1020|961|248|255|271|272|316|394|765|910|
VPS36_HUMAN, Q86VN1, 235|
CDC73_HUMAN, Q6P1J9, 290|315|
UB2D4_HUMAN, Q9Y2X8, 74|
GPKOW_HUMAN, Q92917, 377|
ROA3_HUMAN, P51991, 360|364|373|140|145|149|188|118|126|127|134|148|151|182|199|29|36|73|277|
NKRF_HUMAN, O15226, 172|
S35B2_HUMAN, Q8TB61, 138|
ACAD9_HUMAN, Q9H845, 589|456|47|334|41|
TM109_HUMAN, Q9BVC6, 215|235|46|
HS105_HUMAN, Q92598, 184|726|322|267|
SEPT8_HUMAN, Q92599, 300|
MESH1_HUMAN, Q8N4P3, 146|
CAND1_HUMAN, Q86VP6, 891|878|373|586|372|82|291|797|
CERS6_HUMAN, Q6ZMG9, 92|
NDRG1_HUMAN, Q92597, 231|307|
PHB_HUMAN, P35232, 11|63|
RFA2_HUMAN, P15927, 138|256|
DESP_HUMAN, P15924, 95|172|
GALK2_HUMAN, Q01415, 110|
PPP5_HUMAN, P53041, 434|136|38|80|
CD2AP_HUMAN, Q9Y5K6, 361|88|409|
PLIN3_HUMAN, O60664, 95|251|166|164|46|
LSM7_HUMAN, Q9UK45, 54|62|63|
STRAP_HUMAN, Q9Y3F4, 127|300|28|
CCZ1_HUMAN, P86791, 380|
PRS6A_HUMAN, P17980, 226|185|
TCPA_HUMAN, P17987, 121|131|190|299|422|426|545|126|33|466|538|
NAA15_HUMAN, Q9BXJ9, 425|86|843|
ALG3_HUMAN, Q92685, 435|
SPART_HUMAN, Q8N0X7, 602|

TABLE 3-continued

Protein Modification Sites Targeted by Sulfonyl-Heterocycle Probes and Ligands.

DHX15_HUMAN, O43143, 499|127|177|235|254|323|389|490|710|765|142|686|143|277|408|488|786|13|645|
NOC2L_HUMAN, Q9Y3T9, 162|229|619|
CK5P3_HUMAN, Q96JB5, 168|440|
AKAP1_HUMAN, Q92667, 30|
DI3L2_HUMAN, Q8IYB7, 265|
LRRF1_HUMAN, Q32MZ4, 597|
TTC1_HUMAN, Q99614, 188|244|250|
DNJC7_HUMAN, Q99615, 355|38|145|
TIPRL_HUMAN, O75663, 79|29|108|
EIF3C_HUMAN, Q99613, 884|
SUCA_HUMAN, P53597, 337|78|308|338|54|81|
U2AF2_HUMAN, P26368, 269|463|469|276|462|
EVL_HUMAN, Q9UI08, 39|280|
SYDM_HUMAN, Q6PI48, 237|
MGME1_HUMAN, Q9BQP7, 205|
ACTN4_HUMAN, O43707, 176|108|234|
BUD23_HUMAN, O43709, 164|272|196|
SNR40_HUMAN, Q96DI7, 158|249|
SRR_HUMAN, Q9GZT4, 93|
UBE4A_HUMAN, Q14139, 939|
PLD3_HUMAN, Q8IV08, 437|
MTREX_HUMAN, P42285, 136|649|612|
FKB11_HUMAN, Q9NYL4, 119|121|184|189|
RL7A_HUMAN, P62424, 181|230|102|176|185|245|252|97|
SNX5_HUMAN, Q9Y5X3, 224|232|229|328|324|
ROAA_HUMAN, Q99729, 235|240|332|
COG4_HUMAN, Q9H9E3, 456|
TIM_HUMAN, Q9UNS1, 282|
CSN3_HUMAN, Q9UNS2, 422|
UBP2L_HUMAN, Q14157, 835|858|834|
EIF3A_HUMAN, Q14152, 382|174|499|427|420|63|72|
UBXN7_HUMAN, O94888, 227|
SAFB2_HUMAN, Q14151, 437|732|
VATC1_HUMAN, P21283, 223|28|
MOES_HUMAN, P26038, 134|146|85|270|291|254|64|258|262|263|72|313|296|538|253|568|
BAP29_HUMAN, Q9UHQ4, 90|73|
PLOD3_HUMAN, O60568, 437|438|
TM41B_HUMAN, Q5BJD5, 40|
NUCL_HUMAN, P19338, 467|351|462|473|495|525|402|463|433|294|324|348|370|377|387|398|403|424|477|486|508|513|521|
PUM3_HUMAN, Q15397, 472|
PSB7_HUMAN, Q99436, 34|
IF5A1_HUMAN, P63241, 69|98|127|121|27|34|39|67|68|85|
CARL1_HUMAN, Q5VZK9, 670|
ECSIT_HUMAN, Q9BQ95, 154|
ARF6_HUMAN, P62330, 31|32|58|
PRS10_HUMAN, P62333, 207|132|206|314|378|173|328|
CNN2_HUMAN, Q99439, 12|26|184|231|191|
RBBP7_HUMAN, Q16576, 21|131|20|153|180|155|214|60|
F120A_HUMAN, Q9NZB2, 1020|
MO4L1_HUMAN, Q9UBU8, 239|
PDC10_HUMAN, Q9BUL8, 164|
ACSF3_HUMAN, Q4G176, 175|401|436|544|344|324|563|
RAB10_HUMAN, P61026, 136|161|6|
RAB5B_HUMAN, P61020, 82|89|
MGN2_HUMAN, Q96A72, 43|42|53|50|
ODBA_HUMAN, P12694, 353|120|195|345|356|198|
ARC1B_HUMAN, O15143, 35|
VAC14_HUMAN, Q08AM6, 111|23|
DBLOH_HUMAN, Q9NR28, 150|
AIP_HUMAN, O00170, 202|38|196|316|248|203|
CYFP1_HUMAN, Q7L576, 108|
CD28_HUMAN, P10747, 191|206|209|218|
KCRB_HUMAN, P12277, 100|279|269|125|39|
SMC3_HUMAN, Q9UQE7, 143|
GSHB_HUMAN, P48637, 375|395|172|186|
CGBP1_HUMAN, Q9UFW8, 20|
RNPS1_HUMAN, Q15287, 207|
RAB35_HUMAN, Q15286, 192|
RS3A_HUMAN, P61247, 155|205|31|115|116|152|167|219|222|27|46|56|63|85|94|
MPC1_HUMAN, Q9Y5U8, 12|100|8|
CUL3_HUMAN, Q13618, 58|62|512|
CUL4A_HUMAN, Q13619, 480|
PP14B_HUMAN, Q96C90, 29|
CUL2_HUMAN, Q13617, 107|730|
EZRI_HUMAN, P15311, 85|270|72|64|354|
EHD4_HUMAN, Q9H223, 349|

TABLE 3-continued

Protein Modification Sites Targeted by Sulfonyl-Heterocycle Probes and Ligands.

RS20_HUMAN, P60866, 30|67|
BZW1_HUMAN, Q7L1Q6, 232|208|388|350|
OPA3_HUMAN, Q9H6K4, 111|
PSME1_HUMAN, Q06323, 190|32|
SRSF7_HUMAN, Q16629, 115|14|33|7|
DCPS_HUMAN, Q96C86, 217|
RCC1L_HUMAN, Q96I51, 157|
DNJA2_HUMAN, O60884, 69|35|226|
IF6_HUMAN, P56537, 113|
SH21A_HUMAN, O60880, 100|29|104|
SFR15_HUMAN, O95104, 64|
DJC11_HUMAN, Q9NVH1, 146|81|418|83|
DCTN2_HUMAN, Q13561, 313|289|81|6|
POTEE_HUMAN, Q6S8J3, 918|1062|
EMAL4_HUMAN, Q9HC35, 228|226|
OLA1_HUMAN, Q9NTK5, 203|282|375|323|254|
STIM1_HUMAN, Q13586, 382|
LMAN2_HUMAN, Q12907, 125|
ILF3_HUMAN, Q12906, 22|292|144|891|809|297|365|
ILF2_HUMAN, Q12905, 358|
AIMP1_HUMAN, Q12904, 46|
TMM70_HUMAN, Q9BUB7, 213|215|
SYFB_HUMAN, Q9NSD9, 173|192|372|385|72|176|383|
DCTN4_HUMAN, Q9UJW0, 173|150|
RL36L_HUMAN, Q969Q0, 48|86|
CEP89_HUMAN, Q96ST8, 588|
HACD3_HUMAN, Q9P035, 316|123|319|72|
ATP8_HUMAN, P03928, 47|
PSD10_HUMAN, O75832, 138|160|
SIN3A_HUMAN, Q96ST3, 565|
IWS1_HUMAN, Q96ST2, 762|665|666|
PORED_HUMAN, Q9H8P0, 56|
H2A3_HUMAN, Q7L7L0, 40|37|
ARHG6_HUMAN, Q15052, 644|
MAP4_HUMAN, P27816, 1001|47|
SF3A3_HUMAN, Q12874, 11|394|139|398|92|492|
CHD3_HUMAN, Q12873, 1326|
LMAN1_HUMAN, P49257, 507|87|
PARVB_HUMAN, Q9HBI1, 354|
AN32A_HUMAN, P39687, 131|137|
5NTC_HUMAN, P49902, 210|
TRM6_HUMAN, Q9UJA5, 255|146|145|261|
KTN1_HUMAN, Q86UP2, 503|
HDGR3_HUMAN, Q9Y3E1, 22|
ANXA5_HUMAN, P08758, 260|301|309|86|97|129|133|148|213|250|256|
257|297|308|91|94|101|
CFA20_HUMAN, Q9Y6A4, 184|
TACC3_HUMAN, Q9Y6A5, 403|
RAMAC_HUMAN, Q9BTL3, 91|
DLDH_HUMAN, P09622, 430|143|146|159|
FKB10_HUMAN, Q96AY3, 201|204|
SPB1_HUMAN, Q8IY81, 16|241|727|324|
PFD6_HUMAN, O15212, 16|21|122|15|82|
GSTA4_HUMAN, O15217, 9|
MEMO1_HUMAN, Q9Y316, 54|
AAR2_HUMAN, Q9Y312, 188|
BTD_HUMAN, P43251, 126|
HOOK3_HUMAN, Q86VS8, 323|
RL27A_HUMAN, P46776, 48|109|52|61|110|136|27|55|64|77|92|94|
RL5_HUMAN, P46777, 226|145|183|207|210|219|240|253|44|66|95|99|130|49|79|
10|158|178|197|220|228|241|242|255|43|48|85|31|30|
ZN384_HUMAN, Q8TF68, 270|
RL21_HUMAN, P46778, 156|30|65|13|120|50|60|97|
RL28_HUMAN, P46779, 25|40|102|77|19|22|47|65|84|
GCP60_HUMAN, Q9H3P7, 483|
EFTS_HUMAN, P43897, 288|299|
TIM50_HUMAN, Q3ZCQ8, 122|225|62|250|64|
COX7C_HUMAN, P15954, 19|
VPS35_HUMAN, Q96QK1, 507|662|
PRP8_HUMAN, Q6P2Q9, 1432|219|2294|756|88|902|909|94|225|351|2091|1434|
218|916|932|1930|
LA_HUMAN, P05455, 175|188|23|104|105|148|176|185|191|192|37|
QOR_HUMAN, Q08257, 53|
RAD50_HUMAN, Q92878, 625|
SMCE1_HUMAN, Q969G3, 240|
GDPD1_HUMAN, Q8N9F7, 239|
ZYX_HUMAN, Q15942, 172|316|
RL36_HUMAN, Q9Y3U8, 53|5|62|

TABLE 3-continued

Protein Modification Sites Targeted by Sulfonyl-Heterocycle Probes and Ligands.

CY1_HUMAN, P08574, 199|174|179|218|177|315|318|310|
TCAF1_HUMAN, Q9Y4C2, 542|
VKORL_HUMAN, Q8N0U8, 162|40|
COASY_HUMAN, Q13057, 396|424|
HLTF_HUMAN, Q14527, 30|112|72|
RS6_HUMAN, P62753, 28|48|209|201|211|30|46|58|64|
RL23A_HUMAN, P62750, 144|74|36|117|
NDKB_HUMAN, P22392, 12|67|
ALDOA_HUMAN, P04075, 215|330|138|174|204|214|302|328|85|153|200|87|99|322|111|14|42|140|
RPR1A_HUMAN, Q96P16, 61|
C1TM_HUMAN, Q6UB35, 880|920|
FTO_HUMAN, Q9C0B1, 220|216|214|
DYN1_HUMAN, Q05193, 732|390|597|
RABL6_HUMAN, Q3YEC7, 7|
PABP2_HUMAN, Q86U42, 181|
AAKG1_HUMAN, P54619, 255|
SRP68_HUMAN, Q9UHB9, 618|610|620|249|385|382|
GARS_HUMAN, P41250, 295|374|414|467|249|261|229|264|309|646|
HNRPC_HUMAN, P07910, 137|139|40|157|29|30|42|50|94|223|219|198|105|126|
LIMA1_HUMAN, Q9UHB6, 190|429|452|
CLH2_HUMAN, P53675, 799|
NP1L4_HUMAN, Q99733, 55|85|95|180|186|61|
PDS5A_HUMAN, Q29RF7, 1052|558|
SEPT6_HUMAN, Q14141, 86|338|324|298|
RBM7_HUMAN, Q9Y580, 219|
SMRCD_HUMAN, Q9H4L7, 641|
H2B1N_HUMAN, Q99877, 84|
CENPV_HUMAN, Q7Z7K6, 264|
RD23A_HUMAN, P54725, 188|
ANXA2_HUMAN, P07355, 109|188|235|238|24|30|316|317|
SDF2L_HUMAN, Q9HCN8, 81|201|
G3BP2_HUMAN, Q9UN86, 29|
PARN_HUMAN, O95453, 432|553|
TBCB_HUMAN, Q99426, 107|114|77|133|191|
HNRH1_HUMAN, P31943, 180|195|266|372|82|236|240|243|249|276|306|356|167|185|349|35|73|98|253|246|
SAE2_HUMAN, Q9UBT2, 86|191|84|159|265|144|153|72|
GPSM1_HUMAN, Q86YR5, 150|
G45IP_HUMAN, Q8TAE8, 64|
RAB4B_HUMAN, P61018, 189|
MTFP1_HUMAN, Q9UDX5, 157|21|155|
PRI2_HUMAN, P49643, 381|
SRP54_HUMAN, P61011, 163|154|433|448|
TBC23_HUMAN, Q9NUY8, 150|
EXOC4_HUMAN, Q96A65, 432|
ATPG_HUMAN, P36542, 178|69|77|39|46|79|90|
VATE1_HUMAN, P36543, 56|
RM41_HUMAN, Q8IXM3, 73|71|
NED4L_HUMAN, Q96PU5, 210|
NFM_HUMAN, P07197, 150|401|
QKI_HUMAN, Q96PU8, 204|57|93|
CDC5L_HUMAN, Q99459, 724|
SAR1A_HUMAN, Q9NR31, 154|186|89|27|46|
DDX21_HUMAN, Q9NR30, 221|293|298|434|521|224|320|516|
GLYC_HUMAN, P34896, 82|118|73|34|
GLYM_HUMAN, P34897, 100|105|106|141|176|195|206|292|350|370|96|234|103|181|196|280|297|302|409|464|469|474|
MCM2_HUMAN, P49736, 747|234|486|559|637|726|723|881|216|492|510|728|734|742|
PLSL_HUMAN, P13796, 48|585|124|447|82|444|88|92|96|579|294|449|455|456|328|
PLST_HUMAN, P13797, 52|505|51|121|127|588|
RRP44_HUMAN, Q9Y2L1, 106|826|107|867|
NEUL_HUMAN, Q9BYT8, 245|
ESYT2_HUMAN, A0FGR8, 156|840|845|
SC23A_HUMAN, Q15436, 705|89|329|318|
SC23B_HUMAN, Q15437, 707|78|579|331|674|
SMN_HUMAN, Q16637, 285|
RHG15_HUMAN, Q53QZ3, 248|29|
CPSF6_HUMAN, Q16630, 441|173|
HAUS4_HUMAN, Q9H6D7, 217|
FAF1_HUMAN, Q9UNN5, 515|225|
SUH_HUMAN, Q06330, 74|
ATD3A_HUMAN, Q9NVI7, 399|540|559|421|262|411|442|549|553|562|60|
HIBCH_HUMAN, Q6NVY1, 353|92|
FANCI_HUMAN, Q9NVI1, 795|1225|
KCY_HUMAN, P30085, 49|86|

TABLE 3-continued

Protein Modification Sites Targeted by Sulfonyl-Heterocycle Probes and Ligands.

ECHM_HUMAN, P30084, 137|264|153|128|157|211|282|
PEBP1_HUMAN, P30086, 187|106|120|176|181|81|80|
LUC7L_HUMAN, Q9NQ29, 196|
G6PI_HUMAN, P06744, 144|183|351|174|363|128|142|147|172|211|252|440|447|454|73|366|92|
NPM_HUMAN, P06748, 271|29|67|141|150|202|212|223|236|248|250|257|263|267|273|27|
TMM11_HUMAN, P17152, 162|
TPC_HUMAN, Q9HC21, 59|166|
RTCA_HUMAN, O00442, 226|
TPR_HUMAN, P12270, 422|614|682|877|1552|683|265|1561|735|402|
RL10L_HUMAN, Q96L21, 170|
HDGR2_HUMAN, Q7Z4V5, 18|543|
FAHD1_HUMAN, Q6P587, 52|47|
TRUB1_HUMAN, Q8WWH5, 149|
SPN90_HUMAN, Q9NZQ3, 52|
COPG2_HUMAN, Q9UBF2, 697|
CLIC1_HUMAN, O00299, 119|117|209|214|233|143|93|113|135|192|238|95|
DAZP1_HUMAN, Q96EP5, 111|45|
SRSF1_HUMAN, Q07955, 37|38|112|170|77|
NU107_HUMAN, P57740, 791|
LETM1_HUMAN, O95202, 141|165|422|598|130|150|151|257|274|279|356|603|133|597|
AR6P1_HUMAN, Q15041, 183|124|133|188|198|114|
GRAM4_HUMAN, Q6IC98, 177|386|
RPF2_HUMAN, Q9H7B2, 237|
RT4I1_HUMAN, Q8WWV3, 70|102|206|
DNLI3_HUMAN, P49916, 666|
GUAA_HUMAN, P49915, 185|526|680|208|487|389|604|
AKP13_HUMAN, Q12802, 235|
TMOD3_HUMAN, Q9NYL9, 86|
SPT6H_HUMAN, Q7KZ85, 1431|1184|
GEMI6_HUMAN, Q8WXD5, 94|
H2AJ_HUMAN, Q9BTM1, 40|58|
EXOSX_HUMAN, Q01780, 419|
VINC_HUMAN, P18206, 107|537|822|1133|692|
KTNB1_HUMAN, Q9BVA0, 337|
HNRPQ_HUMAN, O60506, 205|153|223|276|282|356|
IF2A_HUMAN, P05198, 142|141|82|
MPV17_HUMAN, P39210, 87|
TLN1_HUMAN, Q9Y490, 1116|1777|2224|436|70|127|1737|81|2239|1780|83|2133|272|910|1645|156|875|1221|199|
LAT1_HUMAN, Q01650, 19|
MATR3_HUMAN, P43243, 128|158|202|243|289|413|454|474|508|520|784|794|827|171|526|132|245|391|473|478|479|483|487|491|515|522|555|588|829|572|
STA10_HUMAN, Q9Y365, 171|
SYWC_HUMAN, P23381, 100|150|157|316|420|
DPOD2_HUMAN, P49005, 32|
PRAF3_HUMAN, O75915, 182|158|185|
PTTG_HUMAN, P53801, 165|
FIS1_HUMAN, Q9Y3D6, 47|116|46|
TIM16_HUMAN, Q9Y3D7, 86|
EI24_HUMAN, O14681, 335|60|
PDS5B_HUMAN, Q9NTI5, 419|845|
CD82_HUMAN, P27701, 142|261|148|114|263|
H2B3B_HUMAN, Q8N257, 84|
CCD91_HUMAN, Q7Z6B0, 196|
STMN1_HUMAN, P16949, 104|53|80|
PAAF1_HUMAN, Q9BRP4, 84|
HYOU1_HUMAN, Q9Y4L1, 116|213|421|443|476|487|99|531|534|428|431|537|398|433|67|91|480|308|529|913|530|402|904|
RBP56_HUMAN, Q92804, 156|274|427|277|
CNOT4_HUMAN, O95628, 212|
G3BP1_HUMAN, Q13283, 125|56|20|40|50|64|
NAT14_HUMAN, Q8WUY8, 28|
SAMH1_HUMAN, Q9Y3Z3, 360|
VP13C_HUMAN, Q709C8, 2032|995|1512|1528|1745|2224|2357|469|113|1230|179|2033|997|102|2095|175|2090|1062|2092|
FLII_HUMAN, Q13045, 737|1057|1129|1175|1131|
KBL_HUMAN, O75600, 274|
GDAP1_HUMAN, Q8TB36, 195|117|
NUBPL_HUMAN, Q8TB37, 109|
NPM3_HUMAN, O75607, 125|
CTBL1_HUMAN, Q8WYA6, 448|
PDIA5_HUMAN, Q14554, 40|
TBG1_HUMAN, P23258, 82|186|273|86|193|84|
KPRA_HUMAN, Q14558, 101|168|98|103|
PATL1_HUMAN, Q86TB9, 473|474|
RIC8A_HUMAN, Q9NPQ8, 413|

TABLE 3-continued

Protein Modification Sites Targeted by Sulfonyl-Heterocycle Probes and Ligands.

PP4C_HUMAN, P60510, 124|133|
OFUT1_HUMAN, Q9H488, 99|
NELFB_HUMAN, Q8WX92, 99|
IF2B_HUMAN, P20042, 298|278|
RA51C_HUMAN, O43502, 75|
UBA5_HUMAN, Q9GZZ9, 315|53|372|
UCRI_HUMAN, P47985, 101|
NAA50_HUMAN, Q9GZZ1, 36|70|
MUTA_HUMAN, P22033, 364|587|577|110|
GPAA1_HUMAN, O43292, 122|
SNUT1_HUMAN, O43290, 685|712|102|
ABI1_HUMAN, Q8IZP0, 333|
SRGP2_HUMAN, O75044, 170|
ATPA_HUMAN, P25705, 337|343|291|299|311|321|440|476|489|126|132|161|167|175|194|230|239|305|316|427|498|503|531|539|
SERP1_HUMAN, Q9Y6X1, 13|26|
TPPC3_HUMAN, O43617, 34|
TIM44_HUMAN, O43615, 265|242|104|146|157|249|282|73|83|121|138|154|169|130|78|312|105|262|75|165|264|68|144|
NPC2_HUMAN, P61916, 119|
RCC2_HUMAN, Q9P258, 420|142|251|283|303|359|464|258|293|368|422|468|129|
QORX_HUMAN, Q53FA7, 193|
RL15_HUMAN, P61313, 119|127|59|6|62|81|128|14|179|83|93|
RAC2_HUMAN, P15153, 139|154|133|147|153|166|96|123|
FNTA_HUMAN, P49354, 166|
TIF1B_HUMAN, Q13263, 133|208|242|449|458|517|755|188|199|261|272|275|289|779|369|
CPNE3_HUMAN, O75131, 208|203|392|522|523|43|217|
DPYL2_HUMAN, Q16555, 251|32|431|499|290|395|
PO210_HUMAN, Q8TEM1, 1855|1735|
MIC26_HUMAN, Q9BUR5, 82|86|
RAB8A_HUMAN, P61006, 5|176|197|58|
VMP1_HUMAN, Q96GC9, 224|245|348|
ACOC_HUMAN, P21399, 603|
ROA2_HUMAN, P22626, 174|234|331|336|347|131|247|40|41|135|104|112|113|120|137|151|168|17|173|186|22|46|59|94|295|313|
NSDHL_HUMAN, Q15738, 122|349|
P5CR3_HUMAN, Q53H96, 243|
QCR9_HUMAN, Q9UDW1, 11|
TM230_HUMAN, Q96A57, 29|35|
DPP3_HUMAN, Q9NY33, 417|
ELOV5_HUMAN, Q9NYP7, 92|263|267|56|
PAF1_HUMAN, Q8N7H5, 144|359|
PRDX1_HUMAN, Q06830, 120|35|116|194|34|190|185|192|197|67|
ADAS_HUMAN, O00116, 387|390|645|108|389|456|482|
CHD1_HUMAN, O14646, 582|1597|
GPNMB_HUMAN, Q14956, 220|
ACADV_HUMAN, P49748, 276|67|482|
GRP75_HUMAN, P38646, 653|128|181|196|331|652|118|161|230|568|121|135|143|159|175|187|206|234|288|314|340|345|368|394|467|76|625|654|537|106|567|
CKLF3_HUMAN, Q96MX0, 159|
MGST3_HUMAN, O14880, 100|40|149|
PIGL_HUMAN, Q9Y2B2, 220|
SYAC_HUMAN, P49588, 279|667|192|258|266|295|415|690|272|282|338|396|74|782|
SYCC_HUMAN, P49589, 53|60|
PPT1_HUMAN, P50897, 172|215|56|216|165|174|
MCCB_HUMAN, Q9HCC0, 413|177|
ALDOC_HUMAN, P09972, 42|204|138|
CC134_HUMAN, Q9H6E4, 63|64|
RIC8B_HUMAN, Q9NVN3, 445|
PTGR2_HUMAN, Q8N8N7, 106|100|259|265|
TXND5_HUMAN, Q8NBS9, 136|251|262|396|151|277|150|407|278|
MYH14_HUMAN, Q7Z406, 426|
DDX54_HUMAN, Q8TDD1, 159|
ECHB_HUMAN, P55084, 244|331|357|402|71|342|188|332|361|406|72|
SEC13_HUMAN, P55735, 79|
MARE2_HUMAN, Q15555, 194|
EHD3_HUMAN, Q9NZN3, 468|
DCXR_HUMAN, Q7Z4W1, 149|153|
PELO_HUMAN, Q9BRX2, 172|46|
RS12_HUMAN, P25398, 129|127|61|114|112|116|63|83|
PSF3_HUMAN, Q9BRX5, 157|206|
TOE1_HUMAN, Q96GM8, 497|
SAP_HUMAN, P07602, 447|113|418|449|414|188|348|
NMD3_HUMAN, Q96D46, 236|238|
GABPA_HUMAN, Q06546, 173|
FA5_HUMAN, P12259, 2088|
METK1_HUMAN, Q00266, 271|
DHB4_HUMAN, P51659, 414|505|568|676|733|184|260|415|565|645|735|674|477|644|731|164|

TABLE 3-continued

Protein Modification Sites Targeted by Sulfonyl-Heterocycle Probes and Ligands.

THYN1_HUMAN, Q9P016, 147|181|
UXT_HUMAN, Q9UBK9, 20|
LMNB1_HUMAN, P20700, 260|377|121|238|240|268|484|261|37 9|123|134|271|241|483|532|
EIF3B_HUMAN, P55884, 253|272|232|
FUMH_HUMAN, P07954, 465|110|67|292|470|477|263|
HMGB1_HUMAN, P09429, 66, 0,
HOOK1_HUMAN, Q9UJC3, 326|
KIF3A_HUMAN, Q9Y496, 297|
GNL3_HUMAN, Q9BVP2, 118|358|
SF3A1_HUMAN, Q15459, 772|456|
SPTN1_HUMAN, Q13813, 1022|1020|2423|1650|2426|2421|
PROF1_HUMAN, P07737, 129|60|105|108|116|126|127|38|54|70|91|
MTCH2_HUMAN, Q9Y6C9, 95|100|288|
PSA5_HUMAN, P28066, 26|185|187|91|
H2B1H_HUMAN, Q93079, 84|
COX5A_HUMAN, P20674, 123|80|120|87|
ASSY_HUMAN, P00966, 113|151|163|133|112|165|209|229|340|400|
RL32_HUMAN, P62910, 60|95|109|64|67|83|
RL11_HUMAN, P62913, 170|92|154|159|52|67|
GLRX3_HUMAN, O76003, 194|200|204|296|302|80|306|217|245|256|308|79|
TAP1_HUMAN, Q03518, 530|
RL8_HUMAN, P62917, 133|21|46|186|
IF2B3_HUMAN, O00425, 321|
BID_HUMAN, P55957, 144|54|
UBE3C_HUMAN, Q15386, 1030|
MFGM_HUMAN, Q08431, 252|253|
RHEB_HUMAN, Q15382, 131|
SAP18_HUMAN, O00422, 132|
GALT2_HUMAN, Q10471, 367|397|408|434|99|103|420|53|54|42|
ERF3A_HUMAN, P15170, 146|151|208|238|247|96|
GELS_HUMAN, P06396, 160|371|409|465|469|480|239|
HMGCL_HUMAN, P35914, 179|176|
VASP_HUMAN, P50552, 39|16|
SHLB1_HUMAN, Q9Y371, 155|156|163|82|183|80|
RAB1B_HUMAN, Q9H0U4, 116|122|129|170|
MAGT1_HUMAN, Q9H0U3, 106|60|
SAC1_HUMAN, Q9NTJ5, 272|449|271|273|456|483|
RS3_HUMAN, P23396, 107|34|87|141|18|201|75|90|120|
RL22_HUMAN, P35268, 107|48|69|80|
T2FA_HUMAN, P35269, 84|
TSN3_HUMAN, O60637, 140|
ALS2_HUMAN, Q96Q42, 1365|
RCAN1_HUMAN, P53805, 134|
SRSF2_HUMAN, Q01130, 44|92|23|110|
MPPA_HUMAN, Q10713, 478|
HCLS1_HUMAN, P14317, 103|140|175|83|161|177|178|141|151|
GLU2B_HUMAN, P14314, 280|191|279|436|
DHE3_HUMAN, P00367, 135|193|367|171|212|365|477|211|
AT2B4_HUMAN, P23634, 216|
KAD1_HUMAN, P00568, 32|
CLU_HUMAN, O75153, 1212|340|346|
NB5R3_HUMAN, P00387, 151|43|94|248|103|154|156|228|42|80|
PFD5_HUMAN, Q99471, 43|124|42|128|47|
PHB2_HUMAN, Q99623, 77|24|296|
SRSF5_HUMAN, Q13243, 85|
ODPA_HUMAN, P08559, 156|227|242|289|82|158|244|83|142|147|
ABCD3_HUMAN, P28288, 507|513|525|38|39|499|50|
COQ5_HUMAN, Q5HYK3, 127|
PIGU_HUMAN, Q9H490, 119|
SFPQ_HUMAN, P23246, 320|381|470|488|490|602|698|314|330|338|349|413|421|472|
BTF3_HUMAN, P20290, 86|
SND1_HUMAN, Q7KZF4, 109|533|178|217|329|476|661|682|697|728|766|796|878|394|763|386|683|709|
YBOX2_HUMAN, Q9Y2T7, 107|
ARP3B_HUMAN, Q9P1U1, 202|
MMSA_HUMAN, Q02252, 460|
PX11B_HUMAN, O96011, 72|
PTCA_HUMAN, Q14761, 64|
GCDH_HUMAN, Q92947, 413|
ACL6A_HUMAN, O96019, 186|
UBE2T_HUMAN, Q9NPD8, 134|
ARK72_HUMAN, O43488, 225|237|239|260|200|223|242|238|
PARL_HUMAN, Q9H300, 74|373|374|75|
IF4G1_HUMAN, Q04637, 958|1253|
JIP4_HUMAN, O60271, 578|654|518|655|1193|
MSH6_HUMAN, P52701, 166|8|
PHF6_HUMAN, Q8IWS0, 103|105|240|301|195|235|241|127|
PLRG1_HUMAN, O43660, 77|80|

TABLE 3-continued

Protein Modification Sites Targeted by Sulfonyl-Heterocycle Probes and Ligands.

RL37_HUMAN, P61927, 27|39|
TTL12_HUMAN, Q14166, 403|517|244|308|473|192|447|452|
MLEC_HUMAN, Q14165, 82|131|199|239|251|
GIT2_HUMAN, Q14161, 135|
CH60_HUMAN, P10809, 233|223|227|243|385|503|90|125|130|133|156|196|205|218|249|
250|269|292|301|31|352|359|364|387|389|417|462|469|473|
516|523|58|72|75|87|89|91|82|418|202|
SF01_HUMAN, Q15637, 52|147|
TSN_HUMAN, Q15631, 76|
HCDH_HUMAN, Q16836, 264|226|254|311|234|
PGM2_HUMAN, Q96G03, 293|
ARP10_HUMAN, Q9NZ32, 377|
CDC37_HUMAN, Q16543, 155|248|278|135|154|242|276|132|
MD2L1_HUMAN, Q13257, 38|
TCPG_HUMAN, P49368, 247|359|232|274|303|203|21|222|234|248|286|317|
48|529|78|381|138|
DDX6_HUMAN, P26196, 150|440|315|
AP2A1_HUMAN, O95782, 299|
UB2D3_HUMAN, P61077, 134|74|
CLIC5_HUMAN, Q9NZA1, 284|
GPX4_HUMAN, P36969, 59|58|154|
HSP72_HUMAN, P54652, 108|184|
SYAP1_HUMAN, Q96A49, 60|
ESS2_HUMAN, Q96DF8, 409|408|
PP4R2_HUMAN, Q9NY27, 136|
DYL1_HUMAN, P63167, 32|50|36|43|48|49|
PFD2_HUMAN, Q9UHV9, 136|132|121|10|
SRPRB_HUMAN, Q9Y5M8, 22|
SPT5H_HUMAN, O00267, 720|771|787|778|802|155|1015|203|
MCM5_HUMAN, P33992, 332|191|212|403|703|196|218|337|350|407|581|625|677|702|
MCM7_HUMAN, P33993, 297|102|126|137|21|33|333|345|492|580|6|701|88|
221|393|539|562|159|28|335|351|648|89|
MCM4_HUMAN, P33991, 522|193|223|421|471|524|532|714|730|820|693|220|
423|444|455|477|490|719|746|814|858|
RL14_HUMAN, P50914, 14|72|23|53|63|71|79|85|
NACAM_HUMAN, E9PAV3, 1975|1983|
CC50A_HUMAN, Q9NV96, 34|
CNN3_HUMAN, Q15417, 10|182|189|229|261|268|
TMEDA_HUMAN, P49755, 167|169|
TOR1A_HUMAN, O14656, 43|
RBM25_HUMAN, P49756, 755|256|749|734|
RAB14_HUMAN, P61106, 99|
GMFB_HUMAN, P60983, 75|
TCF25_HUMAN, Q9BQ70, 179|
EIF1_HUMAN, P41567, 79|54|30|
SYSC_HUMAN, P49591, 220|224|248|294|401|444|249|448|263|267|
HEMH_HUMAN, P22830, 159|194|209|276|123|113|118|304|
OTOGL_HUMAN, Q3ZCN5, 1734|
RHOA_HUMAN, P61586, 156|42|66|74|118|162|7|
DECR_HUMAN, Q16698, 246|
SNX6_HUMAN, Q9UNH7, 220|311|225|230|307|329|109|
XRN2_HUMAN, Q9H0D6, 642|666|641|256|
UTRO_HUMAN, P46939, 3145|
KT3K_HUMAN, Q9HA64, 45|
SORCN_HUMAN, P30626, 67|68|
TCEA2_HUMAN, Q15560, 271|
PR38A_HUMAN, Q8NAV1, 169|
H15_HUMAN, P16401, 74|113|204|27|35|55|66|78|
GAPD1_HUMAN, Q14C86, 1036|1207|893|460|
DIC_HUMAN, Q9UBX3, 149|182|186|
H13_HUMAN, P16402, 111|76|98|53|
KCRU_HUMAN, P12532, 133|
ACSA_HUMAN, Q9NR19, 647|
PAIRB_HUMAN, Q8NC51, 207|
ARM10_HUMAN, Q8N2F6, 103|155|
PSMD7_HUMAN, P51665, 74|199|
UB2D1_HUMAN, P51668, 74|
TOM20_HUMAN, Q15388, 86|88|
SMHD1_HUMAN, A6NHR9, 234|
CS012_HUMAN, Q9NSK7, 37|
WRB_HUMAN, O00258, 41|91|
NUDT9_HUMAN, Q9BW91, 321|
SNF5_HUMAN, Q12824, 326|
CALX_HUMAN, P27824, 214|229|393|514|100|185|198|70|118|127|182|199|
210|217|220|233|398|458|507|515|516|89|99|87|
NOP58_HUMAN, Q9Y2X3, 187|204|217|338|419|206|40|45|99|
PPIL3_HUMAN, Q9H2H8, 115|141|78|
H33_HUMAN, P84243, 123|15|19|5|57|80|

TABLE 3-continued

Protein Modification Sites Targeted by Sulfonyl-Heterocycle Probes and Ligands.

S23IP_HUMAN, Q9Y6Y8, 871|348|850|
CBX1_HUMAN, P83916, 173|
SP100_HUMAN, P23497, 836|
RL10A_HUMAN, P62906, 107|11|41|106|130|207|212|45|47|
RL24_HUMAN, P83731, 12|11|14|55|113|2|27|35|43|61|69|
TMED4_HUMAN, Q7Z7H5, 218|224|63|
PSB4_HUMAN, P28070, 107|75|
PSB6_HUMAN, P28072, 59|95|124|
RBM39_HUMAN, Q14498, 253|293|475|511|477|
PCM1_HUMAN, Q15154, 1092|1096|
CNDD3_HUMAN, P42695, 1072|
RFC1_HUMAN, P35251, 952|
KCRS_HUMAN, P17540, 134|
MPCP_HUMAN, Q00325, 100|196|208|112|137|209|214|218|234|247|252|304|309|357|99|
IPO5_HUMAN, O00410, 417|530|531|935|940|905|622|714|
DHC24_HUMAN, Q15392, 300|378|301|313|512|
ALG1_HUMAN, Q9BT22, 215|
CELF2_HUMAN, O95319, 508|214|
TR150_HUMAN, Q9Y2W1, 54|603|668|
PAPS2_HUMAN, O95340, 20|
FADS2_HUMAN, O95864,
GBRL1_HUMAN, Q9H0R8, 25|
CD7_HUMAN, P09564, 222|
SURF4_HUMAN, O15260, 24|139|22|
MIC13_HUMAN, Q5XKP0, 112|58|114|
DUS23_HUMAN, Q9BVJ7, 136|
PHF5A_HUMAN, Q7RTV0, 54|100|
TXD12_HUMAN, O95881, 137|70|138|
TXTP_HUMAN, P53007, 161|181|256|276|84|92|149|160|178|21|255|268|273|97|
BIEA_HUMAN, P53004, 98|228|
MYH10_HUMAN, P35580, 13|1868|22|407|580|826|1467|809|1869|
PAXI_HUMAN, P49023, 418|
POTEF_HUMAN, A5A3E0, 1062|
RS19_HUMAN, P39019, 48|115|
AGM1_HUMAN, O95394, 9|
EIF3E_HUMAN, P60228, 256|62|
VTNC_HUMAN, P04004,
ARFG2_HUMAN, Q8N6H7, 358|359|
TMX1_HUMAN, Q9H3N1, 104|217|219|107|222|223|233|
ATP5I_HUMAN, P56385, 30|32|48|55|
ATP5E_HUMAN, P56381, 37|
OSBL8_HUMAN, Q9BZF1, 707|484|482|
CRKL_HUMAN, P46109, 180|177|48|92|251|132|105|127|
CRK_HUMAN, P46108, 108|186|47|
UACA_HUMAN, Q9BZF9, 34|
SC5D_HUMAN, O75845, 268|286|
FACE1_HUMAN, O75844, 253|
PIN4_HUMAN, Q9Y237, 122|71|
CSTF1_HUMAN, Q05048, 213|
PRP16_HUMAN, Q92620, 274|
NU205_HUMAN, Q92621, 66|
QTRT2_HUMAN, Q9H974, 277|
UBC_HUMAN, P0CG48, 59|
UBB_HUMAN, P0CG47, 59|
DNJC8_HUMAN, O75937, 53|129|
ACTY_HUMAN, P42025, 96|38|223|92|
AT2B1_HUMAN, P20020, 220|
PRS6B_HUMAN, P43686, 191|41|239|192|
ILVBL_HUMAN, A1L0T0, 214|216|221|48|
BUD31_HUMAN, P41223, 97|56|
STRN4_HUMAN, Q9NRL3, 126|
ACD10_HUMAN, Q6JQN1, 578|260|584|
RL34_HUMAN, P49207, 36|32|34|13|78|40|
GNPI1_HUMAN, P46926, 34|279|
WDHD1_HUMAN, O75717, 58|845|
COPA_HUMAN, P53621, 249|1177|551|569|628|982|631|634|579|458|
TPC12_HUMAN, Q8WVT3, 411|
SAHH3_HUMAN, Q96HN2, 608|595|
ZN207_HUMAN, O43670, 45|
FMNL1_HUMAN, O95466, 90|973|979|
LONM_HUMAN, P36776, 461|473|565|599|623|394|388|632|
EPN3_HUMAN, Q9H201, 17|
ENOB_HUMAN, P13929, 257|131|44|
H2B1J_HUMAN, P06899, 84|
TECR_HUMAN, Q9NZ01, 296|4|44|77|117|12|16|2|33|55|
TOM40_HUMAN, O96008, 194|
DDB1_HUMAN, Q16531, 245|906|
QCR2_HUMAN, P22695, 109|

TABLE 3-continued

Protein Modification Sites Targeted by Sulfonyl-Heterocycle Probes and Ligands.

SRSF6_HUMAN, Q13247, 138|143|
SDF2_HUMAN, Q99470, 187|189|
SCMC1_HUMAN, Q6NUK1, 272|328|228|332|336|
SRSF9_HUMAN, Q13242, 35|36|17|
LAMP1_HUMAN, P11279, 414|
ABI2_HUMAN, Q9NYB9, 241|
SH3G1_HUMAN, Q99961, 256|170|
DIAP3_HUMAN, Q9NSV4, 21|
TAM41_HUMAN, Q96BW9, 228|
PTER_HUMAN, Q96BW5, 65|
SQOR_HUMAN, Q9Y6N5, 242|434|365|371|65|
GAR1_HUMAN, Q9NY12, 150|
CYFP2_HUMAN, Q96F07, 1078|
OTUB1_HUMAN, Q96FW1, 261|266|258|26|
RL4_HUMAN, P36578, 122|161|211|277|52|184|264|120|157|162|172|175|181|182|219|234|239|259|269|274|294|
RL38_HUMAN, P63173, 41|43|4|9|
ACTN2_HUMAN, P35609, 319|
RPB7_HUMAN, P62487, 17|
PSME3_HUMAN, P61289, 196|
EIF2A_HUMAN, Q9BY44, 182|183|
CHM4A_HUMAN, Q9BY43, 10|15|13|
MACD1_HUMAN, Q9BQ69, 216|232|247|148|138|
LTOR1_HUMAN, Q6IAA8, 40|
IMB1_HUMAN, Q14974, 321|529|448|752|76|757|859|867|661|
RENT1_HUMAN, Q92900, 316|786|318|488|946|
SGPP1_HUMAN, Q9BX95, 19|
ANXA8_HUMAN, P13928, 264|263|
GSTM3_HUMAN, P21266, 201|66|120|71|
AL9A1_HUMAN, P49189, 158|347|
SRSF3_HUMAN, P84103, 13|32|33|
REEP6_HUMAN, Q96HR9, 28|
IF16_HUMAN, Q16666, 20|218|635|645|334|325|372|451|628|695|759|
AKT1_HUMAN, P31749, 326|
MRP1_HUMAN, P33527, 277|
ARF1_HUMAN, P84077, 36|35|58|81|127|59|
DHCR7_HUMAN, Q9UBM7, 382|455|462|468|125|11|13|454|
UBA6_HUMAN, A0AVT1, 663|873|132|
NEK7_HUMAN, Q8TDX7, 201|28|
TKT_HUMAN, P29401, 281|310|456|137|202|275|309|321|447|481|563|564|58|314|16|
LEG3_HUMAN, P17931, 221|
STK24_HUMAN, Q9Y6E0, 295|
MTAP_HUMAN, Q13126, 125|
CATC_HUMAN, P53634, 107|108|
ALKB3_HUMAN, Q96Q83, 127|
CBR1_HUMAN, P16152, 194|
CYC_HUMAN, P99999, 47|49|68|75|26|28|40|74|87|9|73|80|54|89|
EPHA4_HUMAN, P54764, 659|
SYVC_HUMAN, P26640, 601|878|24|300|323|320|
STAT3_HUMAN, P40763, 176|640|686|94|674|642|
PPCE_HUMAN, P48147, 71|190|76|510|
8ODP_HUMAN, P36639, 48|
PSB10_HUMAN, P40306, 31|
HYEP_HUMAN, P07099, 291|
GGPPS_HUMAN, O95749, 30|
HMOX2_HUMAN, P30519, 154|229|268|78|157|42|187|
UBP7_HUMAN, Q93009, 706|106|1091|
PPM1A_HUMAN, P35813, 202|203|
CGL_HUMAN, P32929, 60|
LDLR_HUMAN, P01130, 465|782|
DCTP1_HUMAN, Q9H773, 129|141|102|
HMCS1_HUMAN, Q01581, 47|375|273|267|
RFA1_HUMAN, P27694, 446|326|193|599|196|595|478|498|461|581|256|470|
APEX1_HUMAN, P27695, 128|118|125|
PGES2_HUMAN, Q9H7Z7, 222|141|200|225|
MIF_HUMAN, P14174, 100|76|96|99|78|
MVD1_HUMAN, P53602, 131|
AAPK1_HUMAN, Q13131, 190|243|247|17|257|398|
AMPL_HUMAN, P28838, 438|178|377|494|104|224|384|489|
PYGM_HUMAN, P11217, 574|186|281|614|
PKN1_HUMAN, Q16512, 243|
1433B_HUMAN, P31946, 130|151|21|106|213|50|105|160|214|77|11|13|51|
ATAD2_HUMAN, Q6PL18, 1123|489|
DHB7_HUMAN, P56937, 190|
IDI1_HUMAN, Q13907, 171|37|
CDC42_HUMAN, P60953, 154|72|133|135|150|153|163|166|183|144|
CPT1A_HUMAN, P50416, 186|666|180|514|
MAPK3_HUMAN, Q16644, 263|76|

TABLE 3-continued

Protein Modification Sites Targeted by Sulfonyl-Heterocycle Probes and Ligands.

PDPK1_HUMAN, O15530, 524|
FAS_HUMAN, P49327, 1047|1253|130|1842|1924|1996|2034|222|2269|2454|
2462|277|289|45|470|1707|
KPCD2_HUMAN, Q9BZL6, 178|
PTN11_HUMAN, Q06124, 546|584|
SRPK2_HUMAN, P78362, 118|
TBA3E_HUMAN, Q6PEY2, 108|262|357|224|399|282|272|
VDAC2_HUMAN, P45880, 184|78|236|120|277|85|
MK01_HUMAN, P28482, 113|187|263|64|
NAMPT_HUMAN, P43490, 471|108|195|
CSK21_HUMAN, P68400, 182|257|307|325|
WDR5_HUMAN, P61964, 228|
PPAC_HUMAN, P24666, 132|133|50|120|124|88|58|
KPYM_HUMAN, P14618, 151|105|148|161|175|370|390|83|466|115|135|136|162|166|
186|188|247|256|261|266|270|305|311|322|336|337|367|
433|475|498|62|66|89|
MDHM_HUMAN, P40926, 253|287|56|80|161|105|157|185|203|239|296|301|
45|324|335|329|307|
LGMN_HUMAN, Q99538, 217|221|224|
TBA1C_HUMAN, Q9BQE3, 163|280|401|282|103|108|161|272|312|357|399|112|
326|336|370|394|60|96|262|319|408|224|
MPRI_HUMAN, P11717, 1545|1542|2351|2352|795|
THTM_HUMAN, P25325, 37|40|
ANM5_HUMAN, O14744, 468|304|307|329|
CPT2_HUMAN, P23786, 45|508|538|182|544|56|104|510|457|
THIO_HUMAN, P10599, 85|94|
ERG7_HUMAN, P48449, 430|503|506|
LEG9_HUMAN, O00182, 88|
RAP1A_HUMAN, P62834, 159|40|32|168|173|
PGTB1_HUMAN, P53609, 40|
RASN_HUMAN, P01111, 137|128|
SYYC_HUMAN, P54577, 134|198|123|129|166|289|292|341|346|356|352|52|
TBA4A_HUMAN, P68366, 108|262|357|319|408|399|161|224|312|282|103|272|
TBA1B_HUMAN, P68363, 163|280|401|103|108|161|224|24|262|272|282|312|319|357|399|
408|432|112|304|311|326|336|352|370|394|60|96|
AAKB1_HUMAN, Q9Y478, 126|18|
UBP14_HUMAN, P54578, 285|401|136|151|195|311|417|418|436|381|441|
CATB_HUMAN, P07858, 220|245|215|219|225|227|230|244|256|267|237|209|
ANM8_HUMAN, Q9NR22, 76|
IDE_HUMAN, P14735, 308|364|831|
G6PD_HUMAN, P11413, 112|249|107|118|139|202|322|424|205|497|508|403|
HSP7C_HUMAN, P11142, 108|137|550|107|115|134|149|15|183|288|371|41|431|525|545|
294|126|128|187|246|25|251|257|319|325|328|345|357|384|
497|71|348|535|597|524|526|531|500|589|188|512|451|159|507|
PPGB_HUMAN, P10619, 249|252|
DUS3_HUMAN, P51452, 101|
ULA1_HUMAN, Q13564, 226|199|448|
FDFT_HUMAN, P37268, 14|346|46|139|115|26|30|315|
PREP_HUMAN, Q5JRX3, 921|268|383|76|923|906|979|770|
LDHB_HUMAN, P07195, 244|173|240|282|84|82|308|318|156|248|
TBA1A_HUMAN, Q71U36, 103|108|161|224|262|272|282|312|319|357|399|408|
GSTK1_HUMAN, Q9Y2Q3, 65|163|169|165|54|62|
F262_HUMAN, O60825, 482|
SYUA_HUMAN, P37840, 43|39|
PTN2_HUMAN, P17706, 32|369|
HEXB_HUMAN, P07686, 110|
DNLI1_HUMAN, P18858, 598|823|289|855|487|597|
EF2_HUMAN, P13639, 400|676|265|373|397|443|457|579|634|639|671|730|745|787|175|
367|411|434|760|79|15|152|159|239|252|258|275|283|309|
314|318|42|426|438|439|445|498|512|572|598|629|648|
688|766|90|333|259|
KITH_HUMAN, P04183, 61|181|
GSTO1_HUMAN, P78417, 110|139|11|143|57|
OAT_HUMAN, P04181, 85|
MOT1_HUMAN, P53985, 239|453|450|216|209|
AKT3_HUMAN, Q9Y243, 261|323|
M4K5_HUMAN, Q9Y4K4, 837|
GSTA1_HUMAN, P08263, 147|
GRB2_HUMAN, P62993, 209|52|
GDIR1_HUMAN, P52565, 128|133|144|149|156|175|51|178|141|135|138|
CATG_HUMAN, P08311, 219|
EF1A2_HUMAN, Q05639, 254|56|
CD11B_HUMAN, P21127, 681|
PPME1_HUMAN, Q9Y570, 285|
STA5A_HUMAN, P42229, 694|
G3P_HUMAN, P04406, 251|140|255|314|320|94|276|42|45|49|107|117|139|145|162|
186|194|215|219|227|254|259|263|334|5|55|61|66|84|86|
CATD_HUMAN, P07339, 269|325|

TABLE 3-continued

Protein Modification Sites Targeted by Sulfonyl-Heterocycle Probes and Ligands.

NCOA1_HUMAN, Q15788, 626|
KIF11_HUMAN, P52732, 211|207|932|934|
LYPA2_HUMAN, O95372, 205|
HS71A_HUMAN, P0DMV8, 108|550|107|115|15|183|371|525|545|611|524|431|137|149|134|
STING_HUMAN, Q86WV6, 274|314|240|
GSTP1_HUMAN, P09211, 55|199|50|64|8|80|109|112|119|116|121|189|45|82|4|
NLTP_HUMAN, P22307, 438|453|464|470|511|522|454|524|546|443|491|197|
SOAT1_HUMAN, P35610, 538|283|
GLSK_HUMAN, O94925, 304|249|308|
CHK2_HUMAN, O96017, 445|
PAK2_HUMAN, Q13177, 130|408|453|246|235|
STAT1_HUMAN, P42224, 68|701|
CBP_HUMAN, Q92793, 632|
P3C2B_HUMAN, O00750, 1056|
HSPB1_HUMAN, P04792, 133|23|54|73|
STK26_HUMAN, Q9P289, 336|283|
GSTM2_HUMAN, P28161, 62|69|116|
PPM1B_HUMAN, O75688, 207|208|
1433T_HUMAN, P27348, 128|149|104|118|19|211|48|103|120|157|
158|212|49|74|
RIOK1_HUMAN, Q9BRS2, 83|
ENPL_HUMAN, P14625, 356|404|671|682|95|355|359|401|429|527|539|563|567|575|652|
667|677|678|727|94|271|280|480|258|137|270|285|434|479|
508|534|547|561|586|630|663|683|168|405|593|142|597|
633|455|360|161|
TOP2B_HUMAN, Q02880, 157|172|177|819|
BCAT1_HUMAN, P54687, 161|
CDK1_HUMAN, P06493, 20|15|160|19|286|181|270|245|99|
KPCA_HUMAN, P17252, 285|504|512|515|195|197|209|232|29|316|35|38|517|
ADHX_HUMAN, P11766, 180|335|50|93|101|113|133|188|228|315|338|366|
RIPK1_HUMAN, Q13546, 384|426|
ADK_HUMAN, P55263, 77|
TLK2_HUMAN, Q86UE8, 129|
CPSF3_HUMAN, Q9UKF6, 528|
SCD5_HUMAN, Q86SK9, 137|
BCAT2_HUMAN, O15382, 228|234|111|229|353|
UBP5_HUMAN, P45974, 288|558|223|485|
PLAP_HUMAN, Q9Y263, 477|
ASNS_HUMAN, P08243, 185|555|216|40|536|398|69|
FABP5_HUMAN, Q01469, 34|40|55|
PRP4_HUMAN, O43172, 470|475|
KPCB_HUMAN, P05771, 515|518|617|209|309|35|618|
PEPD_HUMAN, P12955, 128|
SAHH_HUMAN, P23526, 165|39|143|193|221|432|166|226|426|389|
UBP10_HUMAN, Q14694, 77|
GANAB_HUMAN, Q14697, 341|489|113|396|438|498|509|60|664|669|792|854|
277|477|563|462|491|472|899|
HXK1_HUMAN, P19367, 346|749|732|
PP1G_HUMAN, P36873, 255|137|134|
KCC2G_HUMAN, Q13555, 231|517|
AURKB_HUMAN, Q96GD4, 92|
PCNA_HUMAN, P12004, 211|249|114|133|60|138|77|
MTDC_HUMAN, P13995, 234|50|
6PGD_HUMAN, P52209, 137|106|274|
TRAP1_HUMAN, Q12931, 498|317|327|331|344|470|106|559|324|382|560|95|629|
PSA_HUMAN, P55786, 438|224|173|908|
MBD2_HUMAN, Q9UBB5, 196|
ACOD_HUMAN, O00767, 356|189|194|341|357|
OST48_HUMAN, P39656, 385|
ROA1_HUMAN, P09651, 167|341|347|357|366|62|105|106|113|130|144|15|
161|166|350|52|78|8|87|
GTR1_HUMAN, P11166, 256|
EF1A1_HUMAN, P68104, 146|179|255|30|141|167|177|183|254|29|357|418|85|172|
180|212|215|219|244|273|378|386|392|395|408|41|439|
44|444|450|453|457|64|56|
PAK1_HUMAN, Q13153, 429|131|
LDHA_HUMAN, P00338, 14|243|10|127|145|172|239|247|281|83|
149|284|76|81|318|
TAU_HUMAN, P10636, 711|
SYEP_HUMAN, P07814, 1127|701|1077|1130|1221|1504|290|371|374|377|399|507|546|
1269|1132|148|360|370|542|549|407|791|423|864|
PLCG1_HUMAN, P19174, 1253|428|430|783|
ACACA_HUMAN, Q13085, 2027|
AAPK2_HUMAN, P54646, 413|
MK03_HUMAN, P27361, 280|81|204|
SIR2_HUMAN, Q8IXJ6, 104|109|55|
PIN1_HUMAN, Q13526, 23|63|77|
PPIF_HUMAN, P30405, 183|190|73|

TABLE 3-continued

Protein Modification Sites Targeted by Sulfonyl-Heterocycle Probes and Ligands.

PP1A_HUMAN, P62136, 134|137|114|255|306|70|
BIP_HUMAN, P11021, 340|127|160|175|313|568|635|65|209|113|125|152|163|164|
213|273|276|287|326|96|123|154|370|620|621|516|521|579|523|
CD11A_HUMAN, Q9UQ88, 669|
P4HA1_HUMAN, P13674, 378|157|389|
DDX3X_HUMAN, O00571, 243|266|301|343|38|580|255|511|581|
ABD12_HUMAN, Q8N2K0, 293|
RS27_HUMAN, P42677, 31|36|
LGUL_HUMAN, Q04760, 136|170|140|157|
TDT_HUMAN, P04053, 462|
GLNA_HUMAN, P15104, 283|269|336|
FKBP5_HUMAN, Q13451, 57|58|60|278|409|159|54|
CDK3_HUMAN, Q00526, 19|
DUT_HUMAN, P33316, 167|227|193|
CATZ_HUMAN, Q9UBR2, 281|193|280|76|88|
ATR_HUMAN, Q13535, 2067|
PUR9_HUMAN, P31939, 108|104|208|220|303|371|185|192|293|346|362|464|494|558|
137|195|225|294|356|372|389|406|461|477|479|507|290|
SYQ_HUMAN, P47897, 243|422|748|292|
TERA_HUMAN, P55072, 755|211|288|663|754|
CASP7_HUMAN, P55210, 58|
1433F_HUMAN, Q04917, 133|216|217|49|130|131|
DEFM_HUMAN, Q9HBH1, 240|
DHPR_HUMAN, P09417, 154|150|
TE2IP_HUMAN, Q9NYB0, 32|
HS90B_HUMAN, P08238, 306|623|192|211|216|276|301|305|426|430|457|472|484|485|
512|520|56|596|619|155|356|373|107|180|186|199|203|
204|219|275|286|354|399|402|406|423|427|428|435|438|
477|481|505|526|53|538|550|552|557|559|565|568|573|
574|577|607|624|641|646|649|69|72|95|350|347|
PDK1_HUMAN, Q15118, 365|411|207|
SYLC_HUMAN, Q9P2J5, 473|156|183|213|214|275|336|416|666|939|916|944|369|15|
150|278|370|464|491|541|652|716|942|957|983|997|927|240|768|
PP2AA_HUMAN, P67775, 127|265|130|248|267|284|86|218|34|
HS90A_HUMAN, P07900, 314|631|216|309|313|438|465|466|480|492|493|528|604|61|
627|381|434|520|284|204|209|224|435|436|443|446|458|
478|485|499|534|564|58|585|632|84|649|654|657|197|
VATB2_HUMAN, P21281, 371|39|165|
SF3B3_HUMAN, Q15393, 989|109|1166|1041|77|
SPEE_HUMAN, P19623, 278|
CISD1_HUMAN, Q9NZ45, 35|
SYTC_HUMAN, P26639, 543|103|284|298|392|540|55|351|53|
PI51C_HUMAN, O60331, 71|72|
GFPT1_HUMAN, Q06210, 226|553|
PDCD4_HUMAN, Q53EL6, 409|423|
BRD4_HUMAN, O60885, 1054|
BGAL_HUMAN, P16278, 485|488|
PTN6_HUMAN, P29350, 301|168|271|308|
IF4H_HUMAN, Q15056, 86|42|45|130|80|12|
FER_HUMAN, P16591, 714|
PPIB_HUMAN, P23284, 186|
SAHH2_HUMAN, O43865, 514|527|
PB1_HUMAN, Q86U86, 1404|417|126|416|555|
PSIP1_HUMAN, O75475, 420|18|
IDHC_HUMAN, O75874, 135|139|208|246|391|42|
MAP11_HUMAN, P53582, 180|186|291|309|191|311|
PTN1_HUMAN, P18031, 46|323|
NQO1_HUMAN, P15559, 129|43|68|76|
SYIC_HUMAN, P41252, 845|289|369|409|535|540|608|618|626|71|734|94|
680|371|410|514|545|844|127|283|
PDIA6_HUMAN, Q15084, 146|136|150|66|
ERAP2_HUMAN, Q6P179, 826|892|
MAP1B_HUMAN, P46821, 1955|2040|1830|1337|985|1062|1227|2357|1938|496|1796|
KDM1A_HUMAN, O60341, 807|834|242|
HVCN1_HUMAN, Q96D96, 35|
ASAH1_HUMAN, Q13510, 325|
XPO1_HUMAN, O14980, 36|77|1049|1051|594|469|
HXK2_HUMAN, P52789, 398|401|749|27|
ACPH_HUMAN, P13798, 39|
RB_HUMAN, P06400, 790|325|424|329|791|
MPI_HUMAN, P34949, 46|16|
ADA10_HUMAN, O14672, 741|
LKHA4_HUMAN, P09960, 233|573|
DYN2_HUMAN, P50570, 154|231|265|563|726|626|157|240|390|597|125|
DGLB_HUMAN, Q8NCG7, 573|
XPP1_HUMAN, Q9NQW7, 130|128|78|268|296|269|
2ABA_HUMAN, P63151, 134|
DNJA1_HUMAN, P31689, 376|33|381|37|52|

TABLE 3-continued

Protein Modification Sites Targeted by Sulfonyl-Heterocycle Probes and Ligands.

SYK_HUMAN, Q15046, 231|303|95|370|98|
FEN1_HUMAN, P39748, 268|173|83|152|132|135|200|201|252|267|354|80|
AMPD2_HUMAN, Q01433, 145|
AMPD3_HUMAN, Q01432, 422|
VAV_HUMAN, P15498, 400|404|
DCK_HUMAN, P27707, 204|210|207|
PYR1_HUMAN, P27708, 459|1343|
ZAP70_HUMAN, P43403, 164|492|178|292|506|372|
COX1_HUMAN, P00395, 502|
CSK_HUMAN, P41240, 67|64|97|184|18|133|
PTN12_HUMAN, Q05209, 64|
CDK2_HUMAN, P24941, 20|15|19|236|237|
FNTB_HUMAN, P49356, 300|
FKBP4_HUMAN, Q02790, 161|202|220|111|113|225|108|274|426|245|
57|302|280|411|178|383|
TOPK_HUMAN, Q96KB5, 100|156|74|
SYRC_HUMAN, P54136, 384|536|113|230|323|516|92|131|193|
AK1A1_HUMAN, P14550, 210|
OGA_HUMAN, O60502, 805|807|397|
PURA2_HUMAN, P30520, 203|202|206|239|
NMT1_HUMAN, P30419, 420|423|477|482|
IF4A1_HUMAN, P60842, 126|170|197|356|48|50|70|175|391|146|174|177|
193|202|291|369|381|54|68|
ENOA_HUMAN, P06733, 193|281|71|131|189|200|236|257|270|280|287|407|44|
57|103|126|197|199|221|228|239|256|262|28|330|
335|343|358|394|406|420|54|64|80|92|233|60|89|81|422|
IF4E_HUMAN, P06730, 197|34|
PI42C_HUMAN, Q8TBX8, 384|
PYGL_HUMAN, P06737, 204|186|281|539|574|821|76|614|
SYMC_HUMAN, P56192, 201|274|718|668|204|729|
SLK_HUMAN, Q9H2G2, 1044|
PSB9_HUMAN, P28065, 110|
ABHGA_HUMAN, O95870, 222|
DHSO_HUMAN, Q00796, 54|51|25|300|
HPRT_HUMAN, P00492, 105|
PMM2_HUMAN, O15305, 229|
PRKDC_HUMAN, P78527, 115|1411|1437|157|1802|1881|1920|1988|265|2936|3168|3475|
3791|3828|4077|682|799|1086|1192|2004|2743|2965|3705|
3036|1141|1147|117|1193|1412|1456|1612|225|2441|2746|
2829|3172|3485|3550|3552|3603|4048|4085|801|2366|3280|
THIL_HUMAN, P24752, 214|188|219|256|331|407|90|170|190|202|
257|338|66|87|263|268|223|
NEDD4_HUMAN, P46934, 627|
HCD2_HUMAN, Q99714, 168|101|104|105|172|9|
UPP1_HUMAN, Q16831, 230|227|240|291|35|85|
SGPL1_HUMAN, O95470, 22|25|80|91|
NCEH1_HUMAN, Q6PIU2, 300|301|
CSK22_HUMAN, P19784, 308|
SYHC_HUMAN, P12081, 363|
SMCA4_HUMAN, P51532, 718|901|1379|187|507|731|188|
AKT2_HUMAN, P31751, 265|327|
COQ8B_HUMAN, Q96D53, 113|
SPRE_HUMAN, P35270, 170|259|
PNPO_HUMAN, Q9NVS9, 183|
GGH_HUMAN, Q92820, 109|
PGK1_HUMAN, P00558, 199|161|196|324|76|11|133|141|156|184|191|192|267|
272|275|279|291|30|323|332|353|361|382|388|406|
41|48|75|91|97|15|131|139|
ANM1_HUMAN, Q99873, 53|322|
ACLY_HUMAN, P53396, 384|531|682|692|704|1006|1073|247|252|542|579|364|1012|
230|259|331|538|732|86|97|978|836|554|131|1084|517|
GALE_HUMAN, Q14376, 211|230|267|
AMPB_HUMAN, Q9H4A4, 167|640|
CAN1_HUMAN, P07384, 37|
MK14_HUMAN, Q16539, 103|182|258|249|35|
ELAV1_HUMAN, Q15717, 200|109|26|295|63|320|72|92|
THIC_HUMAN, Q9BWD1, 237|235|
FYV1_HUMAN, Q9Y2I7, 92|93|
PPOX_HUMAN, P50336, 140|
TBB6_HUMAN, Q9BUF5, 222|310|36|50|208|183|106|200|281|340|
CDK6_HUMAN, Q00534, 257|43|
PSB1_HUMAN, P20618, 146|133|135|164|158|132|
NDUB1_HUMAN, O75438, 58|
AGAL_HUMAN, P06280, 123|237|
NDUS6_HUMAN, O75380, 46|51|49|100|
PYRD_HUMAN, Q02127, 166|
NU1M_HUMAN, P03886, 43|
TRXR1_HUMAN, Q16881, 298|

TABLE 3-continued

Protein Modification Sites Targeted by Sulfonyl-Heterocycle Probes and Ligands.

NDUS1_HUMAN, P28331, 636|
NDUAA_HUMAN, O95299, 241|339|343|38|181|242|
TBB4B_HUMAN, P68371, 58|36|50|51|59|297|208|183|222|200|
159|106|340|310|281|
KPCD_HUMAN, Q05655, 630|
IMDH1_HUMAN, P20839, 511|233|
HDAC6_HUMAN, Q9UBN7, 728|
NDUS8_HUMAN, O00217, 38|
FKB1A_HUMAN, P62942, 27|83|35|53|45|81|
TBB4A_HUMAN, P04350, 106|50|51|59|208|183|222|200|310|281|340|
NDUA9_HUMAN, Q16795, 234|
PSA1_HUMAN, P25786, 24|6|115|128|
NDUB4_HUMAN, O95168, 6|77|114|7|85|
NDUB8_HUMAN, O95169, 72|90|77|
NDUA3_HUMAN, O95167, 41|
COMT_HUMAN, P21964, 118|180|197|194|
UMPS_HUMAN, P11172, 37|16|22|
AT1A1_HUMAN, P05023, 10|156|843|
GSK3B_HUMAN, P49841, 288|
GSK3A_HUMAN, P49840, 351|355|
VKOR1_HUMAN, Q9BQB6, 152|159|
TOP1_HUMAN, P11387, 211|231|308|239|310|
TOP2A_HUMAN, P11388, 136|151|328|481|522|82|841|640|892|131|
156|606|798|83|893|
HDAC1_HUMAN, Q13547, 87|201|204|221|226|237|303|358|67|72|
218|242|361|74|89|283|
ACPM_HUMAN, O14561, 147|85|151|
NDUB9_HUMAN, Q9Y6M9, 73|65|
HDAC2_HUMAN, Q92769, 304|88|
NDUS2_HUMAN, O75306, 308|
DNMT1_HUMAN, P26358, 1457|975|979|976|99|
PARP1_HUMAN, P09874, 309|310|689|737|775|794|829|889|896|907|
930|344|634|158|324|346|405|633|662|796|893|
933|940|945|949|117|
MP2K2_HUMAN, P36507, 233|101|187|
TBB2A_HUMAN, Q13885, 58|183|200|208|310|36|50|51|59|
222|159|106|340|281|
CD3E_HUMAN, P07766, 111|188|113|158|160|193|
PUR2_HUMAN, P22102, 344|164|417|
MP2K1_HUMAN, Q02750, 97|
IDHP_HUMAN, P48735, 107|179|222|247|258|274|285|311|81|106|112|127|133|
155|166|180|193|199|242|251|256|263|272|275|280|
282|360|384|400|413|426|442|48|67|69|355|
NDUA4_HUMAN, O00483, 62|65|10|63|
CD3D_HUMAN, P04234, 160|
NDUA1_HUMAN, O15239, 60|61|
NDUS7_HUMAN, O75251, 62|55|
PLMN_HUMAN, P00747, 416|
NDUA8_HUMAN, P51970, 168|32|172|
SV2A_HUMAN, Q7L0J3, 480|385|
NU5M_HUMAN, P03915, 455|
CAH2_HUMAN, P00918, 127|40|51|
DPOD1_HUMAN, P28340, 396|545|894|244|
NDUS3_HUMAN, O75489, 245|
FPPS_HUMAN, P14324, 349|295|
LCK_HUMAN, P06239, 192|209|394|441|470|489|
CDK4_HUMAN, P11802, 17|
ALDR_HUMAN, P15121, 178|190|210|179|195|222|240|83|104|
ROCK2_HUMAN, O75116, 1255|
TBB3_HUMAN, Q13509, 106|159|183|200|208|222|310|36|50|
51|59|281|340|
NDUA5_HUMAN, Q16718, 30|
PSB2_HUMAN, P49721, 134|73|147|146|
NDUF4_HUMAN, Q9P032, 24|
PPIA_HUMAN, P62937, 48|79|118|125|131|133|151|155|28|31|
44|49|76|82|91|
TBB1_HUMAN, Q9H4B7, 310|159|
PUR1_HUMAN, Q06203, 94|
IMDH2_HUMAN, P12268, 110|430|459|509|400|233|511|450|
THRB_HUMAN, P00734, 583|603|
RIR1_HUMAN, P23921, 285|316|726|737|485|279|232|486|391|
SSDH_HUMAN, P51649, 519|
TBB2B_HUMAN, Q9BVA1, 58|159|310|36|50|51|59|208|183|222|
200|106|340|281|
TBB5_HUMAN, P07437, 58|106|159|183|200|208|222|281|310|340|
36|50|51|59|103|122|154|216|252|
297|324|336|350|379|
DYR_HUMAN, P00374, 163|

TABLE 3-continued

Protein Modification Sites Targeted by Sulfonyl-Heterocycle Probes and Ligands.

GSHR_HUMAN, P00390, 400|158|
NDUBA_HUMAN, O96000, 115|26|105|29|52|
ITAL_HUMAN, P20701, 332|
PSB8_HUMAN, P28062, 241|133|179|
PNPH_HUMAN, P00491, 91|50|
ADA_HUMAN, P00813, 68|67|323|
TBB8_HUMAN, Q3ZCM7, AT1B3_HUMAN, P54709, 7|
CD2_HUMAN, P06729, 310|
PSB5_HUMAN, P28074, 150|149|228|204|
NDUF2_HUMAN, Q8N183, 38|106|137|32|108|140|20|39|57|
NDUB3_HUMAN, O43676, 39|
TYSY_HUMAN, P04818, 301|135|169|308|
H90B2_HUMAN, Q58FF8, 261|133|198|260|56|138|
SBNO1_HUMAN, A3KN83, 339|
YJU2_HUMAN, Q9BW85, 98|10|
HDHD5_HUMAN, Q9BXW7, 309|328|285|129|279|331|132|177|
H2B1L_HUMAN, Q99880, 44|84|122|117|21|86|121|
HS902_HUMAN, Q14568, 283|
TCPW_HUMAN, Q92526, 109|
BD1L1_HUMAN, Q8NFC6, 84|
RABEK_HUMAN, Q7Z6M1, 87|
SCAF8_HUMAN, Q9UPN6, 64|516|
RL26L_HUMAN, Q9UNX3, 42|41|62|
UE2NL_HUMAN, Q5JXB2, 77|
DD19A_HUMAN, Q9NUU7, 171|
CCD58_HUMAN, Q4VC31, 100|142|139|
TMED8_HUMAN, Q6PL24, 280|
PRRC1_HUMAN, Q96M27, 227|232|
RT26_HUMAN, Q9BYN8, 81|
ISOC1_HUMAN, Q96CN7, 160|162|132|
TBB8L_HUMAN, A6NNZ2, 222|159|281|
BSDC1_HUMAN, Q9NW68, 18|22|73|
ZCCHL_HUMAN, Q96H79, 172|174|
HDDC2_HUMAN, Q7Z4H3, 37|
ARP3C_HUMAN, Q9C0K3, 73|
HDHD1_HUMAN, Q08623, 26|
SFT2C_HUMAN, Q58719, 11|
5NT3B_HUMAN, Q969T7, 60|85|
USP9Y_HUMAN, O00507, 649|368|
AXA2L_HUMAN, A6NMY6, 317|24|
KLH36_HUMAN, Q8N4N3, 435|
BET1_HUMAN, O15155, 86|
RMXL1_HUMAN, Q96E39, 310|
TM6S1_HUMAN, Q9BZW5, 355|
TI23B_HUMAN, Q5SRD1, 52|110|
TTI2_HUMAN, Q6NXR4, 92|97|
ARL17_HUMAN, Q8IVW1, 35|
WDR44_HUMAN, Q5JSH3, 546|446|619|
CR032_HUMAN, Q8TCD1, 39|49|
RBM42_HUMAN, Q9BTD8, 446|
ATP5L_HUMAN, O75964, 22|11|24|35|54|66|
TM205_HUMAN, Q6UW68, 140|
RMD1_HUMAN, Q96DB5, 139|
RM39_HUMAN, Q9NYK5, 211|
TF3C5_HUMAN, Q9Y5Q8, 331|345|184|194|
F118B_HUMAN, Q9BPY3, 307|
PIPSL_HUMAN, A2A3N6, 559|
F136A_HUMAN, Q96C01, 89|99|18|127|138|104|130|
F1142_HUMAN, Q9NRY5, 183|182|
TI17B_HUMAN, O60830, 136|
HS905_HUMAN, Q58FG0, 177|178|46|
LC7L2_HUMAN, Q9Y383, 196|105|186|229|235|371|
SRG2B_HUMAN, P0DMP2, 170|
ALKB4_HUMAN, Q9NXW9, 158|
ANR39_HUMAN, Q53RE8, 65|
SUGP2_HUMAN, Q8IX01, 63|
SC61G_HUMAN, P60059, 16|27|
RM14_HUMAN, Q6P1L8, 51|
SASH3_HUMAN, O75995, 12|
IF5AL_HUMAN, Q6IS14, 69|
PP5D1_HUMAN, E7EU14, 44|
RT06_HUMAN, P82932, 69|
RM16_HUMAN, Q9NX20, 233|
SRSF8_HUMAN, Q9BRL6, 44|23|
AT5L2_HUMAN, Q7Z4Y8, 54|
SF3B5_HUMAN, Q9BWJ5, 18|
PSAL_HUMAN, A6NEC2, 438|224|173|
SMAP_HUMAN, O00193, 84|

TABLE 3-continued

Protein Modification Sites Targeted by Sulfonyl-Heterocycle Probes and Ligands.

TMED9_HUMAN, Q9BVK6, 184|180|226|232|71|
S2540_HUMAN, Q8TBP6, 176|
ETFR1_HUMAN, Q6IPR1, 42|
I2BP1_HUMAN, Q8IU81, 130|315|
FA98B_HUMAN, Q52LJ0, 147|258|256|
ARMC6_HUMAN, Q6NXE6, 427|
LSM6_HUMAN, P62312, 40|
NIBL1_HUMAN, Q96TA1, 258|
RASA2_HUMAN, Q15283, 53|
NOC4L_HUMAN, Q9BVI4, 445|
LMBD2_HUMAN, Q68DH5, 260|274|
PSMA8_HUMAN, Q8TAA3, 126|153|161|165|23|114|
TAF6L_HUMAN, Q9Y6J9, 586|
EF1A3_HUMAN, Q5VTE0, 146|179|255|30|141|167|177|254|29|418|
85|162|165|172|215|219|244|273|378|386|392|41|
439|44|444|450|453|457|64|56|
ATP5S_HUMAN, Q99766, 136|89|
RUSD2_HUMAN, Q8IZ73, 177|
STMP1_HUMAN, E0CX11, 30|41|
S61A2_HUMAN, Q9H9S3, 107|
CC117_HUMAN, Q8IWD4, 231|
S35E1_HUMAN, Q96K37, 111|337|394|
I2BPL_HUMAN, Q9H1B7, 149|459|
RM50_HUMAN, Q8N5N7, 32|34|
ZMAT2_HUMAN, Q96NC0, 21|140|
TBAL3_HUMAN, A6NHL2, 326|406|319|110|
LRC40_HUMAN, Q9H9A6, 595|329|
F10A5_HUMAN, Q8NFI4, 213|151|185|186|
TM9S2_HUMAN, Q99805, 495|
H90B4_HUMAN, Q58FF6, 167|32|
H90B3_HUMAN, Q58FF7, 107|492|190|171|56|195|
ENPLL_HUMAN, Q58FF3, 58|
CAR19_HUMAN, Q96LW7, 85|
RS4Y2_HUMAN, Q8TD47, 54|149|
ZN709_HUMAN, Q8N972, 168|
NPS3A_HUMAN, Q9UFN0, 32|42|
H2B1O_HUMAN, P23527, 84|
P20D2_HUMAN, Q8IYS1, 315|
ANKY2_HUMAN, Q8IV38, 265|262|143|
ACYP1_HUMAN, P07311, 25|
RBM4B_HUMAN, Q9BQ04, 37|
RUS1_HUMAN, Q96GQ5, 51|
PANK4_HUMAN, Q9NVE7, 128|129|258|338|
H2B2D_HUMAN, Q6DRA6, 84|
SPCS2_HUMAN, Q15005, 38|47|
SNX15_HUMAN, Q9NRS6, 64|
SC11C_HUMAN, Q9BY50, 23|
TASOR_HUMAN, Q9UK61, 676|678|
CSK23_HUMAN, Q8NEV1, 182|307|325|
TMM19_HUMAN, Q96HH6, 125|126|
PEPL1_HUMAN, Q8NDH3, 382|
T161A_HUMAN, Q9NX61, 40|41|
TLS1_HUMAN, Q9NZ63, 277|147|221|
ARK74_HUMAN, Q8NHP1, 197|
QRIC1_HUMAN, Q2TAL8, 718|337|
T11L1_HUMAN, Q9NUJ3, 307|
H2B2F_HUMAN, Q5QNW6, 84|
TRAD1_HUMAN, O14545, 558|
PRPS3_HUMAN, P21108, 245|94|
ZN622_HUMAN, Q969S3, 376|
TM256_HUMAN, Q8N2U0, 25|36|38|
RAB1C_HUMAN, Q92928, 122|129|
RALYL_HUMAN, Q86SE5, 34|
POTEJ_HUMAN, P0CG39, 1025|
POTEI_HUMAN, P0CG38, 1062|
RT14_HUMAN, O60783, 47|
RT05_HUMAN, P82675, 137|
ACTBM_HUMAN, Q9BYX7, 362|
RB12B_HUMAN, Q8IXT5, 390|
SMCO4_HUMAN, Q9NRQ5, 10|14|20|
HNRL2_HUMAN, Q1KMD3, 741|264|334|481|625|740|472|668|725|222|
711|726|474|479|626|694|727|
TM214_HUMAN, Q6NUQ4, 47|
SLTM_HUMAN, Q9NWH9, 718|
EMC7_HUMAN, Q9NPA0, 221|225|232|
TM245_HUMAN, Q9H330, 533|586|
MIC10_HUMAN, Q5TGZ0, 72|
SIM15_HUMAN, Q7Z3B0, 53|67|

TABLE 3-continued

Protein Modification Sites Targeted by Sulfonyl-Heterocycle Probes and Ligands.

PSB3_HUMAN, P49720, 104|
ASML_HUMAN, O95671, 418|
YIPF6_HUMAN, Q96EC8, 78|
NT5D2_HUMAN, Q9H857, 110|457|109|
RM46_HUMAN, Q9H2W6, 213|84|216|
TM87A_HUMAN, Q8NBN3, 97|
MYEF2_HUMAN, Q9P2K5, 112|
ISK2_HUMAN, P20155, 77|
RABL3_HUMAN, Q5HYI8, 156|
RU2B_HUMAN, P08579, 75|77|
COXM1_HUMAN, Q7Z7K0, 96|
RL7L_HUMAN, Q6DKI1, 137|233|
DUS3L_HUMAN, Q96G46, 604|
ZCHC8_HUMAN, Q6NZY4, 402|
H2B2C_HUMAN, Q6DN03, 84|
F210A_HUMAN, Q96ND0, 123|231|221|262|
HGB1A_HUMAN, B2RPK0, 16|78|
CNPY3_HUMAN, Q9BT09, 110|54|114|
GXLT1_HUMAN, Q4G148, 413|
TMA16_HUMAN, Q96EY4, 33|
RETR3_HUMAN, Q86VR2, 233|49|
F10C1_HUMAN, Q70Z53, 74|
TIM13_HUMAN, Q9Y5L4, 49|53|
WASC4_HUMAN, Q2M389, 1138|
RM45_HUMAN, Q9BRJ2, 114|126|135|102|256|
H2A1C_HUMAN, Q93077, 58|120|126|37|
H2A1D_HUMAN, P20671, 37|
INT10_HUMAN, Q9NVR2, 281|
THNS1_HUMAN, Q8IYQ7, 549|
ZN573_HUMAN, Q86YE8, 498|
NDK8_HUMAN, O60361, 52|
RBM26_HUMAN, Q5T8P6, 699|822|
HIG2A_HUMAN, Q9BW72, 65|
CMS1_HUMAN, Q9BQ75, 137|103|
VP26B_HUMAN, Q4G0F5, 222|33|55|59|
SR140_HUMAN, O15042, 158|603|614|615|617|
DNJB3_HUMAN, Q8WWF6, 53|
KLC4_HUMAN, Q9NSK0, 572|305|
RDH13_HUMAN, Q8NBN7, 294|
TM209_HUMAN, Q96SK2, 183|
GAG2B_HUMAN, Q13066, 16|
H2A1J_HUMAN, Q99878, 126|
H2B1M_HUMAN, Q99879, 84|
WDR54_HUMAN, Q9H977, 33|
TRIR_HUMAN, Q9BQ61, 153|
TRAM1_HUMAN, Q15629, 113|335|337|342|
LRC47_HUMAN, Q8N1G4, 335|389|
TM14C_HUMAN, Q9P0S9, 81|

REFERENCES

All references listed in the instant disclosure, including but not limited to all patents, patent applications and publications thereof, scientific journal articles, and database entries (including but not limited to UniProt, EMBL, and GENBANK® biosequence database entries and including all annotations available therein) are incorporated herein by reference in their entireties to the extent that they supplement, explain, provide a background for, and/or teach methodology, techniques, and/or compositions employed herein. The discussion of the references is intended merely to summarize the assertions made by their authors. No admission is made that any reference (or a portion of any reference) is relevant prior art. Applicants reserve the right to challenge the accuracy and pertinence of any cited reference.

1. Cravatt B F, Wright A T, Kozarich J W. Activity-based protein profiling: from enzyme chemistry to proteomic chemistry. *Annu Rev Biochem* 2008, 77: 383-414.
2. Sadaghiani A M, Verhelst S H, Bogyo M. Tagging and detection strategies for activity-based proteomics. *Curr Opin Chem Biol* 2007, 11(1): 20-28.
3. Niphakis M J, Cravatt B F. Enzyme inhibitor discovery by activity-based protein profiling. *Annu Rev Biochem* 2014, 83: 341-377.
4. Bachovchin D A, Cravatt B F. The pharmacological landscape and therapeutic potential of serine hydrolases. *Nat Rev Drug Discov* 2012, 11(1): 52-68.
5. Deu E, Verdoes M, Bogyo M. New approaches for dissecting protease functions to improve probe development and drug discovery. *Nat Struct Mol Biol* 2012, 19(1): 9-16.
6. Patricelli M P, Szardenings A K, Liyanage M, Nomanbhoy T K, Wu M, Weissig H, et al. Functional interrogation of the kinome using nucleotide acyl phosphates. *Biochemistry* 2007, 46(2): 350-358.
7. Kumar S, Zhou B, Liang F, Wang W Q, Huang Z, Zhang Z Y. Activity-based probes for protein tyrosine phosphatases. *Proc Natl Acad Sci USA* 2004, 101(21): 7943-7948.
8. Vocadlo D J, Bertozzi C R. A strategy for functional proteomic analysis of glycosidase activity from cell lysates. *Angew Chem Int Ed Engl* 2004, 43(40): 5338-5342.

9. Liu Y, Patricelli M P, Cravatt B F. Activity-based protein profiling: the serine hydrolases. *Proc Natl Acad Sci USA* 1999, 96(26): 14694-14699.
10. Weerapana E, Wang C, Simon G M, Richter F, Khare S, Dillon M B, et al. Quantitative reactivity profiling predicts functional cysteines in proteomes. *Nature* 2010, 468 (7325): 790-795.
11. Hacker S M, Backus K M, Lazear M R, Forli S, Correia B E, Cravatt B F. Global profiling of lysine reactivity and ligandability in the human proteome. *Nat Chem* 2017, 9(12): 1181-1190.
12. Lin S, Yang X, Jia S, Weeks A M, Hornsby M, Lee P S, et al. Redox-based reagents for chemoselective methionine bioconjugation. *Science* 2017, 355(6325): 597-602.
13. Matthews M L, He L, Homing B D, Olson E J, Correia B E, Yates J R, 3rd, et al. Chemoproteomic profiling and discovery of protein electrophiles in human cells. *Nat Chem* 2017, 9(3): 234-243.
14. Parker C G, Galmozzi A, Wang Y, Correia B E, Sasaki K, Joslyn C M, et al. Ligand and Target Discovery by Fragment-Based Screening in Human Cells. *Cell* 2017, 168(3): 527-541 e529.
15. Narayanan A, Jones L H. Sulfonyl fluorides as privileged warheads in chemical biology. *Chem Sci* 2015, 6(5): 2650-2659.
16. Gao B, Zhang L, Zheng Q, Zhou F, Klivansky L M, Lu J, et al. Bifluoride-catalysed sulfur(VI) fluoride exchange reaction for the synthesis of polysulfates and polysulfonates. *Nat Chem* 2017, 9(11): 1083-1088.
17. Dong J, Sharpless K B, Kwisnek L, Oakdale J S, Fokin V V. SuFEx-based synthesis of polysulfates. *Angew Chem Int Ed Engl* 2014, 53(36): 9466-9470.
18. Fahmey D E, Gold A M. Sulfonyl Fluorides as Inhibitors of Esterases. I. Rates of Reaction with Acetylcholinesterase, α-Chymotrypsin, and Trypsin. *Journal of the American Chemical Society* 1963, 85(7): 997-1000.
19. Shannon D A, Gu C, McLaughlin C J, Kaiser M, van der Hoom R A, Weerapana E. Sulfonyl fluoride analogues as activity-based probes for serine proteases. *Chembiochem* 2012, 13(16): 2327-2330.
20. Gu C, Shannon D A, Colby T, Wang Z, Shabab M, Kumari S, et al. Chemical proteomics with sulfonyl fluoride probes reveals selective labeling of functional tyrosines in glutathione transferases. *Chem Biol* 2013, 20(4): 541-548.
21. Zhao Q, Ouyang X, Wan X, Gajiwala K S, Kath J C, Jones L H, et al. Broad-Spectrum Kinase Profiling in Live Cells with Lysine-Targeted Sulfonyl Fluoride Probes. *J Am Chem Soc* 2017, 139(2): 680-685.
22. Yang B, Wu H, Schnier P D, Liu Y, Liu J, Wang N, et al. Proximity-enhanced SuFEx chemical cross-linker for specific and multitargeting cross-linking mass spectrometry. *Proc Natl Acad Sci USA* 2018, 115(44): 11162-11167.
23. Yang X, Michiels T J M, de Jong C, Soethoudt M, Dekker N, Gordon E, et al. An Affinity-Based Probe for the Human Adenosine A2A Receptor. *J Med Chem* 2018, 61(17): 7892-7901.
24. Dong J, Krasnova L, Finn M G, Sharpless K B. Sulfur (VI) fluoride exchange (SuFEx): another good reaction for click chemistry. *Angew Chem Int Ed Engl* 2014, 53(36): 9430-9448.
25. Chen W, Dong J, Plate L, Mortenson D E, Brighty G J, Li S, et al. Arylfluorosulfates Inactivate Intracellular Lipid Binding Protein(s) through Chemoselective SuFEx Reaction with a Binding Site Tyr Residue. *J Am Chem Soc* 2016, 138(23): 7353-7364.
26. Mortenson D E, Brighty G J, Plate L, Bare G, Chen W, Li S, et al. "Inverse Drug Discovery" Strategy To Identify Proteins That Are Targeted by Latent Electrophiles As Exemplified by Aryl Fluorosulfates. *J Am Chem Soc* 2018, 140(1): 200-210.
27. Fadeyi O O, Hoth L R, Choi C, Feng X, Gopalsamy A, Hett E C, et al. Covalent Enzyme Inhibition through Fluorosulfate Modification of a Noncatalytic Serine Residue. *ACS Chem Biol* 2017, 12(8): 2015-2020.
28. Liu Z, Li J, Li S, Li G, Sharpless K B, Wu P. SuFEx Click Chemistry Enabled Late-Stage Drug Functionalization. *J Am Chem Soc* 2018, 140(8): 2919-2925.
29. Adibekian A, Martin B R, Wang C, Hsu K L, Bachovchin D A, Niessen S, et al. Click-generated triazole ureas as ultrapotent in vivo-active serine hydrolase inhibitors. *Nat Chem Biol* 2011, 7(7): 469-478.
30. Ahn K, Boehm M, Brown M F, Calloway J, Che Y, Chen J, et al. Discovery of a Selective Covalent Inhibitor of Lysophospholipase-like 1 (LYPLAL1) as a Tool to Evaluate the Role of this Serine Hydrolase in Metabolism. *ACS Chem Biol* 2016, 11(9): 2529-2540.
31. Bern M, Kil Y J, Becker C. Byonic: advanced peptide and protein identification software. *Curr Protoc Bioinformatics* 2012, *Chapter* 13: Unit13 20.
32. Hornbeck P V, Zhang B, Murray B, Kornhauser J M, Latham V, Skrzypek E. PhosphoSitePlus, 2014: mutations, PTMs and recalibrations. *Nucleic Acids Res* 2015, 43(Database issue): D512-520.
33. Wishart D S, Feunang Y D, Guo A C, Lo E J, Marcu A, Grant J R, et al. *DrugBank* 5.0: a major update to the DrugBank database for 2018. *Nucleic Acids Res* 2018, 46(D1): D1074-D1082.
34. Hentze M W, Castello A, Schwarzl T, Preiss T. A brave new world of RNA-binding proteins. *Nat Rev Mol Cell Biol* 2018, 19(5): 327-341.
35. Yaffe M B. Phosphotyrosine-binding domains in signal transduction. *Nat Rev Mol Cell Biol* 2002, 3(3): 177-186.
36. Shin M, Franks C E, Hsu K L. Isoform-selective activity-based profiling of ERK signaling. *Chem Sci* 2018, 9(9): 2419-2431.
37. Choi E J, Jung D, Kim J S, Lee Y, Kim B M. Chemoselective Tyrosine Bioconjugation through Sulfate Click Reaction. *Chemistry* 2018, 24(43): 10948-10952.
38. Shannon D A, Banerjee R, Webster E R, Bak D W, Wang C, Weerapana E. Investigating the proteome reactivity and selectivity of aryl halides. *J Am Chem Soc* 2014, 136(9): 3330-3333.
39. Humphrey S J, Yang G, Yang P, Fazakerley D J, Stockli J, Yang J Y, et al. Dynamic adipocyte phosphoproteome reveals that Akt directly regulates mTORC2. *Cell Metab* 2013, 17(6): 1009-1020.
40. Lundby A, Secher A, Lage K, Nordsborg N B, Dmytriyev A, Lundby C, et al. Quantitative maps of protein phosphorylation sites across 14 different rat organs and tissues. *Nat Commun* 2012, 3: 876.
41. Hilger M, Bonaldi T, Gnad F, Mann M. Systems-wide analysis of a phosphatase knock-down by quantitative proteomics and phosphoproteomics. *Mol Cell* Proteomics 2009, 8(8): 1908-1920.
42. Song G, Chen L, Zhang B, Song Q, Yu Y, Moore C, et al. Proteome-wide Tyrosine Phosphorylation Analysis Reveals Dysregulated Signaling Pathways in Ovarian Tumors. *Mol Cell Proteomics* 2019, 18(3): 448-460.
43. Song L, Turkson J, Karras J G, Jove R, Haura E B. Activation of Stat3 by receptor tyrosine kinases and cytokines regulates survival in human non-small cell carcinoma cells. *Oncogene* 2003, 22(27): 4150-4165.

44. Hong J Y, Oh I H, McCrea P D. Phosphorylation and isoform use in p120-catenin during development and tumorigenesis. *Biochim Biophys Acta* 2016, 1863(1): 102-114.
45. Hitosugi T, Kang S, Vander Heiden M G, Chung T W, Elf S, Lythgoe K, et al. Tyrosine phosphorylation inhibits PKM2 to promote the Warburg effect and tumor growth. *Sci Signal* 2009, 2(97): ra73.
46. Weerapana E, Simon G M, Cravatt B F. Disparate proteome reactivity profiles of carbon electrophiles. *Nat Chem Biol* 2008, 4(7): 405-407.
47. Manley J L, Kramer A R. A rational nomenclature for serine/arginine-rich protein splicing factors (S R proteins). *Genes Dev* 2010, 24(11): 1073-1074.
48. Hargous Y, Hautbergue G M, Tintaru A M, Skrisovska L, Golovanov A P, Stevenin J, et al. Molecular basis of RNA recognition and TAP binding by the S R proteins SRp20 and 9G8. *EMBO J* 2006, 25(21): 5126-5137.
49. Harris T K, Turner G J. Structural basis of perturbed pKa values of catalytic groups in enzyme active sites. *IUBMB Life* 2002, 53(2): 85-98.
50. Decker C J, Parker R. P-bodies and stress granules: possible roles in the control of translation and mRNA degradation. *Cold Spring Harb Perspect Biol* 2012, 4(9): a012286.
51. Franks C E, Campbell S T, Purow B W, Harris T E, Hsu K L. The Ligand Binding Landscape of Diacylglycerol Kinases. *Cell Chem Biol* 2017, 24(7): 870-880 e875.
52. Chen H, Boutros P C. VennDiagram: a package for the generation of highly-customizable Venn and Euler diagrams in R. *BMC Bioinformatics* 2011, 12: 35.
53. Sigrist C J, de Castro E, Cerutti L, Cuche B A, Hulo N, Bridge A, et al. New and continuing developments at PROSITE. *Nucleic Acids Res* 2013, 41(Database issue): D344-347.
54. Mi H, Muruganujan A, Casagrande J T, Thomas P D. Large-scale gene function analysis with the PANTHER classification system. *Nat Protoc* 2013, 8(8): 1551-1566.
55. Bereman M S, Beri J, Sharma V, Nathe C, Eckels J, MacLean B, et al. An Automated Pipeline to Monitor System Performance in Liquid Chromatography-Tandem Mass Spectrometry Proteomic Experiments. *J Proteome Res* 2016, 15(12): 4763-4769.
56. Wickham H, SpringerLink (Online service), Springer-LINK ebooks—Mathematics and Statistics (2016). ggplot2 Elegant Graphics for Data Analysis. 2nd ed. [S.1.]: Springer International Publishing; 2016.
57. Lin Y, Lang S A. New Synthesis of Diacylamines. *Synthesis-Stuttgart* 1980(2): 119-121.
58. Lin Y-I, Lang S A, Lovell M F, Perkinson N A. New synthesis of 1,2,4-triazoles and 1,2,4-oxadiazoles. *The Journal of Organic Chemistry* 1979, 44(23): 4160-4164.
59. Schreiber, S. L.; Kotz, J. D.; Li, M.; Aube, J.; Austin, C. P.; Reed, J. C.; Rosen, H.; White, E. L.; Sklar, L. A.; Lindsley, C. W.; Alexander, B. R.; Bittker, J. A.; Clemons, P. A.; de Souza, A.; Foley, M. A.; Palmer, M.; Shamji, A. F.; Wawer, M. J.; McManus, O.; Wu, M.; Zou, B.; Yu, H.; Golden, J. E.; Schoenen, F. J.; Simeonov, A.; Jadhav, A.; Jackson, M. R.; Pinkerton, A. B.; Chung, T. D.; Griffin, P. R.; Cravatt, B. F.; Hodder, P. S.; Roush, W. R.; Roberts, E.; Chung, D. H.; Jonsson, C. B.; Noah, J. W.; Severson, W. E.; Ananthan, S.; Edwards, B.; Oprea, T. I.; Conn, P. J.; Hopkins, C. R.; Wood, M. R.; Stauffer, S. R.; Emmitte, K. A.; Team, N. I. H. M. L. P., Advancing Biological Understanding and Therapeutics Discovery with Small-Molecule Probes. *Cell* 2015, 161 (6), 1252-65.
60. Singh, J.; Petter, R. C.; Baillie, T. A.; Whitty, A., The resurgence of covalent drugs. *Nat Rev Drug Discov* 2011, 10 (4), 307-17.
61. Wang, Y.; Dix, M. M.; Bianco, G.; Remsberg, J. R.; Lee, H. Y.; Kalocsay, M.; Gygi, S. P.; Forli, S.; Vite, G.; Lawrence, R. M.; Parker, C. G.; Cravatt, B. F., Expedited mapping of the ligandable proteome using fully functionalized enantiomeric probe pairs. *Nat Chem* 2019, 11 (12), 1113-1123.
62. Backus, K. M.; Correia, B. E.; Lum, K. M.; Forli, S.; Horning, B. D.; Gonzalez-Paez, G. E.; Chatterjee, S.; Lanning, B. R.; Teijaro, J. R.; Olson, A. J.; Wolan, D. W.; Cravatt, B. F., Proteome-wide covalent ligand discovery in native biological systems. *Nature* 2016, 534 (7608), 570-4.
63. Bradshaw, J. M.; McFarland, J. M.; Paavilainen, V. O.; Bisconte, A.; Tam, D.; Phan, V. T.; Romanov, S.; Finkle, D.; Shu, J.; Patel, V.; Ton, T.; Li, X.; Loughhead, D. G.; Nunn, P. A.; Karr, D. E.; Gerritsen, M. E.; Funk, J. O.; Owens, T. D.; Verner, E.; Brameld, K. A.; Hill, R. J.; Goldstein, D. M.; Taunton, J., Prolonged and tunable residence time using reversible covalent kinase inhibitors. *Nat Chem Biol* 2015, 11 (7), 525-31.
64. Yoo, E.; Stokes, B. H.; de Jong, H.; Vanaerschot, M.; Kumar, T.; Lawrence, N.; Njoroge, M.; Garcia, A.; Van der Westhuyzen, R.; Momper, J. D.; Ng, C. L.; Fidock, D. A.; Bogyo, M., Defining the Determinants of Specificity of *Plasmodium* Proteasome Inhibitors. *J Am Chem Soc* 2018, 140 (36), 11424-11437.
65. Patricelli, M. P.; Nomanbhoy, T. K.; Wu, J.; Brown, H.; Zhou, D.; Zhang, J.; Jagannathan, S.; Aban, A.; Okerberg, E.; Herring, C.; Nordin, B.; Weissig, H.; Yang, Q.; Lee, J. D.; Gray, N. S.; Kozarich, J. W., In situ kinase profiling reveals functionally relevant properties of native kinases. *Chem Biol* 2011, 18 (6), 699-710.
66. Zhang, X.; Crowley, V. M.; Wucherpfennig, T. G.; Dix, M. M.; Cravatt, B. F., Electrophilic PROTACs that degrade nuclear proteins by engaging DCAF16. *Nat Chem Biol* 2019, 15 (7), 737-746.
67. Spradlin, J. N.; Hu, X.; Ward, C. C.; Brittain, S. M.; Jones, M. D.; Ou, L.; To, M.; Proudfoot, A.; Ornelas, E.; Woldegiorgis, M.; Olzmann, J. A.; Bussiere, D. E.; Thomas, J. R.; Tallarico, J. A.; McKenna, J. M.; Schirle, M.; Maimone, T. J.; Nomura, D. K., Harnessing the anti-cancer natural product nimbolide for targeted protein degradation. *Nat Chem Biol* 2019, 15 (7), 747-755.
68. Resnick, E.; Bradley, A.; Gan, J.; Douangamath, A.; Krojer, T.; Sethi, R.; Geurink, P. P.; Aimon, A.; Amitai, G.; Bellini, D.; Bennett, J.; Fairhead, M.; Fedorov, O.; Gabizon, R.; Gan, J.; Guo, J.; Plotnikov, A.; Reznik, N.; Ruda, G. F.; Diaz-Saez, L.; Straub, V. M.; Szommer, T.; Velupillai, S.; Zaidman, D.; Zhang, Y.; Coker, A. R.; Dowson, C. G.; Barr, H. M.; Wang, C.; Huber, K. V. M.; Brennan, P. E.; Ovaa, H.; von Delft, F.; London, N., Rapid Covalent-Probe Discovery by Electrophile-Fragment Screening. *J Am Chem Soc* 2019, 141 (22), 8951-8968.
69. Bos, J.; Muir, T. W., A Chemical Probe for Protein Crotonylation. *J Am Chem Soc* 2018, 140 (14), 4757-4760.
70. Wang, R.; Islam, K.; Liu, Y.; Zheng, W.; Tang, H.; Lailler, N.; Blum, G.; Deng, H.; Luo, M., Profiling genome-wide chromatin methylation with engineered posttranslation apparatus within living cells. *J Am Chem Soc* 2013, 135 (3), 1048-56.
71. Bicker, K. L.; Subramanian, V.; Chumanevich, A. A.; Hofseth, L. J.; Thompson, P. R., Seeing citrulline: development of a phenylglyoxal-based probe to visualize protein citrullination. *J Am Chem Soc* 2012, 134 (41), 17015-8.
72. Hahm, H. S.; Toroitich, E. K.; Borne, A. L.; Brulet, J. W.; Libby, A. H.; Yuan, K.; Ware, T. B.; McCloud, R. L.; Ciancone, A. M.; Hsu, K. L., Global targeting of functional tyrosines using sulfur-triazole exchange chemistry. *Nat Chem Biol* 2019. (doi.org/10.1038/s41589-019-0404-5)
73. Grimster, N. P.; Connelly, S.; Baranczak, A.; Dong, J.; Krasnova, L. B.; Sharpless, K. B.; Powers, E. T.; Wilson, I. A.; Kelly, J. W., Aromatic sulfonyl fluorides covalently kinetically stabilize transthyretin to prevent amyloidogenesis while affording a fluorescent conjugate. *J Am Chem Soc* 2013, 135 (15), 5656-68.
74. Zheng, Q.; Woehl, J. L.; Kitamura, S.; Santos-Martins, D.; Smedley, C. J.; Li, G.; Forli, S.; Moses, J. E.; Wolan, D. W.; Sharpless, K. B., SuFEx-enabled, agnostic discovery of covalent inhibitors of human neutrophil elastase. *Proc Natl Acad Sci USA* 2019, 116 (38), 18808-18814.
75. Yang, B.; Wang, N.; Schnier, P. D.; Zheng, F.; Zhu, H.; Polizzi, N. F.; Ittuveetil, A.; Saikam, V.; DeGrado, W. F.; Wang, Q.; Wang, P. G.; Wang, L., Genetically Introducing Biochemically Reactive Amino Acids Dehydroalanine and Dehydrobutyrine in Proteins. *J Am Chem Soc* 2019, 141 (19), 7698-7703.
76. Erlanson, D. A.; Fesik, S. W.; Hubbard, R. E.; Jahnke, W.; Jhoti, H., Twenty years on: the impact of fragments on drug discovery. *Nat Rev Drug Discov* 2016, 15 (9), 605-19.
77. Hopkins, A. L.; Keseru, G. M.; Leeson, P. D.; Rees, D. C.; Reynolds, C. H., The role of ligand efficiency metrics in drug discovery. *Nat Rev Drug Discov* 2014, 13 (2), 105-21.
78. Scott, D. E.; Coyne, A. G.; Hudson, S. A.; Abell, C., Fragment-based approaches in drug discovery and chemical biology. *Biochemistry* 2012, 51 (25), 4990-5003.
79. Electrical Effect Substituent Constants for Correlation Analysis. In *Progress in Physical Organic Chemistry*, pp 119-251.
80. Mann, M., Functional and quantitative proteomics using SILAC. *Nat Rev Mol Cell Biol* 2006, 7 (12), 952-8.
81. Lee, I.; Schindelin, H., Structural insights into E1-catalyzed ubiquitin activation and transfer to conjugating enzymes. *Cell* 2008, 134 (2), 268-78.
82. Chang, T. K.; Shravage, B. V.; Hayes, S. D.; Powers, C. M.; Simin, R. T.; Wade Harper, J.; Baehrecke, E. H., Uba1 functions in Atg7- and Atg3-independent autophagy. *Nat Cell Biol* 2013, 15 (9), 1067-78.
83. Liu, X.; Zhao, B.; Sun, L.; Bhuripanyo, K.; Wang, Y.; Bi, Y.; Davuluri, R. V.; Duong, D. M.; Nanavati, D.; Yin, J.; Kiyokawa, H., Orthogonal ubiquitin transfer identifies ubiquitination substrates under differential control by the two ubiquitin activating enzymes. *Nat Commun* 2017, 8, 14286.
84. Park, E.; Rawson, S.; Li, K.; Kim, B. W.; Ficarro, S. B.; Pino, G. G.; Sharif, H.; Marto, J. A.; Jeon, H.; Eck, M. J., Architecture of autoinhibited and active BRAF-MEK1-14-3-3 complexes. *Nature* 2019, 575 (7783), 545-550.
85. Gavin, A. L.; Huang, D.; Huber, C.; Martensson, A.; Tardif, V.; Skog, P. D.; Blane, T. R.; Thinnes, T. C.; Osborn, K.; Chong, H. S.; Kargaran, F.; Kimm, P.; Zeitjian, A.; Sielski, R. L.; Briggs, M.; Schulz, S. R.; Zarpellon, A.; Cravatt, B.; Pang, E. S.; Teijaro, J.; de la Torre, J. C.; O'Keeffe, M.; Hochrein, H.; Damme, M.; Teyton, L.; Lawson, B. R.; Nemazee, D., PLD3 and PLD4 are single-stranded acid exonucleases that regulate endosomal nucleic-acid sensing. *Nat Immunol* 2018, 19 (9), 942-953.
86. Bezerra, G. A.; Dobrovetsky, E.; Viertlmayr, R.; Dong, A.; Binter, A.; Abramic, M.; Macheroux, P.; Dhe-Paganon, S.; Gruber, K., Entropy-driven binding of opioid peptides induces a large domain motion in human dipeptidyl peptidase III. *Proc Natl Acad Sci USA* 2012, 109 (17), 6525-30.
87. Liu, Q.; Sabnis, Y.; Zhao, Z.; Zhang, T.; Buhrlage, S. J.; Jones, L. H.; Gray, N. S., Developing irreversible inhibitors of the protein kinase cysteinome. *Chem Biol* 2013, 20 (2), 146-59.
88. Simaga, S.; Babic, D.; Osmak, M.; Ilic-Forko, J.; Vitale, L.; Milicic, D.; Abramic, M., Dipeptidyl peptidase III in malignant and non-malignant gynaecological tissue. *Eur J Cancer* 1998, 34 (3), 399-405.
89. Hast, B. E.; Goldfarb, D.; Mulvaney, K. M.; Hast, M. A.; Siesser, P. F.; Yan, F.; Hayes, D. N.; Major, M. B., Proteomic analysis of ubiquitin ligase KEAP1 reveals associated proteins that inhibit NRF2 ubiquitination. *Cancer Res* 2013, 73 (7), 2199-210.
90. Okamura, T.; Singh, S.; Buolamwini, J.; Haystead, T.; Friedman, H.; Bigner, D.; Ali-Osman, F., Tyrosine phosphorylation of the human glutathione S-transferase P1 by epidermal growth factor receptor. *J Biol Chem* 2009, 284 (25), 16979-89.
91. Allocati, N.; Masulli, M.; Di Ilio, C.; Federici, L., Glutathione transferases: substrates, inihibitors and pro-drugs in cancer and neurodegenerative diseases. *Oncogenesis* 2018, 7 (1), 8.
92. Horning, B. D.; Suciu, R. M.; Ghadiri, D. A.; Ulanovskaya, O. A.; Matthews, M. L.; Lum, K. M.; Backus, K. M.; Brown, S. J.; Rosen, H.; Cravatt, B. F., Chemical Proteomic Profiling of Human Methyltransferases. *J Am Chem Soc* 2016, 138 (40), 13335-13343.
93. Lee, J.; Kang, S. U.; Lim, J. O.; Choi, H. K.; Jin, M. K.; Toth, A.; Pearce, L. V.; Tran, R.; Wang, Y.; Szabo, T.; Blumberg, P. M. N-[4-(Methylsulfonylamino) benzyl] thiourea analogues as vanilloid receptor antagonists: analysis of structure-activity relationships for the 'C-Region'. *Bioorg. Med. Chem.* 2004, 12, 371-385.
94. Turner, S. C.; Esbenshade, T. A.; Bennani, Y. L.; Hancock, A. A. A new class of histamine $H_3$-Receptor antagonists: synthesis and structure-Activity relationships of 7,8,9,10-Tetrahydro-6H-cyclohepta[b]quinolones. *Bioorg. Med. Chem. Lett.* 2003, 13, 2131-2135.
95. Raushel, J.; Fokin, V. V. Efficient Synthesis of 1-Sulfonyl-1,2,3-triazoles. *Org. Lett.* 2010, 12(21), 4952-4955.
96. Kheirabadi, M.; Creech, G. S.; Qiao, J. X.; Nirschl, D. S.; Leahy, D. K.; Boy, K. M.; Carter, P. H.; Eastgate, M. D. Leveraging a "Catch-Release" Logic Gate Process for the Synthesis and Nonchromatographic Purification of Thioether- or Amine-Bridged Macrocyclic Peptides. *J Org. Chem.* 2018, 83(8), 4323-4335.
97. Yusubov, M. S.; Yusubova, R. Y.; Nemykin, V. N.; Maskaev, A. V.; Geraskina, M. R.; Kirschning, A.; Zhdankin, V. V. Potassium 4-Iodylbenzenesulfonate: Preparation, Structure, and Application as a Reagent for Oxidative Iodination of Arenes. *Eur. J. Org. Chem.* 2012, 30, 5935-5942.
98. Paoletta, S.; Tosh, D. K.; Finley, A.; Gizewski, E. T.; Moss, S. M.; Gao, Z. G.; Auchampach, J. A.; Salvemini, D.; Jacobson, K. A. Rational Design of Sulfonated $A_3$ Adenosine Receptor-Selective Nucleosides as Pharmacological Tools to Study Chronic Neuropathic Pain. *J. Med. Chem.* 2013, 56(4), 5949-5963.

99. Ware, T. B.; Franks, C. E.; Granade, M. E.; Zhang, M.; Kim, K. B.; Park, K. S.; Gahlmann, A.; Harris, T. E.; Hsu, K. L. Reprogramming fatty acyl specificity of lipid kinases via C1 domain engineering. *Nat. Chem. Biol.* 2020, 16, 170-178.

100. Zhang, L.; Peng, X. M. I Damu, G. L.; Geng, R. X.; Zhou, C. H. Comprehensive review in current developments of imidazole-based medicinal chemistry. *Med. Res. Rev.* 2014, 34(2), 340-437.

101. Lazreg, F., et. al., *Organometallics,* 37, 679-683, 2018.

102. Yamauchi, M., et. al., *Heterocycles,* 80(1), 177-181, 2010.

103. Mangubat-Medina, A. E.; Martin, S. C.; Hanaya, K.; and Ball, Z. T. *J. Am. Chem. Soc.* 2018, 140, 8401-8404.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A tyrosine-reactive compound having a structure of the formula:

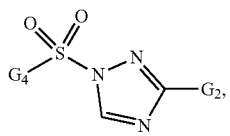

wherein:

$G_2$ is selected from phenyl, pyridyl, thiophenyl, and substituted phenyl; and $G_4$ is selected from the group consisting of cycloalkyl, phenyl, naphthyl, substituted naphthyl, pyridyl, substituted pyridyl, and substituted phenyl.

2. The tyrosine-reactive compound of claim 1, wherein $G_4$ is selected from the group consisting of phenyl, naphthyl, pyridyl, substituted pyridyl, and substituted phenyl.

3. The tyrosine-reactive compound of claim 2, wherein $G_4$ is phenyl or substituted phenyl, wherein the substituted phenyl is para-substituted phenyl and/or phenyl substituted with one or more aryl group substituents selected from the group consisting of halo, alkoxy, cyano, perfluoralkoxy, aryl, —C(=O)—NH(alkyl), —C(=O)—NH(cycloalkyl), and —C(=O)—NH(aralkyl).

4. The tyrosine-reactive compound of claim 1, wherein $G_2$ is substituted phenyl, wherein said substituted phenyl is phenyl substituted with halo, alkoxy, or perfluoroalkyl.

5. The tyrosine-reactive compound of claim 1, wherein the tyrosine reactive compound has a structure of Formula (IV):

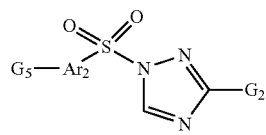

wherein:

$Ar_2$ is selected from the group consisting of phenyl, naphthyl, and pyridyl;

$G_2$ is selected from the group consisting of phenyl, pyridyl, thiophenyl, and substituted phenyl; and $G_5$ is selected from the group consisting of H, halo, perhaloalkyl, alkoxy, cyano, perhaloalkoxy, aryl, —C(=O)—NH(alkyl), —C(=O)—NH(cycloalkyl), and —C(=O)—NH(aralkyl).

6. The tyrosine-reactive compound of claim 5, wherein $G_2$ is substituted phenyl, said substituted phenyl having the structure —$Ar_3$-$G_6$, wherein $Ar_3$ is phenyl and $G_6$ is selected from the group consisting of H, halo, alkoxy, and perhaloalkyl.

7. A pharmaceutical composition comprising an active ingredient comprising a compound having a structure of the formula:

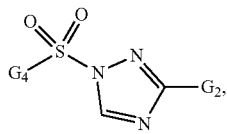

wherein:
  $G_2$ is phenyl, pyridyl, thiophenyl, and substituted phenyl; and
  $G_4$ is selected from the group consisting of cycloalkyl, phenyl, naphthyl, substituted naphthyl, pyridyl, substituted pyridyl, and substituted phenyl.

8. The pharmaceutical composition of claim 7, wherein $G_4$ is cyclopropyl.

9. The pharmaceutical composition of claim 7, wherein $G_4$ is substituted phenyl, substituted naphthyl, or substituted pyridyl, said substituted phenyl, substituted naphthyl, or substituted pyridyl having the structure —$Ar_2$-$(G_5)_y$, wherein y is an integer from 1 to 3; $Ar_2$ is phenyl, naphthyl, or pyridyl; and each $G_5$ is selected from the group consisting of halo, alkoxy, aryloxy, aryl, nitro, —$OCF_3$, perfluoroalkyl, cyano, —C(=O)—O-alkyl, —NHC(=O)-alkyl, and —C(=O)—NRR', wherein R and R' are each selected from H, alkyl, aralkyl, and aryl or wherein R and R' together form an alkylene or substituted alkylene group.

10. The pharmaceutical composition of claim 9, wherein $G_4$ is —$Ar_2$-$G_5$.

11. The pharmaceutical composition of claim 9, wherein $Ar_2$ is phenyl $G_5$ is selected from the group consisting of halo, alkoxy, cyano, perfluoralkoxy, aryl, —C(=O)—NH(alkyl), —C(=O)—NH(cycloalkyl), and —C(=O)—NH(aralkyl).

12. The pharmaceutical composition of claim 7, wherein $G_2$ is substituted phenyl wherein said substituted phenyl is phenyl substituted with one, two or three aryl group substituents selected from halo, alkoxy, nitro, amino, perfluoroalkyl, perfluoroalkoxy, and —C(=O)—O-alkyl.

13. The pharmaceutical composition of claim 7, wherein the compound has a structure of Formula (IV):

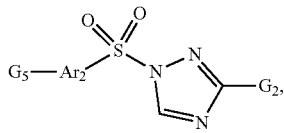

wherein:
  $Ar_2$ is selected from the group consisting of phenyl, naphthyl, and pyridyl;
  $G_2$ is selected from phenyl, pyridyl, thiophenyl, and substituted phenyl; and
  $G_5$ is selected from the group consisting of H, halo, alkoxy, cyano, perfluoralkoxy, aryl, —C(=O)—NH(alkyl), —C(=O)—NH(cycloalkyl), and —C(=O)—NH(aralkyl).

14. The pharmaceutical composition of claim 13, wherein $G_2$ is substituted phenyl having the structure —$Ar_3$-$G_6$, wherein $Ar_3$ is phenyl and wherein $G_6$ is selected from H, alkoxy, perfluoroalkyl, perfluoroalkoxy, —C(=O)—O-alkyl, halo, aryl, alkyl, and amino.

15. The pharmaceutical composition of claim 7, wherein the compound is selected from the group consisting of:

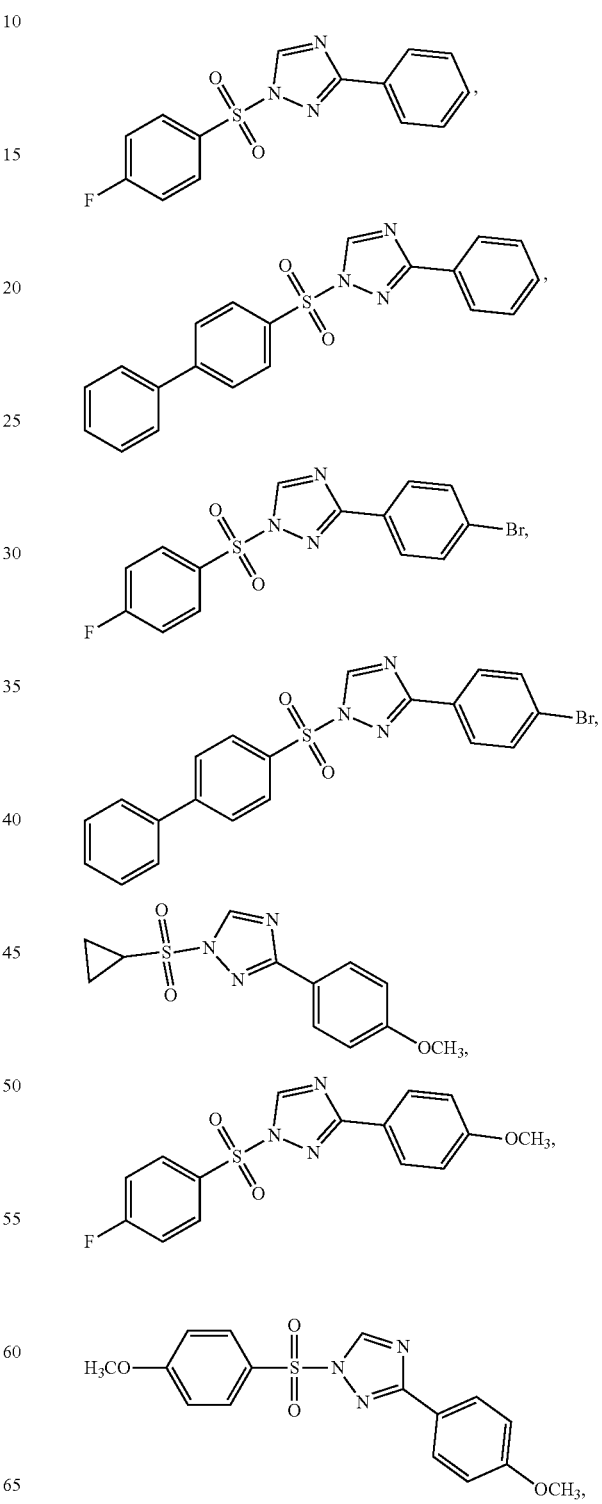

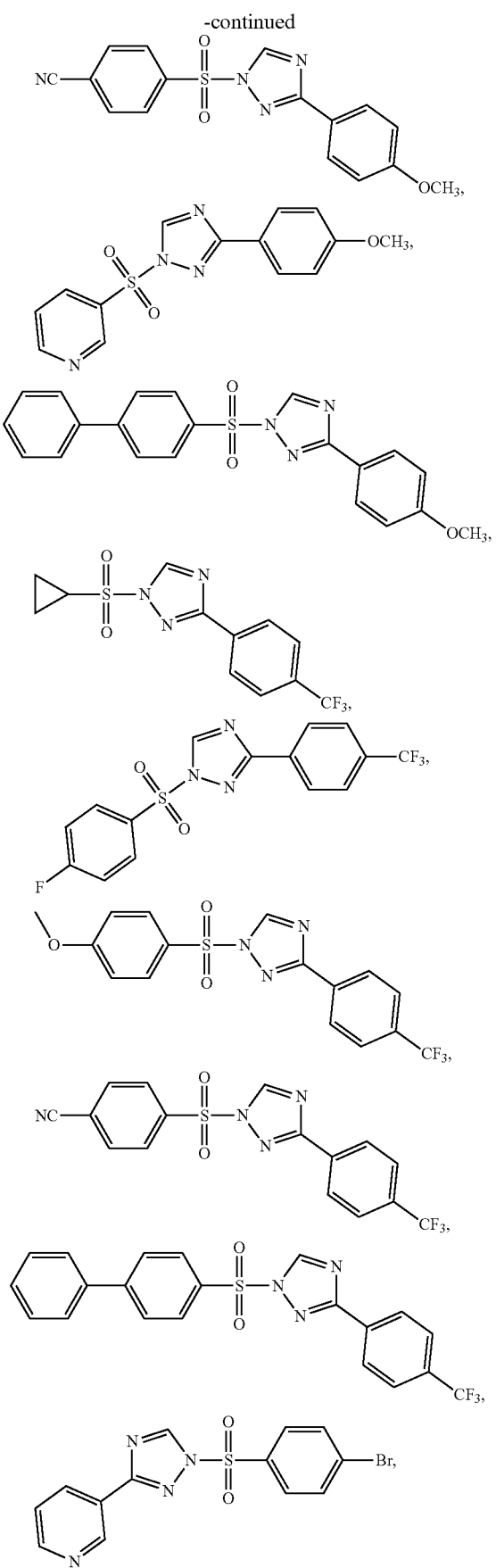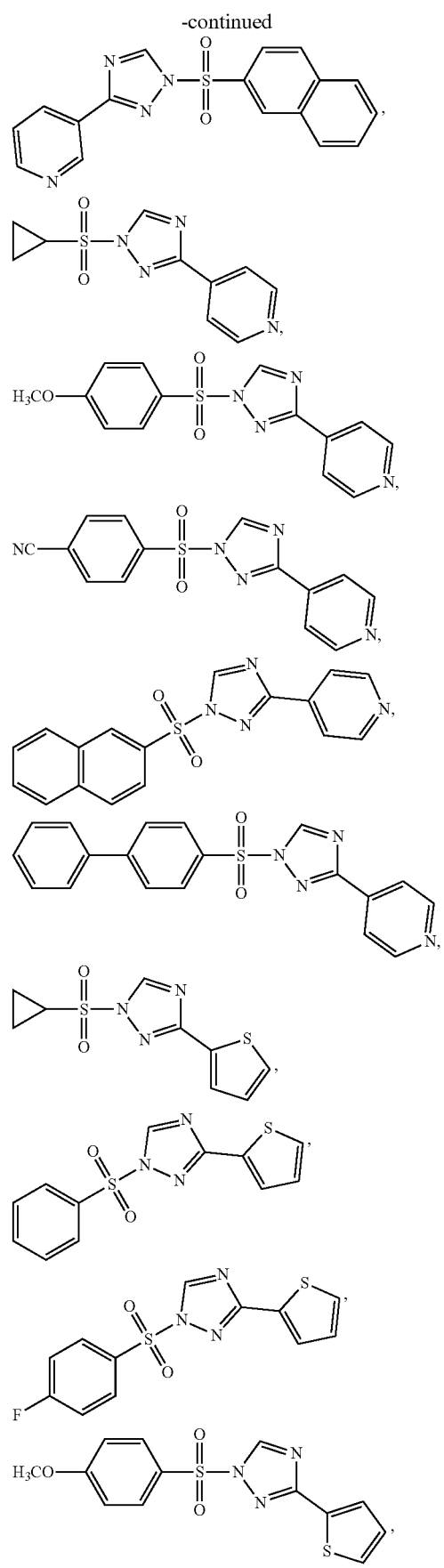

-continued
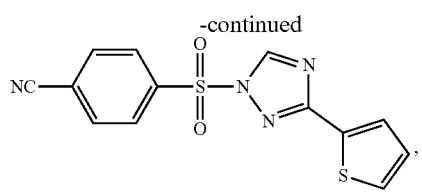
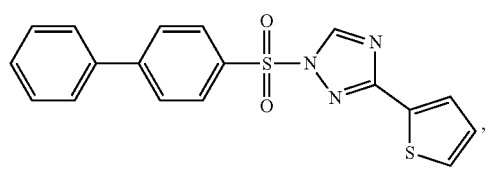
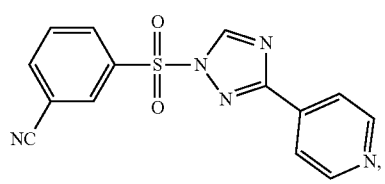
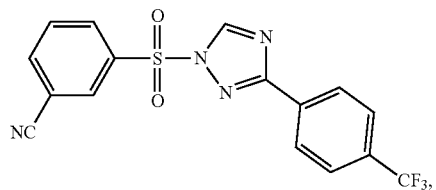
-continued
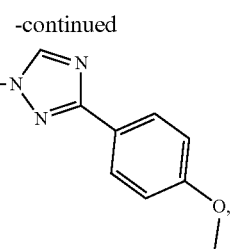
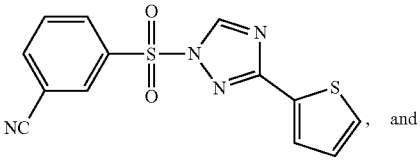
16. The pharmaceutical composition of claim 12, wherein $G_2$ is substituted phenyl, wherein said substituted phenyl is phenyl substituted with one, two or three substituents selected from —$CF_3$, —$OCH_3$, and —$CO_2CH_3$.
* * * * *